US012741989B2

(12) United States Patent
Qian et al.

(10) Patent No.: US 12,741,989 B2
(45) Date of Patent: Sep. 22, 2026

(54) COMPOSITIONS FOR DELIVERY OF ANTISENSE COMPOUNDS

(71) Applicant: Entrada Therapeutics, Inc., Boston, MA (US)

(72) Inventors: Ziqing Qian, Wellesley, MA (US); Xiang Li, Belmont, MA (US); Mahboubeh Kheirabadi, Natick, MA (US); Mohanraj Dhanabal, Boston, MA (US); Haoming Liu, Canton, MA (US); Xiulong Shen, Waltham, MA (US); Kimberli Kamer, Boston, MA (US); Natarajan Sethuraman, Boston, MA (US)

(73) Assignee: Entrada Therapeutics, Inc., Boston, MA (US)

( * ) Notice: Subject to any disclaimer, the term of this patent is extended or adjusted under 35 U.S.C. 154(b) by 878 days.

(21) Appl. No.: 17/757,421

(22) PCT Filed: Dec. 21, 2020

(86) PCT No.: PCT/US2020/066459
§ 371 (c)(1),
(2) Date: Jun. 15, 2022

(87) PCT Pub. No.: WO2021/127650
PCT Pub. Date: Jun. 24, 2021

(65) Prior Publication Data

US 2023/0020092 A1 Jan. 19, 2023

Related U.S. Application Data

(60) Provisional application No. 63/069,984, filed on Aug. 25, 2020, provisional application No. 63/052,286,
(Continued)

(51) Int. Cl.
*C07K 7/64* (2006.01)
*C12N 15/113* (2010.01)

(52) U.S. Cl.
CPC .............. *C07K 7/64* (2013.01); *C12N 15/113* (2013.01); *C12N 2310/11* (2013.01);
(Continued)

(58) Field of Classification Search
CPC ........ C07K 7/64; C07K 19/00; C12N 15/113; C12N 2310/11; C12N 2310/315;
(Continued)

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |

(Continued)

FOREIGN PATENT DOCUMENTS

| | | |
|---|---|---|
| CA | 2417064 A1 | 2/2002 |
| CA | 2455951 A1 | 2/2003 |

(Continued)

OTHER PUBLICATIONS

Fadzen et al., Chimeras of Cell-Penetrating Peptides Demonstrate Synergistic Improvement in Antisense Efficacy. Biochemistry. Sep. 24, 2019;58(38):3980-3989 and S1-S44 Supplemental. doi: 10.1021/acs.biochem.9b00413. Epub Sep. 6, 2019. PMID: 31450889 (Year: 2019).*

(Continued)

*Primary Examiner* — Randall L Beane
(74) *Attorney, Agent, or Firm* — Schwegman Lundberg & Woessner, P.A.

(57) ABSTRACT

Provided herein are compounds comprising cyclic cell penetrating peptides and antisense compounds. Also provided herein are methods of modulating splicing, inhibiting or regulating translation, mediating degradation, blocking
(Continued)

5′-conjugation, click chemistry expansions of nucleotide repeats, and treating disease using the aforementioned compounds.

1 Claim, 90 Drawing Sheets

Specification includes a Sequence Listing.

Related U.S. Application Data filed on Jul. 15, 2020, provisional application No. 63/036,240, filed on Jun. 8, 2020, provisional application No. 62/950,639, filed on Dec. 19, 2019.

(52) U.S. Cl.
CPC .. *C12N 2310/315* (2013.01); *C12N 2310/322* (2013.01); *C12N 2310/3231* (2013.01); *C12N 2310/3233* (2013.01)

(58) Field of Classification Search
CPC ...... C12N 2310/322; C12N 2310/3231; C12N 2310/3233; C12N 2310/3513; C12N 2310/3515; A61K 47/6455; A61K 9/0019; A61K 31/7088
See application file for complete search history.

(56) References Cited

U.S. PATENT DOCUMENTS 5,185,444 A 2/1993 Summerton et al.
5,217,866 A 6/1993 Summerton et al.
5,235,033 A 8/1993 Summerton et al.
5,698,685 A 12/1997 Summerton et al.
5,859,233 A 1/1999 Hirschbein et al.
5,965,536 A 10/1999 Cohen et al.
6,110,889 A 8/2000 Miller et al.
6,251,854 B1 6/2001 Montal et al.
6,355,619 B1 3/2002 Miller et al.
6,593,292 B1 7/2003 Rothbard et al.
6,605,115 B1 8/2003 Cooke et al.
6,649,587 B1 11/2003 Frydman et al.
6,669,951 B2 12/2003 Rothbard et al.
6,730,293 B1 5/2004 Rothbard et al.
6,759,387 B2 7/2004 Rothbard et al.
6,794,545 B1 9/2004 Frydman et al.
6,809,176 B2 10/2004 Blokhin et al.
6,828,105 B2 12/2004 Stein et al.
6,864,355 B1 3/2005 May et al.
6,960,648 B2 11/2005 Bonny
6,982,351 B2 1/2006 Frydman et al.
7,026,347 B2 4/2006 Frydman et al.
7,169,814 B2 1/2007 Rothbard et al.
7,186,825 B2 3/2007 Frydman et al.
7,229,961 B2 6/2007 Rothbard et al.
7,253,207 B2 8/2007 Blokhin et al.
7,279,502 B2 10/2007 Clifford et al.
7,312,244 B2 12/2007 Clifford et al.
7,468,418 B2 12/2008 Iversen et al.
7,585,834 B2 9/2009 Wender et al.
7,816,490 B2 10/2010 Hogan et al.
7,850,949 B2 12/2010 Fang
7,943,762 B2 5/2011 Weller et al.
8,067,571 B2 11/2011 Weller et al.
8,076,476 B2 12/2011 Reeves et al.
8,299,206 B2 10/2012 Fox et al.
8,614,290 B2 12/2013 Wester et al.
8,623,833 B2 1/2014 Rothbard et al.
8,628,750 B2 1/2014 Wester et al.
8,629,112 B2 1/2014 Gombert et al.
8,901,071 B2 12/2014 O'Neil et al.
8,969,551 B2 3/2015 Ueda
9,161,948 B2 10/2015 Hanson
9,169,290 B2 10/2015 Oneil
9,303,075 B2 4/2016 Brinkmann et al.
9,610,362 B2 4/2017 Armstrong
9,745,576 B2 8/2017 De Visser et al.
9,868,767 B2 1/2018 Pei et al.
10,077,443 B2 9/2018 Albaek et al.
10,415,036 B2 9/2019 Torii et al.
10,501,496 B2 12/2019 Pei et al.
10,626,147 B2 4/2020 Pei et al.
10,815,276 B2 10/2020 Pei et al.
10,913,773 B2 2/2021 Pei
11,168,310 B2 11/2021 Sethuraman et al.
11,225,506 B2 1/2022 Pei et al.
11,339,192 B2 5/2022 Pei
11,351,222 B2 6/2022 Pei et al.
11,352,394 B2 6/2022 Pei et al.
11,576,946 B2 2/2023 Pei et al.
11,793,884 B2 10/2023 Pei et al.
2002/0009491 A1 1/2002 Rothbard et al.
2002/0035243 A1 3/2002 Imfeld et al.
2002/0120100 A1 8/2002 Bonny
2002/0127198 A1 9/2002 Rothbard et al.
2003/0022831 A1 1/2003 Rothbard et al.
2003/0032593 A1 2/2003 Wender et al.
2003/0032594 A1 2/2003 Bonny
2003/0072715 A1 4/2003 Frydman et al.
2003/0130356 A1 7/2003 Frydman et al.
2003/0167129 A1 9/2003 Nestor et al.
2004/0152687 A1 8/2004 Frydman et al.
2004/0192665 A1 9/2004 Frydman et al.
2004/0248783 A1 12/2004 Kawabe et al.
2005/0107289 A1 5/2005 Ghadiri et al.
2005/0192210 A1 9/2005 Rothbard et al.
2005/0261249 A1 11/2005 Iversen et al.
2006/0128614 A1 6/2006 Cheng et al.
2006/0141514 A1 6/2006 Rozzelle et al.
2006/0276425 A1 12/2006 Mourich et al.
2007/0004661 A1 1/2007 Stein et al.
2007/0041904 A1 2/2007 Jiang et al.
2007/0129323 A1 6/2007 Stein et al.
2008/0234183 A1 9/2008 Hallbrink et al.
2009/0186802 A1 7/2009 Alluis et al.
2010/0016215 A1 1/2010 Moulton et al.
2010/0130591 A1 5/2010 Sazani et al.
2010/0221235 A1 9/2010 Arranz
2010/0234281 A1 9/2010 Weller et al.
2010/0292148 A1 11/2010 Krippner et al.
2011/0269665 A1 11/2011 Kole
2012/0016005 A1 1/2012 Samarsky et al.
2012/0045393 A1 2/2012 Linder et al.
2012/0156138 A1 6/2012 Smith
2014/0235557 A1 8/2014 De Waard
2014/0294942 A1 10/2014 French et al.
2014/0303071 A1 10/2014 O'neil
2014/0303238 A1 10/2014 Linsley et al.
2014/0329772 A1 11/2014 Linsley et al.
2015/0038671 A1 2/2015 Parang et al.
2015/0297742 A1 10/2015 Strieker et al.
2016/0031941 A1 2/2016 Eckert et al.
2016/0115202 A1 4/2016 Pei et al.
2016/0151512 A1 6/2016 Kim
2017/0112896 A1 4/2017 Briesewitz
2017/0190743 A1 7/2017 Pei et al.
2017/0240961 A1* 8/2017 Drmanac ............ C12Q 1/6869
2017/0304383 A1 10/2017 Briesewitz et al.
2017/0355730 A1* 12/2017 Pei ........................ A61K 38/12
2018/0030094 A1 2/2018 Pei et al.
2018/0030411 A1 2/2018 Kahvejian et al.
2018/0135054 A1 5/2018 Gryaznov et al.
2019/0282654 A1 9/2019 Pei et al.
2019/0284239 A1 9/2019 Pei
2019/0284240 A1 9/2019 Pei et al.
2019/0292208 A1 9/2019 Cai et al.
2019/0309020 A1 10/2019 Pei
2019/0365918 A1 12/2019 Bestwick et al.
2020/0291070 A1 9/2020 Pei
2020/0354697 A1 11/2020 Sethuraman et al.
2020/0377886 A1 12/2020 Passini et al.
2020/0385427 A1 12/2020 Pei et al.
2020/0392498 A1 12/2020 Bradshaw et al.

(56) References Cited

U.S. PATENT DOCUMENTS

2021/0130379 A1 5/2021 Sinha et al.
2022/0177523 A1 6/2022 Pei et al.
2023/0312653 A1 10/2023 Dougherty et al.

FOREIGN PATENT DOCUMENTS

CA 2949705 A1 11/2015
CA 3092062 A1 8/2019
CN 105440105 A 3/2016
CN 106852146 A 6/2017
CN 106852146 B 8/2021
CN 113861268 A 12/2021
EP 1185493 A1 3/2002
EP 1185493 B1 7/2005
EP 1574507 A2 9/2005
EP 1797901 A1 6/2007
EP 2420255 A2 2/2012
EP 2426203 A2 3/2012
EP 2420255 A3 4/2013
EP 3149025 A2 4/2017
EP 3149025 B1 6/2019
EP 3544623 A1 10/2019
EP 3613426 A1 2/2020
HK 1232239 A1 1/2018
HK 1232239 B 4/2020
HK 40019383 10/2020
JP 3791981 B2 6/2006
JP 2009527251 A 7/2009
JP 2010526091 A 7/2010
JP 2012131743 A 7/2012
JP 5909611 B2 4/2016
JP 2016065018 A 4/2016
JP 2017519041 A 7/2017
JP 2020169170 A 10/2020
JP 6807831 B2 12/2020
WO WO-9921877 A1 5/1999
WO WO-0011022 A1 3/2000
WO WO-0113957 A2 3/2001
WO 0152875 A1 7/2001
WO 0231109 A2 4/2002
WO WO-02057313 A2 7/2002
WO WO-02064091 A2 8/2002
WO WO-02067917 A1 9/2002
WO 02092617 A1 11/2002
WO WO-02090503 A2 11/2002
WO WO-03059942 A2 7/2003
WO WO-03070755 A2 8/2003
WO WO-03092631 A2 11/2003
WO WO-03092632 A2 11/2003
WO WO-2004050685 A2 6/2004
WO WO-2006041805 A1 4/2006
WO WO-2006058436 A1 6/2006
WO WO-2006086773 A2 8/2006
WO WO-2007040535 A1 4/2007
WO WO-2007055578 A1 5/2007
WO WO-2007070372 A2 6/2007
WO WO-2007072037 A1 6/2007
WO 2007097561 A1 8/2007
WO WO-2007096662 A2 8/2007
WO WO-2007106554 A2 9/2007
WO WO-2007108749 A1 9/2007
WO WO-2007111993 A2 10/2007
WO WO-2008077194 A1 7/2008
WO 2008134761 A2 11/2008
WO 2009005793 A2 1/2009
WO WO-2009027706 A2 3/2009
WO WO-2009092062 A2 7/2009
WO 2009098450 A2 8/2009
WO 2009098450 A3 10/2009
WO 2010039088 A1 4/2010
WO WO-2010045335 A1 4/2010
WO 2010072406 A1 7/2010
WO WO-2010107832 A1 9/2010
WO WO-2011095218 A1 8/2011
WO WO-2011095607 A1 8/2011
WO WO-2011126010 A1 10/2011
WO WO-2013142184 A1 9/2013
WO 2014052276 A1 4/2014
WO 2014053882 A1 4/2014
WO WO-2014053629 A1 4/2014
WO 2014086835 A1 6/2014
WO 2014190257 A2 11/2014
WO 2014190313 A2 11/2014
WO 2015051030 A2 4/2015
WO 2015148620 A2 10/2015
WO 2015153761 A2 10/2015
WO 2015179434 A1 11/2015
WO 2015179741 A1 11/2015
WO WO-2015179691 A2 11/2015
WO WO-2015179691 A3 2/2016
WO WO-2015179691 A9 3/2016
WO WO-2016033368 A1 3/2016
WO WO-2016044683 A1 3/2016
WO 2016054510 A1 4/2016
WO 2016173214 A1 11/2016
WO WO-2016198676 A1 12/2016
WO 2017044855 A2 3/2017
WO 2017048466 A1 3/2017
WO 2017050836 A1 3/2017
WO WO-2018098231 A1 * 5/2018 ......... A61K 49/0056
WO 2019165183 A1 8/2019
WO 2019217682 A1 11/2019
WO 2020028254 A1 2/2020
WO 2020030927 A1 2/2020
WO 2020102630 A1 5/2020
WO 2020198151 A1 10/2020
WO 2020227194 A1 11/2020
WO 2021041546 A1 3/2021
WO WO-2021041895 A1 3/2021
WO 2021119756 A1 6/2021
WO WO-2021127650 A1 6/2021
WO 2022125984 A1 6/2022
WO 2022125987 A1 6/2022
WO 2022178379 A1 8/2022
WO WO-2022213118 A1 10/2022
WO 2022240757 A1 11/2022
WO 2022240758 A1 11/2022
WO 2022240760 A2 11/2022
WO 2022241408 A1 11/2022
WO 2022251415 A1 12/2022
WO 2022271818 A1 12/2022
WO 2023034817 A4 4/2023
WO 2023034818 A4 5/2023
WO 2023081893 A1 5/2023
WO 2024073042 A1 4/2024

OTHER PUBLICATIONS

Park et al., Cyclic Cell-Penetrating Peptides as Efficient Intracellular Drug Delivery Tools. Mol Pharm. Sep. 3, 2019;16(9):3727-3743. doi: 10.1021/acs.molpharmaceut.9b00633. Epub Aug. 8, 2019. PMID: 31329448 (Year: 2019).*

Wang et al., Construction of cell penetrating peptide vectors with N-terminal stearylated nuclear localization signal for targeted delivery of DNA into the cell nuclei. J Control Release. Oct. 10, 2011;155(1):26-33. doi: 10.1016/j.jconrel.2010.12.009. Epub Dec. 24, 2010. PMID: 21187118 (Year: 2010).*

Greg T. Hermanson, Chapter 2—Functional Targets for Bioconjugation, Bioconjugate Techniques (Third Edition), Academic Press, 2013, pp. 127 and 188, ISBN 9780123822390, https://doi.org/10.1016/B978-0-12-382239-0.00002-9 (Year: 2013).*

Griffin et al., Transglutaminases: nature's biological glues. Biochem J. Dec. 1, 2002;368(Pt 2):377-96. doi: 10.1042/BJ20021234. PMID: 12366374; PMCID: PMC1223021 (Year: 2002).*

Abramova T.V., et al., "Solid-Phase-Supported Synthesis of Morpholinoglycine Oligonucleotide Mimics," The Beilstein Journal of Organic Chemistry, May 20, 2014, vol. 10, pp. 1151-1158.

Alhakamy N.A., et al., "Noncovalently Associated Cell-Penetrating Peptides for Gene Delivery Applications," Therapeutic Delivery, 2013, vol. 4, No. 6, pp. 741-757.

Ali S.A., et al., "A Review of Methods Available to Estimate Solvent-Accessible Surface Areas of Soluble Proteins in the Folded

(56) References Cited

OTHER PUBLICATIONS and Unfolded States," Current Protein and Peptide Science, 2014, vol. 15, No. 3, pp. 456-476 (21 Pages).
Alzani R., et al., "Suramin Induces Deoligomerization of Human Tumor Necrosis Factor Alpha," The Journal of Biological Chemistry, Jun. 15, 1993, vol. 268, No. 17, pp. 12526-12529.
American Chemical Society, Chemical Abstract Service, RN 2478484-06-7, Entered into STN: Sep. 11, 2020, 1 Page.
Angelini A., et al., "Bicyclic Peptide Inhibitor Reveals Large Contact Interface with a Protease Target," ACS Chemical Biology, Feb. 3, 2012, vol. 7, No. 5, pp. 817-821, XP008160873.
Ardi V.C., et al., "Macrocycles that Inhibit the Binding Between Heat Shock Protein 90 and TPR-containing Proteins," ACS Chemical Biology, Dec. 16, 2011, vol. 6, No. 12, pp. 1357-1366 (18 Pages).
Arthanari Y., et al., "Delivery of Therapeutic shRNA and siRNA by Tat Fusion Peptide Targeting Bcr-abl Fusion Gene in Chronic Myeloid Leukemia Cells," Journal of Controlled Release, Apr. 24, 2010, vol. 145, pp. 272-280.
Bedewy W., et al., "Generation of a Cell-Permeable Cycloheptapeptidyl Inhibitor Against the Peptidyl-Prolyl Isomerase Pin1," Organic & Biomolecular Chemistry, May 18, 2017, vol. 15, No. 21, pp. 4540-4543, DOI: 10.1039/C7OB00430C, ISSN 1477-0520, XP055881566.
Bhadra J., et al., "Corrigendum to Synthesis of Phosphorodiamidate Morpholino Oligonucleotides by H-Phosphonate Method" [Tetrahedron Lett. 56 (2015) 4565-4568], Tetrahedron Letters, 2018, vol. 59, pp. 1974-1975.
Bhadra J., et al., "Synthesis of Phosphorodiamidate Morpholino Oligonucleotides by H-Phosphonate Method," Tetrahedron Letters, 2015, vol. 56, pp. 4565-4568.
Bi Y., et al., "siRNA Delivery Using Lipid Nanoparticle Modified with Cell Penetrating Peptide," Nanomedicine: Nanotechnology, Biology, and Medicine, Jul. 17, 2018, vol. 14, No. 5, p. 1878, DOI:10.1016/J.NANO.2017.11.365, ISSN 1549-9634, XP085426707.
Blenke E.O., "Intracellular Delivery Of RNA Therapeutics With Lipid Nanoparticles," Thesis, Utrecht University, Jan. 25, 2017, 164 Pages, XP055556387, [Retrieved on Feb. 13, 2019] Retrieved from URL: https://dspace.library.uu.nl/bitstream/handle/1874/343775/Oude_Blenke.pdf?sequence=1&isAllowed=y.
Borrelli A., et al., "Cell Penetrating Peptides as Molecular Carriers for Anti-Cancer Agents," Molecules, Jan. 1, 2018, vol. 23, No. 2, 295, pp. 1-28, DOI: 10.3390/molecules23020295, XP055633649, Published Jan. 31, 2018.
Cerrato C.P., et al., "Novel Cell-Penetrating Peptide Targeting Mitochondria," The FASEB Journal, Nov. 2015, vol. 29, No. 11, pp. 4589-4599, (12 Pages), Published Online Jul. 20, 2015.
Chen K., et al., "Engineering Cell-Permeable Proteins through Insertion of Cell-Penetrating Motifs into Surface Loops," ACS Chemical Biology, Sep. 18, 2020, vol. 15, No. 9, pp. 2568-2576, (23 Pages), DOI:10.1021/acschembio.0c00593, XP055837925, Accepted Date: Aug. 3, 2020.
Choi J-M., et al., "Cell Permeable NFAT Inhibitory Peptide Sim-2-VIVIT Inhibits T-cell Activation and Alleviates Allergic Airway Inflammation and Hyper-Responsiveness," Immunology Letters, Elsevier B.V, The Netherlands, Jan. 30, 2012, vol. 143, No. 2, pp. 170-176, DOI:10.1016/J.IMLET.2012.01.016, ISSN 0165-2478, XP028478879, Available Online: Feb. 10, 2012.
Claeboe C.D., et al., "3'-Modified Oligonucleotides by Reverse DNA Synthesis," Nucleic Acids Research, Oct. 1, 2003, vol. 31, No. 19, pp. 5685-5691, XP055423008.
Clayton N.P., et al., "Antisense Oligonucleotide-Mediated Suppression of Muscle Glycogen Synthase 1 Synthesis as an Approach for Substrate Reduction Therapy of Pompe Disease," Molecular Therapy-Nucleic Acids, Oct. 28, 2014, vol. 3, No. 10, p. e206, (11 Pages), DOI:10.1038/mtna.2014.57, XP055154181.
Dastpeyman M., et al., "Endosomal Escape Cell-Penetrating Peptides Significantly Enhance Pharmacological Effectiveness and CNS Activity of Systemically Administered Antisense Oligonucleotides," International Journal Of Pharmaceutics, Elsevier, The Netherlands, Feb. 26, 2021, vol. 599, p. 120398 (10 Pages), DOI:10.1016/J.IJPHARM.2021.120398, ISSN: 0378-5173, XP086531660.
Do H., et al., "Difatty Acyl-Conjugated Linear and Cyclic Peptides for siRNA Delivery," ACS Omega, US, Oct. 31, 2017, vol. 2, No. 10, pp. 6939-6957, Published on Oct. 19, 2017, DOI: 10.1021/acsomega.7b00741, ISSN 2470-1343, XP055881634.
Dougherty P.G., et al., "Macrocycles As Protein-protein Interaction Inhibitors," Biochemical Journal, May 13, 2019, vol. 474, No. 7, pp. 1109-1125 (28 Pages).
Dougherty P.G., et al., "Understanding Cell Penetration of Cyclic Peptides," Chemical Reviews, Sep. 11, 2019, vol. 119, No. 17, pp. 10241-10287, 99 Pages, DOI:10.1021/acs.chemrev.9b00008, XP055881368.
D'Souza C., et al., "Structural Parameters Modulating the Cellular Uptake of Disulfide-Rich Cyclic Cell-Penetrating Peptides: MCoTI-II And SFTI-1," European Journal Of Medicinal Chemistry, NL, Dec. 1, 2014, vol. 88, No. 99, pp. 10-18, Available Online on Jun. 24, 2014, DOI: 10.1016/j.ejmech.2014.06.047, ISSN 0223-5234, XP055725965.
Dowdy S.F., "Overcoming Cellular Barriers for RNA Therapeutics," Nature Biotechnology, Mar. 2017, vol. 35, No. 3, pp. 222-229, Published online Feb. 27, 2017.
Dyne Therapeutics: "Building the World's Leading Muscle Disease Company," Company Overview, 39th Annual J.P. Morgan Healthcare Conference, Jan. 13, 2021, pp. 1-31, (31 Pages).
Extended European Search Report for European Application No. 20910565.9, mailed May 2, 2024,9 Pages.
Fosgerau K., et al., "Peptide Therapeutics: Current Status And Future Directions," Drug Discovery Today, Jan. 2015, vol. 20, No. 1, pp. 122-128.
Gu S., et al., "PROTACs: An Emerging Targeting Technique for Protein Degradation in Drug Discovery," BioEssays, John Wiley Sons Ltd, GB, Feb. 23, 2018, vol. 40, No. 4(e1700247), 11 Pages, DOI:10.1002/BIES.201700247, ISSN 0265-9247, XP071526852.
He R., et al., "Peptide Conjugates with Small Molecules Designed to Enhance Efficacy and Safety," Molecules, May 14, 2019, vol. 24, No. 10:1855, 34 Pages.
Hintersteiner M., et al., "Single Bead Labeling Method for Combining Confocal Fluorescence On-Bead Screening and Solution Validation of Tagged One-Bead One-Compound Libraries," Chemical Biology, Jul. 31, 2009, vol. 16, pp. 724-735 (Published on Jul. 30, 2009).
Hölz K., et al., "High-Efficiency Reverse (5'→3') Synthesis of Complex DNA Microarrays," Scientific Reports, Oct. 10, 2018, vol. 8, No. 1, pp. 1-12, XP055685061.
International Application Serial No. PCT/US2022/075691, Article 19 Amendment filed 03- 02-23, 19 pages.
International Application Serial No. PCT/US2022/075693, Article 19 Amendment filed Mar. 17, 23, 18 pages.
International Search Report and Written Opinion for International Application No. PCT/US2023/019452, mailed Jul. 19, 2023, 13 Pages.
International Search Report and Written Opinion for International Application No. PCT/US2023/070154, mailed Mar. 26, 2024, 37 Pages.
Jin J., et al., "The Peptide PROTAC Modality: A Novel Strategy for Targeted Protein Ubiquitination," Theranostics, AU, Jan. 1, 2020, vol. 10, Issue 22, pp. 10141-10153, DOI: 10.7150/thno.46985, ISSN 1838-7640, XP055946116, Published Aug. 8, 2020.
Jirka S.M.G., et al., "Cyclic Peptides to Improve Delivery and Exon Skipping of Antisense Oligonucleotides in a Mouse Model for Duchenne Muscular Dystrophy," Molecular Therapy, US, Jan. 2018, vol. 26, No. 1, 16 Pages, DOI: 10.1016/j.ymthe.2017.10.004, ISSN 1525-0016, XP055436795, Published on Oct. 12, 2017.
Joo S.H, "Cyclic Peptides as Therapeutic Agents and Biochemical Tools," Biomolecules & Therapeutics, 2012, vol. 20, No. 1, pp. 19-26.
Kalafatovic D., et al., "Cell-Penetrating Peptides: Design Strategies Beyond Primary Structure and Amphipathicity," Molecules, Nov. 8, 2017, vol. 22, No. 11, 1929, 38 Pages, DOI:10.3390/molecules22111929, XP055886265, Retrieved from URL: https://www.ncbi.nlm.nih.gov/pmc/articles/PMC6150340/pdf/molecules-22-01929.pdf.

(56) References Cited

OTHER PUBLICATIONS

Kanatsu, K et al. "Discovery and characterization of stereodefined PMO gapmers targeting tau," 2024 bioRxiv May 9, 2024; doi: 10.1101/2024.05.09.591947. preprint.
Khvorova A., et al., "The Chemical Evolution of Oligonucleotide Therapies of Clinical Utility," Nature Biotechnology, Mar. 2017, vol. 35, No. 3, pp. 238-248.
Kreher N.C., et al., "A Novel EEV-Conjugated PMO, ENTR-701, Reduces Nuclear Foci and Corrects Aberrant Splicing in Myotonic Dystrophy Type 1 Preclinical Models," New Directions in Biology and Disease of Skeletal Muscle Conference, Jun. 20, 2020, 1 Page, XP055966142, [Retrieved on Sep. 28, 2022] Retrieved from URL: https://www.entradatx.com/documents/presentations/Entrada_Hicks-ENTR-701-in-DM1-Preclinical-Models_New-Directions-2022.pdf.
Kundu J., et al., "Synthesis of Phosphorodiamidate Morpholino Oligonucleotides Using Trityl and Fmoc Chemistry in an Automated Oligo Synthesizer," The Journal of Organic Chemistry, Jul. 15, 2022, vol. 87, pp. 9466-9478.
Langner H.K., et al., "Synthesis and Characterization of Thiophosphoramidate Morpholino Oligonucleotides and Chimeras," Journal of the American Chemical Society, Aug. 31, 2020, vol. 142, No. 38, pp. 16240-16253, XP055802911, Retrieved from the Internet: URL: https://pubs.acs.org/doi/10.1021/jacs.0c04335.
Leger A.J., et al., "Systemic Delivery of a Peptide-Linked Morpholino Oligonucleotide Neutralizes Mutant RNA Toxicity in a Mouse Model of Myotonic Dystrophy," Nucleic Acid Therapeutics, United States, Apr. 4, 2013, vol. 23, No. 02, pp. 109-117, DOI: 10.1089/nat.2012.0404, XP055096144, Retrieved from URL: http://www.ncbi.nlm.nih.gov/pubmed/23308382.
Lim K.R.Q., et al., "DUX4 Transcript Knockdown with Antisense 2'-O-Methoxyethyl Gapmers for the Treatment of Facioscapulohumeral Muscular Dystrophy," Molecular Therapy, Feb. 2021, vol. 29, No. 2, pp. 548-558.
Lim K.R.Q., et al., "Inhibition of DUX4 Expression With Antisense LNA Gapmers as a Therapy for Facioscapulohumeral Muscular Dystrophy," PNAS, Sep. 1, 2020, vol. 117, No. 35, p. 21823 (Correction pg).
"Canadian Application Serial No. 2,949,705, Examiners Rule 86(2) Requisition mailed Feb. 8, 2023", 4 pgs.
"U.S. Appl. No. 17/530,664, Response filed Mar. 9, 2023 to Restriction Requirement mailed Jan. 12, 2023", 6 pgs.
"International Application Serial No. PCT/US2022/071489, Written Opinion mailed Mar. 1, 2023", 9 pgs.
Lim K.R.Q., et al., "Inhibition of DUX4 Expression With Antisense LNA Gapmers as a Therapy for Facioscapulohumeral Muscular Dystrophy," PNAS, Jul. 14, 2020, vol. 117, No. 28, pp. 16509-16515.
Liu T., et al., "Membrane Permeable Cyclic Peptidyl Inhibitors against Human Peptidylprolyl Isomerase Pin1," Journal of Medicinal Chemistry, 2010, vol. 53, No. 6, pp. 2494-2501, Published online Feb. 24, 2010.
Liu T., et al., "Synthesis and Screening of a Cyclic Peptide Library: Discovery of Small-molecule Ligands Against Human Prolactin Receptor," Bioorganic and Medicinal Chemistry, Feb. 1, 2009, vol. 17, No. 3, pp. 1026-1033, (14 Pages).
Lu-Nguyen N., et al., "Systemic Antisense Therapeutics Inhibiting DUX4 Expression Improves Muscle Function in an FSHD Mouse Model," BIORXIV, Jan. 16, 2021, pp. 1-40, DOI: 10.1101/2021.01.14.426659, XP055944678, Retrieved from URL: https://www.biorxiv.org/content/10.1101/2021.01.14.426659v1.full.pdf.
Ma Y., et al., "Direct Cytosolic Delivery of Cargoes in Vivo by a Chimera Consisting of D-and L-Arginine Residues," Journal of Controlled Release, Epublished on Jul. 21, 2012, vol. 162, No. 2, pp. 286-294.
Marsollier A-C., et al., "Antisense Targeting Of 3' End Elements Involved In DUX4 mRNA Processing Is An Efficient Therapeutic Strategy For Facioscapulohumeral Dystrophy: A New Gene-silencing Approach," Human Molecular Genetics, Jan. 19, 2016, vol. 25, No. 8, pp. 1468-1478.
Meyer D., et al., "Aromatic Interactions with Naphthylalanine in a Beta-Hairpin Peptide," Journal of Peptide Science, Mar. 2, 2013, vol. 19, pp. 277-282.
Mishra A., et al., "Translocation of HIV TAT Peptide and Analogues Induced by Multiplexed Membrane and Cytoskeletal Interactions," Proceedings of the National Academy of Sciences of the United States of America, Oct. 11, 2011, vol. 108, No. 41, pp. 16883-16888.
Paul S., et al., "Synthesis of Phosphorodiamidate Morpholino Oligonucleotides and Their Chimeras Using Phosphoramidite Chemistry," Journal of the American Chemical Society, Dec. 7, 2016, vol. 138, No. 48, pp. 15663-15672, XP055389989.
Sahni A., et al., "Cell-Penetrating Peptides Escape the Endosome by Inducing Vesicle Budding and Collapse," ACS Chemical Biology, Aug. 13, 2020, vol. 15, No. 9, pp. 2485-2492, Sep. 18, 2020, DOI:10.1021/acschembio.0c00478, ISSN 1554-8929, XP055944114.
Sajid M.I., et al., "Applications of Amphipathic And Cationic Cyclic Cell-penetrating Peptides: Significant Therapeutic Delivery Tool," Peptides, Elsevier, Amsterdam, NL, Mar. 29, 2021, vol. 141, 170542, 15 Pages, DOI:10.1016/J.PEPTIDES.2021.170542, ISSN 0196-9781, XP086588682.
Summerton J., et al., "Morpholino Antisense Oligomers: Design, Preparation, and Properties," Antisense & Nucleic Acid Drug Development, 1997, vol. 7, pp. 187-195.
Summerton J.E, "Morpholinos and PNAs Compared," Letters in Peptide Science, KLUWER, 2003, vol. 10, pp. 215-236.
Taylor R.E., et al., "Cell Penetrating Peptides, Novel Vectors for Gene Therapy," Pharmaceutics, Mar. 3, 2020, vol. 12, No. 3, DOI:10.3390/pharmaceutics12030225, XP055868124, Retrieved from URL: https://www.ncbi.nlm.nih.gov/pmc/articles/PMC7150854/pdf/pharmaceutics-12-00225.pdf.
Thakkar A., et al., "Global Analysis of Peptide Cyclization Efficiency," ACS Combinatorial Science, Feb. 11, 2013, vol. 15, pp. 120-129 (21 Pages).
Tian Y., et al., "Achieving Enhanced Cell Penetration of Short Conformationally Constrained Peptides through Amphiphilicity Tuning," Chemical Science, United Kingdom, Jan. 1, 2017, vol. 8, No. 11, pp. 7576-7581, Published on Sep. 13, 2017, DOI: 10.1039/C7SC03614K, ISSN 2041-6520, XP055595333.
Upadhyaya P., et al., "Direct Ras Inhibitors Identified from a Structurally Rigidified Bicyclic Peptide Library," Tetrahedron, Oct. 21, 2014, vol. 70, No. 42, pp. 7714-7720 (15 Pages), DOI: 10.1016/j.tet.2014.05.113.
Wen J., et al., "Rational Design Of Cell-Permeable Cyclic Peptides Containing A D-Pro-L-Pro Motif," Bioorganic Medicinal Chemistry, Oct. 15, 2020, vol. 28, No. 20, 25 Pages, DOI:10.1016/J.BMC.2020.115711, ISSN 0968-0896, XP086296994.
Wolfe J.M., et al., "Machine Learning To Predict Cell-Penetrating Peptides for Antisense Delivery," ACS Central Science, Apr. 5, 2018, vol. 4, No. 4, pp. 512-520, DOI: 10.1021/acscentsci.8b00098, ISSN 2374-7943, XP055692234.
Wolfe J.M., et al., "Perfluoroaryl Bicyclic Cell-Penetrating Peptides for Delivery of Antisense Oligonucleotides," Angewandte Chemie, Wiley-VCH Verlag GmbH & Co. KGaA, DE, Feb. 25, 2018, vol. 130, No. 17, pp. 4846-4849 (12 Pages), DOI:10.1002/ANGE.201801167, ISSN 0044-8249, XP071374322, Version of Record Online: Mar. 14, 2018.
Wu B., et al., "Octa-guanidine Morpholino Restores Dystrophin Expression in Cardiac and Skeletal Muscles and Ameliorates Pathology in Dystrophic mdx Mice," Molecular Therapy, May 1, 2009, vol. 17, No. 5, pp. 864-871, Published online Mar. 10, 2009, DOI: 10.1038/mt.2009.38, XP055651925, [Retrieved on Dec. 11, 2011] Retrieved from URL: https://www.ncbi.nlm.nih.gov/pmc/articles/PMC2835139/pdf/mt200938a.pdf.
Xie J., et al., "Cell-Penetrating Peptides in Diagnosis and Treatment of Human Diseases: From Preclinical Research to Clinical Application," Frontiers in Pharmacology, May 20, 2020, vol. 11, Article 697, 23 Pages, DOI: 10.3389/fphar.2020.00697, XP055965167, Retrieved from URL: https://www.ncbi.nlm.nih.gov/pmc/articles/PMC7251059/pdf/fphar-11-00697.pdf.
Yamagishi Y., et al., "Natural Product-like Macrocyclic N-methyl-peptide Inhibitors Against a Ubiquitin Ligase Uncovered from a

(56) References Cited

OTHER PUBLICATIONS

Ribosome-expressed De Novo Library," ACS Chemistry & Biology, Dec. 23, 2011, vol. 18, pp. 1562-1570, Published Dec. 22, 2011.
Yin H., et al., "Non-viral Vectors for Gene-based Therapy," Nature Reviews Genetics, 2014, vol. 15, pp. 541-555, Published online Jul. 15, 2014.
Yoo J., et al., "Bioreducible Branched Poly(modified nona-arginine) Cell-penetrating Peptide as a Novel Gene Delivery Platform," Journal of Controlled Release, 2017, vol. 246, pp. 142-154, Available online May 8, 2016.
"U.S. Appl. No. 15/312,878, 312 Amendment filed Feb. 12, 2020", 4 pgs.
"U.S. Appl. No. 15/312,878, Examiner Interview Summary mailed Oct. 30, 2019", 4 pgs.
"U.S. Appl. No. 15/312,878, Final Office Action mailed Sep. 9, 2019", 13 pgs.
"U.S. Appl. No. 15/312,878, Non Final Office Action mailed Apr. 8, 2019", 14 pgs.
"U.S. Appl. No. 15/312,878, Notice of Allowance mailed Nov. 25, 2019", 8 pgs.
"U.S. Appl. No. 15/312,878, Preliminary Amendment filed Nov. 21, 2016", 9 pgs.
"U.S. Appl. No. 15/312,878, Response filed Jan. 23, 2019 to Restriction Requirement mailed Nov. 23, 2018", 16 pgs.
"U.S. Appl. No. 15/312,878, Response filed Jul. 8, 2019 to Non Final Office Action mailed Apr. 8, 2019", 20 pgs.
"U.S. Appl. No. 15/312,878, Response filed Oct. 29, 2019 to Final Office Action mailed Sep. 9, 2019", 21 pgs.
"U.S. Appl. No. 15/312,878, Response filed Nov. 14, 2019 to Final Office Action mailed Sep. 9, 2019", 22 pgs.
"U.S. Appl. No. 15/312,878, Restriction Requirement mailed Nov. 23, 2018", 9 pgs.
"U.S. Appl. No. 15/360,719, 312 Amendment filed Aug. 10, 2020", 5 pgs.
"U.S. Appl. No. 15/360,719, 312 Amendment filed Sep. 28, 2020", 4 pgs.
"U.S. Appl. No. 15/360,719, Applicant's Summary of Examiner Interview filed Jun. 3, 2020", 1 pg.
"U.S. Appl. No. 15/360,719, Examiner Interview Summary mailed May 13, 2020", 3 pgs.
"U.S. Appl. No. 15/360,719, Examiner Interview Summary mailed Oct. 30, 2019", 4 pgs.
"U.S. Appl. No. 15/360,719, Final Office Action mailed Feb. 11, 2020", 6 pgs.
"U.S. Appl. No. 15/360,719, Non Final Office Action mailed Aug. 23, 2019", 15 pgs.
"U.S. Appl. No. 15/360,719, Notice of Allowance mailed May 19, 2020", 9 pgs.
"U.S. Appl. No. 15/360,719, Preliminary Amendment filed Feb. 6, 2017", 4 pgs.
"U.S. Appl. No. 15/360,719, PTO Response to Rule 312 Communication mailed Aug. 26, 2020", 2 pgs.
"U.S. Appl. No. 15/360,719, Response filed Jan. 23, 2019 to Restriction Requirement mailed Dec. 5, 2018", 12 pgs.
"U.S. Appl. No. 15/360,719, Response filed Apr. 28, 2020 to Final Office Action mailed Feb. 11, 2020", 11 pgs.
"U.S. Appl. No. 15/360,719, Response filed May 11, 2020 to Final Office Action mailed Feb. 11, 2020", 11 pgs.
"U.S. Appl. No. 15/360,719, Response filed Nov. 25, 2019 to Non Final Office Action mailed Aug. 23, 2019", 18 pgs.
"U.S. Appl. No. 15/360,719, Restriction Requirement mailed Dec. 5, 2018", 7 pgs.
"U.S. Appl. No. 16/852,615, Corrected Notice of Allowability mailed Dec. 7, 2021", 2 pgs.
"U.S. Appl. No. 16/852,615, Examiner Interview Summary mailed Aug. 4, 2021", 2 pgs.
"U.S. Appl. No. 16/852,615, Final Office Action mailed Jun. 29, 2021", 17 pgs.
"U.S. Appl. No. 16/852,615, Non Final Office Action mailed Jan. 25, 2021", 22 pgs.
"U.S. Appl. No. 16/852,615, Notice of Allowance mailed Sep. 22, 2021", 10 pgs.
"U.S. Appl. No. 16/852,615, Preliminary Amendment filed Aug. 21, 2020", 4 pgs.
"U.S. Appl. No. 16/852,615, Response filed Apr. 21, 2021 to Non Final Office Action mailed Jan. 25, 2021", 16 pgs.
"U.S. Appl. No. 16/852,615, Response filed Aug. 27, 2021 to Final Office Action mailed Jun. 29, 2021", 14 pgs.
"U.S. Appl. No. 17/530,664 Preliminary Amendment filed Feb. 24, 2022", 7 pgs.
"U.S. Appl. No. 17/530,664, Restriction Requirement mailed Jan. 12, 2023", 9 pgs.
"Canadian Application Serial No. 2,949,705, Non Final Office Action mailed Feb. 25, 2022", 4 pgs.
"Canadian Application Serial No. 2,949,705, Office Action mailed Apr. 22, 2021", 3 pgs.
"Canadian Application Serial No. 2,949,705, Response filed Aug. 19, 2021 to Office Action mailed Apr. 22, 2021", 56 pgs.
"Canadian Application Serial No. 2,949,705, Response Filed to Non Final Office Action mailed Feb. 25, 2022", 34 pgs.
"Canadian Application Serial No. 2,949,705, Voluntary Amendment filed Nov. 18, 2016", 6 pgs.
"Chinese Application Serial No. 201580034608.9, Office Action mailed Jan. 6, 2020", w/ English translation, 21 pgs.
"Chinese Application Serial No. 201580034608.9, Office Action mailed Sep. 9, 2020", w/ English translation, 10 pgs.
"Chinese Application Serial No. 201580034608.9, Response filed Jan. 25, 2021 to Office Action mailed Sep. 9, 2020", 12 pgs.
"Chinese Application Serial No. 201580034608.9, Response filed May 14, 2020 to Office Action mailed Jan. 6, 2020", w/o English claims, 12 pgs.
"European Application Serial No. 15796259.8, Decision to Grant mailed May 31, 2019", 2 pgs.
"European Application Serial No. 15796259.8, Extended European Search Report mailed Jan. 22, 2018", 5 pgs.
"European Application Serial No. 15796259.8, Intention to Grant mailed Jul. 31, 2018", 143 pgs.
"European Application Serial No. 15796259.8, Intention to Grant mailed Dec. 12, 2018", 145 pgs.
"European Application Serial No. 15796259.8, Response filed Oct. 29, 2018 to Intended to Grant mailed Jul. 31, 2018", 23 pgs.
"European Application Serial No. 19182012.5, Communication Pursuant to Article 94(3) EPC mailed May 27, 2021", 6 pgs.
"European Application Serial No. 19182012.5, Communication Pursuant to Article 94(3) EPC mailed Dec. 5, 2022", 4 pgs.
"European Application Serial No. 19182012.5, Extended European Search Report mailed Jan. 27, 2020", 7 pgs.
"European Application Serial No. 19182012.5, Response filed Sep. 29, 2021 to Communication Pursuant to Article 94(3) EPC mailed May 27, 2021", 7 pgs.
"European Application Serial No. 20903078.2, Response Filed Sep. 5, 2022 to Communication Pursuant to Rules 161 and 162 EPC Filed Jul. 5, 2022", 27 pgs.
"European Application Serial No. Response filed Aug. 24, 2020 to 19182012.5, Extended European Search Report mailed Jan. 27, 2020", 3 pgs.
"Indian Application Serial No. 201617042520, First Examiner Report mailed Aug. 29, 2019", 5 pgs.
"Indian Application Serial No. 201617042520, Response filed Jan. 4, 2020 to First Examiner Report mailed Aug. 29, 2019", 12 pgs.
"International Application Serial No. PCT/US2015/032043, International Preliminary Report on Patentability mailed Dec. 1, 2016", 8 pgs.
"International Application Serial No. PCT/US2015/032043, International Search Report mailed Jan. 14, 2016", 5 pgs.
"International Application Serial No. PCT/US2015/032043, Invitation to Pay Additional Fees mailed Sep. 8, 2015", 2 pgs.
"International Application Serial No. PCT/US2015/032043, Written Opinion mailed Jan. 14, 2016", 6 pgs.

(56) References Cited

OTHER PUBLICATIONS

"International Application Serial No. PCT/US2020/066459, International Preliminary Report on Patentability mailed Jun. 30, 2022", 7 pgs.
"International Application Serial No. PCT/US2022/071489, International Search Report mailed Aug. 5, 2022", 6 pgs.
"International Application Serial No. PCT/US2022/071489, Written Opinion mailed Aug. 5, 2022", 7 pgs.
"Japanese Application Serial No. 2017-513613, Decision of Refusal mailed Dec. 26, 2019", w/ English Translation, 13 pgs.
"Japanese Application Serial No. 2017-513613, Notice of Reasons for Refusal mailed Apr. 18, 2019", w/ English Translation, 11 pgs.
"Japanese Application Serial No. 2017-513613, Response filed Apr. 14, 2020 to Decision of Refusal mailed Dec. 26, 2019", w/ English Translation, 35 pgs.
"Japanese Application Serial No. 2017-513613, Response filed Aug. 8, 2019 to Notice of Reasons for Refusal mailed Apr. 18, 2019", w/ English Translation, 29 pgs.
"Japanese Application Serial No. 2017-513613, Written Amendment filed Jan. 26, 2017", w/ English Translation, 11 pgs.
"Japanese Application Serial No. 2017-513613, Written Amendment filed Aug. 14, 2020", w/ English Translation, 2 pgs.
"Japanese Application Serial No. 2020-072542, Examiners Decision of Final Refusal mailed Apr. 20, 2022", w/ English Translation, 6 pgs.
"Japanese Application Serial No. 2020-072542, Notice of Reasons For Rejection mailed Jun. 30, 2021", w/ English Translation, 11 pgs.
"Japanese Application Serial No. 2020-072542, Office Action mailed Aug. 29, 2022", W/O English Translation, 2 pgs.
"Japanese Application Serial No. 2020-072542, Preliminary Examination Report mailed Nov. 22, 2022", w/ English Translation, 2 pgs.
"Japanese Application Serial No. 2020-072542, Response filed Dec. 15, 2021 to Notice of Reasons For Rejection mailed Jun. 30, 2021", w/ English Translation, 21 pgs.
"Japanese Application Serial No. 2020-072542, Response Filed Sep. 22, 2022 to Office Action mailed Aug. 29, 2022", W/ English Claims, 9 pgs.
"Japanese Application Serial No. 2020-072542, Voluntary Amendment filed May 12, 2020", w/ English Claims, 21 pgs.
Alonso, A, et al., "Protein tyrosine phosphatases in the human genome", Cell, 117(6), (Jun. 2004), 699-711.
Andaloussi, S. E. L., et al., "Design of a peptide-based vector, PepFect6, for efficient delivery of siRNA in cell culture and systemically in vivo", Nucleic acids research 39.9, (May 2011), 3972-3987.
Anderl, J, et al., "Chemical modification allows phallotoxins and amatoxins to be used as tools in cell biology", Beilstein Journal of Organic Chemistry, 8(233), (2012), 2072-2084.
Appelbaum, Jacob S, et al., "Arginine topology controls escape of minimally cationic proteins from early endosomes to the cytoplasm", Chemistry & biology 19.7, (Jul. 2012), 819-830.
Birts, C N, et al., "A cyclic peptide inhibitor of C-terminal binding protein dimerization links metabolism with mitotic fidelity in breast cancer cells", Chem. Sci., 4,., (2013), 3046-3057.
Bolte, S., et al., "A guided tour into subcellular colocalization analysis in light microscopy", J. Microsc., 224(Pt. 3), (Dec. 2006), 213-232.
Burke, T. R. Jr, et al., "Potent Inhibition of Insulin Receptor Dephosphorylation by a Hexamer Peptide Containing the Phosphotyrosyl Mimetic F2Pmp", Biochem. Biophys. Res. Commun. 204(1), (Oct. 1994), 129-134.
Carpenter, A E, et al., "CellProfiler: image analysis software for identifying and quantifying cell phenotypes", Genome Biology, 7:R100, (2006), 11 pgs.
Cascales, L, et al., "Identification and Characterization of a New Family of Cell-Penetrating Peptides", J. Biol. Chem. 286(42), (Oct. 2011), 36932-36943.
Chapman, et al., "", Chem. Soc.Rev., 2012, 41, (2012), 6023-6041.
Chatterjee, Jayanta, et al., "N-methylation of peptides: a new perspective in medicinal chemistry", Accounts of chemical research 41.10, (2008), 1331-1342.
Chen, X, et al., "On-bead screening of combinatorial libraries: Reduction of nonspecific binding by decreasing surface ligand density", J. Comb. Chem. 11, (2009), 604-611.
Cheng, Seng H, et al., "Defective intracellular transport and processing of CFTR is the molecular basis of most cystic fibrosis", Cell 63.4, (1990), 827-834.
Cooley, Christina B, et al., "Oligocarbonate molecular transporters: oligomerization-based syntheses and cell-penetrating studies", Journal of the American Chemical Society 131. 45, (2009), 16401-16403.
Cushing, P. R, et al., "The Relative Binding Affinities of PDZ Partners for CFTR: A Biochemical Basis for Efficient Endocytic Recycling", Biochemistry, 47(38), (2008), 10084-10098.
Cushing, Patrick R, et al., "A Stabilizing Influence: CAL PDZ Inhibition Extends the Half-Life of DeltaF508-CFTR", Angewandte Chemie International Edition 49.51, (2010), 9907-9911.
Deshayes, S., et al., "Cell-penetrating peptides: tools for intracellular delivery of therapeutics", CMLS, Cellular and Molecular Life Sciences, 62(16), (2005), 1839-1849.
Dewan, V, et al., "Cyclic peptide inhibitors of HIV-1 capsid-human lysyl-ERNA synthetase interaction", ACS Chem. Biol. 7(4), (2012), 761-769.
Doyle, D. A, et al., "Crystal Structures of a Complexed and Peptide-Free Membrane Protein-Binding Domain: Molecular Basis of Peptide Recognition by PDZ", Cell, 85(7), (Jun. 1996), 1067-1076.
Driggers, E. M, et al., "The exploration of macrocycles for drug discovery—an underexploited structural class", Nat. Rev. Drug Discov, 7, (Jul. 2008), 608-624.
Duchardt, F, et al., "A Cell-penetrating Peptide Derived from Human Lactoferrin with Conformation-dependent Uptake Efficiency", J. Biol. Chem., 284(52), (Dec. 2009), 36099-36108.
Duchardt, Falk, et al., "A comprehensive model for the cellular uptake of cationic cell-penetrating peptides", Traffic 8.7, (Jul. 2007), 848-866.
Eguchi, Akiko, et al., "Protein transduction domain of HIV-1 Tat protein promotes efficient delivery of DNA into mammalian cells", Journal of Biological Chemistry 276.28, (Jul. 2001), 26204-26210.
Eichler, J, et al., "Novel a-glucosidase inhibitors identified using multiple cyclic peptide combinatorial libraries", Molecular Diversity, 1(4), (Aug. 1996), 233-240.
Elchelby, M, et al., "Increased insulin sensitivity and obesity resistance in mice lacking the protein tyrosine phosphatase-1B gene", Science, 283(5407), (Mar. 1999), 1544-1548.
El-Sayed, Ayman, et al., "Delivery of Macromolecules Using Arginine-Rich Cell-Penetrating Peptides: Ways to Overcome Endosomal Entrapment", The AAPS Journal, 11(1), (2009), 13-22.
Fernandez-Lopez, Sara, et al., "Antibacterial Agents Based on the Cyclic D,L-alpha-peptide Architecture", Nature vol. 412, and Correction page, Nature 414:329 Nov. 2001, (Jul. 26, 2001), 452-455.
Ferrari, Aldo, et al., "Caveolae-mediated internalization of extracellular HIV-1 tat fusion proteins visualized in real time", Molecular therapy 8.2, (2003), 284-294.
Fittipaldi, Antonio, et al., "Cell membrane lipid rafts mediate caveolar endocytosis of HIV-1 Tat fusion proteins", Journal of Biological Chemistry 278.36, (2003), 34141-34149.
Frackenpohl, J, et al., "The Outstanding Biological Stability of ß- and y-Peptides toward Proteolytic Enzymes: An In Vitro Investigation with Fifteen Peptidases", Chembiochem, 2(6), (Jun. 2001), 445-455.
Frankel, A.D., et al., "Cellular Uptake of the Tat Protein From Human Immunodeficiency Virus", Cell: 55.6, (Dec. 1998), 1189-1193.
Frost, J. R, et al., "Macrocyclization of Organa-Peptide Hybrids through a Dual Bio-orthogonal Ligation: Insights from Structure-Reactivity Studies", ChemBioChem 14(1), (Jan. 2013), 147-160.
Futaki, S, et al., "Arginine-rich peptides. An abundant source of membrane-permeable peptides having potential as carriers for intracellular protein delivery", The Journal of Biological Chemistry, 276(8), (2001), 5836-5840.

(56) References Cited

OTHER PUBLICATIONS

Futaki, Shirah, "Membrane-permeable arginine-rich peptides and the translocation mechanisms", Advanced drug delivery reviews 57.4, (2005), 547-558.
Giebel, L. B, et al., "Screening of cyclic peptide phage libraries identifies ligands that bind streptavidin with high affinities", Biochemistry, 34(47), (1995), 15430-15435.
Gobbo, M, et al., "Synthesis and biological activity of some linear and cyclic kinin analogues", International Journal of Peptide & Protein Research, 44(1), Chemical Biology & Drug Design, (Jul. 1994), 1-9.
Goncalves, E, et al., "Binding of Oligoarginine to Membrane Lipids and Heparan Sulfate: Structural and Thermodynamic Characterization of a Cell-Penetrating Peptide", Biochemistry, 44(7), (2005), 2692-2702.
Goun, Elena A, et al., "Molecular transporters: synthesis of oligoguanidinium transporters and their application to drug delivery and real-time imaging", Chem Bio Chem 7.10, (2006), 1497-1515.
Green, M., et al., "Autonomous Functional Domains of Chemically Synthesized Human Immunodeficiency Virus Tat Trans-Activator Protein", Cell, 55, (1988), 1179-1188.
Gupta, Bhawna, et al., "Intracellular delivery of large molecules and small particles by cell-penetrating proteins and peptides", Advanced drug delivery reviews 57.4, (Feb. 2005), 637-651.
Hamill, K. M, et al., "Polymnyxins facilitate entry into mammalian cells", Chem. Sci., 7, (2016), 5059-5068.
Hariton-Gazal, E, et al., "Functional Analysis of Backbone Cyclic Peptides Bearing the Arm Domain of the HIV-1 Rev Protein: Characterization of the Karyophilic Properties and Inhibition of Rev-Induced Gene Expression", Biochemistry, 44(34), (2005), 11555-11566.
He, R, et al., "Recent Advances in PTP1B Inhibitor Development for the Treatment of Type 2 Diabetes and Obesity", Chapter 6 In: New Therapeutic Strategies for Type 2 Diabetes: Small Molecule Approaches, Jones, R. M. (ed.), RSC Drug Discovery Series No. 27, The Royal Society of Chemistry, (2012), 142-176.
Heinis, C, et al., "Phage-encoded combinatorial chemical libraries based on bicyclic peptides", Nat. Chem. Biol. 5, (2009), 502-507.
Herce, H D, et al., "Arginine-rich peptides destabilize the plasma membrane, consistent with a pore formation translocation mechanism of cell-penetrating peptides", Biophysical journal 97.7, (2009), 1917-1925.
Herce, Henry D, et al., "Molecular dynamics simulations suggest a mechanism for translocation of the HIV-1 TAT peptide across lipid membranes", Proceedings of the National Academy of Sciences 104.52, (Dec. 2007), 20805-20810.
Hili, R, et al., "Macrocyclization of Linear Peptides Enabled by Amphoteric Molecules", J. Am. Chern. Soc. 132(9), (2010), 2889-2891.
Hirose, Hisaaki, et al., "Transient focal membrane deformation induced by arginine-rich peptides leads to their direct penetration into cells", Molecular Therapy 20.5, (2012), 984-993.
Holub, J. M, et al., "Improved assays for determining the cytosolic access of peptides, proteins, and their mimetics", Biochemistry, 52(50), (Dec. 2013), 9036-9046.
Horn, M, et al., "Tuning the properties of a novel short cell-penetrating peptide by intramolecular cyclization with a triazole bridge", Chem. Commun. 52, (2016), 2261-2264.
Hoyer, J. A. N, et al., "Peptide vectors for the nonviral delivery of nucleic acids", Accounts of chemical research 45.7, (2012), 1048-4056.
Illsley, N. P, et al., "Membrane chloride transport measured using a chloride sensitive fluorescent probe", Biochemistry, 26(5), (1987), 1215-1219.
Jang, S, et al., "Cell-Penetrating, Dimeric a-Helical Peptides: Nanomolar Inhibitors of HIV-1 Transcription", Angew. Chem. Int. Ed. 53, (2014), 10086-10089.
Jeong, Ji Hoon, et al., "siRNA conjugate delivery systems", Bioconjugate chemistry 20.1, (2009), 5-14.
Jha, D, et al., "CyLoP-1: A Novel Cysteine-Rich Cell-Penetrating Peptide for Cytosolic Delivery of Cargoes", Bioconj. Chem., 22(3), (2011), 319-328.
Jiang, B, et al., "A Selective, Cell-Permeable Nonphosphorylated Bicyclic Peptidyl Inhibitor against Peptidyl-Prolyl Isomerase Pin1", J. Med. Chem., 58, (Jul. 21, 2015), 6306-6312.
Joo, S. H, et al., "High-throughput sequence determination of cyclic peptide library members by partial Edman degradation/mass spectrometry", J. Am. Chem. Soc. 128, (2006), 13000-13009.
Josephson, Lee, et al., "High-efficiency intracellular magnetic labeling with novel superparamagnetic-Tat peptide conjugates", Bioconjugate chemistry 10.2, (1999), 186-191.
Junkes, Christof, et al., "Cyclic antimicrobial R-, W-rich peptides: the role of peptide structure and *E coli* outer and inner membranes in activity and the mode of action", European Biophysics Journal 40.4, (2011), 515-528.
Kaplan, Ian M, et al., "Cationic TAT peptide transduction domain enters cells by macropinocytosis", Journal of Controlled Release 102.1, (2005), 247-253.
Karpurapu, M., et al., "Inhibition of nuclear factor of activated T cells (NFAT) c3 activation attenuates acute lung injury and pulmonary edema in murine models of sepsis", Oncotarget 9(12), (Jan. 25, 2018), 10606-10620.
Kawakami, T, et al., "In Vitro Selection of Multiple Libraries Created by Genetic Code Reprogramming to Discover Macrocyclic Peptides That Antagonize VEGFR2 Activity in Living Cells", ACS Chem. Biol. 8(6), (Apr. 2013), 1205-1214.
Kerem, Bat-Sheva, "Identification of the cystic fibrosis gene: genetic analysis", Science 245, 4922, (1989), 1073-1080.
Kessler, et al., "Conformation and Biological Activity of Cyclic Peptides", Angew. Chem. Int. Ed. Engl. 21, (1982), 512-523.
Kohli, R M, et al., "Biomimetic synthesis and optimization of cyclic peptide antibiotics", Nature, 418, (Aug. 2002), 658-661.
Kritzer, J. A, et al., "Rapid selection of cyclic peptides that reduce a-synucleain toxicity in yeast and animal models", Nature Chemical Biology, 5(9), (Sep. 2009), 655-663.
Kundu, R, et al., "Hybrid Organic-Inorganic Inhibitors of a PDZ Interaction that Regulates the Endocytic Fate of CFTR", Angew. Chem. Int. Ed., 51(29), (Jul. 2012), 7217-7220.
Kwon, Y-U, et al., "Quantitative Comparision of the Relative Cell Permeability of Cyclic and Linear Peptides", Chemistry & Biology, 14(6), (Jun. 2007), 671-677.
Lalonde, M. S, et al., "Inhibition of Both HIV-1 Reverse Transcription and Gene Expression by a Cyclic Peptide that Binds the Tat-Transactivating Response Element (TAR) RNA", PLoS Pathogenes, 7(5), (May 2011), e1002038.
Lamontagne, K. R. Jr, et al., "Protein tyrosine phosphatase PTP1B suppresses p210 bcr-abl-induced transformation of Rat-1 fibroblasts and promotes differentiation of K562 cells", Proc. Natl. Acad. Sci. U.S.A, 95(24), (Nov. 1998), 14094-14099.
Larochelle, Jonathan R, et al., "Fluorescence correlation spectroscopy reveals highly efficient cytosolic delivery of certain penta-arg proteins and stapled peptides", Journal of the American Chemical Society 137.7, (2015), 2536-2541.
Lattig-Tunnemann, Gisela, et al., "Backbone rigidity and static presentation of guanidinium groups increases cellular uptake of arginine-rich cell-penetrating peptides", Nature communications 2, 453, (Aug. 30, 2011), 6 pgs.
Leduc, A M, et al., "Helix-stabilized cyclic peptides as selective inhibitors of steroid receptor-coactivator interactions", Proc. Natl. Acad. Sci. USA 100(20), (Sep. 2003), 11273-11278.
Lee, et al., "Effects of single D-amino acid substitutions on disruption of ß sheet structure and hydrophobicity in cyclic 14-residue antimicrobial peptide analogs related to gramicidin S", J. Peptide Res. 63, (2004), 69-84.
Lee, H J, et al., "PDZ domains and their binding partners: structure, specificity, and modification", Cell Communication and Signaling, 8:8, (2010), 18 pgs.
Lee, J, et al., "Using marine natural products to discover a protease that catalyzes peptide macrocyclization of diverse substrates", J. Am. Chem. Soc. 131(6), (Feb. 2009), 2122-2124.
Lessard, L, et al., "The two faces of PTP1B in cancer", Biochim. Biophys. Acta, 1804(3), (Mar. 2010), 613-619.

(56) References Cited

OTHER PUBLICATIONS

Li, S, et al., "Fluoride enhances the activity of fungicides that destabilize cell membranes", Bioorganic & Medicinal Chemistry Letters, 22(9), (2012), 3317-3322.
Li, S, et al., "Photolithographic synthesis of cyclic peptide arrays using a differential deprotection strategy", Chem. Commun., 5, (2005), 581-583.
Lian, Wenlong, et al., "Cell-permeable bicyclic peptide inhibitors against intracellular proteins", Journal of the American Chemical Society 136.28, (Jul. 2014), 9830-9833.
Lian, Wenlong, et al., "Screening bicyclic peptide libraries for protein-protein interaction inhibitors: discovery of a tumor necrosis factor-a antagonist", Journal of the American Chemical Society 135.32, (2013), 11990-11995.
Liao, et al., "Cell-permeable bicyclic peptidyl inhibitors against T-cell protein tyrosine phosphates from a combinatorial library", Organic & Biomolecular Chemistry, vol. 15, (2017), 9595-9598.
Lin, K-J, et al., "QSAR studies of antimicrobial a, ß-polypeptides", Pharmaceutical Biotechnology, 10(5) (with English Abstract), (2003), 299-303.
Lindgren, Maria, et al., "Classes and Prediction of Cell-Penetrating Peptides", Chapter 1 In: Cell-Penetrating Peptides: Methods and Protocols, Methods in Molecular Biology, vol. 683, Springer Science+ Business Media, LLC, (2011), 3-19.
Liu, Jianquan, et al., "Nanostructured materials designed for cell binding and transduction", Biomacromolecules 2.2, (2001), 362-368.
Liu, R, et al., "A novel peptide-based encoding system for "one-bead one-compound" peptidomimetic and small molecule combinatorial libraries", J. Am. Chem. Soc. 124, (2002), 7678-7680.
Liu, T, et al., "High-throughput screening of one-bead-one compound libraries: identification of cyclic peptidyl inhibitors against calcineurin/NFAT interaction", ACS Comb. Sci. 13(5), (2011), 537-546.
Liu, Tao, et al., "Cyclic peptidyl inhibitors against human Peptidylprolyl Isomerase Pin1", Journal of medicinal chemistry 53.6, (2010), 2494-2501.
Liu, Y, et al., "Multifunctional Tandem Peptide Modified Paclitaxel-Loaded Liposomes for the Treatment of Vasculogenic Mimicry and Cancer Stem Cells in Malignant Glioma", ACS Applied Materials & Interfaces, 7(30), (2015), 16792-16801.
Lu, K P, et al., "The prolyl isomerase PIN1: a pivotal new twist in phosphorylation signalling and disease", Nat. Rev. Mol. Cell Biol 8, (Nov. 2007), 904-916.
Magzoub, M, et al., "Conformational states of the cell-penetrating peptide penetratin when interacting with phospholipid vesicles: effects of surface charge and peptide concentration". Biochim. Biophys. Acta, 1563(1-2), (Jun. 2002), 53-63.
Maiolo, et al., "Effects of cargo molecules on the cellular uptake of arginine-rich cell-penetrating peptides", Biochimica et Biophysica Acta (BBA)-Biomembranes 1712.2, (2005), 161-172.
Maly, D J, et al., "Combinatorial Strategies for Targeting Protein Families: Application to the Proteases", Chembiochem, 3(1), (Jan. 2002), 16-37.
Maly, D J, et al., "Expedient Solid-Phase Synthesis of Fluorogenic Protease Substrates Using the 7-Amino-4-carbamoylmethylcoumarin (ACC) Fluorophore", J.Org. Chern., 67(3), (2002), 910-915.
Mandal, Deendayal, et al., "Cell-penetrating homochiral cyclic peptides as nuclear-targeting molecular transporters", Angewandte Chemie International Edition 50.41, (2011), 9633-9637.
Marsault, E, et al., "Macrocycles Are Great Cycles: Applications, Opportunities, and Challenges of Synthetic Macrocycles in Drug Discovery", J. Med. Chern., 54(7), (2011), 1961-2004.
Martinez-Rodriguez, et al., "Natural Occurrence and Industrial Applications of d-Amino Acids: An Overview", Chemistry & Biodiversity, vol. 7, (2010), 1531-1548.
Meutermans, W. D. F, et al., "Synthesis of Difficult Cyclic Peptides by Inclusion of a Novel Photolabile Auxiliary in a Ring Contraction Strategy", J. Am. Chem. Soc., 1999, 121(42), (1999), 9790-9796.
Millward, S W, et al., "A General Route for Post-Translational Cyclization of mRNA Display Libraries", J. Am. Chem. Soc., 127(41), (2005), 14142-14143.
Millward, S W, et al., "Design of cyclic peptides that bind protein surfaces with antibody-like affinity", ACS Chem. Biol. 2(9), (2007), 625-634.
Ming, Z, et al., "Synthesis of RGD containing peptides and their vasodilation effect", Preparative Biochemistry & Biotechnology, 30(3), (2000), 247-256.
Miranda, E, et al., "A Cyclic Peptide Inhibitor of HIF-1 Heterodimerization That Inhibits Hypoxia Signaling in Cancer Cells", Journal of the American Chemical Society 135(28), (2013), 10418-10425.
Miskolzie, M, et al., "An NMR conformational analysis of cyclic bradykinin mimics. Evidence for ß-turn", Journal of Biomolecular Structure & Dynamics 17(6), (2000), 947-955.
Mitra, Sayantan, et al., "Highly sensitive peptide-based probes for protein tyrosine phosphatase activity utilizing a fluorogenic mimic of phosphotyrosine", Bioorganic & medicinal chemistry letters 15.23, (2005), 5142-5145.
Moore, J. D, et al., "Pin1 inhibitors: Pitfalls, progress and cellular pharmacology", Bioorg. Med. Chem. Lett.,, 23(15), (Aug. 2013), 4283-4291.
Morais Cabral, J H, et al., "Crystal structure of a PDZ domain", Nature, 382, (Aug. 1996), 649-652.
Mosmann, Tim, "Rapid Colorimetric Assay for Cellular Growth and Survival: Application to Proliferation and Cytotoxicity Assays", Journal of Immunological Methods, 65(1-2), (1983), 55-63.
Mueller, Judith, et al., "Comparison of cellular uptake using 22 CPPs in 4 different cell lines", Bioconjugate chemistry 19.12, (2008), 2363-2374.
Muratovska, Aleksandra, et al., "Conjugate for efficient delivery of short interfering RNA (siRNA) into mammalian cells", FEBS letters 558.1-3, (2004), 63-68.
Nakase, Ikuhiko, et al., "Efficient intracellular delivery of nucleic acid pharmaceuticals using cell-penetrating peptides", Accounts of chemical research 45.7, (2012), 1132-1139.
Nakase, Ikuhiko, et al., "Interaction of arginine-rich peptides with membrane-associated proteoglycans is crucial for induction of actin organization and macropinocytosis", Biochemistry 46.2, (2007), 492-501.
Ngu-Schwemlein, M, et al., "In vitro synergy between some cationic amphipathic cyclooctapeptides and antibiotics", Australian Journal of Chemistry, 68(2), (2015), 218-223.
Nguyen, Leonard T, et al., "Serum stabilities of short tryptophan- and arginine-rich antimicrobial peptide analogs", PloS one 5.9, (2010), e12684.
Nischan, N, et al., "Covalent Attachment of Cyclic TAT Peptides to GFP Results in Protein Delivery into Live Cells with Immediate Bioavailability", Angew. Chem. Int. Ed., 54:1950-1953, (2015), S1-S26.
Nori, Aparna, et al., "Tat-conjugated synthetic macromolecules facilitate cytoplasmic drug delivery to human ovarian carcinoma cells", Bioconjugate chemistry 14.1, (Jan.-Feb. 2003), 44-50.
Ocampo-Garcia, B E, "Design and biological evaluation of 99mTc-N2S2-Tat(49-57)-c(RGDyK): A hybrid radiopharmaceutical for tumors expressing a(v)ß(3) integrins", Nuclear Medicine and Biology 40(4), (2013), 481-487.
Oh, D., et al., "Amphiphilic Bicyclic Peptides as Cellular Delivery Agents", ChemMedChem, 9(11), (2014), 2449-2453.
Oh, D., et al., "Antibacterial activities of amphiphilic cyclic cell-penetrating peptides against multidrug-resistant pathogens", Molecular Pharmaceutics 11(10), (2014), 3528-3536.
Oh, D., et al., "Enhanced Cellular Uptake of Short Polyarginine Peptides through Fatty Acylation and Cyclization", Molecular Pharmaceutics, 11(8), (Aug. 4, 2014), 2845-2854.
Okamoto, H, et al., "Conformational transitions of cyclic D,L-Peptides", Journal of Computational Chemistry,, 30(6), (2009), 962-973.
Palm-Apergi, Caroline, et al., "The membrane repair response masks membrane disturbances caused by cell-penetrating peptide uptake", The FASEB Journal 23.1, (2009), 214-223.

(56) References Cited

OTHER PUBLICATIONS

Pawson, T, et al., "Assembly of Cell Regulatory Systems Through Protein Interaction Domains", Science, 300(5618), (Apr. 2003), 445-452.
Pham, Wellington, et al., "Enhancing membrane permeability by fatty acylation of oligoarginine peptides", Chembiochem 5.8, (2004), 1148-1151.
Pomilio, A B, et al., "Naturally-Occurring Cyclopeptides: Structures and Bioactivity", Current Organic Chemistry, 10(16), (Nov. 2006), 2075-2121.
Pooga, M, et al., "Cellular translocation of proteins by transportation", FASEB J. 15(8), (2001), 1451-1453.
Pritz, S, et al., "Synthesis of Biologically Active Peptide Nucleic Acid-Peptide Conjugates by Sortase-Mediated Ligation", Journal of Organic Chemistry 72(10), (2007), 3909-3912.
Qian, Li, et al., "Arginine-rich membrane-permeable peptides are seriously toxic", Pharmacology Research & Perspectives, vol. 5, No. 5, (Oct. 1, 2017), 3 pgs.
Qian, Ziqing, et al., "Discovery and mechanism of highly efficient cyclic cell-penetrating peptides", Biochemistry 55.18, (Apr. 18, 2016), 2601-2612.
Qian, Ziqing, et al., "Early endosomal escape of a cyclic cell-penetrating peptide allows effective cytosolic cargo delivery", Biochemistry 53.24, (Jun. 2014), 4034-4046.
Qian, Ziqing, et al., "Efficient delivery of cyclic peptides into mammalian cells with short sequence motifs", ACS chemical biology 8.2, (Feb. 15, 2013), 423-431.
Qian, Ziqing, et al., "Efficient Delivery of Cyclic Peptides into Mammalian Cells with Short Sequence Motifs", ACS Chem. Biol., 8(2), (2013), 423-431.
Qian, Ziqing, et al., "Enhancing the cell permeability and metabolic stability of peptidy! drugs by reversible bicyclization", Angewandte Chemie International Edition 56.6, (2017), 1525-1529.
Qian, Ziqing, et al., "Intracellular delivery of peptidyl ligands by reversible cyclization: discovery of a PDZ domain inhibitor that rescues CFTR activity", Angewandte Chemie International Edition 54.20, (Mar. 17, 2015), 5874-5878.
Qian, Ziqing, et al., "Monitoring the cytosolic entry of cell-penetrating peptides using a pH- sensitive fluorophore", Chemical Communications 51.11, (2015), 2162-2165.
Qin, C, et al., "Optimization of Antibacterial Cyclic Decapeptides", J. Comb. Chem., 6(3), (2004), 398-406.
Ren, L, et al., "Substrate Specificity of Protein Tyrosine Phosphatases 18, RPTPa, SHP-1, and SHP-2", Biochemistry, 50(12), (2011), 2339-2356.
Rezai, T, et al., "Testing the Conformational Hypothesis of Passive Membrane Permeability Using Synthetic Cyclic Peptide Diastereomers", J. Am. Chem. Soc., 128(8), (2006), 2510-2511.
Rezai, Taha, et al., "Conformational flexibility, internal hydrogen bonding, and passive membrane permeability: successful in silica prediction of the relative permeabilities of cyclic peptides", Journal of the American Chemical Society 128.43, (2006), 14073-14080.
Rhodes, C A, et al., "Cell-Permeable Bicyclic Peptidylinhibitors against NEMO-IkB Kinase Interaction Directly from a Combinatorial Library", JAm Chem Soc.; 140(38), (Sep. 26, 2018), 12102-12110.
Richard, Jean Philippe, et al., "Cellular uptake of unconjugated TAT peptide involves clathrin-dependent endocytosis and heparan sulfate receptors", Journal of Biological Chemistry 280.15, (2005), 15300-15306.
Ricouart, A, et al., "Design of potent protein kinases inhibitors using the bisubstrate approach", Journal of Medicinal Chemistry, 34(1), (1991), 73-78.
Riedl, S J, et al., "Molecular mechanisms of caspase regulation during apoptosis", Nat. Rev. Mol. Cell Biol 5, (Nov. 2004), 897-907.
Roberts, K D, et al., "Efficient synthesis of thioether-based cyclic peptide libraries". Tetrahedron Letters, 39(45), (Nov. 1998), 8357-8360.
Roberts, Kyle E, et al., "Computational design of a PDZ domain peptide inhibitor that rescues CFTR activity", PLoS Comput Biol 8.4, e1002477, (Apr. 2012), 12 pgs.
Rothbard, Jonathan B, et al., "Conjugation of arginine oligomers to cyclosporin A facilitates topical delivery and inhibition of inflammation", Nature medicine 6.11, (2000), 1253-1257.
Rotstein, B. H, et al., "Solvatochromic Reagents for Multicomponent Reactions and their Utility in the Development of Cell-Permeable Macrocyclic Peptide Vectors", Chem. Eur. J., 17, (2011), 12257-12261.
Rueping, Magnus, et al., "Cellular uptake studies with ß-peptides", ChemBioChem 3.2-3, (2002), 257-259.
Rusnati, M, et al., "Multiple Interactions of HIV-1 Tat Protein with Size-defined Heparin Oligosaccharides", J. Biol. Chem., 274(40), (Oct. 1999), 28198-28205.
Saar, Kulliki, et al., "Cell-penetrating peptides: a comparative membrane toxicity study", Analytical biochemistry 345.1, (2005), 55-65.
Sako, Y, et al., "Ribosomal synthesis of bicyclic peptides via two orthogonal inter-side-chain reactions", J. Am. Chem. Soc. 130, (2008), 7232-7234.
Salvado, I, et al., "Membrane-disrupting iridium(III) oligocationic organometallopeptides", Chemical Communications, 52(73):, (2016), 11008-11011.
Schafmeister, C. E, et al., "An All-Hydrocarbon Cross-Linking System for Enhancing the Helicity and Metabolic Stability of Peptides", J. Am. Chern. Soc, 122(24), (2000), 5891-5892.
Schmidt, Nathan, et al., "Arginine-rich cell-penetrating peptides", FEBS letters 584.9, (2010), 1806-1813.
Schwarze, S. R, et al., "In Vivo Protein Transduction: Delivery of a Biologically Active Protein into the Mouse", Science, 285.5433, (Sep. 3, 1999), 1569-1572.
Scott, C. P, et al., "Production of cyclic peptides and proteins in vivo", Proc. Natl. Acad. Sci. U.S. A. 96(24), (Nov. 1999), 13638-13643.
Sela, et al., "Different roles of D-amino acids in immune phenomena", The FASEB Journal, vol. 11, (May 1997), 449-456.
Shirazi, A N, et al., "Cyclic Peptide-Capped Gold Nanoparticles as Drug Delivery Systems", Molecular Pharmaceutics, 11, (2013), 500-511.
Shirazi, A N, et al., "Cyclic peptides containing tryptophan and arginine as Src kinase inhibitors", Bioorganic & Medicinal Chemistry Letters 23, (2013), 3230-3234.
Shirazi, A N, et al., "Design and Biological Evaluation of Cell-Penetrating Peptide-Doxorubicin Conjugates as Prodrugs", Molecular Pharmaceutics 10, (2013), 488-499.
Shirazi, A. N, et al., "Cysteine and arginine-rich peptides as molecular carriers", Bioorg. Med. Chem. Lett., 26, (2016), 656-661.
Siegmund, Reissmann, "Cell penetration: scope and limitations by the application of cell-penetrating peptides", Journal of Peptide Sience, vol. 20, No. 10, (Aug. 11, 2014), 760-784.
Slee, E A, et al., "Benzyloxycarbonyl-Val-Ala-Asp (OMe) fluoromethylketone (Z-VAD.FMK) inhibits apoptosis by blocking the processing of CPP32", Biochemical Journal, 315(1), (Apr. 1996), 21-24.
Songyang, Z, et al., "Recognition of Unique Carboxyl-Terminal Motifs by Distinct PDZ Domains", Science, 275(5296), (Jan. 1997), 73-77.
Stanford, Stephanie M, et al., "High-throughput screen using a single-cell tyrosine phosphatase assay reveals biologically active inhibitors of tyrosine phosphatase CD45", Proceedings of the National Academy of Sciences 109.35, (2012), 13972-13977.
Stewart, J M, et al., "Bradykinin antagonists: Anti-cancer drugs for the new millennium?", Peptides for the New Millennium, Proceedings of the American 312. Peptide Symposium, 16th, Minneapolis, MN, United States, Jun. 26-Jul. 1, 1999 (2000), Meeting, (1999), 219-221.
Stewart, Kelly M, et al., "Cell-penetrating peptides as delivery vehicles for biology and medicine", Organic & biomolecular chemistry 6.13, (2008), 2242-2255.
Suhorutsenko, Julia, et al., "Cell-penetrating peptides, PepFects, show No. evidence of toxicity and immunogenicity in vitro and in vivo", Bioconjugate chemistry 22.11, (Nov. 2011), 2255-2262.

(56) References Cited

OTHER PUBLICATIONS

Sun, Y, et al., "A thioester ligation approach to amphipathic bicyclic peptide library", Org. Lett. 3, (May 2001), 1681-1684.
Tam, J P, et al., "Disulfide bond formation in peptides by dimethyl sulfoxide.Scope and applications", J. Am. Chem. Soc., 113(17), (1991), 6657-6662.
Tavassoli, A, et al., "Inhibition of HIV Budding by a Genetically Selected Cyclic Peptide Targeting the Gag-TSG101 Interaction", ACS Chemical Biology 3(12), (2008), 757-764.
Thakkar, A, et al., "Traceless capping agent for peptide sequencing by partial Edman degradation and mass spectrometry", Anal. Chem. 78, (2006), 5935-5939.
Thornberry, N A, et al., "A combinatorial approach defines specificities of members of the caspase family and granzyme B. Functional relationships established for key mediators of apoptosis", Journal of Biological Chemistry. 272(29), (Jul. 18, 1997), 17907-17911.
Traboulsi, H, et al., "Macrocyclic Cell Penetrating Peptides: A Study of Structure-Penetration Properties", Bioconjugate Chemistry 26, (2015), 405-411.
Trinh, Thi B, et al., "Discovery of a direct Ras inhibitor by screening a combinatorial library of cell-permeable bicyclic peptides", ACS combinatorial science 18.1, 2016, (Dec. 8, 2015), 75-85.
Tse, B. N, et al., "Translation of DNA into a Library of 13 000 Synthetic Small-Molecule Macrocycles Suitable for in Vitro Selection", J. Am. Chem. Soc., 130(46), (2008), 15611-15626.
Turner, R A, et al., "Click chemistry as a macrocyclization tool in the solid-phase synthesis of small cyclic peptides", Org. Lett., 9(24), (Nov. 2007), 5011-5014.
Tyagi, M, et al., "Internalization of HIV-1 Tat requires cell surface heparan sulfate proteoglycans", J. Biol. Chem., 276(5), (Feb. 2001), 3254-3261.
Upadhyaya, Punit, et al., "Inhibition of Ras signaling by blocking Ras-effector interactions with cyclic peptides", Angewandte Chemie International Edition 54.26, Angew. Chem. 127, (May 7, 2015), 7712-7716.
Van Goor, F, et al., "Correction of the F508del-CFTR protein processing defect in vitro by the investigating drug VX-809", Proc. Natl. Acad. Sci. U. S. A., 108(46), (Nov. 2011), 18843-18848.
Varkouhi, Amir K, et al., "Endosomal escape pathways for delivery of biologicals", Journal of Controlled Release 151.3, 220-228, (2011), 9 pgs.
Verdurmen, et al., "Preferential Uptake of L-versus D-Amino Acid Cell-Penetrating Peptides in a Cell Type-Dependent Manner", Chemistry & Biology, vol. 18, (2011), 1000-1010.
Wadia, Jehangir S, et al., "Transmembrane delivery of protein and peptide drugs by TAT-mediated transduction in the treatment of cancer", Advanced drug delivery reviews 57.4, (Feb. 2005), 579-596.
Wallbrecher, R, et al., "Exploration of the Design Principles of a Cell-Penetrating Bicyclic Peptide Scaffold", Bioconjugate Chemistry, 25(5), (Apr. 3, 2014), 955-964.
Wang, C-W, et al., "Increased potency of a novel D-ß-naphthylalanine-substituted antimicrobial peptide against fluconazole-resistant fungal pathogens", FEMS Yeast Research, 9(6), (2009), 967-970.
Wender, P. A, et al., "The design, synthesis, and evaluation of molecules that enable or enhance cellular uptake: Peptoid molecular transporters", Proc. Natl. Acad. Sci. USA, 97(24), (Nov. 2000), 13003-13008.
White, Tina R, et al., "On-resin N-methylation of cyclic peptides for discovery of orally bioavailable scaffolds", Nature chemical biology 7.11, (2011), 810-817.
Wolde, Michael, et al., "Targeting CAL as a negative regulator of ?F508-CFTR cell-surface expression: an rna interference and structure-based mutagenetic approaCH", Journal of Biological Chemistry 282.11, (Mar. 2007), 8099-8109.
Wu, G, et al., "Structural basis of IAP recognition by Smac/DIABLO", Nature, 408(6815), (Dec. 2000), 1008-1012.
Wu, X, et al., "Inhibition of Ras-effector interactions by cyclic peptides", Med. Chem. Commun. 4, (2013), 378-382.
Xie, L, et al., "Cellular Effects of Small Molecule PTP1B Inhibitors on Insulin Signaling", Biochemistry, 42( 44 ), (2003), 12792-12804.
Yin, J., et al., "Genetically encoded short peptide tag for versatile protein labeling by Sfp phosphopantetheinyl transferase", Proc. Natl. Acad. Sci. USA 102(44), (Nov. 2005), 15815-15820.
Zabolotny, J M, et al., "PTP1B regulates leptin signal transduction in vivo", Dev. Cell, 2(4), (Apr. 2002), 489-495.
Zhao, Kun, et al., "Enhanced activity of cyclic transporter sequences driven by phase behavior of peptide-lipid complexes", Soft Matter 8.24, (2012), 6430-6433.
Ziegler, A, et al., "Interaction of the protein transduction domain of HIV-1 Tat with heparan sulfate: binding mechanism and thermodynamic parameters", Biophys. J., 86(1), (Jan. 2004), 254-263.
Ziegler, A, "Thermodynamic studies and binding mechanisms of cell-penetrating peptides with lipids and glycosaminoglycans", Advanced Drug Delivery Reviews, 60(4-5), (Mar. 2008), 580-597.
"U.S. Appl. No. 17/530,664, Final Office Action mailed Dec. 14, 2023", 7 pgs.
"U.S. Appl. No. 17/530,664, Non Final Office Action mailed Jun. 2, 2023", 11 pgs.
"U.S. Appl. No. 17/530,664, Response filed Nov. 30, 2023 to Non Final Office Action mailed Jun. 2, 2023", 5 pgs.
"Chinese Application Serial No. 202280026935.X, Notification to Make Rectification (210302) mailed Oct. 31, 2023", 2 pgs.
"European Application Serial No. 20903078.2, Extended European Search Report mailed Dec. 11, 2023", 12 pgs.
"International Application Serial No. PCT/US2022/071489, International Preliminary Report on Patentability mailed May 26, 2023", 10 pgs.
"Japanese Application Serial No. 2020-072542, Notification of Reasons for Refusal mailed Dec. 7, 2023", w/ English Translation, 7 pgs.
"Korean Application Serial No. 10-2023-7036879, Office Action mailed Nov. 3, 2023", 3 pgs.
"The endosomal escape vehicle platform enhances delivery of oligonucleotides in preclinical models of neuromuscular disorders", Molecular Therapy-Nucleic Acids, vol. 33, [Online]. Retrieved from the Internet: <URL: https://www.ncbi.nlm.nih.gov/pmc/articles/PMC10393622/pdf/main.pdf>, (Sep. 1, 2023), 273-285.
Mozaffari, Saghar, et al., "Amphiphilic Peptides for Efficient siRNA Delivery", Polymers, vol. 11, No. 4, 703, [Online]. Retrieved from the Internet: <URL: https://www.ncbi.nlm.nih.gov/pmc/articles/PMC6523661/pdf/polymers-11-00703.pdf>, (Apr. 17, 2019), 20 pgs.
Panigrahi, Bijayananda, et al., "Cyclic peptide-based nanostructures as efficient siRNA carriers", Artificial Cells, Nanomedicine and Biotechnology, vol. 46, No. sup3, (Oct. 12, 2018), 763-773.
Qian, Ziqing, et al., "Discovery and mechanism of highly efficient cyclic cell-penetrating peptides", Biochemistry 55.18, (2016), 2601-2612.
Shang, Eun Park, et al., "Cyclic Cell-Penetrating Peptides as Efficient Intracellular Drug Delivery Tools", Molecular Pharmaceutics, vol. 16, No. 9, (Sep. 3, 2019), 3727-3743.
Welch, Jade J, et al., "Functional Delivery of siRNA by Disulfide-Constrained Cyclic Amphipathic Peptides", ACS Medicinal Chemistry Letters, vol. 7, No. 6, (Jun. 9, 2016), 584-589.
"International Application Serial No. PCT/US2020/066459, International Search Report mailed Apr. 6, 2021", 4 pgs.
"International Application Serial No. PCT/US2020/066459, Written Opinion mailed Apr. 6, 2021", 5 pgs.
Fadzen, et al., "Chimeras of Cell-Penetrating Peptides Demonstrate Synergistic Improvement in Antisense Efficacy", Biochemistry, vol. 58, Iss. 38, (Aug. 1, 2019), 1-30.
U.S. Appl. No. 18/553,379 filed Sep. 29, 2023, Cyclic Cell Penetrating Peptides.
Hammond S.M., et al., "Delivery of Oligonucleotide-Based Therapeutics: Challenges and Opportunities," EMBO Molecular Medicine, Apr. 6, 2021, vol. 13, 23 pages.
Inagaki M., et al., "N-Benzoyl-Protected Peptide Nucleic Acid (PNA) Monomers Expand the Range of Nucleobases Available for PNA-DNA Chimera," Chemistry Letters, The Chemical Society of Japan, Jan. 1, 2019, vol. 48, pp. 341-344.

(56) References Cited

OTHER PUBLICATIONS

Iranian Notice of Refusal for IR Application No. 140250140003006562, Aug. 10, 2024, 15 pages.
Juliano R.L, "The Delivery of Therapeutic Oligonucleotides," Nucleic Acids Research, Apr. 15, 2016, vol. 44, No. 14, pp. 6518-6548.
Laurent Q., et al., "Oligonucleotide Phosphorothioates Enter Cells by Thiol-Mediated Uptake," Angewandte International Edition Chemie, Aug. 23, 2021, vol. 60, 6 pages.
Li C., et al., "Fully Automated Fast-Flow Synthesis of Antisense Phosphorodiamidate Morpholino Oligomers," Nature Communications, Jul. 20, 2021, vol. 12:4396, pp. 1-8.
Milligan J.F., et al., "Current Concepts in Antisense Drug Design," Journal of Medicinal Chemistry, Jul. 9, 1993, vol. 36, No. 14, pp. 1923-1937.
Muslehiddinoglu J., et al., "Technical Considerations for Use of Oligonucleotide Solution API," Nucleic Acid Therapeutics, Aug. 6, 2020, vol. 30, No. 04, pp. 189-197.
Paunovska K., et al., "Drug Delivery Systems for RNA Therapeutics," Nature Reviews Genetics, Jan. 4, 2022, 16 pages.
Rinaldi C., et al., "Antisense Oligonucleotides: The Next Frontier For Treatment of Neurological Disorders," Nature Reviews Neurology, London, Jan. 1, 2018, vol. 14, No. 1, pp. 9-21 (32 Pages), DOI: 10.1038/nrneurol.2017.148, ISSN: 1759-4758, XP055851467, Retrieved from URL: https://www.nature.com/articles/nrneurol.2017.148.pdf.

* cited by examiner

5′-conjugation, amide chemistry

3′-conjugation, amide chemistry

RT-PCR analysis demonstrating exon skipping in muscle

PMO-A

PMO-T

PMO-C

PMO-G

SEQUENCE LISTING

```
<160> NUMBER OF SEQ ID NOS: 272

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 1

Phe Xaa Arg Arg Arg
1               5


<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 2

Phe Xaa Arg Arg Arg Cys
1               5


<210> SEQ ID NO 3
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (6)..(6)
<223> OTHER INFORMATION: Selenocysteine

<400> SEQUENCE: 3

Phe Xaa Arg Arg Arg Xaa
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
<220> FEATURE:
```

<221> NAME/KEY: MOD_RES
<222> LOCATION: (4)..(4)
<223> OTHER INFORMATION: L-2-naphthylalanine

<400> SEQUENCE: 4

Arg Arg Arg Xaa Phe
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 5

Arg Arg Arg Arg Xaa Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 6

Phe Xaa Arg Arg Arg Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 7

Phe Xaa Arg Arg Arg Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 8

Phe Xaa Arg Arg Arg Arg
1 5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 9

Phe Xaa Arg Arg Arg Arg
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 10

Phe Xaa Arg Arg Arg Arg
1 5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 11

Arg Arg Phe Arg Xaa Arg
1 5

<210> SEQ ID NO 12

<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-2-naphthylalanine

<400> SEQUENCE: 12

Phe Arg Arg Arg Arg Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (5)..(5)
<223> OTHER INFORMATION: L-2-naphthylalanine

<400> SEQUENCE: 13

Arg Arg Phe Arg Xaa Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-2-naphthylalanine

<400> SEQUENCE: 14

Arg Arg Xaa Phe Arg Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Cys Arg Arg Arg Arg Phe Trp
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: L-2-naphthylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 16

Phe Phe Xaa Arg Arg Arg Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-2-naphthylalanine

<400> SEQUENCE: 17

Phe Phe Xaa Arg Arg Arg Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-2-naphthylalanine

<400> SEQUENCE: 18

Arg Phe Arg Phe Arg Xaa Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Selenocysteine

<400> SEQUENCE: 19

Xaa Arg Arg Arg Arg Phe Trp
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Cys Arg Arg Arg Arg Phe Trp
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 21

Phe Xaa Arg Arg Arg Arg Gln Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 22

Phe Xaa Arg Arg Arg Arg Gln Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 23

Phe Xaa Arg Arg Arg Arg Arg Gln
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 24

Phe Xaa Arg Arg Arg Arg Arg Gln 1 5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine
<220> FEATURE:
<221> NAME/KEY: MOD_RES
<222> LOCATION: (8)..(8)
<223> OTHER INFORMATION: L-norleucine

<400> SEQUENCE: 25

Arg Arg Arg Arg Xaa Phe Asp Xaa Cys
1 5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 26

Phe Xaa Arg Arg Arg
1 5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Phe Trp Arg Arg Arg
1 5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-2-naphthylalanine

<400> SEQUENCE: 28

Arg Arg Arg Xaa Phe
1 5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

-continued

Arg Arg Arg Trp Phe
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 30

Phe Xaa Arg Arg Arg Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Phe Phe Arg Arg Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 32

Phe Phe Arg Arg Arg
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: D-amino acid

<400> SEQUENCE: 33

Phe Phe Arg Arg Arg
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Phe Arg Phe Arg Arg
1 5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Phe Arg Arg Phe Arg
1 5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Phe Arg Arg Arg Phe
1 5

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 37

Gly Xaa Arg Arg Arg
1 5

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct

<400> SEQUENCE: 38

Phe Phe Phe Arg Ala
1 5

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Phe Phe Phe Arg Arg
1 5

<210> SEQ ID NO 40
<211> LENGTH: 6
<212> TYPE: PRT

<213> ORGANISM: Artificial Sequence
<220> FEATURE:
<223> OTHER INFORMATION: Synthetic Construct

<400> SEQUENCE: 40

Phe Phe Arg Arg Arg Arg
1 5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Phe Arg Arg Phe Arg Arg
1 5

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct

<400> SEQUENCE: 42

Phe Arg Arg Arg Phe Arg
1 5

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct

<400> SEQUENCE: 43

Arg Phe Phe Arg Arg Arg
1 5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Arg Phe Arg Arg Phe Arg
1 5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Phe Arg Phe Arg Arg Arg
1 5

<210> SEQ ID NO 46
<211> LENGTH: 6
<212> TYPE: PRT
<213> ORGANISM: Artificial Sequence
<220> FEATURE:
<223> OTHER INFORMATION: Synthetic Construct

<400> SEQUENCE: 46

Phe Phe Phe Arg Arg Arg
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct

<400> SEQUENCE: 47

Phe Phe Arg Arg Arg Phe
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct

<400> SEQUENCE: 48

Phe Arg Phe Phe Arg Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct

<400> SEQUENCE: 49

Arg Arg Phe Phe Phe Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Construct

<400> SEQUENCE: 50

Phe Phe Arg Phe Arg Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Phe Phe Arg Arg Phe Arg
1               5

<210> SEQ ID NO 52
<211> LENGTH: 6
<212> TYPE: PRT
<213> ORGANISM: Artificial Sequence
<220> FEATURE:

<223> OTHER INFORMATION: Synthetic Construct

<400> SEQUENCE: 52

Phe Arg Arg Phe Phe Arg
1 5

<210> SEQ ID NO 53
<211> LENGTH: 6
<212> TYPE: PRT
<213> ORGANISM: Artificial Sequence
<220> FEATURE:
<223> OTHER INFORMATION: Synthetic Construct

<400> SEQUENCE: 53

Phe Arg Arg Phe Arg Phe
1 5

<210> SEQ ID NO 54
<211> LENGTH: 6
<212> TYPE: PRT
<213> ORGANISM: Artificial Sequence
<220> FEATURE:
<223> OTHER INFORMATION: Synthetic Construct

<400> SEQUENCE: 54

Phe Arg Phe Arg Phe Arg
1 5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Arg Phe Phe Arg Phe Arg
1 5

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 56

Gly Xaa Arg Arg Arg Arg
1 5

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Phe Phe Phe Arg Arg Arg Arg
1 5

<210> SEQ ID NO 58
<211> LENGTH: 7

<212> TYPE: PRT
<213> ORGANISM: Artificial Sequence
<220> FEATURE:
<223> OTHER INFORMATION: Synthetic Construct

<400> SEQUENCE: 58

Arg Phe Phe Arg Arg Arg Arg
1 5

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Arg Arg Phe Phe Arg Arg Arg
1 5

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct

<400> SEQUENCE: 60

Arg Phe Phe Phe Arg Arg Arg
1 5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Arg Arg Phe Phe Phe Arg Arg
1 5

<210> SEQ ID NO 62
<211> LENGTH: 7
<212> TYPE: PRT
<213> ORGANISM: Artificial Sequence
<220> FEATURE:
<223> OTHER INFORMATION: Synthetic Construct

<400> SEQUENCE: 62

Phe Phe Arg Arg Phe Arg Arg
1 5

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Phe Phe Arg Arg Arg Arg Phe
1 5

<210> SEQ ID NO 64
<211> LENGTH: 7
<212> TYPE: PRT

<213> ORGANISM: Artificial Sequence
<220> FEATURE:
<223> OTHER INFORMATION: Synthetic Construct

<400> SEQUENCE: 64

Phe Arg Arg Phe Phe Arg Arg
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic Construct

<400> SEQUENCE: 65

Phe Phe Phe Arg Arg Arg Arg Arg
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Phe Phe Phe Arg Arg Arg Arg Arg Arg
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 67

Phe Xaa Arg Arg Arg Arg
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(2)
<223> OTHER INFORMATION: L-4-fluorophenylalanine

<400> SEQUENCE: 68

Xaa Xaa Arg Arg Arg Arg
1               5

<210> SEQ ID NO 69

<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 69

Phe Phe Phe Arg Arg Arg
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 70

Phe Phe Phe Arg Arg Arg
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 71

Phe Phe Phe Arg Arg Arg
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)

<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 72

Phe Phe Phe Arg Arg Arg
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 73

Phe Phe Xaa Arg Arg Arg
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 74

Phe Xaa Phe Arg Arg Arg
1               5

<210> SEQ ID NO 75
<211> LENGTH: 6
<212> TYPE: PRT
<213> ORGANISM: Artificial Sequence
<220> FEATURE:

<223> OTHER INFORMATION: Synthetic Construct
<220> FEATURE:
<221> NAME/KEY: MOD_RES
<222> LOCATION: (1)..(1)
<223> OTHER INFORMATION: D-2-naphthylalanine
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 75

Xaa Phe Phe Arg Arg Arg
1 5

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 76

Phe Xaa Arg Arg Arg
1 5

<210> SEQ ID NO 77
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 77

Phe Xaa Arg Arg Arg
1 5

<210> SEQ ID NO 78
<211> LENGTH: 8
<212> TYPE: PRT
<213> ORGANISM: Artificial Sequence
<220> FEATURE:

-continued

<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 78

Lys Phe Phe Arg Arg Arg Arg Asp
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: L-2,3-diaminopropionic acid
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 79

Xaa Phe Phe Arg Arg Arg Arg Asp
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(8)
<223> OTHER INFORMATION: disulfide bond

<400> SEQUENCE: 80

Cys Trp Trp Arg Arg Arg Arg Cys
1               5

<210> SEQ ID NO 81
<211> LENGTH: 9
<212> TYPE: PRT
<213> ORGANISM: Artificial Sequence
<220> FEATURE:

<223> OTHER INFORMATION: Synthetic Construct
<220> FEATURE:
<221> NAME/KEY: DISULFID
<222> LOCATION: (1)..(9)
<223> OTHER INFORMATION: disulfide bond

<400> SEQUENCE: 81

Cys Trp Trp Trp Arg Arg Arg Arg Cys
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(8)
<223> OTHER INFORMATION: disulfide bond

<400> SEQUENCE: 82

Cys Phe Trp Arg Arg Arg Arg Cys
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: DISULFID
<222> LOCATION: (1)..(8)
<223> OTHER INFORMATION: disulfide bond

<400> SEQUENCE: 83

Cys Trp Trp Trp Arg Arg Arg Cys
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(7)
<223> OTHER INFORMATION: D-amino acid

<400> SEQUENCE: 84

Xaa Xaa Arg Glu Arg Arg Glu
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(7)
<223> OTHER INFORMATION: D-amino acid

<400> SEQUENCE: 85

Xaa Xaa Arg Arg Arg Arg Glu
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(3)
<223> OTHER INFORMATION: L-2-naphthylalanine
<220> FEATURE:
<221> NAME/KEY: MOD_RES
<222> LOCATION: (5)..(7)
<223> OTHER INFORMATION: D-amino acid

<400> SEQUENCE: 86

Xaa Xaa Xaa Arg Arg Arg Glu
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(3)
<223> OTHER INFORMATION: L-2-naphthylalanine
<220> FEATURE:
<221> NAME/KEY: MOD_RES
<222> LOCATION: (5)..(6)
<223> OTHER INFORMATION: D-amino acid

<400> SEQUENCE: 87

Xaa Xaa Xaa Arg Arg Arg Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(7)
<223> OTHER INFORMATION: D-amino acid

<400> SEQUENCE: 88

Xaa Xaa Phe Arg Arg Arg Glu
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (5)..(6)
<223> OTHER INFORMATION: D-amino acid

<400> SEQUENCE: 89

Xaa Xaa Phe Arg Arg Arg Glu
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(7)
<223> OTHER INFORMATION: D-amino acid

<400> SEQUENCE: 90

Xaa Xaa Phe Arg Arg Arg Glu
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(6)
<223> OTHER INFORMATION: D-amino acid

<400> SEQUENCE: 91

Xaa Xaa Phe Arg Arg Arg Glu
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-2-naphthylalanine
<220> FEATURE:
<221> NAME/KEY: MOD_RES
<222> LOCATION: (5)..(6)
<223> OTHER INFORMATION: D-amino acid

<400> SEQUENCE: 92

Xaa Xaa Xaa Arg Arg Arg Glu
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-2-naphthylalanine
<220> FEATURE:
<221> NAME/KEY: MOD_RES
<222> LOCATION: (5)..(7)
<223> OTHER INFORMATION: D-amino acid

<400> SEQUENCE: 93

Xaa Xaa Xaa Arg Arg Arg Glu
1               5

<210> SEQ ID NO 94
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Arg is modified with pimelic acid
<220> FEATURE:
<221> NAME/KEY: MISC_FEATURE
<222> LOCATION: (1)..(4)
<223> OTHER INFORMATION: Cyclization between Arg is modified with pimelic acid and Arg is modified with lysine peptoid residue
<220> FEATURE:
<221> NAME/KEY: MOD_RES
<222> LOCATION: (4)..(4)
<223> OTHER INFORMATION: Arg is modified with lysine peptoid residue

<400> SEQUENCE: 94

Arg Gln Arg Arg Gly Arg Arg Arg
1               5

<210> SEQ ID NO 95
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (2)..(19)
<223> OTHER INFORMATION: Cys residues jopined by disulfide bond

<400> SEQUENCE: 95

Lys Cys Phe Gln Trp Gln Arg Asn Met Arg Lys Val Arg Gly Pro Pro
1               5                   10                  15

Val Ser Cys

<210> SEQ ID NO 96
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(11)
<223> OTHER INFORMATION: Cyclization between Lys and Glu
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid

<400> SEQUENCE: 96

Lys Arg Arg Arg Gly Arg Lys Lys Arg Arg Glu
1               5                   10

<210> SEQ ID NO 97

<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(12)
<223> OTHER INFORMATION: Cyclization between Lys and Glu
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid

<400> SEQUENCE: 97

Lys Arg Arg Arg Arg Arg Arg Arg Arg Arg Arg Glu
1               5                   10

<210> SEQ ID NO 98
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
<223> OTHER INFORMATION: D-amino acid

<400> SEQUENCE: 98

Arg Val Arg Thr Arg Gly Lys Arg Arg Ile Arg Arg Pro Pro
1               5                   10

<210> SEQ ID NO 99
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
<223> OTHER INFORMATION: D-amino acid

<400> SEQUENCE: 99

Arg Thr Arg Thr Arg Gly Lys Arg Arg Ile Arg Val Pro Pro
1               5                   10

<210> SEQ ID NO 100
<211> LENGTH: 8
<212> TYPE: PRT
<213> ORGANISM: Artificial Sequence
<220> FEATURE:
<223> OTHER INFORMATION: synthetic construct

<400> SEQUENCE: 100

```
Trp Arg Trp Arg Trp Arg Trp Arg
1               5


<210> SEQ ID NO 101
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (4)..(21)
<223> OTHER INFORMATION: Cys residues jopined by disulfide bond
<220> FEATURE:
<221> NAME/KEY: DISULFID
<222> LOCATION: (11)..(23)
<223> OTHER INFORMATION: Cys residues jopined by disulfide bond
<220> FEATURE:
<221> NAME/KEY: DISULFID
<222> LOCATION: (17)..(29)
<223> OTHER INFORMATION: Cys residues jopined by disulfide bond

<400> SEQUENCE: 101

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp


<210> SEQ ID NO 102
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(10)
<223> OTHER INFORMATION: Macrocyclization by multicomponent reaction
      with aziridine aldehyde and isocyanide
<220> FEATURE:
<221> NAME/KEY: MOD_RES
<222> LOCATION: (2)..(2)
<223> OTHER INFORMATION: L-3-cyclohexyl-alanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: L-cyclohexylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (6)..(6)
<223> OTHER INFORMATION: L-cyclohexylalanine
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: L-cyclohexylalanine
<220> FEATURE:
<221> NAME/KEY: MOD_RES
<222> LOCATION: (9)..(9)
<223> OTHER INFORMATION: D-amino acid

<400> SEQUENCE: 102
```

Pro Xaa Arg Xaa Arg Xaa Arg Xaa Arg Gly
1 5 10

<210> SEQ ID NO 103
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ser is modified with trimesic acid
<220> FEATURE:
<221> NAME/KEY: MISC_FEATURE
<222> LOCATION: (1)..(13)
<223> OTHER INFORMATION: N-terminal amine and side chains of two L-2,3-diaminopropionic acid residues bicyclized with trimesic acid
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: L-4-(phosphonodifluoromethyl)phenylalanine
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-naphthylalanine
<220> FEATURE:
<221> NAME/KEY: MOD_RES
<222> LOCATION: (13)..(13)
<223> OTHER INFORMATION: L-2,3-diaminopropionic acid

<400> SEQUENCE: 103

Ser Val Pro Xaa His Xaa Phe Xaa Arg Arg Arg Arg Xaa
1 5 10

<210> SEQ ID NO 104
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-alanine is modified with trimesic acid
<220> FEATURE:
<221> NAME/KEY: MOD_RES
<222> LOCATION: (1)..(1)
<223> OTHER INFORMATION: D-amino acid
<220> FEATURE:
<221> NAME/KEY: MISC_FEATURE
<222> LOCATION: (1)..(17)
<223> OTHER INFORMATION: N-terminal amine and side chains of two L-2,3-diaminopropionic acid residues bicyclized with trimesic acid
<220> FEATURE:
<221> NAME/KEY: MOD_RES
<222> LOCATION: (2)..(2)
<223> OTHER INFORMATION: sarcosine
<220> FEATURE:
<221> NAME/KEY: MOD_RES
<222> LOCATION: (4)..(4)
<223> OTHER INFORMATION: D-phosphothreonine
<220> FEATURE:
<221> NAME/KEY: MOD_RES
<222> LOCATION: (5)..(5)
<223> OTHER INFORMATION: L-homoproline
<220> FEATURE:

<221> NAME/KEY: MOD_RES
<222> LOCATION: (6)..(6)
<223> OTHER INFORMATION: L-naphthylalanine
<220> FEATURE:
<221> NAME/KEY: MOD_RES
<222> LOCATION: (9)..(9)
<223> OTHER INFORMATION: D-alanine
<220> FEATURE:
<221> NAME/KEY: MOD_RES
<222> LOCATION: (10)..(10)
<223> OTHER INFORMATION: L-2,3-diaminopropionic acid
<220> FEATURE:
<221> NAME/KEY: MOD_RES
<222> LOCATION: (12)..(12)
<223> OTHER INFORMATION: L-naphthylalanine
<220> FEATURE:
<221> NAME/KEY: MOD_RES
<222> LOCATION: (17)..(17)
<223> OTHER INFORMATION: L-2,3-diaminopropionic acid

<400> SEQUENCE: 104

Ala Xaa Asp Xaa Xaa Xaa Arg Ala Xaa Xaa Phe Xaa Arg Arg Arg Arg
1               5                   10                  15

Xaa

<210> SEQ ID NO 105
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(15)
<223> OTHER INFORMATION: Three Cys side chains bicyclized with
      tris(bromomethyl)benzene

<400> SEQUENCE: 105

Cys Arg Arg Ser Arg Arg Gly Cys Gly Arg Arg Ser Arg Arg Cys Gly
1               5                   10                  15

<210> SEQ ID NO 106
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(2)
<223> OTHER INFORMATION: linked by dodecanoyl moiety

<400> SEQUENCE: 106

Lys Arg Arg Arg Arg
1               5

<210> SEQ ID NO 107
<211> LENGTH: 16
<212> TYPE: PRT
<213> ORGANISM: Artificial Sequence
<220> FEATURE:
<223> OTHER INFORMATION: synthetic construct

<400> SEQUENCE: 107

Leu Lys Lys Leu Cys Lys Leu Leu Lys Lys Leu Cys Lys Leu Ala Gly
1               5                   10                  15

<210> SEQ ID NO 108
<211> LENGTH: 9
<212> TYPE: PRT

<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(9)
<223> OTHER INFORMATION: Cyclization between Lys and Glu

<400> SEQUENCE: 108

Arg Arg Arg Arg Lys Arg Arg Arg Glu
1               5

<210> SEQ ID NO 109
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(9)
<223> OTHER INFORMATION: Cyclization between Lys and Glu

<400> SEQUENCE: 109

Arg Arg Arg Lys Arg Arg Arg Arg Glu
1               5

<210> SEQ ID NO 110
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(9)
<223> OTHER INFORMATION: Cyclization between Lys and Glu

<400> SEQUENCE: 110

Arg Arg Lys Arg Arg Arg Arg Arg Glu
1               5

<210> SEQ ID NO 111
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(9)
<223> OTHER INFORMATION: Cyclization between Lys and Glu

<400> SEQUENCE: 111

Arg Lys Arg Arg Arg Arg Arg Arg Glu
1               5

<210> SEQ ID NO 112
<211> LENGTH: 8
<212> TYPE: PRT
<213> ORGANISM: Artificial Sequence
<220> FEATURE:
<223> OTHER INFORMATION: synthetic construct

<400> SEQUENCE: 112

Cys Arg Cys Arg Cys Arg Cys Arg
1               5

<210> SEQ ID NO 113

<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MISC_FEATURE
<222> LOCATION: (1)..(12)
<223> OTHER INFORMATION: Cyclization by the click reaction between L-propargylglycine and L-6-Azido-2-amino-hexanoic
<220> FEATURE:
<221> NAME/KEY: MOD_RES
<222> LOCATION: (12)..(12)
<223> OTHER INFORMATION: L-6-Azido-2-amino-hexanoic

<400> SEQUENCE: 113

Xaa Leu Arg Lys Arg Leu Arg Lys Phe Arg Asn Xaa
1               5                   10

<210> SEQ ID NO 114
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(4)
<223> OTHER INFORMATION: L-2,3-diaminopropionic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(8)
<223> OTHER INFORMATION: L-2,3-diaminopropionic acid

<400> SEQUENCE: 114

Thr Xaa Xaa Xaa Phe Leu Xaa Xaa Thr
1               5

<210> SEQ ID NO 115
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: L-2-amino-3-guanidinylpropionic acid
<220> FEATURE:
<221> NAME/KEY: MOD_RES
<222> LOCATION: (3)..(3)
<223> OTHER INFORMATION: L-2,3-diaminopropionic acid
<220> FEATURE:
<221> NAME/KEY: MOD_RES
<222> LOCATION: (4)..(4)
<223> OTHER INFORMATION: L-2-amino-3-guanidinylpropionic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(8)
<223> OTHER INFORMATION: L-2-amino-3-guanidinylpropionic acid

<400> SEQUENCE: 115

Thr Xaa Xaa Xaa Phe Leu Xaa Xaa Thr
1 5

<210> SEQ ID NO 116
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 116

Phe Xaa Arg Arg Arg Arg
1 5

<210> SEQ ID NO 117
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: L-2-naphthylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 117

Phe Phe Xaa Arg Arg Arg Arg
1 5

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 118

Phe Xaa Arg Arg Arg Arg
1 5

```
<210> SEQ ID NO 119
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 119

Phe Xaa Arg Arg Arg Arg Arg
1               5


<210> SEQ ID NO 120
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 120

Phe Xaa Arg Arg Arg Arg
1               5


<210> SEQ ID NO 121
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: D-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 121

Phe Xaa Arg Arg Arg Arg
1               5
```

-continued

<210> SEQ ID NO 122
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 122

Phe Xaa Arg Arg Arg Arg Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 123

Arg Arg Phe Arg Xaa Arg Gln
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-2-naphthylalanine

<400> SEQUENCE: 124

Phe Phe Xaa Arg Arg Arg Arg
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-2-naphthylalanine

<400> SEQUENCE: 125

Arg Phe Arg Phe Arg Xaa Arg
1               5

<210> SEQ ID NO 126
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2-naphthylalanine

<400> SEQUENCE: 126

Phe Xaa Arg Arg Arg
1 5

<210> SEQ ID NO 127
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-2-naphthylalanine

<400> SEQUENCE: 127

Phe Arg Arg Arg Arg Xaa
1 5

<210> SEQ ID NO 128
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (5)..(5)
<223> OTHER INFORMATION: L-2-naphthylalanine

<400> SEQUENCE: 128

Arg Arg Phe Arg Xaa Arg
1 5

<210> SEQ ID NO 129
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-2-naphthylalanine

<400> SEQUENCE: 129

Arg Arg Xaa Phe Arg Arg
1 5

<210> SEQ ID NO 130
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(4)
<223> OTHER INFORMATION: D-amino acid

```
<220> FEATURE:
<221> NAME/KEY: MOD_RES
<222> LOCATION: (6)..(6)
<223> OTHER INFORMATION: D-amino acid

<400> SEQUENCE: 130

Phe Xaa Phe Arg Arg Arg
1               5


<210> SEQ ID NO 131
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 131

Pro Lys Lys Lys Arg Lys Val
1               5


<210> SEQ ID NO 132
<211> LENGTH: 19
<212> TYPE: PRT
<213> ORGANISM: Artificial Sequence
<220> FEATURE:
<223> OTHER INFORMATION: nuclear localization sequence

<400> SEQUENCE: 132

Asn Leu Ser Lys Arg Pro Ala Ala Ile Lys Lys Ala Gly Gln Ala Lys
1               5                   10                  15

Lys Lys Lys


<210> SEQ ID NO 133
<211> LENGTH: 9
<212> TYPE: PRT
<213> ORGANISM: Artificial Sequence
<220> FEATURE:
<223> OTHER INFORMATION: nuclear localization sequence

<400> SEQUENCE: 133

Pro Ala Ala Lys Arg Val Lys Leu Asp
1               5


<210> SEQ ID NO 134
<211> LENGTH: 11
<212> TYPE: PRT
<213> ORGANISM: Artificial Sequence
<220> FEATURE:
<223> OTHER INFORMATION: nuclear localization sequence

<400> SEQUENCE: 134

Arg Gln Arg Arg Asn Glu Leu Lys Arg Ser Phe
1               5                   10


<210> SEQ ID NO 135
<211> LENGTH: 41
<212> TYPE: PRT
<213> ORGANISM: Artificial Sequence
<220> FEATURE:
<223> OTHER INFORMATION: nuclear localization sequence

<400> SEQUENCE: 135

Arg Met Arg Lys Phe Lys Asn Lys Gly Lys Asp Thr Ala Glu Leu Arg
1               5                   10                  15

Arg Arg Arg Val Glu Val Ser Val Glu Leu Arg Lys Ala Lys Lys Asp
            20                  25                  30
```

Glu Gln Ile Leu Lys Arg Arg Asn Val
        35                  40

<210> SEQ ID NO 136
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 136

Val Ser Arg Lys Arg Pro Arg Pro
1               5

<210> SEQ ID NO 137
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 137

Pro Pro Lys Lys Ala Arg Glu Asp
1               5

<210> SEQ ID NO 138
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 138

Pro Gln Pro Lys Lys Lys Pro Leu
1               5

<210> SEQ ID NO 139
<211> LENGTH: 12
<212> TYPE: PRT
<213> ORGANISM: Artificial Sequence
<220> FEATURE:
<223> OTHER INFORMATION: nuclear localization sequence

<400> SEQUENCE: 139

Ser Ala Leu Ile Lys Lys Lys Lys Lys Met Ala Pro
1               5                   10

<210> SEQ ID NO 140
<211> LENGTH: 5
<212> TYPE: PRT
<213> ORGANISM: Artificial Sequence
<220> FEATURE:
<223> OTHER INFORMATION: nuclear localization sequence

<400> SEQUENCE: 140

Asp Arg Leu Arg Arg
1               5

<210> SEQ ID NO 141
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 141

```
Pro Lys Gln Lys Lys Arg Lys
1               5


<210> SEQ ID NO 142
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 142

Arg Lys Leu Lys Lys Lys Ile Lys Lys Leu
1               5                   10


<210> SEQ ID NO 143
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 143

Arg Glu Lys Lys Lys Phe Leu Lys Arg Arg
1               5                   10


<210> SEQ ID NO 144
<211> LENGTH: 20
<212> TYPE: PRT
<213> ORGANISM: Artificial Sequence
<220> FEATURE:
<223> OTHER INFORMATION: nuclear localization sequence

<400> SEQUENCE: 144

Lys Arg Lys Gly Asp Glu Val Asp Gly Val Asp Glu Val Ala Lys Lys
1               5                   10                  15

Lys Ser Lys Lys
            20


<210> SEQ ID NO 145
<211> LENGTH: 17
<212> TYPE: PRT
<213> ORGANISM: Artificial Sequence
<220> FEATURE:
<223> OTHER INFORMATION: nuclear localization sequence

<400> SEQUENCE: 145

Arg Lys Cys Leu Gln Ala Gly Met Asn Leu Glu Ala Arg Lys Thr Lys
1               5                   10                  15

Lys


<210> SEQ ID NO 146
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (2)..(2)
<223> OTHER INFORMATION: L-2-naphthylalanine

<400> SEQUENCE: 146

Phe Xaa Arg Arg Arg Arg Gln
```

1               5

<210> SEQ ID NO 147
<211> LENGTH: 16
<212> TYPE: DNA
<213> ORGANISM: Artificial Sequence
<220> FEATURE:
<223> OTHER INFORMATION: immunostimulatory nucleic acid

<400> SEQUENCE: 147
taacgttgag gggcat 16

<210> SEQ ID NO 148
<211> LENGTH: 18
<212> TYPE: DNA
<213> ORGANISM: Artificial Sequence
<220> FEATURE:
<223> OTHER INFORMATION: antisense compound phosphorodiamidate
      morpholino oligomer (PMO) with a C6-thiol 5' modification
<220> FEATURE:
<221> NAME/KEY: misc_feature
<222> LOCATION: (1)..(1)
<223> OTHER INFORMATION: C6-thiol 5' modification
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: modified_base
<222> LOCATION: (1)..(18)
<223> OTHER INFORMATION: linked by non-ionic phosphorodiamidate
      intersubunit linkages

<400> SEQUENCE: 148
gctattacct taacccag 18

<210> SEQ ID NO 149
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: L-2-naphthylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: gamma-glutamate
<220> FEATURE:
<221> NAME/KEY: MOD_RES
<222> LOCATION: (9)..(10)
<223> OTHER INFORMATION: beta-alanine
<220> FEATURE:
<221> NAME/KEY: MOD_RES
<222> LOCATION: (11)..(11)
<223> OTHER INFORMATION: modiified with maleimide

<400> SEQUENCE: 149

```
Phe Phe Xaa Arg Arg Arg Arg Xaa Xaa Xaa Lys
1               5                   10


<210> SEQ ID NO 150
<211> LENGTH: 23
<212> TYPE: DNA
<213> ORGANISM: Artificial Sequence
<220> FEATURE:
<223> OTHER INFORMATION: RT-PCR primer

<400> SEQUENCE: 150

cgtaaacggc cacaagttca gcg                                              23


<210> SEQ ID NO 151
<211> LENGTH: 24
<212> TYPE: DNA
<213> ORGANISM: Artificial Sequence
<220> FEATURE:
<223> OTHER INFORMATION: RT-PCR primer

<400> SEQUENCE: 151

gtggtgcaga tgaacttcag ggtc                                             24


<210> SEQ ID NO 152
<211> LENGTH: 17
<212> TYPE: DNA
<213> ORGANISM: Artificial Sequence
<220> FEATURE:
<223> OTHER INFORMATION: antisense compound

<400> SEQUENCE: 152

gctattacct taaccca                                                     17


<210> SEQ ID NO 153
<211> LENGTH: 21
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(21)
<223> OTHER INFORMATION: 6 membered morpholine rings replace deoxyribose
      rings
<220> FEATURE:
<221> NAME/KEY: modified_base
<222> LOCATION: (1)..(21)
<223> OTHER INFORMATION: linked by non-ionic phosphorodiamidate
      intersubunit linkages

<400> SEQUENCE: 153

gtaactgtat ttggtacttc c                                                21


<210> SEQ ID NO 154
<211> LENGTH: 25
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages
<220> FEATURE:
```

<221> NAME/KEY: misc_feature
<222> LOCATION: (25)..(25)
<223> OTHER INFORMATION: conjugated to CP12 peptide

<400> SEQUENCE: 154
cttcttcttc ttcttcttct tcttc 25

<210> SEQ ID NO 155
<211> LENGTH: 18
<212> TYPE: DNA
<213> ORGANISM: Artificial Sequence
<220> FEATURE:
<223> OTHER INFORMATION: antisense compound
<220> FEATURE:
<221> NAME/KEY: misc_feature
<222> LOCATION: (1)..(1)
<223> OTHER INFORMATION: conjugated to CP12 peptide
<220> FEATURE:
<221> NAME/KEY: modified_base
<222> LOCATION: (1)..(18)
<223> OTHER INFORMATION: 2'-O-MOE ribonucleotides
<220> FEATURE:
<221> NAME/KEY: misc_feature
<222> LOCATION: (1)..(18)
<223> OTHER INFORMATION: linked by phosphorothioate bonds

<400> SEQUENCE: 155
cttcttcttc ttcttctt 18

<210> SEQ ID NO 156
<211> LENGTH: 19
<212> TYPE: DNA
<213> ORGANISM: Artificial Sequence
<220> FEATURE:
<223> OTHER INFORMATION: antisense compound
<220> FEATURE:
<221> NAME/KEY: misc_feature
<222> LOCATION: (1)..(19)
<223> OTHER INFORMATION: linked by phosphorothioate bonds
<220> FEATURE:
<221> NAME/KEY: modified_base
<222> LOCATION: (1)..(1)
<223> OTHER INFORMATION: locked nucleic acid
<220> FEATURE:
<221> NAME/KEY: misc_feature
<222> LOCATION: (1)..(1)
<223> OTHER INFORMATION: conjugated to CP12 peptide
<220> FEATURE:
<221> NAME/KEY: modified_base
<222> LOCATION: (3)..(4)
<223> OTHER INFORMATION: locked nucleic acid
<220> FEATURE:
<221> NAME/KEY: modified_base
<222> LOCATION: (6)..(7)
<223> OTHER INFORMATION: locked nucleic acid
<220> FEATURE:
<221> NAME/KEY: modified_base
<222> LOCATION: (9)..(10)
<223> OTHER INFORMATION: locked nucleic acid
<220> FEATURE:
<221> NAME/KEY: modified_base
<222> LOCATION: (12)..(13)
<223> OTHER INFORMATION: locked nucleic acid
<220> FEATURE:
<221> NAME/KEY: modified_base
<222> LOCATION: (15)..(16)
<223> OTHER INFORMATION: locked nucleic acid
<220> FEATURE:
<221> NAME/KEY: modified_base
<222> LOCATION: (18)..(19)
<223> OTHER INFORMATION: locked nucleic acid

<400> SEQUENCE: 156
tcttcttctt cttcttctt 19

```
<210> SEQ ID NO 157
<211> LENGTH: 18
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: misc_feature
<222> LOCATION: (1)..(18)
<223> OTHER INFORMATION: linked by non-ionic phosphorodiamidate
      intersubunit linkages
<220> FEATURE:
<221> NAME/KEY: misc_feature
<222> LOCATION: (18)..(18)
<223> OTHER INFORMATION: conjugated to CP12 peptide

<400> SEQUENCE: 157

gctattacct taacccag                                                    18


<210> SEQ ID NO 158
<211> LENGTH: 18
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: misc_feature
<222> LOCATION: (1)..(18)
<223> OTHER INFORMATION: linked by non-ionic phosphorodiamidate
      intersubunit linkages
<220> FEATURE:
<221> NAME/KEY: misc_feature
<222> LOCATION: (18)..(18)
<223> OTHER INFORMATION: conjugated to CP12 peptide and lipid group

<400> SEQUENCE: 158

gctattacct taacccag                                                    18


<210> SEQ ID NO 159
<211> LENGTH: 18
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: misc_feature
<222> LOCATION: (1)..(18)
<223> OTHER INFORMATION: linked by non-ionic phosphorodiamidate
      intersubunit linkages
<220> FEATURE:
<221> NAME/KEY: misc_feature
<222> LOCATION: (18)..(18)
<223> OTHER INFORMATION: conjugated to CP1212 peptide

<400> SEQUENCE: 159

gctattacct taacccag                                                    18
```

<210> SEQ ID NO 160
<211> LENGTH: 18
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: conjugated to Pip peptide

<400> SEQUENCE: 160
gctattacct taacccag 18

<210> SEQ ID NO 161
<211> LENGTH: 24
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(24)
<223> OTHER INFORMATION: 6 membered morpholine rings replace deoxyribose rings
<220> FEATURE:
<221> NAME/KEY: misc_feature
<222> LOCATION: (1)..(24)
<223> OTHER INFORMATION: linked by non-ionic phosphorodiamidate intersubunit linkages
<220> FEATURE:
<221> NAME/KEY: misc_feature
<222> LOCATION: (24)..(24)
<223> OTHER INFORMATION: conjugated to CP12 peptide

<400> SEQUENCE: 161
gggcatttta atatatctct gaac 24

<210> SEQ ID NO 162
<211> LENGTH: 24
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(24)
<223> OTHER INFORMATION: 6 membered morpholine rings replace deoxyribose rings
<220> FEATURE:
<221> NAME/KEY: misc_feature
<222> LOCATION: (1)..(24)
<223> OTHER INFORMATION: linked by non-ionic phosphorodiamidate intersubunit linkages
<220> FEATURE:
<221> NAME/KEY: misc_feature
<222> LOCATION: (24)..(24)
<223> OTHER INFORMATION: conjugated to CP12 peptide

<400> SEQUENCE: 162
ggccaaacct cggcttacct gaaa 24

<210> SEQ ID NO 163
<211> LENGTH: 24
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(24)
<223> OTHER INFORMATION: 6 membered morpholine rings replace deoxyribose rings
<220> FEATURE:
<221> NAME/KEY: misc_feature
<222> LOCATION: (1)..(24)
<223> OTHER INFORMATION: linked by non-ionic phosphorodiamidate intersubunit linkages
<220> FEATURE:
<221> NAME/KEY: misc_feature
<222> LOCATION: (24)..(24)
<223> OTHER INFORMATION: conjugated to CP12 peptide and lipid group

<400> SEQUENCE: 163
ggccaaacct cggcttacct gaaa 24

<210> SEQ ID NO 164
<211> LENGTH: 21
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(21)
<223> OTHER INFORMATION: 6 membered morpholine rings replace deoxyribose rings
<220> FEATURE:
<221> NAME/KEY: misc_feature
<222> LOCATION: (1)..(21)
<223> OTHER INFORMATION: linked by non-ionic phosphorodiamidate intersubunit linkages
<220> FEATURE:
<221> NAME/KEY: misc_feature
<222> LOCATION: (21)..(21)
<223> OTHER INFORMATION: conjugated to CP12 peptide

<400> SEQUENCE: 164
gtaactgtat ttggtacttc c 21

<210> SEQ ID NO 165
<211> LENGTH: 25
<212> TYPE: DNA
<213> ORGANISM: Artificial Sequence
<220> FEATURE:
<223> OTHER INFORMATION: antisense compound
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 165
ccaactgtcc tcaaaagcag gaata 25

<210> SEQ ID NO 166
<211> LENGTH: 25
<212> TYPE: DNA
<213> ORGANISM: Artificial Sequence
<220> FEATURE:

<223> OTHER INFORMATION: antisense compound
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 166
ccgggtctgc cgcccgctcc gccct 25

<210> SEQ ID NO 167
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 2'-O-MOE ribonucleotides
<220> FEATURE:
<221> NAME/KEY: misc_feature
<222> LOCATION: (1)..(18)
<223> OTHER INFORMATION: linked by phosphorothioate bonds
<220> FEATURE:
<221> NAME/KEY: modified_base
<222> LOCATION: (3)..(3)
<223> OTHER INFORMATION: 5-methyl cytosine
<220> FEATURE:
<221> NAME/KEY: modified_base
<222> LOCATION: (6)..(6)
<223> OTHER INFORMATION: 5-methyl cytosine
<220> FEATURE:
<221> NAME/KEY: modified_base
<222> LOCATION: (9)..(9)
<223> OTHER INFORMATION: 5-methyl cytosine
<220> FEATURE:
<221> NAME/KEY: modified_base
<222> LOCATION: (12)..(12)
<223> OTHER INFORMATION: 5-methyl cytosine
<220> FEATURE:
<221> NAME/KEY: modified_base
<222> LOCATION: (15)..(15)
<223> OTHER INFORMATION: 5-methyl cytosine
<220> FEATURE:
<221> NAME/KEY: modified_base
<222> LOCATION: (18)..(18)
<223> OTHER INFORMATION: 5-methyl cytosine

<400> SEQUENCE: 167
ttcttcttct tcttcttc 18

<210> SEQ ID NO 168
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(4)
<223> OTHER INFORMATION: 2'-O-MOE ribonucleotides
<220> FEATURE:
<221> NAME/KEY: modified_base
<222> LOCATION: (1)..(1)
<223> OTHER INFORMATION: 5-methyl cytosine
<220> FEATURE:
<221> NAME/KEY: modified_base
<222> LOCATION: (4)..(4)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (16)..(16)
<223> OTHER INFORMATION: 5-methyl cytosine
<220> FEATURE:
<221> NAME/KEY: modified_base
<222> LOCATION: (19)..(19)
<223> OTHER INFORMATION: 5-methyl cytosine

<400> SEQUENCE: 168
cttcttcttc ttcttcttct 20

<210> SEQ ID NO 169
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (2)..(2)
<223> OTHER INFORMATION: 5-methyl cytosine
<220> FEATURE:
<221> NAME/KEY: modified_base
<222> LOCATION: (5)..(5)
<223> OTHER INFORMATION: 5-methyl cytosine
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: modified_base
<222> LOCATION: (20)..(20)
<223> OTHER INFORMATION: 5-methyl cytosine

<400> SEQUENCE: 169
tcttcttctt cttcttcttc 20

<210> SEQ ID NO 170
<211> LENGTH: 19
<212> TYPE: RNA
<213> ORGANISM: Artificial Sequence
<220> FEATURE:

<223> OTHER INFORMATION: antisense oligonucleotide
<220> FEATURE:
<221> NAME/KEY: misc_feature
<222> LOCATION: (1)..(4)
<223> OTHER INFORMATION: linked by phosphorothioate bonds
<220> FEATURE:
<221> NAME/KEY: modified_base
<222> LOCATION: (1)..(19)
<223> OTHER INFORMATION: 2'-fluoro ribonucleotides
<220> FEATURE:
<221> NAME/KEY: misc_feature
<222> LOCATION: (17)..(19)
<223> OTHER INFORMATION: linked by phosphorothioate bonds

<400> SEQUENCE: 170
gaagaagaag aagaagaag 19

<210> SEQ ID NO 171
<211> LENGTH: 19
<212> TYPE: RNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(3)
<223> OTHER INFORMATION: linked by phosphorothioate bonds
<220> FEATURE:
<221> NAME/KEY: modified_base
<222> LOCATION: (1)..(19)
<223> OTHER INFORMATION: 2'-fluoro ribonucleotides
<220> FEATURE:
<221> NAME/KEY: misc_feature
<222> LOCATION: (16)..(19)
<223> OTHER INFORMATION: linked by phosphorothioate bonds

<400> SEQUENCE: 171
cuucuucuuc uucuucuuc 19

<210> SEQ ID NO 172
<211> LENGTH: 19
<212> TYPE: RNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(4)
<223> OTHER INFORMATION: linked by phosphorothioate bonds
<220> FEATURE:
<221> NAME/KEY: misc_feature
<222> LOCATION: (1)..(1)
<223> OTHER INFORMATION: conjugated to CPP12
<220> FEATURE:
<221> NAME/KEY: modified_base
<222> LOCATION: (1)..(1)
<223> OTHER INFORMATION: amidated
<220> FEATURE:
<221> NAME/KEY: modified_base
<222> LOCATION: (1)..(19)
<223> OTHER INFORMATION: 2'-fluoro ribonucleotides
<220> FEATURE:
<221> NAME/KEY: misc_feature
<222> LOCATION: (17)..(19)
<223> OTHER INFORMATION: linked by phosphorothioate bonds

<400> SEQUENCE: 172
gaagaagaag aagaagaag 19

<210> SEQ ID NO 173
<211> LENGTH: 19
<212> TYPE: RNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(3)
<223> OTHER INFORMATION: linked by phosphorothioate bonds
<220> FEATURE:
<221> NAME/KEY: modified_base
<222> LOCATION: (1)..(19)
<223> OTHER INFORMATION: 2'-fluoro ribonucleotides
<220> FEATURE:
<221> NAME/KEY: misc_feature
<222> LOCATION: (16)..(19)
<223> OTHER INFORMATION: linked by phosphorothioate bonds

<400> SEQUENCE: 173
cuucuucuuc uucuucuuc 19

<210> SEQ ID NO 174
<211> LENGTH: 19
<212> TYPE: RNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(19)
<223> OTHER INFORMATION: 2'-fluoro ribonucleotides
<220> FEATURE:
<221> NAME/KEY: misc_feature
<222> LOCATION: (17)..(19)
<223> OTHER INFORMATION: linked by phosphorothioate bonds
<220> FEATURE:
<221> NAME/KEY: modified_base
<222> LOCATION: (19)..(19)
<223> OTHER INFORMATION: amidated
<220> FEATURE:
<221> NAME/KEY: misc_feature
<222> LOCATION: (19)..(19)
<223> OTHER INFORMATION: conjugated to CPP12

<400> SEQUENCE: 174
gaagaagaag aagaagaag 19

<210> SEQ ID NO 175
<211> LENGTH: 19
<212> TYPE: RNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(3)
<223> OTHER INFORMATION: linked by phosphorothioate bonds
<220> FEATURE:
<221> NAME/KEY: modified_base
<222> LOCATION: (1)..(19)
<223> OTHER INFORMATION: 2'-fluoro ribonucleotides
<220> FEATURE:
<221> NAME/KEY: misc_feature
<222> LOCATION: (16)..(19)
<223> OTHER INFORMATION: linked by phosphorothioate bonds

<400> SEQUENCE: 175
cuucuucuuc uucuucuuc 19

<210> SEQ ID NO 176
<211> LENGTH: 21
<212> TYPE: DNA
<213> ORGANISM: Artificial Sequence
<220> FEATURE:
<223> OTHER INFORMATION: antisense oligonucleotide
<220> FEATURE:

<221> NAME/KEY: modified_base
<222> LOCATION: (1)..(19)
<223> OTHER INFORMATION: ribonucleotides

<400> SEQUENCE: 176
gaagaagaag aagaagaagt t 21

<210> SEQ ID NO 177
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(19)
<223> OTHER INFORMATION: ribonucleotides

<400> SEQUENCE: 177
cuucuucuuc uucuucuuct t 21

<210> SEQ ID NO 178
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(19)
<223> OTHER INFORMATION: ribonucleotides

<400> SEQUENCE: 178
gcuauaccag cgucgucaut t 21

<210> SEQ ID NO 179
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(19)
<223> OTHER INFORMATION: ribonucleotides

<400> SEQUENCE: 179
atgacgacgc tggtatagct t 21

<210> SEQ ID NO 180
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(19)
<223> OTHER INFORMATION: ribonucleotides

<400> SEQUENCE: 180
gagugucuau uugaugaaut t 21

<210> SEQ ID NO 181
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(19)
<223> OTHER INFORMATION: ribonucleotides

<400> SEQUENCE: 181
auucaucaaa uagacacuct t 21

<210> SEQ ID NO 182
<211> LENGTH: 17
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(17)
<223> OTHER INFORMATION: 2'-O-MOE ribonucleotides
<220> FEATURE:
<221> NAME/KEY: modified_base
<222> LOCATION: (1)..(2)
<223> OTHER INFORMATION: 5-methyl cytosine
<220> FEATURE:
<221> NAME/KEY: misc_feature
<222> LOCATION: (1)..(17)
<223> OTHER INFORMATION: linked by phosphorothioate bonds
<220> FEATURE:
<221> NAME/KEY: modified_base
<222> LOCATION: (4)..(4)
<223> OTHER INFORMATION: 5-methyl cytosine
<220> FEATURE:
<221> NAME/KEY: modified_base
<222> LOCATION: (10)..(10)
<223> OTHER INFORMATION: 5-methyl cytosine

<400> SEQUENCE: 182
cctcaaaagc aggaaua 17

<210> SEQ ID NO 183
<211> LENGTH: 15
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(15)
<223> OTHER INFORMATION: linked by phosphorothioate bonds
<220> FEATURE:
<221> NAME/KEY: modified_base
<222> LOCATION: (1)..(15)
<223> OTHER INFORMATION: 2'-O-MOE ribonucleotides
<220> FEATURE:
<221> NAME/KEY: modified_base
<222> LOCATION: (1)..(2)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (10)..(11)
<223> OTHER INFORMATION: 5-methyl cytosine
<220> FEATURE:
<221> NAME/KEY: modified_base
<222> LOCATION: (13)..(15)
<223> OTHER INFORMATION: 5-methyl cytosine

<400> SEQUENCE: 183
ccgggtctgc cgccc 15

<210> SEQ ID NO 184

<211> LENGTH: 17
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(17)
<223> OTHER INFORMATION: 6 membered morpholine rings replace deoxyribose rings
<220> FEATURE:
<221> NAME/KEY: misc_feature
<222> LOCATION: (1)..(17)
<223> OTHER INFORMATION: linked by non-ionic phosphorodiamidate intersubunit linkages

<400> SEQUENCE: 184
cctcaaaagc aggaata 17

<210> SEQ ID NO 185
<211> LENGTH: 15
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(15)
<223> OTHER INFORMATION: 6 membered morpholine rings replace deoxyribose rings
<220> FEATURE:
<221> NAME/KEY: misc_feature
<222> LOCATION: (1)..(15)
<223> OTHER INFORMATION: linked by non-ionic phosphorodiamidate intersubunit linkages

<400> SEQUENCE: 185
ccgggtctgc cgccc 15

<210> SEQ ID NO 186
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 186
ccaactgtcc tcaaaagcag gaata 25

<210> SEQ ID NO 187
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)

<223> OTHER INFORMATION: linked by non-ionic phosphorodiamidate
      intersubunit linkages

<400> SEQUENCE: 187
ccgggtctgc cgcccgctcc gccct 25

<210> SEQ ID NO 188
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 188
cttcttcttc ttcttcttct tcttc 25

<210> SEQ ID NO 189
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 2'-O-MOE ribonucleotides
<220> FEATURE:
<221> NAME/KEY: misc_feature
<222> LOCATION: (1)..(18)
<223> OTHER INFORMATION: linked by phosphorothioate bonds

<400> SEQUENCE: 189
cttcttcttc ttcttctt 18

<210> SEQ ID NO 190
<211> LENGTH: 19
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(19)
<223> OTHER INFORMATION: linked by phosphorothioate bonds
<220> FEATURE:
<221> NAME/KEY: modified_base
<222> LOCATION: (1)..(1)
<223> OTHER INFORMATION: locked nucleic acid
<220> FEATURE:
<221> NAME/KEY: modified_base
<222> LOCATION: (3)..(4)
<223> OTHER INFORMATION: locked nucleic acid
<220> FEATURE:
<221> NAME/KEY: modified_base
<222> LOCATION: (6)..(7)
<223> OTHER INFORMATION: locked nucleic acid
<220> FEATURE:
<221> NAME/KEY: modified_base
<222> LOCATION: (9)..(10)
<223> OTHER INFORMATION: locked nucleic acid
<220> FEATURE:
<221> NAME/KEY: modified_base
<222> LOCATION: (12)..(13)

<223> OTHER INFORMATION: locked nucleic acid
<220> FEATURE:
<221> NAME/KEY: modified_base
<222> LOCATION: (15)..(16)
<223> OTHER INFORMATION: locked nucleic acid
<220> FEATURE:
<221> NAME/KEY: modified_base
<222> LOCATION: (18)..(19)
<223> OTHER INFORMATION: locked nucleic acid

<400> SEQUENCE: 190
tcttcttctt cttcttctt 19

<210> SEQ ID NO 191
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides

<400> SEQUENCE: 191
cttcttcttc ttcttcttct 20

<210> SEQ ID NO 192
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides

<400> SEQUENCE: 192
tcttcttctt cttcttcttc 20

<210> SEQ ID NO 193
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(18)
<223> OTHER INFORMATION: linked by phosphorothioate bonds
<220> FEATURE:
<221> NAME/KEY: modified_base
<222> LOCATION: (1)..(18)
<223> OTHER INFORMATION: 2'-O-MOE ribonucleotides

<400> SEQUENCE: 193

```
cttcttcttc ttcttctt                                              18


<210> SEQ ID NO 194
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(1)
<223> OTHER INFORMATION: modifed with an alkyne moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 194

acagacaata aataccgagg                                            20


<210> SEQ ID NO 195
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(1)
<223> OTHER INFORMATION: modified with a cycloctyne moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 195

acagacaata aataccgagg                                            20


<210> SEQ ID NO 196
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
```

<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 196
acagacaata aataccgagg 20

<210> SEQ ID NO 197
<211> LENGTH: 16
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(16)
<223> OTHER INFORMATION: linked by phosphorothioate bonds
<220> FEATURE:
<221> NAME/KEY: modified_base
<222> LOCATION: (1)..(1)
<223> OTHER INFORMATION: modified with a cyclooctyne moiety
<220> FEATURE:
<221> NAME/KEY: modified_base
<222> LOCATION: (1)..(3)
<223> OTHER INFORMATION: S-constrained ethyl motif backboned residues
<220> FEATURE:
<221> NAME/KEY: modified_base
<222> LOCATION: (14)..(16)
<223> OTHER INFORMATION: S-constrained ethyl motif backboned residues
<220> FEATURE:
<221> NAME/KEY: modified_base
<222> LOCATION: (16)..(16)
<223> OTHER INFORMATION: modified with a primary amine moiety

<400> SEQUENCE: 197
acaataaata ccgagg 16

<210> SEQ ID NO 198
<211> LENGTH: 16
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(16)
<223> OTHER INFORMATION: linked by phosphorothioate bonds
<220> FEATURE:
<221> NAME/KEY: modified_base
<222> LOCATION: (1)..(1)
<223> OTHER INFORMATION: modified with a cyclooctyne moiety
<220> FEATURE:
<221> NAME/KEY: modified_base
<222> LOCATION: (1)..(3)
<223> OTHER INFORMATION: S-constrained ethyl motif backboned residues
<220> FEATURE:
<221> NAME/KEY: modified_base
<222> LOCATION: (14)..(16)
<223> OTHER INFORMATION: S-constrained ethyl motif backboned residues
<220> FEATURE:
<221> NAME/KEY: misc_feature
<222> LOCATION: (16)..(16)
<223> OTHER INFORMATION: conjugated to CP12 peptide

<400> SEQUENCE: 198
acaataaata ccgagg 16

```
<210> SEQ ID NO 199
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 199

cggagcggtt gtgaactggc                                                  20


<210> SEQ ID NO 200
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(1)
<223> OTHER INFORMATION: modified with an alkyne moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 200

cggagcggtg tgaactggca                                                  20


<210> SEQ ID NO 201
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
```

<223> OTHER INFORMATION: 2'-O-MOE ribonucleotides

<400> SEQUENCE: 201
acagacaata aataccgagg 20

<210> SEQ ID NO 202
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(1)
<223> OTHER INFORMATION: modified with a alkyne moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: misc_feature
<222> LOCATION: (20)..(20)
<223> OTHER INFORMATION: conjugated to a CPP12 peptide through a PEG12
moiety

<400> SEQUENCE: 202
acagacaata aataccgagg 20

<210> SEQ ID NO 203
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: misc_feature
<222> LOCATION: (1)..(1)
<223> OTHER INFORMATION: conjugated to a CPP12 peptide through a Peg12-
Lys-click moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides

<400> SEQUENCE: 203
acagacaata aataccgagg 20

<210> SEQ ID NO 204
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: misc_feature
<222> LOCATION: (1)..(1)
<223> OTHER INFORMATION: conjugated the a CPP12 peptide through a PEG12-
click moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides

<400> SEQUENCE: 204
acagacaata aataccgagg 20

<210> SEQ ID NO 205
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: misc_feature
<222> LOCATION: (1)..(1)
<223> OTHER INFORMATION: conjugated to a aCPP12-K(CPP12) peptide through
a PEG12-K-click moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 205
acagacaata aataccgagg 20

<210> SEQ ID NO 206
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: misc_feature
<222> LOCATION: (1)..(1)
<223> OTHER INFORMATION: conjugated to Ac-NLS-Lys(CPP12) peptide through
a PEG12-K-click moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides

<400> SEQUENCE: 206
acagacaata aataccgagg 20

<210> SEQ ID NO 207
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine + SMCC moiety

<400> SEQUENCE: 207
acagacaata aataccgagg 20

<210> SEQ ID NO 208
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(21)
<223> OTHER INFORMATION: 6 membered morpholine rings replace deoxyribose
rings
<220> FEATURE:
<221> NAME/KEY: misc_feature
<222> LOCATION: (1)..(21)
<223> OTHER INFORMATION: linked by non-ionic phosphorodiamidate
intersubunit linkages
<220> FEATURE:
<221> NAME/KEY: modified_base
<222> LOCATION: (21)..(21)
<223> OTHER INFORMATION: amidated

<400> SEQUENCE: 208
cagcagcagc agcagcagca g 21

<210> SEQ ID NO 209
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(21)
<223> OTHER INFORMATION: 6 membered morpholine rings replace deoxyribose
rings
<220> FEATURE:
<221> NAME/KEY: misc_feature
<222> LOCATION: (1)..(21)
<223> OTHER INFORMATION: linked by non-ionic phosphorodiamidate
intersubunit linkages
<220> FEATURE:
<221> NAME/KEY: misc_feature
<222> LOCATION: (21)..(21)
<223> OTHER INFORMATION: conjugated to CP12 peptides

<400> SEQUENCE: 209
cagcagcagc agcagcagca g 21

<210> SEQ ID NO 210
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(1)
<223> OTHER INFORMATION: modified with an alkyne moiety
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 210
acagacaata aataccgagg 20

<210> SEQ ID NO 211
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(20)
<223> OTHER INFORMATION: linked by phosphorothioate bonds
<220> FEATURE:
<221> NAME/KEY: modified_base
<222> LOCATION: (1)..(5)
<223> OTHER INFORMATION: 2'-O-MOE ribonucleotides
<220> FEATURE:
<221> NAME/KEY: modified_base
<222> LOCATION: (16)..(20)
<223> OTHER INFORMATION: 2'-O-MOE ribonucleotides
<220> FEATURE:
<221> NAME/KEY: modified_base
<222> LOCATION: (20)..(20)
<223> OTHER INFORMATION: modified with a primary amine moiety

<400> SEQUENCE: 211
cggagcggtt gtgaactggc 20

<210> SEQ ID NO 212
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 212
ccataataaa gggctcag 18

<210> SEQ ID NO 213
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 213
cagctggagt ttatcttttg 20

<210> SEQ ID NO 214
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 214
ggccaaacct cggcttacct gaaa 24

<210> SEQ ID NO 215
<211> LENGTH: 20
<212> TYPE: RNA
<213> ORGANISM: Artificial Sequence
<220> FEATURE:
<223> OTHER INFORMATION: exemplary RNA sequence

<400> SEQUENCE: 215
aagaagaaga agaagaagaa 20

<210> SEQ ID NO 216
<211> LENGTH: 24
<212> TYPE: RNA
<213> ORGANISM: Artificial Sequence
<220> FEATURE:
<223> OTHER INFORMATION: exemplary RNA sequence

<400> SEQUENCE: 216
aagaagaaga agaagaagaa gaag 24

<210> SEQ ID NO 217
<211> LENGTH: 17
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: May be conjugated to a chemical moiety
<220> FEATURE:
<221> NAME/KEY: misc_feature
<222> LOCATION: (17)..(17)
<223> OTHER INFORMATION: May be conjugated to a chemical moiety

<400> SEQUENCE: 217
gctattacct taaccca 17

<210> SEQ ID NO 218
<211> LENGTH: 24
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: May be conjugated to a chemical moiety
<220> FEATURE:
<221> NAME/KEY: misc_feature
<222> LOCATION: (24)..(24)
<223> OTHER INFORMATION: May be conjugated to a chemical moiety

<400> SEQUENCE: 218
ggccaaacct cggcttacct gaaa 24

<210> SEQ ID NO 219
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: May be conjugated to a chemical moiety
<220> FEATURE:
<221> NAME/KEY: misc_feature
<222> LOCATION: (20)..(20)
<223> OTHER INFORMATION: May be conjugated to a chemical moiety

<400> SEQUENCE: 219
gtaactgtat ttggtacttc 20

<210> SEQ ID NO 220
<211> LENGTH: 14
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: May be conjugated to a chemical moiety
<220> FEATURE:
<221> NAME/KEY: misc_feature
<222> LOCATION: (14)..(14)
<223> OTHER INFORMATION: May be conjugated to a chemical moiety

<400> SEQUENCE: 220
ctgtatttgg tact 14

<210> SEQ ID NO 221
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 221
gctattacct taacccag 18

<210> SEQ ID NO 222
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a -C6-NH2 moeity

<400> SEQUENCE: 222
gctattacct taacccag 18

<210> SEQ ID NO 223
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a cyclooctyne moeity
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 223
gctattacct taacccag 18

<210> SEQ ID NO 224
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-PEG12 moeity
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 224
gctattacct taacccag 18

<210> SEQ ID NO 225
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a CPP12-PEG12-TFP moeity

<400> SEQUENCE: 225
gctattacct taacccag 18

<210> SEQ ID NO 226
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a CPP1212-TFP moeity

<400> SEQUENCE: 226
gctattacct taacccag 18

<210> SEQ ID NO 227
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(bidentate-no linker)-PEG12 moeity
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 227
gctattacct taacccag 18

<210> SEQ ID NO 228
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(bidentate-PEG4)-PEG12 moeity

```
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: misc_feature
<222> LOCATION: (1)..(18)
<223> OTHER INFORMATION: linked by non-ionic phosphorodiamidate
      intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 228

gctattacct taacccag                                                  18


<210> SEQ ID NO 229
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(bidentate-PEG12)-PEG12
      moeity
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: misc_feature
<222> LOCATION: (1)..(18)
<223> OTHER INFORMATION: linked by non-ionic phosphorodiamidate
      intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 229

gctattacct taacccag                                                  18


<210> SEQ ID NO 230
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(tridentate-no linker)-
      PEG12 moeity
<220> FEATURE:
<221> NAME/KEY: modified_base
<222> LOCATION: (1)..(18)
<223> OTHER INFORMATION: 6 membered morpholine rings replace deoxyribose
      rings
<220> FEATURE:
<221> NAME/KEY: misc_feature
<222> LOCATION: (1)..(18)
<223> OTHER INFORMATION: linked by non-ionic phosphorodiamidate
      intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 230
```

gctattacct taacccag 18

<210> SEQ ID NO 231
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(tridentate-PEG4)-PEG12 moeity
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 231
gctattacct taacccag 18

<210> SEQ ID NO 232
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(tridentate-PEG12)-PEG12 moeity
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 232
gctattacct taacccag 18

<210> SEQ ID NO 233
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 6 membered morpholine rings replace deoxyribose rings
<220> FEATURE:
<221> NAME/KEY: misc_feature
<222> LOCATION: (1)..(18)

<223> OTHER INFORMATION: linked by non-ionic phosphorodiamidate
intersubunit linkages
<220> FEATURE:
<221> NAME/KEY: misc_feature
<222> LOCATION: (18)..(18)
<223> OTHER INFORMATION: modified with a NLS-ss-CPP12 moeity

<400> SEQUENCE: 233
gctattacct taacccag 18

<210> SEQ ID NO 234
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a Ac-NLS-Lys(CPP12)-PEG12-K(N3)
moeity
<220> FEATURE:
<221> NAME/KEY: modified_base
<222> LOCATION: (1)..(18)
<223> OTHER INFORMATION: 6 membered morpholine rings replace deoxyribose
rings
<220> FEATURE:
<221> NAME/KEY: misc_feature
<222> LOCATION: (1)..(18)
<223> OTHER INFORMATION: linked by non-ionic phosphorodiamidate
intersubunit linkages
<220> FEATURE:
<221> NAME/KEY: misc_feature
<222> LOCATION: (18)..(18)
<223> OTHER INFORMATION: modified with a Lissamine Rho moeity

<400> SEQUENCE: 234
gctattacct taacccag 18

<210> SEQ ID NO 235
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)
<223> OTHER INFORMATION: 6 membered morpholine rings replace deoxyribose
rings
<220> FEATURE:
<221> NAME/KEY: misc_feature
<222> LOCATION: (1)..(18)
<223> OTHER INFORMATION: linked by non-ionic phosphorodiamidate
intersubunit linkages
<220> FEATURE:
<221> NAME/KEY: misc_feature
<222> LOCATION: (18)..(18)
<223> OTHER INFORMATION: modified with a click-K-PEG12-Lys(CPP12)-NLS-Ac
moeity

<400> SEQUENCE: 235
gctattacct taacccag 18

<210> SEQ ID NO 236
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(18)

<223> OTHER INFORMATION: 6 membered morpholine rings replace deoxyribose rings
<220> FEATURE:
<221> NAME/KEY: misc_feature
<222> LOCATION: (1)..(18)
<223> OTHER INFORMATION: linked by non-ionic phosphorodiamidate intersubunit linkages
<220> FEATURE:
<221> NAME/KEY: misc_feature
<222> LOCATION: (18)..(18)
<223> OTHER INFORMATION: modified with a click-Lys(N3)-miniPEG-NLS-ss-PEG12-CPP12 moeity

<400> SEQUENCE: 236
gctattacct taacccag 18

<210> SEQ ID NO 237
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 237
ggccaaacct cggcttacct gaaat 25

<210> SEQ ID NO 238
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a C3-NH2 moiety

<400> SEQUENCE: 238
ggccaaacct cggcttacct gaaat 25

<210> SEQ ID NO 239
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a cyclooctyne moiety
<220> FEATURE:
<221> NAME/KEY: modified_base
<222> LOCATION: (1)..(25)

<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 239
ggccaaacct cggcttacct gaaat 25

<210> SEQ ID NO 240
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a NH2-C3 moiety
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a C3-NH2 moiety

<400> SEQUENCE: 240
ggccaaacct cggcttacct gaaat 25

<210> SEQ ID NO 241
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a C4-cyclooctyne moiety

<400> SEQUENCE: 241
ggccaaacct cggcttacct gaaat 25

<210> SEQ ID NO 242
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-PEG12-ValCitPABC moiety
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 242
ggccaaacct cggcttacct gaaat 25

<210> SEQ ID NO 243
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-PEG12-NH moiety
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a NH-PEG12-CPP12 moiety

<400> SEQUENCE: 243
ggccaaacct cggcttacct gaaat 25

<210> SEQ ID NO 244
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a C3-NH-PEG12-CPP12 moiety

<400> SEQUENCE: 244
ggccaaacct cggcttacct gaaat 25

<210> SEQ ID NO 245
<211> LENGTH: 25
<212> TYPE: DNA
<213> ORGANISM: Artificial Sequence
<220> FEATURE:
<223> OTHER INFORMATION: antisense oligonucleotide
<220> FEATURE:

```
<221> NAME/KEY: misc_feature
<222> LOCATION: (1)..(1)
<223> OTHER INFORMATION: modified with a CPP12-PEG12-Cys-ss-Cys-Lys(N3)-
      cyclooctyne moiety
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 245

ggccaaacct cggcttacct gaaat                                          25


<210> SEQ ID NO 246
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-PEG12-Lys(N3)-cyclooctyne
      moiety
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 246

ggccaaacct cggcttacct gaaat                                          25


<210> SEQ ID NO 247
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-PEG12-Prodisulfide moiety
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 247

ggccaaacct cggcttacct gaaat                                          25


<210> SEQ ID NO 248
<211> LENGTH: 25
<212> TYPE: DNA
<213> ORGANISM: Artificial Sequence
<220> FEATURE:
<223> OTHER INFORMATION: antisense oligonucleotide
```

```
<220> FEATURE:
<221> NAME/KEY: misc_feature
<222> LOCATION: (1)..(1)
<223> OTHER INFORMATION: modified with a CPP12-PEG24 moiety
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 248

ggccaaacct cggcttacct gaaat                                           25


<210> SEQ ID NO 249
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages
<220> FEATURE:
<221> NAME/KEY: misc_feature
<222> LOCATION: (25)..(25)
<223> OTHER INFORMATION: modified with a C3NH-C6-CPP12 moiety

<400> SEQUENCE: 249

ggccaaacct cggcttacct gaaat                                           25


<210> SEQ ID NO 250
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a CPP12-(bidentate-no linker)-
      PEG12 moiety
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 250

ggccaaacct cggcttacct gaaat                                           25


<210> SEQ ID NO 251
<211> LENGTH: 25
<212> TYPE: DNA
<213> ORGANISM: Artificial Sequence
<220> FEATURE:
<223> OTHER INFORMATION: antisense oligonucleotide
```

<220> FEATURE:
<221> NAME/KEY: misc_feature
<222> LOCATION: (1)..(1)
<223> OTHER INFORMATION: modified with a CPP12-(bidentate-PEG12)-PEG12 moiety
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 251
ggccaaacct cggcttacct gaaat 25

<210> SEQ ID NO 252
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a C3-NH-CPP1212 moiety

<400> SEQUENCE: 252
ggccaaacct cggcttacct gaaat 25

<210> SEQ ID NO 253
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)..(1)
<223> OTHER INFORMATION: modified with a T9-PEG12-CPP12-PEG12 moiety
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages

<400> SEQUENCE: 253
ggccaaacct cggcttacct gaaat 25

<210> SEQ ID NO 254
<211> LENGTH: 25
<212> TYPE: DNA
<213> ORGANISM: Artificial Sequence
<220> FEATURE:
<223> OTHER INFORMATION: antisense oligonucleotide -continued
<220> FEATURE:
<221> NAME/KEY: misc_feature
<222> LOCATION: (1)..(1)
<223> OTHER INFORMATION: modified with a Ac-MSP-PEG12-Lys(CPP12-PEG12)-
      K(N3) moiety
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages

<400> SEQUENCE: 254
ggccaaacct cggcttacct gaaat 25

<210> SEQ ID NO 255
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages
<220> FEATURE:
<221> NAME/KEY: misc_feature
<222> LOCATION: (25)..(25)
<223> OTHER INFORMATION: modified with a C3NH-PEG4-BCN+Lys(N3)-miniPEG-
      NLS-ss-bA-bA-CPP12 moiety

<400> SEQUENCE: 255
ggccaaacct cggcttacct gaaat 25

<210> SEQ ID NO 256
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose
      rings
<220> FEATURE:
<221> NAME/KEY: misc_feature
<222> LOCATION: (1)..(25)
<223> OTHER INFORMATION: linked by non-ionic phosphorodiamidate
      intersubunit linkages
<220> FEATURE:
<221> NAME/KEY: misc_feature
<222> LOCATION: (25)..(25)
<223> OTHER INFORMATION: modified with a C3NH-PEG4-BCN+Ac-NLS-
      Lys(CPP12)-PEG12-K(N3) moiety

<400> SEQUENCE: 256
ggccaaacct cggcttacct gaaat 25

<210> SEQ ID NO 257
<211> LENGTH: 25
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(25)
<223> OTHER INFORMATION: 6 membered morpholine rings replace deoxyribose rings
<220> FEATURE:
<221> NAME/KEY: misc_feature
<222> LOCATION: (1)..(25)
<223> OTHER INFORMATION: linked by non-ionic phosphorodiamidate intersubunit linkages
<220> FEATURE:
<221> NAME/KEY: misc_feature
<222> LOCATION: (25)..(25)
<223> OTHER INFORMATION: modified with a click-K-PEG12-Lys(CPP12)-NLS-Ac moiety

<400> SEQUENCE: 257
ggccaaacct cggcttacct gaaat 25

<210> SEQ ID NO 258
<211> LENGTH: 12
<212> TYPE: PRT
<213> ORGANISM: Artificial Sequence
<220> FEATURE:
<223> OTHER INFORMATION: T9 peptide

<400> SEQUENCE: 258

Ser Lys Thr Phe Asn Thr His Pro Gln Ser Thr Pro
1 5 10

<210> SEQ ID NO 259
<211> LENGTH: 7
<212> TYPE: PRT
<213> ORGANISM: Artificial Sequence
<220> FEATURE:
<223> OTHER INFORMATION: MSP peptide

<400> SEQUENCE: 259

Ala Ser Ser Leu Asn Ile Ala
1 5

<210> SEQ ID NO 260
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 260
ggccaaacct cggcttacct gaaat 25

<210> SEQ ID NO 261
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 261
cagaattctg ccaattgctg ag 22

<210> SEQ ID NO 262
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 262
ttcttcagct tgtgtcatcc 20

<210> SEQ ID NO 263
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 263
cccagtctac caccctatca gagc 24

<210> SEQ ID NO 264
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 264
cctgccttta aggcttcctt 20

<210> SEQ ID NO 265
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(21)
<223> OTHER INFORMATION: 6 membered morpholine rings replace deoxyribose rings
<220> FEATURE:
<221> NAME/KEY: misc_feature
<222> LOCATION: (1)..(21)
<223> OTHER INFORMATION: linked by non-ionic phosphorodiamidate intersubunit linkages
<220> FEATURE:
<221> NAME/KEY: misc_feature
<222> LOCATION: (21)..(21)
<223> OTHER INFORMATION: modified with a primary amine moiety

<400> SEQUENCE: 265
gtaactgtat ttggtacttc c 21

<210> SEQ ID NO 266
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(21)
<223> OTHER INFORMATION: 6 membered morpholine rings replace deoxyribose rings
<220> FEATURE:
<221> NAME/KEY: misc_feature
<222> LOCATION: (1)..(21)
<223> OTHER INFORMATION: linked by non-ionic phosphorodiamidate intersubunit linkages
<220> FEATURE:
<221> NAME/KEY: misc_feature
<222> LOCATION: (21)..(21)
<223> OTHER INFORMATION: modified with a PEG12CPP12 moiety

<400> SEQUENCE: 266

-continued

```
gtaactgtat ttggtacttc c                                              21


<210> SEQ ID NO 267
<211> LENGTH: 15
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(15)
<223> OTHER INFORMATION: 6 membered morpholine rings replace deoxyribose
      rings
<220> FEATURE:
<221> NAME/KEY: misc_feature
<222> LOCATION: (1)..(15)
<223> OTHER INFORMATION: linked by non-ionic phosphorodiamidate
      intersubunit linkages
<220> FEATURE:
<221> NAME/KEY: misc_feature
<222> LOCATION: (15)..(15)
<223> OTHER INFORMATION: modified with a CPP12-PEG12-K(CPP12)-PEG12-TFP
      moiety

<400> SEQUENCE: 267

ctgtatttgg tactt                                                     15


<210> SEQ ID NO 268
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(21)
<223> OTHER INFORMATION: 6 membered morpholine rings replace deoxyribose
      rings
<220> FEATURE:
<221> NAME/KEY: misc_feature
<222> LOCATION: (1)..(21)
<223> OTHER INFORMATION: linked by non-ionic phosphorodiamidate
      intersubunit linkages
<220> FEATURE:
<221> NAME/KEY: misc_feature
<222> LOCATION: (21)..(21)
<223> OTHER INFORMATION: modified with a CPP12-PEG12-K(CPP12)-PEG12-TFP
      moiety

<400> SEQUENCE: 268

gtaactgtat ttggtacttc c                                              21


<210> SEQ ID NO 269
<211> LENGTH: 21
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(21)
<223> OTHER INFORMATION: 6 membered morpholine rings replace deoxyribose
      rings
<220> FEATURE:
<221> NAME/KEY: misc_feature
<222> LOCATION: (1)..(21)
<223> OTHER INFORMATION: linked by non-ionic phosphorodiamidate
      intersubunit linkages
<220> FEATURE:
<221> NAME/KEY: misc_feature
<222> LOCATION: (21)..(21)
<223> OTHER INFORMATION: modified with a Ac-NLS-Lys(CPP12)-PEG12-K(N3)
      moiety
```

-continued

<400> SEQUENCE: 269
gtaactgtat ttggtacttc c 21

<210> SEQ ID NO 270
<211> LENGTH: 15
<212> TYPE: DNA
<213> ORGANISM: Homo sapiens

<400> SEQUENCE: 270
ctgtatttgg tactt 15

<210> SEQ ID NO 271
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 271
ctcagacatg ccgctgct 18

<210> SEQ ID NO 272
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 272
ttgagctgga tggttctctc cg 22

COMPOSITIONS FOR DELIVERY OF ANTISENSE COMPOUNDS

CROSS-REFERENCE TO RELATED APPLICATIONS

This application is a U.S. National Stage Filing under 35 U.S.C. 371 from International Application No. PCT/US2020/066459, filed on Dec. 21, 2020, and published as WO 2021/127650, which claims priority to U.S. Application No. 62/970,639, filed Dec. 19, 2019, U.S. Application No. 63/036,240, filed Jun. 8, 2020, U.S. Application No. 63/052,286, filed Jul. 15, 2020, and U.S. Application No. 63/069,984, filed Aug. 25, 2020, each of which is incorporated by reference herein in its entirety.

INCORPORATION BY REFERENCE OF SEQUENCE LISTING

This application contains a Sequence Listing which has been submitted electronically in ST25 format and hereby incorporated by reference in its entirety. Said ST25 file, created on Sep. 20, 2025, is named 5892003us1.txt and is 104,334 bytes in size.

BACKGROUND

Therapeutic antisense compounds include e.g., antisense oligonucleotides, small interfering RNA (siRNA), microRNA (miRNA), ribozymes, immune stimulating nucleic acids, antagomir, antimir, microRNA mimic, supermir, Ul adaptors, CRISPR machinery and aptamers. These oligonucleotide containing compounds act via a variety of mechanisms. The therapeutic applications of antisense compounds are extremely broad, since these compounds can be synthesized with any nucleotide sequence directed against virtually any target gene or genomic segments.

A major problem for the use of antisense compounds in therapeutics is their limited ability to gain access to the intracellular compartment when administered systemically. Intracellular delivery of antisense compounds can be facilitated by use of carrier systems such as polymers, cationic liposomes or by chemical modification of the construct, for example by the covalent attachment of cholesterol molecules. However, intracellular delivery efficiency is low. Improved delivery systems are still required to increase the potency of these antisense compounds.

There is an unmet need for effective compositions to deliver antisense compounds to intracellular compartments so as to treat diseases caused by, e.g., aberrant gene transcription, splicing and/or translation.

SUMMARY

Compositions for delivering nucleic acids are described herein.

In some embodiments, provided herein is a compound comprising: (a) a cyclic cell penetrating peptide (cCPP) sequence and (b) an antisense compound (AC) that is complementary to a target sequence in a pre-mRNA sequence.

In some embodiments, provided herein is a compound comprising a cCPP and an AC that is complementary to a target in a pre-mRNA sequence, wherein the AC comprises at least one modified nucleotide or nucleic acid selected from a phosphorothioate (PS) nucleotide, a phosphorodiamidate morpholino nucleotide, a locked nucleic acid (LNA), a peptide nucleic acid (PNA), a nucleotide comprising a 2'-O-methyl (2'-OMe) modified backbone, a 2'O-methoxy-ethyl (2'-MOE) nucleotide, a 2',4' constrained ethyl (cEt) nucleotide, and a 2'-deoxy-2'-fluoro-beta-D-arabinonucleic acid (2'F-ANA), and wherein hybridization of the AC with the target sequence reduces or prevents splicing, inhibits or regulates translation, mediates degradation, or blocks expansions of nucleotide repeats.

In some embodiments, provided herein is a compound comprising a cCPP and an AC that is complementary to a target in a pre-mRNA sequence, wherein the AC comprises small interfering RNA (siRNA), microRNA (miRNA), ribozymes, immune stimulating nucleic acids, antisense, antagomir, antimir, microRNA mimic, supermir, Ul adaptor, aptamer, or a CRISPR gene-editing machinery.

In some embodiments, provided herein is a compound comprising a cCPP and an AC that is complementary to a target in a pre-mRNA sequence, wherein the cCPP is conjugated to the 5' end or the 3' end of the AC.

In some embodiments, provided herein is a compound comprising a cCPP and an AC that is complementary to a target in a pre-mRNA sequence, further comprising a linker (L), which conjugates the cCPP to the AC.

In some embodiments, provided herein is a compound comprising a cCPP and an AC that is complementary to a target in a pre-mRNA sequence further comprising L, wherein the L is covalently bound to the side chain of an amino acid on the CPP.

In some embodiments, provided herein is a compound having a structure according to Formula I-A or Formula I-B:

cCPP—L—AC or (I-A)

AC—L—cCPP, (I-B)

wherein L of Formula I-A is covalently bound to the side chain of an amino acid on the CPP and to the 5' end of the AC, and L of Formula I-B is covalently bound to the side chain of an amino acid on the CPP and the 3' end of the AC.

In some embodiments, provided herein is a compound comprising a cCPP and an AC that is complementary to a target in a pre-mRNA sequence further comprising L, wherein L comprises one or more D or L amino acids, each of which is optionally substituted; alkylene, alkenylene, alkynylene, carbocyclyl, or heterocyclyl, each of which is optionally substituted; or —($R^1$—X—$R^2$)z-, wherein each of $R^1$ and $R^2$, at each instance, are independently selected from alkylene, alkenylene, alkynylene, carbocyclyl, and heterocyclyl, each X is independently $NR^3$, —$NR^3$C(O)—, S, and O, wherein $R^3$ is independently selected from H, alkyl, alkenyl, alkynyl, carbocyclyl, and heterocyclyl, each of which is optionally substituted, and z is an integer from 1 to 20; or combinations thereof.

In some embodiments, provided herein is a compound comprising a cCPP and an AC that is complementary to a target in a pre-mRNA sequence further comprising L, comprising one or more D or L amino acids; —($R^1$—X—$R^2$)z-, wherein each of $R^1$ and $R^2$, at each instance, are independently alkylene, each X is independently $NR^3$, —$NR^3$C(O)—, S, and O, wherein $R^3$ is independently selected from H and alkyl, and z is an integer from 1 to 20; or combinations thereof.

In some embodiments, provided herein is a compound comprising a cCPP and an AC that is complementary to a target in a pre-mRNA sequence further comprising L, wherein the linker is conjugated to the AC through a bonding group (M).

In some embodiments, provided herein is a compound comprising a cCPP and an AC that is complementary to a target in a pre-mRNA sequence further comprising L, wherein the linker is conjugated to the AC through a bonding group (M), wherein M is selected from the group consisting of:

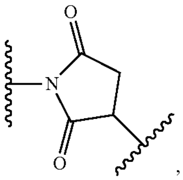, 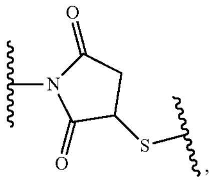, 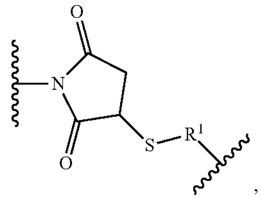, 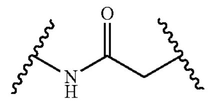, 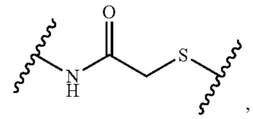,

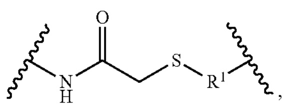, 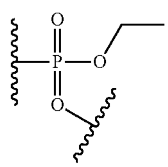, 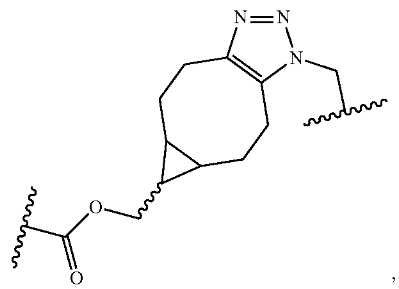,

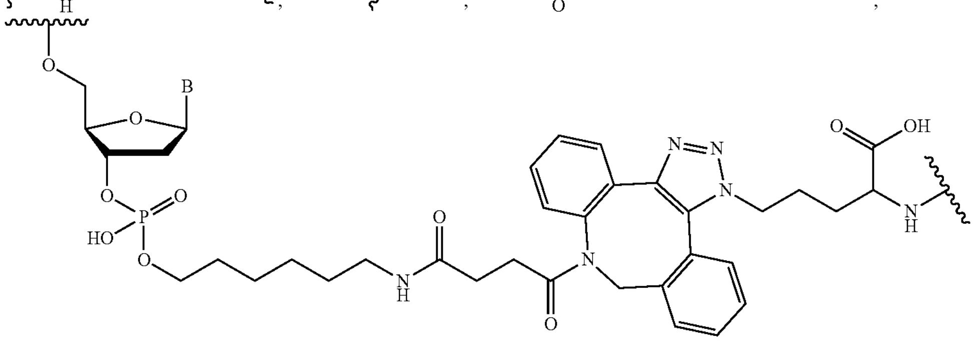, and

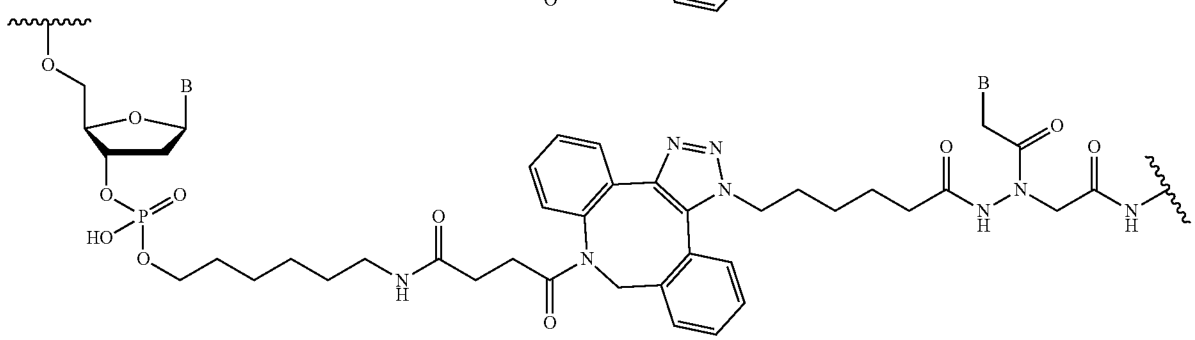.

wherein: $R^1$ is alkylene, cycloalkyl, or

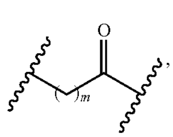, wherein m is 0 to 10 wherein each R is independently an alkyl, alkenyl, alkynyl, carbocyclyl, or heterocyclyl.

In some embodiments, provided herein is a compound comprising a cCPP and an AC that is complementary to a target in a pre-mRNA sequence further comprising L, wherein the linker is conjugated to the AC through a bonding group (M), wherein M is

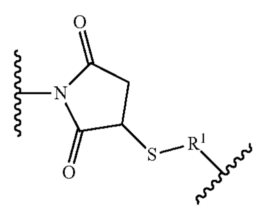.

In some embodiments, provided herein is a compound comprising a cCPP and an AC that is complementary to a target in a pre-mRNA sequence further comprising L, wherein the linker is conjugated to the AC through a bonding group (M), wherein M is selected from the group consisting of:

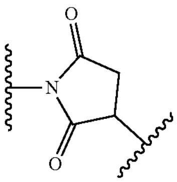, 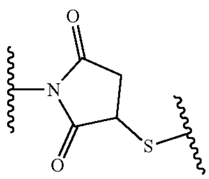, 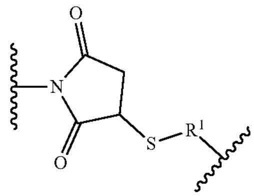, 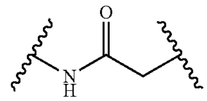, 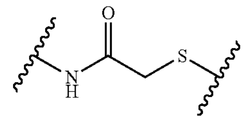,

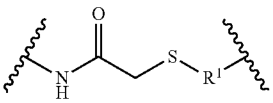, 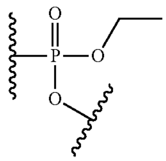, 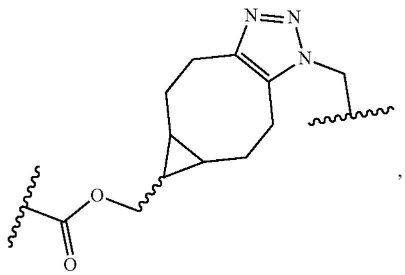,

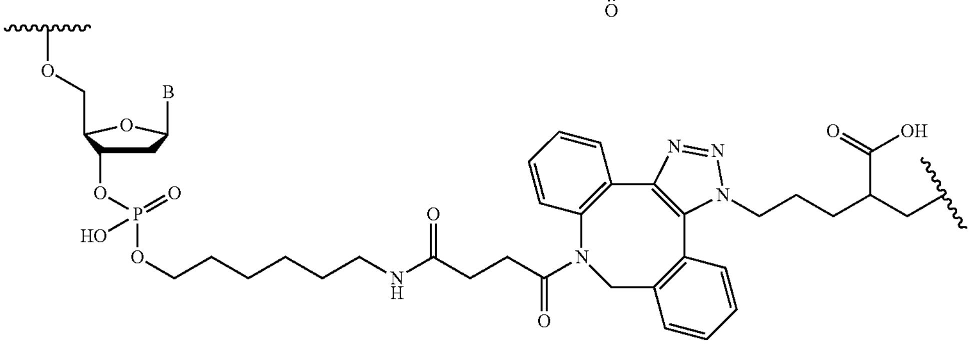, and

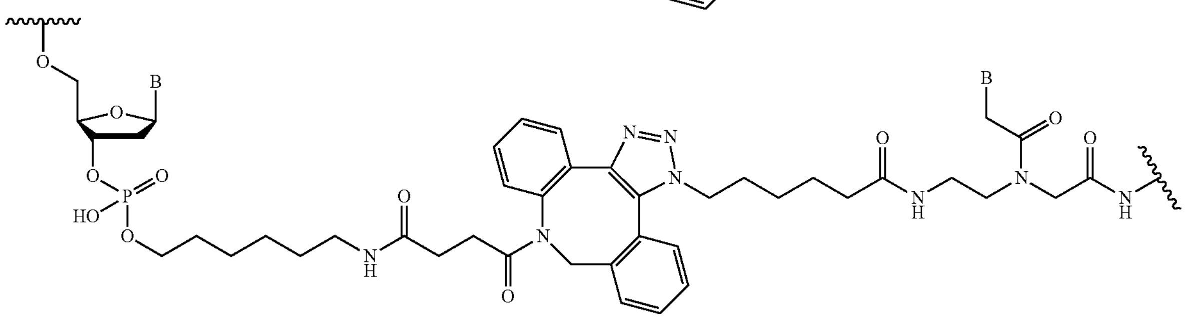;

wherein: $R^1$ is alkylene, cycloalkyl, or

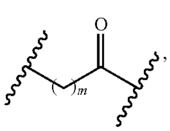, wherein m is 0 to 10 wherein each R is independently an alkyl, alkenyl, alkynyl, carbocyclyl, or heterocyclyl, wherein $R^1$ is

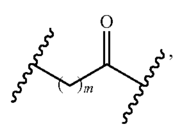, and m is 2.

In some embodiments, provided herein is a compound comprising a cCPP and an AC that is complementary to a target in a pre-mRNA sequence further comprising L, wherein L has the following structure:

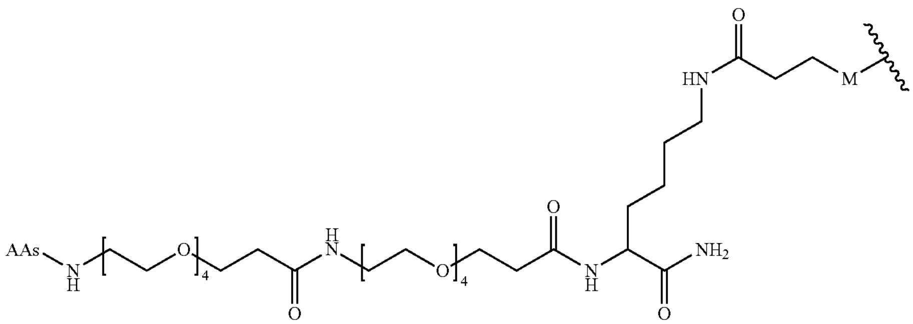
wherein $AA_s$ is a side chain or terminus of an amino acid on the CPP.
In some embodiments, provided herein is a compound having a following structure:
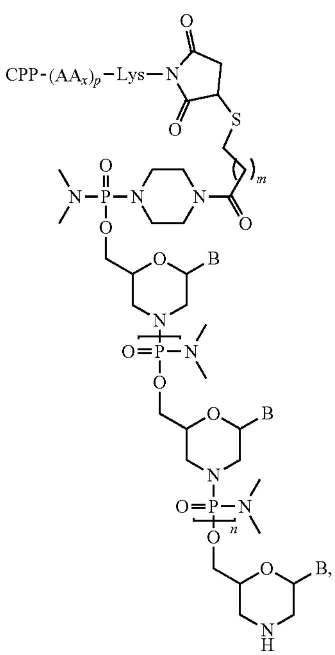
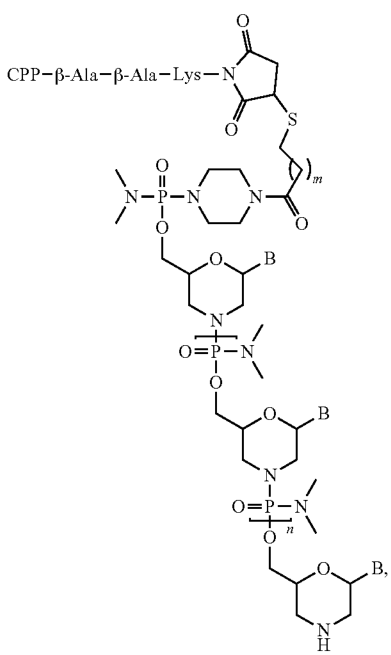
or -continued

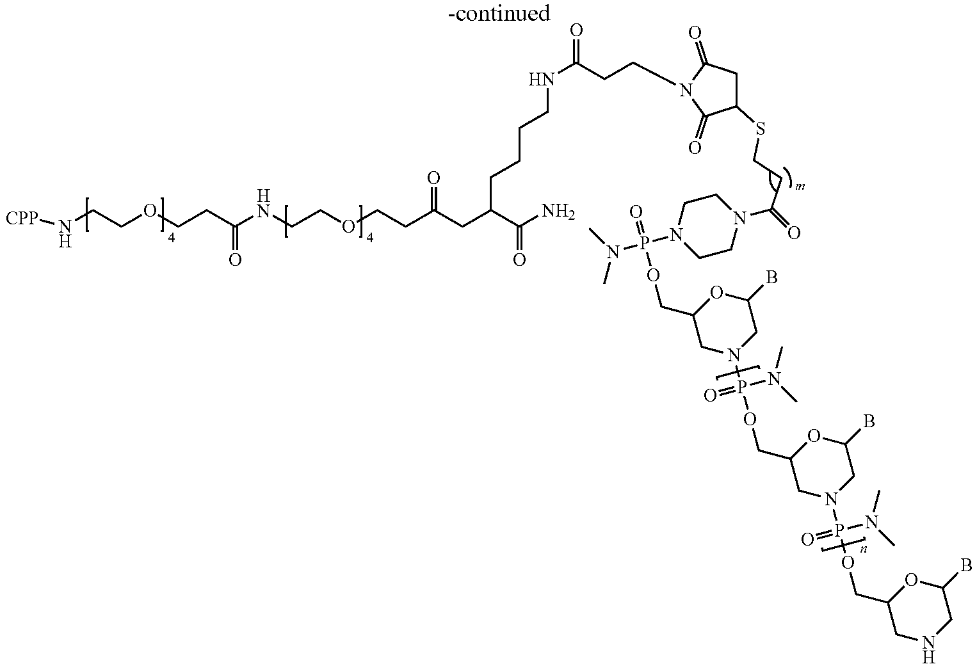

wherein each B is independently a nucleobase; each $AA_x$ is independently an amino acid; m is 1 to 10; and n is an integer from 1 to 50.

In some embodiments, provided herein is a compound comprising a cCPP and an AC that is complementary to a target in a pre-mRNA sequence, wherein the cCPP has a sequence comprising Formula III:

III

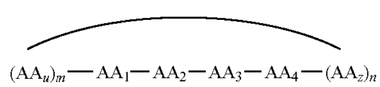

wherein: each of $AA_1$, $AA_2$, $AA_3$, and $AA_4$, are independently selected from a D or L amino acid, each of $AA_u$ and $AA_z$, at each instance and when present, are independently selected from a D or L amino acid, and m and n are independently selected from a number from 0 to 6; and wherein: at least two amino acids are independently arginine, and at least two amino acids are independently a hydrophobic amino acid.

In some embodiments, provided herein is a compound comprising a cCPP and an AC that is complementary to a target in a pre-mRNA sequence, wherein the cCPP has a sequence comprising any one of Formula IV-A-D:

IV-A

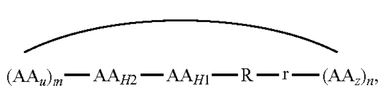

IV-B

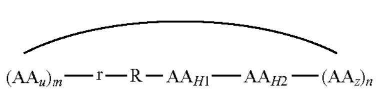

IV-C

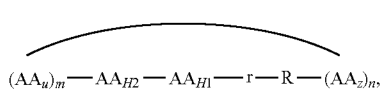

and

-continued

IV-D

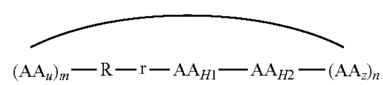

wherein: each of $AA_{H1}$ and $AA_{H2}$ are independently a D or L hydrophobic amino acid;

at each instance and when present, each of $AA_U$ and $AA_Z$ are independently a D or L amino acid; and m and n are independently selected from a number from 0 to 6.

In some embodiments, provided herein is a compound comprising a cCPP and an AC that is complementary to a target in a pre-mRNA sequence further comprising L, wherein the linker is conjugated to the AC through a bonding group (M), wherein M and covalently bound to the 5' end of the AC or the 3' end of the AC.

In some embodiments, provided herein is a compound comprising a cCPP and an AC that is complementary to a target in a pre-mRNA sequence, wherein the AC is complementary to a target sequence comprising an intron, comprising by an exon, or bridging an intron/exon junction.

In some embodiments, provided herein is a compound comprising a cCPP and an AC that is complementary to a target in a pre-mRNA sequence, wherein the AC is complementary to a target sequence comprising an intronic silencer sequence (ISS) or terminal stem loop (TSL) sequence of the target pre-mRNA.

In some embodiments, provided herein is a compound comprising a cCPP and an AC that is complementary to a target in a pre-mRNA sequence, wherein the AC is complementary to part or all of a splice site.

In some embodiments, provided herein is a compound comprising a cCPP and an AC that is complementary to a target in a pre-mRNA sequence, wherein the AC is complementary to part or all of a splice site, wherein the splice site is a splice donor site, a splice acceptor site, a cryptic splice site, or a mutation-induced aberrant splice site.

In some embodiments, provided herein is a compound comprising a cCPP and an AC that is complementary to a target in a pre-mRNA sequence, wherein hybridization of the AC with its target sequence results in exon skipping or exon inclusion.

In some embodiments, provided herein is a compound comprising a cCPP and an AC that is complementary to a target in a pre-mRNA sequence, wherein the AC is complementary to at least a portion of expended nucleotide repeats in target mRNA.

In some embodiments, provided herein is a compound comprising a cCPP and an AC that is complementary to a target in a pre-mRNA sequence, wherein hybridization of the AC with the target sequence blocks transcription of at least a portion of the nucleotide repeats.

In some embodiments, provided herein is a compound comprising a cCPP and an AC that is complementary to a target in a pre-mRNA sequence, wherein the AC is 5-50 nucleotides in length.

In some embodiments, provided herein is a compound comprising a cCPP and an AC that is complementary to a target in a pre-mRNA sequence, wherein the AC comprises one or more modified nucleotides or nucleic acids that affect one or more of nuclease resistance, pharmacokinetics, and affinity.

In some embodiments, provided herein is a compound comprising a cCPP and an AC that is complementary to a target in a pre-mRNA sequence, wherein the AC comprises one or more phosphorodiamidate morpholino nucleosides, 2-O-methylated nucleosides, and/or locked nucleic acids (LNAs).

In some embodiments, provided herein is a compound comprising a cCPP and an AC that is complementary to a target in a pre-mRNA sequence, wherein the target gene is involved in the pathogenesis of a disease.

In some embodiments, provided herein is a compound comprising a cCPP and an AC that is complementary to a target in a pre-mRNA sequence, wherein the target gene is involved in the pathogenesis of a genetic disease.

In some embodiments, provided herein is a compound comprising a cCPP and an AC that is complementary to a target in a pre-mRNA sequence, wherein the target gene is involved in the pathogenesis of a cancer, an autoimmune disease, an inflammatory disease, or an infection.

In some embodiments, provided herein is a compound comprising a cCPP and an AC that is complementary to a target in a pre-mRNA sequence, wherein the target sequence in the pre-mRNA comprises a mutation-induced aberrant splice site.

In some embodiments, provided herein is a compound comprising a cCPP and an AC that is complementary to a target in a pre-mRNA sequence, wherein hybridization of the AC with the target sequence suppresses aberrant splicing of the target pre-mRNA.

In some embodiments, provided herein is a compound comprising a cCPP and an AC that is complementary to a target in a pre-mRNA sequence, wherein hybridization of the AC with the target sequence induces expression of one or more protein isomers encoded by the target gene.

In some embodiments, provided herein is a compound comprising a cCPP and an AC that is complementary to a target in a pre-mRNA sequence, wherein hybridization of the AC with the target sequence suppresses expression of one or more protein isomers encoded by the target gene.

In some embodiments, provided herein is a compound comprising a cCPP and an AC that is complementary to a target in a pre-mRNA sequence, wherein the target protein produced by splicing and translation of the target pre-mRNA is not functional or is less functional than a wild type target protein in the absence of AC hybridization to the target sequence.

In some embodiments, provided herein is a compound comprising a cCPP and an AC that is complementary to a target in a pre-mRNA sequence, wherein hybridization of the AC with the target sequence suppresses expression of the target protein that would have been expressed from the target pre-mRNA in the absence of AC hybridization.

In some embodiments, provided herein is a compound comprising a cCPP and an AC that is complementary to a target in a pre-mRNA sequence, wherein hybridization of the AC with the target sequence results in expression of a re-spliced target protein having one or more improved functions or characteristics compared to the expressed target protein in the absence of AC hybridization.

In some embodiments, provided herein is a compound comprising a cCPP and an AC that is complementary to a target in a pre-mRNA sequence, wherein the one or more improved characteristics comprise function and/or activity.

In some embodiments, provided herein is a compound comprising a cCPP and an AC that is complementary to a target in a pre-mRNA sequence, wherein the re-spliced target protein comprises an active fragment of a wild type target protein.

In some embodiments, provided herein is a compound comprising a cCPP and an AC that is complementary to a target in a pre-mRNA sequence, wherein hybridization of the AC with the target sequence results in expression of a re-spliced target protein that ameliorates or rescues aspects of a disease phenotype associated with the target gene.

In some embodiments, provided herein is a compound comprising a cCPP and an AC that is complementary to a target in a pre-mRNA sequence, further comprising a nuclear localization signal (NLS).

In some embodiments, provided herein is a compound comprising a cCPP and an AC that is complementary to a target in a pre-mRNA sequence further comprising an NLS, wherein the C-terminus of the NLS sequence is conjugated to the CPP.

In some embodiments, provided herein is a pharmaceutical composition comprising a compound comprising a cCPP and an AC that is complementary to a target in a pre-mRNA sequence.

In some embodiments, provided herein is a compound comprising a cCPP and an AC that is complementary to a target in a pre-mRNA sequence.

In some embodiments, provided herein is a method of modulating the splicing of a target pre-mRNA in a subject in need thereof, comprising administering a compound comprising a cCPP and an AC that is complementary to a target in a pre-mRNA sequence.

In some embodiments, provided herein is a method of modulating the splicing of a target pre-mRNA in a subject in need thereof, comprising administering a compound comprising a cCPP and an AC that is complementary to a target in a pre-mRNA sequence, wherein the compound suppresses expression of the target protein translated from the target pre-mRNA in the absence of the compound.

In some embodiments, provided herein is a method of modulating the splicing of a target pre-mRNA in a subject in need thereof, comprising administering a compound comprising a cCPP and an AC that is complementary to a target in a pre-mRNA sequence, wherein administration of the compound results in the expression of a re-spliced target protein.

In some embodiments, provided herein is a method of modulating the splicing of a target pre-mRNA in a subject in need thereof, comprising administering a compound comprising a cCPP and an AC that is complementary to a target in a pre-mRNA sequence, wherein administration of the compound results in the expression of a re-spliced target protein, wherein the re-spliced target protein has one or more improved characteristics compared to the target protein.

In some embodiments, provided herein is a method of modulating the splicing of a target pre-mRNA in a subject in need thereof, comprising administering a compound comprising a cCPP and an AC that is complementary to a target in a pre-mRNA sequence, wherein administration of the compound results in the expression of a re-spliced target protein, wherein the re-spliced target protein has one or more improved characteristics compared to the target protein, wherein the one or more improved characteristics are selected from the list consisting of: function, activity, binding, and enzymatic activity.

In some embodiments, provided herein is a method of modulating the splicing of a target pre-mRNA in a subject in need thereof, comprising administering a compound comprising a cCPP and an AC that is complementary to a target in a pre-mRNA sequence, wherein administration of the compound results in the increased expression of one or more protein isomers encoded by the target gene.

In some embodiments, provided herein is a method of modulating the splicing of a target pre-mRNA in a subject in need thereof, comprising administering a compound comprising a cCPP and an AC that is complementary to a target in a pre-mRNA sequence, wherein administration of the compound results in the decreased expression of one or more protein isomers encoded by the target gene.

In some embodiments, provided herein is a method of modulating the splicing of a target pre-mRNA in a subject in need thereof, comprising administering a compound comprising a cCPP and an AC that is complementary to a target in a pre-mRNA sequence, wherein administration of the compound results in increased expression of a wild type target protein or an active fragment of a wild type target protein.

In some embodiments, provided herein is a method of modulating the splicing of a target pre-mRNA in a subject in need thereof, comprising administering a compound comprising a cCPP and an AC that is complementary to a target in a pre-mRNA sequence, wherein the compound modulates splicing of exon 2, 8, 11, 17, 19, 23, 29, 40, 41, 42, 43, 44, 45, 46, 48, 49, 50, 51, 52, 53, 55, and 59 of DMD.

In some embodiments, provided herein is a method of modulating the splicing of a target pre-mRNA in a subject in need thereof, comprising administering a compound comprising a cCPP and an AC that is complementary to a target in a pre-mRNA sequence, wherein the compound modulates splicing of exon 2, 8, 11, 23 43, 44, 45, 50, 51, 53, and 55 of DMD.

In some embodiments, provided herein is a method of modulating the splicing of a target pre-mRNA in a subject in need thereof, comprising administering a compound comprising a cCPP and an AC that is complementary to a target in a pre-mRNA sequence, wherein the compound modulates splicing of exon 2, 23, 44, or 51 of DMD.

In some embodiments, provided herein is a method of modulating the splicing of a target pre-mRNA in a subject in need thereof, comprising administering a compound comprising a cCPP and an AC that is complementary to a target in a pre-mRNA sequence, wherein the AC is selected from Table B1-B3.

In some embodiments, provided herein is a method of modulating the splicing of a target pre-mRNA in a subject in need thereof comprising administering a compound comprising a cCPP and an AC that is complementary to a target in a pre-mRNA sequence, wherein the compound modulates splicing of exon 1, exon 2, exon 3, exon 4, exon 5, exon 6, exon 7a, and exon 7b of CD33.

In some embodiments, provided herein is a method of modulating the splicing of a target pre-mRNA in a subject in need thereof comprising administering a compound comprising a cCPP and an AC that is complementary to a target in a pre-mRNA sequence, wherein the AC is selected from Table C.

In some embodiments, provided herein is a method of treating a genetic disease in a subject in need thereof, comprising administering a compound comprising a cCPP and an AC that is complementary to a target in a pre-mRNA sequence.

In some embodiments, provided herein is a method of treating a genetic disease in a subject in need thereof, comprising administering a compound comprising a cCPP and an AC that is complementary to a target in a pre-mRNA sequence, wherein administration of the compound modulates splicing or expression of a target gene, degrades mRNA, stabilizes mRNA, or sterically blocks mRNA.

In some embodiments, provided herein is a method of treating a genetic disease in a subject in need thereof, comprising administering a compound comprising a cCPP and an AC that is complementary to a target in a pre-mRNA sequence, wherein administration of the compound modulates splicing of the target pre-mRNA.

In some embodiments, provided herein is a method of treating a genetic disease in a subject in need thereof, comprising administering a compound comprising a cCPP and an AC that is complementary to a target in a pre-mRNA sequence, wherein administration of the compound results in an increase in the expression of a wild type target protein or an active fragment thereof.

In some embodiments, provided herein is a method of treating a genetic disease in a subject in need thereof, comprising administering a compound comprising a cCPP and an AC that is complementary to a target in a pre-mRNA sequence, wherein administration of the compound results in expression of a re-spliced target protein that is more highly expressed, functional, and/or active than the target protein expressed in the absence of the compound.

In some embodiments, provided herein is a method of treating a genetic disease in a subject in need thereof, comprising administering a compound comprising a cCPP and an AC that is complementary to a target in a pre-mRNA sequence, wherein administration of the compound results in expression of a re-spliced target protein that is more highly expressed, functional, and/or active than the target protein expressed in the absence of the compound, wherein the re-spliced target protein comprises an active fragment of a wild type target protein.

In some embodiments, provided herein is a method of treating a genetic disease in a subject in need thereof, comprising administering a compound comprising a cCPP and an AC that is complementary to a target in a pre-mRNA sequence, wherein the genetic disease is a central nervous system disorder, a neuromuscular disorder, or a musculoskeletal disorder.

In some embodiments, provided herein is a method of treating a genetic disease in a subject in need thereof, comprising administering a compound comprising a cCPP and an AC that is complementary to a target in a pre-mRNA sequence, wherein the genetic disease is Duchenne muscular dystrophy, R thalassemia, dystrophin Kobe, osteogenesis imperfect, cystic fibrosis, Merosin-deficient congenital muscular dystrophy type 1A, or spinal muscular atrophy.

In some embodiments, provided herein is a method of treating a genetic disease in a subject in need thereof, comprising administering a compound comprising a cCPP and an AC that is complementary to a target in a pre-mRNA sequence, wherein the disease is Duchenne muscular dystrophy.

In some embodiments, provided herein is a method of treating a genetic disease in a subject in need thereof, comprising administering a compound comprising a cCPP and an AC that is complementary to a target in a pre-mRNA sequence, wherein the AC is selected from Table B1-B3.

In some embodiments, provided herein is a method of treating a genetic disease in a subject in need thereof, comprising administering a compound comprising a cCPP and an AC that is complementary to a target in a pre-mRNA sequence, wherein the AC has a nucleic acid sequence of 5'-GCTATTACCTTAACCCA-3' (SEQ ID NO: 152).

In some embodiments, provided herein is a method of treating a genetic disease in a subject in need thereof, comprising administering a compound comprising a cCPP and an AC that is complementary to a target in a pre-mRNA sequence, wherein the AC is a phosphorodiamidate morpholino oligomer (PMO).

In some embodiments, provided herein is a method of treating a genetic disease in a subject in need thereof, comprising administering a compound comprising a cCPP and an AC that is complementary to a target in a pre-mRNA sequence, wherein the AC has a nucleic acid sequence of 5'-GTAACTGTATTTGGTACTTCC-3' (SEQ ID NO: 153).

In some embodiments, provided herein is a method of treating a genetic disease in a subject in need thereof, comprising administering a compound comprising a cCPP and an AC that is complementary to a target in a pre-mRNA sequence, wherein the AC is a phosphorodiamidate morpholino oligomer (PMO).

In some embodiments, provided herein is a method of treating a genetic disease in a subject in need thereof, comprising administering a compound comprising a cCPP and an AC that is complementary to a target in a pre-mRNA sequence, resulting in a splicing increase in the expression of a wild type target protein or an active fragment thereof in muscle tissue, diaphragm tissue, quadriceps, and/or heart tissue.

In some embodiments, provided herein is a method of treating a genetic disease in a subject in need thereof, comprising administering a compound comprising a cCPP and an AC that is complementary to a target in a pre-mRNA sequence, resulting in a splicing increase in the expression of a wild type target protein or an active fragment thereof in heat tissue.

In some embodiments, provided herein is a method of treating a genetic disease in a subject in need thereof, comprising administering a compound comprising a cCPP and an AC that is complementary to a target in a pre-mRNA sequence, wherein administration of the compound blocks transcription of at least a portion of the trinucleotide repeats.

In some embodiments, provided herein is a method of treating a genetic disease in a subject in need thereof, comprising administering a compound comprising a cCPP and an AC that is complementary to a target in a pre-mRNA sequence, wherein administration of the compound reduces the length and/or number of expanded nucleotide repeats an expressed protein.

In some embodiments, provided herein is a method of treating a genetic disease in a subject in need thereof, comprising administering a compound comprising a cCPP and an AC that is complementary to a target in a pre-mRNA sequence, wherein the genetic disease is Fragile X, Friedreich's ataxia (FRDA), Huntington's Disease (HD), Myotonic dystrophy type 1 (DM1), Myotonic dystrophy type 2 (DM2), Spinal and bulbar muscular atrophy (SBMA), Spinal cerebellar ataxia type 1 (SCA1), Spinal cerebellar ataxia type 2 (SCA2), or Spinal cerebellar ataxia type 3 (SCA3).

In some embodiments, provided herein is a method of treating a genetic disease in a subject in need thereof, comprising administering a compound comprising a cCPP and an AC that is complementary to a target in a pre-mRNA sequence, wherein the genetic disease is Fragile X, Friedreich's ataxia (FRDA), Huntington's Disease (HD), Myotonic dystrophy type 1 (DM1).

In some embodiments, provided herein is a method of treating a genetic disease in a subject in need thereof, comprising administering a compound comprising a cCPP and an AC that is complementary to a target in a pre-mRNA sequence, wherein the genetic disease is FRDA, and the AC is selected from Table 8.

In some embodiments, provided herein is a method of treating a genetic disease in a subject in need thereof, comprising administering a compound comprising a cCPP and an AC that is complementary to a target in a pre-mRNA sequence, wherein the disease is DM1, and the AC is selected from Table 7.

In some embodiments, provided herein is a method of treating a genetic disease in a subject in need thereof, comprising administering a compound comprising a cCPP and an AC that is complementary to a target in a pre-mRNA sequence, wherein the AC comprises a gapmer, which hybridizes with the target RNA and catalyzes degradation of the target.

In some embodiments, provided herein is a method of treating a genetic disease in a subject in need thereof, comprising administering a compound comprising a cCPP and an AC that is complementary to a target in a pre-mRNA sequence, wherein the AC comprises a gapmer, which hybridizes with the target RNA and catalyzes degradation of the target, wherein the AC is selected from Table 8.

In some embodiments, provided herein is a method of treating Fragile X, Friedreich's ataxia (FRDA), Huntington's Disease (HD), Myotonic dystrophy type 1 (DM1), Myotonic dystrophy type 2 (DM2), Spinal and bulbar muscular atrophy (SBMA), Spinal cerebellar ataxia type 1 (SCA1), Spinal cerebellar ataxia type 2 (SCA2), or Spinal cerebellar ataxia type 3 (SCA3), comprising administering a compound comprising a cCPP and an AC that is complementary to a target in a pre-mRNA sequence, wherein the AC comprises a sequence that is complementary to a trinucleotide repeat in a target mRNA sequence, and the AC hybridizes with the target mRNA sequence to blocks transcription of the trinucleotide repeat.

In some embodiments, provided herein is a method of treating a genetic disease in a subject in need thereof, comprising administering a compound comprising a cCPP and an AC that is complementary to a target in a pre-mRNA sequence, wherein the genetic disease is FRDA, and the AC is selected from Table 8.

In some embodiments, provided herein is a method of treating a genetic disease in a subject in need thereof, comprising administering a compound comprising a cCPP and an AC that is complementary to a target in a pre-mRNA sequence, wherein the disease is DM1, and the AC is selected from Table 7.

In some embodiments, provided herein is a method of blocking or degrading nucleotide repeat expansions in RNA comprising administering a compound comprising a cCPP and an AC that is complementary to a target in a pre-mRNA sequence, wherein the AC comprises an antisense oligonucleotide sequence that is complementary to at least a portion of the nucleotide repeats in the target RNA.

In some embodiments, provided herein is a method of blocking or degrading nucleotide repeat expansions in RNA comprising administering a compound comprising a cCPP and an AC that is complementary to a target in a pre-mRNA sequence, wherein the administration prevents or reduces translation of at least a portion of the nucleotide repeats.

In some embodiments, provided herein is a method of blocking or degrading nucleotide repeat expansions in RNA comprising administering a compound comprising a cCPP and an AC that is complementary to a target in a pre-mRNA sequence, wherein the nucleotide repeats expansions are trinucleotide repeat expansions, pentanucleotide repeat expansions, or hexanucleotide repeat expansions.

In some embodiments, provided herein is a method of blocking or degrading nucleotide repeat expansions in RNA comprising administering a compound comprising a cCPP and an AC that is complementary to a target in a pre-mRNA sequence, wherein the nucleotide repeat expansions comprises expansions of CAG repeats, CGG repeats, GCC repeats, GAA repeats, or CUG repeats.

In some embodiments, provided herein is a method of blocking or degrading nucleotide repeat expansions in RNA comprising administering a compound comprising a cCPP and an AC that is complementary to a target in a pre-mRNA sequence, wherein the nucleotide repeat expansions are located in the FMRI gene, HTT gene, ATP7B gene, DMPK gene, or FX gene.

In some embodiments, provided herein is a method of blocking or degrading nucleotide repeat expansions in RNA comprising administering a compound comprising a cCPP and an AC that is complementary to a target in a pre-mRNA sequence, wherein the nucleotide repeat expansions are located in the DMPK gene or FX gene.

In some embodiments, provided herein is a method of blocking or degrading nucleotide repeat expansions in RNA comprising administering a compound comprising a cCPP and an AC that is complementary to a target in a pre-mRNA sequence, wherein the gene is FXN, and the AC is selected from Table 8.

In some embodiments, provided herein is a method of blocking or degrading nucleotide repeat expansions in RNA comprising administering a compound comprising a cCPP and an AC that is complementary to a target in a pre-mRNA sequence, wherein the gene is DMPK, and the AC is selected from Table 9.

In some embodiments, provided herein is a compound comprising a cCPP is selected from Table 4 or a method comprising administering a cCPP selected from Table 4.

In some embodiments, provided herein is a compound and/or method comprising cCPP12.

BRIEF DESCRIPTION OF THE DRAWINGS

FIG. 7A shows the amide bond formation between peptides with carboxylic acid group or with TFP activated ester and primary amine residues at the 5' end of AC. FIG. 7B shows the conjugation of secondary amine or primary amine modified AC at 3' and peptide-TFP ester through amide bond formation. FIG. 7C shows the conjugation of peptide-azide to the 5' cyclooctyne modified AC via cupper-free azide-alkyne cycloaddition. FIG. 7D demonstrates another exemplary conjugation between 3' modified cyclooctyne ACs or 3' modified azide ACs and CPP containing linker-azide or linker-alkyne/cyclooctyne moiety, via a cupper-free azide-alkyne cycloaddition or cupper catalyzed azide-alkyne cycloaddition, respectively (click reaction).

FIG. 9 shows a schematic of preparation of CPP12-$PMO^{DMD}$ (also called “PMO-DMD”) and CPP12-$PMO^{DMD}$ (also called “EEV12-$PMO^{DMD}$”).

FIG. 22C and FIG. 22D illustrate the percentage of splicing correction of DMD in the heart and diaphragm on electrophoresis gels. Alpha-actinin is included as a positive control.

of HeLa-654 cells treated for 24 hr with medium, 2 μM of PMO-LSR (ENTR-0059, Table 1) with transfection reagent, endoporter (6 μL/mL) or CPP-NLS-PMO-LSR (ENTR-0168, Table 1), as described in Example 1.

Figure 39:
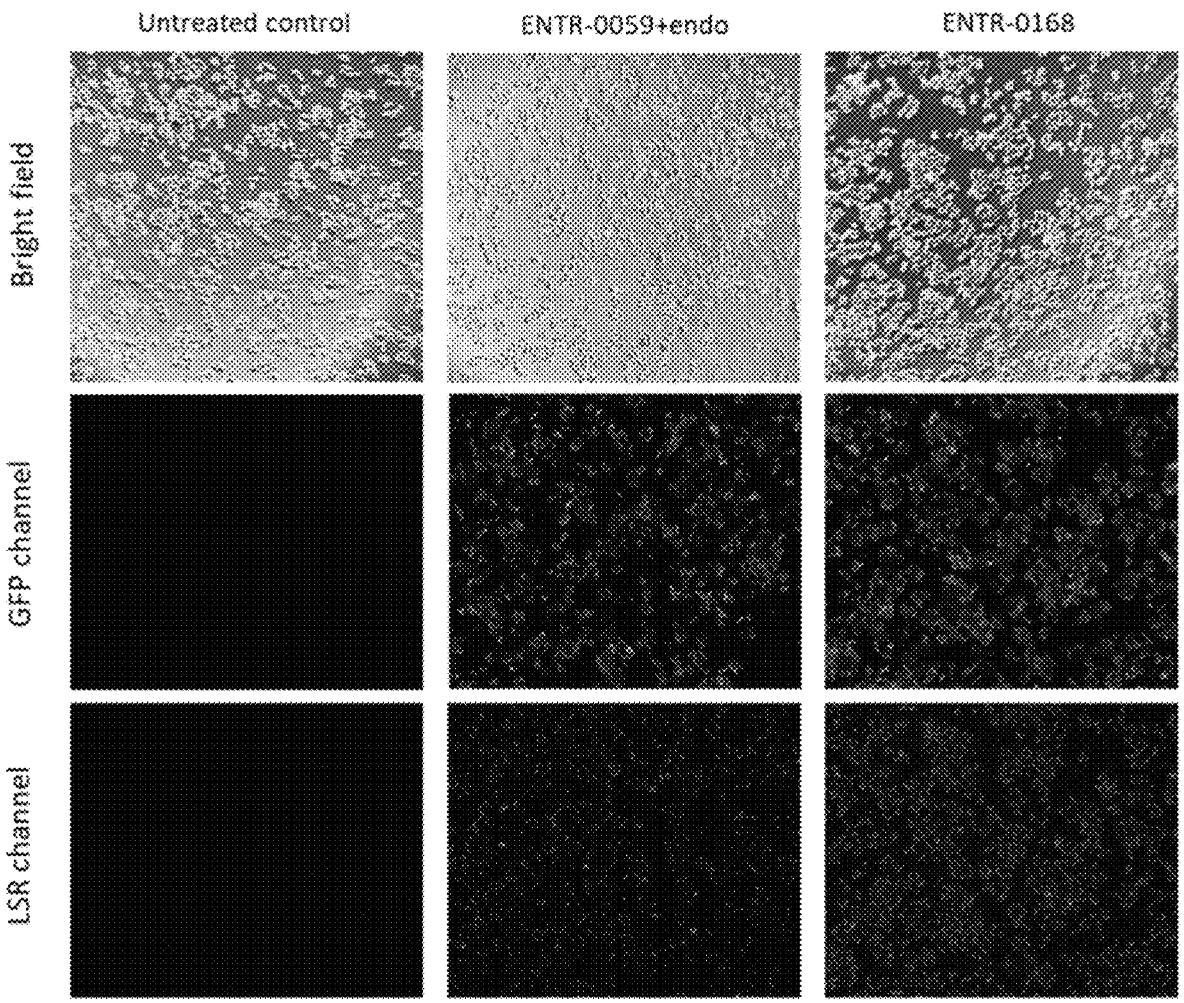

FIG. 39 shows the bright field microscopy (top) and fluorescence microscopy (GFP channel, middle; LSR channel, bottom) imaging of HeLa-654 cells treated with 2 μM of PMO-LSR (ENTR-0059, Table 1)+endoporter (6 μL/mL) and CPP-NLS-PMO-LSR (ENTR-0168, Table 1) post 24 hours, as described in Example 1.

Figure 40:
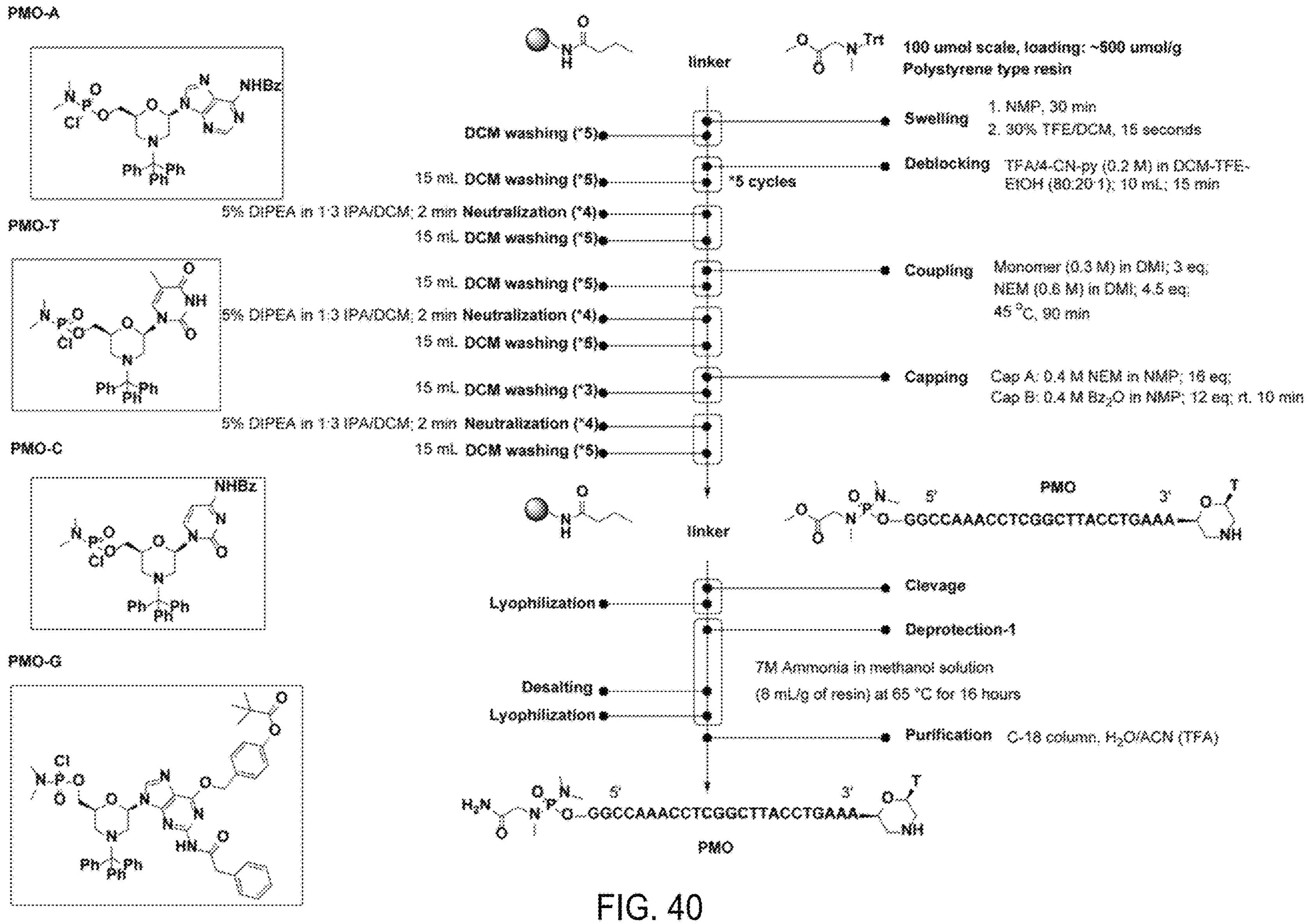

FIG. 40 shows a schematic preparation of the PMO oligo and the monomers used for assembling the PMO oligo (SEQ ID NO: 214).

Figure 41:
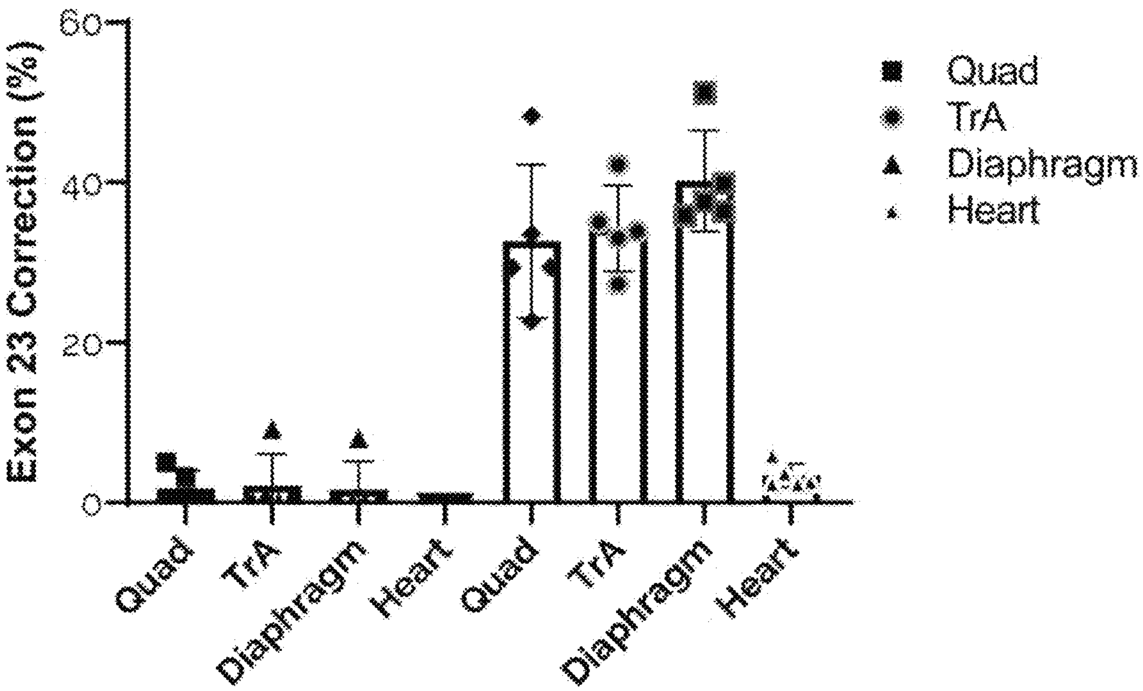

FIG. 41 shows the RT-PCR result of exon skipping activities of PMO alone (ENTR-0013, Table B1) (24 mpk) and CPP12-PMO$^{DMD}$ (ENTR-0098, Table B2) (30 mpk) in C57BL/10J mouse. Various muscle groups were analyzed at 1 week post intravenous injection (Quad=quadriceps, TrA=transverse abdominis, Diaphragm=Diaphragm muscles, Heart=cardiac muscle).

FIGS. 42A-D shows the RT-PCR result of exon skipping activities in quadriceps (FIG. 42A), transverse abdominis (FIG. 42B), diaphragm (FIG. 42C), and heart (FIG. 42D) in C57BL/10ScSn-Dmdmdx/J (MDX) mice after intravenous injection of CPP12-PMO$^{DMD}$(ENTR-0098, Table 3) at 10 and 30 mpk.

FIGS. 43A-D show the RT-PCR result of exon skipping activities in quadriceps (FIG. 43A), transverse abdominis (FIG. 43B), diaphragm (FIG. 43C), and heart (FIG. 43D) in MDX mice after a single 30 mpk intravenous injection of CPP12-PMO$^{DMD}$ (ENTR-0098, Table B2) analyzed at 1 week, 2 weeks, and 4 weeks post injection.

Figure 44:
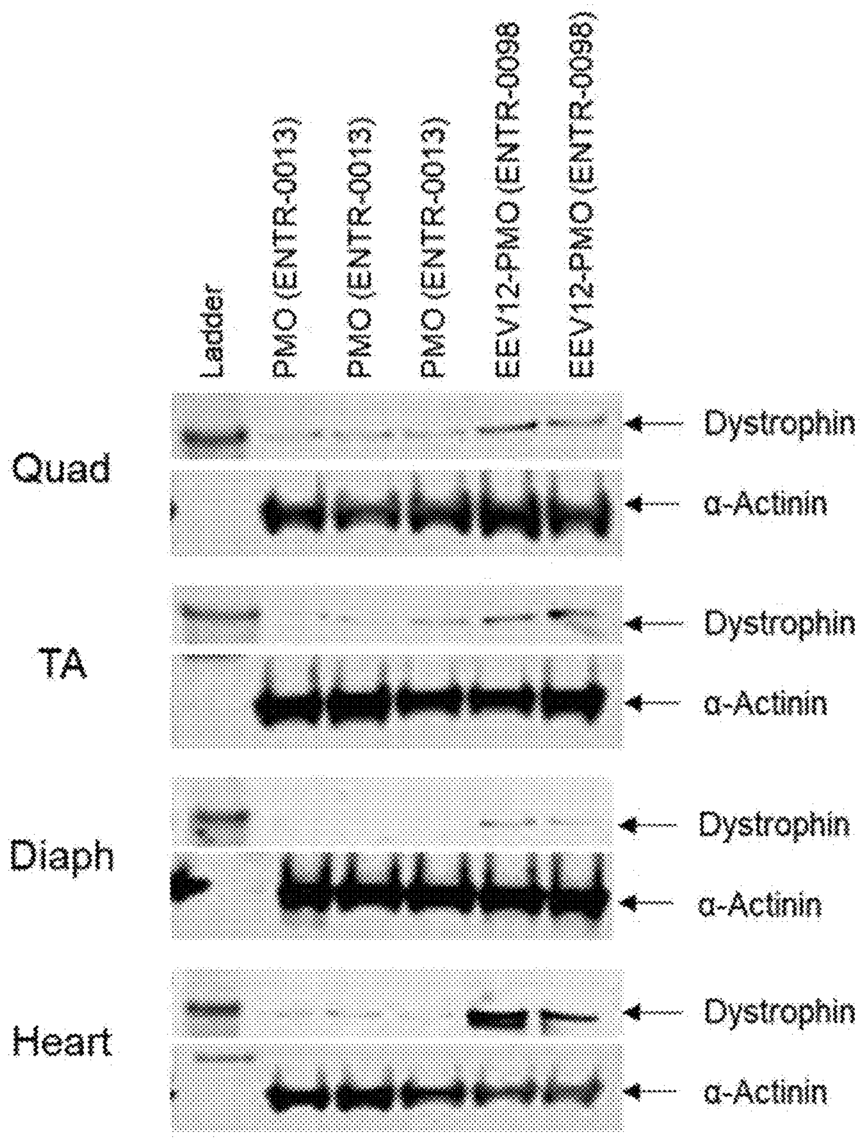
Figure 45A:
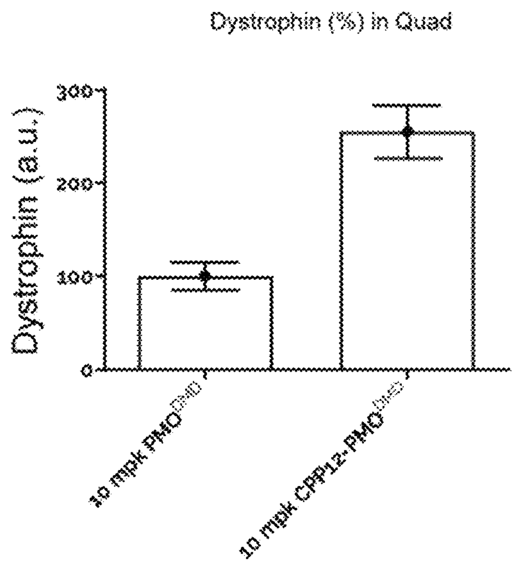
Figure 45B:
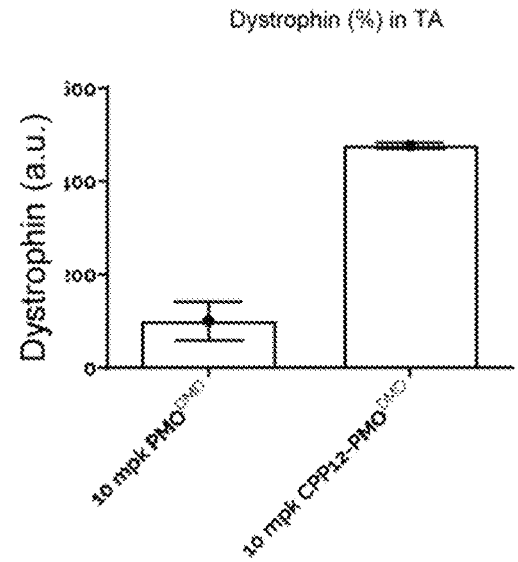
Figure 45C:
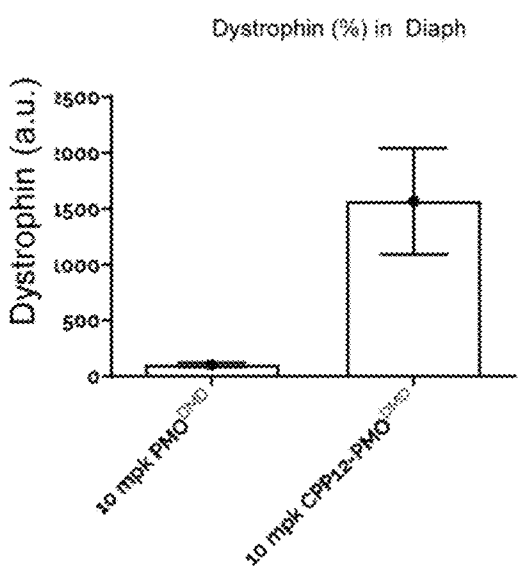
Figure 45D:
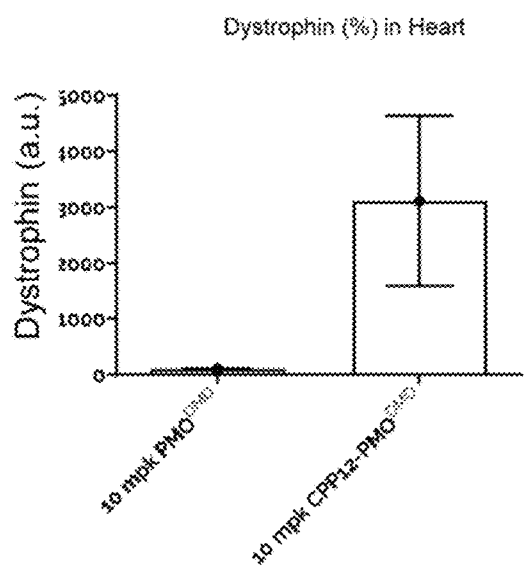

FIG. 44 shows Western Blots of exon-23 corrected dystrophin and α-actinin in various muscle groups of MDX mice 1 week post single intravenous injection of PMO$^{DMD}$ (8 mpk, ENTR-0013, Table 2) or CPP12-PMO$^{DMD}$ (10 mpk, ENTR-0098, Table 3) in various muscle groups (quadriceps, Quad; transverse abdominis, TA; diaphragm, and heart.

FIGS. 45A-D show the amount of exon-23 corrected dystrophin detected by Western Blot 1-week post single intravenous injection of PMO$^{DMD}$ (ENTR-0013, Table 2) or CPP12-PMO$^{DMD}$(ENTR-0098, Table B2) in the quadriceps (Quad) (FIG. 45A), transverse abdominis (TA) (FIG. 45B), diaphragm (FIG. 45C), and heart (FIG. 45D) of MDX mice. The level of dystrophin correction after PMO injection is calibrated as 100%. Alpha-actinin is used as loading control.

Figure 46A:
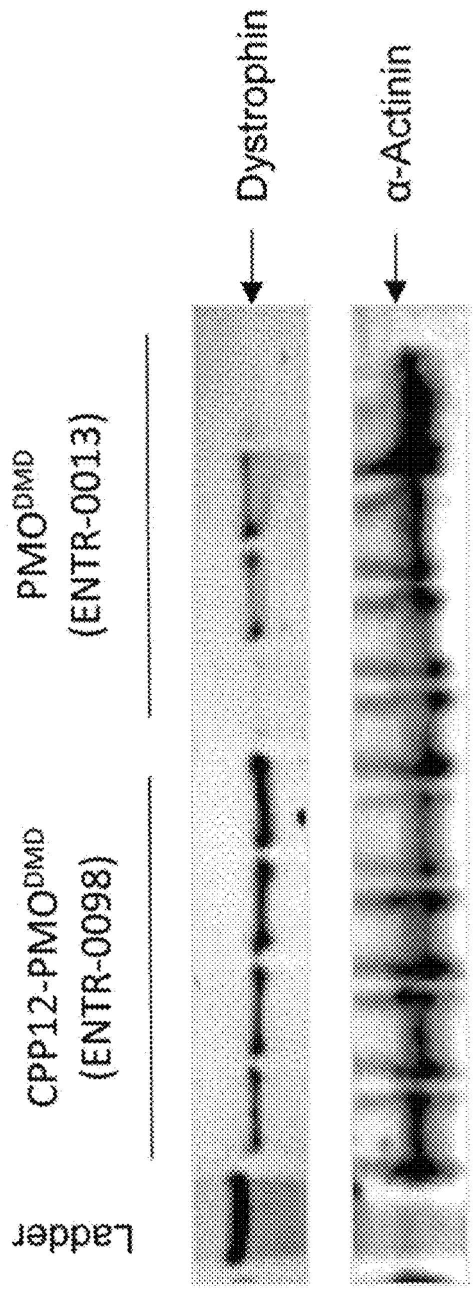
Figure 46B:
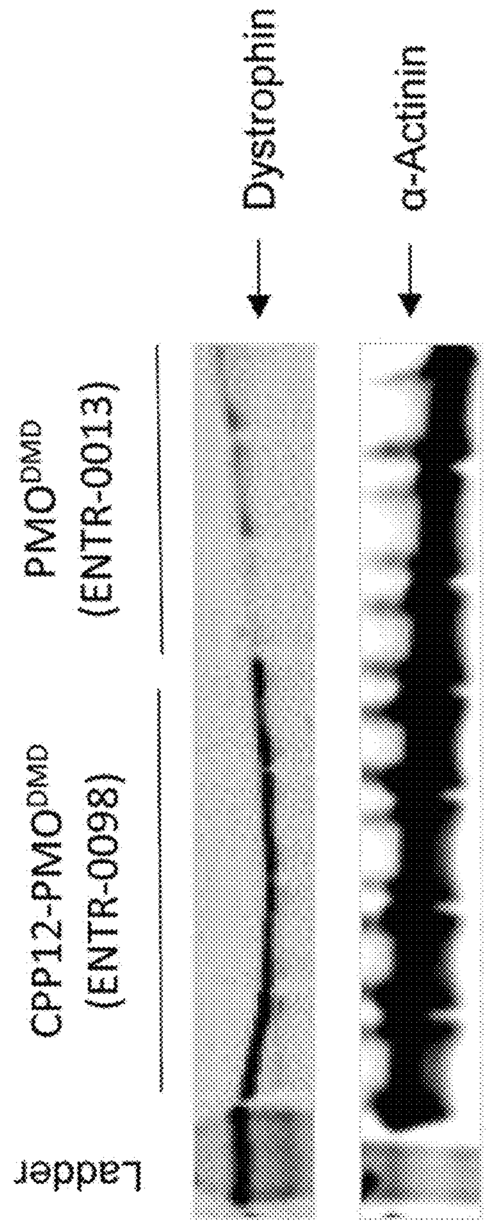

FIGS. 46A-B show Western Blots of exon-23 corrected dystrophin and α-actinin in the heart 2-week (FIG. 46A) or 4-week (FIG. 46B) after intravenous injection in MDX mice at 24 mpk of PMO$^{DMD}$ (ENTR-0013, Table B1) or 30 mpk CPP12-PMO$^{DMD}$ (ENTR-0098, Table B2).

Figure 47:
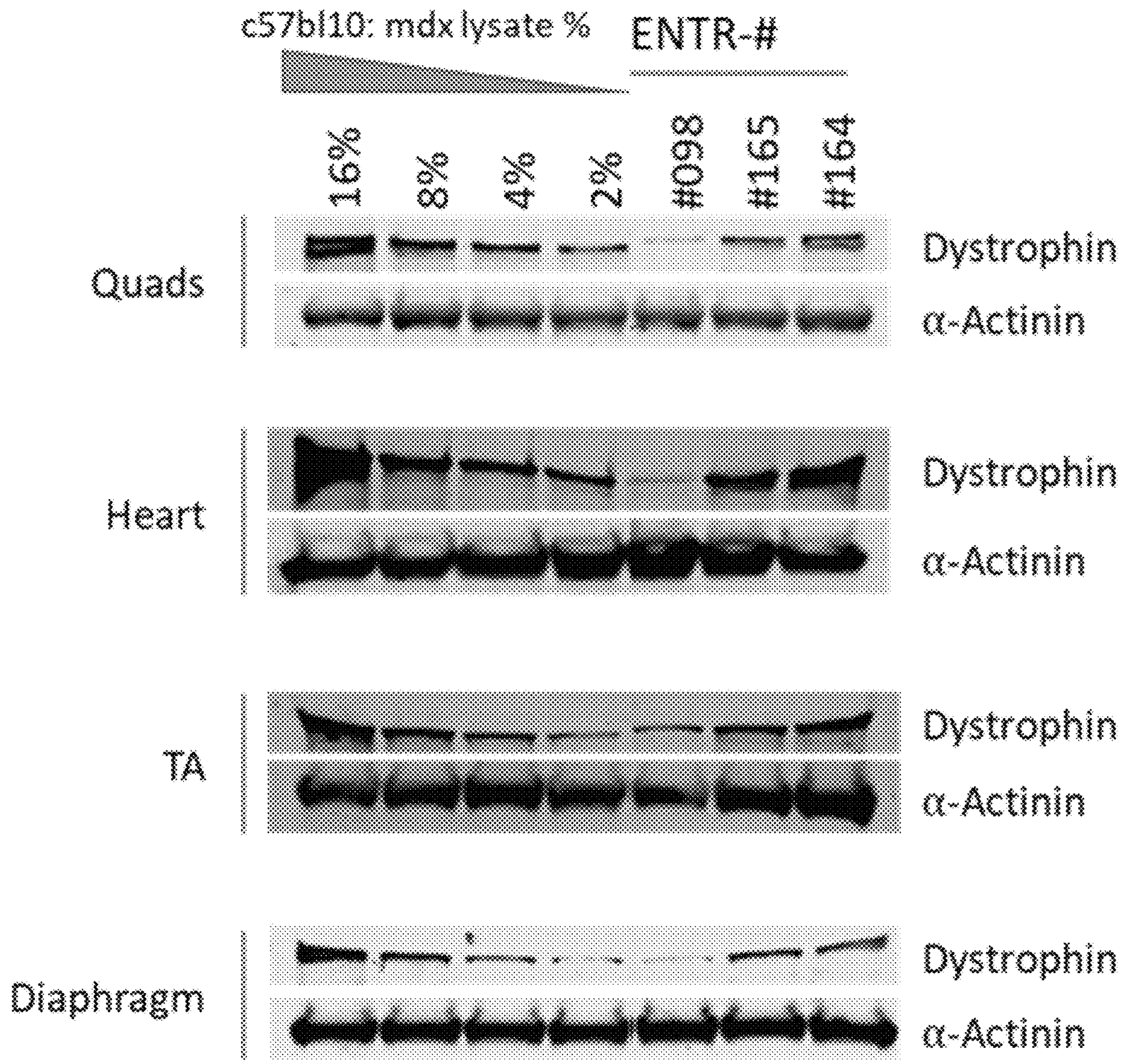
Figure 48A:
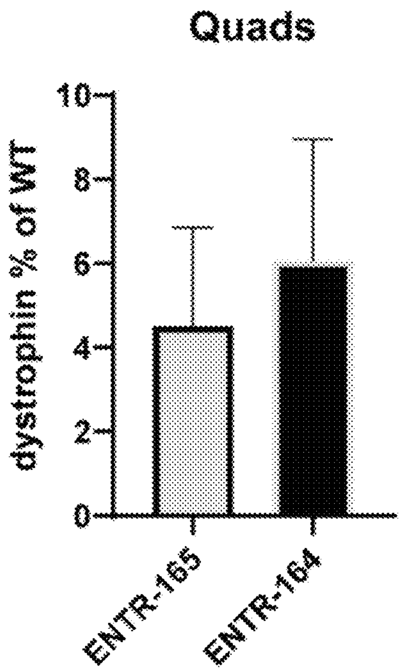
Figure 48B:
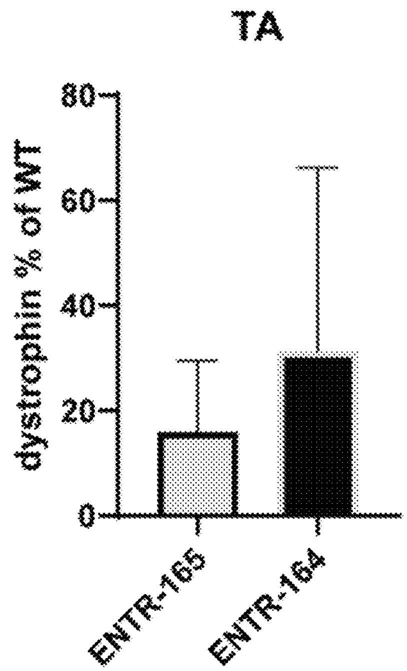
Figure 48C:
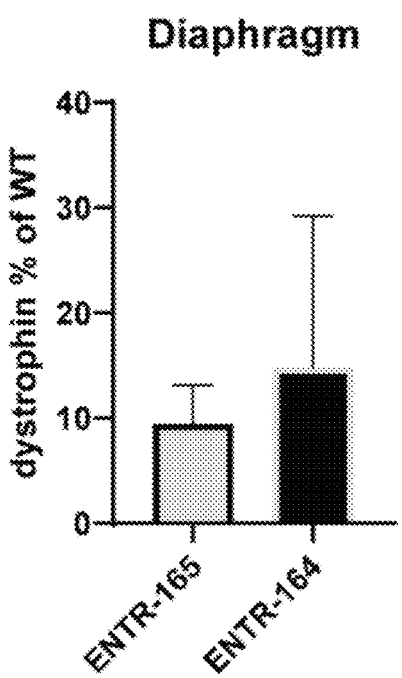
Figure 48D:
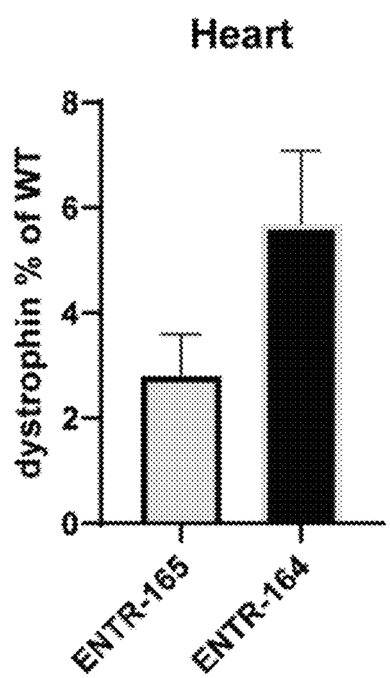
Figure 49B:
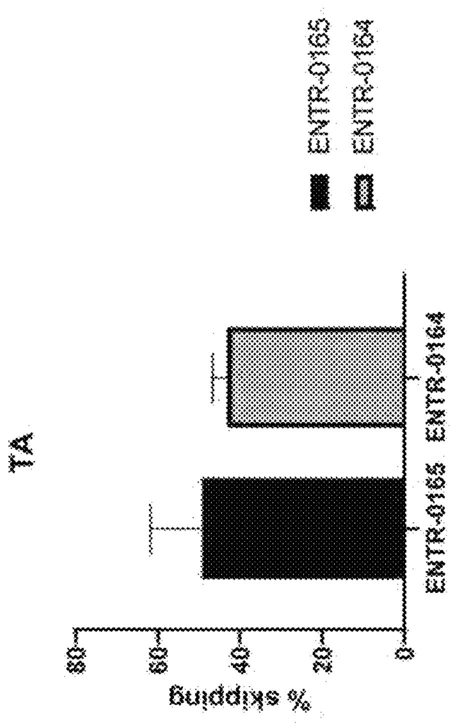
Figure 49A:
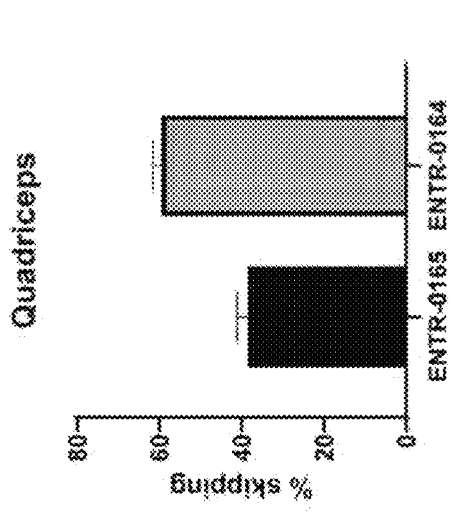
Figure 49D:
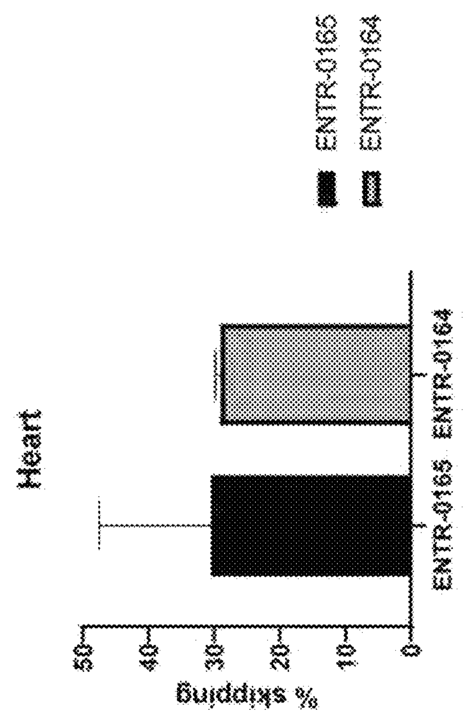
Figure 49C:
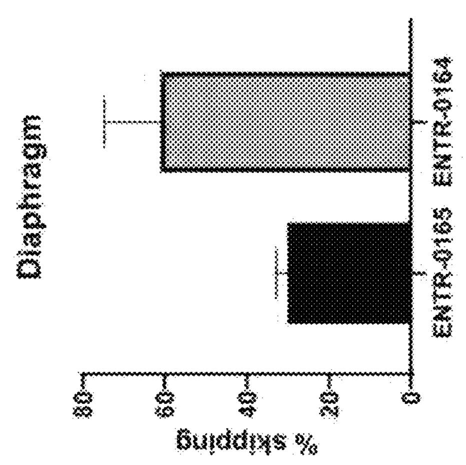

FIG. 47 shows Western Blots of exon-23 corrected dystrophin and α-actinin in various muscle groups of MDX mice 1 week post single intravenous injection of CPP12-PMO$^{DMD}$ (20 mpk, ENTR-0098, Table B2), or CPP12-NLS-PMO (20 mpk, construct ENTR-0164 or ENTR-0165, Table B3) in various muscle groups (quadriceps, Quad; heart; transverse abdominis, TA; and diaphragm). Alpha-actinin is used as loading control.

FIGS. 48A-D show the amount of exon-23 corrected dystrophin detected by Western Blot 1-week post single intravenous injection of CPP12-NLS-PMO constructs (20 mpk, construct ENTR-0164 or ENTR-0165, Table 4) in the quadriceps (Quad) (FIG. 48A), transverse abdominis (TA) (FIG. 48B), diaphragm (FIG. 48C), and heart (FIG. 48D) of MDX mice. Data is shown as % of dystrophin level in wild type animal (C57BL/10). Alpha-actinin as loading control.

FIGS. 49A-D show the RT-PCR result of exon skipping activities in the quadriceps (Quad) (FIG. 49A), transverse abdominis (TA) (FIG. 49B), diaphragm (FIG. 49C), and heart (FIG. 49D) of MDX mice at 1-week post single intravenous injection of CPP12-NLS-PMO constructs (20 mpk, construct ENTR-0164 or ENTR-0165, Table B3)

Figure 50:
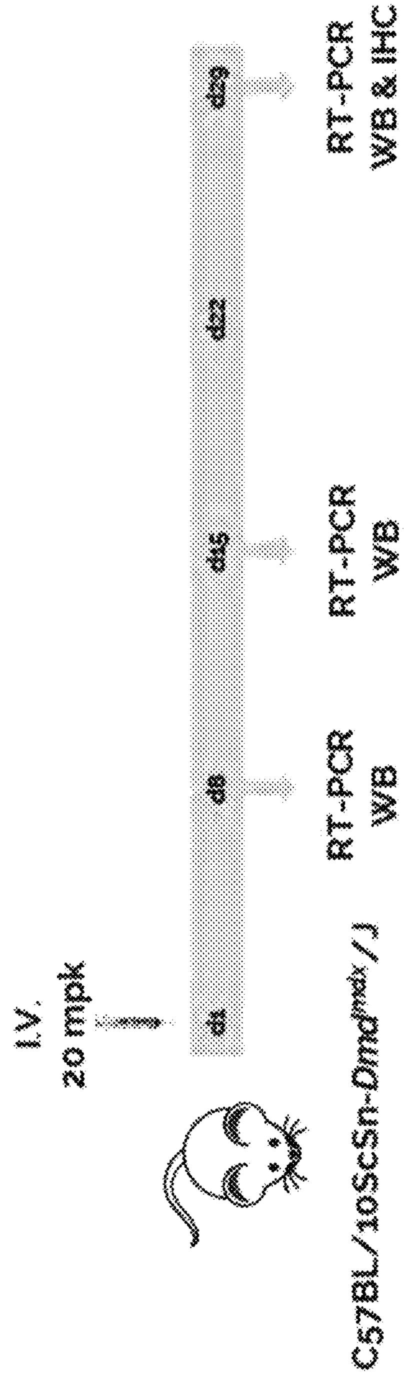

FIG. 50 shows the study design of to evaluate the duration of effects of ENTR-201 in MDX (C57BL/10ScSn-Dmd$^{mdx}$/J) mice.

FIGS. 51A-D show the RT-PCR result of exon skipping activities of PBS vehicle or CPP12-NLS-PMO construct (ENTR-201, Table 4) in heart (FIG. 51A), diaphragm (FIG. 51B), quadricep (FIG. 51C), and transverse abdominis (TrA) (FIG. 51D) in MDX mice 1-week, 2-week, or 4-week post single IV injection at 20 mpk.

FIGS. 52A-D show the amount of exon-23 corrected dystrophin detected by Western Blot in the heart (FIG. 52A), diaphragm (FIG. 52B), quadricep (FIG. 52C), and transverse abdominis (TrA) (FIG. 52D) of MDX mice 1-week, 2-week, or 4-week post single intravenous injection of PBS vehicle or CPP12-NLS-PMO construct (ENTR-201, Table 4). Data is shown as % of dystrophin level in wild type animal (C57BL/10). Alpha-actinin as loading control.

Figure 53:
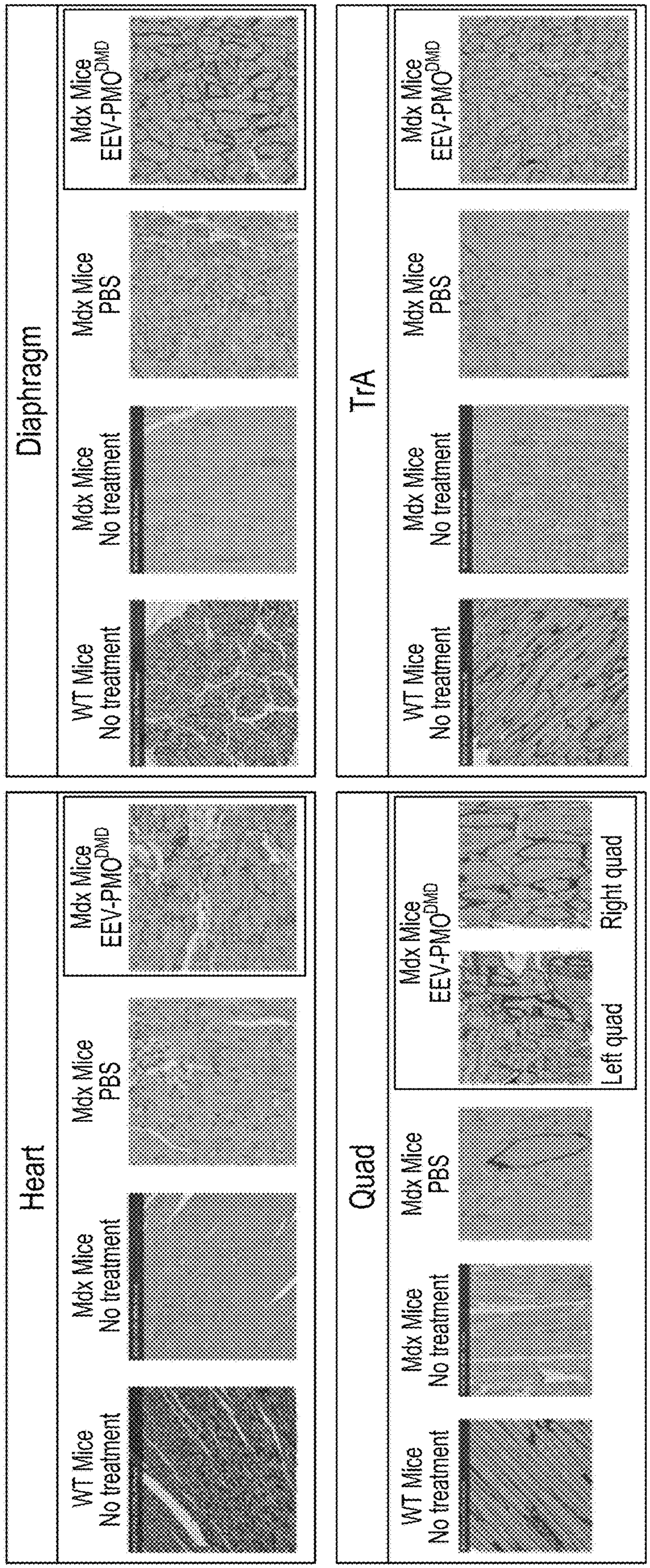

FIG. 53 shows immunohistochemistry of muscle groups in mdx mice 4 weeks post single IV injection of ENTR-201 at 20 mpk and PBS vehicle.

Figure 54:
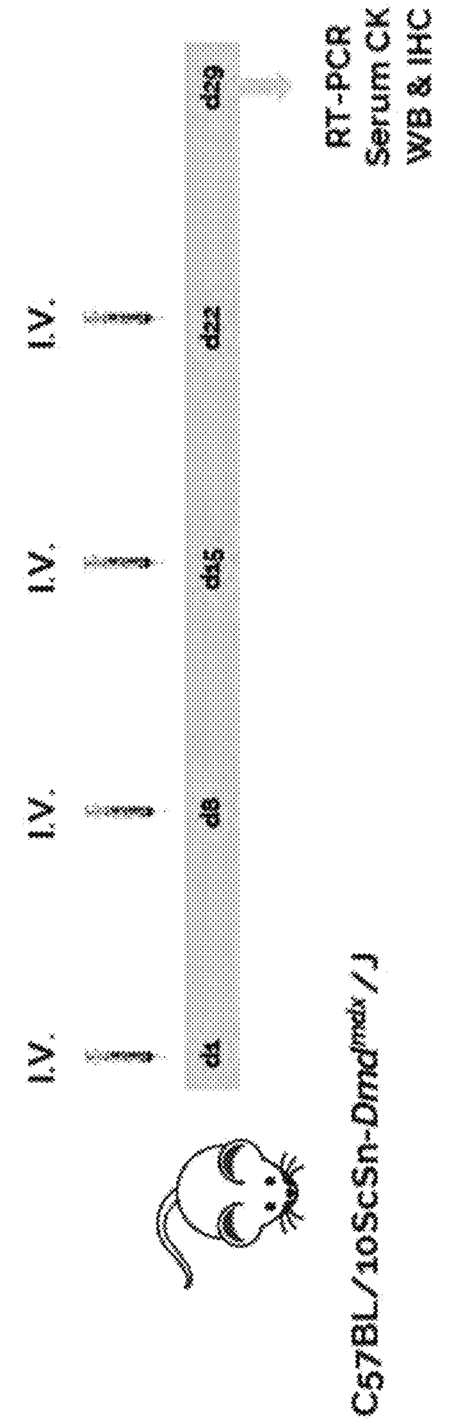
Figure 55A:
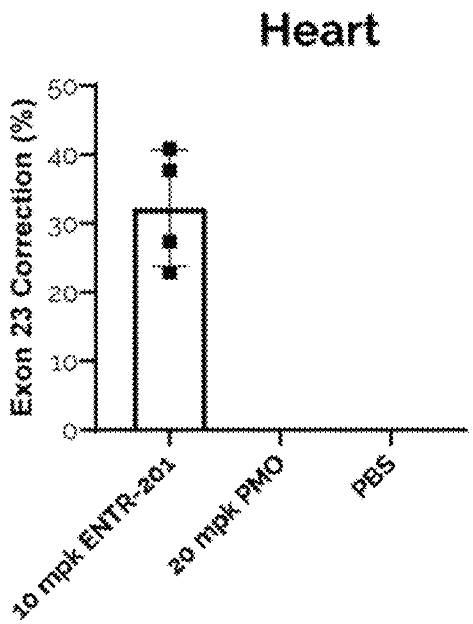
Figure 55B:
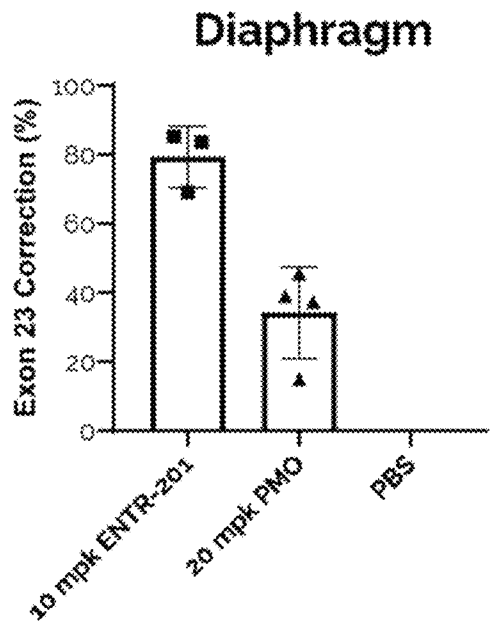
Figure 55C:
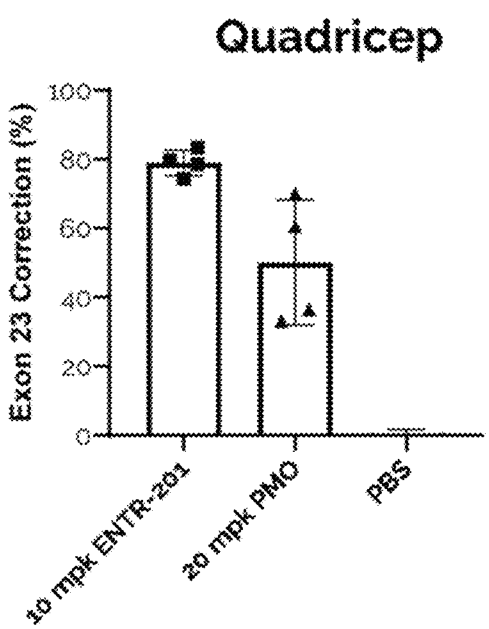
Figure 55D:
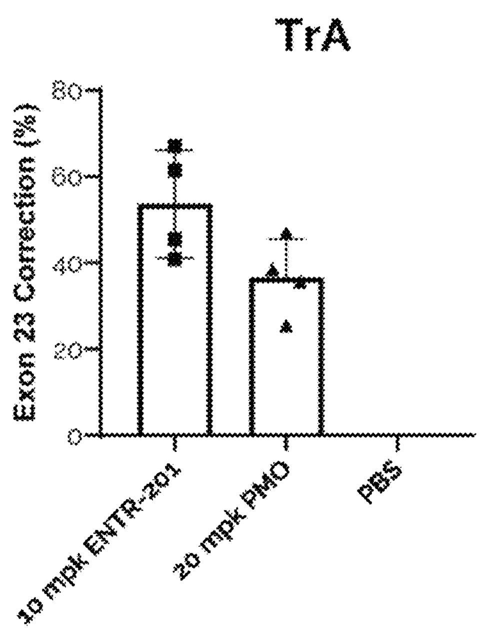
Figure 56A:
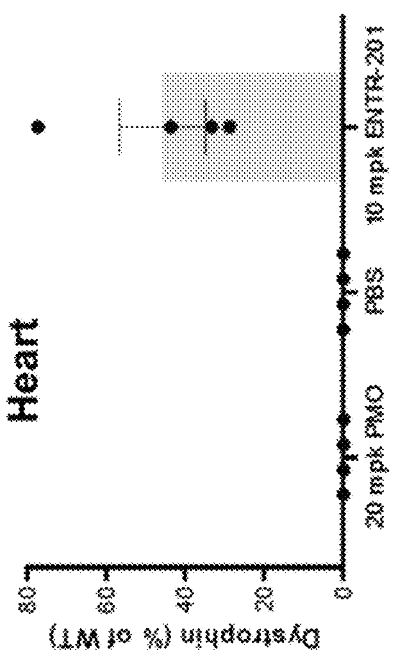
Figure 56B:
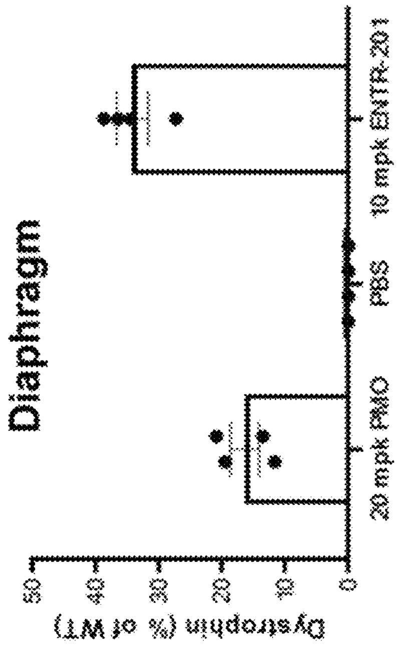
Figure 56C:
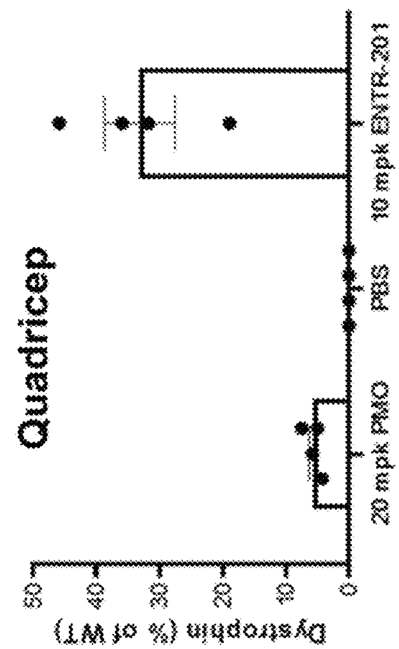
Figure 56D:
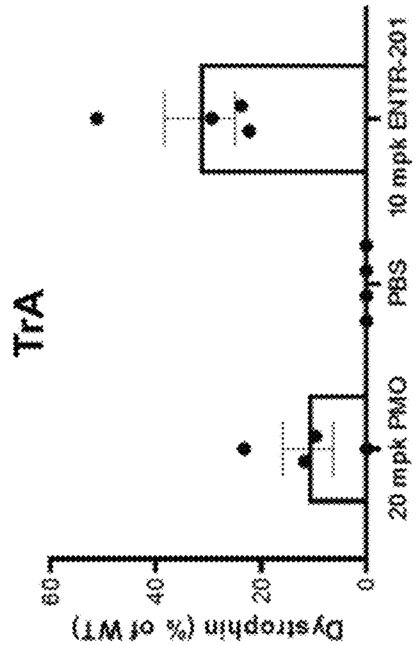

FIG. 54 shows the study design to evaluate the efficacy of CPP12-NLS-PMO construct (ENTR-201, Table 4) at 10 mg/kg or PMO itself (ENTR-0013, Table B2) after repeated dose in MDX (C57BL/10ScSn-Dmd$^{mdx}$/J) mice. QW, weekly dosage.

FIGS. 55A-D show the RT-PCR result of exon skipping activities of 4 weekly IV dosage of vehicle, CPP12-NLS-PMO construct (ENTR-201 at 10 mpk) or PMO alone (ENTR-013, at 20 mpk) in heart (FIG. 55A), diaphragm (FIG. 55B), quadricep (FIG. 55C), and transverse abdominis (TrA) (FIG. 55D) of MDX mice.

FIGS. 56A-D show the amount of exon-23 corrected dystrophin protein detected by Western Blot in the heart (FIG. 56A), diaphragm (FIG. 56B), quadricep (FIG. 56C), and transverse abdominis (TrA) (FIG. 56D) muscles of MDX mice after 4 weekly IV dosage of vehicle, CPP12-NLS-PMO construct (ENTR-201 at 10 mpk) or PMO alone (ENTR-013, at 20 mpk). Data is shown as % of dystrophin level in wild type animal (C57BL/10). Alpha-actinin as loading control.

Figure 57:
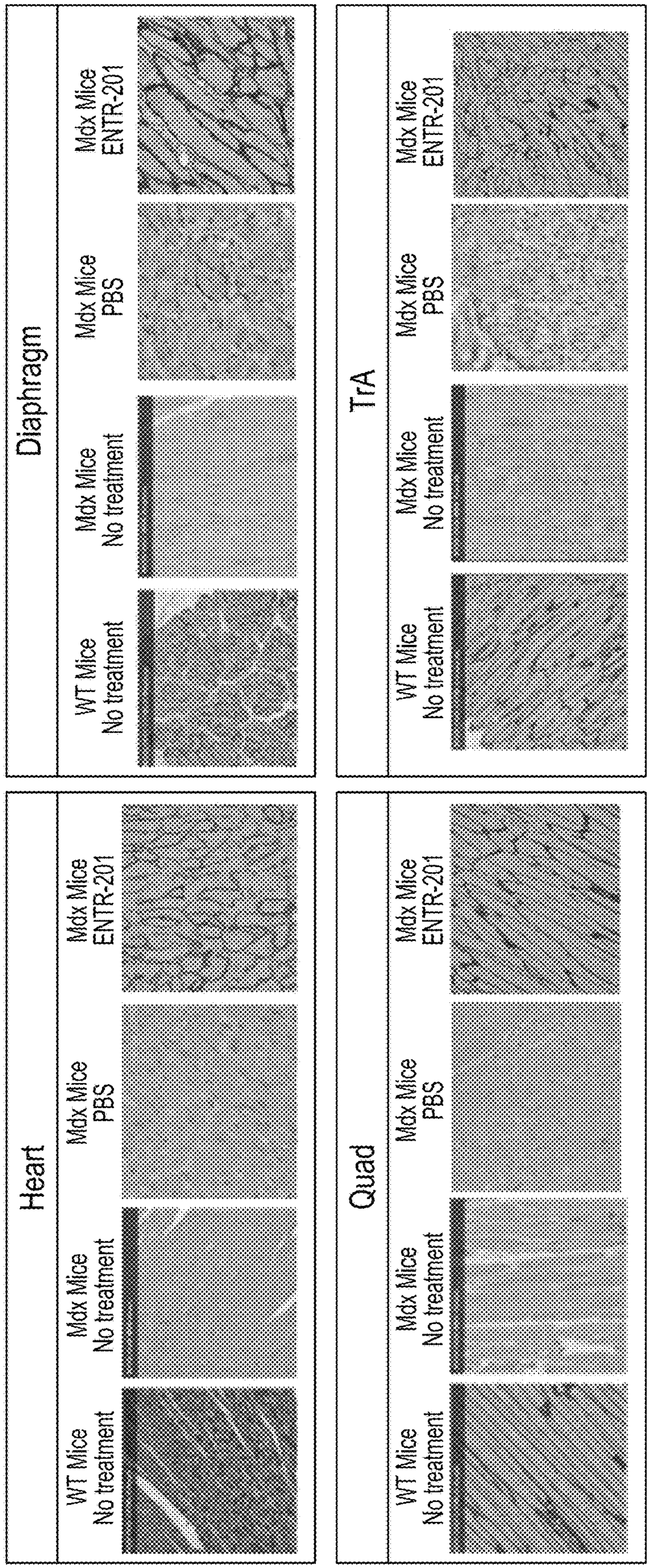

FIG. 57 shows immunohistochemistry of muscle groups in mdx mice analyzed one week after 4 weekly dosages of ENTR-201 at 10 mpk and vehicle.

Figure 58:
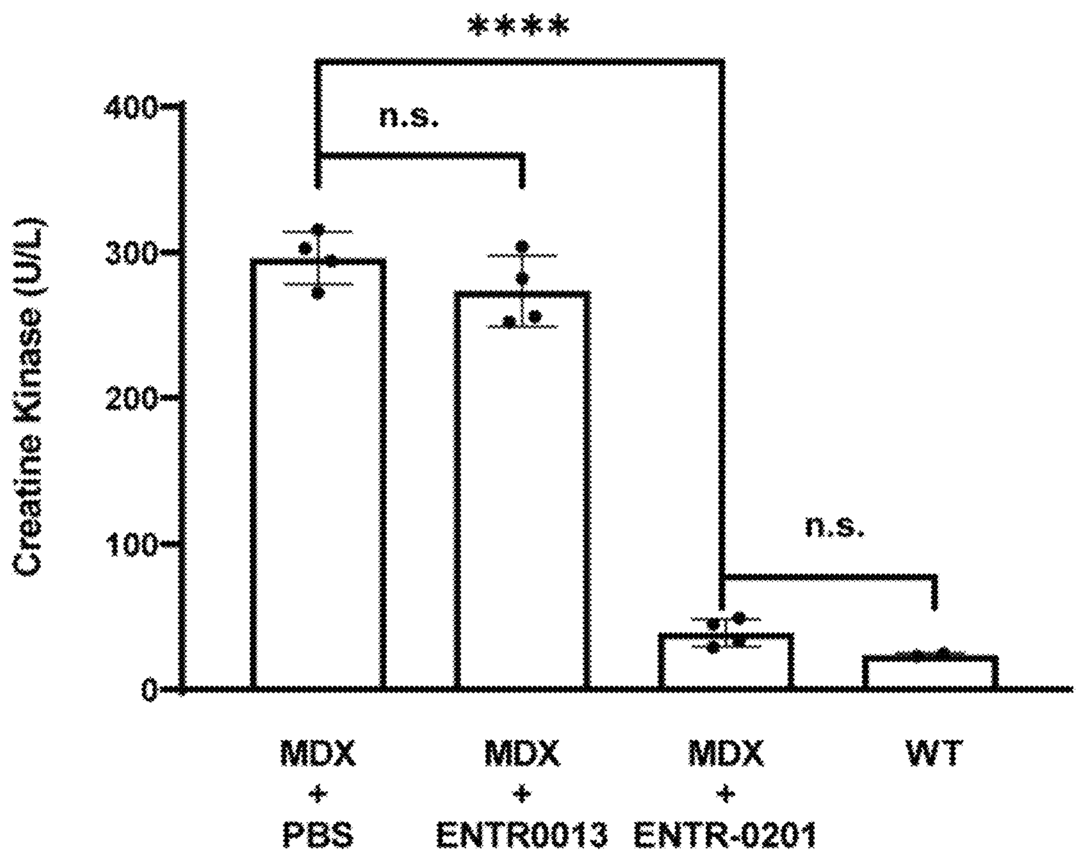

FIG. 58 shows serum creatine kinase level in the serum of mdx mice analyzed one week after 4 weekly dosages of ENTR-201 at 10 mpk, PMO alone (ENTR-0013) at 20 mpk or vehicle. All data are reported as mean values +/−SEM. Statistical differences between treatment groups and control groups were evaluated by one-tailed t-test for statistical significance.

Figure 59:
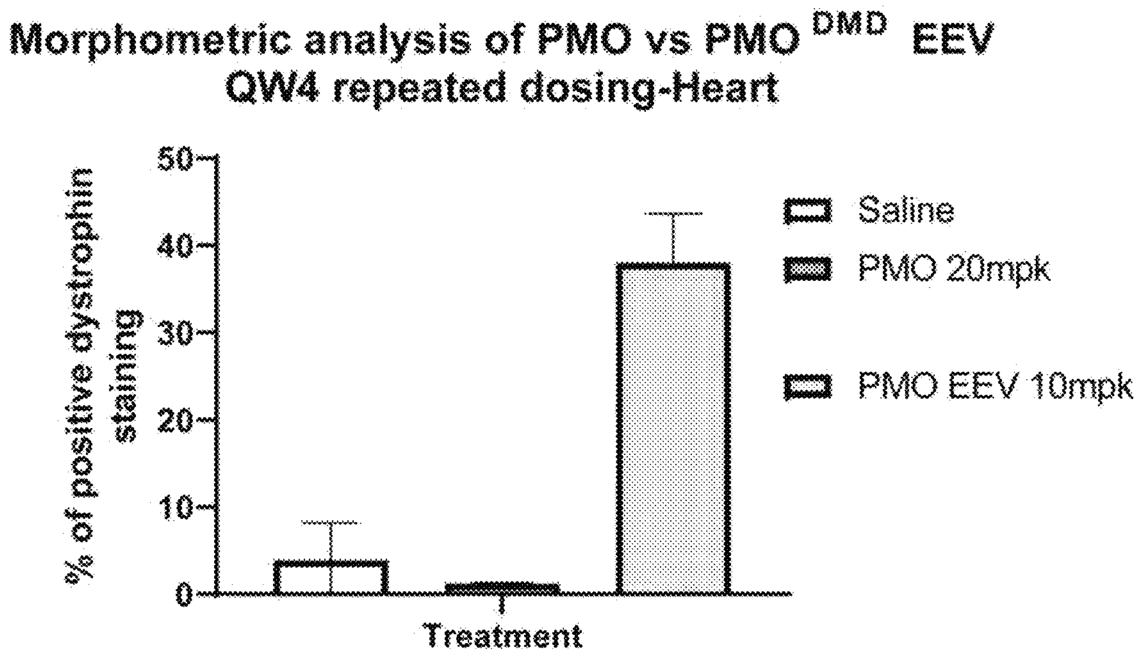

FIG. 59 shows quantification of dystrophin staining intensity in the heart tissue using Halo membrane algorithm version 1.7 after 4 weekly dosages of ENTR-201 at 10 mpk, PMO alone at 20 mpk, or vehicle. Data is presented as % of dystrophin level among different treatment groups, CPP12-NLS-PMO construct (ENTR-201 at 10 mpk) or PMO alone (ENTR-013, at 20 mpk).

Figure 60B:
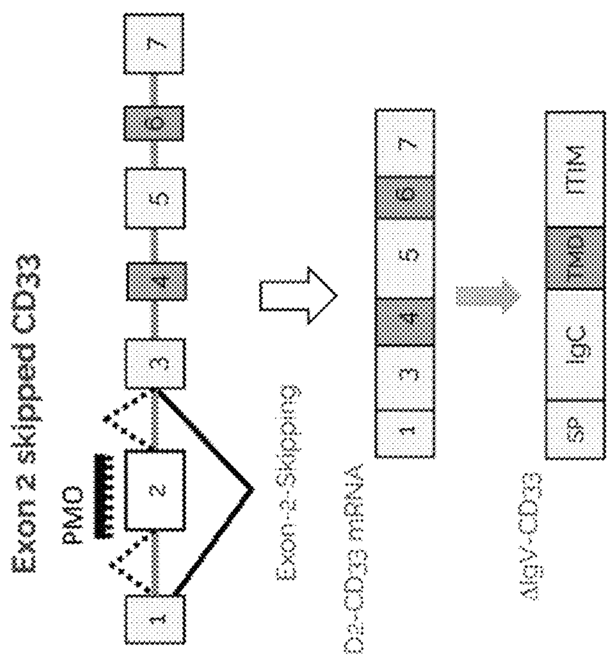
Figure 60A:
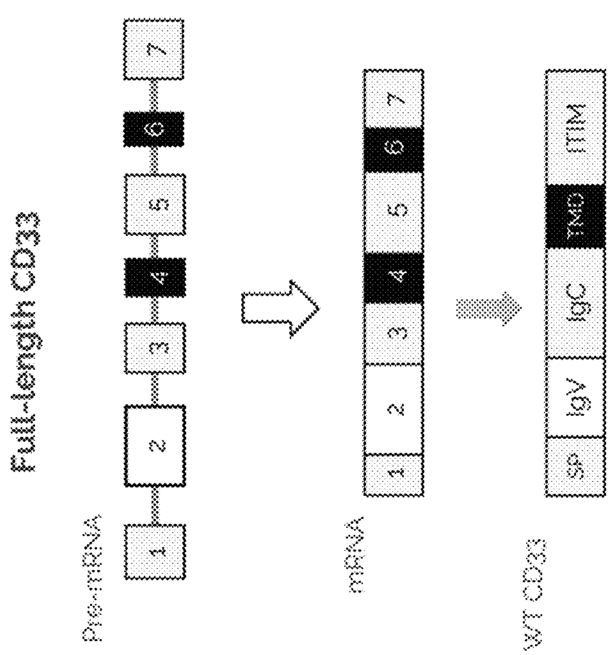

FIGS. 60A-B shows a schematic of CD33 PMO oligo design. PMO oligo targeting exon 2 of CD33 gene (also known as PMO$^{CD33}$) induces Exon-2-skipping of CD33 pre-mRNA, resulting in a truncated mature mRNA lacking exon 2 (D2-CD33) (FIG. 60B). The resulting protein translated from D2-CD33 mRNA lacks the extracellular IgV domain (ΔIgV-CD33), resulting in non-functional CD33 protein. FIG. 60A shows translation of wild-type CD33.

Figure 61A:
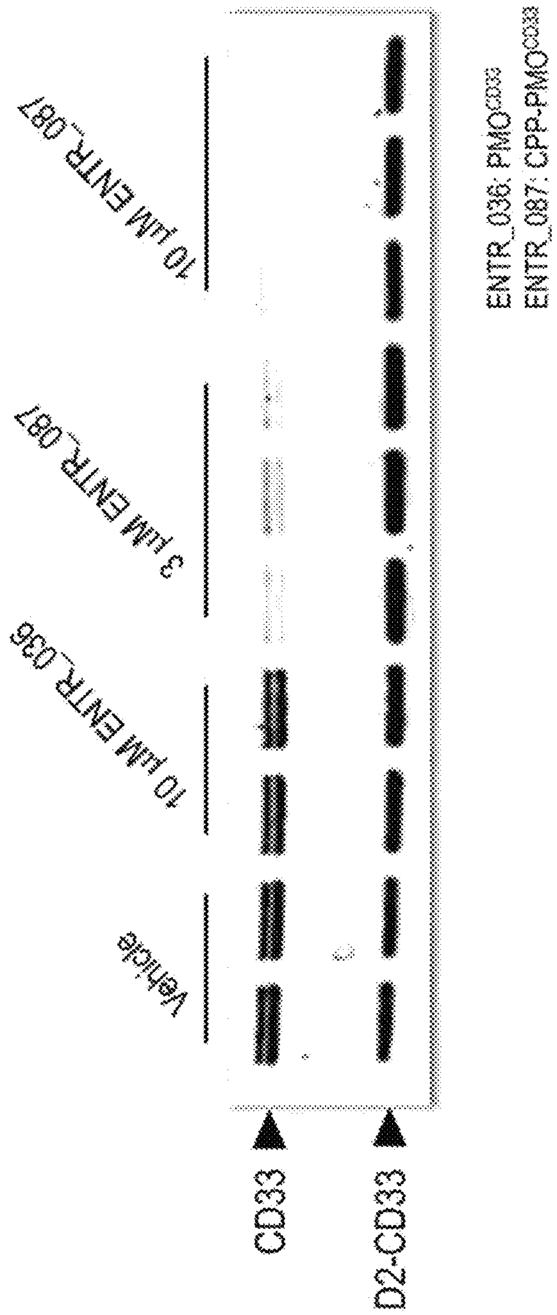
Figure 61B:
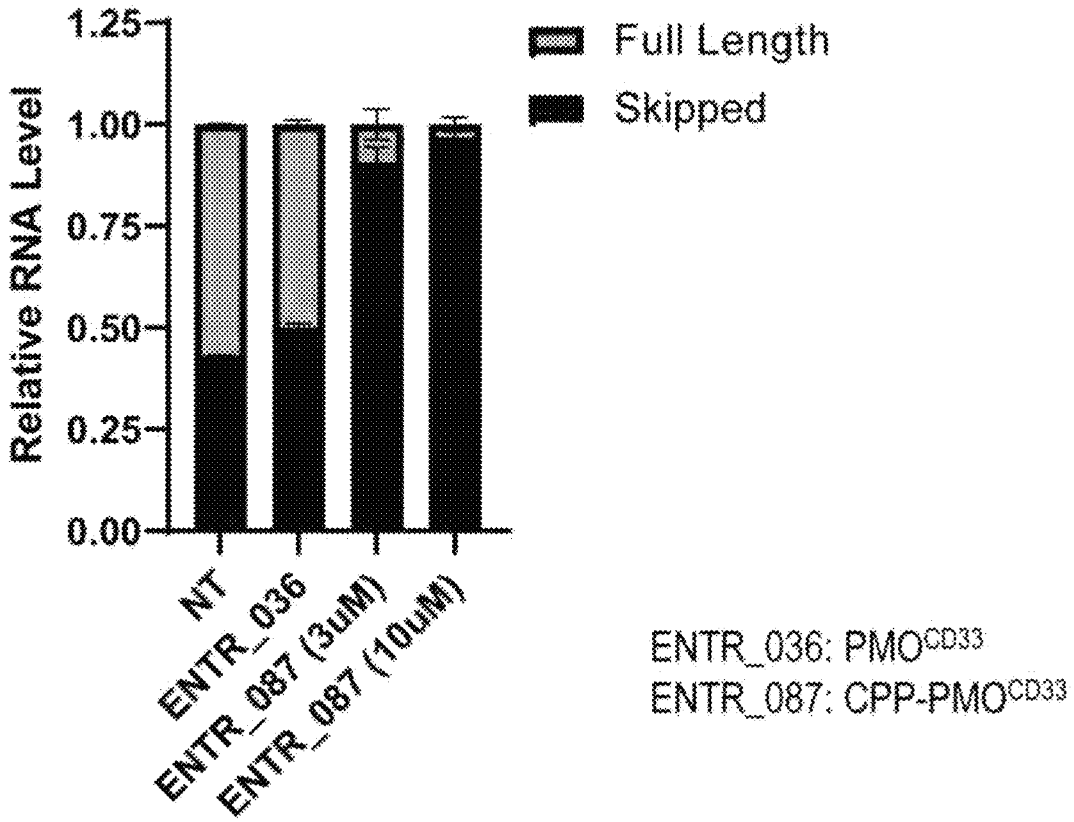

FIGS. 61A-B show a RT-PCR analysis of exon 2 skipping of CD33 (FIG. 61A) and quantification of full length CD33 versus D2-CD33 transcripts (FIG. 61B) after treatment with CPP-PMO$^{CD33}$ (ENTR-087, TABLE 5) or PMO$^{CD33}$ (ENTR-036, TABLE 5). PMO$^{CD33}$ is an antisense compound that targets exon 2 of CD33.

Figure 62A:
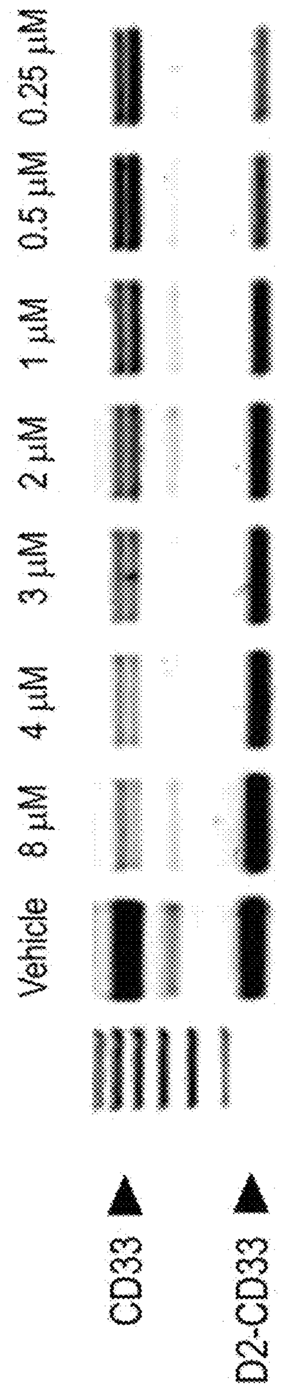
Figure 62B:
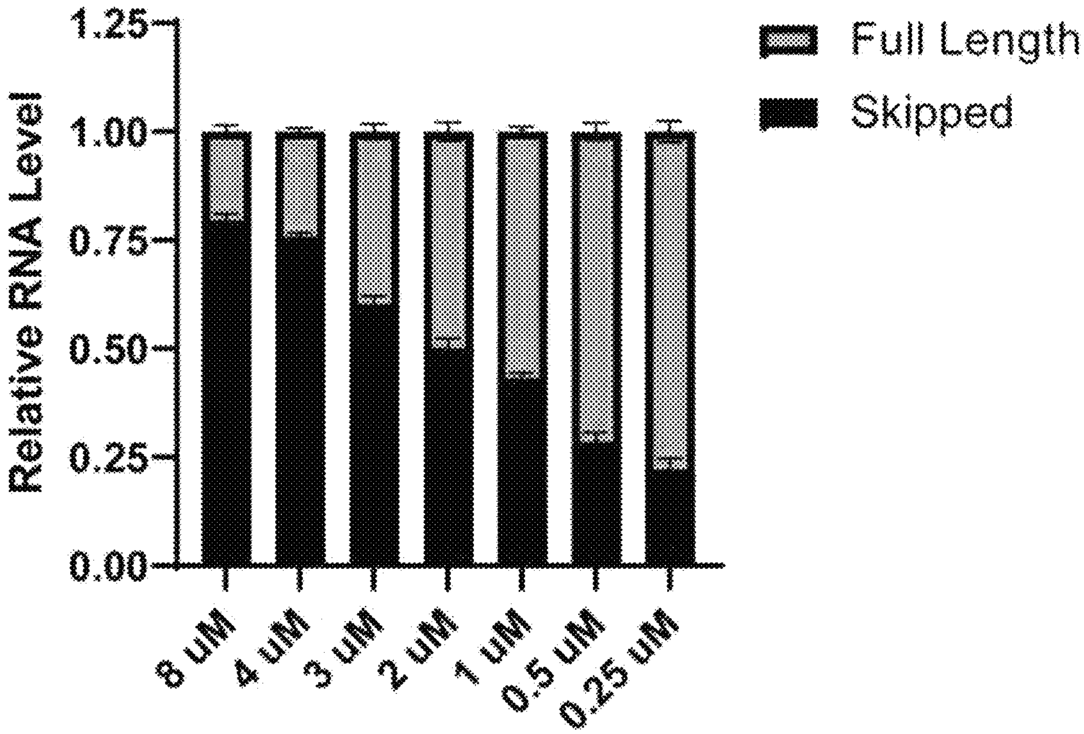

FIGS. 62A-B show the dose dependence of RT-PCR analysis of exon 2 skipping of CD33 (FIG. 62A) and quantification of full length CD33 versus D2-CD33 transcripts by dose (FIG. 62B) after treatment with CPP-PMO$^{CD33}$ (ENTR-087, TABLE 5). The PMO targeted exon 2 of CD33.

Figure 63:
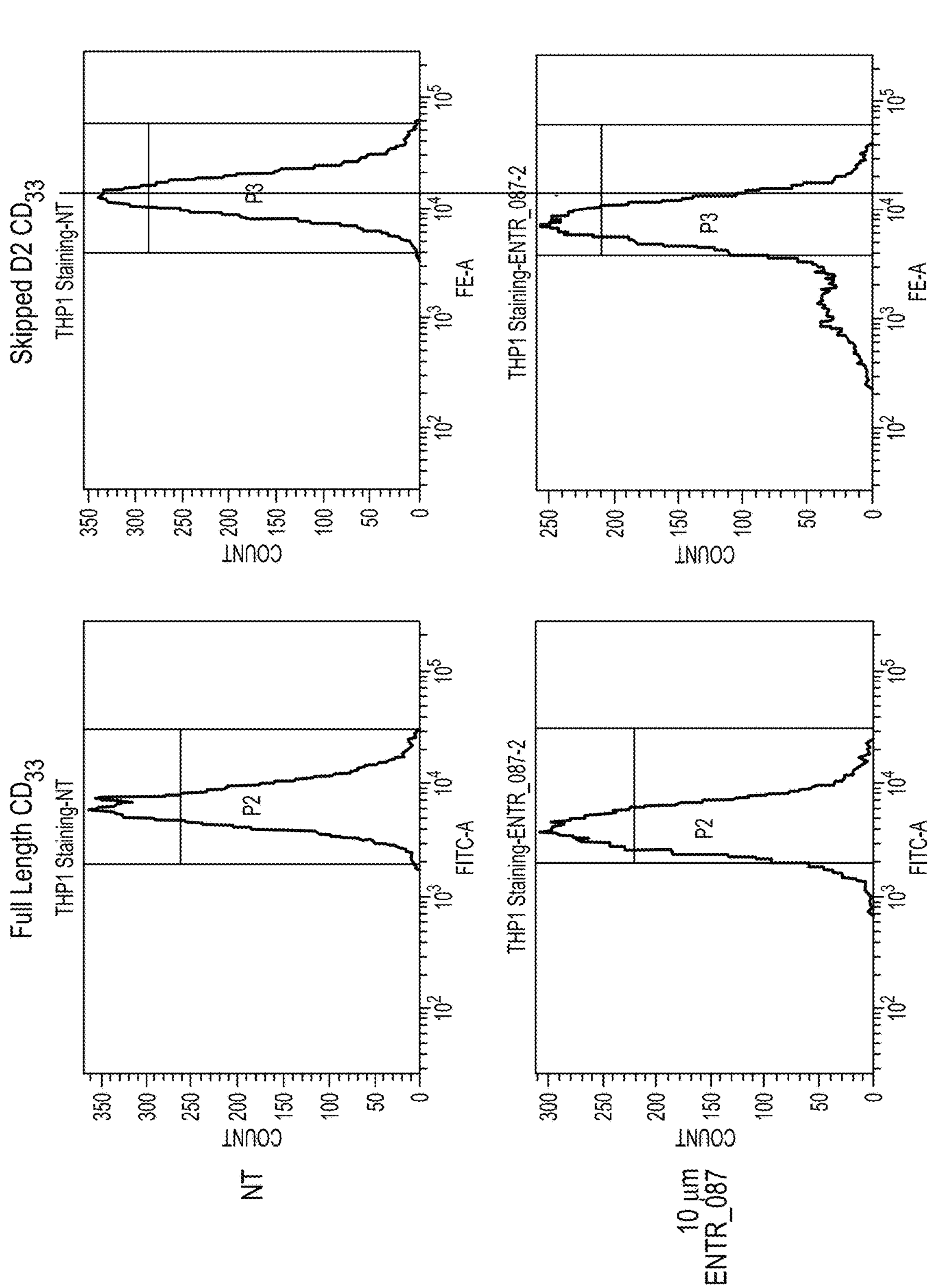

FIG. 63 shows flow cytometry analysis of THP1 cells after treatment with CPP-PMO$^{CD33}$ compared to untreated ("NT") cells.

Figure 64:
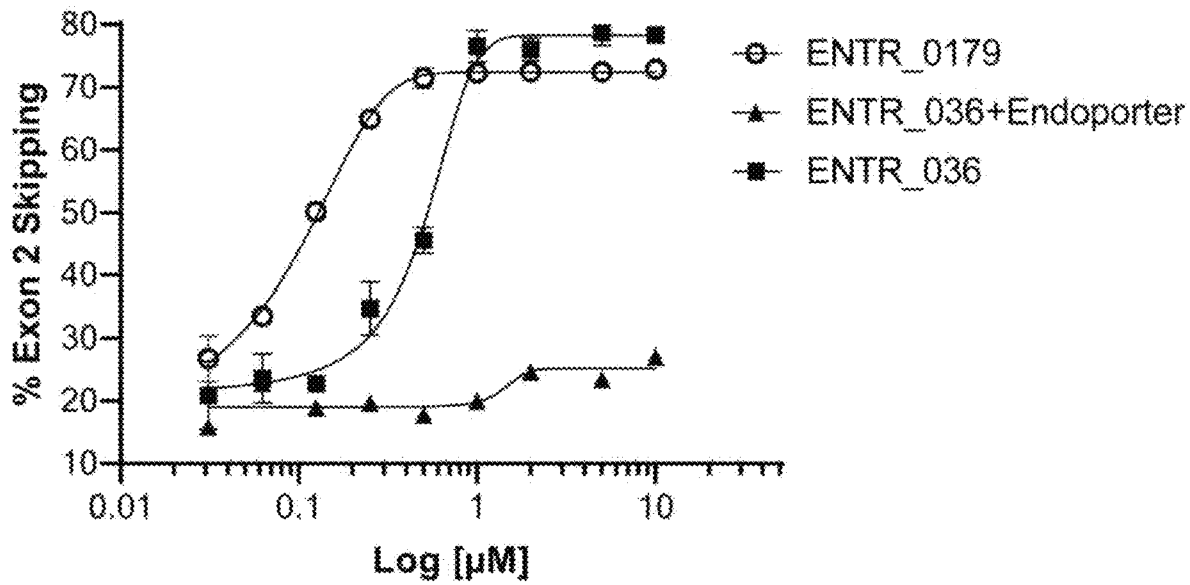

FIG. 64 shows RT-PCR analysis of exon 2 skipping of CD33 gene. Differentiated THP1 cells were treated with CPP-NLS-PMO$^{CD33}$ (ENTR-179, TABLE 5), PMO$^{CD33}$ (ENTR-036, Table C) with and without Endoporter transfection reagent (6 μL/mL).

Figure 65:
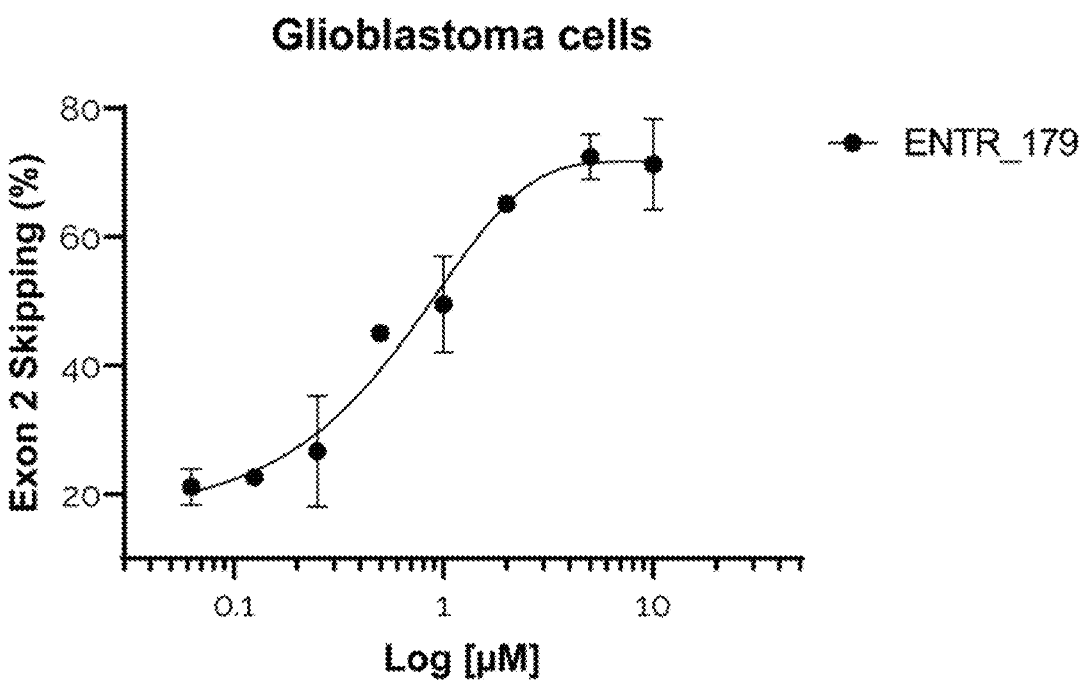

FIG. 65 shows RT-PCR analysis of exon 2 skipping of CD33 gene in glioblastoma cells. Human glioblastoma cells were treated with various dose (from 0.0625 μM to 10 μM) of CPP-NLS-PMO$^{CD33}$ (ENTR-179, Table C).

Figure 66A:
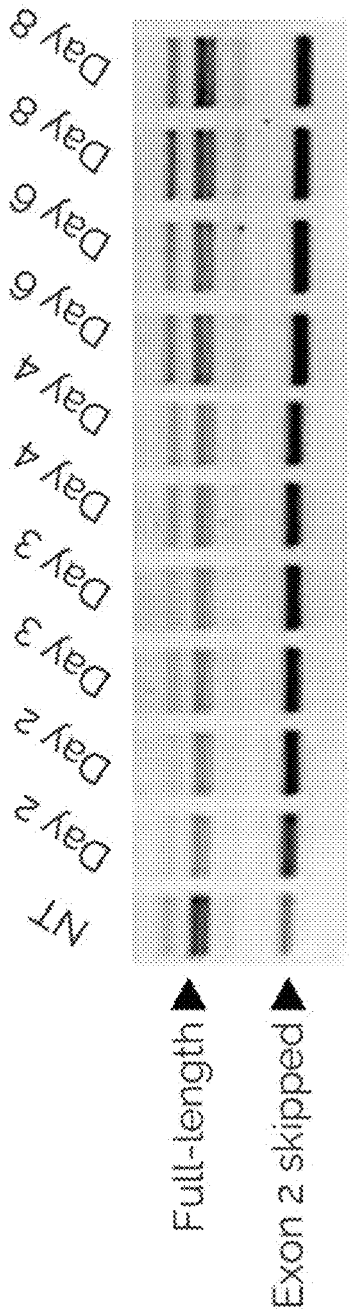
Figure 66B:
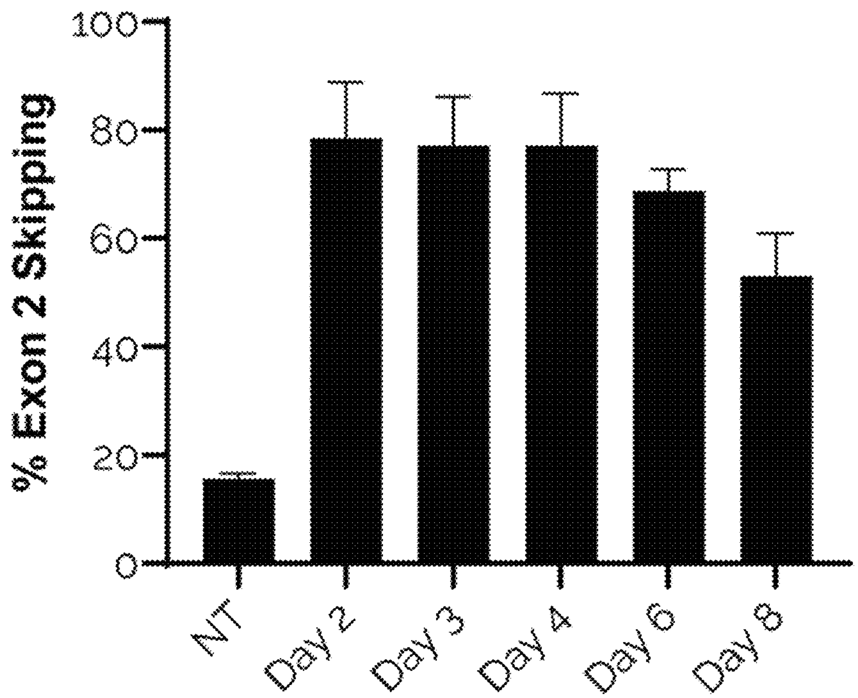

FIGS. 66A-B show RT-PCR analysis and quantification of exon 2 skipping of CD33 gene in THP1 cells in a time course study. Differentiated THP1 cells were treated with CPP-PMO$^{CD33}$ (ENTR-087") for 24 hr before washed and cultured with compound-free media. Cells were harvested at Day 2, 3, 4, 6, and 8 post treatment.

Figure 67:
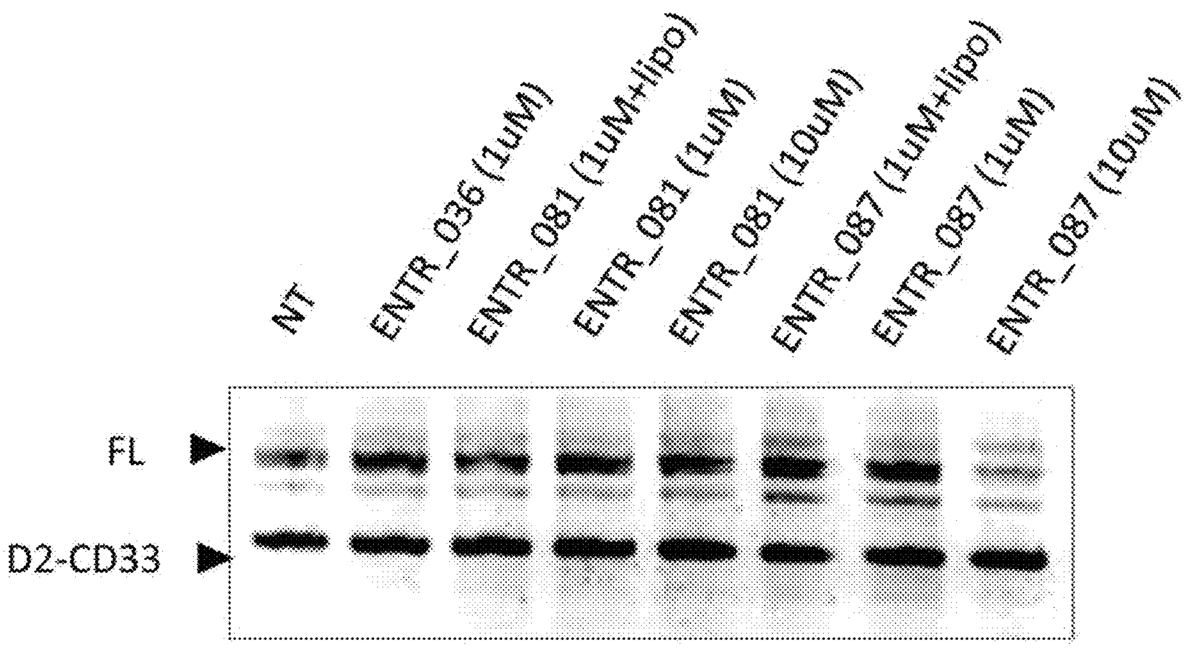

FIG. 67 shows RT-PCR analysis of exon 2 skipping of CD33 gene in THP1 cells treated by CPP-PMO$^{CD33}$ (ENTR-087, Table C), CPP-PMO$^{CD33}$ (ENTR-081, TABLE 5), or PMO$^{CD33}$ (ENTR-036, TABLE 5) with or without transfection reagent.

Figure 68A:
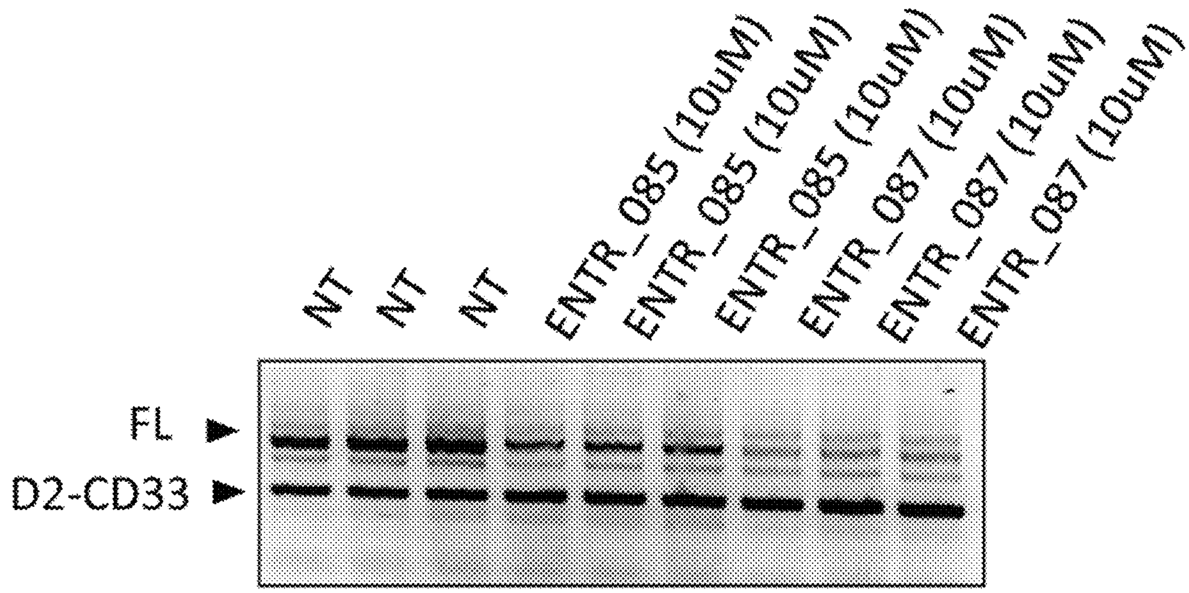
Figure 68B:
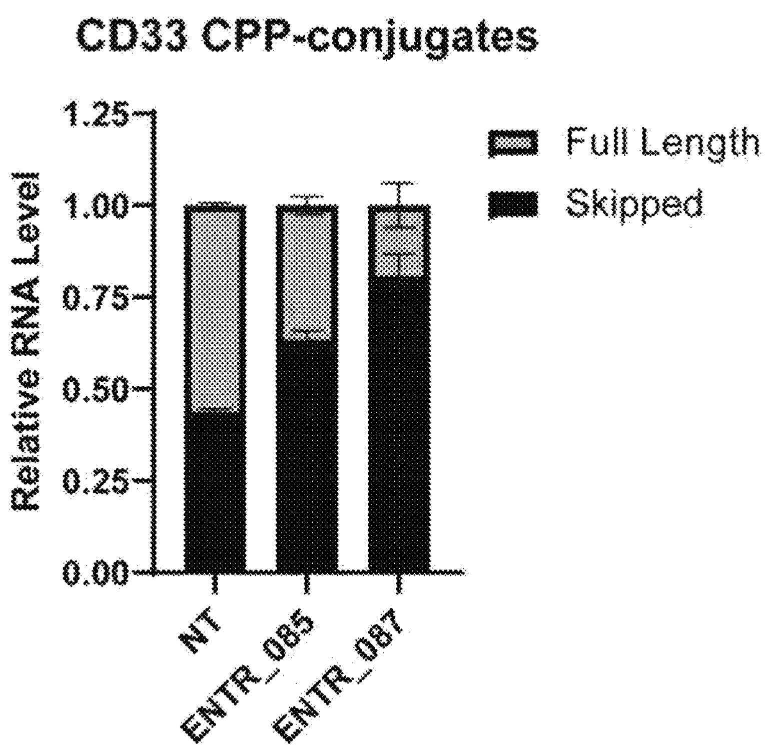

FIGS. 68A-B show RT-PCR analysis (FIG. 68A) and quantification of exon 2 skipping of CD33 gene (FIG. 68B) in THP1 cells. Differentiated THP1 cells were treated with CPP-PMO$^{CD33}$ with two different PMO sequences (15-mer in ENTR-085 and 21-mer ENTR-087) for 24 hrs.

Figure 69:
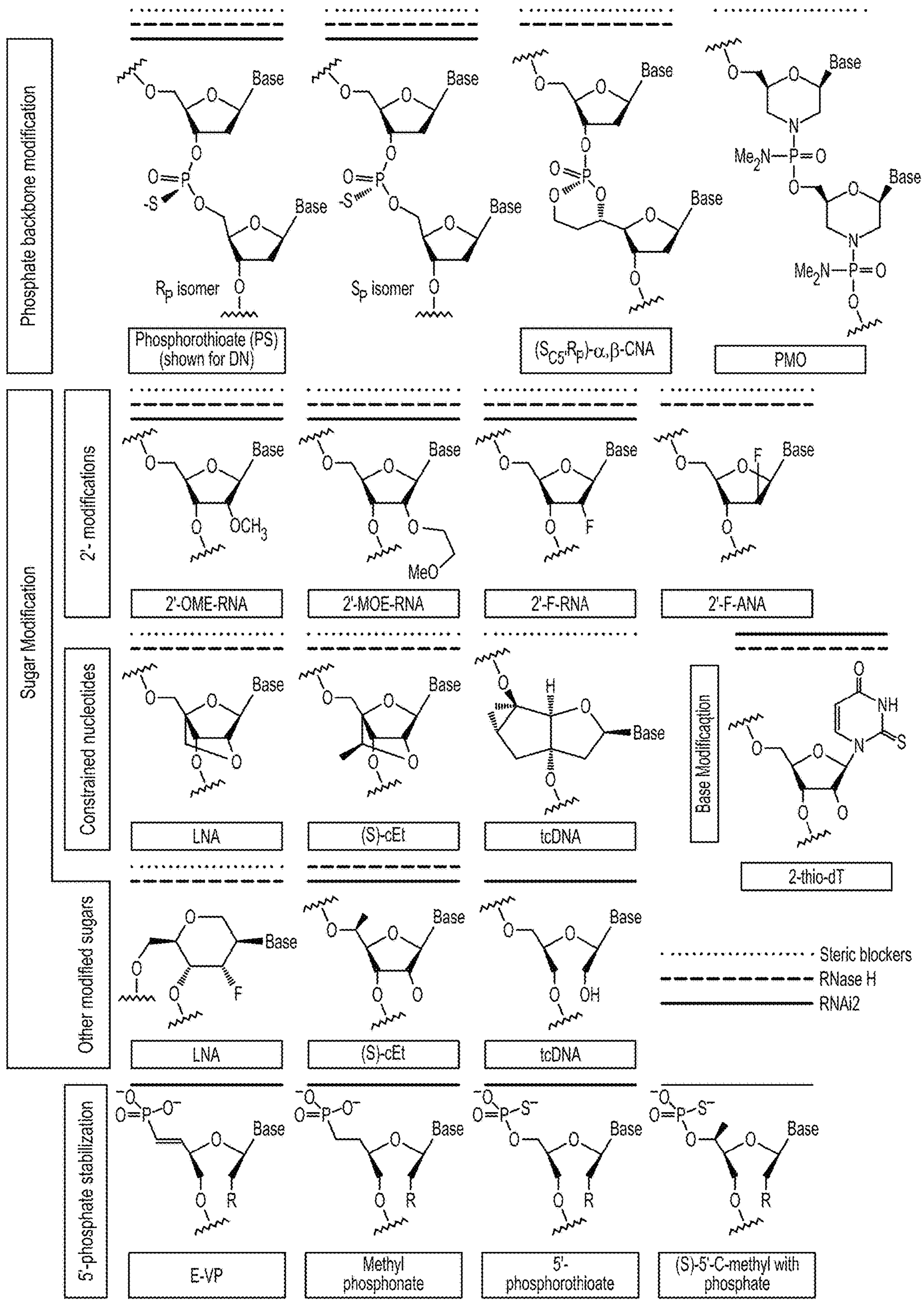

FIG. 69 shows nucleosides used in the antisense oligonucleotides of the disclosure.

DETAILED DESCRIPTION

Definitions

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non limiting examples of inorganic or metal salts include lithium, sodium, calcium, potassium, magnesium salts and the like.

As used herein, "treat," "treating," "treatment" and variants thereof, refers to any administration of the disclosed compounds that partially or completely alleviates, ameliorates, relieves, inhibits, delays onset of, reduces severity of, and/or reduces incidence of one or more symptoms or features of a disease as described herein.

As used herein, "therapeutically effective" refers to an amount of a disclosed compound which confers a therapeutic effect on a patient. In some embodiments, the therapeutically effective amount is an amount sufficient to treat a disease in a subject in need thereof.

As used herein, "cell penetrating peptide" or "CPP" refers to any cyclic peptide which is capable of penetrating a cell membrane. Cell penetrating peptides may also be referred to as an endosomal escape vehicle or EEV. In some embodiments, the CPP is cyclic, and is represented as "cCPP". The cyclic cell penetrating peptide is also capable of directing a compound (e.g., AC) to penetrate the membrane of a cell. In some embodiments, the cCPP delivers the AC to the cytosol of the cell. In some embodiments, the cCPP delivers the AC to the cellular location where the target sequence on pre-mRNA is located.

As used herein, "linker" or "L" refers to a moiety which that covalently bonds two or more moieties (e.g., a cCPP and an AC or a cCPP and CRISPR gene-editing machinery). In some embodiments, the linker can be natural or non-natural amino acid or polypeptide. In other embodiments, the linker is a synthetic compound containing two or more appropriate functional groups suitable to bind a CPP and an AC, to thereby form the compounds disclosed herein. In yet another embodiment, the linker comprises an M moiety to thereby conjugate the CPP to the AC. For example, in some embodiments, the cCPP may be covalently bound to the AC via a linker. For example, in some embodiments, the cCPP may be covalently bound to the CRISPR gene-editing machinery via a linker.

As used herein, "polypeptide" refers to a string of at least two amino acids attached to one another by a peptide bond. There is no upper limit to the number of amino acids that can be included in a polypeptide. Further, polypeptides may include non-natural amino acids, amino acid analogs, or other synthetic molecules that are capable of integrating into a polypeptide.

As used herein, the term "sequence identity" refers to the percentage of amino acids between two polypeptide sequences that are the same and in the same relative position. As such one polypeptide sequence has a certain percentage of sequence identity compared to another polypeptide sequence. For sequence comparison, typically one sequence acts as a reference sequence, to which test sequences are compared. Those of ordinary skill in the art will appreciate that two sequences are generally considered to be "substantially identical" if they contain identical residues in corresponding positions. In some embodiments, the sequence identity between two amino acid sequences may be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), in the version that exists as of the date of filing. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment)

In other embodiments, sequence identity may be determined using the Smith-Waterman algorithm, in the version that exists as of the date of filing.

As used herein, "sequence homology" refers to the percentage of amino acids between two polypeptide sequences that are homologous and in the same relative position. As such one polypeptide sequence has a certain percentage of sequence homology compared to another polypeptide sequence. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains, and substitution of one amino acid for another of the same type may often be considered a "homologous" substitution.

As is well known in this art, amino acid sequences may be compared using any of a variety of algorithms, including those available in commercial computer programs such as BLASTP, gapped BLAST, and PSI-BLAST, in existence as of the date of filing. Exemplary such programs are described in Altschul, et al., Basic local alignment search tool, *J. Mol. Biol.,* 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology.

As used herein, the term "nuclear localization sequence" (NLS) refers to an amino acid sequence which induces transport of molecules comprising such sequences or linked to such sequences into the nucleus of eukaryotic cells. Non-limiting examples of nuclear localization sequences include the nuclear localization sequence of the SV40 virus large T-antigen the minimal functional unit of which is the seven amino acid sequence PKKKRKV (SEQ ID NO: 131), the nucleoplasmin bipartite NLS with the sequence NLSKRPAAIKKAGQAKKKK (SEQ ID NO: 132), the c-myc nuclear localization sequence having the amino acid sequence PAAKRVKLD (SEQ ID NO: 133) or RQRRNELKRSF (SEQ ID NO: 134), the sequence RMRKFKNKGKDTAELRRRRVEVSVELRKAKKDEQILKRRNV (SEQ ID NO: 135) of the IBB domain from importin-alpha, the sequences VSRKRPRP (SEQ ID NO: 136) and PPKKARED (SEQ ID NO: 137) of the myoma T protein, the sequence PQPKKKPL (SEQ ID NO: 138) of human p53, the sequence SALIKKKKKMAP (SEQ ID NO: 139) of mouse c-abl IV, the sequences DRLRR (SEQ ID NO: 140) and PKQKKRK (SEQ ID NO: 141) of the influenza virus NS1, the sequence RKLKKKIKKL (SEQ ID NO: 142) of the Hepatitis virus delta antigen and the sequence REKKKFLKRR (SEQ ID NO: 143) of the mouse Mxl protein, the sequence KRKGDEVDGVDEVAKKKSKK (SEQ ID NO: 144) of the human poly(ADP-ribose) polymerase and the sequence RKCLQAGMNLEARKTKK (SEQ ID NO: 145) of the steroid hormone receptors (human) glucocorticoid. International Publication No. 2001/038547 describes additional examples of NLSs and is incorporated by reference herein in its entirety.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. The alkylene chain is attached, directly or indirectly, to the cCPP through a single bond and, directly or indirectly, to the AC through a single bond. Unless stated otherwise specifically in the specification, an alkylene chain can be optionally substituted as described herein.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. The alkenylene chain is attached, directly or indirectly, to the cCPP through a single bond and, directly or indirectly, to the AC through a single bond. Unless stated otherwise specifically in the specification, an alkenylene chain can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain, having from two to forty carbon atoms, and having one or more carbon-carbon triple bonds. Non-limiting examples of $C_2$-$C_{40}$ alkynylene include ethynylene, propargylene and the like. The alkynylene chain is attached, directly or indirectly, to the CPP through a single bond and, directly or indirectly, to the AC through a single bond. Unless stated otherwise specifically in the specification, an alkynylene chain can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Unless stated otherwise specifically in the specification, the carbocyclyl can be a monocyclic, bicyclic, tricyclic or tetracyclic ring system, which can include fused or bridged ring systems Carbocyclic rings include aryls and cycloalkyl, cycloalkenyl, and cycloalkynyl as defined herein. Unless stated otherwise specifically in the specification, a carbocyclyl group can be optionally substituted. In some embodiments, the carbocyclyl divalent, and is attached, directly or indirectly, to the CPP through a single bond and, directly or indirectly, to the AC through a single bond. Unless stated otherwise specifically in the specification, a heterocyclyl group can be optionally substituted.

"Cycloalkyl" refers to a stable non-aromatic monocyclic or polycyclic fully saturated hydrocarbon having from 3 to 40 carbon atoms and at least one ring, wherein the ring consists solely of carbon and hydrogen atoms, which can include fused or bridged ring systems. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. In some embodiments, the cycloalkyl divalent and is attached, directly or indirectly, to the CPP through a single bond and, directly or indirectly, to the AC through a single bond. Unless otherwise stated specifically in the specification, a cycloalkyl group can be optionally substituted.

"Cycloalkenyl" refers to a stable non-aromatic monocyclic or polycyclic hydrocarbon having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyls include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. In some embodiments, cycloalkenyl is divalent and is attached, directly or indirectly, to the CPP through a single bond and, directly or indirectly, to the AC through a single bond. Unless otherwise stated specifically in the specification, a cycloalkenyl group can be optionally substituted.

"Cycloalkynyl" refers to a stable non-aromatic monocyclic or polycyclic hydrocarbon having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyls include, for example, cycloheptynyl, cyclooctynyl, and the like. The cycloalkynyl is attached, directly or indirectly, to the CPP through a single bond and, directly or indirectly, to the AC through a single bond. Unless otherwise stated specifically in the specification, a cycloalkynyl group can be optionally substituted.

"Aryl" refers to a hydrocarbon ring system comprising hydrogen, 6 to 40 carbon atoms and at least one aromatic ring. For purposes of this disclosure, the aryl can be a monocyclic, bicyclic, tricyclic or tetracyclic ring system, which can include fused or bridged ring systems. Aryls include, but are not limited to, aryl divalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl divalent and is attached, directly or indirectly, to the CPP through a single bond and, directly or indirectly, to the AC through a single bond. Unless stated otherwise specifically in the specification, an aryl group can be optionally substituted.

"Heterocyclyl," "heterocyclic ring" or "heterocycle" refers to a stable 3- to 22-membered ring system which consists of two to fourteen carbon atoms and from one to eight heteroatoms selected from the group consisting of nitrogen, oxygen and sulfur. Heterocyclyl or heterocyclic rings include heteroaryls as defined below. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, succinimidyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl is divalent and is attached, directly or indirectly, to the CPP through a single bond and, directly or indirectly, to the AC through a single bond. Unless stated otherwise specifically in the specification, a heterocyclyl group can be optionally substituted.

"Heteroaryl" refers to a 5- to 22-membered aromatic ring comprising hydrogen atoms, one to fourteen carbon atoms, one to eight heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl is divalent and is attached, directly or indirectly, to the CPP through a single bond and, directly or indirectly, to the AC through a single bond. Unless stated otherwise specifically in the specification, a heteroaryl group can be optionally substituted.

The term "ether" used herein refers to a divalent moiety having a formula $—[(R_1)_m—O—(R^2)_n]_z—$ wherein each of m, n, and z are independently selected from 1 to 40, and $R^1$ and $R^2$ are independently selected from an alkylene. Examples include polyethylene glycol. The ether is attached, directly or indirectly, to the CPP through a single bond and, directly or indirectly, to the AC through a single bond. Unless stated otherwise specifically in the specification, the ether can be optionally substituted.

The term "substituted" used herein means any of the above groups (i.e., alkylene, alkenylene, alkynylene, aryl, carbocyclyl, cycloalkyl, cycloalkenyl, cycloalkynyl, heterocyclyl, heteroaryl, and/or ether) wherein at least one hydrogen atom is replaced by a bond to a non-hydrogen atoms such as, but not limited to: a deuterium atom; a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the above groups are replaced by a substituent listed in this paragraph, and the substituent then forms a covalent bond with the CPP or AC. The resulting bonding group can be considered a "substituent." For example, In some embodiments, any of the above groups can be substituted at a first position with a carboxylic acid (i.e., $—C(=O)OH$) which forms an amide bond with an appropriate amino acid CPP (e.g., lysine), and also substituted at a second position with either an electrophilic group (e.g., $—C(=O)H$, $—CO_2R_g$, -halide, etc.) or a nucleophilic group ($—NH_2$, $—NHR_g$, $—OH$, etc.) which forms a bond with the 5' end of an AC or alternatively which forms a bond with the 3' end of AC. The resulting bond, e.g., amide bond, can be considered a "substituent." In some embodiments, the second position is substituted with a thiol group which forms a disulfide bond with a thiol group attached to the AC. The resulting disulfide is encompassed by the term substituent.

As used herein, the symbol

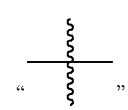

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

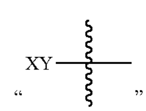

indicates that the chemical entity "XY" is bonded to another chemical entity via the point of attachment bond. Furthermore, the specific point of attachment to the non-depicted chemical entity can be specified by inference. For example, the compound $CH_3-R^3$, wherein $R^3$ is H or

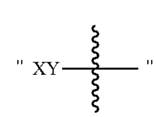

infers that when $R^3$ is "XY", the point of attachment bond is the same bond as the bond by which $R^3$ is depicted as being bonded to $CH_3$.

As used herein, the terms "antisense compound" and "AC" are used interchangeably to refer to a polymeric nucleic acid structure which is at least partially complementary to a target nucleic acid molecule to which it (the AC) hybridizes. The AC may be a short (in some embodiments, less than 50 base pair) polynucleotide or polynucleotide homologue comprising a sequence complimentary to a target sequence in a target pre-mRNA strand. The AC may be formed of natural nucleic acids, synthetic nucleic acids, nucleic acid homologues, or any combination thereof. In some embodiments, the AC comprises oligonucleosides. In some embodiments, AC comprises antisense oligonucleotides. In some embodiments, the AC comprises conjugate groups. Nonlimiting examples of ACs include, but are not limited to, primers, probes, antisense oligonucleotides, external guide sequence (EGS) oligonucleotides, alternate splicers, siRNAs, oligonucleotides, oligonucleosides, oligonucleotide analogs, oligonucleotide mimetics, and chimeric combinations of these. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound. In some embodiments, an AC modulates (increases, decreases, or changes) expression of a target nucleic acid.

The terms "pre-mRNA" and "primary transcript" as used herein refer to a newly synthesized eukaryotic mRNA molecule directly after DNA transcription. A pre-mRNA must be capped with a 5' cap, modified with a 3' poly-A tail, and spliced to produce a mature mRNA sequence.

As used herein, the terms "target nucleic acid" and "target sequence" refer to the nucleic acid sequence to which the antisense compound binds or hybridizes. Target nucleic acids include, but are not limited to, RNA (including, but not limited to pre-mRNA and mRNA or portions thereof), cDNA derived from such RNA, as well as non-translated RNA, such as miRNA. For example, in some embodiments, a target nucleic acid can be a cellular gene (or mRNA transcribed from such gene) whose expression is associated with a particular disorder or disease state, or a nucleic acid molecule from an infectious agent.

As used herein, the terms "splicing" and "processing" refer to the modification of a pre-mRNA following transcription, in which introns are removed and exons are joined. Splicing occurs in a series of reactions that are catalyzed by a large RNA-protein complex composed of five small nuclear ribonucleoproteins (snRNPs) referred to as a spliceosome. Within an intron, a 3' splice site, a 5' splice site, and a branch site are required for splicing. The RNA components of snRNPs interact with the intron and may be involved in catalysis The "target pre-mRNA" is the pre-mRNA comprising the target sequence to which the AC hybridizes.

The "target mRNA" is the mRNA sequence resulting from splicing of the target pre-mRNA sequence. In some embodiments, the target mRNA does not encode a functional protein. In some embodiments, the target mRNA retains one or more intron sequences.

The "target gene" of the present disclosure refers to the gene that encodes the target pre-mRNA.

The "target protein" refers to the amino acid sequence encoded by the target mRNA. In some embodiments, the target protein may not be a functional protein.

"Wild type target protein" refers to a native, functional protein isomer produced by a wild type, normal, or unmutated version of the target gene. The wild type target protein also refers to the protein resulting from a target pre-mRNA that has been properly spliced.

A "re-spliced target protein", as used herein, refers to the protein encoded by the mRNA resulting from the splicing of the target pre-mRNA to which the AC hybridizes. Re-spliced target protein may be identical to a wild type target protein, may be homologous to a wild type target protein, may be a functional variant of a wild type target protein, or may be an active fragment of a wild type target protein.

As used herein, "functional fragment" or "active fragment" refers to a portion of a eukaryotic wild type target protein that exhibits an activity, such as one or more activities of a full-length wild type target protein, or that possesses another activity. In some embodiments, a re-spliced target protein that shares at least one biological activity of wild type target protein is considered to be an active fragment of the wild type target protein. Activity can be any percentage of activity (i.e., more or less) of the full-length wild type target protein, including but not limited to, about 1% of the activity, about 2%, about 3%, about 4%, about 5%, about 10%, about 20%, about 30%, about 40%, about 50%, about 60%, about 70%, about 80%, about 90%, about 95%, about 96%, about 97%, about 98%, about 99%, about 100%, about 200%, about 300%, about 400%, about 500%, or more (including all values and ranges inbetween these values) activity compared to the wild type target protein. Thus, in some embodiments, the active fragment may retain at least a portion of one or more biological activities of wild type target protein. In other embodiments, the active fragment may enhance one or more biological activities of wild type target protein.

As used herein, the term "nucleoside" means a glycosylamine comprising a nucleobase and a sugar. Nucleosides includes, but are not limited to, natural nucleosides, abasic nucleosides, modified nucleosides, and nucleosides having mimetic bases and/or sugar groups. A "natural nucleoside" or "unmodified nucleoside" is a nucleoside comprising a natural nucleobase and a natural sugar. Natural nucleosides include RNA and DNA nucleosides.

As used herein, the term "natural sugar" refers to a sugar of a nucleoside that is unmodified from its naturally occurring form in RNA (2'-OH) or DNA (2'-H).

As used herein, the term "nucleotide" refers to a nucleoside having a phosphate group covalently linked to the sugar. Nucleotides may be modified with any of a variety of substituents.

As used herein, the term "nucleobase" refers to the base portion of a nucleoside or nucleotide. A nucleobase may comprise any atom or group of atoms capable of hydrogen bonding to a base of another nucleic acid. A natural nucleobase is a nucleobase that is unmodified from its naturally occurring form in RNA or DNA.

As used herein, the term "heterocyclic base moiety" refers to a nucleobase comprising a heterocycle.

As used herein "oligonucleoside" refers to an oligonucleotide in which the internucleoside linkages do not contain a phosphorus atom.

As used herein, the term "oligonucleotide" refers to an oligomeric compound comprising a plurality of linked nucleotides or nucleosides. In certain embodiment, one or more nucleotides of an oligonucleotide is modified. In some embodiments, an oligonucleotide comprises ribonucleic acid (RNA) or deoxyribonucleic acid (DNA). In some embodiments, oligonucleotides are composed of natural and/or modified nucleobases, sugars and covalent internucleoside linkages, and may further include non-nucleic acid conjugates.

As used herein "internucleoside linkage" refers to a covalent linkage between adjacent nucleosides.

As used herein "natural internucleotide linkage" refers to a 3' to 5' phosphodiester linkage.

As used herein, the term "modified internucleoside linkage" refers to any linkage between nucleosides or nucleotides other than a naturally occurring internucleoside linkage.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound as described herein.

As used herein, the term "mixed-backbone antisense oligonucleotide" refers to an antisense oligonucleotide wherein at least one internucleoside linkage of the antisense oligonucleotide is different from at least one other internucleotide linkage of the antisense oligonucleotide.

As used herein, the term "nucleobase complementarity" refers to a nucleobase that is capable of base pairing with another nucleobase. For example, in DNA, adenine (A) is complementary to thymine (T). For example, in RNA, adenine (A) is complementary to uracil (U). In some embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a pair of nucleobases that do not form hydrogen bonds with one another or otherwise support hybridization.

As used herein, the term "complementary" refers to the capacity of an oligomeric compound to hybridize to another oligomeric compound or nucleic acid through nucleobase complementarity. In some embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% nucleobase complementary to a target nucleic acid.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In some embodiments, an antisense oligonucleotide specifically hybridizes to more than one target site. In some embodiments, an oligomeric compound specifically hybridizes with its target under stringent hybridization conditions.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

As used herein, the term "2'-modified" or "2'-substituted" means a sugar comprising substituent at the 2' position other than H or OH. 2'-modified monomers, include, but are not limited to, BNA's and monomers (e.g., nucleosides and nucleotides) with 2'-substituents, such as allyl, amino, azido, thio, O-allyl, O-C1-C10 alkyl, —OCF3, O—(CH2)2—O—CH3, 2'—O($CH_2$)2SCH3, O—(CH2)2—O—N(Rm)(Rn), or O—CH2—C(═O)—N(Rm)(Rn), where each Rm and Rn is, independently, H or substituted or unsubstituted C1-C10 alkyl.

As used herein, the term "MOE" refers to a 2'-O-methoxyethyl substituent.

As used herein, the term "high-affinity modified nucleotide" refers to a nucleotide having at least one modified nucleobase, internucleoside linkage or sugar moiety, such that the modification increases the affinity of an antisense compound comprising the modified nucleotide to a target nucleic acid. High-affinity modifications include, but are not limited to, BNAs, LNAs and 2'-MOE.

As used herein the term "mimetic" refers to groups that are substituted for a sugar, a nucleobase, and/or internucleoside linkage in an AC. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein, the term "bicyclic nucleoside" or "BNA" refers to a nucleoside wherein the furanose portion of the nucleoside includes a bridge connecting two atoms on the furanose ring, thereby forming a bicyclic ring system. BNAs include, but are not limited to, α-L-LNA, β-D-LNA, ENA, Oxyamino BNA (2'-O—N(CH3)—CH2-4') and Aminooxy BNA (2'-N(CH3)—O—CH2-4').

As used herein, the term "4' to 2' bicyclic nucleoside" refers to a BNA wherein the bridge connecting two atoms of the furanose ring bridges the 4' carbon atom and the 2' carbon atom of the furanose ring, thereby forming a bicyclic ring system.

As used herein, the term "subcutaneous administration" refers to administration just below the skin. "Intravenous administration" means administration into a vein.

As used herein, the term "dose" refers to a specified quantity of a pharmaceutical agent provided in a single administration. In some embodiments, a dose may be administered in two or more boluses, tablets, or injections. For example, In some embodiments, where subcutaneous administration is desired, the desired dose requires a volume not easily accommodated by a single injection. In such embodiments, two or more injections may be used to achieve the desired dose. In some embodiments, a dose may be administered in two or more injections to minimize injection site reaction in an individual.

As used herein, the term "dosage unit" refers to a form in which a pharmaceutical agent is provided. In some embodiments, a dosage unit is a vial comprising lyophilized antisense oligonucleotide. In some embodiments, a dosage unit is a vial comprising reconstituted antisense oligonucleotide.

Below is a list of abbrevations found herein: TFP refers to tetrafluorophenyl; Dap refers to diammonium phosphate; BCN refers to Nbenzyloxycarbonyloxy-5-norbornene-2,3-dicarboximide; PYAOP is tripyrrolidinophosphonium hexafluorophosphate; DIPEA is N,N-Diisopropylethylamine. Pip6a refers to a peptide with a sequence of.

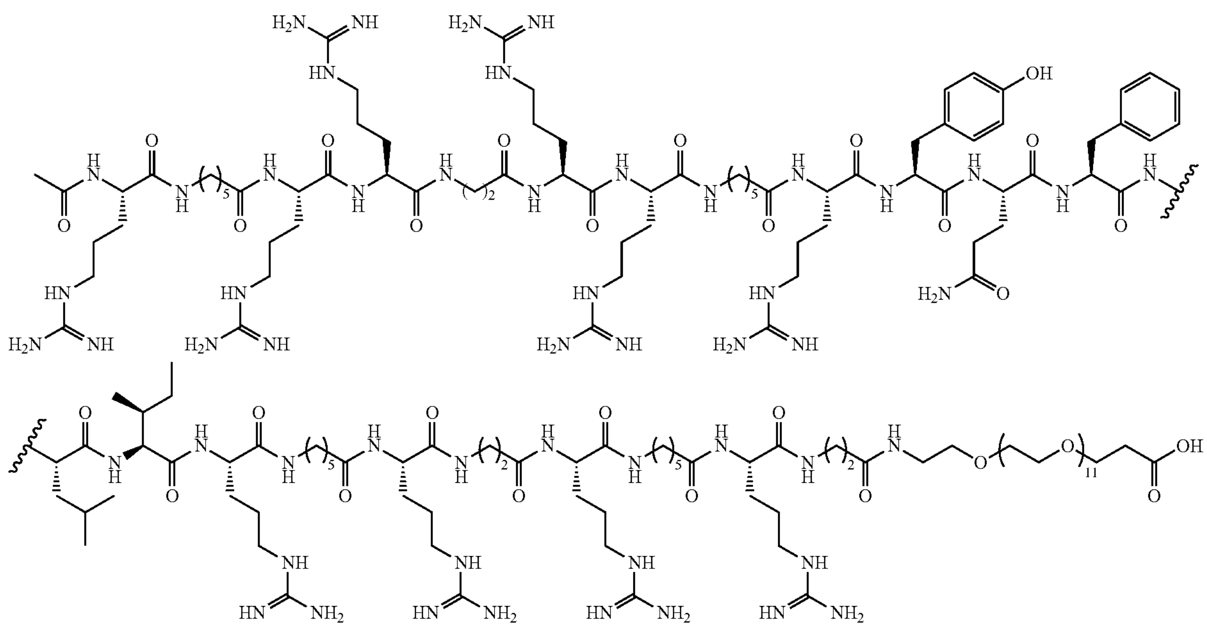

As used herein, a "locked nucleic acid" or "LNA" refers to a nucleotide modified such that the 2'-hydroxyl group of the ribosyl sugar ring is linked to the 4' carbon atom of the sugar ring via a methylene groups, thereby forming a 2'-C,4'-C-oxymethylene linkage. LNAs include, but are not limited to, α-L-LNA, and R-D-LNA.

As used herein, the term "cap structure" or "terminal cap moiety" refers to chemical modifications, which have been incorporated at either end of an AC.

As used herein, the term "parenteral administration," refers to administration through injection or infusion. Parenteral administration includes, but is not limited to, subcutaneous administration, intravenous administration, or intramuscular administration.

Compounds

Disclosed herein, in various embodiments, are compounds for treating disease. The compounds described herein comprise a cell-penetrating peptide and an antisense compound (AC). The compounds are designed to deliver an antisense compound (AC) intracellularly to subjects in need thereof Upon cell entry, the AC binds to the target mRNA or pre-mRNA. By doing so, the compounds disclosed herein reduce or prevent splicing, inhibit or regulate translation, mediate degradation, or block expansions of nucleotide repeats.

When the compounds of the disclosure reduce or prevent splicing, the resulting re-spliced target protein may be more functional than the target protein produced by the splicing of the target pre-mRNA in the absence of the AC. In some embodiments, the re-spliced target protein increases target protein function by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, about 100%, about 150%, about 200%, about 250%, about 300%, about 350%, about 400%, about 450%, about 500%, or more, compared to the function of the target protein produced by splicing, inclusive of all values and ranges therebetween. In some embodiments, the re-spliced target protein restores function to about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100% of the function of a wild type target protein, inclusive of all values and ranges therebetween.

Similarly, the compounds of the disclosure can inhibit or regulate translation, mediate degradation, or block expansions of nucleotide repeats of a target by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100% of the function of a wild type target protein, inclusive of all values and ranges therebetween.

In various embodiments, the compounds disclosed herein have an AC moiety and/or CRISPR gene-editing machinery and cell penetrating activity (e.g., a cCPP), such that the compounds are able to traverse the cell membrane and bind to target pre-mRNA in vivo. In some embodiments, the compounds comprise: a) at least one CPP moiety; and b) at least one AC and/or at least one CRISPR gene-editing machinery, wherein the CPP is coupled, directly or indirectly, to the AC and/or CRISPR gene-editing machinery. In some embodiments, the compounds comprise 1, 2, 3, 4, 5, 6, 7, 8, 9, 10, or more AC moieties. In some embodiments, the compounds comprise 1, 2, 3, 4, 5, 6, 7, 8, 9, 10, or more CPP moieties. In some embodiments, the compounds comprise 1, 2, 3, 4, 5, 6, 7, 8, 9, 10, or more CRISPR gene-editing machinery. In some embodiments, the compounds comprise one AC moiety. In some embodiments, the compounds comprise two AC moieties. As used herein, "coupled" can refer to a covalent or non-covalent association between the CPP to the AC, including fusion of the CPP to the AC and chemical conjugation of the CPP to the AC. A non-limiting example of a means to non-covalently attach the CPP to the AC is through the streptavidin/biotin interaction, e.g., by conjugating biotin to CPP and fusing AC to streptavidin. In the resulting compound, the CPP is coupled to the AC via non-covalent association between biotin and streptavidin.

In some embodiments, the CPP is conjugated, directly or indirectly, to the AC to thereby form a CPP-AC conjugate. Conjugation of the AC to the CPP may occur at any appropriate site on these moieties. For example, in some embodiments, the 5' or the 3' end of the AC may be conjugated to the C-terminus, the N-terminus, or a side chain of an amino acid in the CPP.

In some embodiments, the AC is covalently linked to the CPP. Covalent linkage, as used herein, refer to constructs where a linear CPP moiety is covalently linked to the 5' and/or 3' end of the AC moiety. Such conjugates may alternatively be described as having a cell penetrating moiety and an oligonucleotide moiety. Methods of covalent linkage are well-known in the art. A covalently-linked AC-CPP conjugate, in accordance with certain embodiments of the disclosure, includes the AC component and the linear CPP component associated with one another by linkers.

In other embodiments, the AC may be chemically conjugated to the CPP through a moiety on the 5' or 3' end of the AC. In still other embodiments, the AC may be conjugated to the CPP through a side chain of an amino acid on the CPP. Any amino acid side chain on the CPP which is capable of forming a covalent bond, or which may be so modified, can be used to link AC to the CPP. The amino acid on the CPP can be a natural or non-natural amino acid. In some embodiments, the amino acid on the CPP used to conjugate the AC is aspartic acid, glutamic acid, glutamine, asparagine, lysine, ornithine, 2,3-diaminopropionic acid, or analogs thereof, wherein the side chain is substituted with a bond to the AC or linker. In particular embodiments, the amino acid is lysine, or an analog thereof In other embodiments, the amino acid is glutamic acid, or an analog thereof. In further embodiments, the amino acid is aspartic acid, or an analog thereof.

In some embodiments of the present disclosure, the compounds further comprise a linker (L), which conjugates the CPP to AC. In some embodiments, L conjugates the CPP to the 5' or the 3' end of the AC. In some embodiments of the present disclosure, the compounds further comprise a linker (L), which conjugates a CPP to CRISPR gene-editing machinery. In some embodiments, L conjugates the CPP to the gRNA. In some embodiments, L conjugates the CPP to the nuclease.

In some embodiments, compounds comprising an AC moiety and CPP comprise a nuclear localization sequence (NLS). In some embodiments, the NLS is coupled to the AC. In some embodiments, the NLS is coupled to the CPP. In some embodiments, the NLS is coupled to the AC and the CPP. Coupling between the NLS, AC, CPP, or combinations thereof, may be non-covalent or covalent. In some embodiments, the NLS is attached through a peptide bond to the N-terminus of the CPP. In some embodiments, the NLS is attached through a peptide bond to the C-terminus of the CPP. In some embodiments, the NLS is attached to the CPP through a side chain of an amino acid in the CPP. In some embodiments, the NLS is attached to the CPP through a side chain of a lysine which is conjugated to the side chain of a glutamine in the CPP. In some embodiments, the NLS is conjugated to the 5' or 3' end of an AC. In some embodiments, the NLS is coupled to a linker. In some embodiments, the NLS is coupled to a linker via the C-terminus of an NLS and a CPP through a side chain on the CPP and/or NLS. For example, an NLS may comprise a terminal lysine which is then coupled to a CPP containing a glutamine through an amide bond. When the NLS contains a terminal lysine, and the side chain of the lysine is used to attach the CPP, the C- or N-terminus may be attached to the linker on the AC.

In some embodiments, the CPP is cyclic (as described herein), and referred to herein as a cCPP. There are numerous possible configurations for the compounds disclosed herein. In some embodiments, the compounds of the disclosure are exocyclic compounds wherein AC is conjugated to the side chain of an amino acid in the cCPP. In some embodiments, the compounds disclosed herein have structure (i.e., exocyclic) according to Formula I-A or Formula I-A1:

$$\text{CPP—L—AC} \quad \text{or} \tag{I-A}$$

$$\text{AC—L—CPP,} \tag{I-A1}$$

wherein L is covalently bound to the side chain of an amino acid on the CPP and to the 5' end of the AC, the backbone of the AC, or the 3' end of the AC.

In some embodiments, the compounds (e.g., exocyclic compounds) disclosed herein have a structure according to Formula I-A:

(I-A)

CPP—L—AC, wherein L is covalently bound to the side chain of an amino acid on the CPP and to the 5' or 3' end of the AC.

In some embodiments, the compound of the present disclosure is a compound of Formula (I) having the structure:

(I)

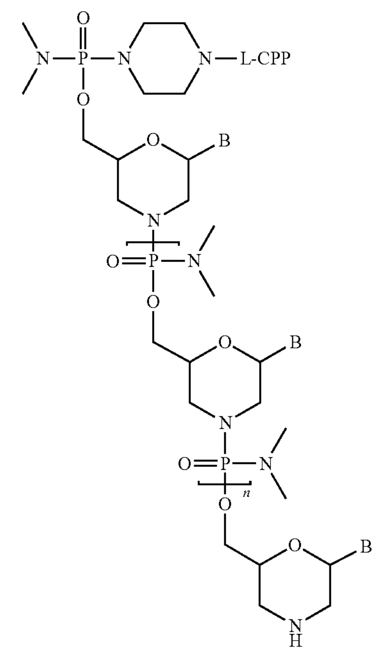

wherein.

B is each independently a nucleobase that is complementary to a base in the target sequence;

n is 1 to 50; and

L is a linker.

In some embodiments, n is an integer from 5 to 50, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, inclusive of all subranges therebetween. In some embodiments, n is an integer from 1 to 40. In some embodiments, n is an integer from 1 to 30. In some embodiments, n is an integer from 1 to 20. In some embodiments, n is an integer from 1 to 10.

L may be any appropriate moiety which conjugates CPP (e.g., as described herein) to a AC moiety. Thus, prior to conjugation to the CPP and AC, the linker has two or more functional groups, each of which are independently capable of forming a covalent bond to the CPP moiety and the AC moiety. In various embodiments of the present disclosure, L is covalently bound to the 5' end of the AC or the 3' end of the AC. In some embodiments, L is covalently bound to the 5' end of the AC. In other embodiments, L is covalently bound to the 3' end of the AC. In still other embodiments, L is covalently bound to the backbone of the AC.

L may be any appropriate moiety which conjugates CPP (e.g., as described herein) to an oligonucleotide. Thus, prior to conjugation to the CPP and the AC, the linker has two or more functional groups, each of which are independently capable of forming a covalent bond to the CPP moiety and the AC. In various embodiments of the present disclosure, L is covalently bound to a nucleophilic moiety on the AC. In some embodiments, the nucleophilic moiety is conjugated to the AC so that the AC can be attached to the CPP through L. In some embodiments, L is covalently bound to a piperazine moiety on the AC. In some embodiments, L is covalently bound to a side chain or terminus of an amino acid on the CPP. In certain embodiments, L is covalently bound to the side chain of an amino acid on the CPP.

In various embodiments of the present disclosure, L comprises (i) one or more D or L amino acids, each of which is optionally substituted; (ii) alkylene, alkenylene, alkynylene, carbocyclyl, or heterocyclyl, each of which is optionally substituted; or (iii) —($R^1$—X—$R^2$)z-, wherein each of $R^1$ and $R^2$, at each instance, are independently selected from alkylene, alkenylene, alkynylene, carbocyclyl, and heterocyclyl, each X is independently $NR^3$, —NR $^3$C(O)—, S, and O, wherein $R^3$ is H, alkyl, alkenyl, alkynyl, carbocyclyl, or heterocyclyl, each of which is optionally substituted, and z is an integer from 1 to 50; or (iv) combinations thereof. In some embodiments, L comprises one or more D or L amino acids, each of which is optionally substituted. In other embodiments, L comprises alkylene, alkenylene, alkynylene, carbocyclyl, or heterocyclyl, each of which is optionally substituted. In still other embodiments, L comprises —($R^1$—X—$R^2$)z-, wherein each of $R^1$ and $R^2$, at each instance, are independently selected from alkylene, alkenylene, alkynylene, carbocyclyl, and heterocyclyl, each X is independently $NR^3$, —NR $^3$C(O)—, S, and O, wherein $R^3$ is H, alkyl, alkenyl, alkynyl, carbocyclyl, or heterocyclyl, each of which is optionally substituted, and z is an integer from 1 to 50; or combinations thereof. In certain embodiments, L is an ether, which is optionally substituted. In more specific embodiments, L comprises —($CH_2$—O—$CH_2$)z-, wherein Z is an integer from 1-50. In more specific embodiments, L comprises —($CH_2$—O—$CH_2$)z-, wherein Z is an integer from 1-25 (e.g., 12), and one or more D or L amino acids, such as and lysine. For example, in various embodiments, L comprises a polyethylene glycol moiety, having from 1 to 50 ethylene glycol units, and a lysine residue. In other specific embodiments, L comprises —($CH_2$—S—$CH_2$)z-, wherein z is an integer from 1-50. In still other specific embodiments, L comprises —($CH_2$—$NR^3$—$CH_2$)z-, wherein $R^3$ is H, —C(O), alkyl, alkenyl, alkynyl, carbocyclyl, or heterocyclyl, each of which is optionally substituted, and z is an integer from 1-50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, inclusive of all subranges therebetween. In some embodiments, z is an integer from 10-15. In a specific embodiment, z is 12.

In some embodiments, the CPP is attached to the AC through a linker ("L"). In some embodiments, the linker is conjugated to the AC through a bonding group ("M").

As discussed above, L or M may be covalently bound to AC at any suitable location on AC. In various embodiments of the present disclosure, L or M is covalently bound to the 3' end of AC or the 5' end of AC. In some embodiments, L or M is covalently bound to the backbone of AC.

In some embodiments, L is bound to the side chain of aspartic acid, glutamic acid, glutamine, asparagine, or lysine, or a modified side chain of glutamine or asparagine (e.g., a reduced side chain having an amino group), on the CPP. In particular embodiments, the L is bound to the side chain of lysine on the CPP.

In some embodiments, L has a structure according to Formula (II):

(II)

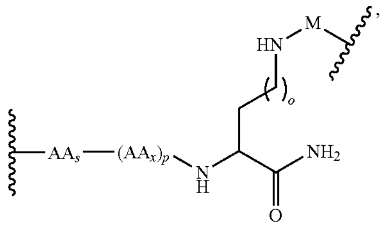

wherein

M is a group that conjugates L to an oligonucleotide;

$AA_s$ is a side chain or terminus of an amino acid on the CPP;

$AA_x$ is an amino acid;

o is an integer from 0 to 10; and p is an integer from 0 to 5.

In some embodiments, L has a structure according to Formula (III):

(III)

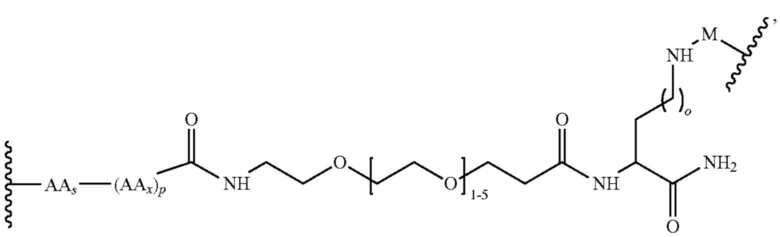

wherein

M is a group that conjugates L to an oligonucleotide;

$AA_s$ is a side chain or terminus of an amino acid on the CPP;

$AA_x$ is an amino acid;

o is an integer from 0 to 10; and p is an integer from 0 to 5.

L or M may be covalently bound to the AC at any suitable location on the AC (e.g., the 3' or 5' end). In various embodiments of the present disclosure, M is covalently bound to a nucleophilic moiety on the AC. In some embodiments, the nucleophilic moiety is a nitrogen-containing moiety. In some embodiments, M is covalently bound to a piperazine moiety of the AC.

In some embodiments of Formula (II), M comprises an alkylene, alkenylene, alkynylene, carbocyclyl, or heterocyclyl, each of which is optionally substituted. In some embodiments, M is selected from the group consisting of:

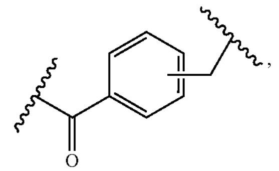

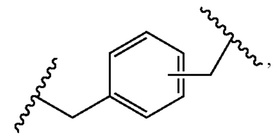

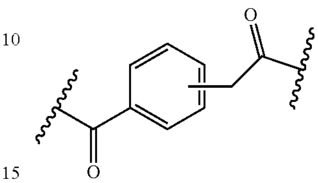

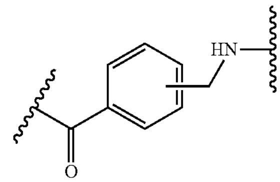

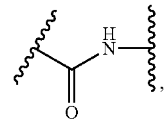

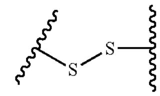

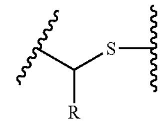

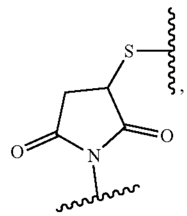

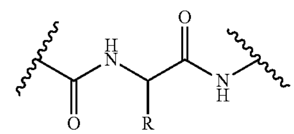

-continued

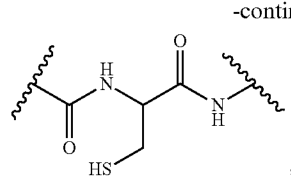

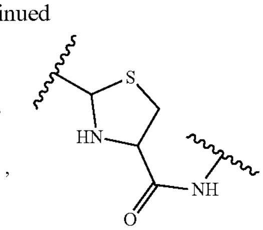

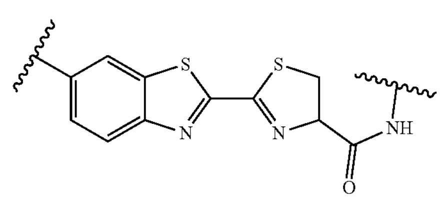

-continued
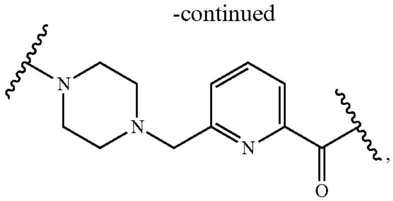
and
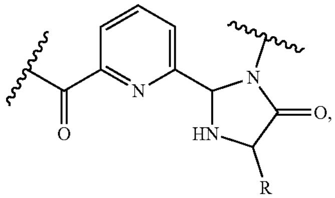
wherein R is alkyl, alkenyl, alkynyl, carbocyclyl, or heterocyclyl.
In some embodiments, M is selected from the group consisting of:
wherein: $R^1$ is alkylene, cycloalkyl, or
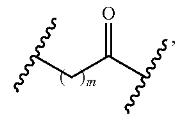
wherein m is 0 to 10. In some embodiments, M is
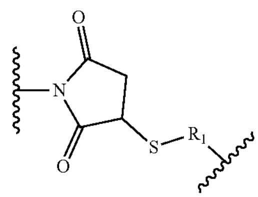
, $R^1$ is
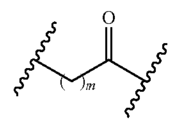
,
m is 0 to 10.
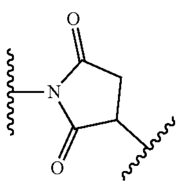
,
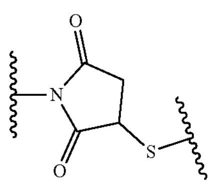
,
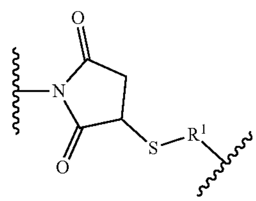
,
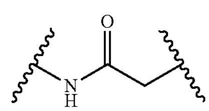
,
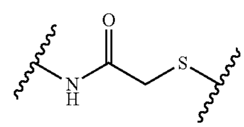
, and
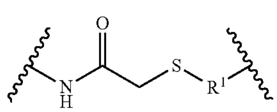
,
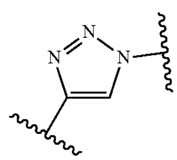
,
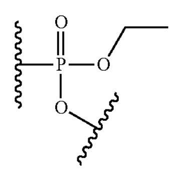
,
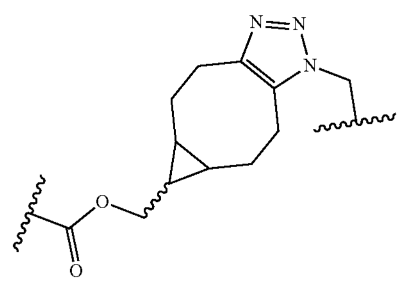
,
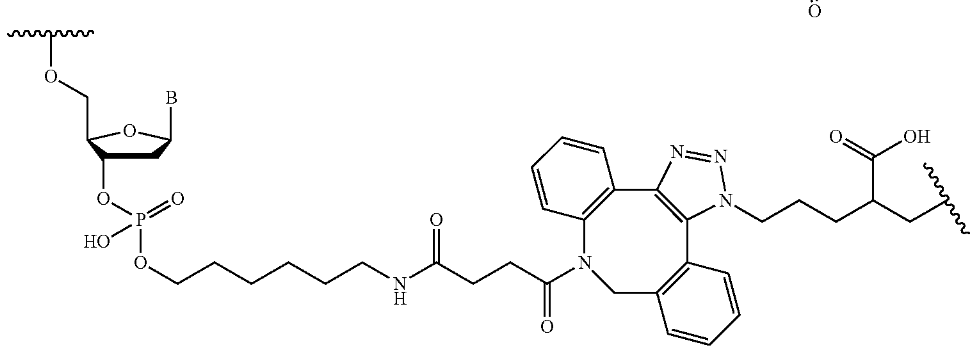
, and
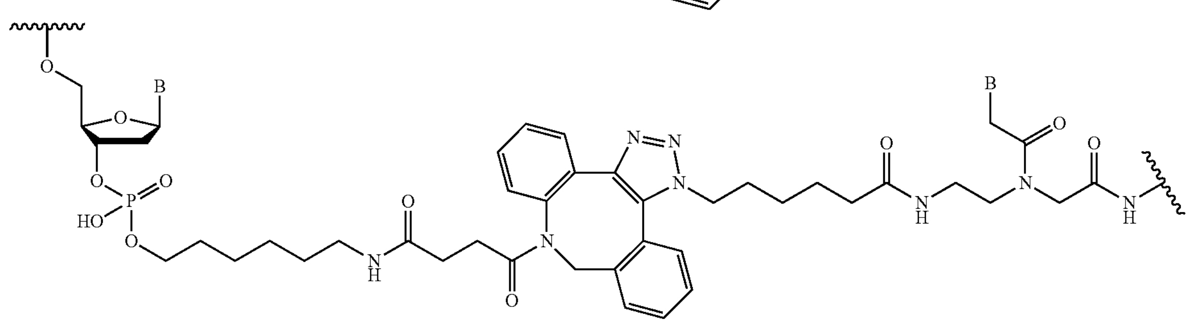
.

In some embodiments, M is a heterobifunctional cross-linker, e.g.,

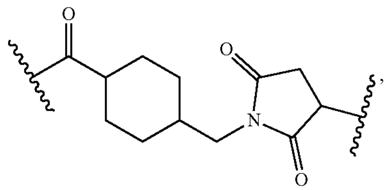 [SMILES: *C(=O)C1CCC(CN2C(=O)CC(*)C2=O)CC1]

which is disclosed in Williams et al. *Curr. Protoc Nucleic Acid Chem.* 2010, 42, 4.41.1-4.41.20, incorporated herein by reference its entirety.

In some embodiments, m is an integer from 0 to 10, e.g., 0, 1, 2, 3, 4, 5, 6, 7, 8, 9, and 10. In some embodiments, m is an integer from 1 to 5. In some embodiments, m is an integer from 1 to 3. In some embodiments, m is 1. In some embodiments, m is 2. In some embodiments, m is 3. In some embodiments, m is 4. In some embodiments, m is 5.

In some embodiments, $AA_s$ is a side chain or terminus of an amino acid on the CPP. Non-limiting examples of $AA_s$ include aspartic acid, glutamic acid, glutamine, asparagine, or lysine, or a modified side chain of glutamine or asparagine (e.g., a reduced side chain having an amino group).

In some embodiments, each $AA_x$ is independently a natural or non-natural amino acid. In some embodiments, one or more $AA_x$ is a natural amino acid. In some embodiments, one or more $AA_x$ is a non-natural amino acid. In some embodiments, one or more $AA_x$ is a f-amino acid. In some embodiments, the f-amino acid is β-alanine.

In some embodiments, o is an integer from 0 to 10, e.g., 0, 1, 2, 3, 4, 5, 6, 7, 8, 9, and 10. In some embodiments, o is 0, 1, 2, or 3. In some embodiments, o is 0. In other embodiments, o is 1. In still other embodiments, o is 2. In yet another embodiment, o is 3.

In some embodiments, p is 0 to 5, e.g., 0, 1, 2, 3, 4, or 5. In some embodiments, p is 0. In other embodiments, p is 1. In still other embodiments p is 2. In yet other embodiments, p is 3. In another embodiment, p is 4. In still another embodiment, p is 5.

In some embodiments, L has a structure according to Formula II-A or Formula II-B:

(II-A)

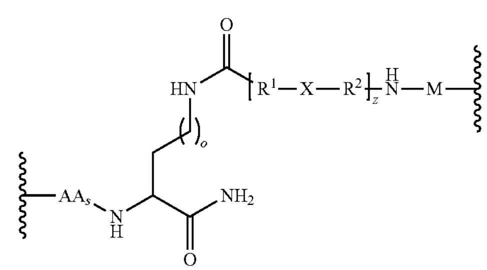

or (II-B)

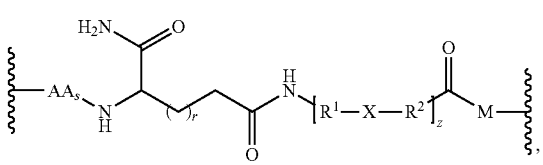

wherein M, $AA_s$, each —($R^1$—X—$R^2$)z-, and o are defined as above for Formula (II); and r is 0 or 1.

In some embodiments, r is 0. In some embodiments, r is 1.

In some embodiments, each of $R^1$ and $R^2$, at each instance, are independently selected from alkylene, alkenylene, alkynylene, carbocyclyl, and heterocyclyl, each of which is optionally substituted.

In some embodiments, each X is independently $NR^3$, —$NR^3C(O)$—, S, and O, and wherein $R^3$ is independently selected from H, alkyl, alkenyl, alkynyl, carbocyclyl, and heterocyclyl, each of which is optionally substituted.

In some embodiments, L has a structure according to Formula II-A' or II-B':

(II-A')

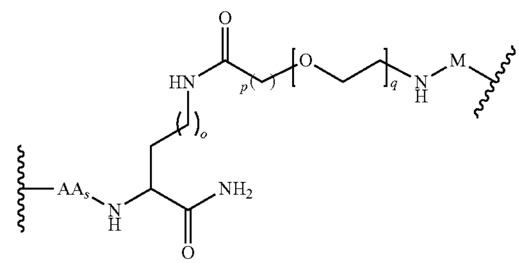

(II-B')

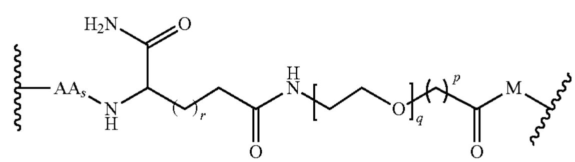

wherein each of M, $AA_s$, o, p, and r are defined above.

In some embodiments, q is an integer from 1 to 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, inclusive of all ranges and values therebetween. In other embodiments, q is an integer from 5-20. In other embodiments, q is an integer from 10-15.

In some embodiments, L has a structure according to Formula (IIc):

(IIc)

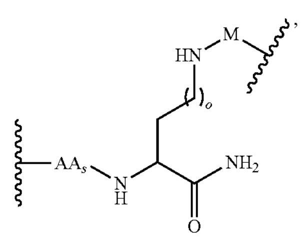

wherein:

M, $AA_s$ and o are as defined above for Formula I.

Other non-limiting examples of suitable L groups include:
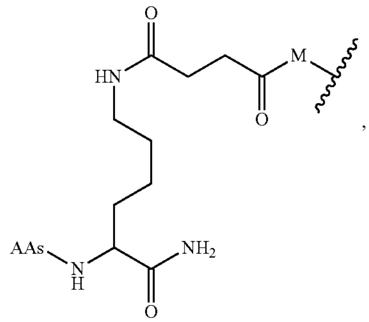
,
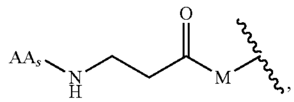
,
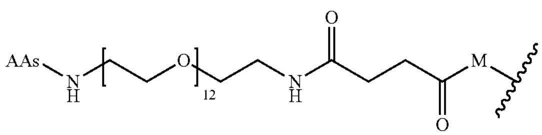
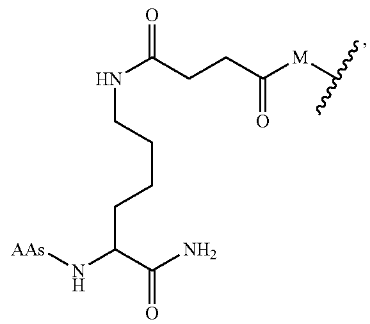
,
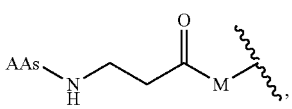
,
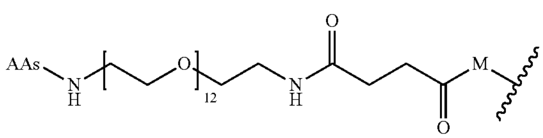
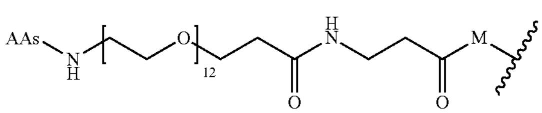
,
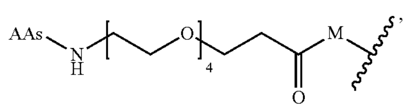
,
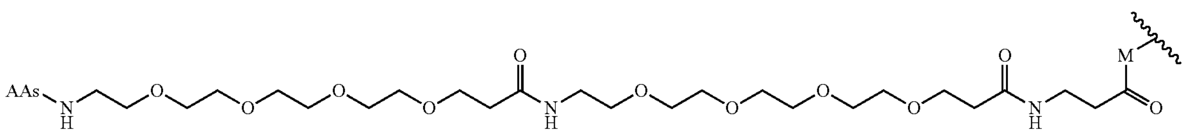
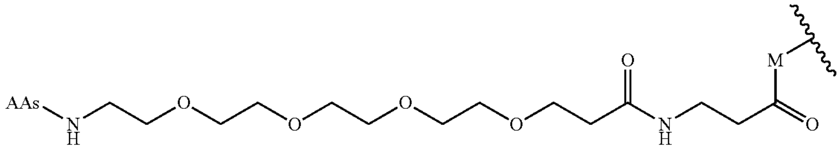
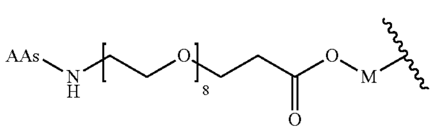
,
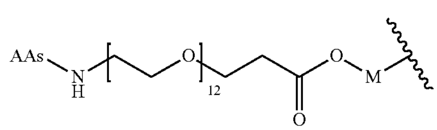
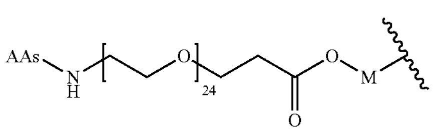
,
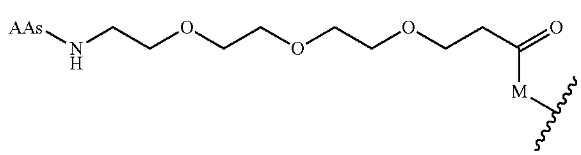
, -continued
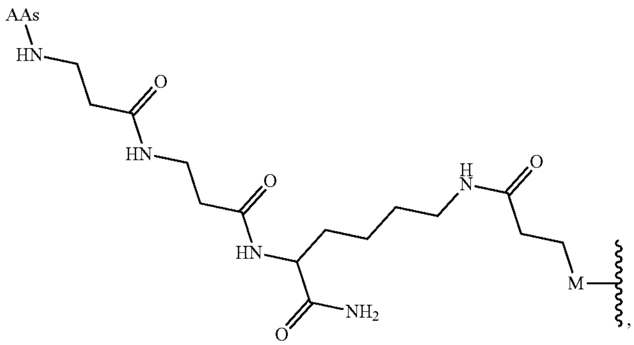,
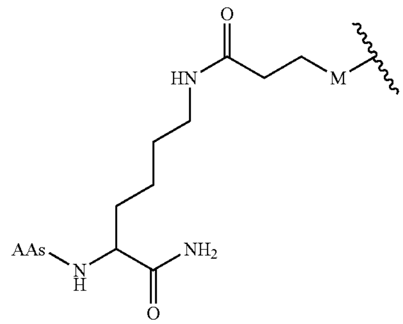
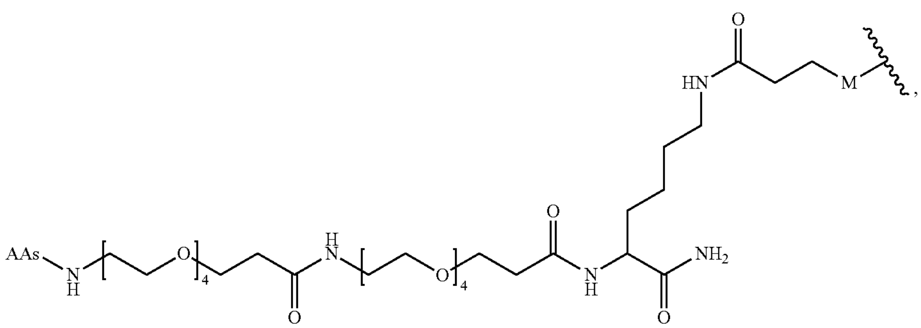,
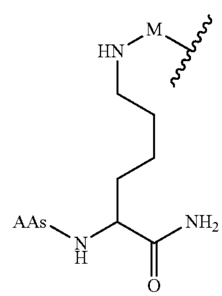
and
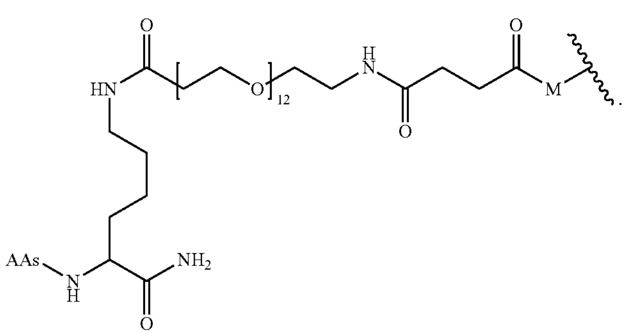.

In some embodiments, L and M have the following structure:

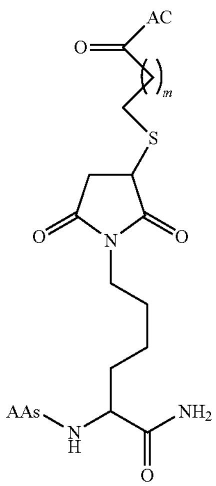

In some embodiments, the present disclosure provides a compound of Formula (Ia) having the structure:

(Ia)

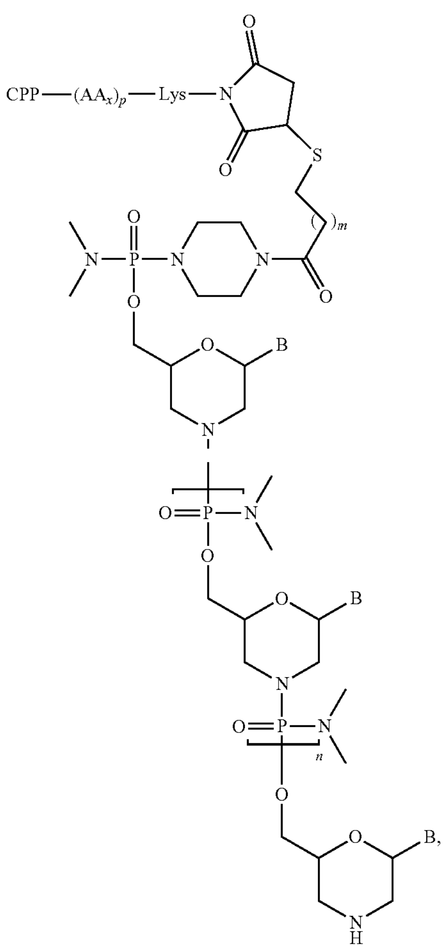

wherein:

m, n, p, $AA_x$, and B are as defined above.

In some embodiments, the present disclosure provides a compound of Formula (Ib) having the structure:

(Ib)

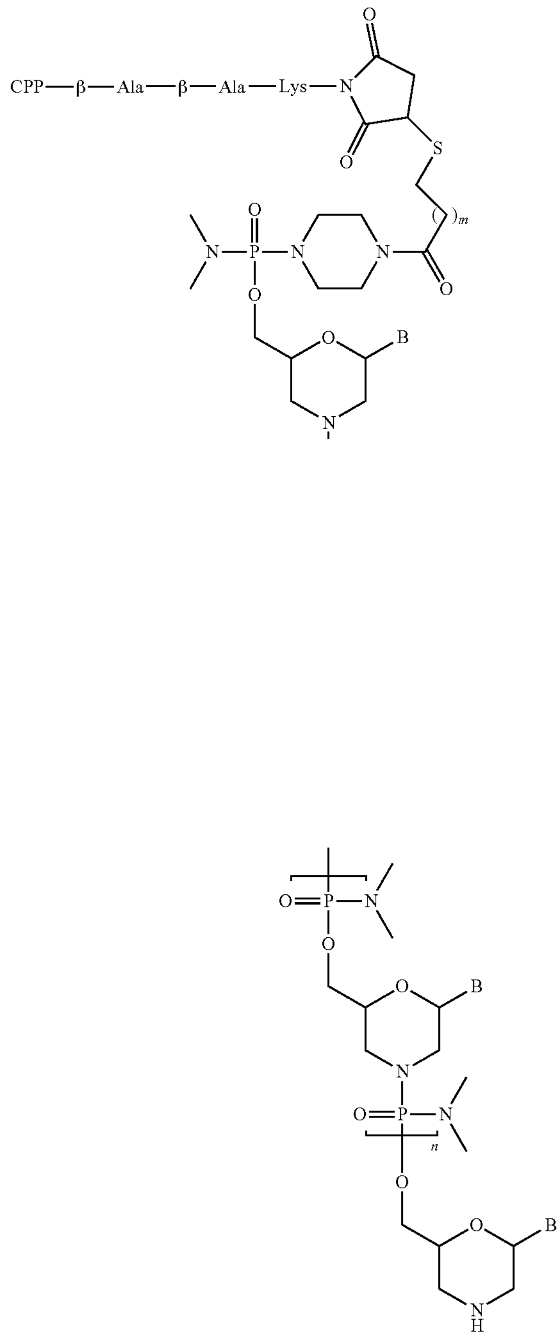

wherein:

m, n, and B are as defined above.

In some embodiments, the present disclosure provides a compound of Formula (Ic) having the structure:

(Ic)

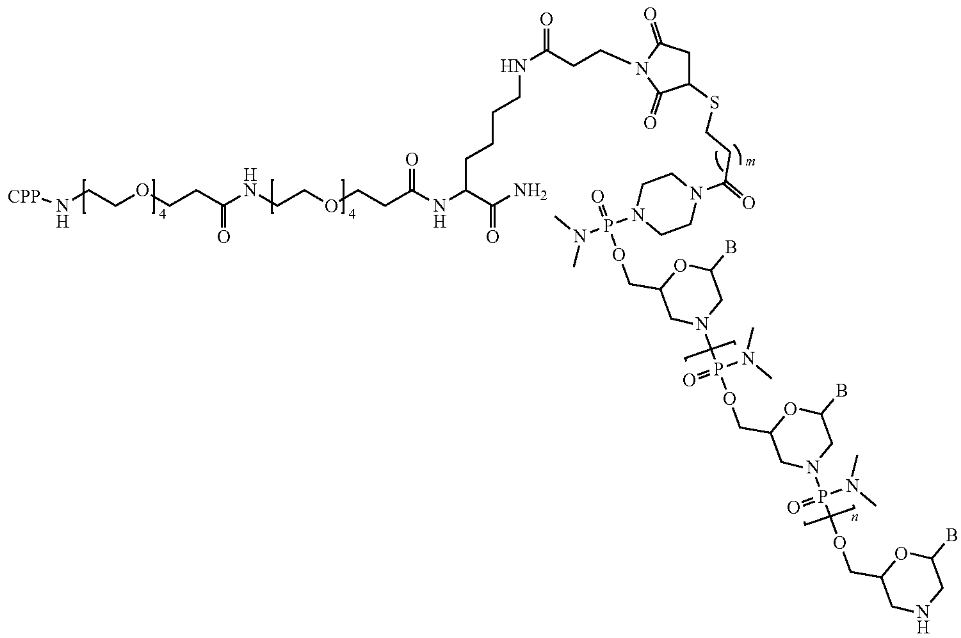

wherein:

m, n, and B are as defined above.

In some embodiments, the L contains a group which may be cleaved after cytosolic uptake of the compounds of the disclosure to release the AC. Non-limiting examples of physiologically cleavable linking group include carbonate, thiocarbonate, thioester, disulfide, sulfoxide, hydrazine, protease-cleavable dipeptide linker, and the like.

In some embodiments, a precursor to L also contains a thiol group, which forms a disulfide bond with the side chain of cysteine or cysteine in the CPP or attached to the 5' or 3' end of the AC.

Accordingly, in various embodiments, the compounds disclosed herein (e.g., the compounds for Formula (I-A) have the following structure:

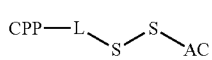

In some embodiments, the disulfide bond is formed between a thiol group on L, and the side chain of cysteine or an amino acid analog having a thiol group on CPP or attached to the 5' or 3' end of the AC. Non-limiting examples of amino acid analogs having a thiol group which can be used with the compounds disclosed herein include:

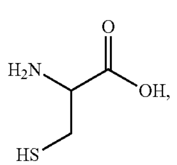

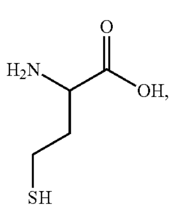

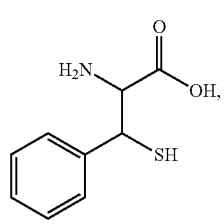

-continued

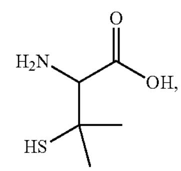

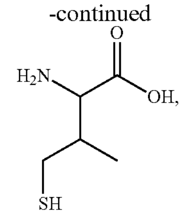

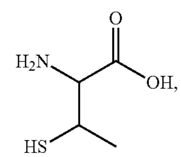

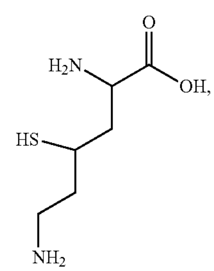

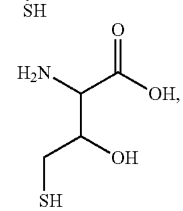

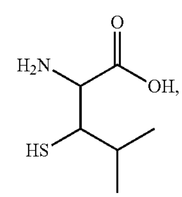

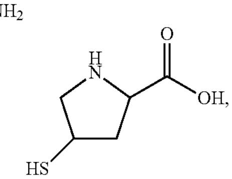

or

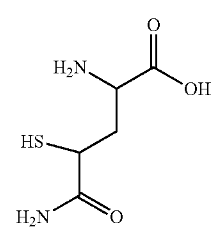

One skilled in the art will recognize that the amino acid analogs depicted above are shown as precursors, i.e., prior to incorporation into the compounds. When incorporated in the compounds of the present disclosure, the N- and C-termini are independently substituted to form peptide bonds, and the hydrogen on the thiol group is replaced with a bond to another sulfur atom to thereby form a disulfide.

Non-limiting examples of unconjugated AC structures (i.e. prior to conjugation to the CPP) are provided below. Underlining represents the antisense oligonucleotide (SEQ ID NO: 217). The antisense oligonucleotide sequences shown below are for illustrative purposes only, and can be substituted for another antisense oligonucleotide sequence depending on the target of interest.

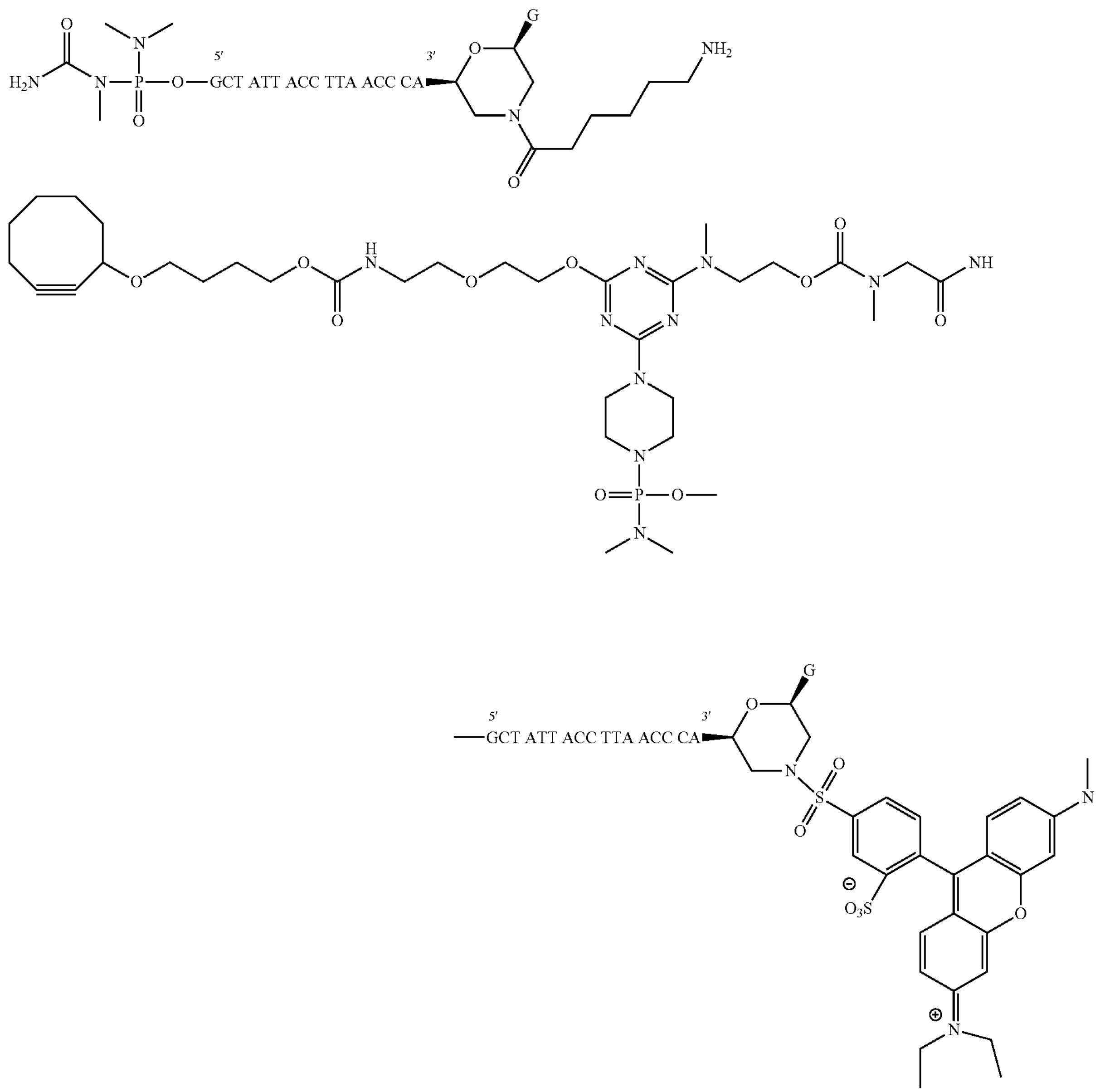

Cell-Penetrating Peptides

As discussed above, the compounds disclosed herein comprise cell-penetrating peptides (CPPs).

The CPP may be or include any amino sequence which facilitates cellular uptake of the compounds disclosed herein. Suitable CPPs for use in the compounds and methods described herein can include naturally occurring sequences, modified sequences, and synthetic sequences. In embodiments, the total number of amino acids in the CPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the CPPs disclosed herein comprise about 4 to about to about 13 amino acids. In particular embodiments, the CPPs disclosed herein comprise about 6 to about 10 amino acids, or about 6 to about 8 amino acids.

Each amino acid in the CPP may be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

| Amino Acid Abbreviations | | |
|---|---|---|
| Amino Acid | Abbreviations* L-amino acid | Abbreviations* D-amino acid |
| Alanine | Ala (A) | ala (a) |
| Allo-isoleucine | AIle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| glutamic acid | Glu (E) | glu (e) |
| glutamine | Gln (Q) | gln (q) |
| glycine | Gly (G) | gly (g) |
| histidine | His (H) | his (h) |
| Homoproline (aka pipecolic acid) | Pip (Θ) | pip (θ) |
| isoleucine | Ile (I) | ile (i) |
| leucine | Leu (L) | leu (l) |
| lysine | Lys (K) | lys (k) |
| methionine | Met (M) | met (m) |
| napthylalanine | Nal (Φ) | nal (φ) |
| norleucine | Nle (Ω) | nle |
| phenylalanine | Phe (F) | phe (F) |
| phenylglycine | Phg (Ψ) | phg |
| 4-(phosphonodifluoromethyl) phenylalanine | $F_2$Pmp (Λ) | $f_2$pmp |
| proline | Pro (P) | pro (p) |
| sarcosine | Sar (Ξ) | sar |
| selenocysteine | Sec (U) | sec (u) |
| serine | Ser (S) | ser (s) |
| threonine | Thr (T) | thr (y) |
| tyrosine | Tyr (Y) | tyr (y) |
| tryptophan | Trp (W) | trp (w) |
| valine | Val (V) | val (v) |
| Tert-butyl-alanine | Tle | tle |
| Penicillamine | Pen | pen |
| Homoarginine | HomoArg | homoarg |
| Nicotinyl-lysine | Lys(NIC) | lys(NIC) |
| Triflouroacetyl-lysine | Lys(TFA) | lys(TFA) |
| Methyl-leucine | MeLeu | meLeu |
| 3-(3-benzothienyl)-alanine | Bta | bta |

*single letter abbreviations: when shown in capital letters herein it indicates the L-amino acid form, when shown in lower case herein it indicates the D-amino acid form.

Non-limiting examples of linear CPPs include Polyarginine (e.g., $R_9$ or $R_{11}$), Antennapedia sequences, HIV-TAT, Penetratin, Antp-3A (Antp mutant), Buforin II. Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In various embodiments, the cell-penetrating peptides of the present disclosure are cyclic cell-penetrating peptides (cCPPs). In some embodiment, CPPs are cyclized to form cCPP by forming a peptide bond between the N- and C-termini of two amino acids in a peptide sequence. In some embodiments, the cCPPs may include any combination of at least two arginines and at least two hydrophobic amino acids. In some embodiments, the cCPPs may include any combination of two to three arginines and at least two hydrophobic amino acids.

In some embodiments, the cCPP used in compounds described herein has a structure comprising Formula III:

III

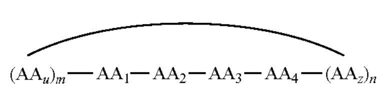

wherein:

each of $AA_1$, $AA_2$, $AA_3$, and $AA_4$, are independently selected from a D or L amino acid, each of $AA_u$ and $AA_z$, at each instance and when present, are independently selected from a D or L amino acid, and m and n are independently selected from a number from 0 to 6; and wherein:

at least two of $AA_u$, when present, $AA_1$, $AA_2$, $AA_3$, $AA_4$, and $AA_z$, when present, are independently arginine, and at least two of $AA_u$, when present, $AA_1$, $AA_2$, $AA_3$, $AA_4$, and $AA_z$, when present, are independently a hydrophobic amino acid.

In some embodiments, each hydrophobic amino acid is independently selected from is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of certain of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents.

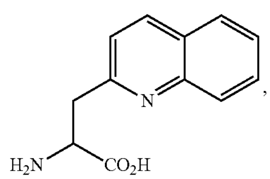

, 3-(2-quinolyl)-alanine

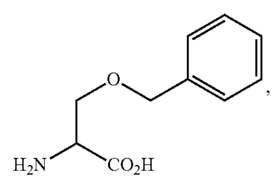

,

O-benzylserine

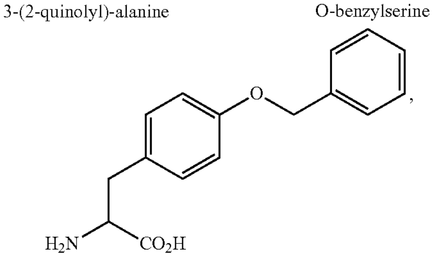

, 3-(4-(benzyloxy)phenyl)-alanine

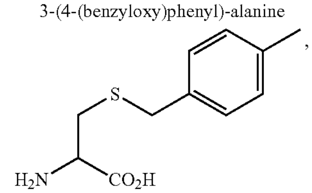

,

S-(4-methylbenzyl)cysteine

-continued

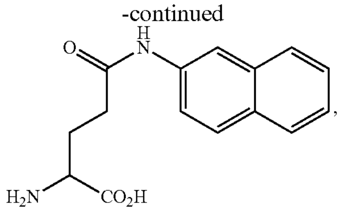

$N^5$-(naphthalen-2-yl)glutamine

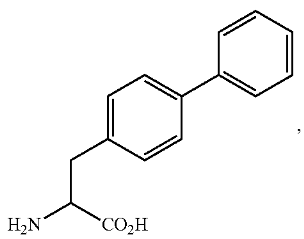

,

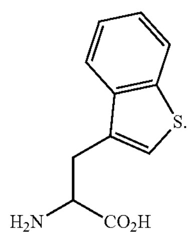

3-(1,1′-biphenyl-4-yl)-alanine 3-(3-benzothienyl)-alanine

The optional substituent can be any atom or group which does not significantly reduce (e.g., by more than 50%) the cytosolic delivery efficiency of the cCPP, e.g., compared to an otherwise identical sequence which does not have the substituent. In some embodiments, the optional substituent can be a hydrophobic substituent or a hydrophilic substituent. In some embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a cCPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1):140-144), Engleman, et al. (Ann. Rev, of Biophys. Biophys. Chem.. 1986; 1986(15):321-53), Kyte and Doolittle 3. Mol. Biol. 1982; 157(1):105-132), Hoop and Woods (Proc. Natl. Acad. Sci. U.S.A 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

Amino Acid Hydrophobicity

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the cCPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the cCPPs described herein comprise at least two consecutive hydrophobic amino acids and at least two consecutive arginines. In further embodiments, one hydrophobic amino acid is adjacent to one of the arginines. In still other embodiments, the cCPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the cCPPs described herein (e.g., the cCPPs according to Formula 2) can have one of the following sequences:

$AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid. Accordingly, in some embodiments, the cCPPs used in the compounds described herein comprise a structure according any of Formula IV-A-D:

IV-A

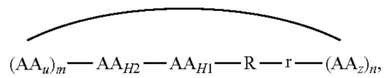

IV-B

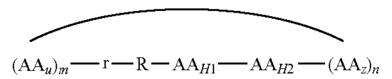

IV-C

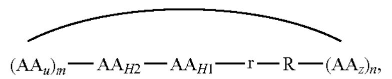

IV-D

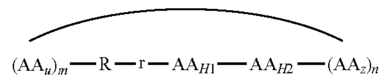

wherein:

each of $AA_{H1}$ and $AA_{H2}$ are independently a hydrophobic amino acid;

at each instance and when present, each of $AA_U$ and $AA_Z$ are independently any amino acid; and m and n are independently selected from a number from 0 to 6.

In some embodiments, the total number of amino acids (including r, R, $AA_{H1}$, $AA_{H2}$), in the CPPs of Formula 4-A to 4-D are in the range of 6 to 10. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, or norleucine, each of which is optionally substituted with one or more substituents. In particular embodiments, each hydrophobic amino acid is independently a hydrophobic aromatic amino acid. In some embodiments, the aromatic hydrophobic amino acid is piperidine-2-carboxylic acid, naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

In some embodiments, each of $AA_{H1}$ and $AA_{H2}$ are independently a hydrophobic amino acid having a hydrophobicity value which is greater than that of glycine. In other embodiments, each of $AA_{H1}$ and $AA_{H2}$ are independently a hydrophobic amino acid having a hydrophobicity value which is greater than that of alanine. In still other embodiments, each of $AA_{H1}$ and $AA_{H2}$ are independently an hydrophobic amino acid having a hydrophobicity value which is greater than that of phenylalanine, e.g., as measured using the hydrophobicity scales described above, including Eisenberg and Weiss (Proc. Natl. Acad. Sci. U.S.A 1984; 81(1): 140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also found to improve the cytosolic uptake of the cCPP (and the attached cargo). For example, in some embodiments, the cCPPs disclosed herein may include $AA_{H1}$-D-Arg or D-Arg-$AA_{H1}$. In other embodiments, the cCPPs disclosed herein may include $AA_{H1}$-L-Arg or L-Arg-$AA_{H1}$.

The size of the hydrophobic amino acid on the N- or C-terminal of the D-Arg or an L-Arg, or a combination thereof (i.e., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, $AA_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of $AA_{H1}$ and $AA_{H2}$ have a combined SASA of at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $AA_{H2}$ is a hydrophobic amino acid with a side chain having a SASA that is less than or equal to the SASA of the hydrophobic side chain of $AA_{H1}$. By way of example, and not by limitation, a cCPP having a Nal-Arg motif exhibits improved cytosolic delivery efficiency compared to an otherwise identical CPP having a Phe-Arg motif, a cCPP having a Phe-Nal-Arg motif exhibits improved cytosolic delivery efficiency compared to an otherwise identical cCPP having a Nal-Phe-Arg motif; and a phe-Nal-Arg motif exhibits improved cytosolic delivery efficiency compared to an otherwise identical cCPP having a nal-Phe-Arg motif.

As used herein, "hydrophobic surface area" or "SASA" refers to the surface area (reported as square Ångstroms; Å$^2$) of an amino acid side chain that is accessible to a solvent. In particular embodiments, SASA is calculated using the 'rolling ball' algorithm developed by Shrake & Rupley (*J Mol Biol.* 79 (2): 35-271), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In some embodiments, the SASA values described herein are based on the theoretical values listed in Table 3 below, as reported by Tien, et al. (PLOS ONE 8(11): e80635. https://doi.org/10.1371/joumnal.pone.0080635, which is herein incorporated by reference in its entirety for all purposes.

TABLE 3

Amino Acid SASA Values

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the cCPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the cCPP does not include a hydrophobic amino acid having a side chain which is larger (as described herein) than at least one of $AA_1$ or $AA_{H2}$. In further embodiments, the cCPP does not include a hydrophobic amino acid with a side chain having a surface area greater than $AA_{H1}$. For example, in embodiments in which at least one of $AA_{H1}$ or $AA_{H2}$ is phenylalanine, the cCPP does not further include a naphthylalanine (although the cCPP may include at least one hydrophobic amino acid which is smaller than $AA_{H1}$ and $AA_{H2}$, e.g., leucine). In still other embodiments, the cCPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the cCPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the cCPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_{H1}$ can be D-nal, D-trp, or D-phe. In another non-limiting example, when arginine is L-Arg, $AA_{H1}$ can be L-Nal, L-Trp, or L-Phe.

In some embodiments, the cCPPs described herein include at least three arginines. Accordingly, in some embodiments, the cCPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R—R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the cCPPs have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AAH_1$ and $AAH_2$ can be selected to improve cytosolic uptake efficiency, e.g., as described above, where $AAH_1$ has the same chirality as the adjacent arginine, and $AAH_1$ and $AAH_2$ have the opposite chirality.

In some embodiments, the cCPPs described herein include three hydrophobic amino acids. Accordingly, in some embodiments, the cCPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any hydrophobic amino acid described above, e.g., piperidine-2-carboxylic acid, naphthylalanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AAH_1$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In some embodiments, $AA_{H1}$ and $AA_{H2}$ have the opposite chirality. Accordingly, in some embodiments, the cCPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-$AA_{H1}$ and L-$AA_{H2}$ is L-Nal. In other particular embodiments, L-$AA_{H1}$ is L-Nal.

As discussed above, the disclosure provides for various modifications to a cCPP which may improve cytosolic delivery (also called uptake) efficiency. In some embodiments, improved cytosolic uptake efficiency can be measured by comparing the cytosolic delivery efficiency of the cCPP having the modified sequence to a proper control sequence. In some embodiments, the control sequence does not include a particular modification (e.g., matching chirality of R and $AA_{H1}$) but is otherwise identical to the modified sequence. In other embodiments, the control has the following sequence: cyclic(FΦRRRRQ) (SEQ ID NO: 146). In some embodiments, improved cytosolic uptake efficiency can be measured by comparing the cytosolic delivery efficiency of a compound described herein having a cCPP to a control compound that does not have a cCPP.

As used herein cytosolic delivery efficiency refers to the ability of a cCPP to traverse a cell membrane and enter the cytosol. In embodiments, cytosolic delivery efficiency of the cCPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a cCPP (or a cCPP-AC conjugate) over the concentration of the CPP (or the CPP-AC conjugate) in the growth medium. Relative cytosolic delivery efficiency refers to the concentration of a cCPP in the cytosol compared to the concentration of a control cCPP in the cytosol. Quantification can be achieved by fluorescently labeling the cCPP (e.g., with a FITC dye) and measuring the fluorescence intensity using techniques well-known in the art.

In particular embodiments, relative cytosolic delivery efficiency is determined by comparing (i) the amount of a compound containing a cCPP and oligonucleotide sequence internalized by a cell type (e.g., HeLa cells) to (ii) the amount of the control cCPP internalized by the same cell type. To measure relative cytosolic delivery efficiency, the cell type may be incubated in the presence of a cCPP for a specified period of time (e.g., 30 minutes, 1 hour, 2 hours, etc.) after which the amount of the cCPP internalized by the cell is quantified using methods known in the art, e.g., fluorescence microscopy. Separately, the same concentration of the control cCPP is incubated in the presence of the cell type over the same period of time, and the amount of the control cCPP internalized by the cell is quantified.

In other embodiments, relative cytosolic delivery efficiency can be determined by measuring the $IC_{50}$ of a cCPP having a modified sequence for an intracellular target, and comparing the $IC_{50}$ of the cCPP having the modified sequence to a proper control sequence (as described herein).

In some embodiments, the relative cytosolic delivery efficiency of the cCPP-AC conjugates described herein in the range of from about 1% to about 1000% compared to cCPP, e.g., about 5%, about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, about 590%, about 600%, about 610%, about 620%, about 630%, about 640%, about 650%, about 660%, about 670%, about 680%, about 690%, about 700%, about 710%, about 720%, about 730%, about 740%, about 750%, about 760%, about 770%, about 780%, about 790%, about 800%, about 810%, about 820%, about 830%, about 840%, about 850%, about 860%, about 870%, about 880%, about 890%, about 900%, about 910%, about 920%, about 930%, about 940%, about 950%, about 960%, about 970%, about 980%, about 990%, about 1000%, inclusive of all values and subranges therebetween In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

In some embodiments, the cCPP may be or include any of the sequences listed in Table 4. That is, the cCPPs used in the compounds disclosed herein may comprise any one of the sequences listed in Table 4, along with additional amino acids to form a cyclic sequence, or the sequences in the Table 4 may be cyclized (via a peptide bond) to form a cCPP. In some embodiments, the amino acids listed in Table 4 further include a glutamine residue or other amino acid that has a side chain that allows for conjugation of the AC.

TABLE 4 cCPP sequences

| ID | Sequence | SEQ ID NO |
|---|---|---|
| PCT 1 | FΦRRR | 1 |
| PCT 2 | FΦRRRC | 2 |
| PCT 3 | FΦRRRU | 3 |
| PCT 4 | RRRPF | 4 |
| PCT 5 | RRRRΦF | 5 |
| PCT 6 | FΦRRRR | 6 |
| PCT 7 | FφrRrR | 7 |
| PCT 8 | FφrRrR | 8 |
| PCT 9 | FΦRRRR | 9 |
| PCT 10 | fΦRrRr | 10 |
| PCT 11 | RRFRΦR | 11 |
| PCT 12 | FRRRRΦ | 12 |
| PCT 13 | rRFRΦR | 13 |
| PCT 14 | RRΦFRR | 14 |
| PCT 15 | CRRRRFW | 15 |
| PCT 16 | FfΦRrRr | 16 |
| PCT 17 | FFΦRRRR | 17 |
| PCT 18 | RFRFRΦR | 18 |
| PCT 19 | URRRRFW | 19 |

TABLE 4-continued

| cCPP sequences | | |
|---|---|---|
| ID | Sequence | SEQ ID NO |
| PCT 20 | CRRRRFW | 20 |
| PCT 21 | FΦRRRRQK | 21 |
| PCT 22 | FΦRRRRQC | 22 |
| PCT 23 | fΦRrRrRQ | 23 |
| PCT 24 | FΦRRRRRQ | 24 |
| PCT 25 | RRRRΦFDΩC | 25 |
| PCT 26 | FΦRRR | 26 |
| PCT 27 | FWRRR | 27 |
| PCT 28 | RRRΦF | 28 |
| PCT 29 | RRRWF | 29 |
| SAR 1 | FΦRRRR | 30 |
| SAR 19 | FFRRR | 31 |
| SAR 20 | FFrRr | 32 |
| SAR 21 | FFRrR | 33 |
| SAR 22 | FRFRR | 34 |
| SAR 23 | FRRFR | 35 |
| SAR 24 | FRRRF | 36 |
| SAR 25 | GΦRRR | 37 |
| SAR 26 | FFFRA | 38 |
| SAR 27 | FFFRR | 39 |
| SAR 28 | FFRRRR | 40 |
| SAR 29 | FRRFRR | 41 |
| SAR 30 | FRRRFR | 42 |
| SAR 31 | RFFRRR | 43 |
| SAR 32 | RFRRFR | 44 |
| SAR 33 | FRFRRR | 45 |
| SAR 34 | FFFRRR | 46 |
| SAR 35 | FFRRRF | 47 |
| SAR 36 | FRFFRR | 48 |
| SAR 37 | RRFFFR | 49 |
| SAR 38 | FFRFRR | 50 |
| SAR 39 | FFRRFR | 51 |
| SAR 40 | FRRFFR | 52 |
| SAR 41 | FRRFRF | 53 |
| SAR 42 | FRFRFR | 54 |
| SAR 43 | RFFRFR | 55 |
| SAR 44 | GΦRRRR | 56 |
| SAR 45 | FFFRRRR | 57 |
| SAR 46 | RFFRRRR | 58 |
| SAR 47 | RRFFRRR | 59 |
| SAR 48 | RFFFRRR | 60 |
| SAR 49 | RRFFFRR | 61 |
| SAR 50 | FFRRFRR | 62 |
| SAR 51 | FFRRRRF | 63 |
| SAR 52 | FRRFFRR | 64 |
| SAR 53 | FFFRRRRR | 65 |
| SAR 54 | FFFRRRRRR | 66 |
| SAR 55 | FΦRrRr | 67 |
| SAR 56 | XXRRRR | 68 |
| SAR 57 | FfFRrR | 69 |
| SAR 58 | fFfrRr | 70 |
| SAR 59 | fFfRrR | 71 |
| SAR 60 | FfFrRr | 72 |
| SAR 61 | fFφrRr | 73 |
| SAR 62 | fΦfrRr | 74 |
| SAR 63 | φFfrRr | 75 |
| SAR 64 | FΦrRr | 76 |
| SAR 65 | fΦrRr | 77 |
| SAR 66 | Ac-(Lys-fFRrRrD) | 78 |
| SAR 67 | Ac-(Dap-fFRrRrD) | 79 |
| SAR 68 | CWWRRRRC<br>S—S | 80 |
| SAR 69 | CWWVRRRRC<br>S—S | 81 |
| SAR 70 | CFWRRRRC<br>S—S | 82 |
| SAR 71 | CWWWRRRC<br>S—S | 83 |
| Pin1 15 | Pip-Nal-Arg-Glu-arg-arg-glu | 84 |
| Pin1 16 | Pip-Nal-Arg-Arg-arg-arg-glu | 85 |
| Pin1 17 | Pip-Nal-Nal-Arg-arg-arg-glu | 86 |
| Pin1 18 | Pip-Nal-Nal-Arg-arg-arg-Glu | 87 |
| Pin1 19 | Pip-Nal-Phe-Arg-arg-arg-glu | 88 |
| Pin1 20 | Pip-Nal-Phe-Arg-arg-arg-Glu | 89 |
| Pin1 21 | Pip-Nal-phe-Arg-arg-arg-glu | 90 |
| Pin1 22 | Pip-Nal-phe-Arg-arg-arg-Glu | 91 |
| Pin1 23 | Pip-Nal-nal-Arg-arg-arg-Glu | 92 |
| Pin1 24 | Pip-Nal-nal-Arg-arg-arg-glu | 93 |
| Rev-13 | [Pim-RQRR-Nlys]GRRR[b] | 94 |
| hLF | KCFQWQRNMRKVRGPPVSC | 95 |
| cTat | [KrRrGrKkRrE][c] | 96 |
| cR10 | [KrRrRrRrRrE][c] | 97 |
| L-50 | [RVRTRGKRRIRRpP] | 98 |
| L-51 | [RTRTRGKRRIRVpP] | 99 |
| $[WR]_4$ | [WRWRWRWR] | 100 |
| MCOTI-II | [GGVCPKILKKCRRDSDCPGACICRGNGYCGSGSD] | 101 |
| Rotstein et al. Chem. Eur. J. 2011 | [P-Cha-r-Cha-r-Cha-r-Cha-r-G][d] | 102 |
| Lian et al. J. Am. Chem. Soc. 2014 | Tm(SvP-$F_2$Pmp-H)-Dap-(FΦRRRR-Dap)][f] | 103 |
| Lian et al. J. Am. Chem. Soc. 2014 | [Tm(a-Sar-D-pThr-Pip-ΦRAa)-Dap-(FΦRRRR-Dap)][f] | 104 |
| IA8b | [CRRSRRGCGRRSRRCG][g] | 105 |
| Dod-$[R_5]$ | [K(Dod)RRRR] | 106 |
| LK-3 | | 107 |
| | RRRR-[KRRRE][c] | 108 |
| | RRR-[KRRRRE][c] | 109 |
| | RR-[KRRRRRE][c] | 110 |
| | R-[KRRRRRRE][c] | 111 |
| $[CR]_4$ | [CRCRCRCR] | 112 |
| cyc3 | [Pra-LRKRLRKFRN-AzK][h] | 113 |
| PMB | T-Dap-[Dap-Dap-f-L-Dap-Dap-T] | 114 |
| GPMB | T-Agp-[Dap-Agp-f-L-Agp-Agp-T] | 115 |
| cCPP1 | FΦRRRR | 116 |
| cCPP12 | FfΦRrRr | 117 |
| cCPP9 | fΦRrRr | 118 |
| cCPP11 | fΦRrRrR | 119 |
| cCPP18 | FφrRrR | 120 |
| cCPP13 | FφrRrR | 121 |
| cCPP6 | FΦRRRRR | 122 |
| cCPP3 | RRFRΦRQ | 123 |
| cCPP7 | FFΦRRRR | 124 |
| cCPP8 | RFRFRΦR | 125 |
| cCPP5 | FΦRRR | 126 |
| cCPP4 | FRRRRΦ | 127 |
| cCPP10 | rRFRΦR | 128 |
| cCPP2 | RRΦFRR | 129 |
| cCPP62 | fΦfrRr | 130 |

Φ, L-2-naphthylalanine; Pim, pimelic acid; Nlys, lysine peptoid residue; D-pThr, D-phosphothreonine; Pip, L-piperidine-2-carboxylic acid; Cha, L-3-cyclohexyl-alanine; Tm, trimesic acid; Dap, L-2,3-diaminopropionic acid; Sar, sarcosine; $F_2$Pmp, L-difluorophosphonomethyl phenylalanine; Dod, dodecanoyl; Pra, L-propargylglycine; AzK, L-6-Azido-2-amino-hexanoic; Agp, L-2-amino-3-guanidinylpropionic acid; [b]Cyclization between Pim and Nlys; [c]Cyclization between Lys and Glu; [d]Macrocyclization by multicomponent reaction with aziridine aldehyde and isocyanide; [e]Cyclization between the main-chain of Gln residue; [f]N-terminal amine and side chains of two Dap residues bicyclized with Tm; [g]Three Cys side chains bicyclized with tris(bromomethyl)benzene; [h]Cyclization by the click reaction between Pra and Azk.

Additionally, the cCPP used in the compounds and methods described herein can include any sequence disclosed in: U.S. application Ser. No. 15/312,878; U.S. application Ser. No. 15/360,719; International PCT Application Publication No. WO/2018/089648 (including the corresponding US publication), and International PCT Application Publication No. WO 2018/098231, each of which is incorporated by reference in its entirety for all purposes.

In some embodiments, provided herein are ACs conjugated to cCPP12. Non-limiting examples of the structures of ACs conjugated to cCPP12 are provided below. Underlining represents the antisense oligonucleotide (SEQ ID NO: 217). The antisense oligonucleotide sequences shown below are for illustrative purposes only, and can be substituted for another antisense oligonucleotide sequence depending on the target of interest.

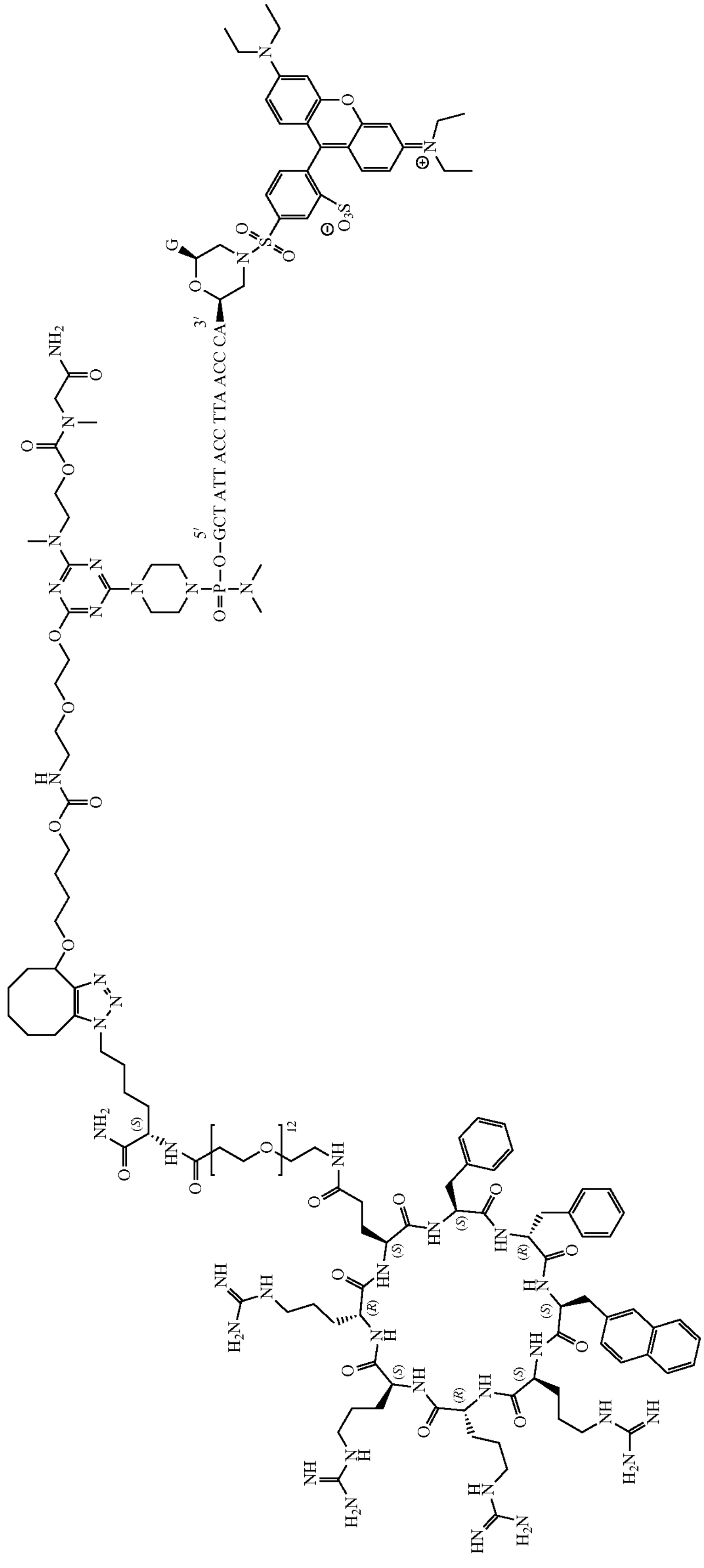

-continued
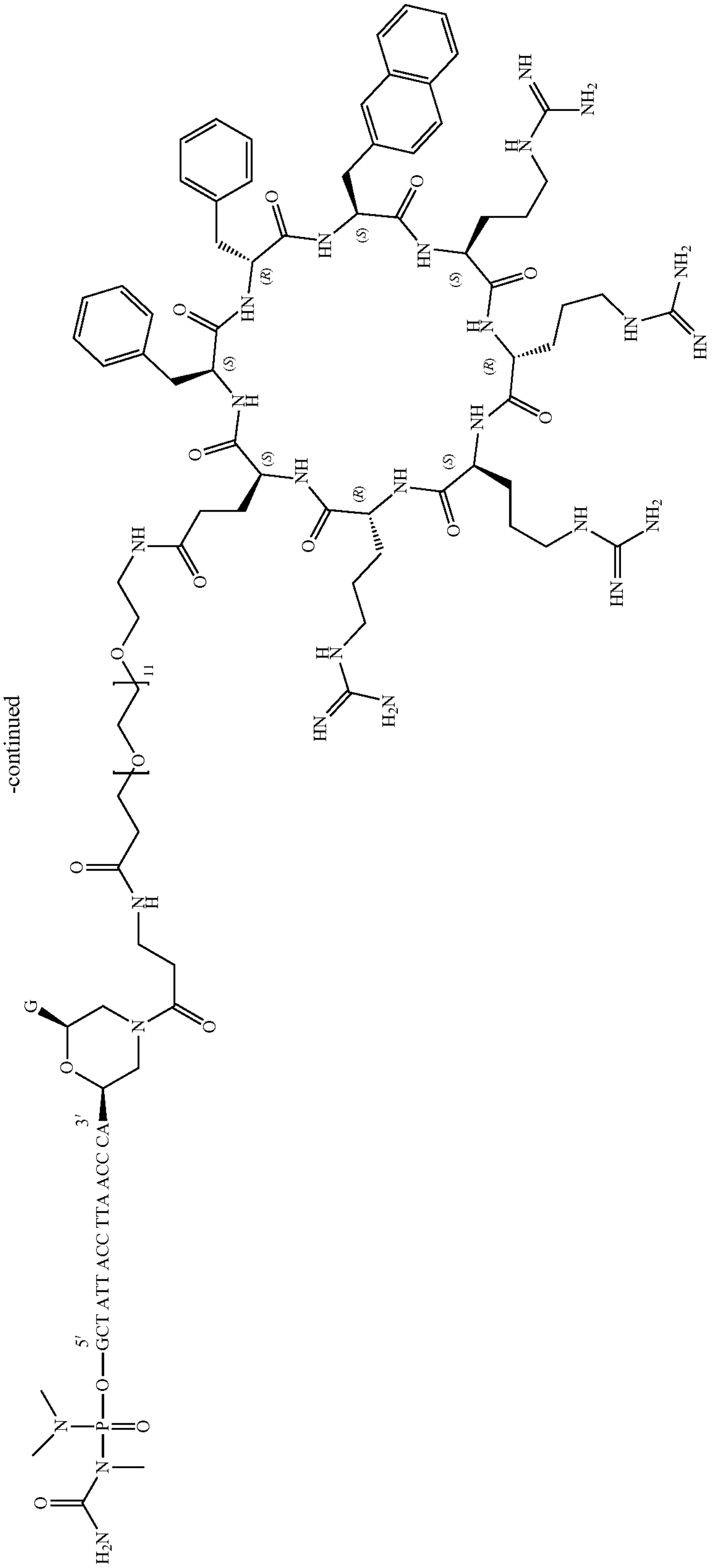

In some embodiments, provided herein are ACs that are conjugated to two CPPs. Non-limiting examples of the structures of ACCs that are conjugated to two CPPs are provided below. Underlining represents the antisense oligonucleotide (SEQ ID: 217). The antisense oligonucleotide sequences shown below are for illustrative purposes only, and can be substituted for another antisense oligonucleotide sequence depending on the target of interest.

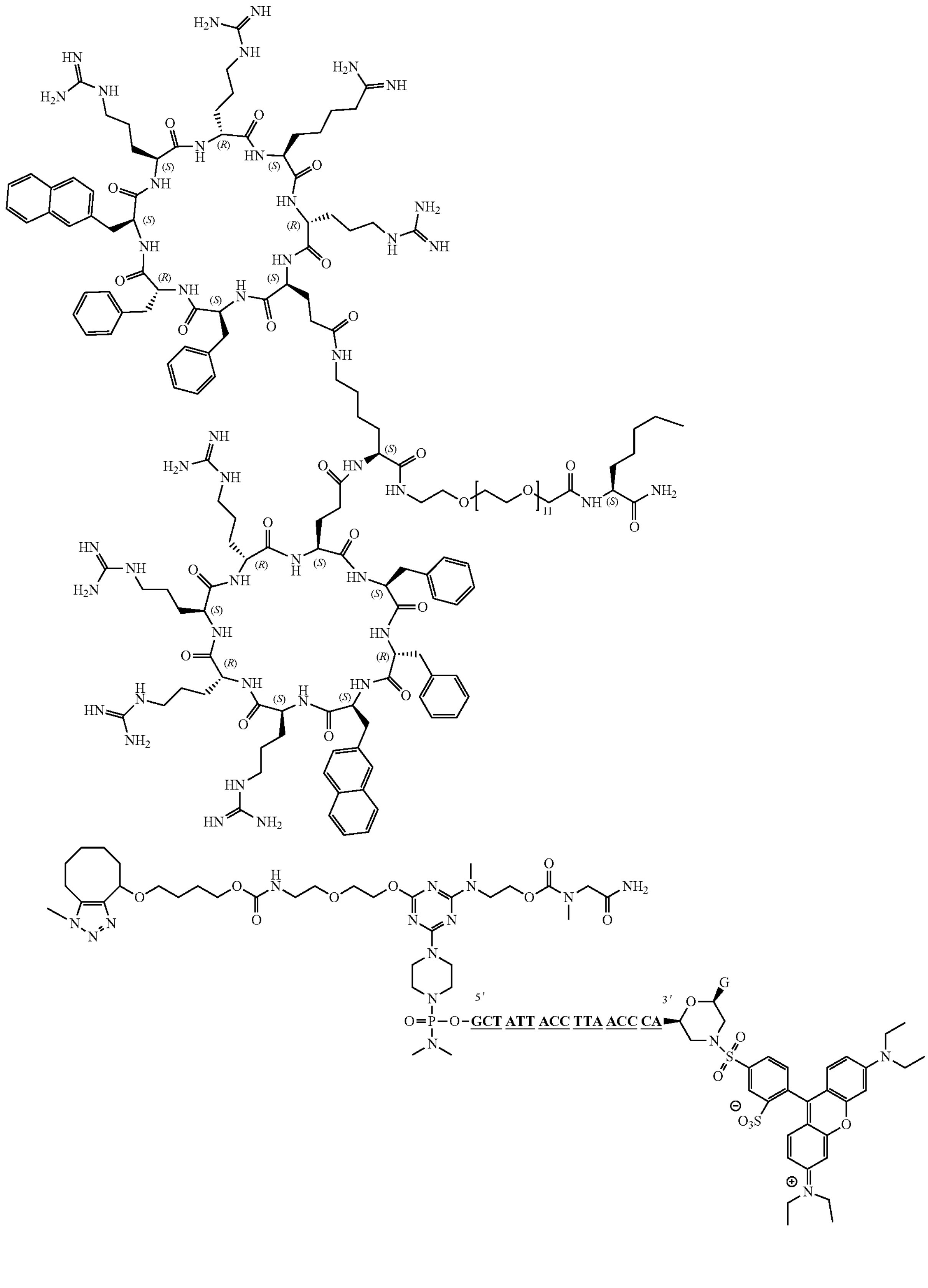

-continued
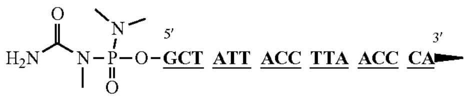
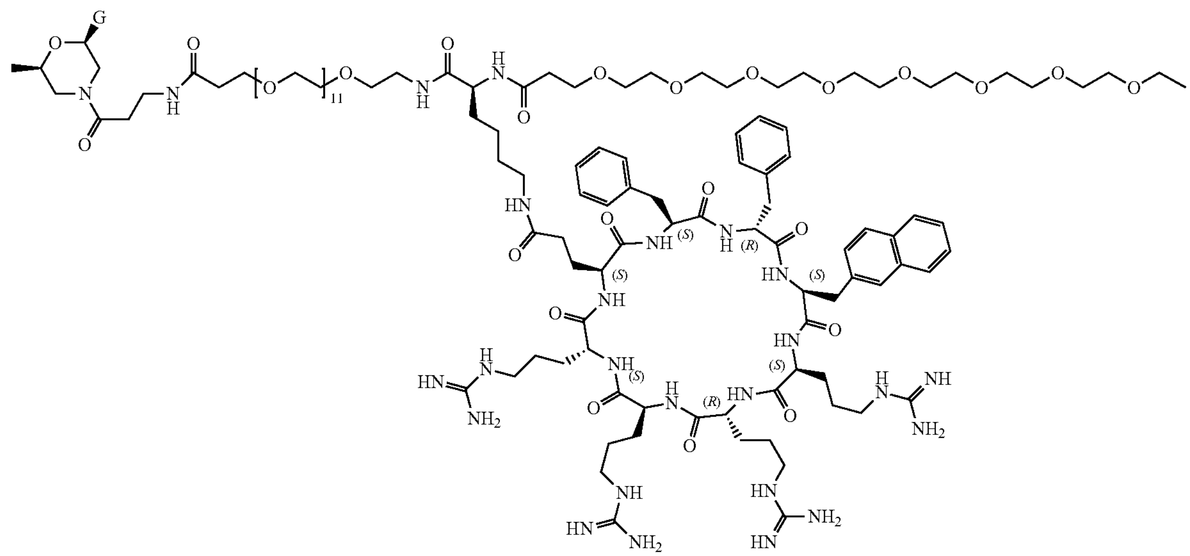
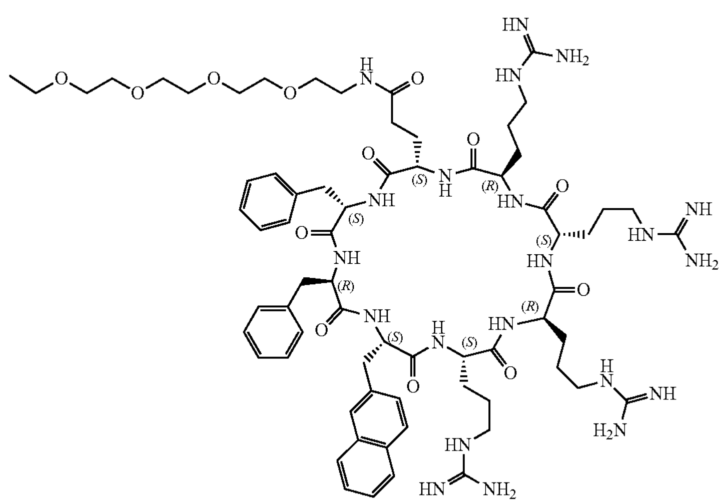

-continued
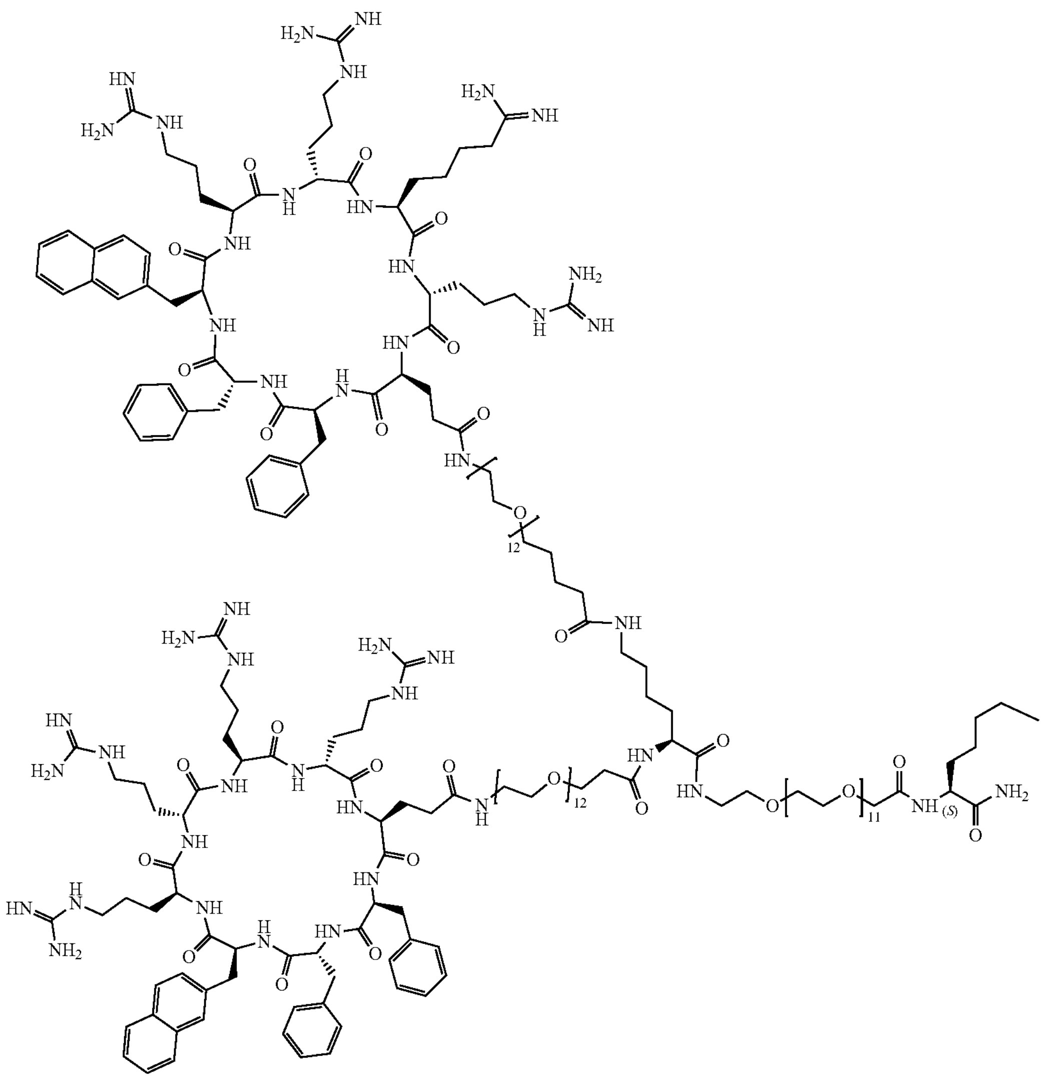
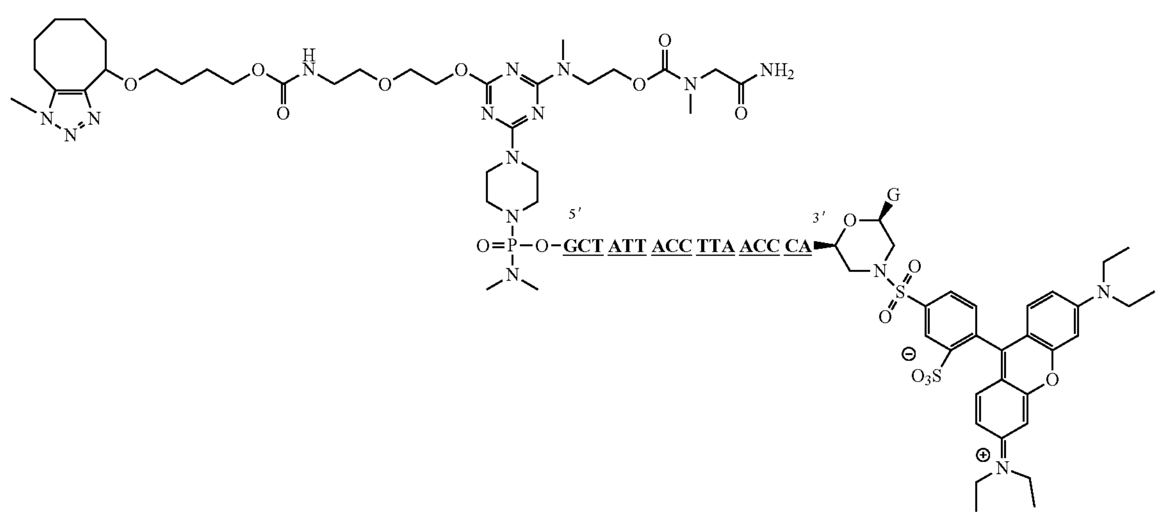

-continued

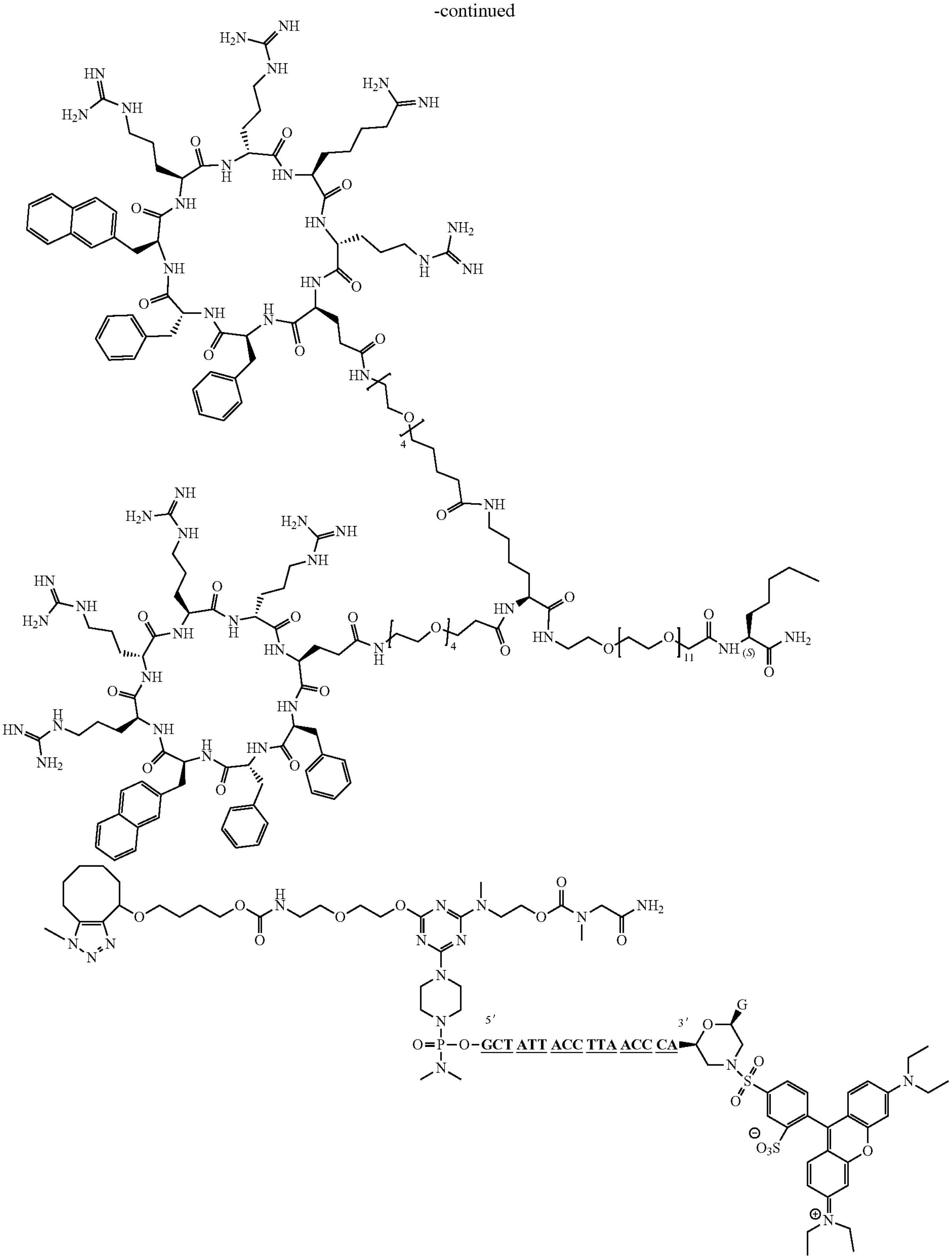

In some embodiments, provided herein are ACs that are conjugated to three CPPs. Non-limiting examples of the structures of ACCs that are conjugated to three CPPs are provided below. Underlining represents the antisense oligonucleotide (SEQ ID NO: 217). The antisense oligonucleotide sequences shown below are for illustrative purposes only, and can be substituted for another antisense oligonucleotide sequences depending on the target of interest.

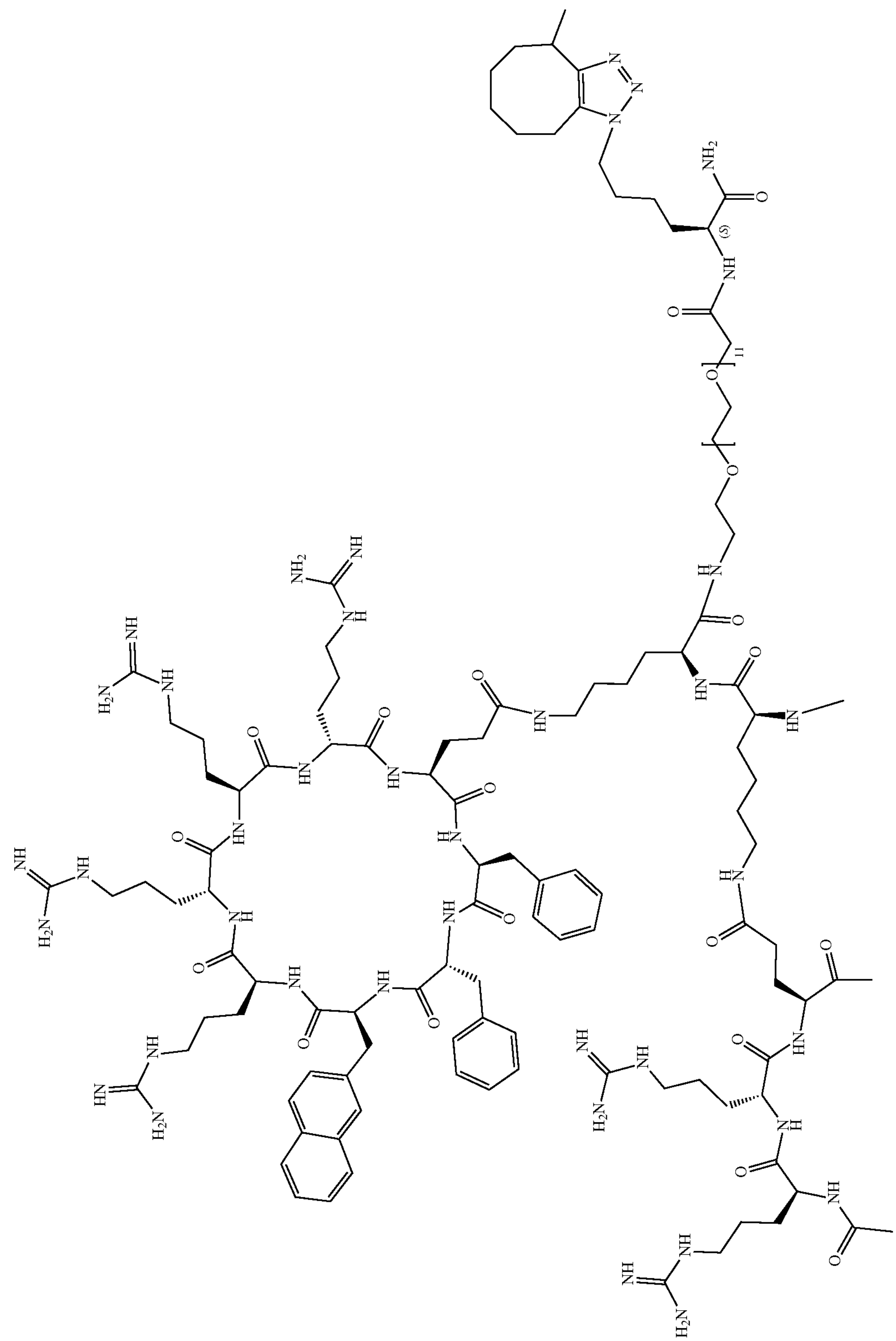

-continued
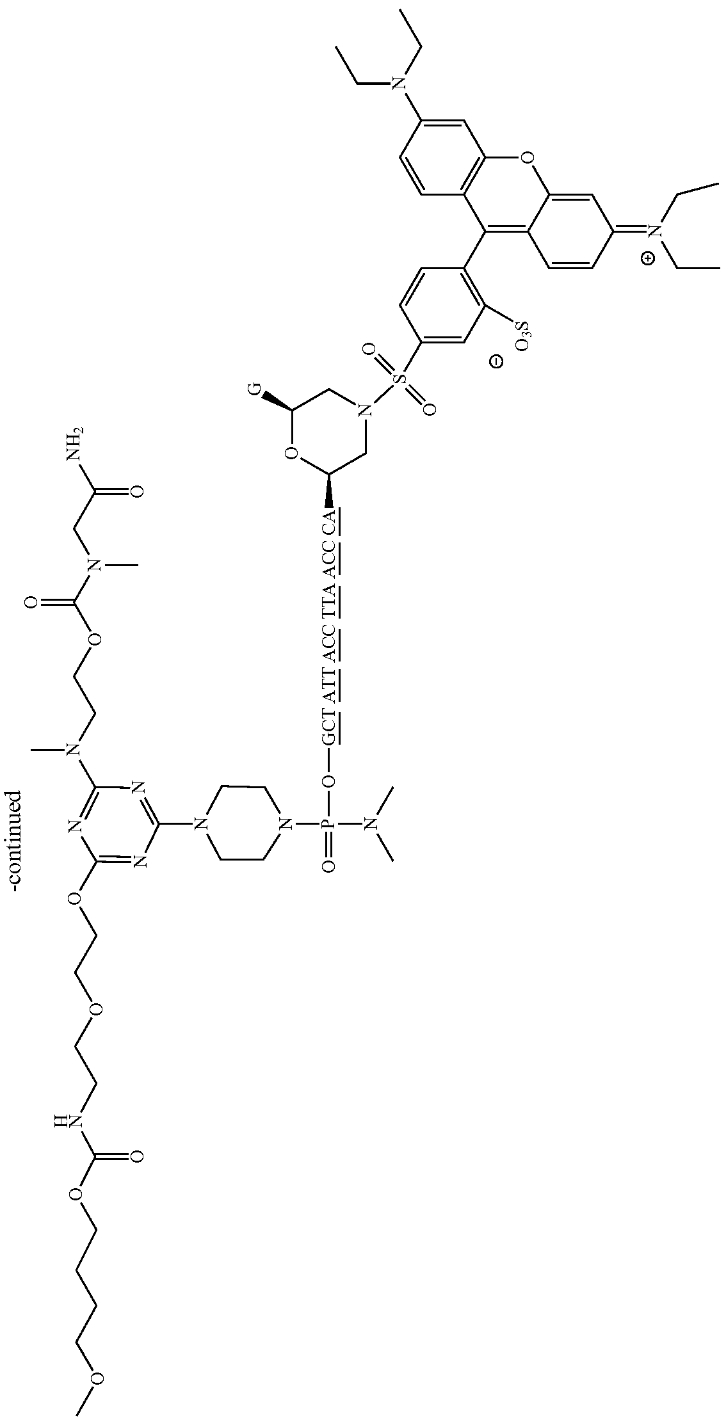

-continued
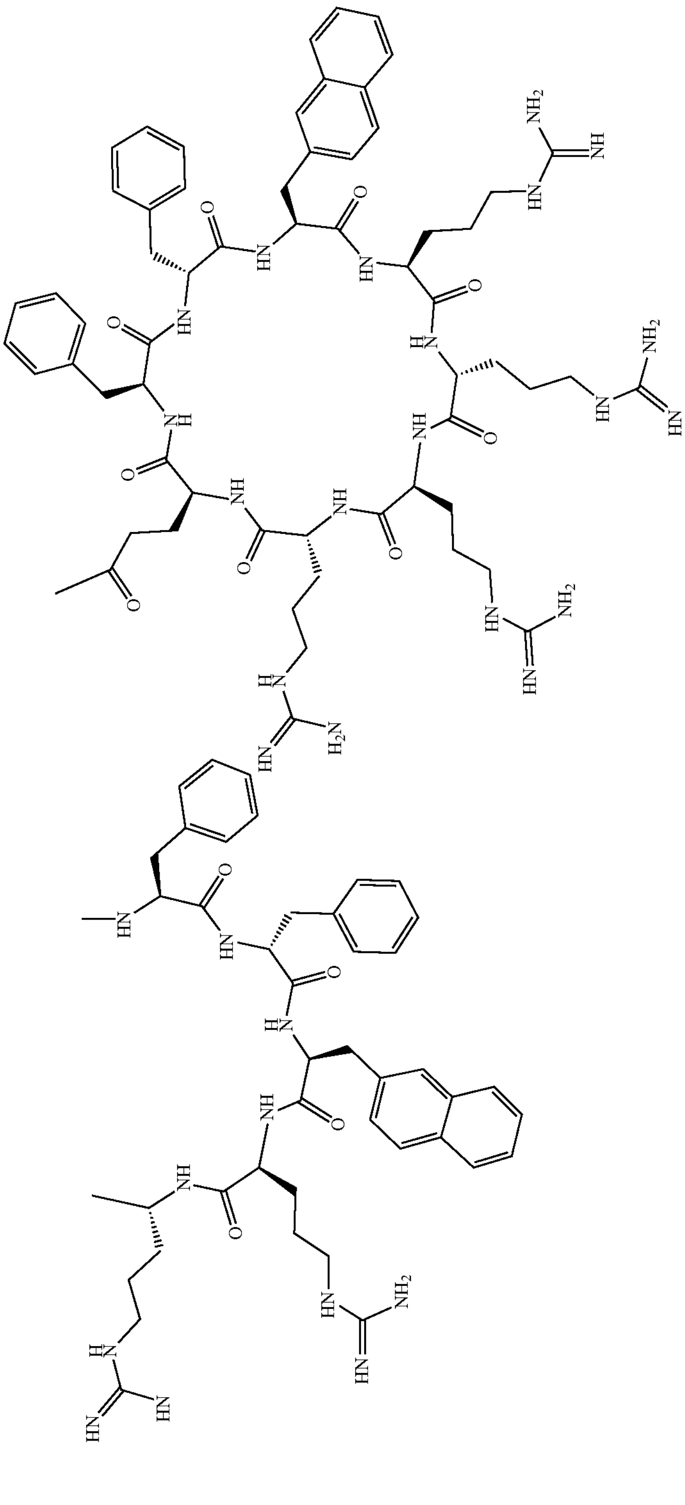

-continued
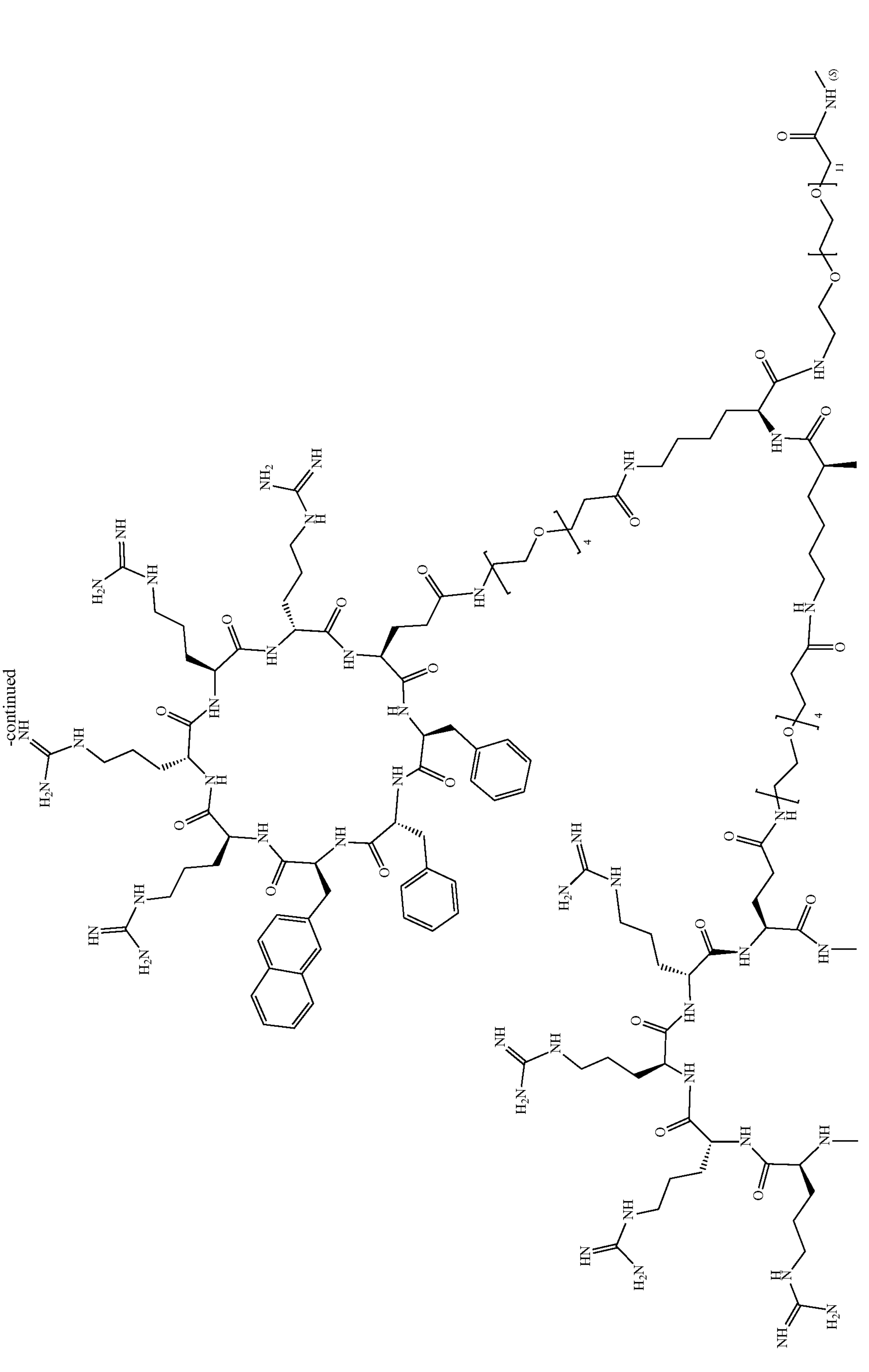

-continued
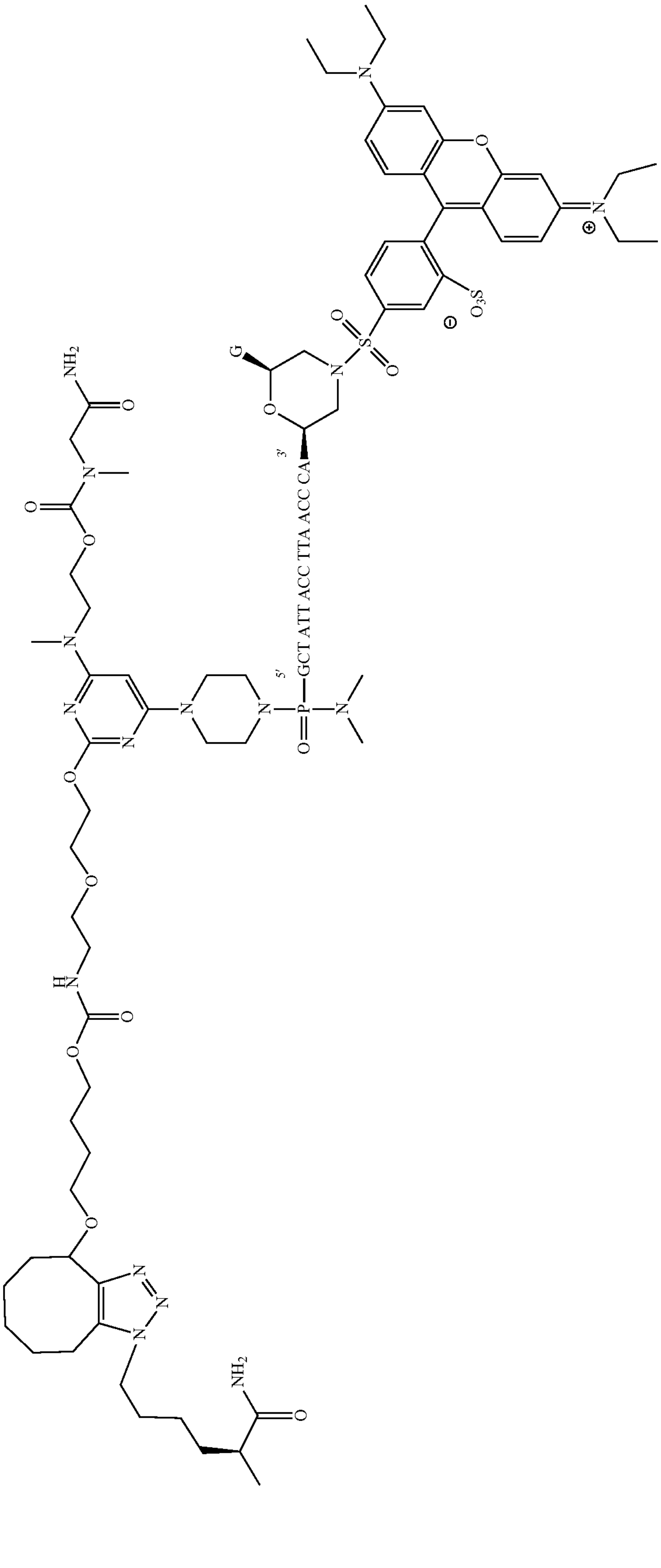

-continued
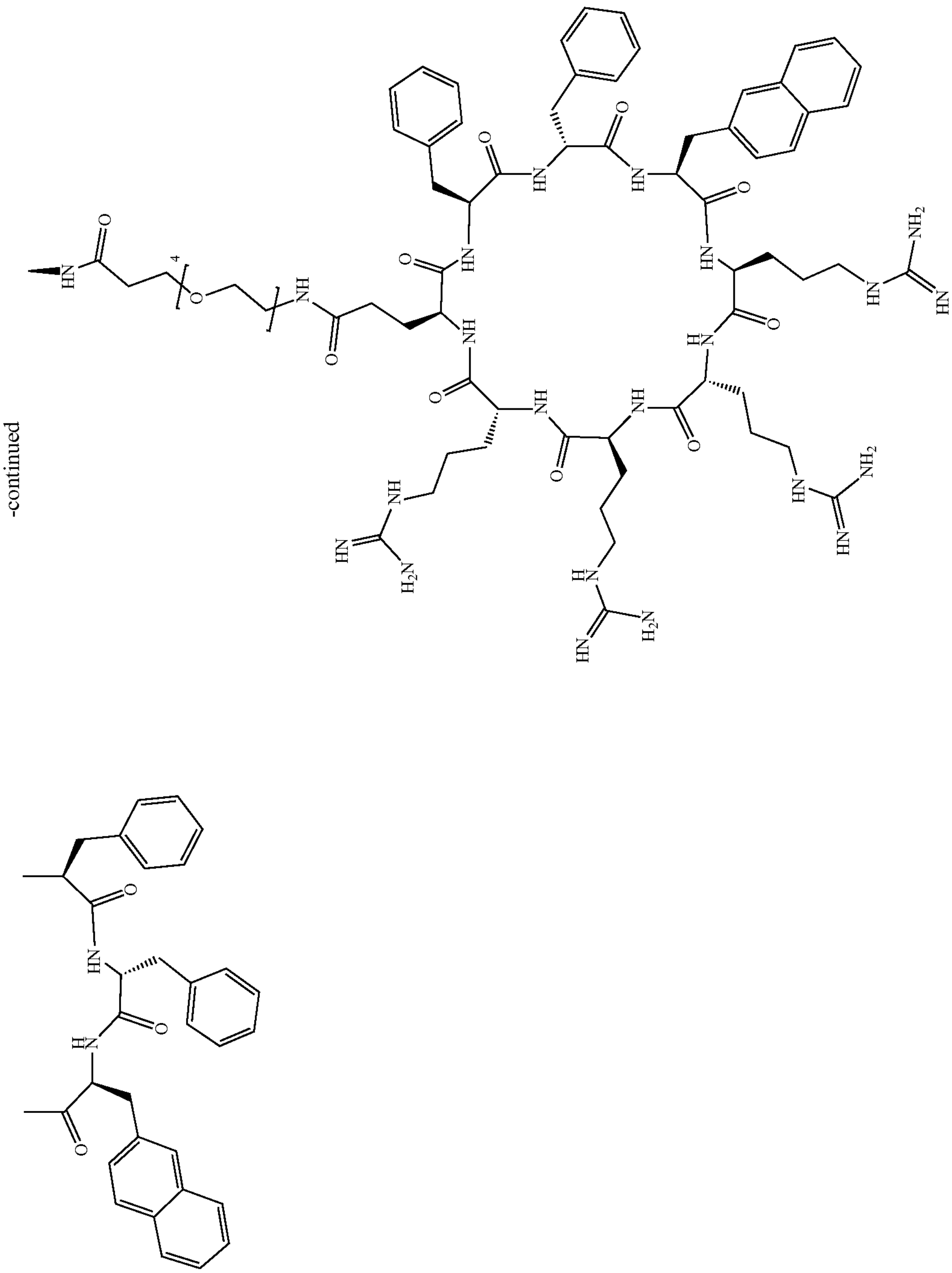

-continued
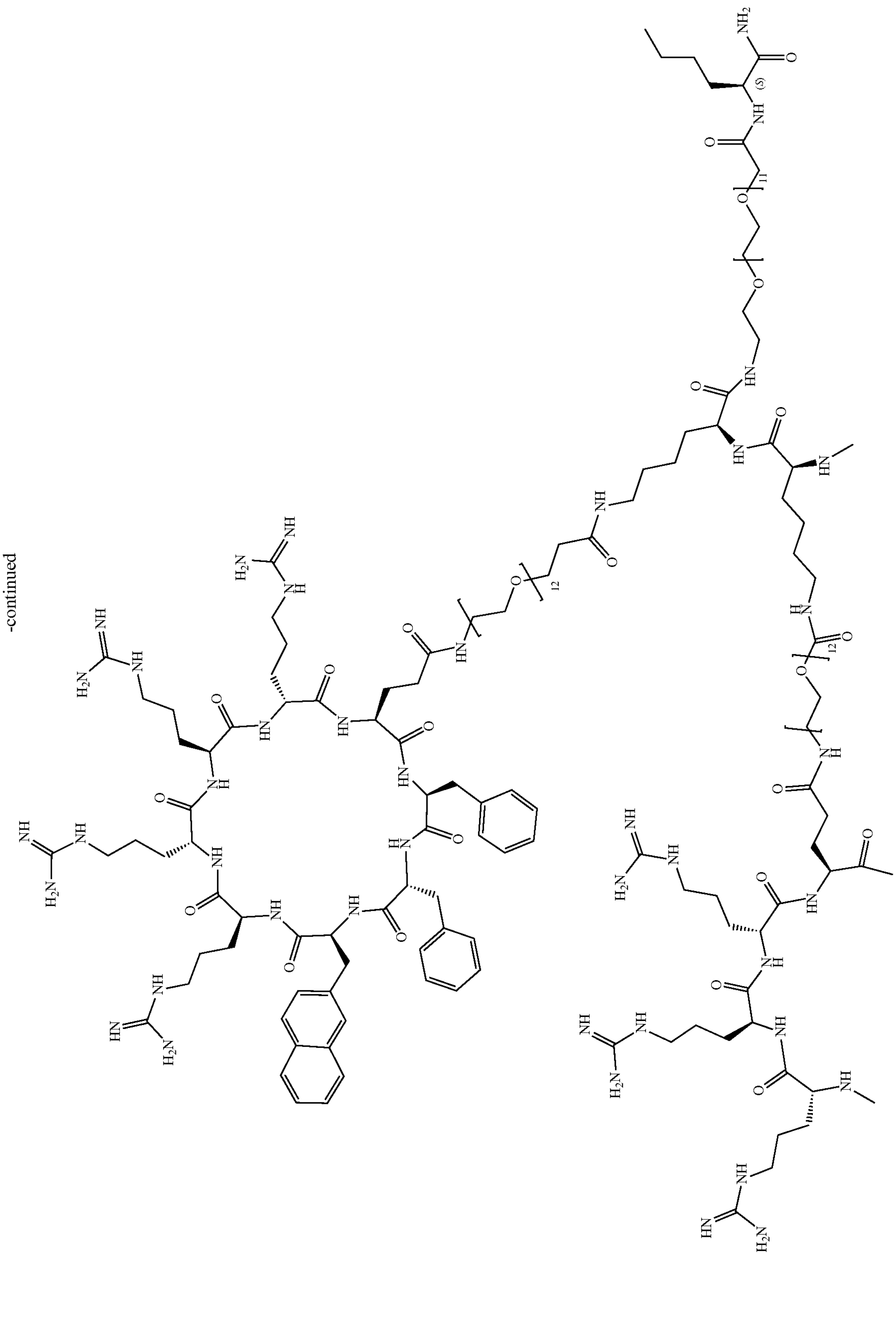

-continued
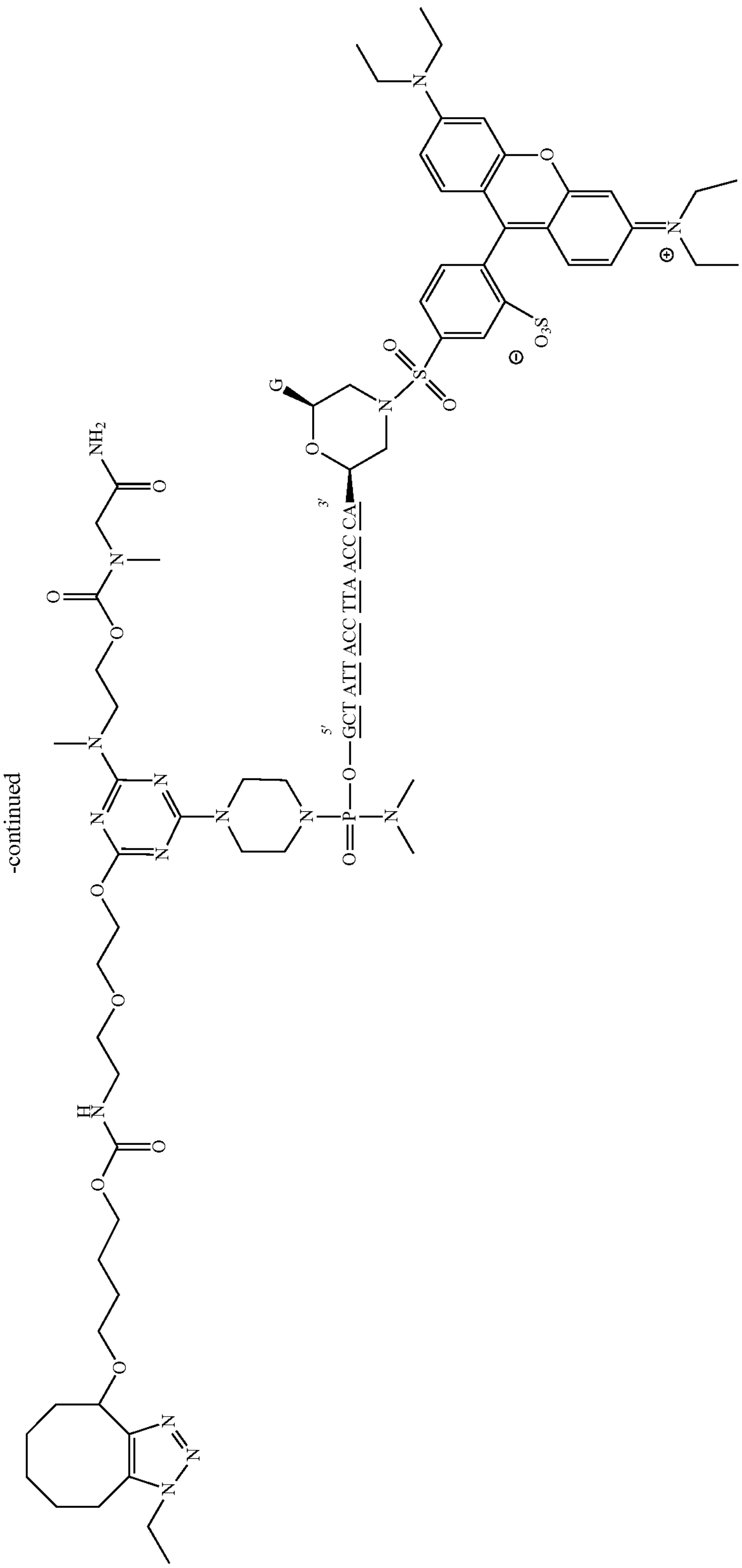

-continued
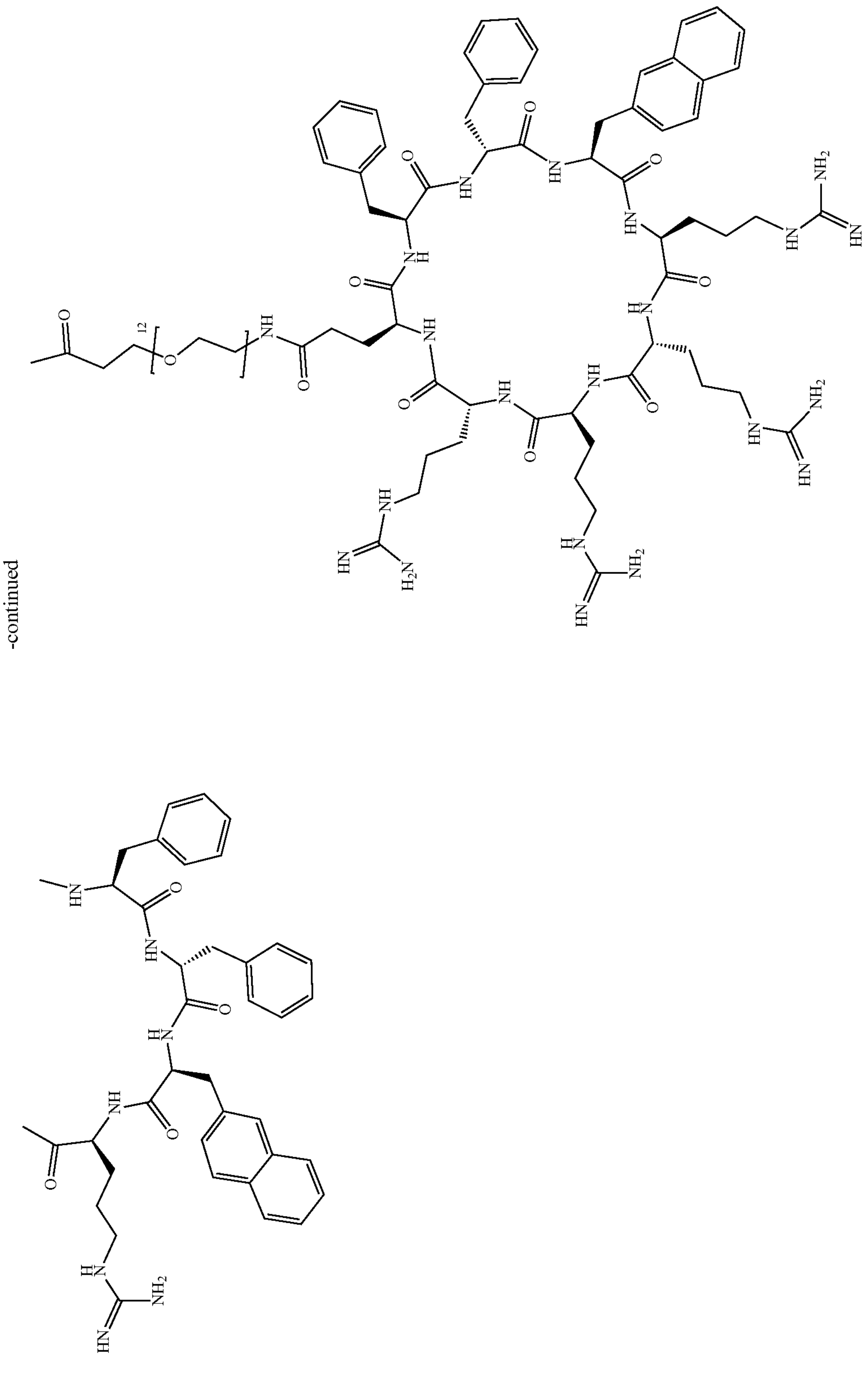

In some embodiments, the AC is independently selected from one of the following structures. Underlining represents the antisense oligonucleotide (SEQ ID NO: 217). The antisense oligonucleotide sequences shown below are for illustrative purposes only, and can be substituted for another antisense oligonucleotide depending on the target of interest.
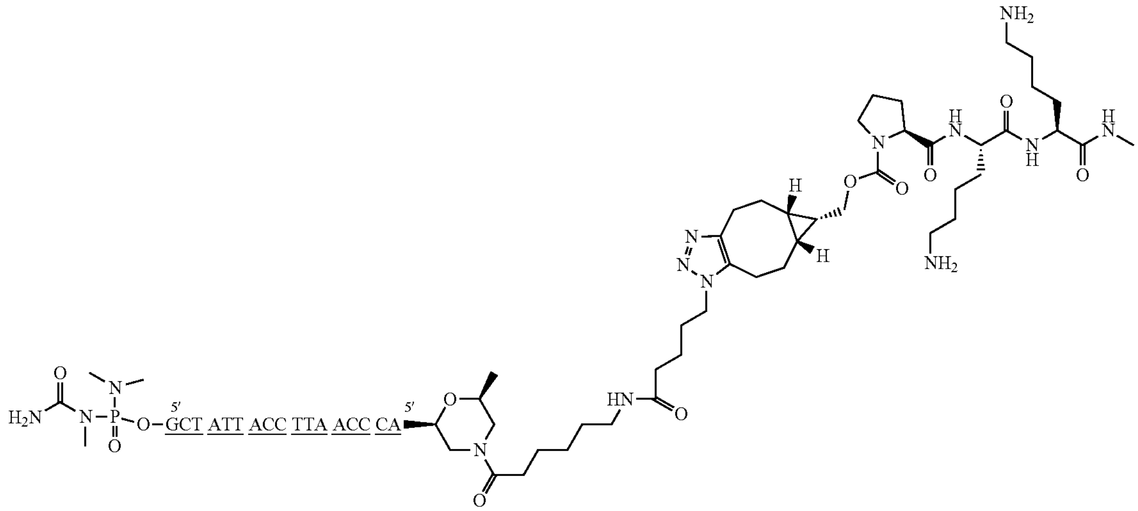
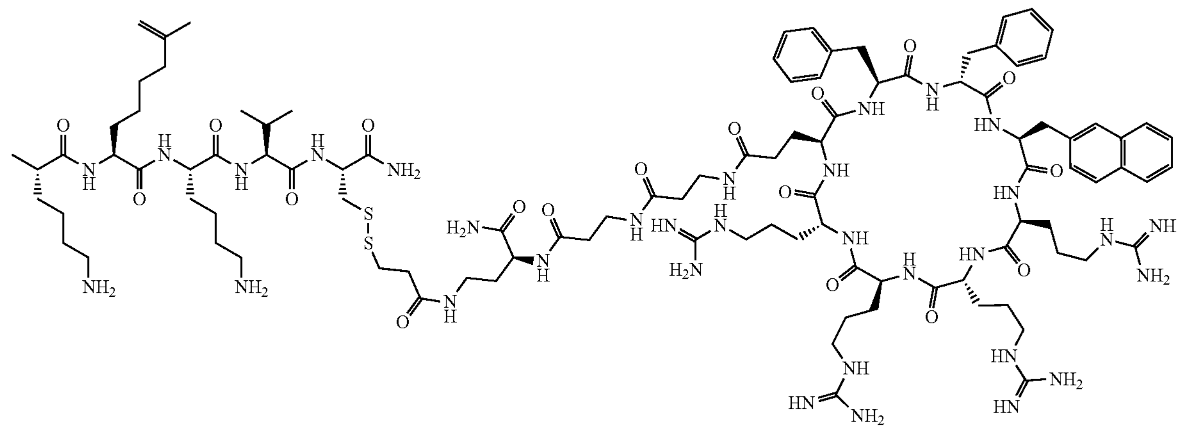
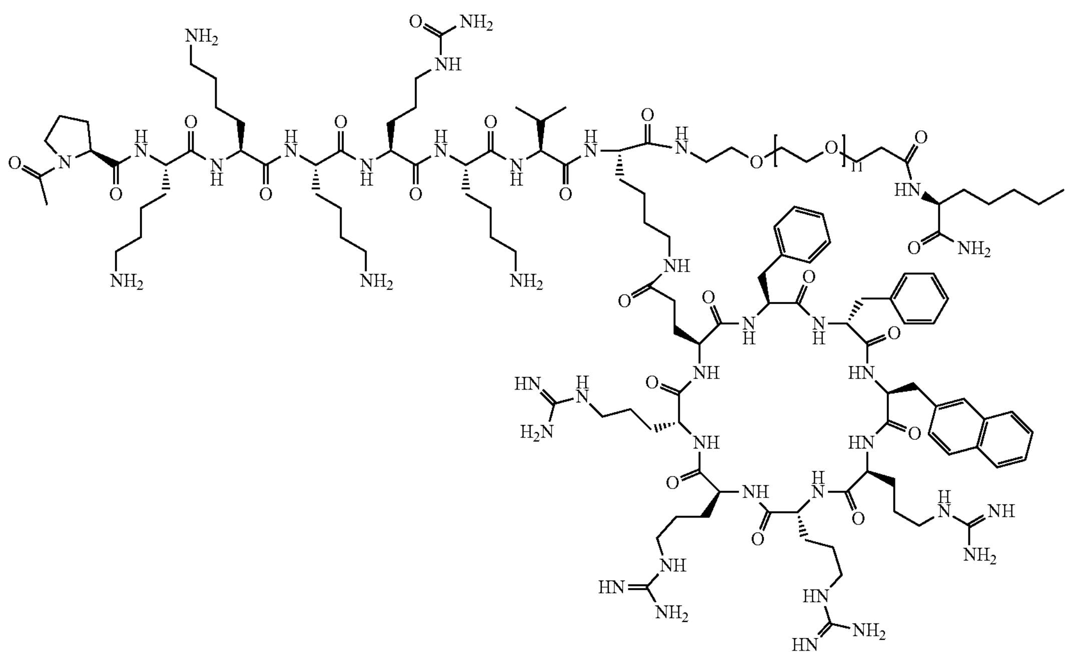

-continued
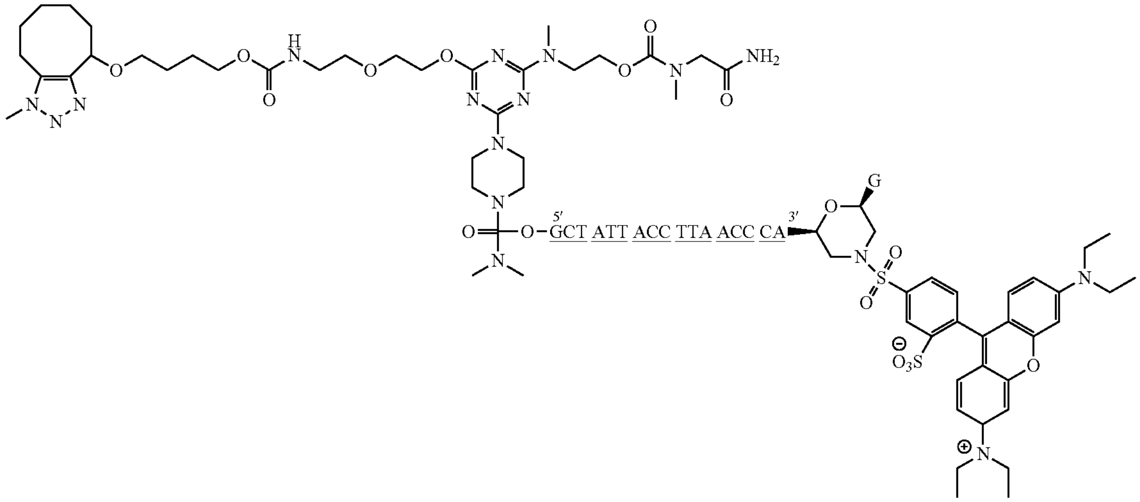
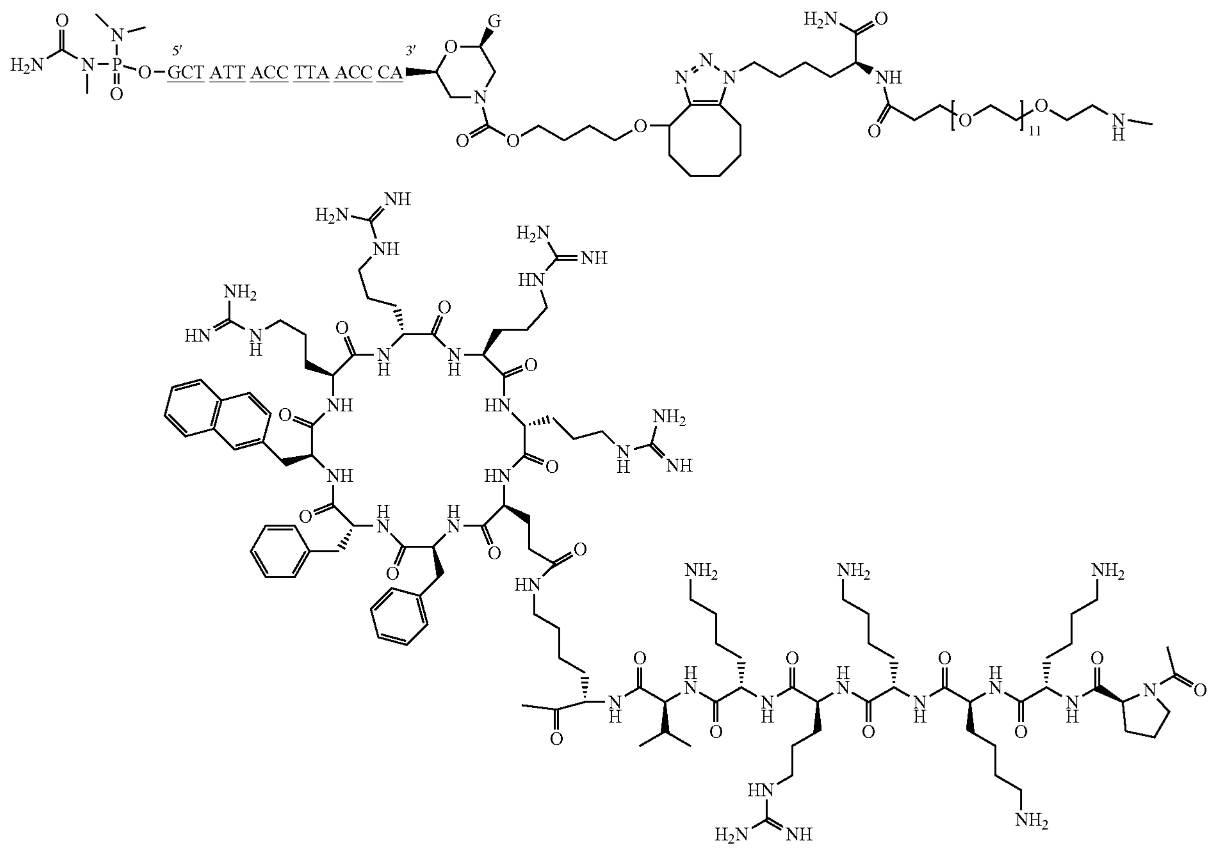
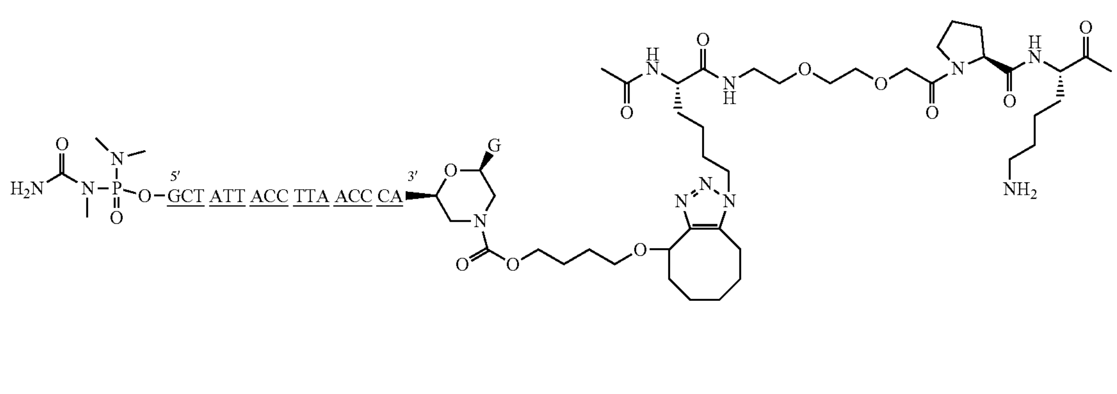

-continued
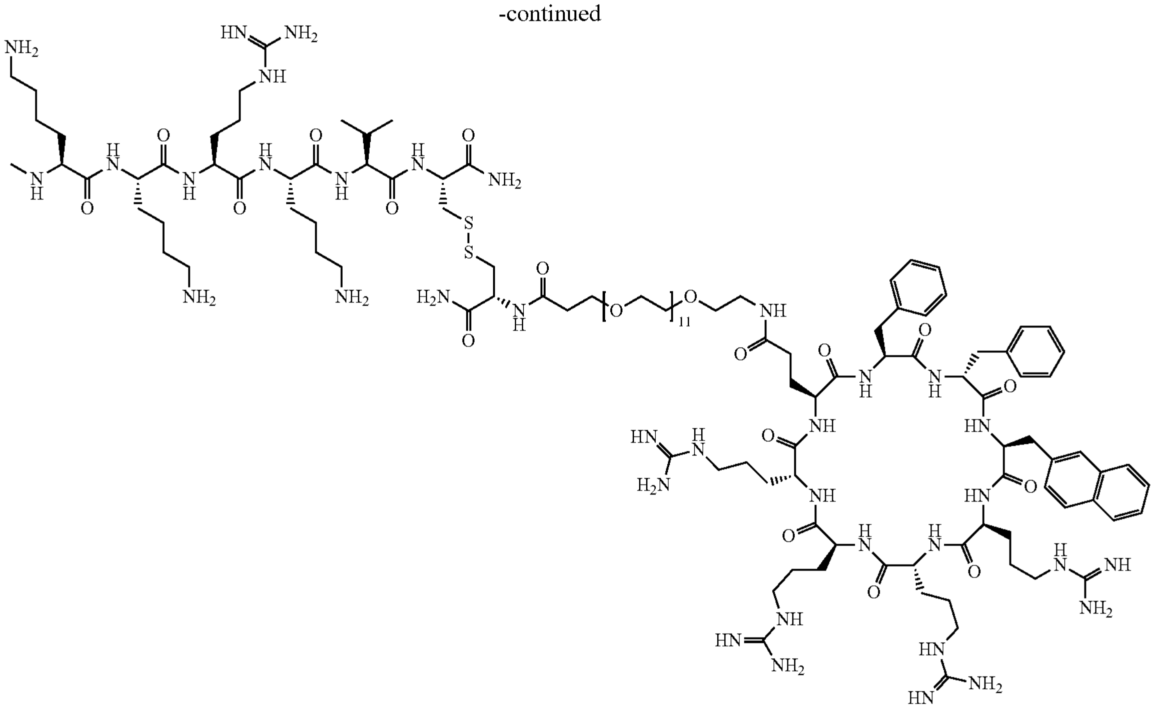
In some embodiments, the compounds of the disclosure have the following structure:
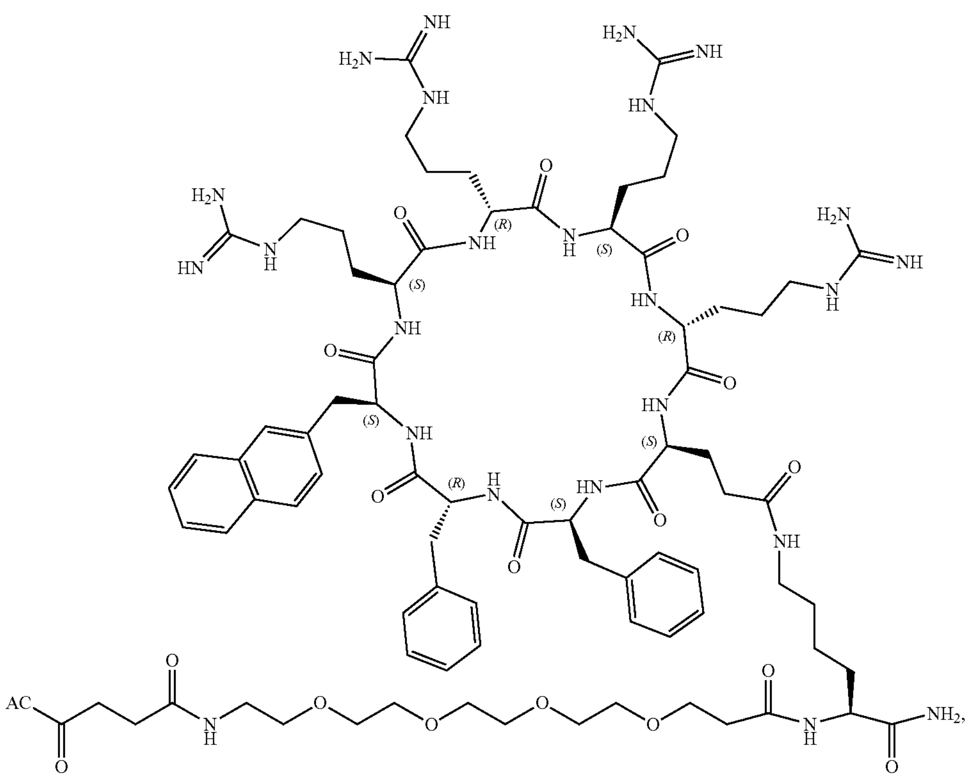

-continued
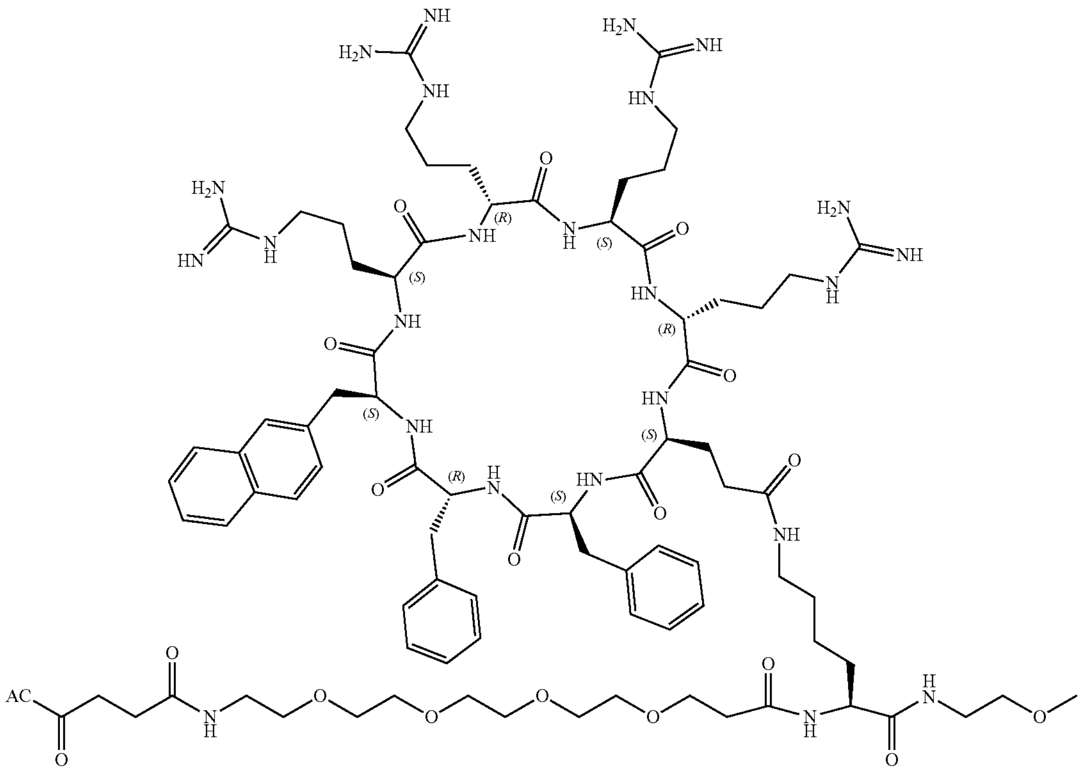
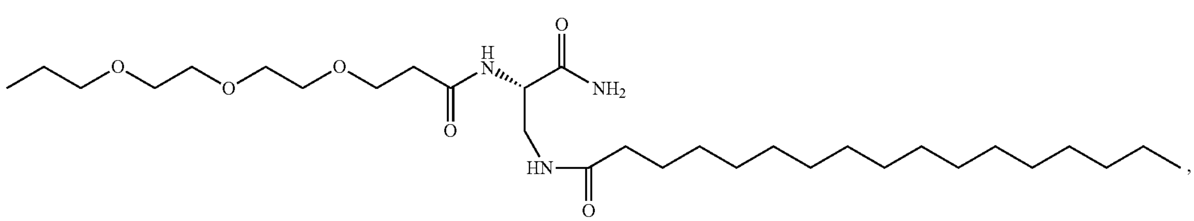
,

-continued
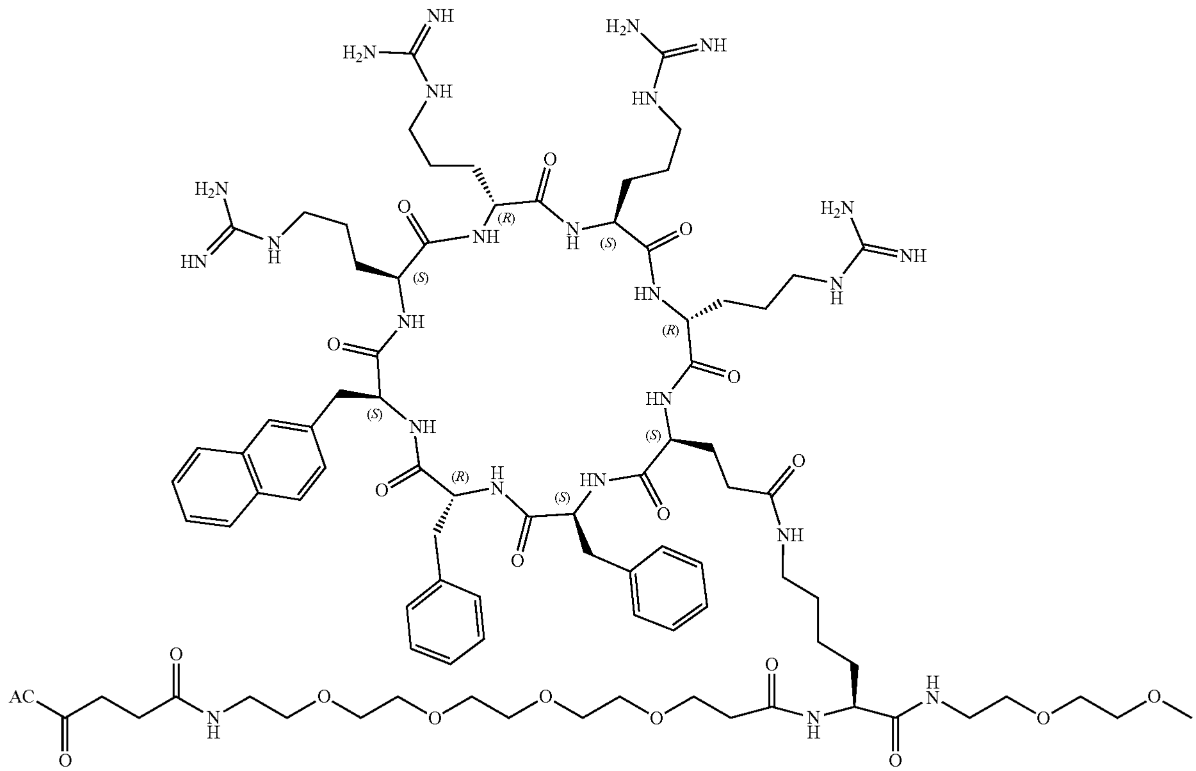
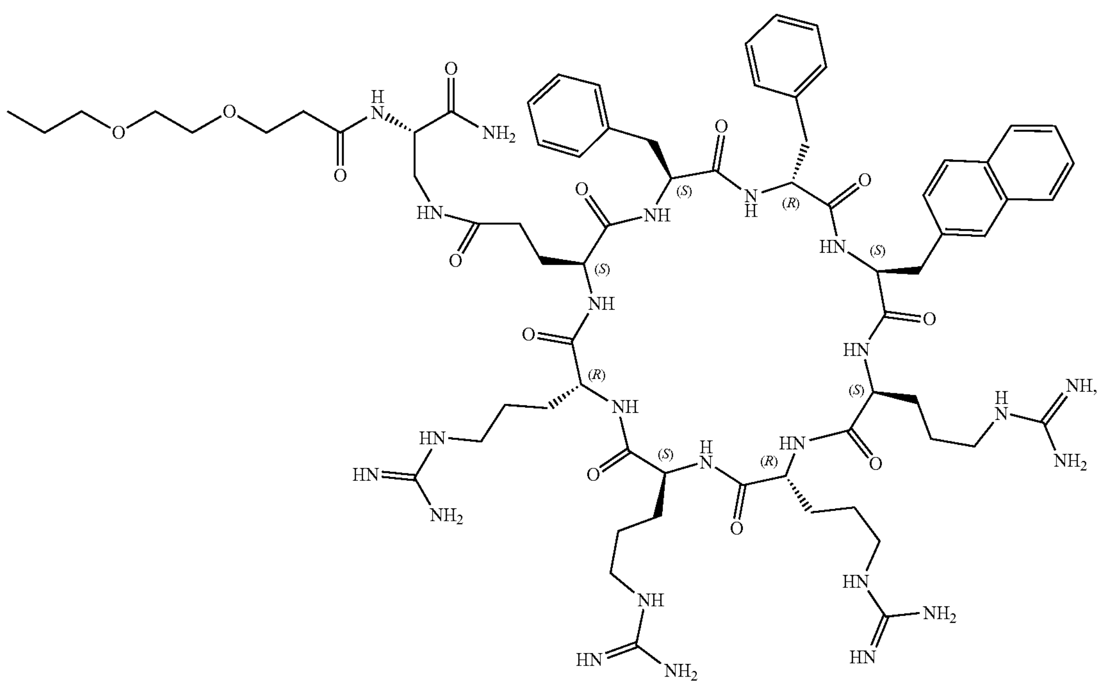
,

-continued

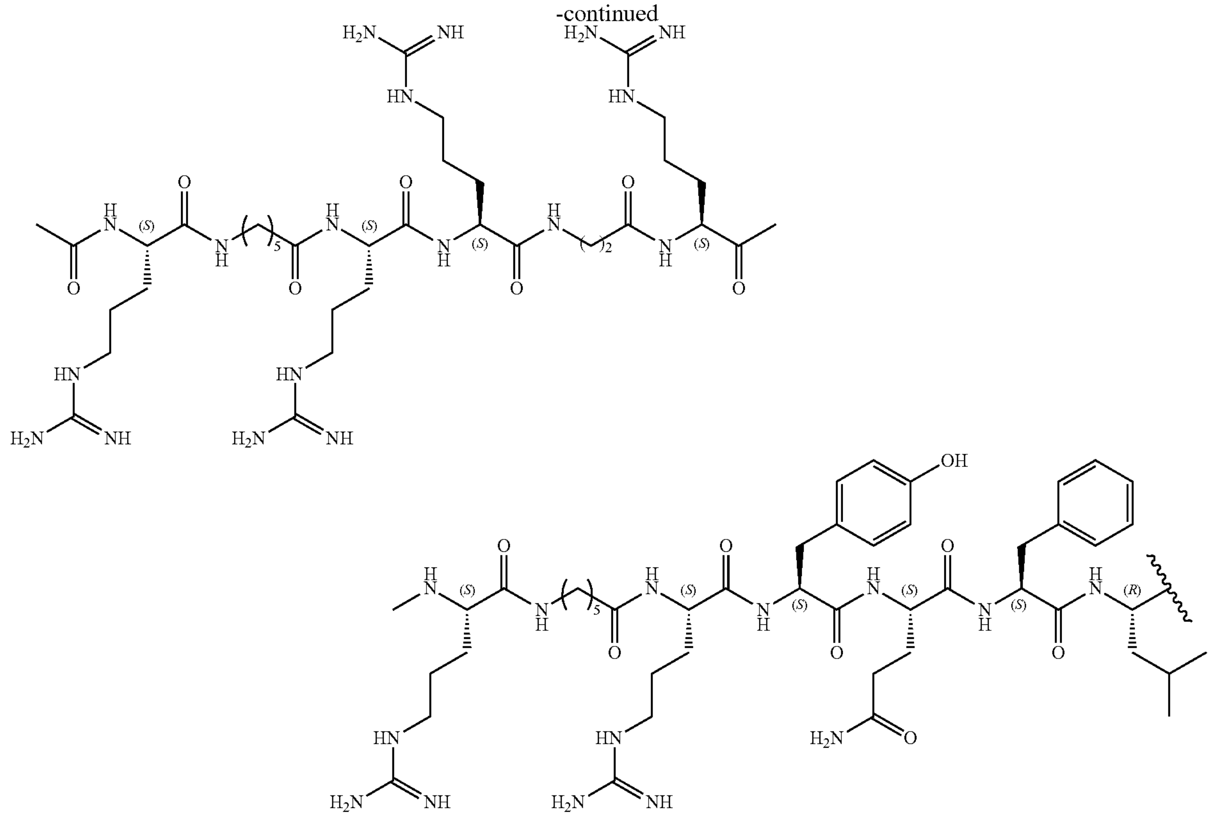

Oligonucleotides

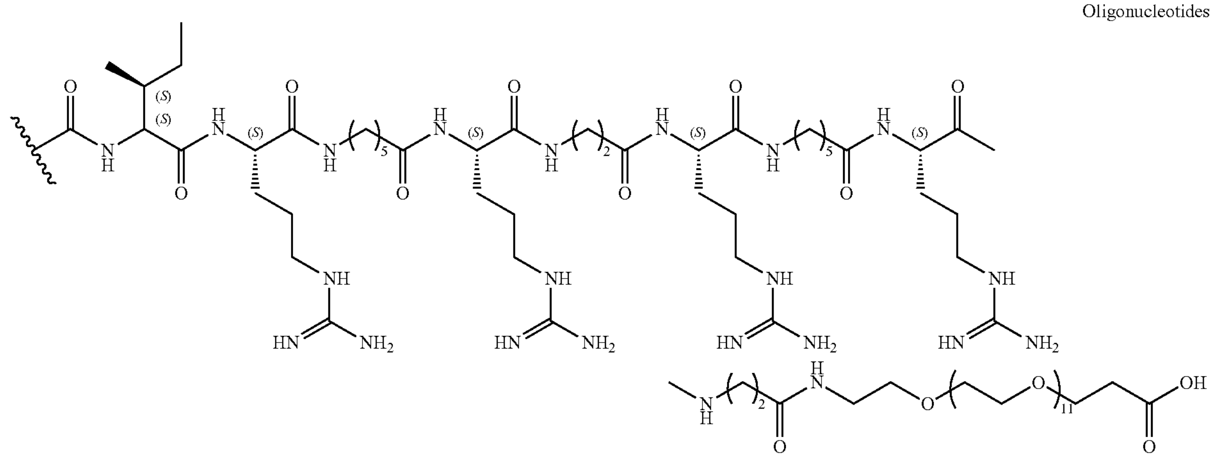

Oligonucleotides

In various embodiments, the compounds disclosed herein comprise a cell penetrating peptide conjugated to an antisense compound (AC). In some embodiments, the AC comprises an antisense oligonucleotide, siRNA, microRNA, antagomir, aptamer, ribozyme, immunostimulatory oligonucleotide, decoy oligonucleotide, supermir, miRNA mimic, miRNA inhibitor, U1 adaptor, or combinations thereof.

Antisense Oligonucleotides

In various embodiments, the oligonucleotide moiety of the present invention is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g. a target gene mRNA.

Figure 31:
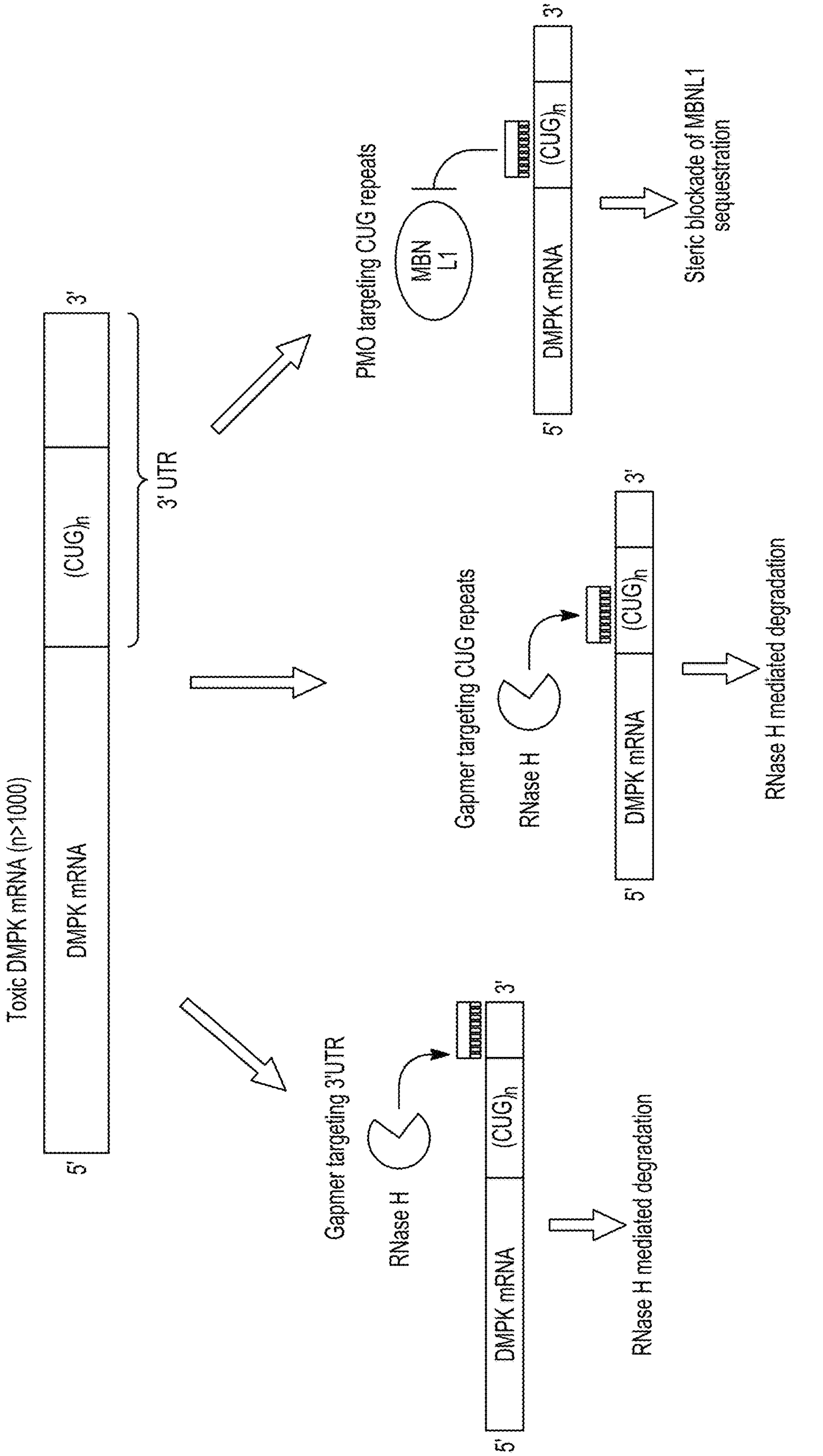
FIG. 31 shows various mechanisms by which antisense compounds modulate expression of DMPK.
Figure 32:
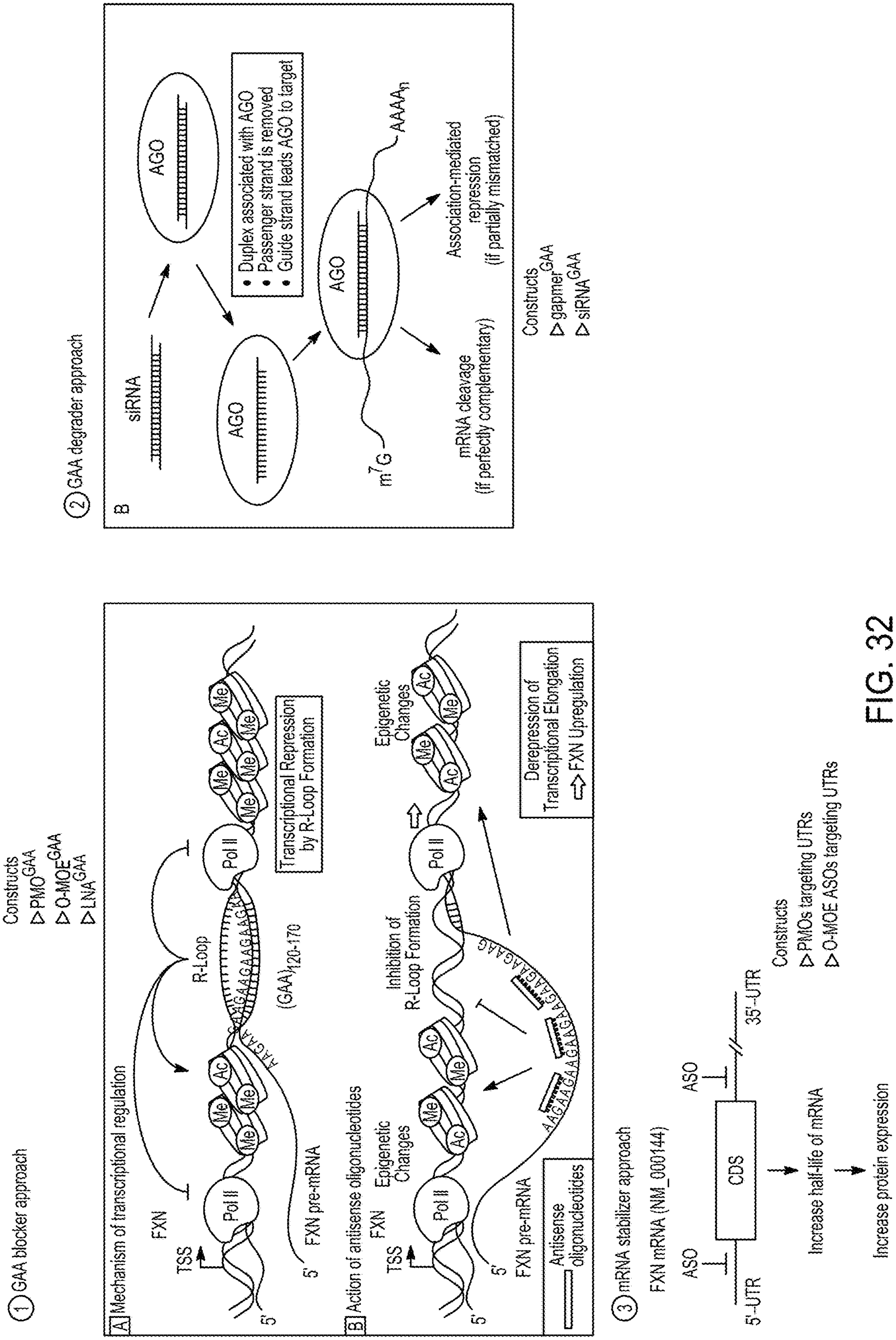
FIG. 32 shows mechanisms by which antisense compounds modulate transcription, degrade mRNA, and stabilize mRNA (SEQ ID NOs: 215 and 216).

The antisense oligonucleotides may modulate one or more aspects of protein transcription, translation, and expression. The antisense oligonucleotides described herein modulate aspects of transcription, translation, and expression through various mechanisms as shown in FIGS. 31 and 32.

In some embodiments, antisense oligonucleotides block expansions of nucleotide repeats (e.g., trinucleotide repeat expansions, pentanucleotide repeat expansions, or hexanucleotide repeat expansions). FIG. 32 shows an exemplary mechanism through which an AC blocks trinucleotide repeats. In some embodiments, the antisense oligonucleotide blocks transcription of the trinucleotide repeat. The following review article describes additional applications for steric blocking antisense oligonucleotides and is incorporated by reference herein in its entirety: Roberts et al. Nature Reviews Drug Discovery (2020) 19: 673-694.

Several diseases are associated with expanded nucleotide repeats, for example, Fragile X mental retardation 1, Friedreich's ataxia (FRDA), Huntington's Disease, myotonic dystrophy type 1 (DM1), myotonic dystrophy type 2 (DM2), spinal and bulbar muscular atrophy, spinal cerebellar ataxia type 1, spinal cerebellar ataxia type 2, and spinal cerebellar ataxia type 3. Table 5 provides examples of nucleotide repeat disorders, and characteristics of genes with expanded nucleotide repeats. The following document describes exemplary oligonucleotides for treating tandem repeat diseases and is incorporated by reference herein in its entirety: Zain et al. Neurotherapeutics. 2019; 16(2): 248-262.

TABLE 5

Tandem Repeat Diseases

| Disease (abbreviation) | Gene | Normal repeat length | Expanded repeat length | Gene product | Repeat sequence | Location of Repeat |
|---|---|---|---|---|---|---|
| Fragile X mental retardation 1 (Fragile X) | FMR1 | 5-55 | >200 | Fragile X mental retardation protein | CGG•CCG | 5' UTR |
| Friedreich's ataxia (FRDA) | FXN | 5-34 | 66-1700 | Frataxin | GAA•CTT | Intron |
| Huntington's Disease (HD) | HTT | 6-35 | 36-250 | Huntingtin | CAG•CTG | Exon |
| Myotonic dystrophy type 1 (DM1) | DMPK | 5-34 | >50 | Dystrophia myotonica protein kinase | CTG•CAG | 3' UTR |
| Myotonic dystrophy type 2 (DM2) | CNBP | 11-26 | 75-11,000 | Cellular nucleic acid-binding protein | CCTG•CAGG | Intron |
| Spinal and bulbar muscular atrophy (SBMA) | AR | 9-34 | 38-68 | Androgen receptor | CAG•CTG | Exon |
| Spinal cerebellar ataxia type 1 (SCA1) | ATXN1 | 6-44 | 39-82 | Ataxin 1 | CAG•CTG | Exon |
| Spinal cerebellar ataxia type 2 (SCA2) | ATXN2 | 12-44 | 55-87 | Ataxin 2 | CAG•CTG | Exon |
| Spinal cerebellar ataxia type 3 (SCA3) | ATXN3 | 12-44 | 55-87 | Ataxin 3 | CAG•CTG | Exon |

In some embodiments, the antisense oligonucleotide is complementary to trinucleotide repeats, such as CAG repeats, CGG repeats, GCC repeats, GAA repeats, or CUG repeats. In some embodiments, the trinucleotide repeat is a CAG repeat. In some embodiments, the target RNA sequence comprises at least 10 trinucleotide repeats (e.g., CAG, CGG, GCC, GAA, or CUG repeats), e.g., at least 5, at least 10, at least 15, at least 20, at least 25, at least 30, at least 35, at least 40, at least 45, at least 50, at least 60, at least 70, at least 80, at least 90, at least 100, at least 150, at least 200, at least 300, at least 400, at least 500, at least 600, at least 700, at least 800, at least 900, at least 1000 at least 2000 trinucleotide repeats. In some embodiments, the AC is complementary sequence comprises to at least 5, at least 10, at least 15, at least 20, at least 25, at least 30, at least 35, at least 40, at least 45, at least 50, at least 60, at least 70, at least 80, at least 90, at least 100, at least 150, at least 200, at least 300, at least 400, at least 500, at least 600, at least 700, at least 800, at least 900, at least 1000 at least 2000 of the trinucleotide repeats in the target mRNA.

In some embodiments, the compounds disclosed herein block at least 1, at least 5, at least 10, at least 15, at least 20, at least 25, at least 30, at least 35, at least 40, at least 45, at least 50, at least 60, at least 70, at least 80, at least 90, at least 100, at least 150, at least 200, at least 300, at least 400, at least 500, at least 600, at least 700, at least 800, at least 900, at least 1000 at least 2000 nucleotide repeats. In some embodiments, the compound disclosed herein prevent translation of at least 1, at least 5, at least 10, at least 15, at least 20, at least 25, at least 30, at least 35, at least 40, at least 45, at least 50, at least 60, at least 70, at least 80, at least 90, at least 100, at least 150, at least 200, at least 300, at least 400, at least 500, at least 600, at least 700, at least 800, at least 900, at least 1000 at least 2000 of the nucleotide repeats in the target mRNA.

In some embodiments, the compounds of the disclosure result in decreased translation of the nucleotide repeats about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the expanded repeat length in the disease state.

Examples of AC sequences for FRDA and DM1 are provided in Table 8. When cells were transfected with these sequences, translation of at least a portion of the expanded repeat was blocked.

In some embodiments, the antisense oligonucleotide degrades trinucleotide repeats. In some embodiments, after binding of an antisense oligonucleotide to a target mRNA, the target mRNA is degraded by RNase H.

In some embodiments, a pair of antisense oligonucleotides are utilized to stabilize target mRNA. In some embodiments, a pair of antisense oligonucleotides are utilized to stabilize the coding region of a target mRNA also referred to herein as a "CDS". In some embodiments, a first antisense oligonucleotide binds 5' of the mRNA CDS, and a second antisense oligonucleotide binds 3' of the mRNA CDS.

In some embodiments, an antisense oligonucleotide increases the half-life of an mRNA. In some embodiments, an antisense oligonucleotide increases the half-life of a target mRNA. In some embodiments, an antisense oligonucleotide increases expression of the protein product of an mRNA (FIG. 32).

In some embodiments, the antisense oligonucleotides to a target sequence within a target pre-mRNA modulates one or more aspects of pre-mRNA splicing. As used herein, modulation of splicing refers to altering the processing of a pre-mRNA transcript such that the spliced mRNA molecule contains either a different combination of exons as a result of exon skipping or exon inclusion, a deletion in one or more exons, or the deletion or addition of a sequence not normally found in the spliced mRNA (e.g., an intron sequence). In some embodiments, antisense oligonucleotides hybridization to a target sequence comprised by a pre-mRNA molecule restores native splicing to a mutated pre-mRNA sequence. In some embodiments, antisense oligonucleotides hybridization results in alternative splicing of the target pre-mRNA. In some embodiments, antisense oligonucleotides hybridization results in exon inclusion or exon skipping of one or more exons. In some embodiments, the skipped exon sequence comprises a frameshift mutation, a nonsense mutation, or a missense mutation. In some embodiments, the skipped exon sequence comprises a nucleic acid deletion, substitution, or insertion. In some embodiments, the skipped exon itself does not comprise a sequence mutation, but a neighboring intron comprises a mutation leading to a frameshift mutation or a nonsense mutation. In some embodiments, antisense oligonucleotides hybridization to a target sequence within a target pre-mRNA prevents inclusion of an intron sequence in the mature mRNA molecule. In some embodiments, antisense oligonucleotides hybridization to a target sequence within a target pre-mRNA results in preferential expression of a wild type target protein isomer. In some embodiments, antisense oligonucleotides hybridization to a target sequence within a target pre-mRNA results in expression of a re-spliced target protein comprising an active fragment of a wild type target protein.

The antisense mechanism functions via hybridization of an antisense oligonucleotide compound with a target nucleic acid. In some embodiments, the antisense oligonucleotide hybridizing to its target sequence suppresses expression of the target protein. In some embodiments, the antisense oligonucleotide hybridizing to its target sequence suppresses expression of one or more wild type target protein isomers. In some embodiments, the antisense oligonucleotide hybridizing to its target sequence upregulates expression of the target protein. In some embodiments, the antisense oligonucleotide hybridizing to its target sequence increases expression of one or more wild type target protein isomers.

In other embodiments, the antisense compound of the present invention can inhibit gene expression by binding to a complementary mRNA. Binding to the target mRNA can lead to inhibition of gene expression either by preventing translation of complementary mRNA strands by binding to it or by leading to degradation of the target mRNA. Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, or about 15 to about 30 nucleotides. The term also encompasses antisense oligonucleotides that may not be fully complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829). Further, examples of antisense inhibition have been demonstrated with the nuclear protein cyclin, the multiple drug resistance gene (MDG1), ICAM-1, E-selectin, STK-1, striatal GABAA receptor and human EGF (Jaskulski et ai, Science. 1988 Jun. 10; 240(4858): 1544-6; Vasanthakumar and Ahmed, Cancer Commun. 1989; 1(4):225-32; Peris et ai, Brain Res Mol Brain Res. 1998 Jun. 15; 57(2): 310-20; U.S. Pat. Nos. 5,801,154; 5,789,573; 5,718,709 and 5,610,288). Furthermore, antisense constructs have also been described that inhibit and can be used to treat a variety of abnormal cellular proliferations, e.g. cancer (U.S. Pat. Nos. 5,747,470; 5,591,317 and 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, Tm, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et ai, Nucleic Acids Res. 1997, 25(17):3389-402).

RNA Interference Nucleic Acids

In some embodiments, the oligonucleotide moiety of the present invention is a RNA interference (RNAi) molecule or a small interfering RNA molecule. RNA interference methods using RNAi or siRNA molecules may be used to disrupt the expression of a gene or polynucleotide of interest.

Small interfering RNAs (siRNAs) are RNA duplexes normally 16-30 nucleotides long that can associate with a cytoplasmic multi-protein complex known as RNAi-induced silencing complex (RISC). RISC loaded with siRNA mediates the degradation of homologous mRNA transcripts, therefore siRNA can be designed to knock down protein expression with high specificity. Unlike other antisense technologies, siRNA function through a natural mechanism evolved to control gene expression through non-coding RNA. A variety of RNAi reagents, including siRNAs targeting clinically relevant targets, are currently under pharmaceutical development, as described, e.g., in de Fougerolles, A. et al, Nature Reviews 6:443-453 (2007).

While the first described RNAi molecules were RNA: RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S. and Christian, A. T., (2003) Molecular Biotechnology 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded oligonucleotides comprising two separate strands, i.e. a sense strand and an antisense strand, e.g., small interfering RNA (siRNA); double-stranded oligonucleotide comprising two separate strands that are linked together by non-nucleotidyl linker; oligonucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule.

A single strand siRNA compound may be sufficiently long that it can enter the RISC and participate in RISC mediated cleavage of a target mRNA. A single strand siRNA compound is at least 14, and in other embodiments at least 15, 20, 25, 29, 35, 40, or 50 nucleotides in length. In certain embodiments, it is less than 200, 100, or 60 nucleotides in length.

Hairpin siRNA compounds may have a duplex region equal to or at least 17, 18, 19, 29, 21, 22, 23, 24, or 25 nucleotide pairs. The duplex region may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the same side of the hairpin and in some embodiments on the antisense side of the hairpin.

A "double stranded siRNA compound" as used herein, is an siRNA compound which includes more than one, and in some cases two, strands in which interchain hybridization can form a region of duplex structure.

The antisense strand of a double stranded siRNA compound may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to21 nucleotides in length. As used herein, term "antisense strand" means the strand of an siRNA compound that is sufficiently complementary to a target molecule, e.g. a target RNA.

The sense strand of a double stranded siRNA compound may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded siRNA compound may be equal to or at least, 14, 15, 16 17, 18, 19, 20, 21, 22, 23, 24, 25, 29, 40, or 60 nucleotide pairs in length, It may be equal to or less than 200, 100, or 50, nucleotides pairs in length, Ranges may be 15-30, 17 to 23, 19 to 23, and 19 to 21 nucleotides pairs in length.

In many embodiments, the siRNA compound is sufficiently large that it can be cleaved by an endogenous molecule, e.g., by Dicer, to produce smaller siRNA compounds, e.g., siRNAs agents The sense and antisense strands may be chosen such that the double-stranded siRNA compound includes a single strand or unpaired region at one or both ends of the molecule. Thus, a double-stranded siRNA compound may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In one embodiment, both ends of an siRNA molecule will have a 3' overhang. In some embodiments, the overhang is 2 nucleotides.

In certain embodiments, the length for the duplexed region is between 15 and 30, or 18, 19, 20, 21, 22, and 23 nucleotides in length, e.g., in the ssiRNA (siRNA with sticky overhangs) compound range discussed above. ssiRNA compounds can resemble in length and structure the natural Dicer processed products from long dsiRNAs. Embodiments in which the two strands of the ssiRNA compound are linked, e.g., covalently linked are also included. Hairpin, or other single strand structures which provide the required double stranded region, and a 3' overhang are also within the invention.

The siRNA compounds described herein, including double-stranded siRNA compounds and single-stranded siRNA compounds can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an ssiRNA compound of 21 to 23 nucleotides.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in certain embodiments, the siRNA compound specifically discriminates a single-nucleotide difference. In this case, the siRNA compound only mediates RNAi if exact complementary is found in the region (e.g., within 7 nucleotides of) the single-nucleotide difference.

MicroRNAs

In some embodiments, the oligonucleotide moiety of the present invention is a microRNA molecule. MicroRNAs (miRNAs) are a highly conserved class of small RNA molecules that are transcribed from DNA in the genomes of plants and animals, but are not translated into protein. Processed miRNAs are single stranded −17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3 '-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "miRBase: microRNA sequences, targets and gene nomenclature" Griffiths-Jones S, Grocock RJ, van Dongen S, Bateman A, Enright AJ. NAR, 2006, 34, Database Issue, D140-D144; "The microRNA Registry" Griffiths-Jones S. NAR, 2004, 32, Database Issue, D109-D111; and also at http://www.mirbase.org/.

Antagomirs

In some embodiments, the oligonucleotide moiety of the present invention is an antagomir. Antagomirs are RNA-like oligonucleotides that harbor various modifications for RNAse protection and pharmacologic properties, such as enhanced tissue and cellular uptake. They differ from normal RNA by, for example, complete 2-0-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. patent application Ser. Nos. 11/502,158 and 11/657,341 (the disclosure of each of which are incorporated herein by reference).

An antagomir can include ligand-conjugated monomer subunits and monomers for oligonucleotide synthesis. Exemplary monomers are described in U.S. application Ser. No. 10/916,185, filed on Aug. 10, 2004. An antagomir can have a ZXY structure, such as is described in PCT Application No. PCT/US2004/07070 filed on Mar. 8, 2004. An antagomir can be complexed with an amphipathic moiety. Exemplary amphipathic moieties for use with oligonucleotide agents are described in PCT Application No. PCT/US2004/07070, filed on Mar. 8, 2004.

Aptamers

In some embodiments, the oligonucleotide moiety of the present invention is an aptamer. Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1: 10-16 (1997), Famulok, Curr. Opin. Struct. Biol. 9:324-9(1999), and Hermann and Patel, Science 287:820-5 (2000). Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, the term "aptamer" also includes "secondary aptamers" containing a consensus sequence derived from comparing two or more known aptamers to a given target. In some embodiments, the aptamer is an "intracellular aptamer", or "intramer", which specifically recognize intracellular targets. See Famulok et al., Chem Biol. 2001, October, 8(10):931-939; Yoon and Rossi, Adv Drug Deliv Rev. 2018, September, 134:22-35, each incorporated by reference herein.

Ribozymes

In some embodiments, the oligonucleotide moiety of the present invention is a ribozyme. Ribozymes are RNA molecules complexes having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al, Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374): 173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions, In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis 6 virus, group I intron or RNaseP RNA (in association with an RNA guide sequence) or *Neurospora* VS RNA motif, for example. Specific examples of hammerhead motifs are described by Rossi et al. Nucleic Acids Res. 1992 Sep. 11; 20(17):4559-65.

Examples of hairpin motifs are described by Hampel et al. (Eur. Pat. Appl. Publ. No. EP 0360257), Hampel and Tritz, Biochemistry 1989 June 13; 28(12):4929-33; Hampel et al, Nucleic Acids Res. 1990 Jan. 25; 18(2):299-304 and U.S. Pat. No. 5,631,359. An example of the hepatitis virus motif is described by Perrotta and Been, Biochemistry. 1992 Dec. 1; 31(47): 11843-52; an example of the RNaseP motif is described by Guerrier-Takada et al, Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(1 1):2795-9); and an example of the Group I intron is described in U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem Π bases to shorten RNA synthesis times and reduce chemical requirements.

Immunostimulatory Oligonucleotides

In some embodiments, the oligonucleotide moiety of the present invention is an immunostimulatory oligonucleotide. Immunostimulatory oligonucleotides (ISS; single- or double-stranded) are capable of inducing an immune response when administered to a subject, which may be a mammal or other patient. ISS include, e.g., certain palindromes leading to hairpin secondary structures (see Yamamoto S., et al. (1992) J. Immunol. 148: 4072-4076), or CpG motifs, as well as other known ISS features (such as multi-G domains, see WO 96/11266).

The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. In a specific embodiment, the nucleic acid comprises the sequence 5' TAACGTTGAGGGGCAT 3' (SEQ ID NO: 147). In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine.

Additional specific nucleic acid sequences of oligonucleotides (ODNs) suitable for use in the compositions and methods of the invention are described in Raney et al, Journal of Pharmacology and Experimental Therapeutics, 298:1185-1192 (2001). In certain embodiments, ODNs used in the compositions and methods of the present invention have a phosphodiester ("PO") backbone or a phosphorothioate ("PS") backbone, and/or at least one methylated cytosine residue in a CpG motif.

Decoy Oligonucleotides

In some embodiments, the oligonucleotide moiety of the present invention is a decoy oligonucleotide. Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest, 2000, 106: 1071-1075, which is expressly incorporated by reference herein, in its entirety.

Supermir

In some embodiments, the oligonucleotide moiety of the present invention is a supermir. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target, This term includes oligonucleotides composed of naturally-occurring nucleobases, sugars and covalent internucleoside (backbone) linkages and which contain at least one non-naturally-occurring portion which functions similarly. Such modified or substituted oligonucleotides are preferred over native forms because of desirable properties such as, for example, enhanced cellular uptake, enhanced affinity for nucleic acid target and increased stability in the presence of nucleases. In a preferred embodiment, the supermir does not include a sense strand, and in another preferred embodiment, the supermir does not self-hybridize to a significant extent.

A supermir featured in the invention can have secondary structure, but it is substantially single-stranded under physiological conditions. A supermir that is substantially single-stranded is single-stranded to the extent that less than about 50% {e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or n nucleotides, e.g., 5 nuclotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

miRNA Mimics

In some embodiments, the oligonucleotide moiety of the present invention is an miRNA mimic. miRNA mimics represent a class of molecules that can be used to imitate the gene silencing ability of one or more miRNAs. Thus, the term “microRNA mimic” refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). miRNA mimics can be comprised of nucleic acid (modified or modified nucleic acids) including oligonucleotides comprising, without limitation, RNA, modified RNA, DNA, modified DNA, locked nucleic acids, or 2'-0,4'-C-ethylene-bridged nucleic acids (ENA), or any combination of the above (including DNA-RNA hybrids). In addition, miRNA mimics can comprise conjugates that can affect delivery, intracellular compartmentalization, stability, specificity, functionality, strand usage, and/or potency. In one design, miRNA mimics are double stranded molecules (e.g., with a duplex region of between about 16 and about 31 nucleotides in length) and contain one or more sequences that have identity with the mature strand of a given miRNA. Modifications can comprise 2' modifications (including 2'-0 methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality. In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3 ' overhang.

miRNA Inhibitor

In some embodiments, the oligonucleotide moiety of the present invention is an miRNA inhibitor. The terms “anti-mir” “microRNA inhibitor”, “miR inhibitor”, or “miRNA inhibitor” are synonymous and refer to oligonucleotides or modified oligonucleotides that interfere with the ability of specific miRNAs. In general, the inhibitors are nucleic acid or modified nucleic acids in nature including oligonucleotides comprising RNA, modified RNA, DNA, modified DNA, locked nucleic acids (LNAs), or any combination of the above.

Modifications include 2' modifications (including 2'-0 alkyl modifications and 2' F modifications) and internucleotide modifications (e.g. phosphorothioate modifications) that can affect delivery, stability, specificity, intracellular compartmentalization, or potency. In addition, miRNA inhibitors can comprise conjugates that can affect delivery, intracellular compartmentalization, stability, and/or potency. Inhibitors can adopt a variety of configurations including single stranded, double stranded (RNA/RNA or RNA/DNA duplexes), and hairpin designs, in general, microRNA inhibitors comprise contain one or more sequences or portions of sequences that are complementary or partially complementary with the mature strand (or strands) of the miRNA to be targeted, in addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, or U). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. Micro-RNA inhibitors, when double stranded, may include mismatches between nucleotides on opposite strands. Furthermore, micro-RNA inhibitors may be linked to conjugate moieties in order to facilitate uptake of the inhibitor into a cell. For example, a micro-RNA inhibitor may be linked to cholesteryl 5-(bis(4-methoxyphenyl)(phenyl)methoxy)-3 hydroxypentylcarbamate) which allows passive uptake of a micro-RNA inhibitor into a cell. Micro-RNA inhibitors, including hairpin miRNA inhibitors, are described in detail in Vermeulen et al., “Double-Stranded Regions Are Essential Design Components Of Potent Inhibitors of RISC Function,” RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

U1 adaptor

In some embodiments, the oligonucleotide moiety of the present invention is a U1 adaptor. U1 adaptors inhibit polyA sites and are bifunctional oligonucleotides with a target domain complementary to a site in the target gene's terminal exon and a ‘U1 domain’ that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant Mol Biol 49:77-95). Nucleotides 2-11 of the 5'end of U1 snRNA base pair bind with the 5'ss of the pre mRNA. In one embodiment, oligonucleotides of the invention are U1 adaptors. In one embodiment, the Ul adaptor can be administered in combination with at least one other iRNA agent.

Antisense Compounds (ACs)

According to the present disclosure, an antisense compound (AC) is employed in order to alter one or more aspects of the splicing, translation, or expression of a target gene, e.g., by altering the splicing of a eukaryotic target pre-mRNA. The AC according to the disclosure comprises a nucleic acid sequence that is complementary to a sequence found within a target pre-mRNA sequence. The use of these ACs provides a direct genetic approach that has the ability to modulate splicing of specific disease-causing genes. The principle behind antisense technology is that an antisense compound, which hybridizes to a target nucleic acid, modulates gene expression activities such as splicing or translation through one of a number of antisense mechanisms. The sequence-specificity of the AC makes this technique extremely attractive as a therapeutic to selectively modulate the splicing of pre-mRNA involved in the pathogenesis of any one of a variety of diseases. Antisense technology is an effective means for changing the expression of one or more specific gene products and can therefore prove to be useful in a number of therapeutic, diagnostic, and research applications.

The compounds described herein may contain one or more asymmetric centers and thus give rise to enantiomers, diastereomers, and other stereoisomeric configurations that may be defined, in terms of absolute stereochemistry, as (R) or (S), a or 3, or as (D) or (L). Included in the antisense compounds provided herein are all such possible isomers, as well as their racemic and optically pure forms.

Antisense Compound Hybridization Site

Antisense mechanisms rely on hybridization of the antisense compound to the target nucleic acid. Accordingly, the present disclosure provides antisense compounds that are complementary to a target nucleic acid. In some embodiments, the target nucleic acid sequence is present in a pre-mRNA molecule.

Pre-mRNA molecules are made in the nucleus and are processed before or during transport to the cytoplasm for translation. Processing of the pre-mRNAs includes addition of a 5' methylated cap and an approximately 200-250 base poly(A) tail to the 3' end of the transcript. The next step in mRNA processing is splicing of the pre-mRNA, which occurs in the maturation of 90-95% of mammalian mRNAs. Introns (or intervening sequences) are regions of a primary transcript (or the DNA encoding it) that are not included in the coding sequence of the mature mRNA. Exons are regions of a primary transcript that remain in the mature mRNA when it reaches the cytoplasm. The exons are spliced together to form the mature mRNA sequence. Splice junctions are also referred to as splice sites with the 5' side of the junction often called the "5' splice site," or "splice donor site" and the 3' side called the "3' splice site" or "splice acceptor site." In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

In some embodiments, the AC hybridizes with a sequence in a splice site. In some embodiments, the AC hybridizes with a sequence comprising part of a splice site. In some embodiments, the AC hybridizes with a sequence comprising all of a splice site. In some embodiments, the AC hybridizes with a sequence comprising part or all of a splice donor site. In some embodiments, the AC hybridizes with a sequence comprising part or all of a splice acceptor site. In some embodiments, the AC hybridizes with a sequence comprising part or all of a cryptic splice site. In some embodiments, the AC hybridizes with a sequence comprising an exon/intron junction.

Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS) and terminal stem loop (TSL) sequences. As used herein, the terms "intronic silencer sequences (ISS)" and "terminal stem loop (TSL)" refer to sequence elements within introns and exons, respectively, that control alternative splicing by the binding of trans-acting protein factors within a pre-mRNA thereby resulting in differential use of splice sites. Typically, intronic silencer sequences are between 8 and 16 nucleotides and are less conserved than the splice sites at exon-intron junctions. Terminal stem loop sequences are typically between 12 and 24 nucleotides and form a secondary loop structure due to the complementarity, and hence binding, within the 12-24 nucleotide sequence.

In some embodiments, the AC hybridizes with a sequence comprising part or all of an intronic silencer sequence. In some embodiments, the AC hybridizes with a sequence comprising part or all of a terminal stem loop.

Up to 50% of human genetic diseases resulting from a point mutation are caused by aberrant splicing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers).

In some embodiments, the AC hybridizes with a sequence comprising part or all of an aberrant splice site resulting from a mutation in the target gene. In some embodiments, the AC hybridizes with a sequence comprising part or all of a regulatory element. Also provided are antisense compounds targeted to cis regulatory elements. In some embodiments, the regulatory element is in an exon. In some embodiments, the regulatory element is in an intron.

In some embodiments, the AC may be specifically hybridizable with a translation initiation codon region, a 5' cap region, an intron/exon junction, a coding sequence, a translation termination codon region or sequences in the 5'- or 3'-untranslated region. In some embodiments, the AC may hybridize with part or all of a pre-mRNA splice site, an exon-exon junction, or an intron-exon junction. In some embodiments, the AC may hybridize with an aberrant fusion junction due to a rearrangement or a deletion. In some embodiments, the AC may hybridize with particular exons in alternatively spliced mRNAs.

In some embodiments, the AC hybridizes with a sequence between 5 and 50 nucleic acids in length, which can also be referred to as the length of the AC. In some embodiments, the AC is between 5 and 10, 10 and 15, 15 and 20, 20 and 25, 25 and 30, 30 and 35, 35 and 40, 40 and 45, or 45 and 50 nucleic acids in length. In some embodiments, the AC is approximately 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleic acids in length. In some embodiments, the AC is approximately 10 nucleic acids in length. In some embodiments, the AC is approximately 15 nucleic acids in length. In some embodiments, the AC is approximately 20 nucleic acids in length. In some embodiments, the AC is approximately 25 nucleic acids in length. In some embodiments, the AC is approximately 30 nucleic acids in length.

In some embodiments, the AC may be less than 100 percent complementary to a target nucleic acid sequence. As used herein, the term "percent complementary" refers to the number of nucleobases of an AC that have nucleobase complementarity with a corresponding nucleobase of an oligomeric compound or nucleic acid divided by the total length (number of nucleobases) of the AC. One skilled in the art recognizes that the inclusion of mismatches is possible without eliminating the activity of the antisense compound. Therefore, in some embodiments, an AC may contain up to about 20% nucleotides that disrupt base pairing of the AC to the target nucleic acid. In some embodiments, the ACs contain no more than about 15%, no more than about 10%, no more than 5%, or no mismatches. In some embodiments, the ACs are at least 80%, at least 85%, at least 90%, at least 95%, at least 96%, at least 97%, at least 98%, at least 99% or 100% complementary to a target nucleic acid. Percent complementarity of an oligonucleotide is calculated by dividing the number of complementary nucleobases by the total number of nucleobases of the oligonucleotide. Percent complementarity of a region of an oligonucleotide is calculated by dividing the number of complementary nucleobases in the region by the total number of nucleobases region.

In some embodiments, incorporation of nucleotide affinity modifications allows for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

Antisense Mechanisms

The ACs according to the present disclosure may modulate one or more aspects of protein transcription, translation, and expression. In some embodiments, the AC hybridizing to a target sequence within a target pre-mRNA modulates one or more aspects of pre-mRNA splicing. As used herein, modulation of splicing refers to altering the processing of a pre-mRNA transcript such that the spliced mRNA molecule contains either a different combination of exons as a result of exon skipping or exon inclusion, a deletion in one or more exons, or the deletion or addition of a sequence not normally found in the spliced mRNA (e.g., an intron sequence). In some embodiments, AC hybridization to a target sequence comprised by a pre-mRNA molecule restores native splicing to a mutated pre-mRNA sequence. In some embodiments, AC hybridization results in alternative splicing of the target pre-mRNA. In some embodiments, AC hybridization results in exon inclusion or exon skipping of one or more exons. In some embodiments, the skipped exon sequence comprises a frameshift mutation, a nonsense mutation, or a missense mutation. In some embodiments, the skipped exon sequence comprises a nucleic acid deletion, substitution, or insertion. In some embodiments, the skipped exon itself does not comprise a sequence mutation, but a neighboring intron comprises a mutation leading to a frameshift mutation or a nonsense mutation. In some embodiments, AC hybridization to a target sequence within a target pre-mRNA prevents inclusion of an intron sequence in the mature mRNA molecule. In some embodiments, AC hybridization to a target sequence within a target pre-mRNA results in preferential expression of a wild type target protein isomer. In some embodiments, AC hybridization to a target sequence within a target pre-mRNA results in expression of a re-spliced target protein comprising an active fragment of a wild type target protein.

In some embodiments, the AC regulates transcription, translation, or protein expression through steric blocking. The following review article describes the mechanisms of steric blocking and applications thereof and is incorporated by reference herein in its entirety: Roberts et al. Nature Reviews Drug Discovery (2020) 19: 673-694.

The antisense mechanism functions via hybridization of an antisense compound with a target nucleic acid. In some embodiments, the AC hybridizing to its target sequence suppresses expression of the target protein. In some embodiments, the AC hybridizing to its target sequence suppresses expression of one or more wild type target protein isomers. In some embodiments, the AC hybridizing to its target sequence upregulates expression of the target protein. In some embodiments, the AC hybridizing to its target sequence increases expression of one or more wild type target protein isomers.

The efficacy of the ACs of the present disclosure may be assessed by evaluating the antisense activity effected by their administration. As used herein, the term "antisense activity" refers to any detectable and/or measurable activity attributable to the hybridization of an antisense compound to its target nucleic acid. Such detection and or measuring may be direct or indirect. In some embodiments, antisense activity is assessed by detecting and or measuring the amount of target protein. In some embodiments, antisense activity is assessed by detecting and or measuring the amount of re-spliced target protein. In some embodiments, antisense activity is assessed by detecting and/or measuring the amount of target nucleic acids and/or cleaved target nucleic acids and/or alternatively spliced target nucleic acids Antisense Compound Design Design of ACs according to the present disclosure will depend upon the sequence being targeted. Targeting an AC to a particular target nucleic acid molecule can be a multi-step process. The process usually begins with the identification of a target nucleic acid whose expression is to be modulated. As used herein, the terms "target nucleic acid" and "nucleic acid encoding a target gene" encompass DNA encoding a selected target gene, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent.

One of skill in the art will be able to design, synthesize, and screen antisense compounds of different nucleobase sequences to identify a sequence that results in antisense activity. For example, one may design an antisense compound that alters splicing of a target pre-mRNA or inhibits expression of a target protein. Methods for designing, synthesizing and screening antisense compounds for antisense activity against a preselected target nucleic acid can be found, for example in "Antisense Drug Technology, Principles, Strategies, and Applications" Edited by Stanley T. Crooke, CRC Press, Boca Raton, Florida, which is incorporated by reference in its entirety for any purpose.

In some embodiments, the present invention provides antisense compounds comprising oligonucleotides. Certain oligonucleotides comprise 8 to 30 linked nucleosides. In some embodiments, the antisense compounds comprise modified nucleosides, modified internucleoside linkages and/or conjugate groups.

In some embodiments, the antisense compound is a "tricyclo-DNA (tc-DNA)", which refers to a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs.

Exemplary Nucleosides

In some embodiments, the invention provides antisense compounds comprising linked nucleosides. In some embodiments, some or all of the nucleosides are modified nucleosides. In some embodiments, one or more nucleoside comprises a modified nucleobase. In some embodiments, one or more nucleosides comprises a modified sugar. Chemically modified nucleosides are routinely used for incorporation into antisense compounds to enhance one or more properties, such as nuclease resistance, pharmacokinetics or affinity for a target RNA. Non-limiting examples of nucleosides are provided in FIG. 69 and in Khvorova et al. Nature Biotechnology (2017) 35: 238-248, which is incorporated by reference herein in its entirety.

In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The terms modified nucleobase and nucleobase mimetic can overlap but generally a modified nucleobase refers to a nucleobase that is fairly similar in structure to the parent nucleobase, such as for example a 7-deaza purine, a 5-methyl cytosine, or a G-clamp, whereas a nucleobase mimetic would include more complicated structures, such as for example a tricyclic phenoxazine nucleobase mimetic. Methods for preparation of the above noted modified nucleobases are well known to those skilled in the art.

In some embodiments, ACs provided herein comprise one or more nucleosides having a modified sugar moiety. In some embodiments, the furanosyl sugar ring of a natural nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R1)(R2) for the ring oxygen at the 4'-position. Modified sugar moieties are well known and can be used to alter, typically increase, the affinity of the antisense compound for its target and/or increase nuclease resistance. A representative list of modified sugars includes but is not limited to non-bicyclic substituted sugars, especially non-bicyclic 2'-substituted sugars having a 2'-F, 2'-OCH3 or a 2'-O(CH2)2—OCH3 substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,600,032; and WO 2005/121371.

In some embodiments, nucleosides comprise bicyclic modified sugars (BNA's), including LNA (4'—(CH2)—O—2' bridge), 2'-thio-LNA (4'—(CH2)—S-2' bridge),, 2'-amino-LNA (4'—(CH2)—NR-2' bridge),, ENA (4'—(CH2)2—O—2' bridge), 4'—(CH2)3-2' bridged BNA, 4'—(CH2CH(CH3))-2' bridged BNA" cEt (4'—(CH(CH3)—O—2' bridge), and cMOE BNAs (4'—(CH(CH2OCH3)—O—2' bridge). Certain such BNA's have been prepared and disclosed in the patent literature as well as in scientific literature (See, e.g., Srivastava, et al. J. Am. Chem. Soc. 2007, ACS Advanced online publication, 10.1021/ja071106y, Albaek et al. J. Org. Chem., 2006, 71, 7731-7740, Fluiter, et al. Chembiochem 2005, 6, 1104-1109, Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; WO 94/14226; WO 2005/021570; Singh et al., J. Org. Chem., 1998, 63, 10035-10039, WO 2007/090071; Examples of issued US patents and published applications that disclose BNAs include, for example, U.S. Pat. Nos. 7,053,207; 6,268,490; 6,770,748; 6,794,499; 7,034,133; and 6,525,191; and U.S. Pre-Grant Publication Nos. 2004-0171570; 2004-0219565; 2004-0014959; 2003-0207841; 2004-0143114; and 20030082807.

Also provided herein are "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene ($—CH_2—$) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +100° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

An isomer of LNA that has also been studied is alpha-L-LNA which has been shown to have superior stability against a 3'-exonuclease. The alpha-L-LNA's were incorporated into antisense gapmers and chimeras that showed potent antisense activity (Frieden et al., Nucleic Acids Research, 2003, 21, 6365-6372).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Exemplary Internucleoside Linkages

Described herein are internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH2-N(CH3)—O—CH2-), thiodiester (—O—C(O)—S—), thionocarbamate (—O—C(O)(NH)—S—); siloxane (—O—Si(H)2—O—); and N,N'-dimethylhydrazine (—CH2-N(CH3)—N(CH3)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

In some embodiments, a phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage.

Conjugate Groups

In some embodiments, ACs are modified by covalent attachment of one or more conjugate groups. In general, conjugate groups modify one or more properties of the attached AC including but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an AC. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In some embodiments, the conjugate group is a polyethylene glycol (PEG), and the PEG is conjugated to either the AC or the CPP.

Certain conjugate groups amenable to the present invention include lipid moieties such as a cholesterol moiety (Letsinger et al., Proc. Natl. Acad. Sci. USA, 1989, 86, 6553); cholic acid (Manoharan et al., Bioorg. Med. Chem. Lett., 1994, 4, 1053); a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al., Tetrahedron Lett., 1995, 36, 3651; Shea et al., Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al., Biochim. Biophys. Acta, 1995, 1264, 229); or an octadecylamine or hexylamino-carbonyl-oxycholesterol moiety (Crooke et al., J. Pharmacol. Exp. Ther., 1996,277,923).

Linking groups or bifunctional linking moieties such as those known in the art are amenable to the compounds provided herein. Linking groups are useful for attachment of chemical functional groups, conjugate groups, reporter groups and other groups to selective sites in a parent compound such as for example an AC. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. Any of the linkers described here may be used. In some embodiments, the linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In some embodiments, the AC may be linked to a 10 arginine-serine dipeptide repeat. ACs linked to 10 arginine-serine dipeptide repeats for the artificial recruitment of splicing enhancer factors have been applied in vitro to induce inclusion of mutated BRCA1 and SMN2 exons that otherwise would be skipped. See Cartegni and Krainer 2003, incorporated by reference herein.

In some embodiments, the AC may be between 5 and 50 nucleotides in length. In some embodiments, the AC may be 5-10 nucleotides in length. In some embodiments, the AC may be 10-15 nucleotides in length. In some embodiments, the AC may be 15-20 nucleotides in length. In some embodiments, the AC may be 20-25 nucleotides in length. In some embodiments, the AC may be 25-30 nucleotides in length. In some embodiments, the AC may be 30-35 nucleotides in length. In some embodiments, the AC may be 35-40 nucleotides in length. In some embodiments, the AC may be 40-45 nucleotides in length. In some embodiments, the AC may be 45-50 nucleotides in length.

Clustered Regularly Interspaced Short Palindromic Repeats (CRISPR) Gene-Editing Machinery In some embodiments, the compounds disclosed herein comprise one or more CPP (or cCPP) conjugated to CRISPR gene-editing machinery. As used herein, "CRISPR gene-editing machinery" refers to protein, nucleic acids, or combinations thereof, which may be used to edit a genome. Non-limiting examples of gene-editing machinery include gRNAs, nucleases, nuclease inhibitors, and combinations and complexes thereof. The following patent documents describe CRISPR gene-editing machinery: U.S. Pat. Nos. 8,697,359, 8,771,945, 8,795,965, 8,865,406, 8,871,445, 8,889,356, 8,895,308, 8,906,616, 8,932,814, 8,945,839, 8,993,233, 8,999,641, U.S. patent application Ser. No. 14/704,551, and U.S. patent application Ser. No. 13/842,859. Each of the aforementioned patent documents is incorporated by reference herein in its entirety.

In some embodiments, a linker conjugates the CPP (or cCPP) to the CRISPR gene-editing machinery. Any linker described in this disclosure or that is known to a person of skill in the art may be utilized.

gRNA

In some embodiments, the compounds comprise the CPP (or cCPP) is conjugated to a gRNA. A gRNA targets a genomic loci in a prokaryotic or eukaryotic cell.

In some embodiments, the gRNA is a single-molecule guide RNA (sgRNA). A sgRNA comprises a spacer sequence and a scaffold sequence. A spacer sequence is a short nucleic acid sequence used to target a nuclease (e.g., a Cas9 nuclease) to a specific nucleotide region of interest (e.g., a genomic DNA sequence to be cleaved). In some embodiments, the spacer may be about 17-24 base pairs in length, such as about 20 base pairs in length. In some embodiments, the spacer may be about 15, about 16, about 17, about 18, about 19, about 20, about 21, about 22, about 23, about 24, about 25, about 26, about 27, about 28, about 29, or about 30 base pairs in length. In some embodiments, the spacer may be at least 15, at least 16, at least 17, at least 18, at least 19, at least 20, at least 21, at least 22, at least 23, at least 24, at least 25, at least 26, at least 27, at least 28, at least 29, or at least 30 base pairs in length. In some embodiments, the spacer may be 15, 16, 17, 18, 19, 20, 21, 22, 23, 24, 25, 26, 27, 28, 29, or 30 base pairs in length. In some embodiments, the spacer sequence has between about 40% to about 80% GC content.

In some embodiments, the spacer targets a site that immediately precedes a 5' protospacer adjacent motif (PAM). The PAM sequence may be selected based on the desired nuclease. For example, the PAM sequence may be any one of the PAM sequences shown in Table 5 below, wherein N refers to any nucleic acid, R refers to A or G, Y refers to C or T, W refers to A or T, and V refers to A or C or G.

TABLE 6

Exemplary Nucleases and PAM sequences

| PAM sequence (5' to 3') | Nuclease | Isolated from |
|---|---|---|
| NGG | SpCas9 | *Streptococcus pyogenes* |
| NGRRT or NGRRN | SaCas9 | *Staphylococcus aureus* |
| NNNNGATT | NmeCas9 | *Neisseria meningitidis* |
| NNNNRYAC | CjCas9 | *Campylobacter jejuni* |
| NNAGAAW | StCas9 | *Streptococcus thermophiles* |
| TTTV | LbCpf1 | *Lachnospiraceae bacterium* |
| TTTV | AsCpf1 | *Acidaminococcus* sp. |

In some embodiments, a spacer may target a sequence of a mammalian gene, such as a human gene. In some embodiments, the spacer may target a mutant gene. In some embodiments, the spacer may target a coding sequence. In some embodiments, the spacer may target an exonic sequence.

The scaffold sequence is the sequence within the sgRNA that is responsible for nuclease (e.g., Cas9) binding. The scaffold sequence does not include the spacer/targeting sequence. In some embodiments, the scaffold may be about 1 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, or about 120 to about 130 nucleotides in length. In some embodiments, the scaffold may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60,about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, or about 125 nucleotides in length. In some embodiments, the scaffold may be at least 10, at least 20, at least 30, at least 40, at least 50, at least 60, at least 70, at least 80, at least 90, at least 100, at least 110, at least 120, or at least 125 nucleotides in length.

In some embodiments, the gRNA is a dual-molecule guide RNA, e.g, crRNA and tracrRNA. In some embodiments, the gRNA may further comprise a polyA tail.

In some embodiments, a compound comprising a CPP is conjugated to a nucleic acid comprising a gRNA. In some embodiments, the nucleic acid comprises about 1, 2, 3, 4, 5, 6, 7, 8, 9, 10, 11, 12, 13, 14, 15, 16, 17, 18, 19, or 20 gRNAs. In some embodiments, the gRNAs recognize the same target. In some embodiments, the gRNAs recognize different targets. In some embodiments, the nucleic acid comprising a gRNA comprises a sequence encoding a promoter, wherein the promoter drives expression of the gRNA.

Nuclease

In some embodiments, the compounds comprise a cell penetrating peptide conjugated to a nuclease. In some embodiments, the nuclease is a Type II, Type V-A, Type V-B, Type VC, Type V-U, Type VI-B nuclease. In some embodiments, the nuclease is a transcription, activator-like effector nuclease (TALEN), a meganuclease, or a zinc-finger nuclease. In some embodiments, the nuclease is a Cas9, Cas12a (Cpf1), Cas12b, Cas12c, Tnp-B like, Cas13a (C2c2), Cas13b, or Cas14 nuclease. For example, in some embodiments, the nuclease is a Cas9 nuclease or a Cpf1 nuclease.

In some embodiments, the nuclease is a modified form or variant of a Cas9, Cas12a (Cpf1), Cas12b, Cas12c, Tnp-B like, Cas13a (C2c2), Cas13b, or Cas14 nuclease. In some embodiments, the nuclease is a modified form or variant of a TAL nuclease, a meganuclease, or a zinc-finger nuclease. A "modified" or "variant" nuclease is one that is, for example, truncated, fused to another protein (such as another nuclease), catalytically inactivated, etc. In some embodiments, the nuclease may have at least 80%, at least 85%, at least 90%, at least 95%, at least 98%, at least 99%, or 100% sequence identity to a naturally occurring Cas9, Cas12a (Cpf1), Cas12b, Cas12c, Tnp-B like, Cas13a (C2c2), Cas13b, Cas14 nuclease, or a TALEN, meganuclease, or zinc-finger nuclease. In embodiments, the nuclease is a Cas9 nuclease derived from *S. pyogenes* (SpCas9). In some embodiments, a nuclease has at least 90%, at least 95%, at least 96%, at least 97%, at least 98%, or at least 99% sequence identity to a Cas9 nuclease derived from *S. pyogenes* (SpCas9). In embodiments, the nuclease is a Cas9 derived from *S. aureus* (SaCas9). In some embodiments, the nuclease has at least 90%, at least 95%, at least 96%, at least 97%, at least 98%, or at least 99% sequence identity to a Cas9 derived from *S. aureus* (SaCas9). In embodiments, the Cpf1 is a Cpf1 enzyme from Acidaminococcus (species BV3L6, UniProt Accession No. U2UMQ6). In some embodiments, the nuclease has at least 90%, at least 95%, at least 96%, at least 97%, at least 98%, or at least 99% sequence identity to a Cpf1 enzyme from Acidaminococcus (species BV3L6, UniProt Accession No. U2UMQ6).

In some embodiments, the Cpf1 is a Cpf1 enzyme from Lachnospiraceae (species ND2006, UniProt Accession No. A0A182DWE3). In some embodiments, the nuclease has at least 90%, at least 95%, at least 96%, at least 97%, at least 98%, or at least 99% sequence identity to a Cpf1 enzyme from Lachnospiraceae. In some embodiments, a sequence encoding the nuclease is codon optimized for expression in mammalian cells. In some embodiments, the sequence encoding the nuclease is codon optimized for expression in human cells or mouse cells.

In some embodiments, a compound comprising a CPP is conjugated to a nuclease. In some embodiments, the nuclease is a soluble protein.

In some embodiments, a compound comprising a CPP is conjugated to a nucleic acid encoding a nuclease. In some embodiments, the nucleic acid encoding a nuclease comprises a sequence encoding a promoter, wherein the promoter drives expression of the nuclease.

gRNA and Nuclease Combinations

In some embodiments, the compounds comprise one or more CPP (or cCPP) conjugated to a gRNA and a nuclease. In some embodiments, the one or more CPP (or cCPP) are conjugated to a nucleic acid encoding a gRNA and/or a nuclease. In some embodiments, the nucleic acid encoding a nuclease and a gRNA comprises a sequence encoding a promoter, wherein the promoter drives expression of the nuclease and the gRNA. In some embodiments, the nucleic acid encoding a nuclease and a gRNA comprises two promoters, wherein a first promoter controls expression of the nuclease and a second promoter controls expression of the gRNA. In some embodiments, the nucleic acid encoding a gRNA and a nuclease encodes 1, 2, 3, 4, 5, 6, 7, 8, 9, 10, 11, 12, 13, 14, 15, 16, 17, 18, 19, or 20 gRNAs. In some embodiments, the gRNAs recognize different targets. In some embodiments, the gRNAs recognize the same target.

In some embodiments, the compounds comprise a cell penetrating peptide (or cCPP) conjugated to a ribonucleoprotein (RNP) comprising a gRNA and a nuclease.

In some embodiments, a composition comprising: (a) a CPP conjugated to a gRNA and (b) a nuclease is delivered to a cell. In some embodiments, a composition comprising: (a) a CPP conjugated to a nuclease and (b) an gRNA is delivered to a cell.

In some embodiments, a composition comprising: (a) a first CPP conjugated to a gRNA and (b) a second CPP conjugated to a nuclease is delivered to a cell. In some embodiments, the first CPP and second CPP are the same. In some embodiments, the first CPP and second CPP are different.

Genetic Element of Interest

In some embodiments, the compounds disclosed herein comprise a cell penetrating peptide conjugated to a genetic element of interest. In some embodiments, a genetic element of interest replaces a genomic DNA sequence cleaved by a nuclease. Non-limiting examples of genetic elements of interest include genes, a single nucleotide polymorphism, promoter, or terminators.

Nuclease Inhibitors

In some embodiments, the compounds disclosed herein comprise a cell penetrating peptide conjugated to an inhibitor of a nuclease (e.g. Cas9). A limitation of gene editing is potential off-target editing. The delivery of a nuclease inhibitor will limit off-target editing. In some embodiments, the nuclease inhibitor is a polypeptide, polynucleotide, or small molecule. Exemplary nuclease inhibitors are described in U.S. Publication No. 2020/087354, International Publication No. 2018/085288, U.S. Publication No. 2018/0382741, International Publication No. 2019/089761, International Publication No. 2020/068304, International Publication No. 2020/041384, and International Publication No. 2019/076651, each of which is incorporated by reference herein in its entirety.

Mechanism of Modulation and Target Molecules

Many types of oligonucleotides are capable of modulating gene transcription, translation and/or protein function in cells. Non-limiting examples of such oligonucleotides include, e.g., small interfering RNA (siRNA), microRNA (miRNA), antisense oligonucleotides, ribozymes, plasmids, immune stimulating nucleic acids, antisense, antagomir, antimir, microRNA mimic, supermir, Ul adaptor, and aptamer. Additional examples include DNA-targeting, triplex-forming oligonucleotide, strand-invading oligonucleotide, and synthetic guide strand for CRISPR/Cas, These nucleic acids act via a variety of mechanisms. See Smith and Zain, Annu Rev Pharmacol Toxicol. 2019, 59:605-630, incorporated by reference herein.

Splice-switching antisense oligonucleotides are short, synthetic, antisense, modified nucleic acids that base-pair with a pre-mRNA and disrupt the normal splicing repertoire of the transcript by blocking the RNA-RNA base-pairing or protein-RNA binding interactions that occur between components of the splicing machinery and the pre-mRNA. Splicing of pre-mRNA is required for the proper expression of the vast majority of protein-coding genes, and thus, targeting the process offers a means to manipulate protein production from a gene. Splicing modulation is particularly valuable in cases of disease caused by mutations that lead to disruption of normal splicing or when interfering with the normal splicing process of a gene transcript may be therapeutic. Such antisense oligonucleotides offer an effective and specific way to target and alter splicing in a therapeutic manner. See Havens and Hastings, Nucleic Acids Res. 2016 Aug. 19; 44(14):6549-6563, incorporated by reference herein.

In the case of siRNA or miRNA, these nucleic acids can down-regulate intracellular levels of specific proteins through a process termed RNA interference (RNAi). Following introduction of siRNA or miRNA into the cell cytoplasm, these double-stranded RNA constructs can bind to a protein termed RISC. The sense strand of the siRNA or miRNA is displaced from the RISC complex providing a template within RISC that can recognize and bind mRNA with a complementary sequence to that of the bound siRNA or miRNA. Having bound the complementary mRNA the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models, as well as in clinical studies.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts, Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, Trends in Biotech. 14:376-387 (1996)). Antisense can also affect cellular activity by hybridizing specifically with chromosomal DNA.

Immune-stimulating nucleic acids include deoxyribonucleic acids and ribonucleic acids. In the case of deoxyribonucleic acids, certain sequences or motifs have been shown to illicit immune stimulation in mammals. These sequences or motifs include the CpG motif, pyrimidine-rich sequences and palindromic sequences. It is believed that the CpG motif in deoxyribonucleic acids is specifically recognized by an endosomal receptor, tolllike receptor 9 (TLR-9), which then triggers both the innate and acquired immune stimulation pathway. Certain immune stimulating ribonucleic acid sequences have also been reported. It is believed that these RNA sequences trigger immune activation by binding to toll-like receptors 6 and 7 (TLR-6 and TLR-7). In addition, double-stranded RNA is also reported to be immune stimulating and is believe to activate via binding to TLR-3.

Non-limiting examples of mechanism and targets of antisense oligonucleotides (ASOs) to modulate gene transcription, translation and/or protein function are illustrated in Table 7A and 7B.

TABLE 7A

Mechanism of ASO Modulation and Target Molecules

| Types | Location of target | Subcellular Location | Mechanism |
|---|---|---|---|
| mRNA | Intracellular | cytoplasm | inhibition of translation |
| Pre-mRNA | Intracellular | nucleus | alternate splicing |
| micro-RNA | Intracellular | cytoplasm and nucleus | miRNA inhibition or activation |
| long non-Coding RNA | Intracellular | cytoplasm and nucleus | inhibition of IncRNA function |
| Telomerase RNA component | Intracellular | cytoplasm and nucleus | inhibition of telomerase |
| Protein | Extra- and intracellular | cytoplasm and nucleus | inhibition of protein target |

TABLE 7B

Mechanism of ASO Modulation and Target Molecules

| Mechanism | Target | Description | Examples of drugs |
|---|---|---|---|
| Regulation of pre-mRNA splicing | pre-mRNA | ASOs bind to pre-mRNA and alter the splicing by steric blocking, which result in disruption of the recognition by splicing factors | Nusinersen, Eteplirsen |
| Regulation of RNA translation by recruiting RNase H | pre-mRNA and mRNA | ASOs containing DNA bases bind to target RNA and induce the cleavage of RNA by RNase H | Mipomersen, Inotersen |
| Regulation of RNA translation by steric blocking | mRNA | ASOs and duplex RNA can both sterically block the translation machinery to inhibit RNA translation or enhance RNA translation by blocking aberrant sites that reduce RNA translation | |
| Regulation of RNA translation by RNAi | mRNA | siRNA and miRNA inhibit translation by RNA interference and induce the cleavage of target RNA | Patisiran, Inclisiran, Fitusiran, Givosiran |
| Regulation of protein activity by binding with target proteins | protein | Aptamers bind with target proteins as antagonists | Pegaptanib |

Clustered regularly interspaced short palindromic repeats (CRISPR) and associated Cas proteins constitute the CRISPR-Cas system. CRISPR-Cas is a mechanism for gene-editing. The RNA-guided (e.g., gRNA) Cas9 endonuclease specifically targets and cleaves DNA in a sequence-dependent manner. The Cas9 endonuclease can be substituted with any nuclease of the disclosure. The gRNA targets a nuclease (e.g., a Cas9 nuclease) to a specific nucleotide region of interest (e.g., a genomic DNA sequence to be cleaved) and cleaves genomic DNA. Genomic DNA can then be replaced with a genetic element of interest.

Diseases and Target Genes

The human genome comprises more than 40,000 genes, approximately half of which correspond to protein-coding genes. However, the number of human protein species is predicted to be orders of magnitude higher due to single amino acid polymorphisms, post translational modifications, and, importantly, alternative splicing. RNA splicing, generally taking place in the nucleus, is the process by which precursor messenger RNA (pre-mRNA) is transformed into mature messenger RNA (mRNA) by removing non-coding regions (introns) and joining together the remaining coding regions (exons). The resulting mRNA can then be exported from the nucleus and translated into protein. Alternative splicing, or differential splicing, is a regulated process during gene expression that results in a single gene coding for multiple proteins. In this process, particular exons of a gene may be included within or excluded from the final, processed mRNA produced from that gene. While alternative splicing is a normal phenomenon in eukaryotic organisms, and contributes to the biodiversity of proteins encoded by a genome, abnormal variations in splicing are heavily implicated in disease. A large proportion of human genetic disorders result from splicing variants; abnormal splicing variants contribute to the development of cancer; and splicing factor genes are frequently mutated in different types of cancer.

About 10% of ~80,000 mutations reported in the human gene mutation database (HGMD) affect splice sites. In the HGMD, there are 3390 disease-causing mutations that occur at the +1 donor splice site. These mutations affect 2754 exons in 901 genes. The prevalence is even higher for neuromuscular disorders (NMDs) due to the unusually large size and multiexonic structure of genes encoding muscle structural proteins, further highlighting the importance of these mutations in NMDs.

Previously, the correction of point mutations, e.g. splice site mutations, has been attempted via the homology-directed repair (HDR) pathway, which is extremely inefficient in post-mitotic tissues such as skeletal muscles, hampering its therapeutic utility in NMD. In addition, standard gene therapy approaches to reintroduce corrected coding regions into the genome are impeded by the large size of genes encoding, e.g., muscular structural proteins. Furthermore, many existing therapies rely on inefficient introduction of the therapeutic compound into the disease cells, such that in vivo treatment is impractical and higher toxicities are experienced.

The target gene of the present disclosure may be any eukaryotic gene comprising one or more introns and one or more exons. In some embodiments, the target gene is a mammalian gene. In some embodiments, the mammal is a human, mouse, bovine, rat, pig, horse, chicken, sheep, or the like. In some embodiments, the target gene is a human gene.

In some embodiments, the target gene is a gene comprising mutations leading to aberrant splicing. In some embodiments, the target gene is a gene that comprises one or more mutations. In some embodiments, the target gene is a gene that comprises one or more mutations, such that transcription and translation of the target gene does not lead to a functional protein. In some embodiments, the target gene is a gene that comprises one or more mutations, such that transcription and translation of the target gene leads to a target protein that is less active or less functional than a wild type target protein.

In some embodiments, the target gene is a gene underlying a genetic disorder. In some embodiments, the target gene has abnormal gene expression in the central nervous system. In some embodiments, the target gene is a gene involved in the pathogenesis of a neuromuscular disorder (NMD). In some embodiments, the target gene is a gene involved in the pathogenesis of a musculoskeletal disorder (NMD). In some embodiments, the neuromuscular disease is Pompe disease, and the target gene is GYS1.

Antisense compounds may be used to target genes comprising mutations that lead to aberrant splicing underlying a genetic disease in order to redirect splicing to give a desired splice product (Kole, Acta Biochimica Polonica, 1997, 44, 231-238).

CRISPR gene-editing machinery may be used to target aberrant genes for removal or to regulate gene transcription and translation.

In some embodiments, the disease is β-thalassemia (Dominski and Kole, Proc. Natl. Acad. Sci. USA, 1993, 90, 8673-8677; Sierakowska et al., Nucleosides & Nucleotides, 1997, 16,1173-1182; Sierakowska et al., Proc. Natl. Acad. Sci. USA, 1996, 93, 12840-44; Lacerra et al., Proc. Natl. Acad. Sci. USA, 2000, 97, 9591-9596).

In some embodiments, the disease is dystrophin Kobe (Takeshima et al., J. Clin. Invest., 1995, 95, 515-520).

In some embodiments, the disease is Duchenne muscular dystrophy (Dunckley et al. Nucleosides & Nucleotides, 1997, 16, 1665-1668; Dunckley et al. Human Mol. Genetics, 1998, 5, 1083-90). In some embodiments, the target gene is the DMD gene, which codes for dystrophin. The protein consists of an N-terminal domain that binds to actin filaments, a central rod domain, and a C-terminal cysteine-rich domain that binds to the dystrophin-glycoprotein complex (Hoffman et al. 1987; Koenig et al. 1988; Yoshida and Ozawa 1990). Mutations in the DMD gene that interrupt the reading frame result in a complete loss of dystrophin function, which causes severe Duchenne muscular dystrophy (DMD) [MIM 310200]). The milder Becker muscular dystrophy (BMD [MIM 300376]), on the other hand, is the result of mutations in the same gene that are not frameshifting and result in an internally deleted but partially functional dystrophin that has retained its N- and C-terminal ends (Koenig et al. 1989; Di Blasi et al. 1996). Over two-thirds of patients with DMD and BMD have a deletion of >1 exon (den Dun-nen et al. 1989). Remarkably, patients have been described who exhibit very mild BMD and who lack up to 67% of the central rod domain (England et al. 1990; Winnard et al. 1993; Mirabella et al. 1998). This suggests that, despite large deletions, a partially functional dystrophin can be generated, provided that the deletions render the transcript in frame. These observations have led to the idea of using ACs to alter splicing so that the open reading frame is restored and the severe DMD phenotype is converted into a milder BMD phenotype. Several studies have shown therapeutic AC-induced single-exon skipping in cells derived from the mdx mouse model (Dunckley et al. 1998; Wilton et al. 1999; Mann et al. 2001, 2002; Lu et al. 2003) and various DMD patients (Takeshima et al. 2001; van Deutekom et al. 2001; Aartsma-Rus et al. 2002, 2003; De Angelis et al. 2002). In some embodiments, the AC of the present disclosure is used to skip one or more exons selected from exons 2, 8, 11, 17, 19, 23, 29, 40, 41, 42, 43, 44, 45, 46, 48, 49, 50, 51, 52, 53, 55, and 59 of DMD. See Aartsma-Rus et al. 2002, incorporated by reference herein. In some embodiments, the AC of the present disclosure is used to skip one or more exons selected from exons 8, 11, 43, 44, 45, 50, 51, 53, and 55 of DMD. Of all patients with DMD, ~75% would benefit from the skipping of these exons. The skipping of exons flanking out-of-frame deletions or an in-frame exon containing a nonsense mutation can restore the reading frame and induce the synthesis of BMD-like dystrophins in treated cells. (van Deutekom et al. 2001; Aartsma-Rus et al. 2003). In some embodiments, the AC hybridizing to its target sequence within a target DMD pre-mRNA induces the skipping of one or more exons. In some embodiments, the AC induces expression of a re-spliced target protein comprising an active fragment of dystrophin.Non-limiting examples of AC for exon 52 are described in US Pub. No. 2019/0365918, which is incorporated by reference in its entirety for all purposes.

In some embodiments, provided herein are compounds comprising an AC and CPP that target the DMD gene. Non-limiting examples of the aforementioned compounds are shown below. The antisense oligonucleotide is underlined (SEQ ID NO: 218).

ENTR-0088:

ENTR-0088
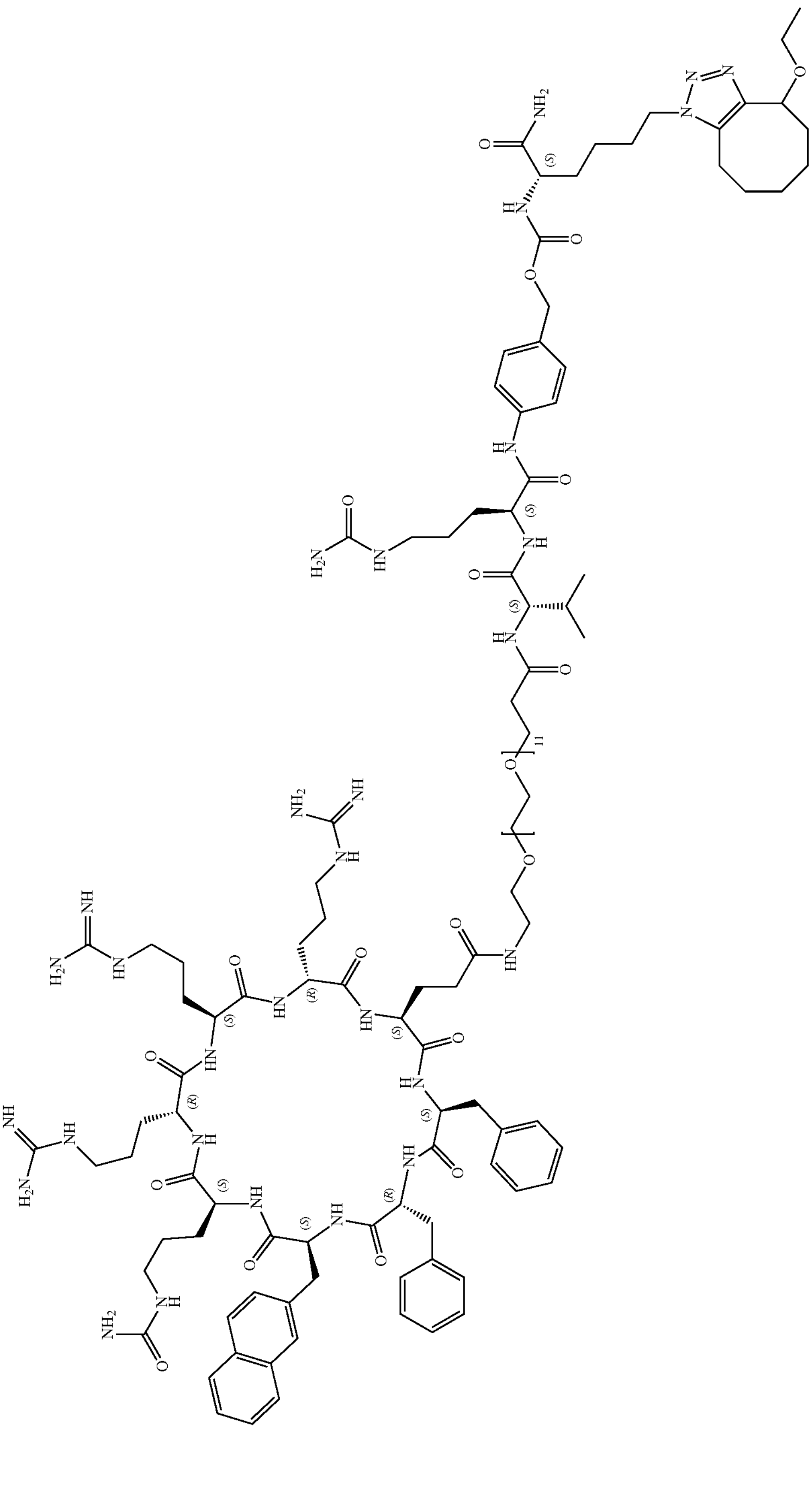

-continued
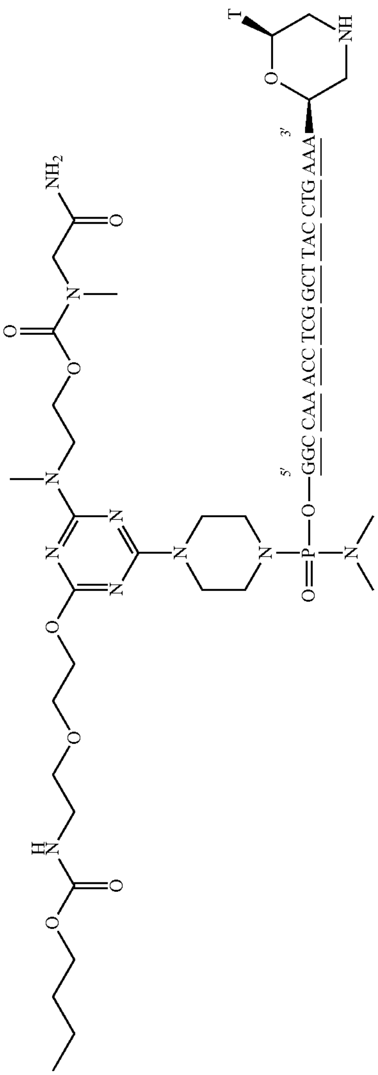

ENTR-0093
-continued
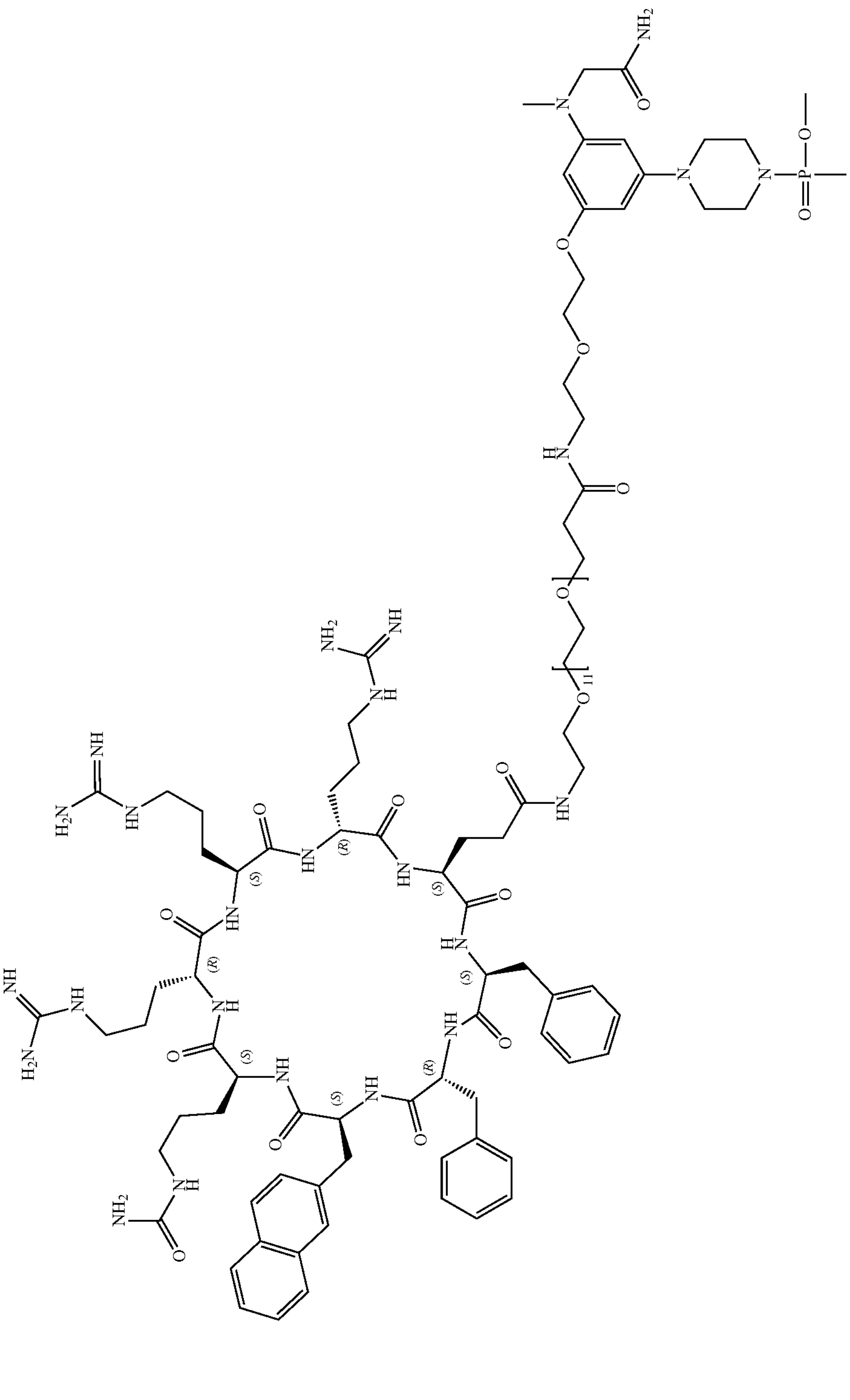

-continued
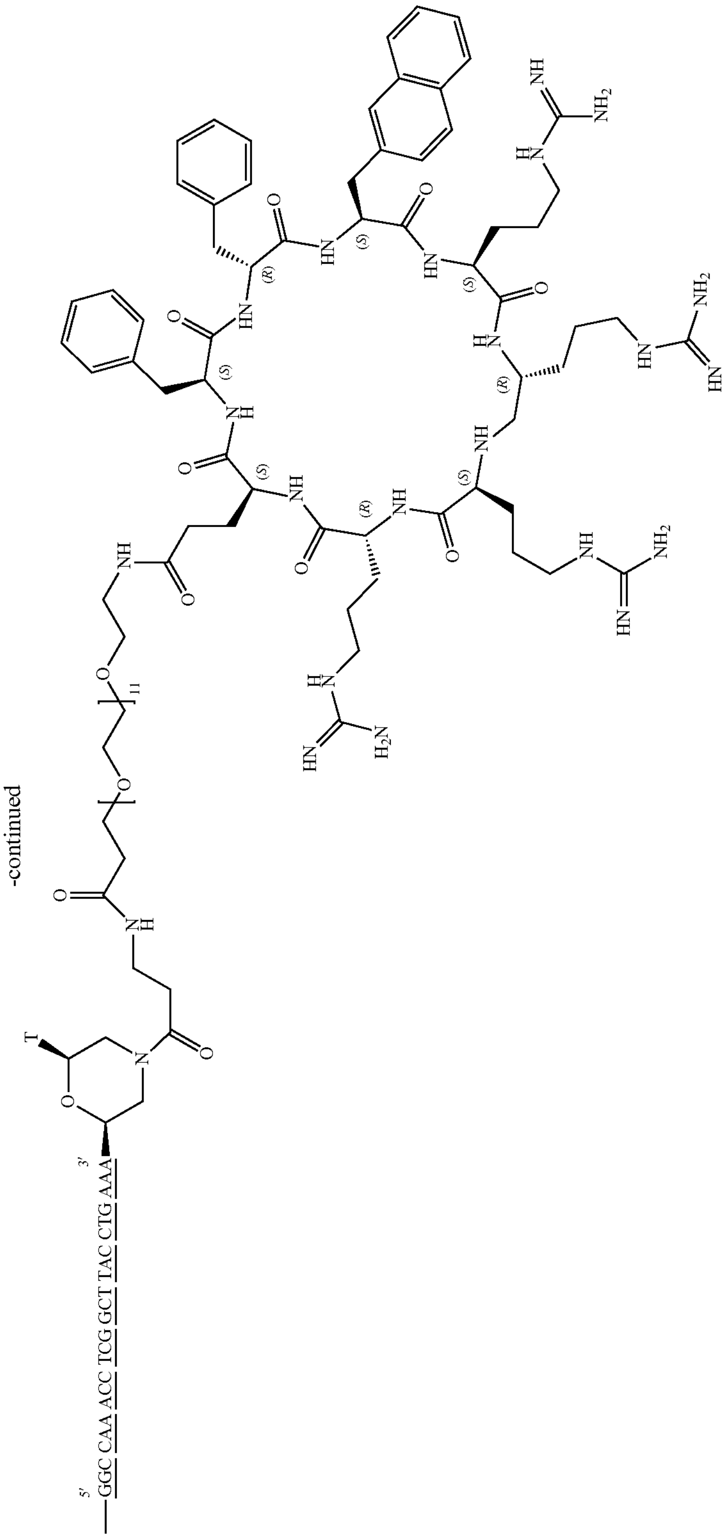

-continued
ENTR-0098
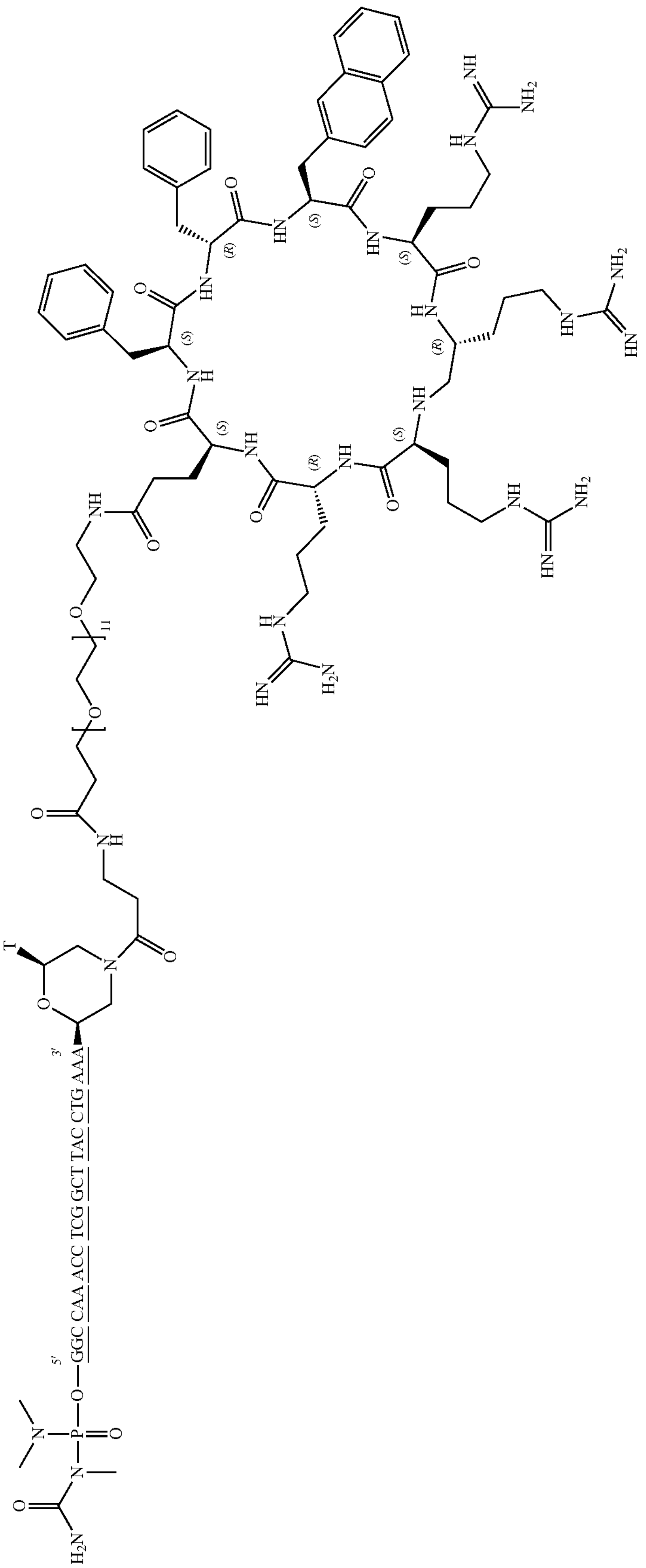

ENTR-0099
-continued
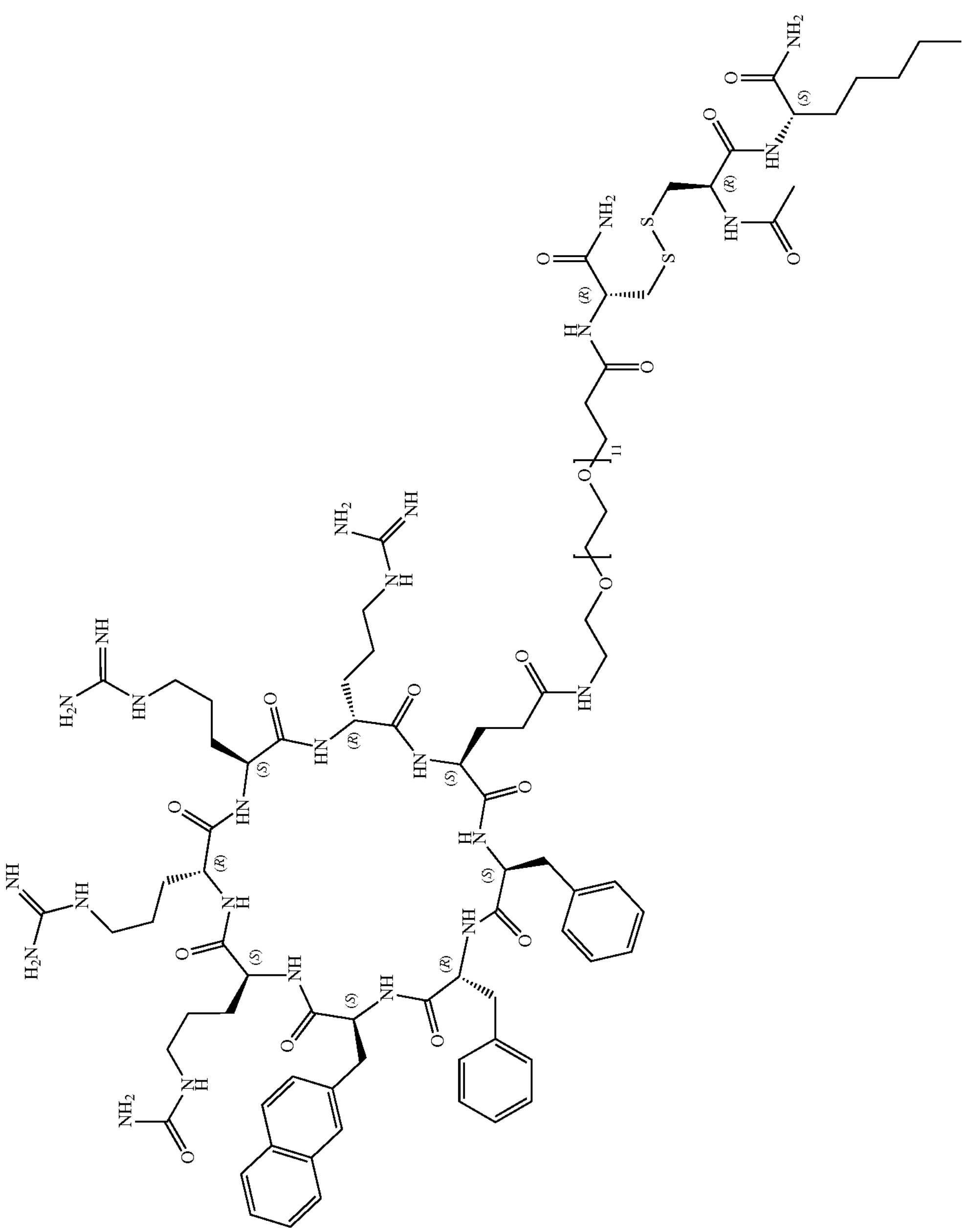

-continued
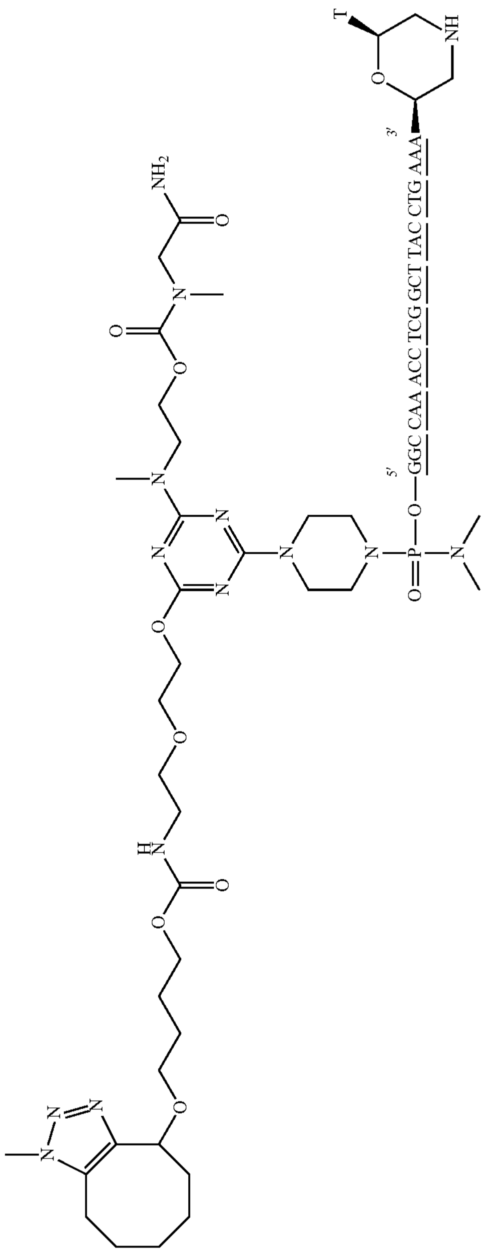

-continued
ENTR-0014
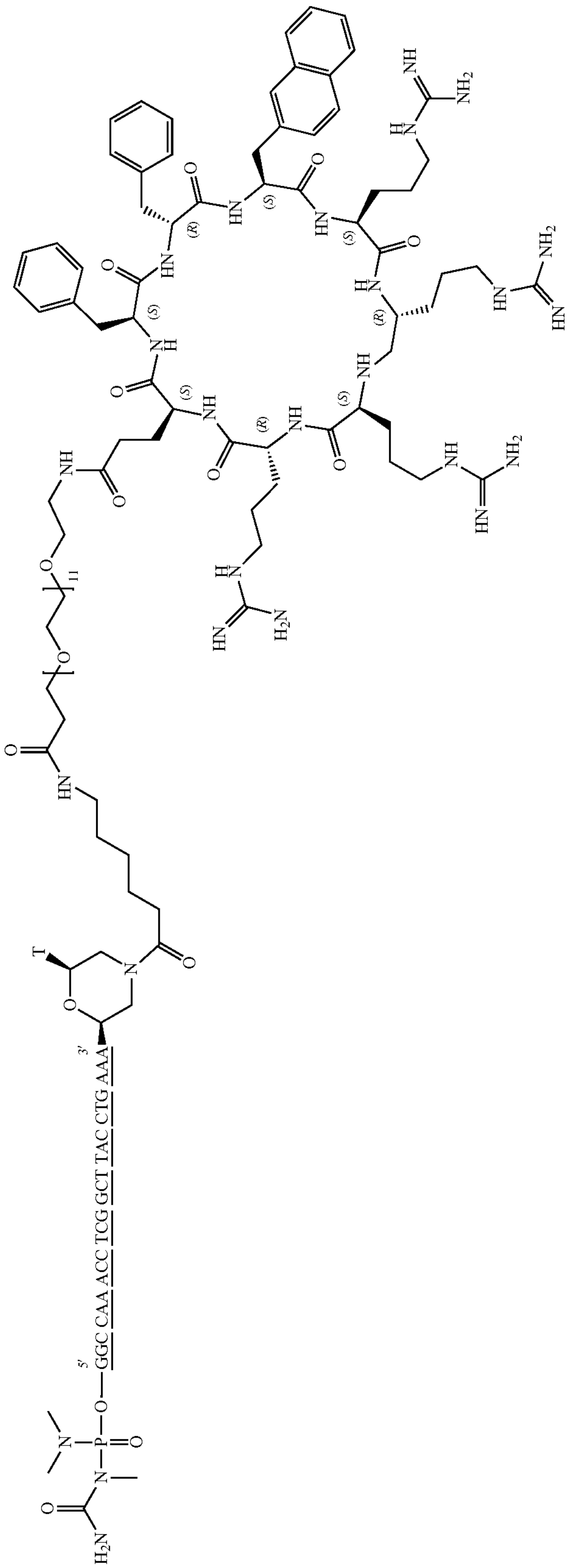

ENTR-0100
-continued
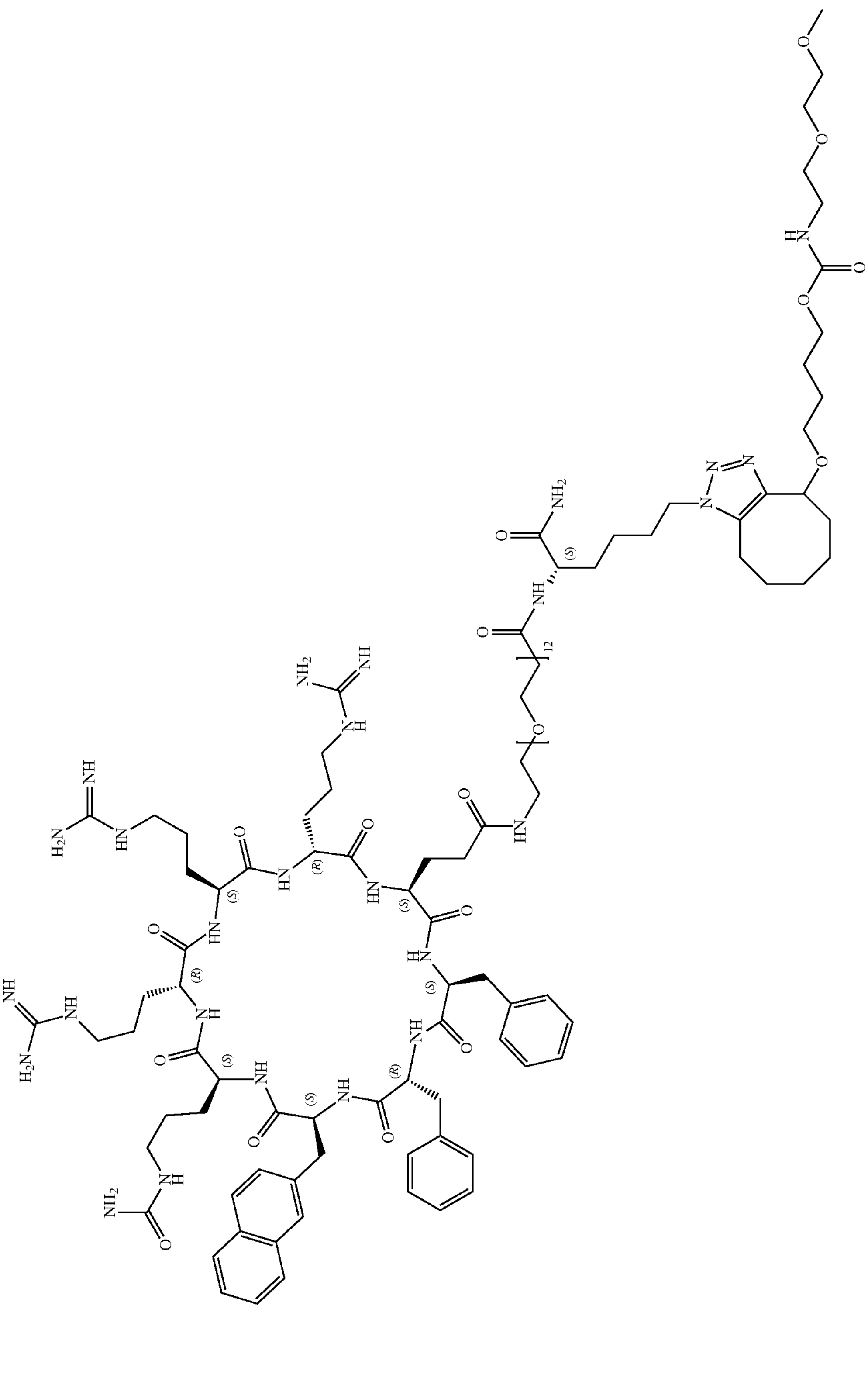

-continued
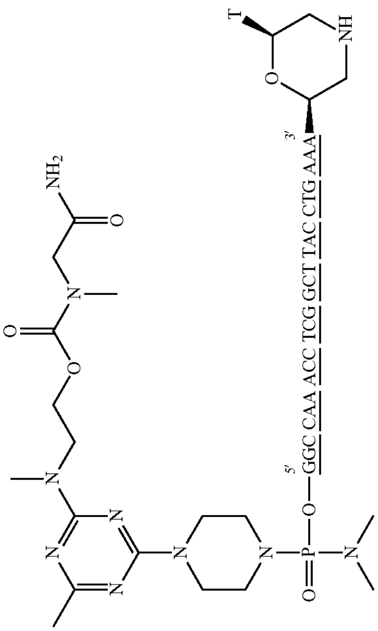

ENTR-0115
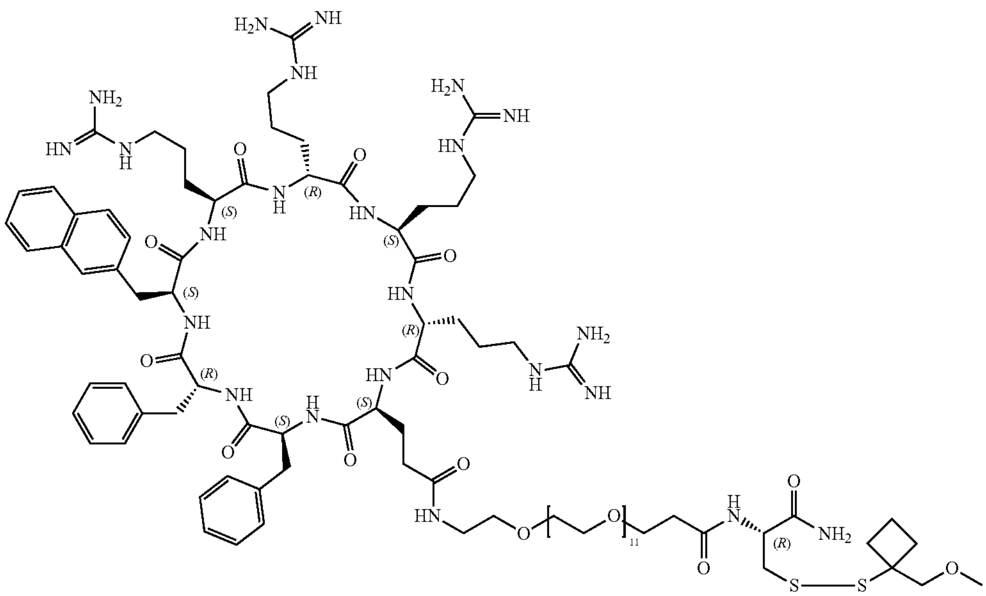
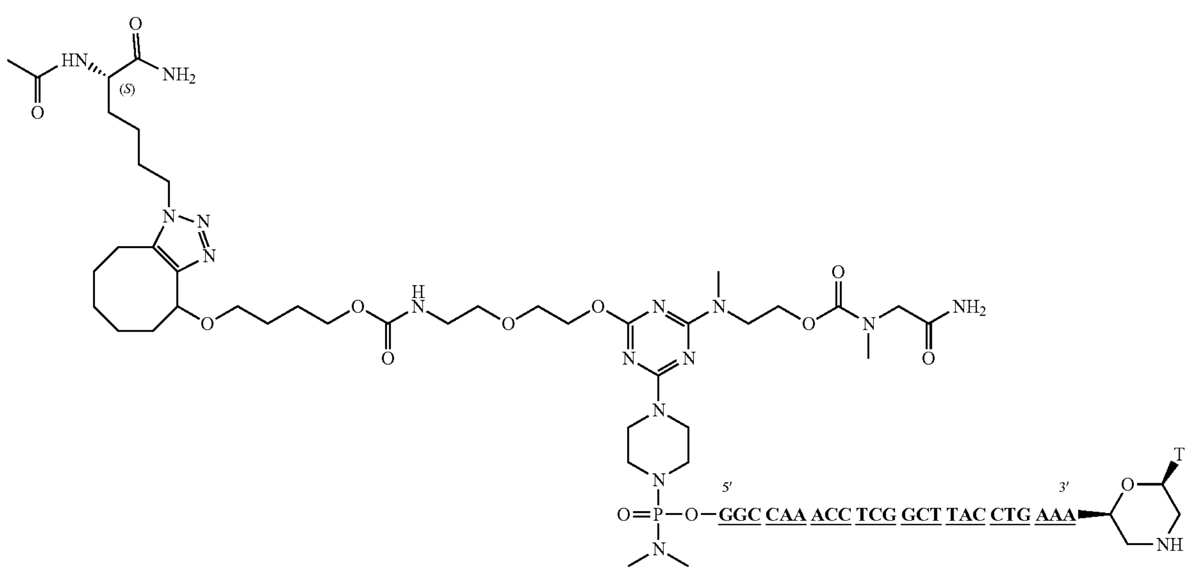

-continued
ENTR-0120
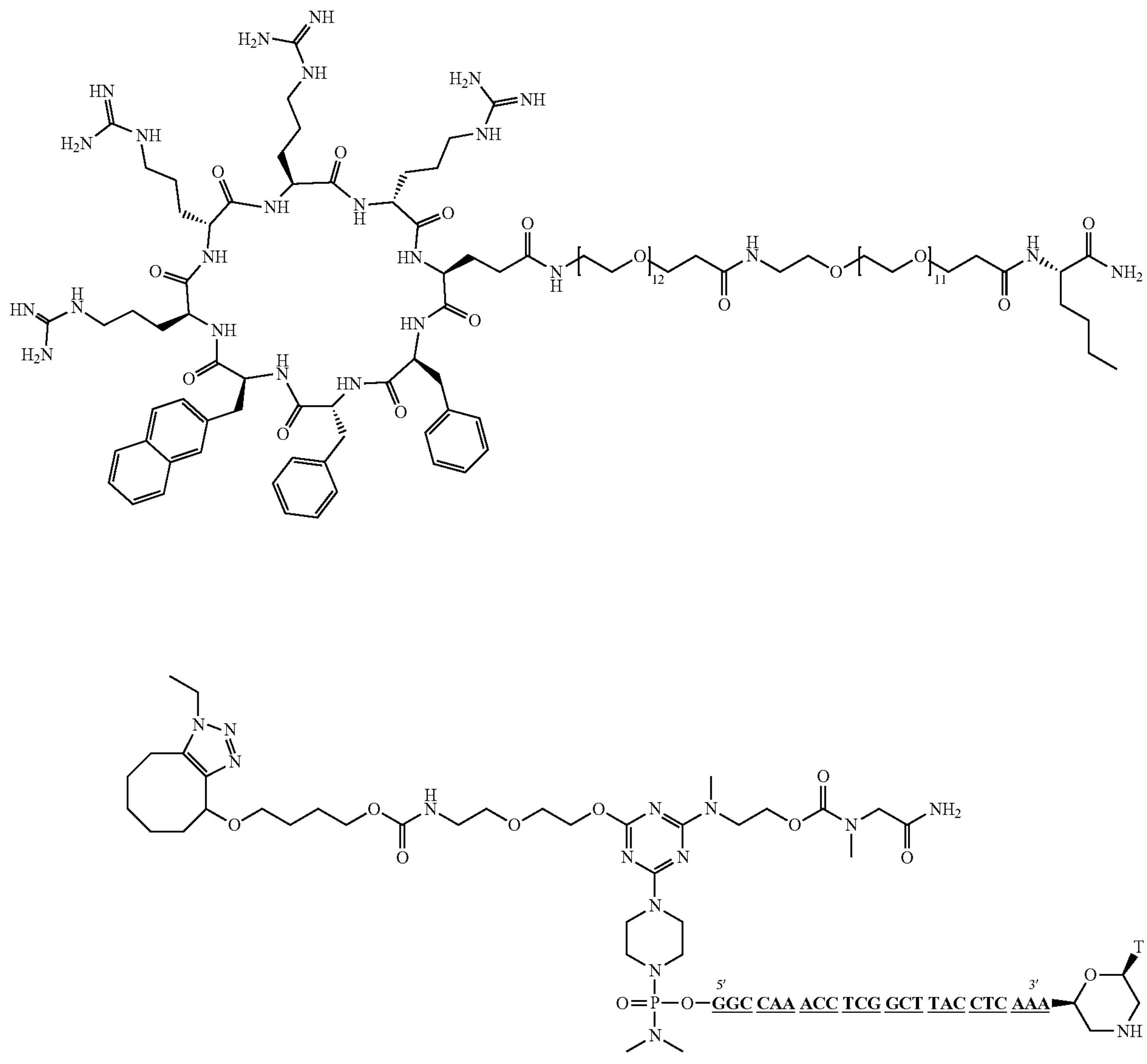
ENTR-0161
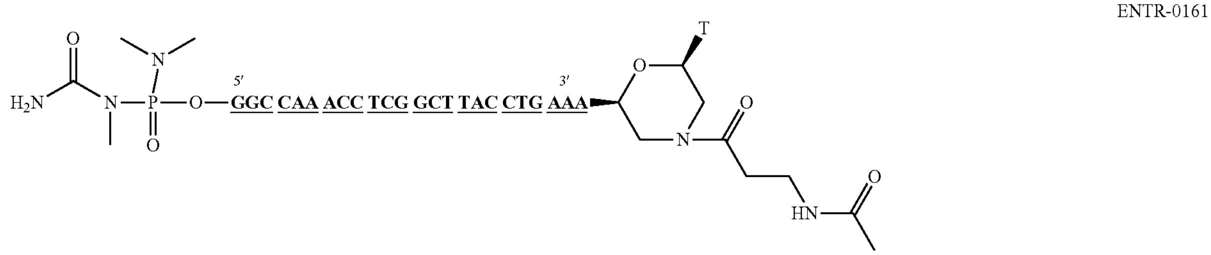

-continued
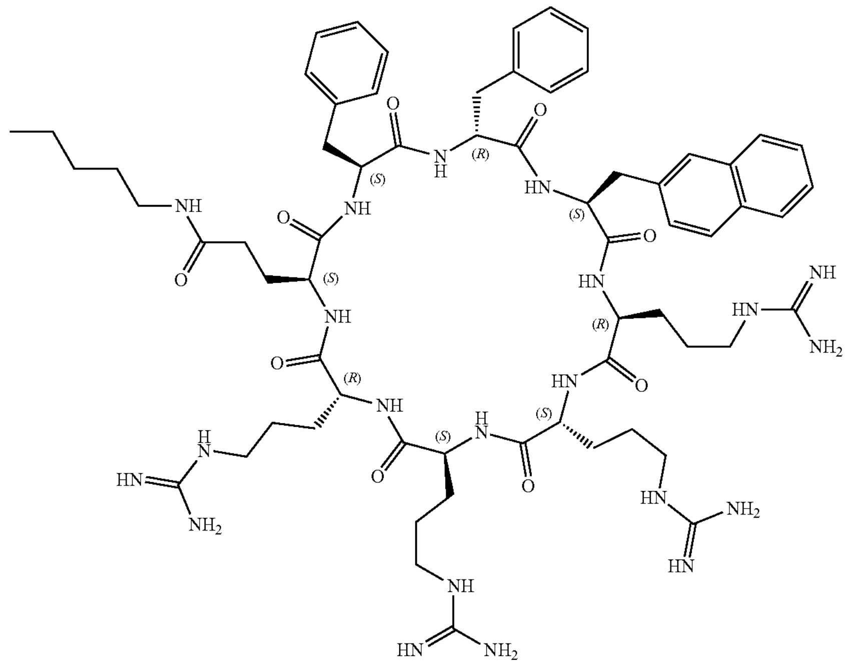
ENTR-0089
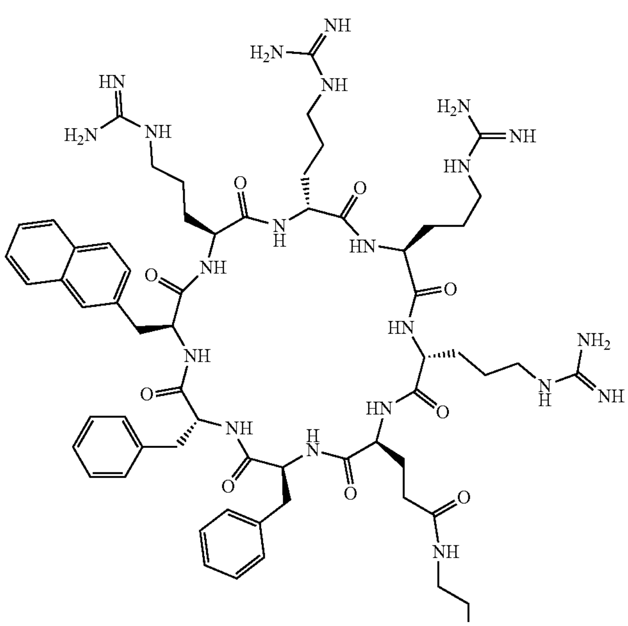

-continued
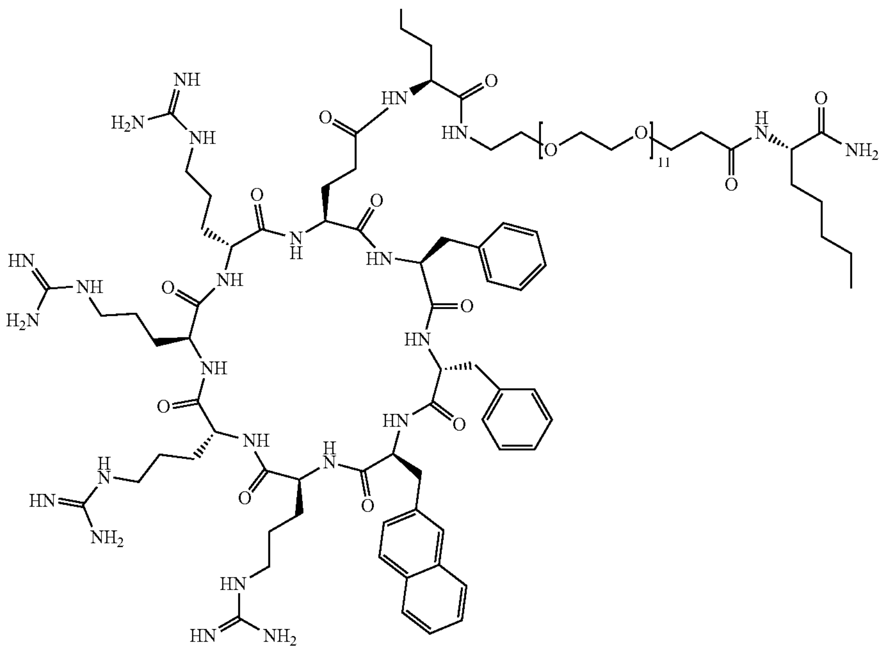
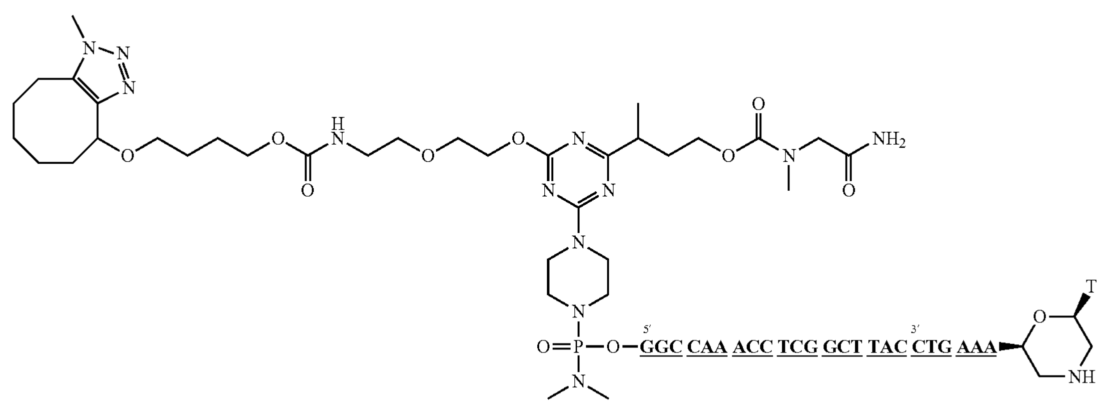
ENTR-0119
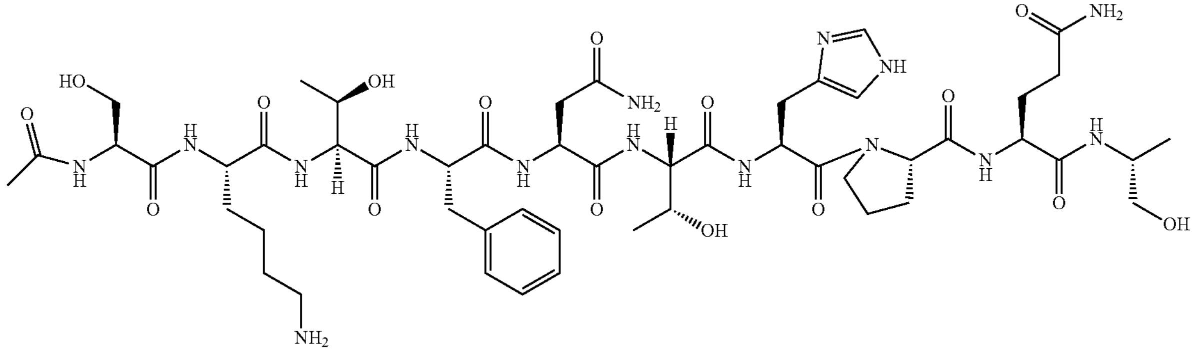

-continued
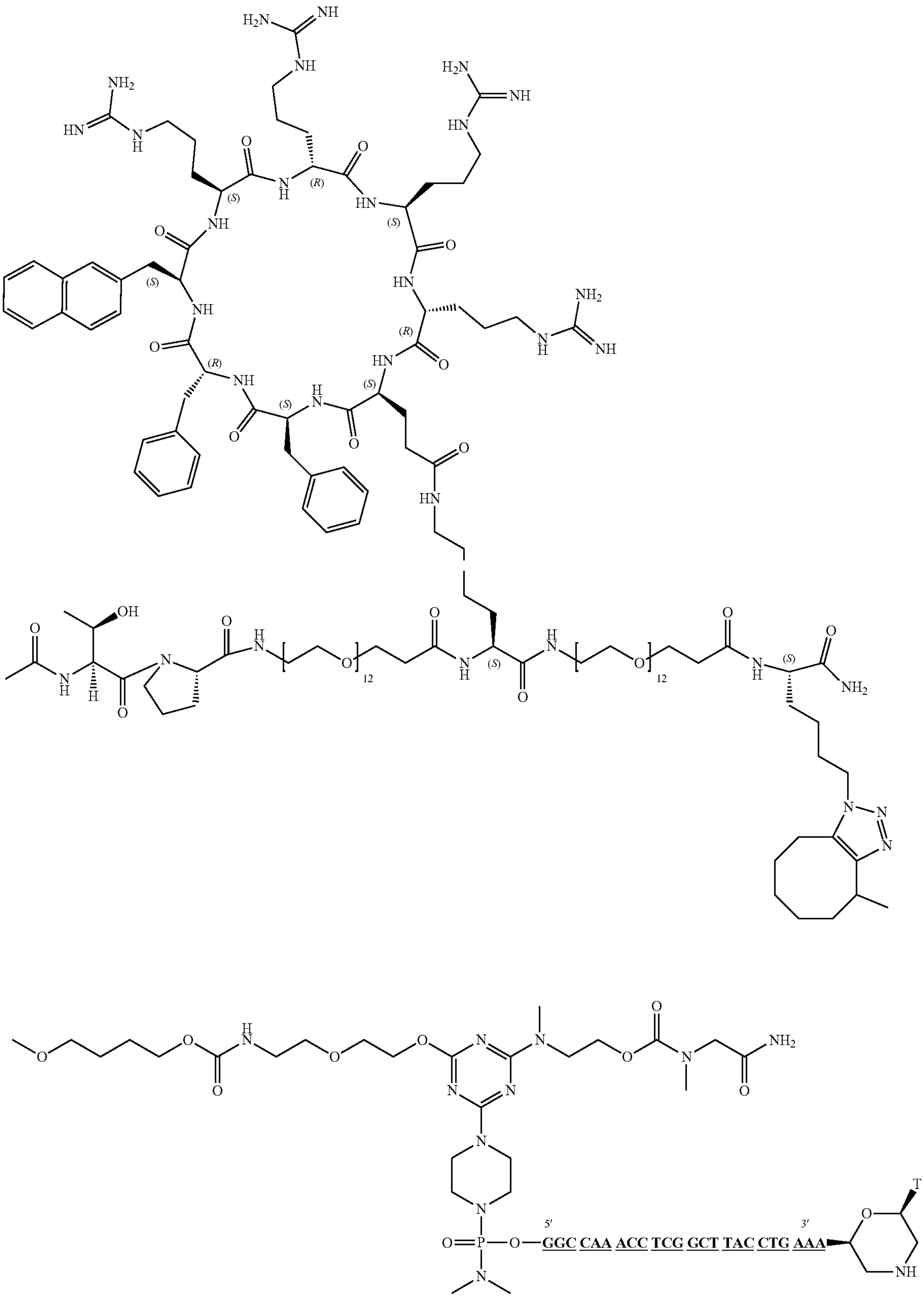

-continued
ENTR-0092
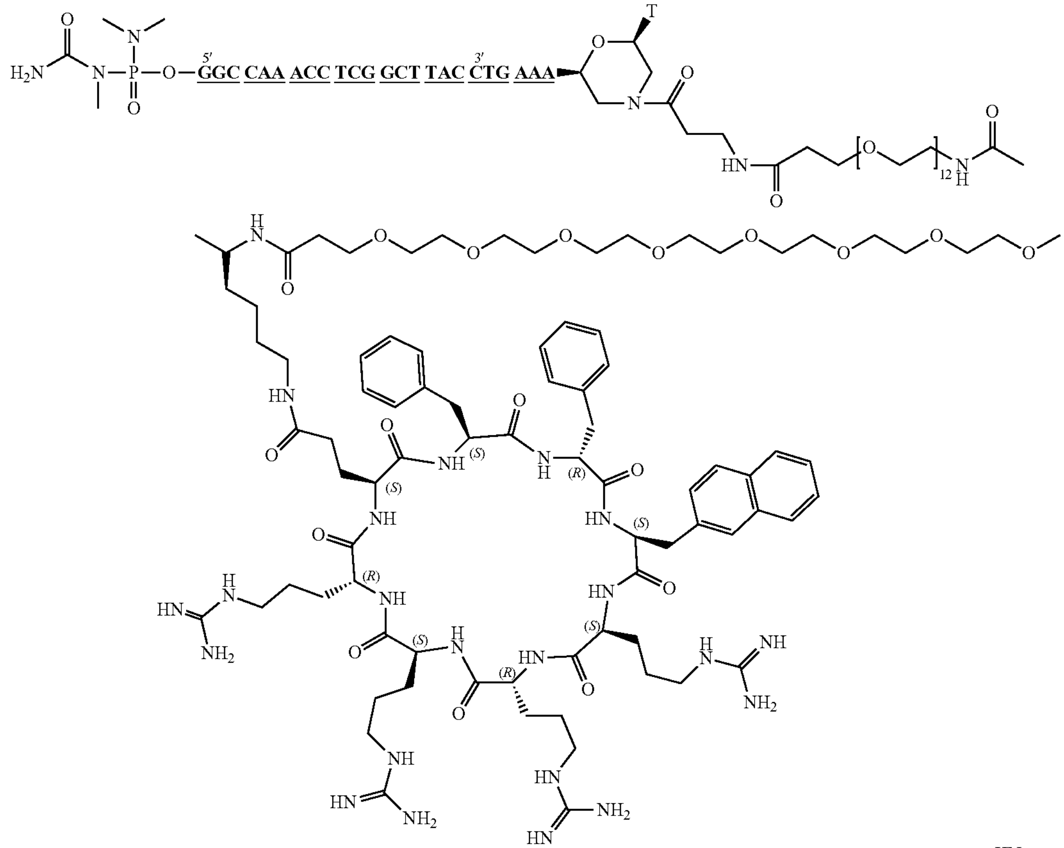
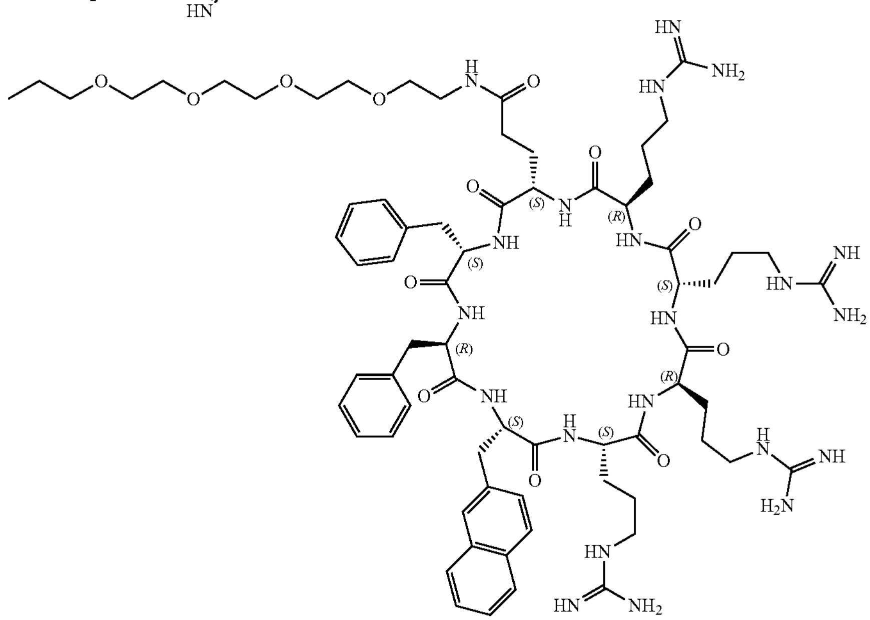
ENTR-0163
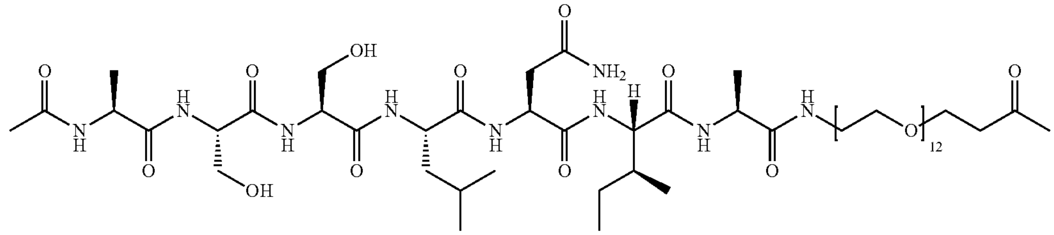

-continued

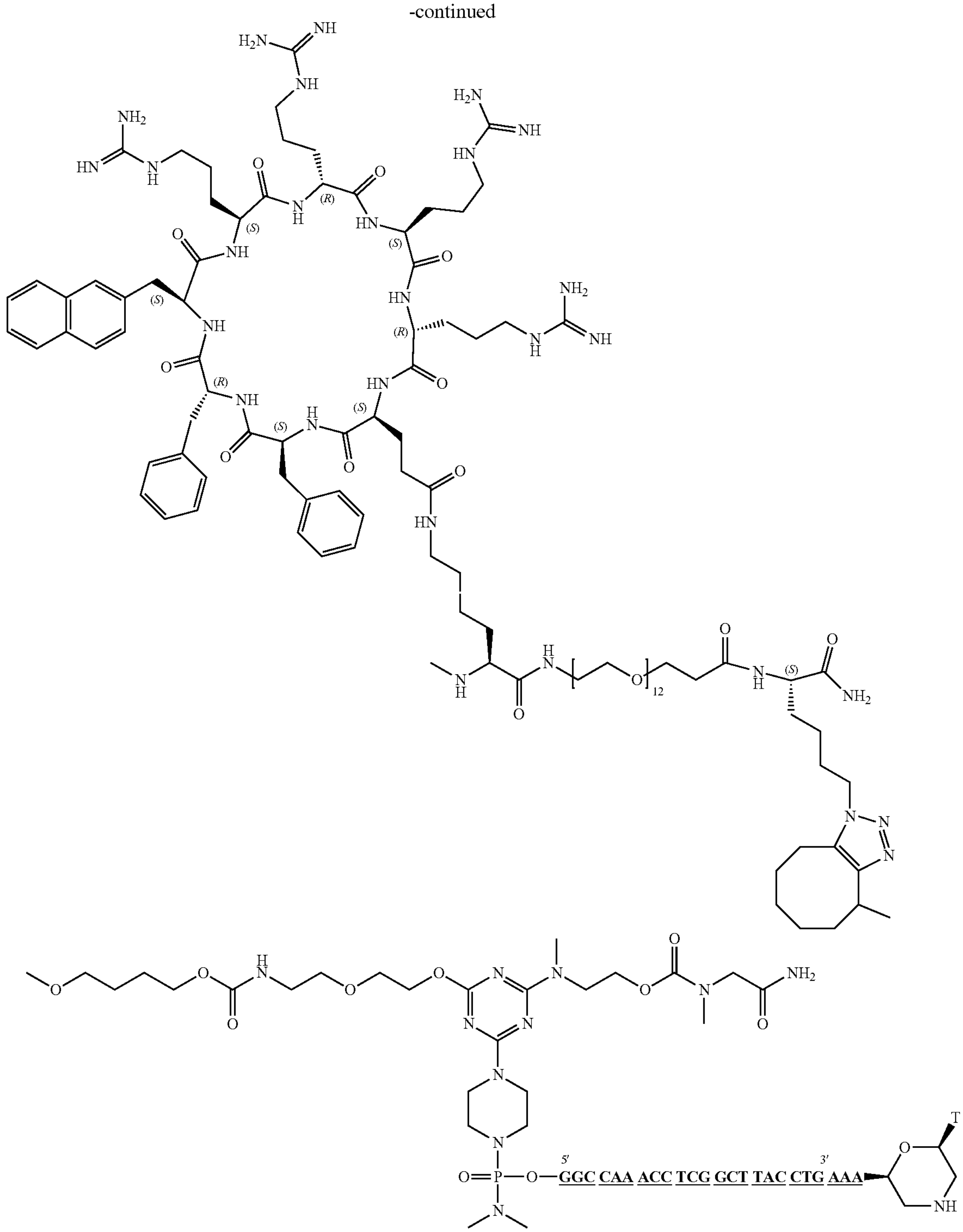

In some embodiments, the disease is an ocular disease. In some embodiments, the ocular disease is refractive errors, macular degeneration, cataracts, diabetic retinopathy, glaucoma, amblyopia, or strabismus. In some embodiments, the target gene is VEGF, ABCA4, CEP290, RHO, USH2A, OPA1, CNGB3, PRPF31, RPGR.

In some embodiments, the disease is associated with insulin resistance. In some embodiments, the disease is diabetes. In some embodiments, the target gene is PTP.

In some embodiments, the disease is a CNS disorder. In some embodiments, the disease is Alzheimer's Disease (AD) (Zhao et al. Gerontology 2019; 65:323-331). In some embodiments, the target gene is the CD33 gene. The CD33 gene maps on chromosome 19q13.33 in humans encoding a 67-kDa transmembrane glycoprotein. Human CD33 binds preferentially to alpha-2,6-linked sialic acid. CD33 is expressed exclusively on immune cells. CD33 is an inhibitory receptor that recruits inhibitory proteins such as SHP phosphatases via its immunoreceptor tyrosine-based inhibition motif (ITIM). CD33 is also involved in adhesion processes in immune or malignant cells, inhibition of cytokine release by monocytes, immune cell growth and survival through the inhibition of proliferation, and induction of apoptosis. Polymorphisms of CD33 have been implicated in modulating AD susceptibility. rs3865444C is an allele associated with an increased risk of AD in European, Chinese, and North American populations due to increased expression of CD33. The skipping of exon 2 of CD33 leads to a decreased expression of CD33 and an increased expression of D2-CD33, which is a CD33 isoform that lacks a ligand binding domain. Expression of D2-CD33 is associated with a decreased risk of developing AD. In some embodiments, the AC of the present disclosure is used to skip an exon of CD33 selected from the group consisting of exon 1, exon 2, exon 3, exon 4, exon 5, exon 6, exon 7a, and exon 7b. In some embodiments, the exon is exon 2. In some embodiments, the AC hybridizing to its target sequence within a target CD33 pre-mRNA induces the skipping of one or more exons. In some embodiments, the AC induces expression of a re-spliced target protein comprising an inactive fragment of CD33.

In some embodiments, the disease is cancer (Laszlo et al. Oncotarget. 2016 Jul. 12; 7(28): 43281-43294.). In some embodiments, the cancer is acute myeloid leukemia (AML). In some embodiments, the cancer is glioma, thyroid cancer, lung cancer, colorectal cancer, head and neck cancer, stomach cancer, liver cancer, pancreatic cancer, renal cancer, urothelial cancer, prostate cancer, testis cancer, breast cancer, cervical cancer, endometrial cancer, ovarian cancer, or melanoma. In some embodiments, the target gene is the CD33 gene. Each of the aforementioned cancers express CD33. In some embodiments, the AC of the present disclosure is used to skip an exon of CD33. In some embodiments, the exon is selected from exon 1, exon 2, exon 3, exon 4, exon 5, exon 6, exon 7a, and exon 7b. In some embodiments, the target gene is Myc, STAT3, MDM4, ERRB4, BCL2L1, GLDC, PKM2, MCL1, MDM2, BRCA2, IL5R, FGFR1, MSTR1, USP5, or CD33.

In some embodiments, provided herein are compounds comprising an AC and CPP that target the CD33 gene. Non-limiting examples of the aforementioned compounds are shown below. The antisense oligonucleotide is underlined (SEQ ID NOs: 219 and 220).

ENTR-0036
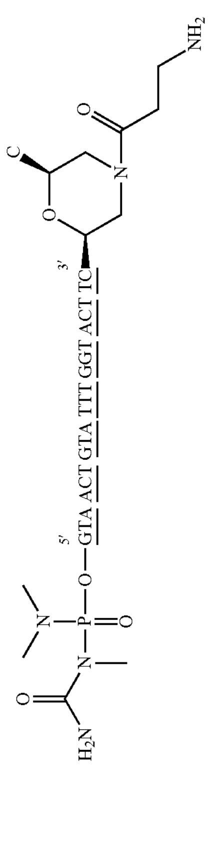
ENTR-0081
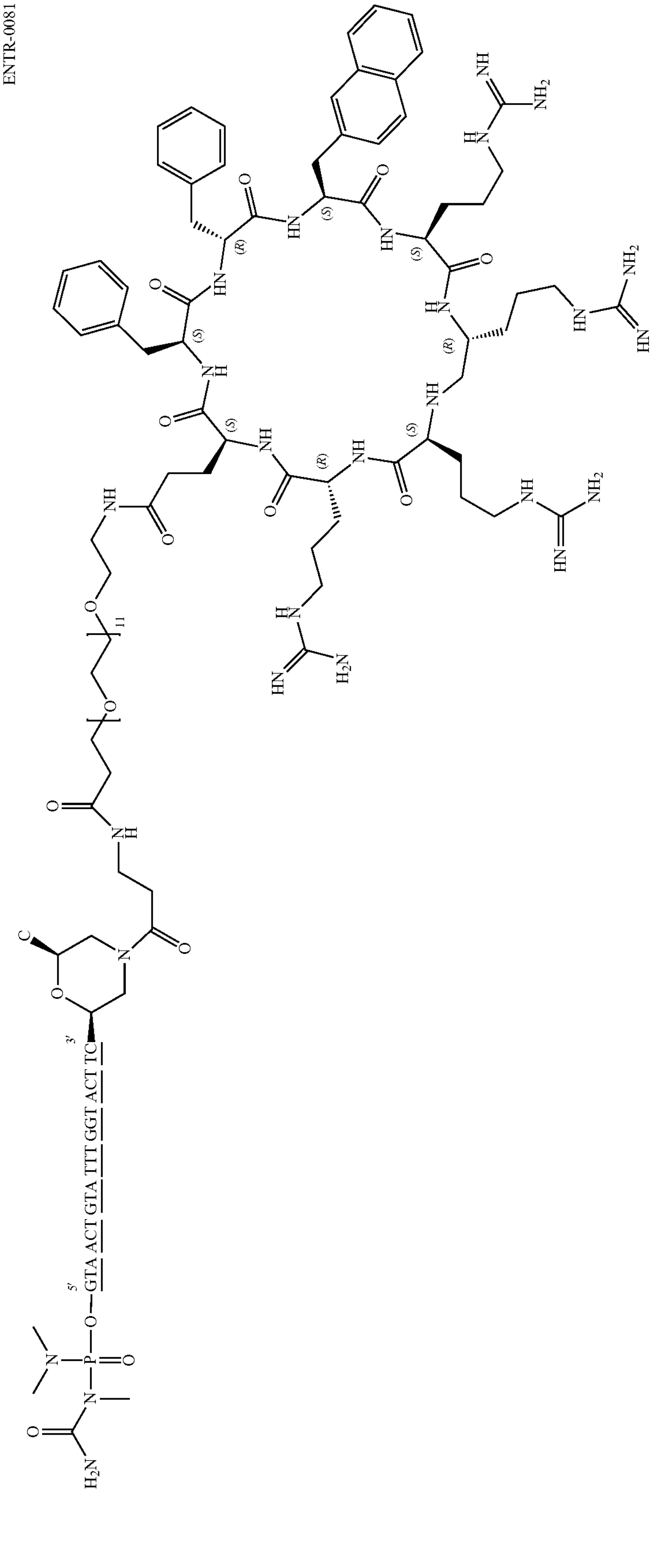

ENTR-0087
-continued
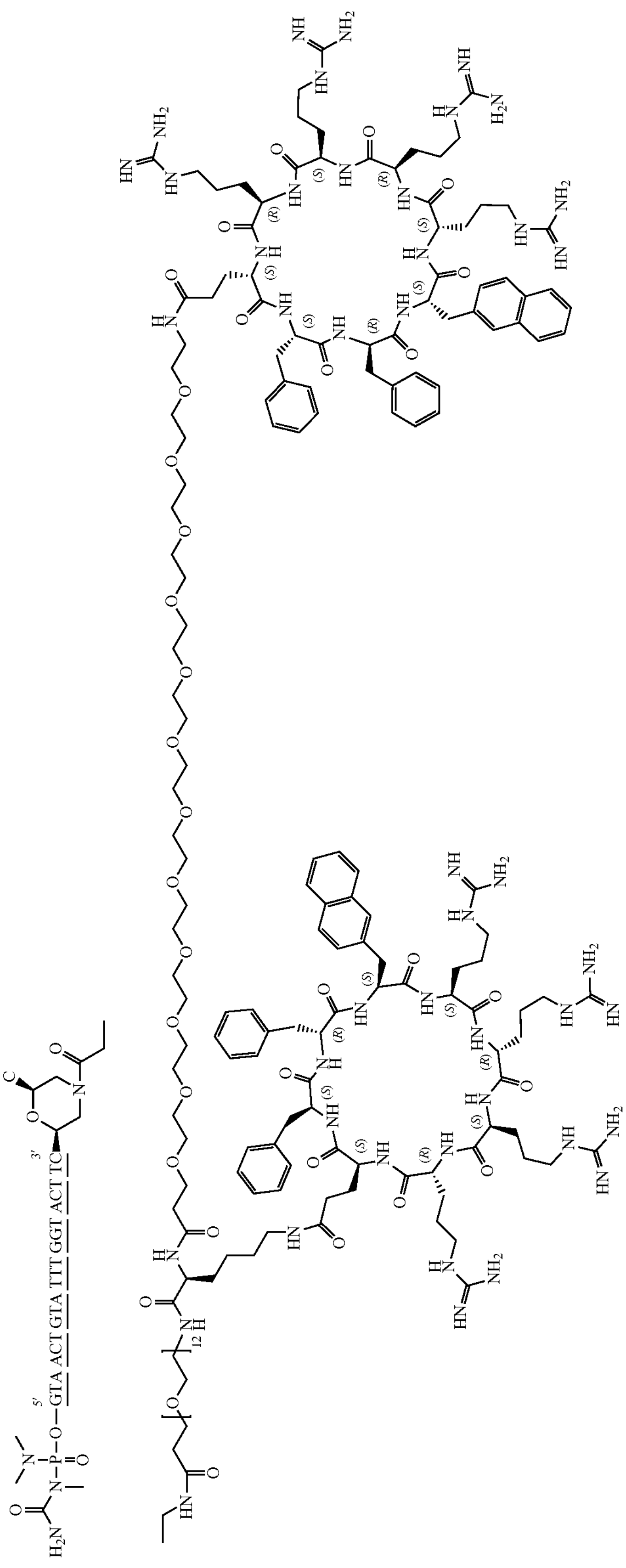

-continued
ENTR-0085
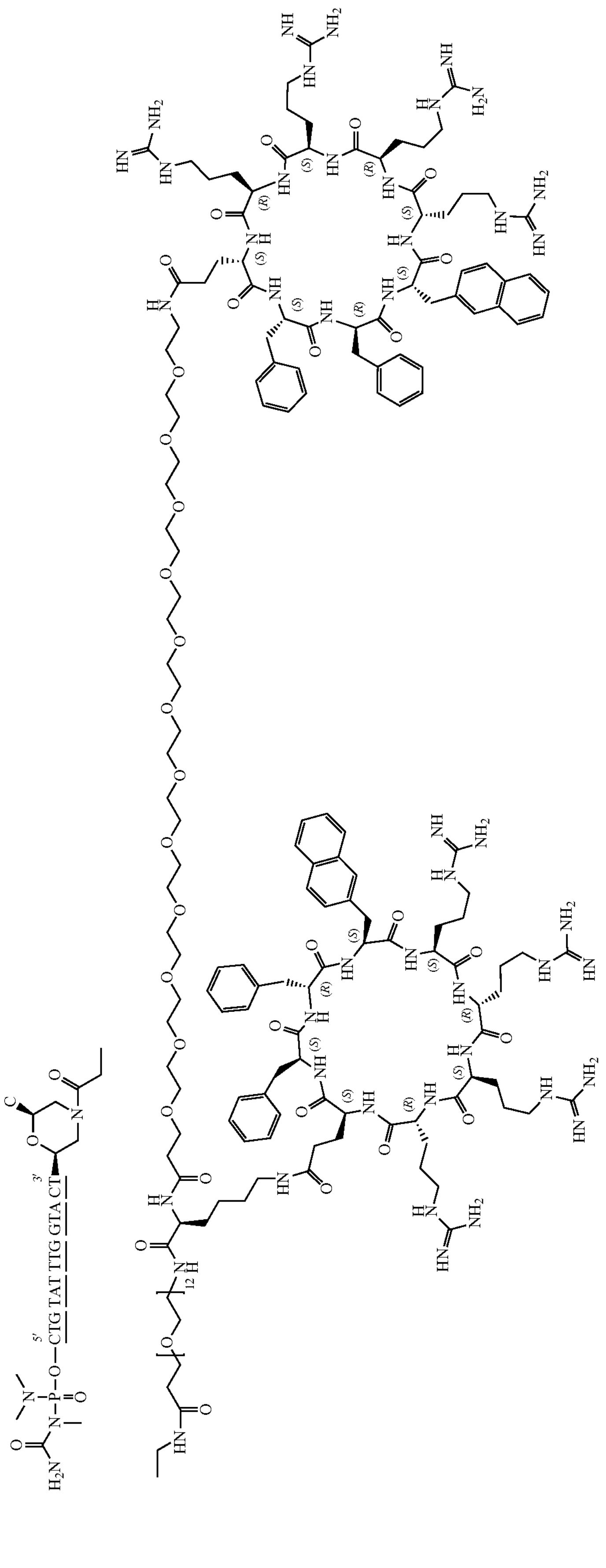

-continued
ENTR-0179
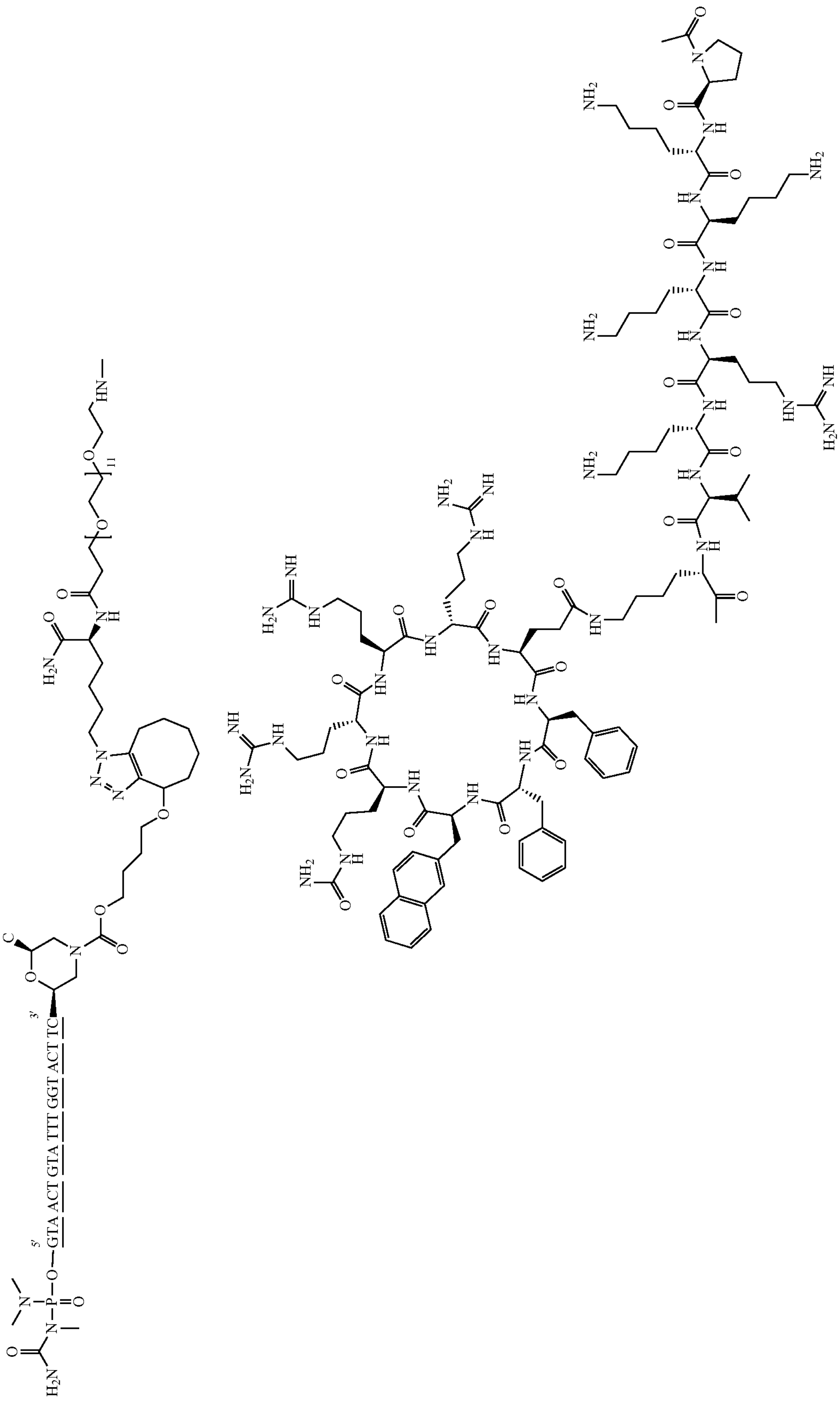

In some embodiments, the disease is an inflammatory or autoimmune disease. In some embodiments, the target gne is NLRP3 or CD6.

In some embodiments, the disease is osteogenesis imperfecta (Wang and Marini, J. Clin Invest., 1996, 97, 448-454).

In some embodiments, the disease is cystic fibrosis (Friedman et al., J. Biol. Chem., 1999, 274, 36193-36199).

In some embodiments, the disease is Merosin-deficient congenital muscular dystrophy type 1A (MDC1A). MDC1A is an autosomal recessive neuromuscular disease characterized by neonatal onset of muscle weakness, hypotonia, dysmyelinating neuropathy, and minor brain abnormalities. Splice site mutations are estimated to affect ~40% of the MDC1A patient population. Causative mutations are located in the LAMA2 gene, which encodes the a2 chain (Lama2) of laminin-211 (or merosin) heterotrimeric protein complex expressed in the basement membrane of muscle and Schwann cells. In MDC1A, laminin-211 loses its proper interactions with receptors such as integrin 0701 and dystroglycan, resulting in muscle and Schwann cells apoptosis and degeneration, which leads to fibrosis and loss of muscle function. In some embodiments, the AC hybridizes with a LAMA2 target pre-mRNA. So far, development of therapeutic strategies for MDC1A have been mainly focused on preventing fibrosis and apoptosis. The degree of LAMA2 deficiency highly correlates with the clinical severity in patients and mouse models. The lack of a functional Lama2 leads to the development of severe muscle atrophy and hind limb paralysis in mice. Therefore, restoration of LAMA2 expression holds a tremendous potential for the treatment of MDC1A. It has previously been demonstrated that muscle-specific overexpression of Laminin-211 in merosin-deficient mice improved muscle pathology, but not the associated paralysis, indicating that correction of the peripheral neuropathy requires restoration of Lama2 beyond skeletal muscles. In some embodiments, the AC restores proper splicing to the gene.

In some embodiments, antisense compounds may be used to alter the ratio of the long and short forms of bcl-x pre-mRNA. See U.S. Pat. Nos. 6,172,216; 6,214,986; Taylor et al., Nat. Biotechnol. 1999, 17, 1097-1100, each incorporated herein by reference. An increasing number of genes and gene products have been implicated in apoptosis. One of these is bcl-2, which is an intracellular membrane protein shown to block or delay apoptosis. Overexpression of bcl-2 has been shown to be related to hyperplasia, autoimmunity and resistance to apoptosis, including that induced by chemotherapy (Fang et al., J. Immunol. 1994, 153, 4388-4398). A family of bcl-2-related genes has been described. All bcl-2 family members share two highly conserved domains, BH1 and BH2. These family members include, but are not limited to, A-1, mcl-1, bax and bcl-x. Bcl-x was isolated using a bcl-2 cDNA probe at low stringency due to its sequence homology with bcl-2. Bcl-x was found to function as a bcl-2-independent regulator of apoptosis (Boise et al., Cell, 1993, 74, 597-608). Two isoforms of bcl-x were reported in humans. Bcl-xl (long) contains the highly conserved BH1 and BH2 domains. When transfected into an IL-3 dependent cell line, bcl-xl inhibited apoptosis during growth factor withdrawal in a manner similar to bcl-2. In contrast, the bcl-x short isoform, bcl-xs, which is produced by alternative splicing and lacks a 63-amino acid region of exon 1 containing the BH1 and BH2 domains, antagonizes the anti-apoptotic effect of either bcl-2 or bcl-xl. As numbered in Boise et al., Cell, 1993 74:, 597-608, the bcl-x transcript can be categorized into regions described by those of skill in the art as follows: nucleotides 1-134, 5' untranslated region (5'-UTR); nucleotides 135-137, translation initiation codon (AUG); nucleotides 135-836, coding region, of which 135-509 are the shorter exon 1 of the bcl-xs transcript and 135-698 are the longer exon 1 of the bcl-xl transcript; nucleotides 699-836, exon 2; nucleotides 834-836, stop codon; and nucleotides 837-926, 3' untranslated region (3'-UTR). Between exons 1 and 2 (between nucleotide 698 and 699) an intron is spliced out of the pre-mRNA when the mature bcl-xl (long) mRNA transcript is produced. An alternative splice from position 509 to position 699 produces the bcl-xs (short) mRNA transcript which is 189 nucleotides shorter than the long transcript, encoding a protein product (bcl-xs) which is 63 amino acids shorter than bcl-xl. Thus nucleotide position 698 is sometimes referred to in the art as the "5' splice site" and position 509 as the "cryptic 5' splice site," with nucleotide 699 sometimes referred to as the "3' splice site." In some embodiments, the AC hybridizes with a sequence comprising the cryptic 5' splice site of the bcl-x pre-mRNA, thereby inhibiting production of the short isoform and increasing the ratio of bcl-xl to bcl-xs isoforms.

In some embodiments, the AC promotes skipping of specific exons containing premature termination codons. See Wilton et al., Neuromuscul. Disord., 1999, 9, 330-338, incorporated by reference herein.

In some embodiments, the AC counteracts or corrects aberrant splicing in a target pre-mRNA. See U.S. Pat. No. 5,627,274 and WO 94/26887, each of which is incorporated by reference herein, and which disclose compositions and methods for combating aberrant splicing in a pre-mRNA molecule containing a mutation using antisense oligonucleotides which do not activate RNAse H.

In some embodiments, the disease is proximal spinal muscular atrophy (SMA). SMA is a genetic, neurodegenerative disorder characterized by the loss of spinal motor neurons. SMA is an autosomal recessive disease of early onset and is currently the leading cause of death among infants. SMA is caused by the loss of both copies of survival of motor neuron 1 (SMN1), a protein that is part of a multi-protein complex thought to be involved in snRNP biogenesis and recycling. A nearly identical gene, SMN2, exists in a duplicated region on chromosome 5 ql3. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Drainer, Nat. Genet., 2002, 30, 377-384). In some embodiments, the AC is targeted to intron 6, exon 7 or intron 7 of SMN2. In some embodiments, the AC modulates splicing of SMN2 pre-mRNA. In some embodiments, modulation of splicing results in an increase in exon 7 inclusion.

In some embodiments, the target gene is the beta globin gene. See Sierakowska et al. 1996, incorporated by reference herein. In some embodiments, the target gene is the cystic fibrosis transmembrane conductance regulator gene. See Friedman et al. 1999, incorporated by reference herein. In some embodiments, the target gene is the BRCA1 gene. In some embodiments, the target gene is the eIF4E gene. In some embodiments, the target gene is a gene involved in the pathogenesis of Duchenne muscular dystrophy, spinal muscular atrophy, or Steinert myotonic dystrophy. In some embodiments, the target gene is a DMD gene. In some embodiments, the target gene is BRCA1. In some embodiments, the target gene is a gene encoding a muscular structural protein. In some embodiments, the target gene is a gene implicated in a neuromuscular disorder (NMD). In some embodiments, the target gene is a gene implicated in cancer.

In some embodiments, the target gene is a gene that is subject to alternative splicing. In some embodiments, the present compounds and methods may be used to preferentially increase the ratio of a protein isoform by preferentially increasing the splicing of the target pre-mRNA to produce the mRNA encoding that isoform.

In some embodiments, the disease is a disease that is caused by repeat expansions of nucleotide repeat (e.g., trinucleotide repeat expansions, tetranucleotide repeat expansions, pentanucleotide repeat expansions, or hexanucleotide repeat expansions). In some embodiments, the disease is Huntington's disease, Huntington disease-like 2 (HDL2), myotonic dystrophy, spinocerebellar ataxia, spinal and bulbar muscular atrophy (SBMA), dentatorubral-pallidoluysian atrophy (DRPLA), amyotrophic lateral sclerosis, frontotemporal dementia, Fragile X syndrome, fragile X mental retardation 1 (FMR1), fragile X mental retardation 2 (FMR2), Fragile XE mental retardation (FRAXE), Friedreich's ataxia (FRDA), fragile X-associated tremor/ataxia syndrome (FXTAS), myoclonic epilepsy, oculopharyngeal muscular dystrophy (OPMD), or syndromic or non-syndromic X-linked mental retardation. In some embodiments, the disease is Huntington's disease. In some embodiments, the disease is amyotrophic lateral sclerosis. In some embodiments, the disease is a form of spinocerebellar ataxia (e.g., SCA1, SCA2, SAC3/MJD, SCA6, SCA7, SCA8, SCA10, SCA12, or SCA17).

In some embodiments, the disease is Friedreich's ataxia. In some embodiments, the target gene is FXN, which encodes for frataxin. In some embodiments, the compounds provided herein comprise an antisense oligonucleotide that targets FXN. Exemplary oligonucleotides that target FX are provided in Table 8.

TABLE 8

Exemplary Oligonucleotides targeting FXN

| Oligo chemistry | Name (oligo chemistry) | Design | Target |
|---|---|---|---|
| MOE blocker | M-4 | 5'- TT$^{m}$C TT$^{m}$C TT$^{m}$C TT$^{m}$C TT$^{m}$C TT$^{m}$C-3' (all 2'-O-MOE, all PS bonds, m = 5-methyl C) (SEQ ID NO: 167) | FXN (GAA)n |
| MOE gapmer | Gap-0039 | 5'- $^{m}$**CTT** $^{m}$**CTT** $^{m}$CTT $^{m}$CTT $^{m}$CTT $^{m}$**CTT** $^{m}$**CT**-3' (all PS bonds, not bold = DNA, bold = 2-MOE, m = 5-methyl C)(SEQ ID NO: 168) | FXN (GAA)n |
| MOE gapmer | Gap-0040 | 5' - **T**$^{m}$**CT** **T**$^{m}$**C**T T$^{m}$CT T$^{m}$CT T$^{m}$CT **T**$^{m}$**CT** **T**$^{m}$**C**-3' (all PS bonds, not-bold = DNA, bold = 2-MOE, m = 5-methyl C)(SEQ ID NO: 169) | FXN (GAA)n |
| 2'-F, siRNA | ENTR-siRNA-0027 | ss 5'-GSASAS GAA GAA GAA GAA GASASG-3' (SEQ ID NO: 170)<br>as 5'-CSUSUC UUC UUC UUC UUC SUSUSC-3' (SEQ ID NO: 171)<br>(all 2'-F, S = PS bond) | FXN (GAA)n |
| 2'-F, siRNA EEV | ENTR-siRNA-0027A | ss $CPP_{12}$-NH-5'-GSASAS GAA GAA GAA GAA GASASG-3' (SEQ ID NO: 172)<br>as 5'-CSUSUC UUC UUC UUC UUC SUSUSC-3' (SEQ ID NO: 173)<br>(all 2'-F, S = PS bond) | FXN (GAA)n |
| 2'-F, siRNA EEV | ENTR-siRNA-0027B | ss 5'-GSASAS GAA GAA GAA GAA GASASG-3'-NH-$CPP_{12}$ (SEQ ID NO: 174)<br>as 5'-CSUSUC UUC UUC UUC UUC SUSUSC-3' (SEQ ID NO: 175)<br>(all 2'-F, S = PS bond) | FXN (GAA)n |
| siRNA | siGAA | ss 5'-GAAGAAGAAGAAGAAGAAGT$_{d}$T$_{d}$-3' (SEQ ID NO: 176)<br>as 5'-CUUCUUCUUCUUCUUCUUCT$_{d}$T$_{d}$-3' (d = DNA)(SEQ ID NO: 177) | FXN (GAA)n |
| siRNA | Control (Ctrl) | as 5'-GCUAUACCAGCGUCGUCAUT$_{d}$T$_{d}$-3' (SEQ ID NO: 178)<br>ss 5'-ATGACGACGCTGGTATAGCT$_{d}$T$_{d}$-3' (d = DNA)(SEQ ID NO: 179) | Mismatched negative control |
| siRNA | siExon2 | ss 5'-GAGUGUCUAUUUGAUGAAUT$_{d}$T$_{d}$-3' (SEQ ID NO: 180)<br>as 5'-AUUCAUCAAAUAGACACUCT$_{d}$T$_{d}$-3' (d = DNA)(SEQ ID NO: 181) | FXN exon2, positive control for transfection |
| MOE blocker | ET4 | 5'-$^{m}$C$^{m}$CT $^{m}$CAA AAG $^{m}$CAG GAA UA-3' (all 2'-O-MOE, all PS bonds, m = 5-methyl C) (SEQ ID NO: 182) | FXN 3'-UTR |
| MOE blocker | ET14 | 5'-$^{m}$C$^{m}$CG GGT $^{m}$CTG $^{m}$C$^{m}$CG $^{m}$C$^{m}$C$^{m}$C-3' (all 2'-O-MOE, all PS bonds, m = 5-methyl C) (SEQ ID NO: 183) | FXN 5'-UTR |

TABLE 8-continued

| Exemplary Oligonucleotides targeting FXN | | | |
|---|---|---|---|
| Oligo chemistry | Name (oligo chemistry) | Design | Target |
| PMO | ENTR-Oligo-0180 | 5'-CCT CAA AAG CAG GAA TA-3' (all PMO monomers)(SEQ ID NO: 184) | FXN 3'-UTR |
| PMO | ENTR-Oligo-0181 | 5'-CCG GGT CTG CCG CCC-3' (all PMO monomers)(SEQ ID NO: 185) | FXN 5'-UTR |
| PMO | ENTR-Oligo-0182 | 5'-CCA ACT GTC CTC AAA AGC AGG AAT A-3' (all PMO monomers)(SEQ ID NO: 186) | FXN 3'-UTR |
| PMO | ENTR-Oligo-0183 | 5'-CCG GGT CTG CCG CCC GCT CCG CCC T-3' (all PMO monomers)(SEQ ID NO: 187) | FXN 5'-UTR |
| PMO | ENTR-Oligo-0000 | 5'-CTT CTT CTT CTT CTT CTT CTT CTT C-3' (all PMO monomers)(SEQ ID NO: 188) | FXN (GAA)n |
| O-MOE | ENTR-Oligo-0002 | 5'-CTT CTT CTT CTT CTT CTT-3' (all 2'-O-MOE RNA monomers, all PS bonds)(SEQ ID NO: 189) | FXN (GAA)n |
| LNA | ENTR-Oligo-0004 | 5'-LnT-dC-LnT-LnT-dC-LnT-LnT-dC-LnT-LnT-dC-LnT-LnT-dC-LnT-LnT-dC-LnT-LnT-3' (LnT = LNA T; dC = DNA C; all PS bonds) (SEQ ID NO: 190) | FXN (GAA)n |
| Gapmer (all PS bonds) | ENTR-Oligo-0039 | 5'- **CTTCT**TCTTCTTCTT**CTTCT**-3' (all PS bonds, non-bold-DNA, bold = 2-MOE)(SEQ ID NO: 191) | FXN (GAA)n |
| Gapmer (all PS bonds) | ENTR-Oligo-0040 | 5' - **TCTTC**TTCTTCTTCT**TCTTC**-3' (all PS bonds, non-bold = DNA, bold = 2-MOE)(SEQ ID NO: 192) | FXN (GAA)n |
| MOE (all PS bonds) | ENTR-Oligo-0041 | 5'-CTT CTT CTT CTT CTT CTT-3' (all 2'-O-MOE RNA monomers, all PS bonds)(SEQ ID NO: 193) | FXN (GAA)n |

In some embodiments, the disease is a form of myotonic dystrophy (e.g., myotonic dystrophy type 1 or myotonic dystrophy type 2). In some embodiments, the target gene is the DMPK gene, which encodes myotonic-protein kinase. In some embodiments, the compounds provided herein comprise an antisense oligonucleotide that targets DMPK. Exemplary oligonucleotides that target DMPK are provided in Table 9.

TABLE 9

| Exemplary Oligonucleotides targeting DMPK | | | |
|---|---|---|---|
| Oligo ID | Oligo name | Target | Sequence (5'-3') |
| ENTR-Oligo-0022 | DMPK-2MOE-M+N+H (quote as DM+N+H) | DMPK | alkyne-5'-**ACAGA**CAATAAATACC**GAGG**-3'-primary amine (all PS bonds, black = DNA, black = 2-MOE)(SEQ ID NO: 194) |
| ENTR-Oligo-0023 | DMPK-2MOE-M+N+H-dual modification-1 | DMPK | cycloctyne-5'-**ACAGA**CAATAAATACC**GAGG**-3'-primary amine (all PS bonds, black = DNA, black = 2-MOE)(SEQ ID NO: 195) |
| ENTR-Oligo-0023A | DMPK-2MOE-M+N+H-NH2-1 | DMPK | 5'-**ACAGA**CAATAAATACC**GAGG**-3'-primary amine (all PS bonds, black = DNA, black = 2-MOE)(SEQ ID NO: 196) |
| ENTR-Oligo-0028 | DMPK-cEt-M+N+H | DMPK | cyclooctyne-5'-**ACA**ATAAATACCG**AGG**-(3'-primary amine (all PS bonds, black = DNA, bold = (s)-cEt)(SEQ ID NO: 197) |
| ENTR-Oligo-0029 | DMPK-cEt-M+N+H-CP12 | DMPK | cyclooctyne-5'-**ACA**ATAAATACCG**AGG**-3'-CP12 (all PS bonds, black = DNA, bold = (s)-cEt)(SEQ ID NO: 198) |

TABLE 9-continued

| Exemplary Oligonucleotides targeting DMPK | | | |
|---|---|---|---|
| Oligo ID | Oligo name | Target | Sequence (5'-3') |
| ENTR-Oligo-0031 | DMPK-2MOE-H-2 (quote as DH-1) | DMPK | 5'- **CGGAG**CGGTTGTGAA**CTGGC** -3'-primary amine (all PS bonds, non-bold = DNA, bold = 2-MOE)(SEQ ID NO: 199) |
| ENTR-Oligo-0032 | DMPK-2MOE-N-2 (wrongly labeled as DM-1 in quote) | DMPK | alkyne-5'- **CGGAG**CGGTGTGAAC**TGGCA** -3'-primary amine (20 bases, all PS bonds, non-bold = DNA, bold = 2-MOE)(SEQ ID NO: 200) |
| ENTR-Oligo-0053 | DMPK-2MOE-M+N+H | DMPK | 5'-**ACAGA**CAATAAATAC**CGAGG**-3' (all PS bonds, non-bold = DNA, bold = 2-MOE)(SEQ ID NO: 201) |
| ENTR-oligo-0077 | ENTR-oligo-0022-PEG12-CPP12-Amide | DMPK | alkyne-5'-**ACAGA**CAATAAATAC**CGAGG**-3'-PEG12-CPP12 (all PS bonds, non-bold = DNA, bold = 2-MOE)(SEQ ID NO: 202) |
| ENTR-oligo-0078 | CPP12-PEG12-click-ENTR-oligo-0022 | DMPK | CPP12-PEG12-Lys-click-5'-**ACAGA**CAATAAATAC**CGAGG**-3' (all PS bonds, non-bold = DNA, bold = 2-MOE) (SEQ ID NO: 203) |
| ENTR-oligo-0189 | ETRDWUXI-617+ ENTR-oligo-0023 (click) | DMPK | 204) CPP12-PEG12-click-5'-**ACAGA**CAATAAATAC**CGAGG**-3'-primary amine (all PS bonds, non-bold = DNA, bold = 2-MOE)(SEQ ID NO: |
| ENTR-oligo-0190 | ETRDWUXI-642+ ENTR-oligo-0023 (click) | DMPK | CPP12-K(CPP12) PEG12-K-click-5'-**ACAGA**CAATAAATAC**CGAGG**-3'-primary amine (all PS bonds, non-bold = DNA, bold = 2-MOE)(SEQ ID NO: 205) |
| ENTR-oligo-0191 | ETRDWUXI-684+ ENTR-oligo-0023 (click) | DMPK | Ac-NLS-Lys(CPP12)-PEG12-K-click-5'-**ACAGA**CAATAAATAC**CGAGG**-3'-primary amine (all PS bonds, non-bold = DNA, bold = 2-MOE)(SEQ ID NO: 206) |
| ENTR-oligo-0192 | ENTR-oligo-0023a+SMCC | DMPK | 5'-**ACAGA**CAATAAATAC**CGAGG**-3'-primary amine+SMCC (all PS bonds, non-bold = DNA, bold = 2-MOE)(SEQ ID NO: 207) |
| ENTR-Oligo-0071 | PMOCAG | DMPK | 5'-CAG CAG CAG CAG CAG CAG CAG-3'-NH2 (all PMO monomers)(SEQ ID NO: 208) |
| ENTR-Oligo-0034 | PMOCAG-CP12 | DMPK | 5'-CAG CAG CAG CAG CAG CAG CAG-3' -CP12 (all PMO monomers)(SEQ ID NO: 209) |
| ENTR-Oligo-0022 | DMPK-2MOE-M+N+H (quote as DM+N+H) | DMPK | alkyne-5'-**ACAGA**CAATAAATAC**CGAGG**-3'-primary amine (all PS bonds, non-bold = DNA, bold-2-MOE)(SEQ ID NO: 210) |
| ENTR-Oligo-0031 | DMPK-2MOE-H-2 (quote as DH-1) | DMPK | 5'- **CGGAG**CGGTTGTGAA**CTGGC**-3'-primary amine (all PS bonds, non-bold = DNA, bold = 2-MOE)(SEQ ID NO: 211) |

In some embodiments, the disease is Dravet syndrome. Dravet syndrome is a severe and progressive genetic epilepsy. Dravet syndrome is an autosomal dominant condition caused by more than 1250 de novo mutations in SCN1A, resulting in 50% NaV1.1 protein expression. Dravet syndrome is caused by pathogenic mutation or deletion of the SCN1A gene in 85% of patients. Existing antiepileptic drug sonly address the occurrence of seizures, and more than 90% of Dravet syndrome patients still report suffering from incomplete seizure control. In some embodiments, the antisense oligonucleotide targets SCN1A. In some embodiments, the antisense oligonucleotide targeting SCN1A has a sequence of 5'-CCATAATAAAGGGCTCAG-3' (SEQ ID NO: 212). In some embodiments, the efficacy of antisense compounds targeting SCN1A is evaluated in a mouse model. Non-limiting examples of mouse models include mouse models with a targeted deletion of SCN1A exon 1 (Scn1a$^{tm1Kea}$) and exon 26 (Scn1a$^{tm1Wac}$), mouse models with specific point mutation knock-ins, such as Scn1a R$^{1407}$X, Scn1a R1648H, and Scn1a E1099X, and a transgenic mouse model expressing a bacterial artificial chromosome (BAC) with a human SCN1A R1648H mutation. In some embodiments, the efficacy of antisense compounds targeting SCN1A is evaluated in an in vitro model, for example, in wild-type fibroblasts.

In some embodiments, the disease is Fragile X Syndrome (FXS). FXS is the most common form of inherited intellectual and developmental disease. FXS is caused by silenced expression of fragile X mental retardation protein (FMRP) due to the presence of >200 CGG trinucleotide repeats in FMR1 which encodes for FMRP. FMRP is encoded by FMR1. In some embodiments, an antisense compound of the disclosure targets FMR1. In some embodiments, the efficacy of antisense compounds targeting FMR1 is evaluated in a mouse model (e.g., those described in Dahlhaus et al.), which is incorporated by reference herein in its entirety: Dahlhaus, R. (2018). Of men and mice: modeling the fragile X syndrome. Frontiers in molecular neuroscience, 11, 41.

In some embodiments, the disease is Fragile X tremor ataxia syndrome (FXTAS). FXTAS is a late-onset, progressive neurodegenerative disorder characterized by cerebellar ataxia and intention tremor. FXTAS is caused by an FMRI premutation, which is defined as having 55 to 200 CGG repeats in the 5' untranslated region of FMR1. In some embodiments, an antisense compound of the disclosure targets FMR1.

Figure 33:
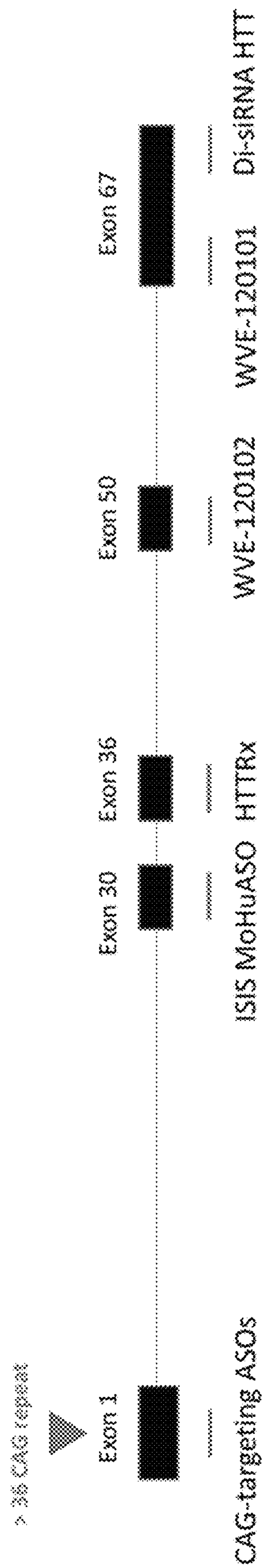
FIG. 33 shows exemplary antisense oligonucleotides and their pre-mRNA HTT targets.

In some embodiments, the disease is Huntington's Disease (HD). HD is an autosomal dominant disease, characterized by cognitive decline, psychiatric illness, and chorea. HD is often fatal. HD is caused by an expanded CAG triplet repeat in the HTT gene, which results in the production of mutant huntingtin protein (mHTT). Accumulation of mHTT causes progressive loss of neurons in the brain. In some embodiments, the target gene is HTT In some embodiments, an antisense compound of the disclosure targets HTT. In some embodiments, the efficacy of antisense compounds and/or oligonucleotides are evaluated in in vivo models. Exemplary models are described in Pouladi et al. which is incorporated by reference herein in its entirety: Pouladi, Mahmoud A., et al. "Choosing an animal model for the study of Huntington's disease." *Nature Reviews Neuroscience* 14.10 (2013): 708-721. In some embodiments, the antisense oligonucleotide is non-allele selective. In some embodiments, the non-allele selective antisense oligonucleotide is an HTTRx gapmer (Ionis) or a divalent siRNA (UMass). In some embodiments, the antisense oligonucleotide is allele selective. In some embodiments, the allele selective antisense oligonucleotide is a stereopure gapmer targeting a single nucleotide polymorphism in HTT. In some embodiments, the antisense oligonucleotide targets exon 1, exon 30, exon 36, exon 50, or exon 67 of HTT. Exemplary antisense oligonucleotides and their pre-mRNA targets for HD are illustrated in FIG. 33. The following references describe exemplary antisense oligonucleotides and are incorporated herein by reference in their entirety: Yu, Dongbo, et al. *Cell* 150.5 (2012): 895-908; Alterman, *Julia* F., et al. Nature biotechnology 37.8 (2019): 884-894. Tabrizi, Sarah J., et al. *New England Journal of Medicine* 380.24 (2019): 2307-2316.; Kordasiewicz, Holly B., et al. *Neuron* 74.6 (2012): 1031-1044.

In some embodiments, the disease is Wilson's Disease (WD). WD is a recessive fatal copper homeostasis disorder, typically diagnosed in patients between the ages of 5 and 35, leading to hepatic and neurologic symptoms due to free copper accumulation. WD is caused by loss-of-function mutations in the ATP7B gene. ATP7B encodes copper-transporting ATPase 2, which is a transmembrane copper transporter and responsible in the transport of copper from the liver to other parts of the body. In some embodiments, provided herein is an antisense oligonucleotide or compound thereof that targets ATP7B. In some embodiments, the antisense oligonucleotide or compound thereof targets a T1934G (or Met-645-Arg) mutation in ATP7B. The aforementioned ATP7B variant is described in Merico et al. which is incorporated by reference herein in its entirety: Merico, Daniele, et al. *NPJ Genomic Medicine* 5.1 (2020): 1-7. In some embodiments, the antisense oligonucleotide has a sequence of 5'-CAGCTGGAGTTTATCTTTTG-3' (SEQ ID NO: 213).

In some embodiments of this aspect, the sequence of the corresponding gene underlying such diseases is prone to forming clusters of RNA comprises tandem nucleotide repeats (e.g., multiple nucleotide repeats comprising at least 10, 15, 20, 25, 30, 40, 50, 60, 70 or more adjacent repeated nucleotide sequences). In some embodiments, the tandem nucleotide repeats are trinucleotide repeats. The trinucleotide repeat sequences may be CAG repeats, CGG repeats, GCC repeats, GAA repeats, or CUG repeats. In some embodiments, the trinucleotide repeat is a CAG repeat. In some embodiments, the RNA sequence comprises at least 10 trinucleotide repeats (e.g., CAG, CGG, GCC, GAA, or CUG repeats), e.g., at least 10, at least 15, at least 20, at least 25, at least 30, at least 35, at least 40, at least 45, at least 50, at least 60, or at least 70 trinucleotide repeats. In some embodiments, the target gene is selected from the group consisting of FMR1, AFF2, FXN, DMPK, SCA8, PPP2R2B, ATN1, DRPLA, HTT, AR, ATXN1, ATXN2, ATXN3, CACNA1A, ATXN7, TBP. See U.S. Pat. Appl. Publ. No. 2016/0355796 and U.S. Pat. Appl. Publ. No. 2018/0344817, each of which is incorporated by reference herein, and which discloses diseases and corresponding genes prone to forming and/or expanding tandem nucleotide repeats.

In some embodiments, an AC of the disclosure is administered to treat any disease described by the disclosure, for example, Huntington's disease, Huntington disease-like 2 (HDL2), myotonic dystrophy, spinocerebellar ataxia, spinal and bulbar muscular atrophy (SBMA), dentatorubral-pallidoluysian atrophy (DRPLA), amyotrophic lateral sclerosis, frontotemporal dementia, Fragile X syndrome, fragile X mental retardation 1 (FMR1), fragile X mental retardation 2 (FMR2), Fragile XE mental retardation (FRAXE), Friedreich's ataxia (FRDA), fragile X-associated tremor/ataxia syndrome (FXTAS), myoclonic epilepsy, oculopharyngeal muscular dystrophy (OPMD), syndromic or non-syndromic X-linked mental retardation, Cystic fibrosis, proximal spinal muscular atrophy, of Duchenne muscular dystrophy, spinal muscular atrophy, Steinert myotonic dystrophy, Merosin-deficient congenital muscular dystrophy type 1A, osteogenesis imperfect, cancer, glioma, thyroid cancer, lung cancer, colorectal cancer, head and neck cancer, stomach canker, liver cancer, pancreatic cancer, renal cancer, urothelial cancer, prostate cancer, testis cancer, breast cancer, cervical cancer, endometrial cancer, ovarian cancer, melanoma, or Alzheimer's Disease. In some embodiments, an AC of the disclosure is administered to a patient diagnosed with a disease of the disclosure at a dose of between about 0.1 mg/kg and about 1000 mg/kg, for example, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg, about 50 mg/kg, about 51 mg/kg, about 52 mg/kg, about 53 mg/kg, about 54 mg/kg, about 55 mg/kg, about 56 mg/kg, about 57 mg/kg, about 58 mg/kg, about 59 mg/kg, about 60 mg/kg, about 61 mg/kg, about 62 mg/kg, about 63 mg/kg, about 64 mg/kg, about 65 mg/kg, about 66 mg/kg, about 67 mg/kg, about 68 mg/kg, about 69 mg/kg, about 70 mg/kg, about 71 mg/kg, about 72 mg/kg, about 73 mg/kg, about 74 mg/kg, about 75 mg/kg, about 76 mg/kg, about 77 mg/kg, about 78 mg/kg, about 79 mg/kg, about 80 mg/kg, about 81 mg/kg, about 82 mg/kg, about 83 mg/kg, about 84 mg/kg, about 85 mg/kg, about 86 mg/kg, about 87 mg/kg, about 88 mg/kg, about 89 mg/kg, about 90 mg/kg, about 91 mg/kg, about 92 mg/kg, about 93 mg/kg, about 94 mg/kg, about 95 mg/kg, about 96 mg/kg, about 97 mg/kg, about 98 mg/kg, about 99 mg/kg, about 100 mg/kg, about 110 mg/kg, about 120 mg/kg, about 130 mg/kg, about 140 mg/kg, about 150 mg/kg, about 160 mg/kg, about 170 mg/kg, about 180 mg/kg, about 190 mg/kg, about 200 mg/kg, about 210 mg/kg, about 220 mg/kg, about 230 mg/kg, about 240 mg/kg, about 250 mg/kg, about 260 mg/kg, about 270 mg/kg, about 280 mg/kg, about 290 mg/kg, about 300 mg/kg, about 310 mg/kg, about 320 mg/kg, about 330 mg/kg, about 340 mg/kg, about 350 mg/kg, about 360 mg/kg, about 370 mg/kg, about 380 mg/kg, about 390 mg/kg, about 400 mg/kg, about 410 mg/kg, about 420 mg/kg, about 430 mg/kg, about 440 mg/kg, about 450 mg/kg, about 460 mg/kg, about 470 mg/kg, about 480 mg/kg, about 490 mg/kg, about 500 mg/kg, about 510 mg/kg, about 520 mg/kg, about 530 mg/kg, about 540 mg/kg, about 550 mg/kg, about 560 mg/kg, about 570 mg/kg, about 580 mg/kg, about 590 mg/kg, about 600 mg/kg, about 610 mg/kg, about 620 mg/kg, about 630 mg/kg, about 640 mg/kg, about 650 mg/kg, about 660 mg/kg, about 670 mg/kg, about 680 mg/kg, about 690 mg/kg, about 700 mg/kg, about 710 mg/kg, about 720 mg/kg, about 730 mg/kg, about 740 mg/kg, about 750 mg/kg, about 760 mg/kg, about 770 mg/kg, about 780 mg/kg, about 790 mg/kg, about 800 mg/kg, about 810 mg/kg, about 820 mg/kg, about 830 mg/kg, about 840 mg/kg, about 850 mg/kg, about 860 mg/kg, about 870 mg/kg, about 880 mg/kg, about 890 mg/kg, about 900 mg/kg, about 910 mg/kg, about 920 mg/kg, about 930 mg/kg, about 940 mg/kg, about 950 mg/kg, about 960 mg/kg, about 970 mg/kg, about 980 mg/kg, about 990 mg/kg, or about 1000 mg/kg, including all values and ranges therein and in between.

In some embodiments, an AC of the disclosure is a gapmer oligonucleotide as disclose in U.S. Pat. No. 9,550,988, the disclosure of which is incorporated by reference herein.

In some embodiments, an AC of the disclosure comprises the sequence and/or structure of any one of the ACs targeting SMN2 disclosed in U.S. Pat. No. 8,361,977, the disclosure of which is incorporated by reference herein.

In some embodiments, an AC of the disclosure comprises the sequence and/or structure of any one of the ACs targeting DMD, SMN2, or DMPK disclosed in U.S. Patent Publication No. 2017/0260524, the disclosure of which is incorporated by reference herein.

In some embodiments, an AC of the disclosure comprises the sequence and/or structure of any one of the ACs or oligonucleotides disclosed in U.S. Patent Publications US20030235845A1, US20060099616A1, US 2013/0072671 A1, US 2014/0275212 A1, US 2009/0312532 A1, US20100125099A1, US 2010/0125099 A1, US 2009/0269755 A1, US 2011/0294753 A1, US 2012/0022134 A1, US 2011/0263682 A1, US 2014/0128592 A1, US 2015/0073037 A1, and US20120059042A1, the contents of each of which are incorporated herein in their entirety for all purposes.

Re-Spliced Target Proteins

The "target protein" is the amino acid sequence resulting from transcription and translation of the target gene. The "re-spliced target protein" as used herein refers to the protein encoded as a result of binding of the AC to the target pre-mRNA transcribed from the target gene. The "wild type target protein" refers to a naturally occurring, correctly translated protein isomer resulting from proper splicing of the target pre-mRNA encoded by a wild type target gene. The present compounds and methods may result in a re-spliced target protein containing one or more amino acid substitutions, deletions, and/or insertions as compared to a wild type target protein, while retaining some wild type target protein activity. In some embodiments, the re-spliced target protein produced by administration of the present compounds is homologous to a wild type target protein. In some embodiments, the re-spliced target protein has an amino acid sequence that is at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% or more identical to a wild type target protein. In some embodiments, the re-spliced target protein is substantially identical to a wild type target protein. In some embodiments, the amino acid sequence of the re-spliced target protein is at least 50% identical to the amino acid sequence of a wild type target protein. In some embodiments, the amino acid sequence of the re-spliced target protein is at least 75% identical to the amino acid sequence of a wild type target protein. In some embodiments, the amino acid sequence of the re-spliced target protein is at least 90% identical to the amino acid sequence of a wild type target protein. In some embodiments, the re-spliced target protein is a truncated version of a wild type target protein.

In some embodiments, the re-spliced target protein can rescue one or more phenotypes or symptoms of a disease associated with the transcription and translation of the target gene. In some embodiments, the re-spliced target protein can rescue one or more phenotypes or symptoms of a disease associated with the expression of the target protein. In some embodiments, the re-spliced target protein is an active fragment of a wild type target protein. In some embodiments, the re-spliced target protein functions in a substantially similar manner to the wild type target protein. In some embodiments, the re-spliced target protein allows the cell to function substantially similar to a similar cell which expresses a wild type target protein. In some embodiments, the re-spliced target protein does not cure the disease associated with the target gene or with the target protein, but ameliorates one or more symptoms of the disease. In some embodiments, the re-spliced target protein results in an improvement of target protein function of about 1%, about 2%, about 3%, about 4%, about 5%, about 6%, about 7%, about 8%, about 9%, about 10%, about 15%, about 205, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the re-spliced target protein may have an amino acid sequence that is reduced from the size of a wild type target protein by about 1 or more amino acids, e.g., about 5, about 10, about 15, about 20, about 25, about 30, about 35, about 40, about 45, about 50, about 55, about 60, about 65, about 70, about 75, about 80, about 90, about 95, about 100, about 105, about 110, about 115, about 120, about 125, about 130, about 135, about 140, about 145, about 150, about 155, about 160, about 165, about 170, about 175, or about 180 or more amino acids.

In some embodiments, the re-spliced target protein may have one or more properties that are improved relative to the target protein. In some embodiments, the re-spliced target protein may have one or more properties that are improved relative to a wild type target protein. In some embodiments, the enzymatic activity or stability may be enhanced by promoting different splicing of the target pre-mRNA. In some embodiments, the re-spliced target protein may have a sequence identical or substantially similar to a wild type target protein isomer having improved properties compared to another wild type target protein isomer.

In some embodiments, one or more properties of the target protein are either not present (eliminated) or are reduced in the re-spliced target protein. In some embodiments, one or more properties of the wild type target protein are either not present (eliminated) or are reduced in the re-spliced target protein. Non-limiting examples of properties that may be reduced or eliminated include immunogenic, angiogenic, thrombogenic, aggregation, and ligand-binding activity.

In some embodiments, the re-spliced target protein contains one or more amino acid substitutions compared to a wild type target protein. In some embodiments, the substitutions may be conservative substitutions or non-conservative substitutions. Examples of conservative amino acid substitutions include substitution of one amino acid for another amino acid within one from one of the following groups: basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). In some embodiments, structurally similar amino acids are substituted to reverse the charge of a residue (e.g., glutamine for glutamic acid or vice-versa, aspartic acid for asparagine or vice-versa). In some embodiments, tyrosine is substituted for phenylalanine or vice-versa. Other non-limiting examples of amino acid substitutions are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In some embodiments, the re-spliced target protein may comprise a substitution, deletion, and/or insertion at one or more (e.g., several) positions compared to a wild type target protein. In some embodiments, the number of amino acid substitutions, deletions and/or insertions comprised by the re-spliced target protein amino acid sequence is not more than 200, not more than 150, not more than 100, not more than 50, not more than 40, not more than 30, not more than 20, or not more than 10, e.g., 1, 2, 3, 4, 5, 6, 7, 8, 9, or 10.

In some embodiments, cCPP may be conjugated, via the linker, to the 5' or 3' end of the AC. In some embodiments, the linker further comprises an amino acid (e.g., lysine) to facilitate chemical conjugation of the AC to a side chain of an amino acid on the cCCP In some embodiments, a water-soluble polymer can be conjugated to the AC.

Methods of Treatment

The present disclosure provides a method of treating disease in a subject in need thereof, comprising administering a compound disclosed herein. In some embodiments, the disease is any of the diseases provided in the present disclosure. In some embodiments, the target gene is any of the target genes provided in the present disclosure.

In various embodiments, treatment refers to partial or complete alleviation, amelioration, relief, inhibition, delaying onset, reducing severity and/or incidence of one or more symptoms in a subject.

In some embodiments, a method is provided for altering the expression of a target gene in a subject in need thereof, comprising administering a compound disclosed herein. In some embodiments, the treatment results in the lowered expression of a target protein. In some embodiments, the treatment results in the expression of a re-spliced target protein. In some embodiments, the treatment results in the preferential expression of a wild type target protein isomer.

In some embodiments, treatment according to the present disclosure results in decreased expression of a target protein in a subject by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject before the treatment or of one or more control individuals with similar disease without treatment.

In some embodiments, treatment according to the present disclosure results in increased expression of a re-spliced target protein in a subject by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject before the treatment or of one or more control individuals with similar disease without treatment.

In some embodiments, treatment according to the present disclosure results in increased or decreased expression of a wild type target protein isomer in a subject by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject before the treatment or of one or more control individuals with similar disease without treatment.

In some embodiments, treatment according to the present disclosure results in decreased expression of a target protein in a subject's muscle tissue, diaphragm tissue, quadriceps, or heart by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject's muscle tissue, diaphragm tissue, quadriceps, or heart before the treatment, compared to one or more control individuals with similar disease without treatment, or compared to treatment with an AC not conjugated to a cyclic CPP disclosed herein.

In some embodiments, treatment according to the present disclosure results in increased expression of a re-spliced target protein in a subject's muscle tissue, diaphragm tissue, quadriceps, or heart by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 350%, about 400%, about 450%, about 500%, about 550%, about 600%, about 650%, about 700%, about 750%, about 800, about 850%, about 900%, about 950%, or about 1000% or more, as compared to the average level of the target protein in the subject's muscle tissue, diaphragm tissue, quadriceps, or heart before the treatment, compared to one or more control individuals with similar disease without treatment, or compared to treatment with an AC not conjugated to a cyclic CPP disclosed herein.

In some embodiments, treatment according to the present disclosure results in increased or decreased expression of a wild type target protein isomer in a subject's muscle tissue, diaphragm tissue, quadriceps, or heart by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject's muscle tissue, diaphragm tissue, quadriceps, or heart before the treatment, compared to one or more control individuals with similar disease without treatment, or compared to treatment with an AC not conjugated to a cyclic CPP disclosed herein.

In some embodiments, treatment according to the present disclosure results in decreased expression of a target protein in a subject's heart by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject's heart before the treatment, compared to one or more control individuals with similar disease without treatment, or compared to treatment with an AC not conjugated to a cyclic CPP disclosed herein.

In some embodiments, treatment according to the present disclosure results in increased expression of a re-spliced target protein in a subject's heart by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 350%, about 400%, about 450%, about 500%, about 550%, about 600%, about 650%, about 700%, about 750%, about 800, about 850%, about 900%, about 950%, or about 1000% or more, as compared to the average level of the target protein in the subject's heart before the treatment, compared to one or more control individuals with similar disease without treatment, or compared to treatment with an AC not conjugated to a cyclic CPP disclosed herein.

In some embodiments, treatment according to the present disclosure results in increased or decreased expression of a wild type target protein isomer in a subject by more than about 5%, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%, as compared to the average level of the target protein in the subject's heart before the treatment, compared to one or more control individuals with similar disease without treatment, or compared to treatment with an AC not conjugated to a cyclic CPP disclosed herein.

The terms, "improve," "increase," "reduce," "decrease," and the like, as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with the same disease, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having a disease or having the potential to develop a disease. The individual may have a disease mediated by aberrant gene expression or aberrant gene splicing. In various embodiments, the individual having the disease may have wild type target protein expression or activity levels that are less than about 1-99% of normal protein expression or activity levels in an individual not afflicted with the disease. In some embodiments, the range includes, but is not limited to less than about 80-99%, less than about 65-80%, less than about 50-65%, less than about 30-50%, less than about 25-30%, less than about 20-25%, less than about 15-20%, less than about 10-15%, less than about 5-10%, less than about 1-5% of normal thymidine phosphorylase expression or activity levels. In some embodiments, the individual may have target protein expression or activity levels that are 1-500% higher than normal wild type target protein expression or activity levels. In some embodiments, the range includes, but is not limited to, greater than about 1-10%, about 10-50%, about 50-100%, about 100-200%, about 200-300%, about 300-400%, about 400-500%, or about 500-1000%.

In some embodiments, the individual is an individual who has been recently diagnosed with the disease. Typically, early treatment (treatment commencing as soon as possible after diagnosis) is important to minimize the effects of the disease and to maximize the benefits of treatment.

Methods of Making

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopentyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thioanisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

The above polymers, such as PEG groups, can be attached to the AC under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the AC (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., α-iodo acetic acid, α-bromoacetic acid, α-chloroacetic acid). If attached to the AC by reductive alkylation, the polymer selected should have a single reactive aldehyde so that the degree of polymerization is controlled. See, for example, Kinstler et al., Adv. Drug. Delivery Rev. 54: 477-485 (2002); Roberts et al., Adv. Drug Delivery Rev. 54: 459-476 (2002); and Zalipsky et al., Adv. Drug Delivery Rev. 16: 157-182 (1995).

In order to direct covalently link the AC to the CPP, appropriate amino acid residues of the CPP may be reacted with an organic derivatizing agent that is capable of reacting with a selected side chain or the N- or C-termini of an amino acids. Reactive groups on the peptide or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art.

Methods of making AC and conjugating AC to linear CPP are generally described in US Pub. No. 2018/0298383, which is herein incorporated by reference for all purposes. The methods may be applied to the cyclic CPPs disclosed herein.

Synthetic schemes are provided in FIG. 7A-7D, FIG. 8, and FIG. 9

Non-limiting examples of CPPs containing reactive groups (e.g., TFP) for conjugation to an AC are shown below. Although each of the below examples contain CPP12, any CPP can be substituted for CPP12.

TFP-PEG-K(CPP12):

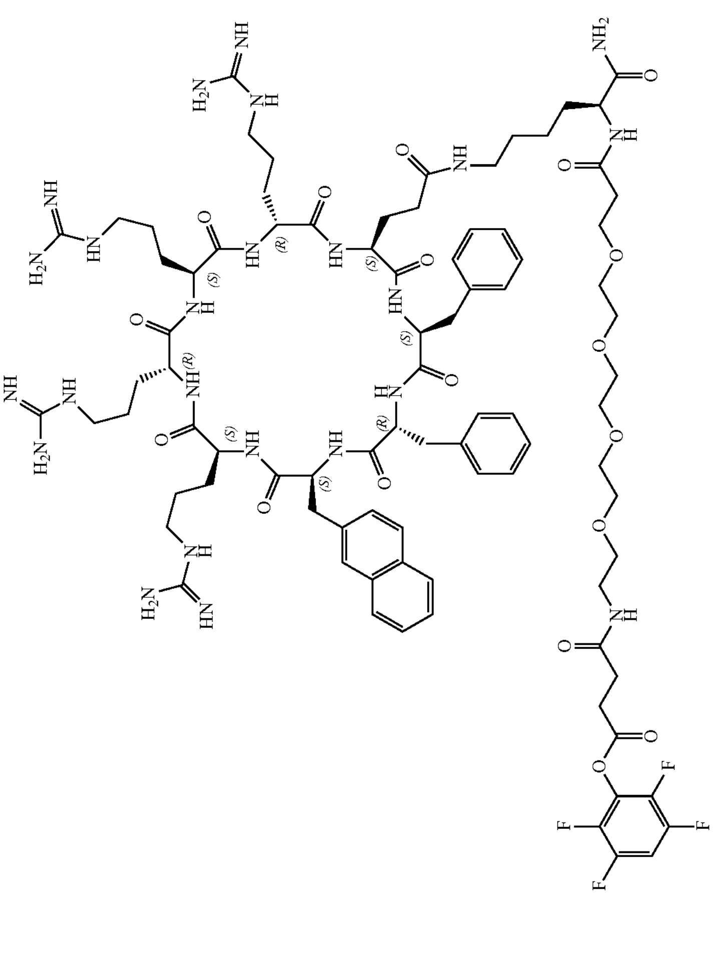
TFP-$PEG_4$-K(CPP12)-$PEG_4$-Dap(palmitoyl)

-continued
ala
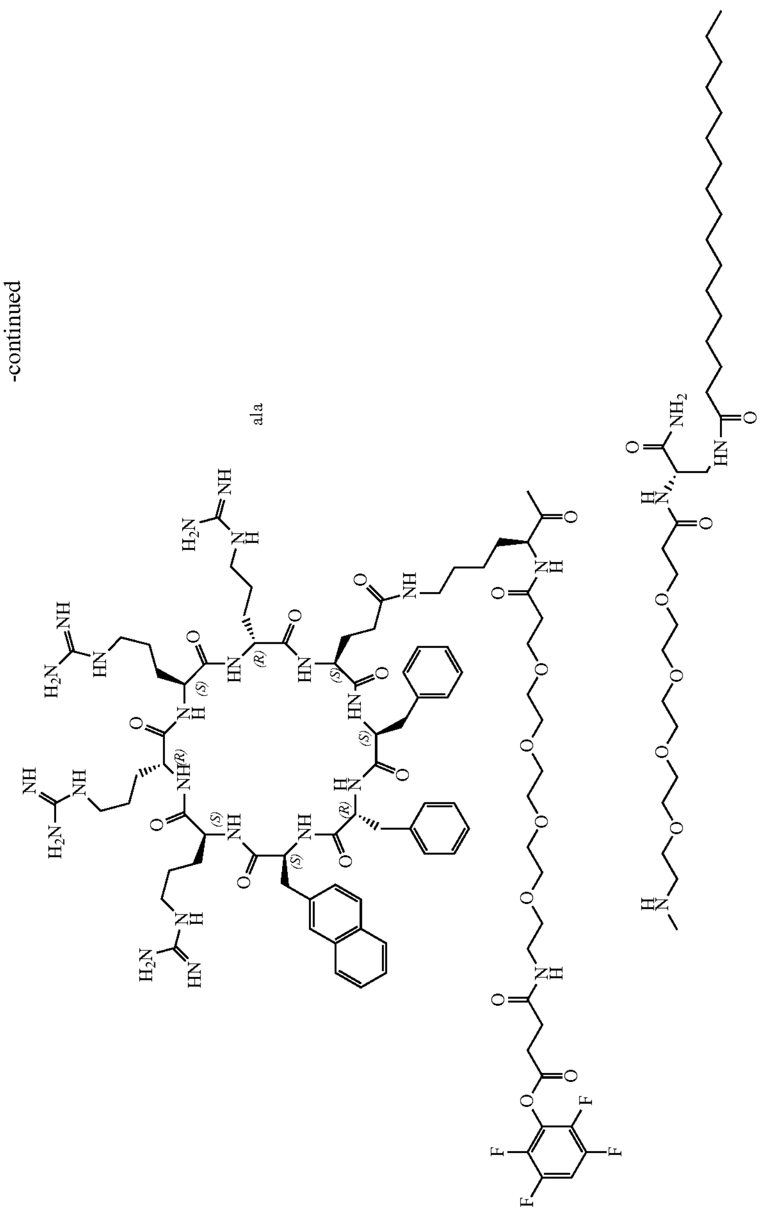
TFP-PEG$_4$-K(CPP12)-PEG$_4$-Dap(CPP12)

-continued
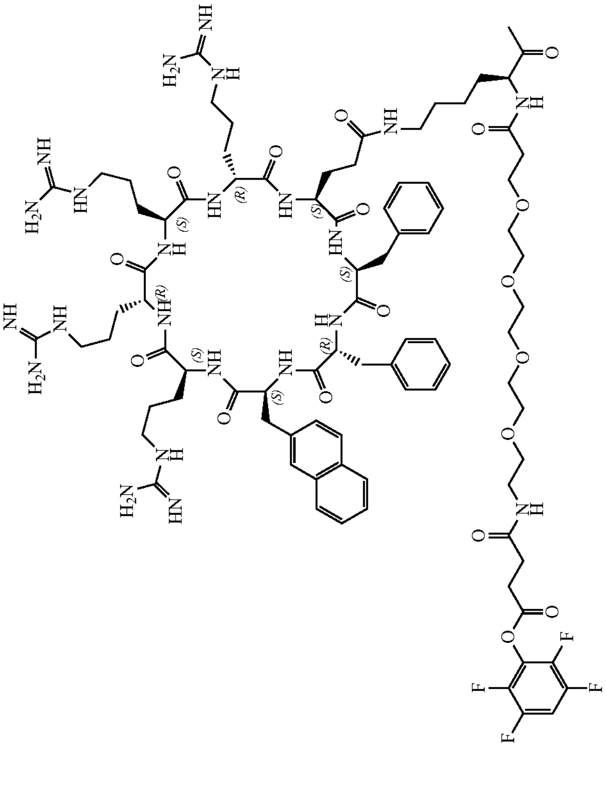
ala
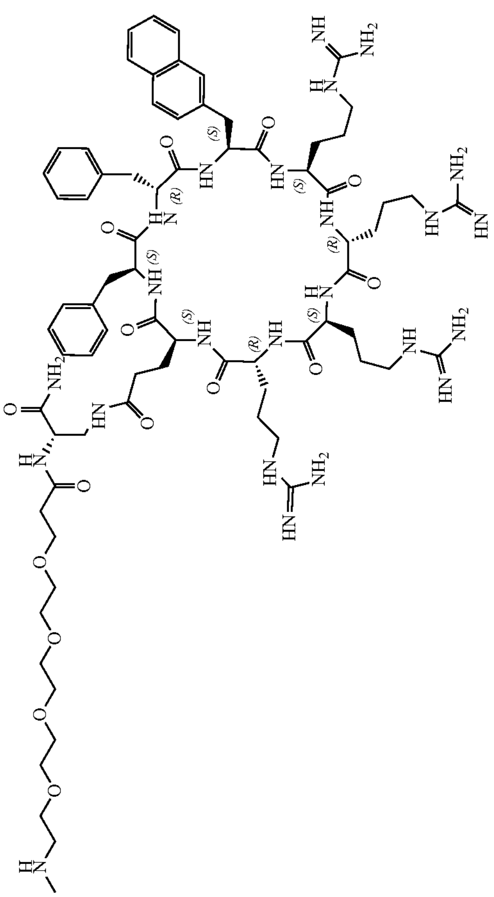
TFP-Pip6a

-continued
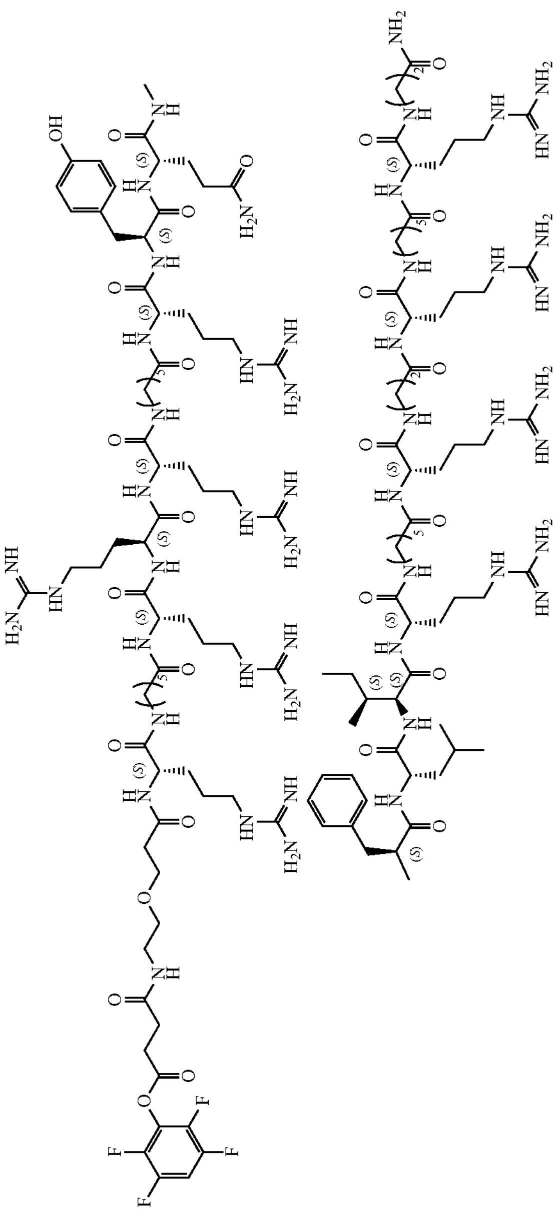
CPP12-PEG12-TFP

-continued
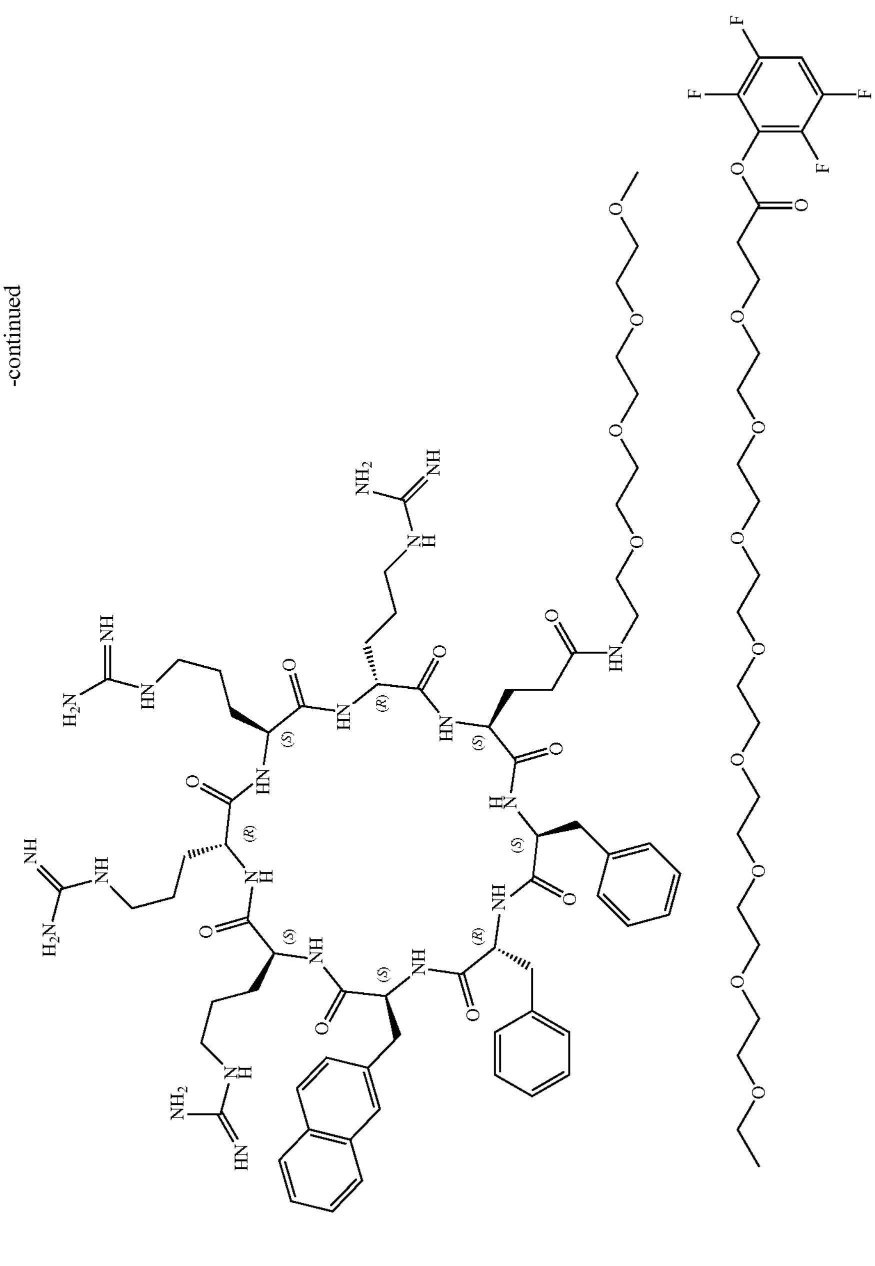
CPP12-PEG12-K(CPP12)-PEG12-TFP ETRD-peptide-344

-continued
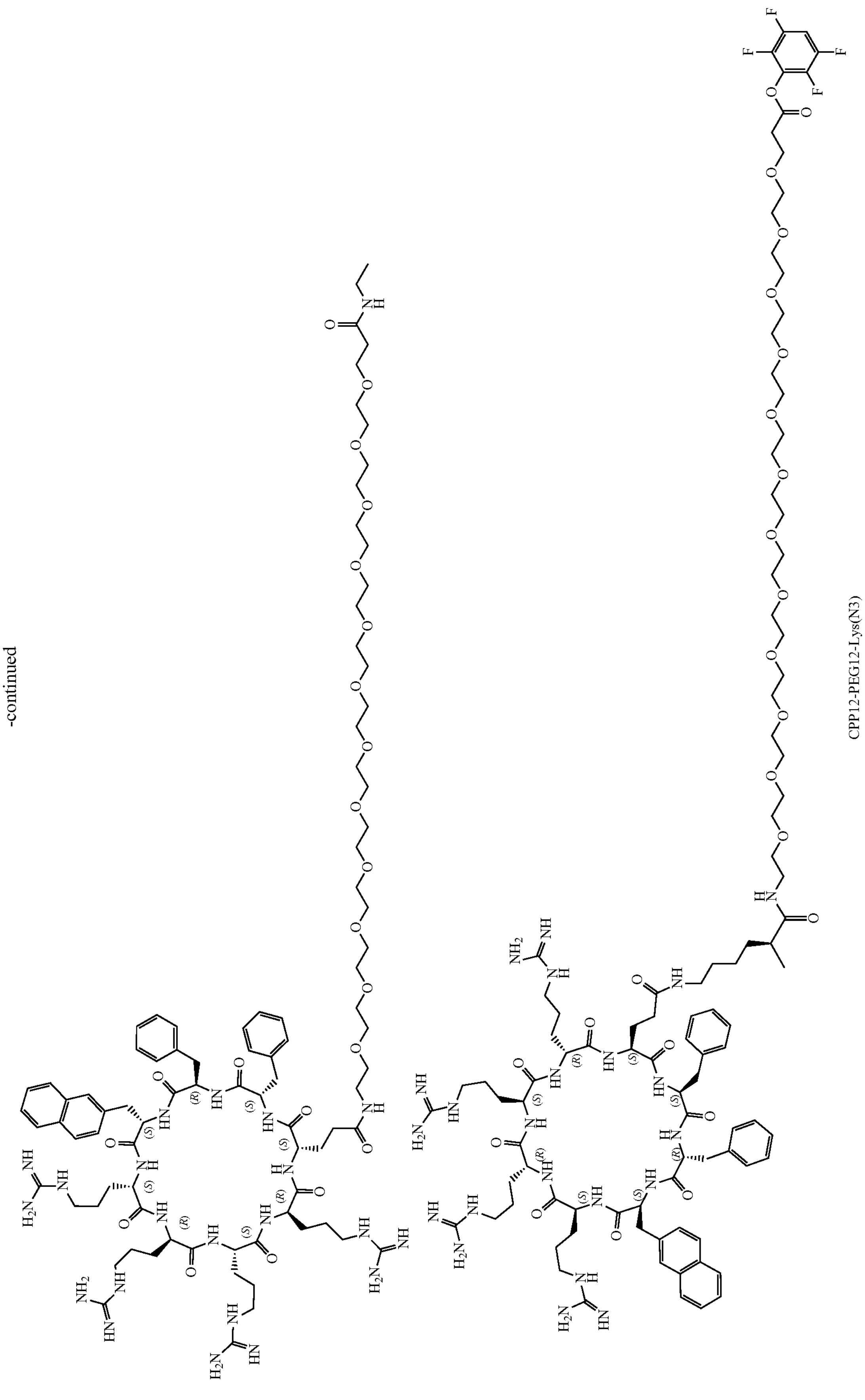
CPP12-PEG12-Lys(N3)

-continued
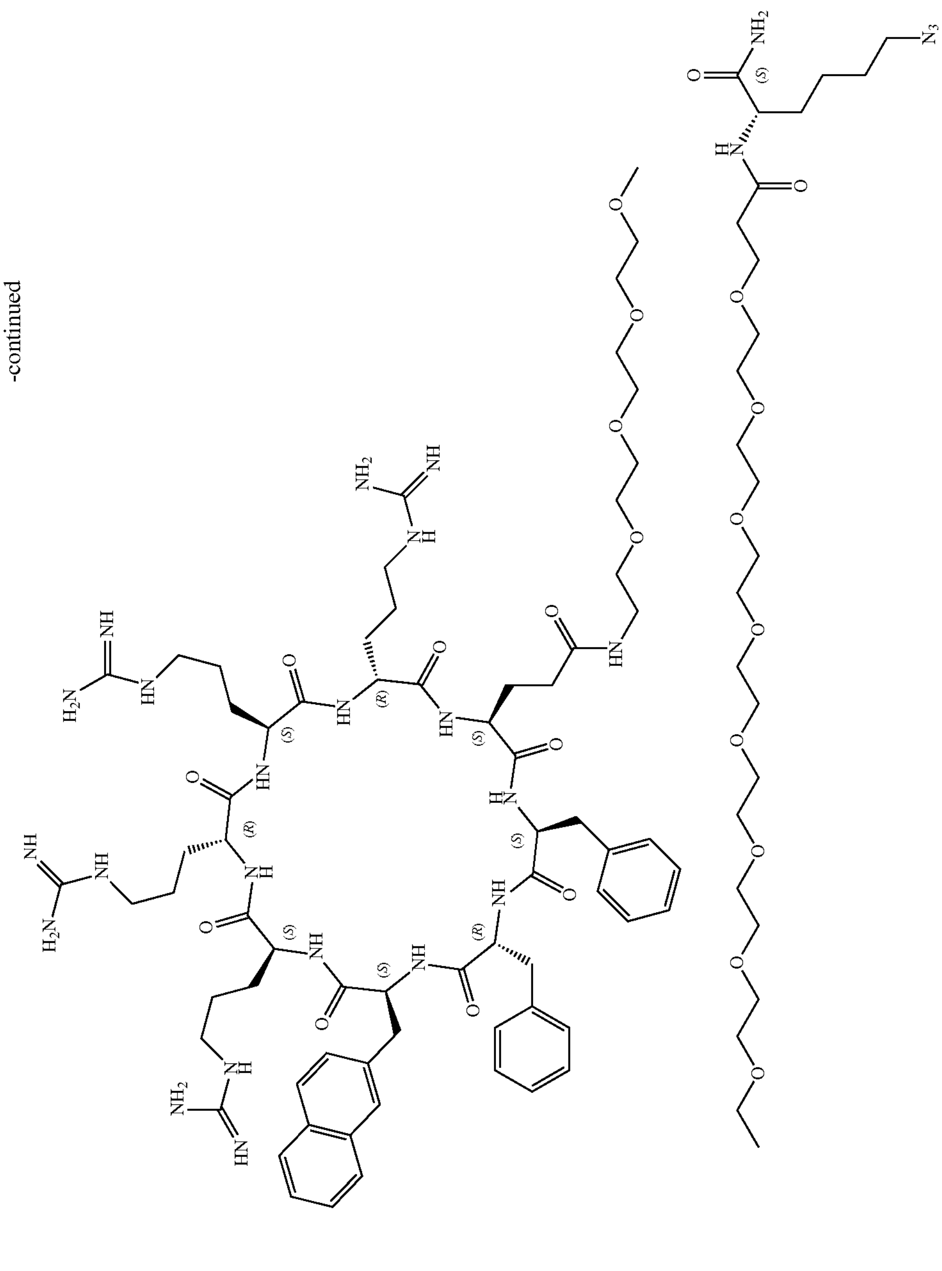
CPP-12-K(CPP12)-PEG12-K(N3)

-continued
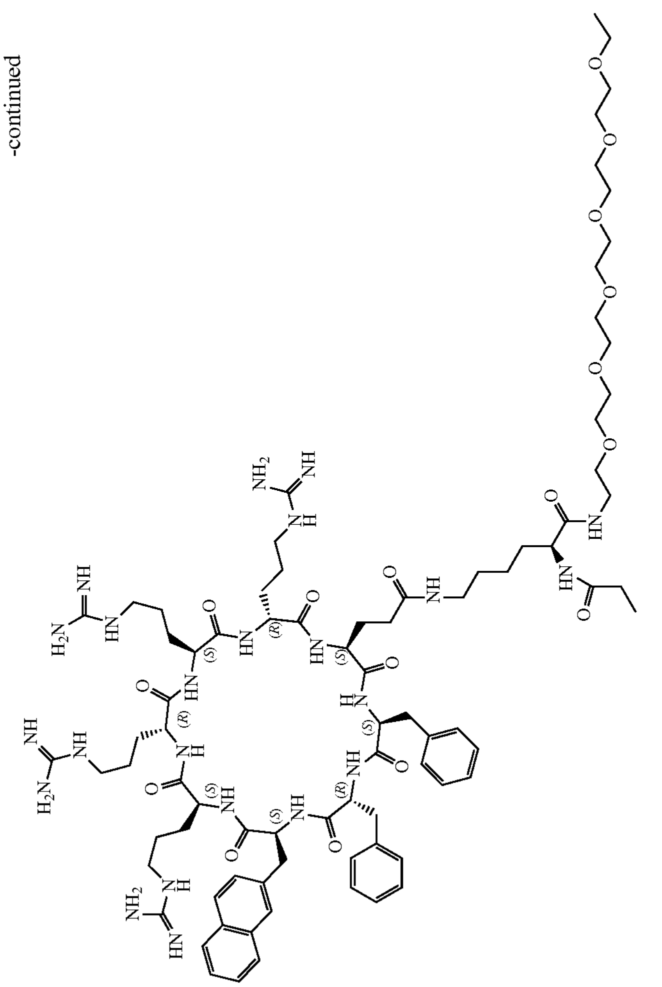

-continued
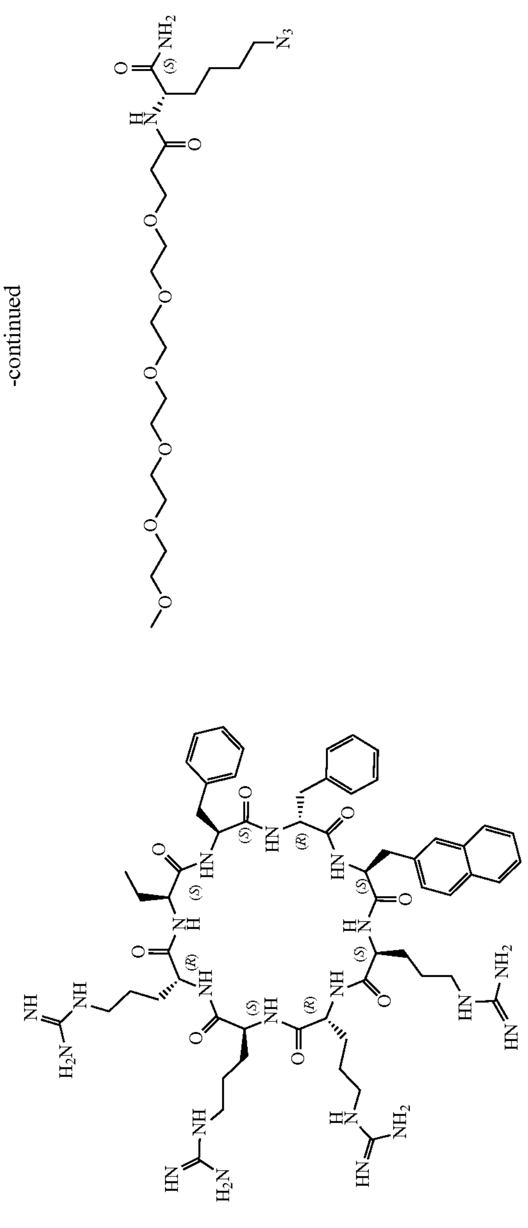
CPP12-PEG4-K(PEG4-CPP12)-PEG12-K(N3)

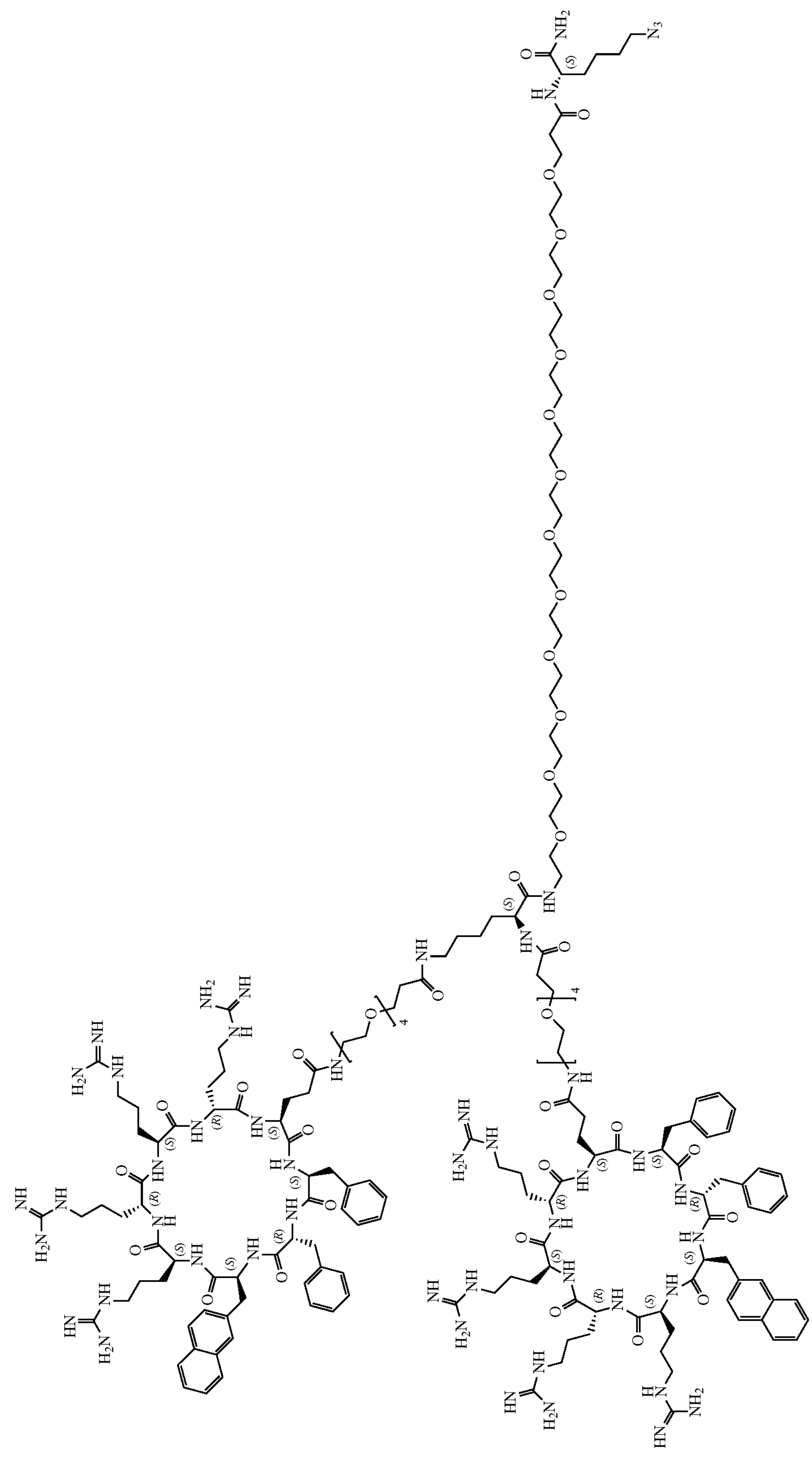
CPP12-PEG4-K(PEG4-CPP12)-PEG12-K(N3)

-continued
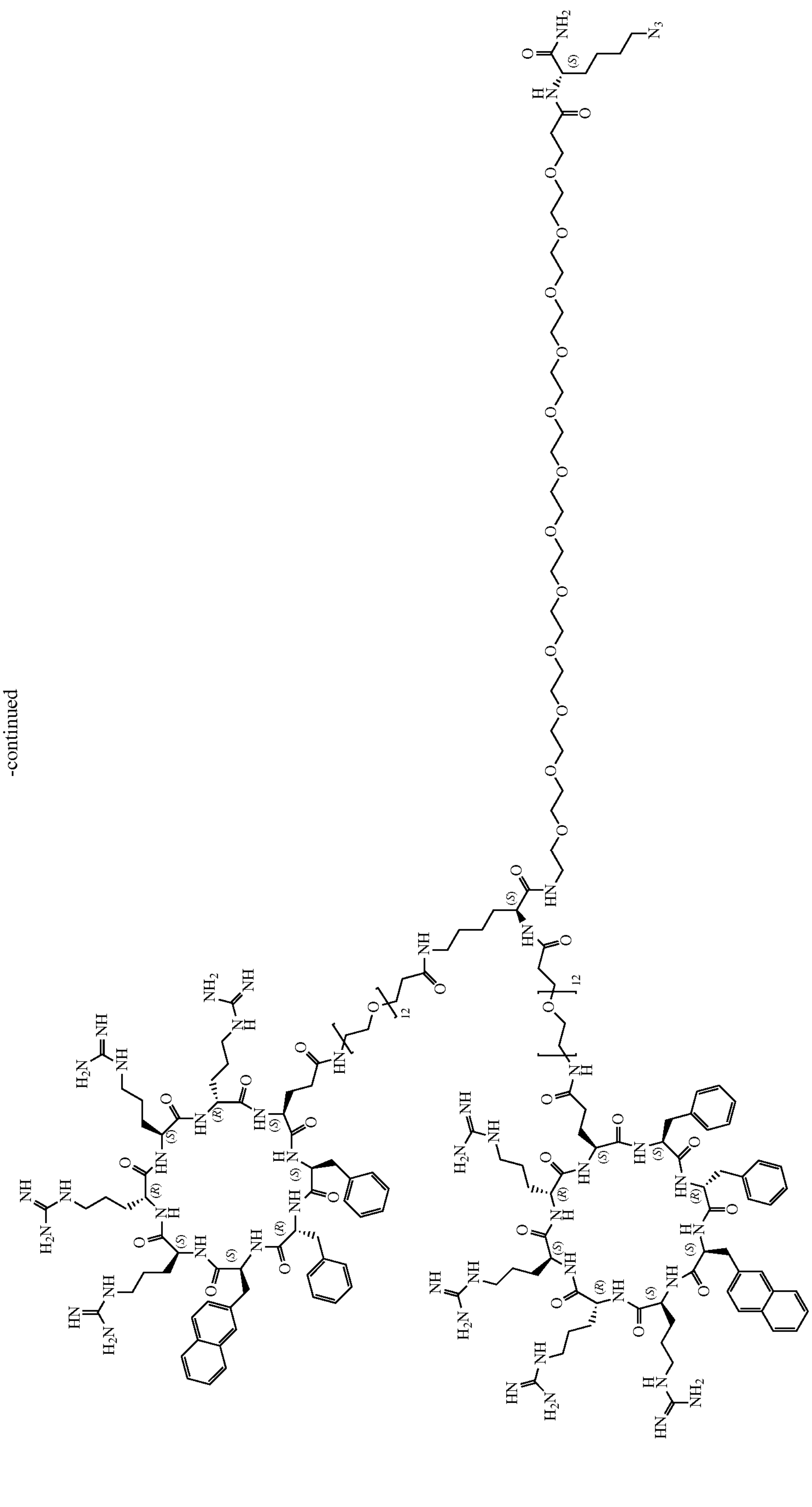
CPP12-PEG12-K(PEG12-CPP12)-PEG12-K(N3)

-continued
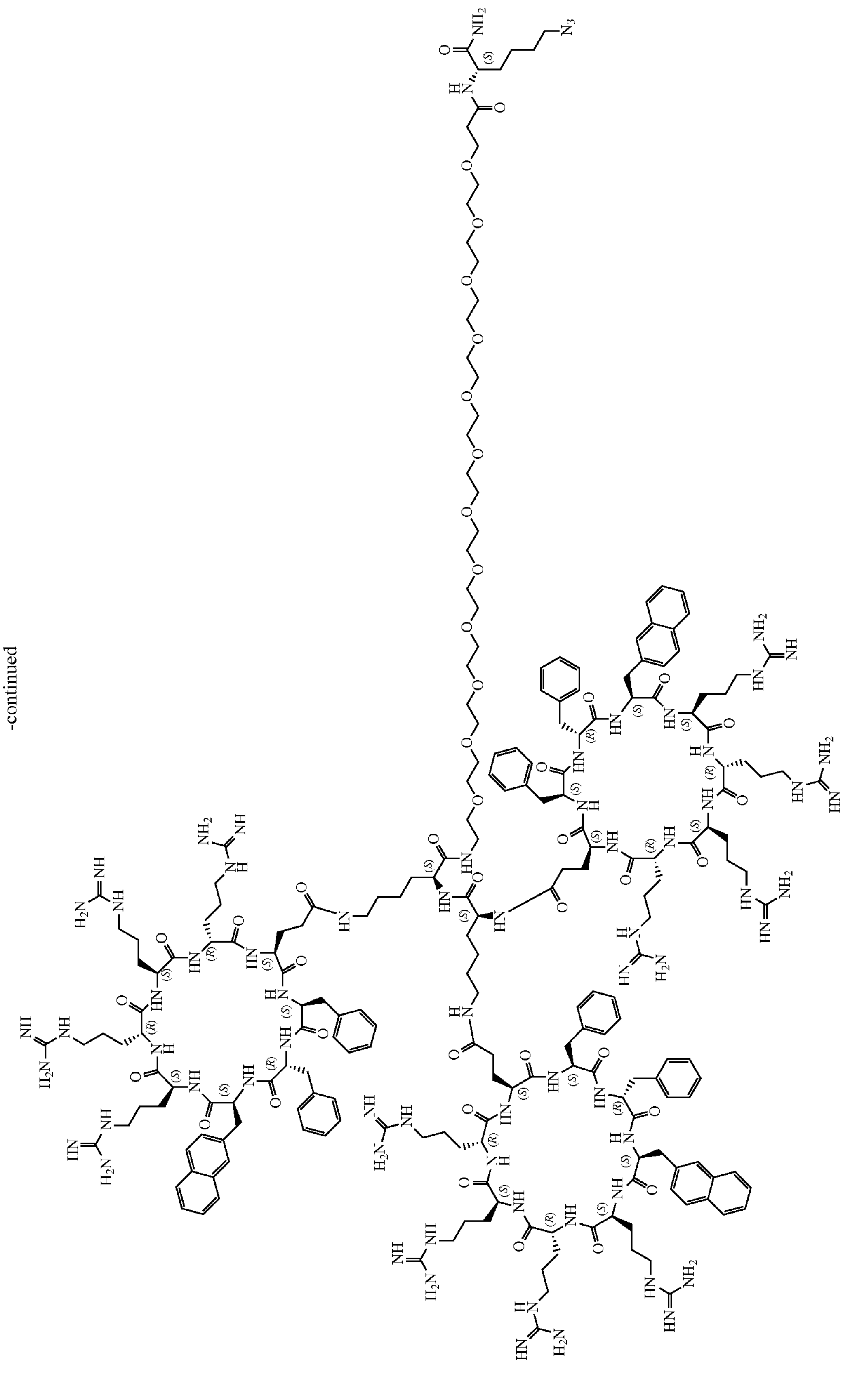
CPP12-K(CPP12)-K(CPP12)-PEG12-K(N3)

-continued
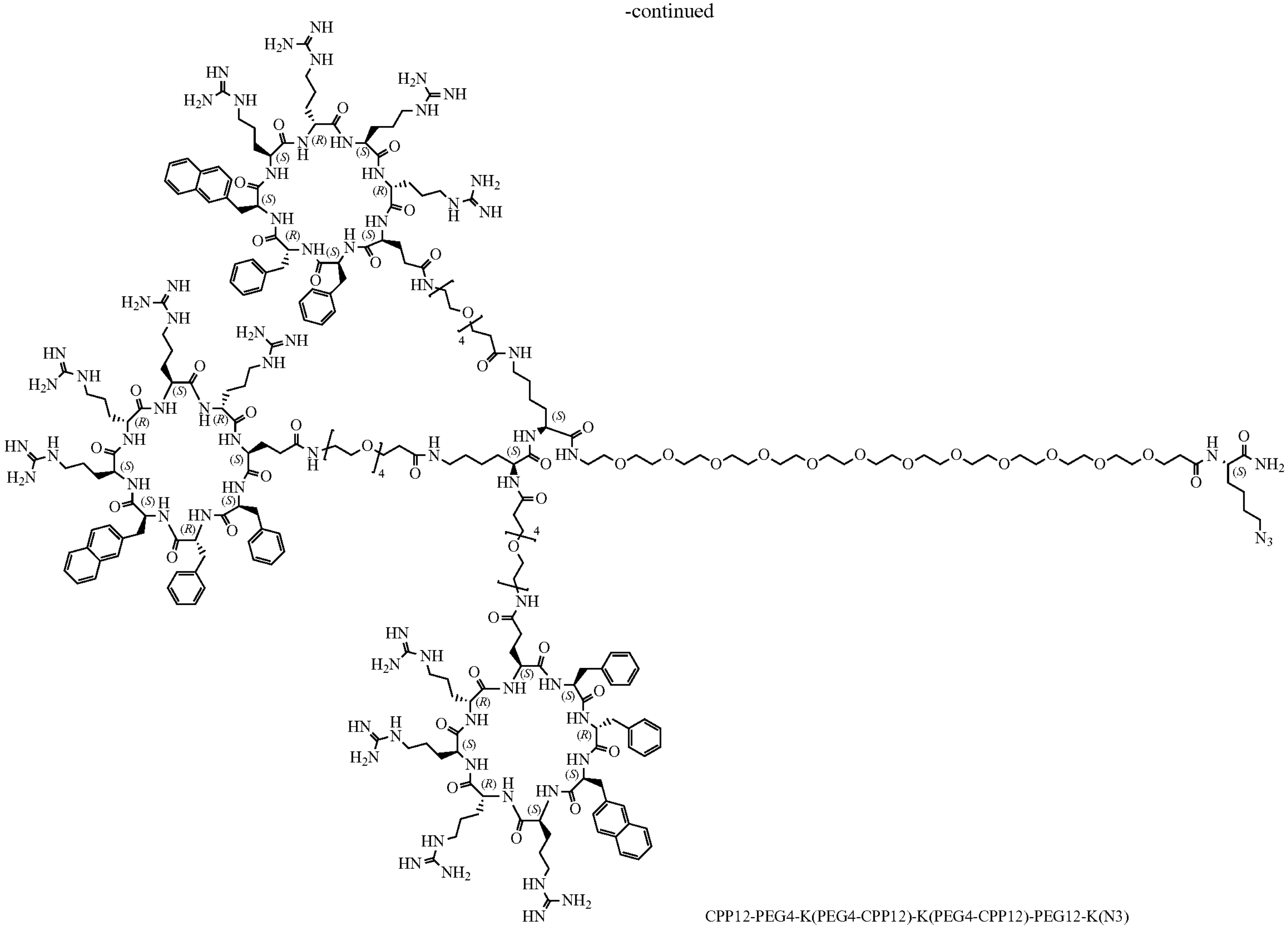
CPP12-PEG4-K(PEG4-CPP12)-K(PEG4-CPP12)-PEG12-K(N3)

-continued
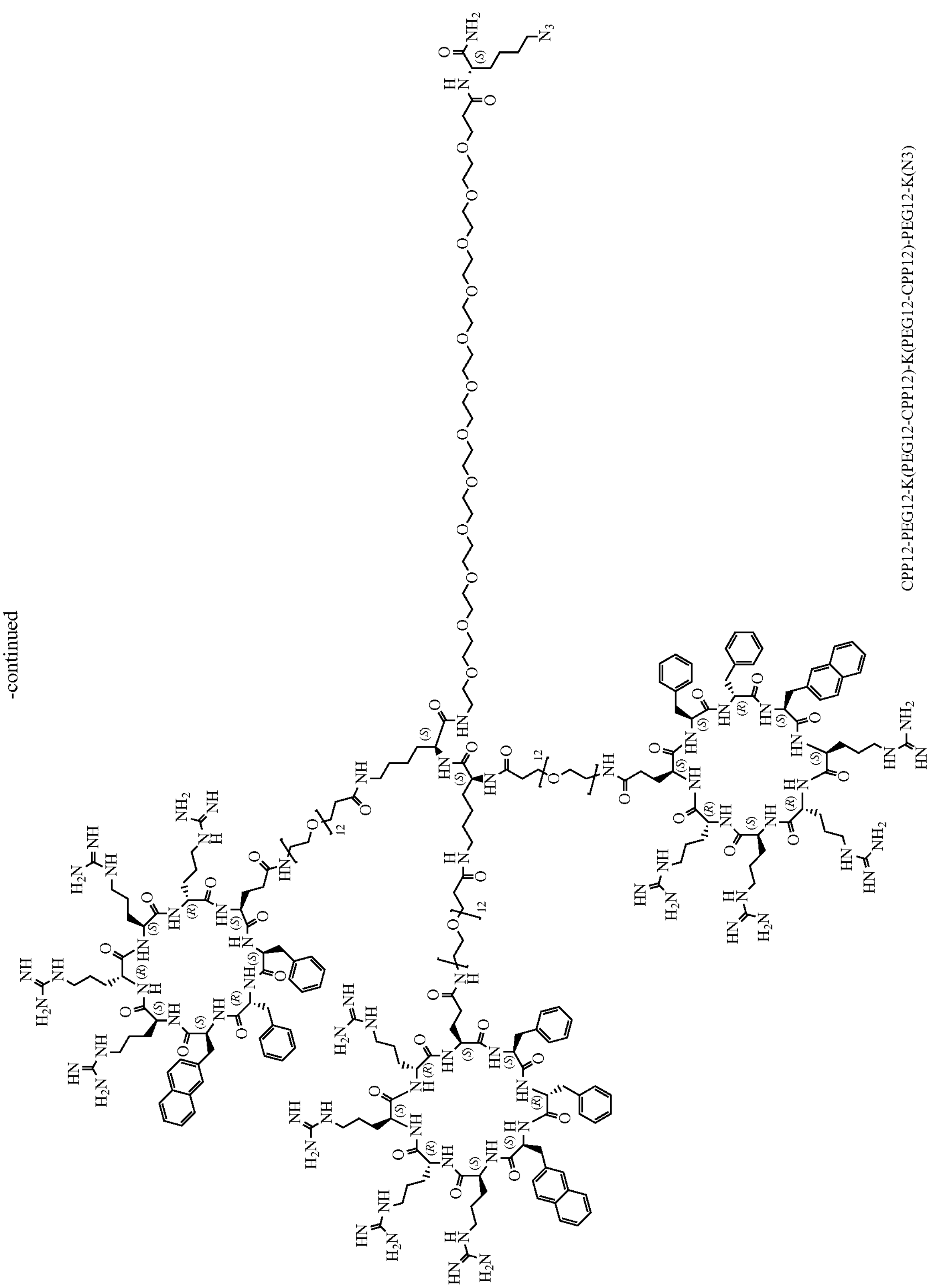
CPP12-PEG12-K(PEG12-CPP12)-K(PEG12-CPP12)-PEG12-K(N3)

-continued
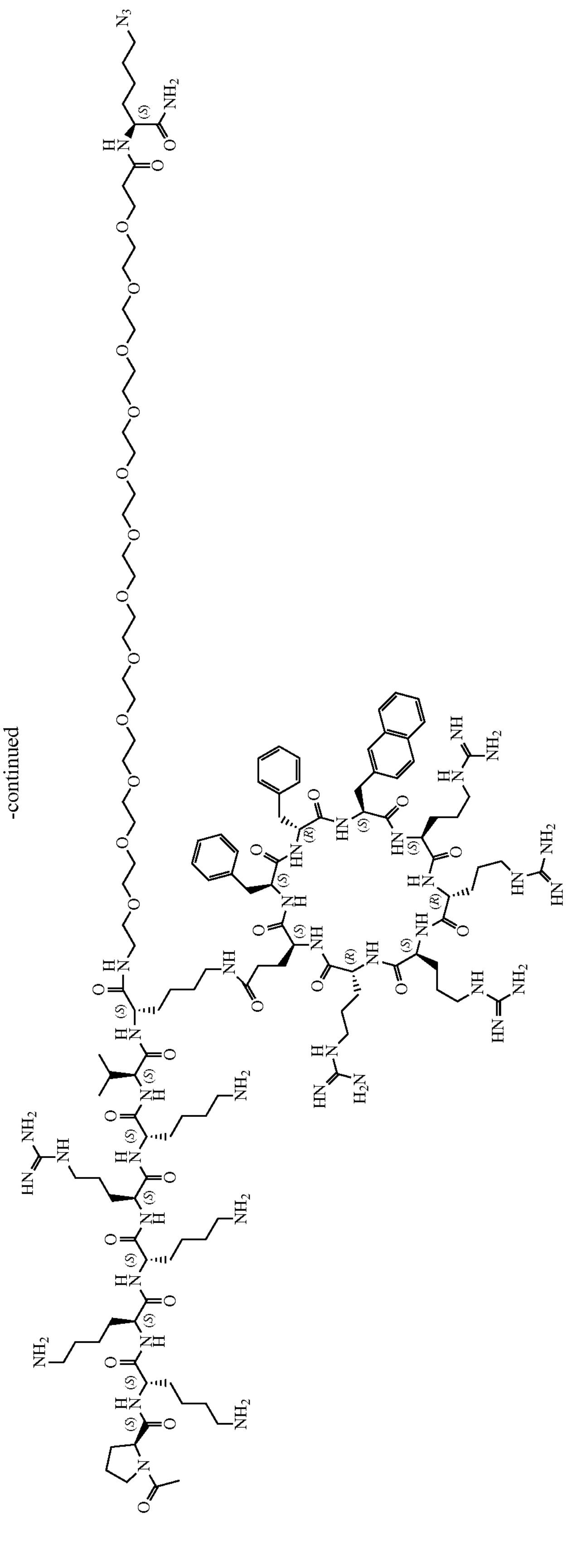
Ac-NLS-Lys(CPP12)-PEG12-K(N3)

-continued
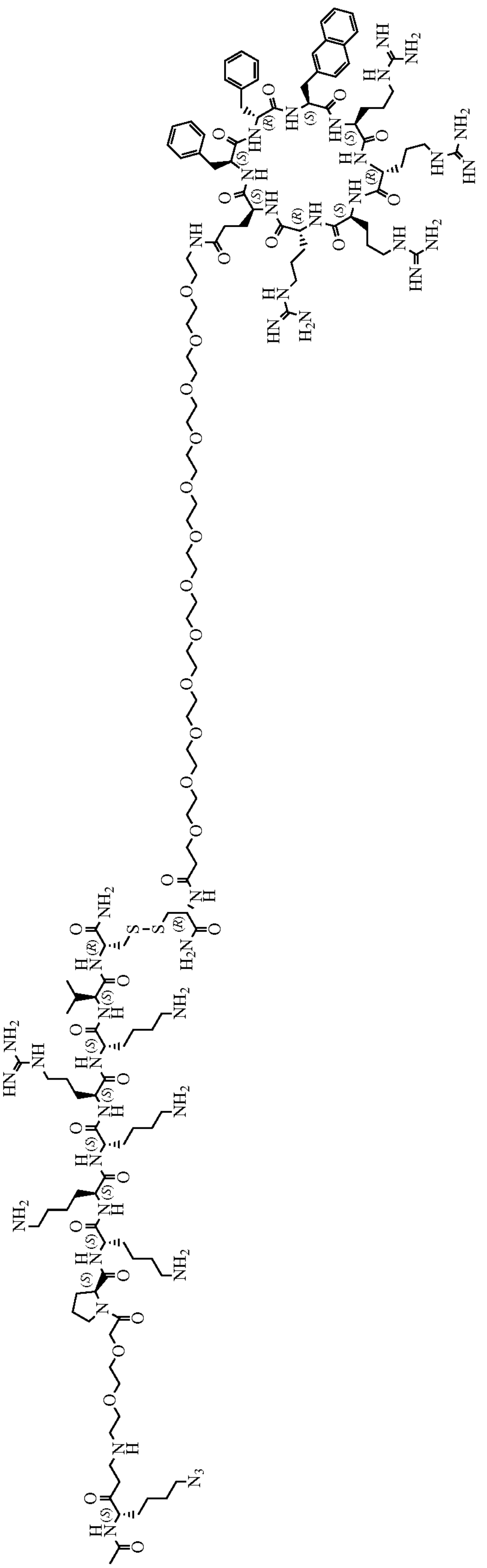
Lys(N3)-miniPEG-NLS-ss-PEG12-CPP12

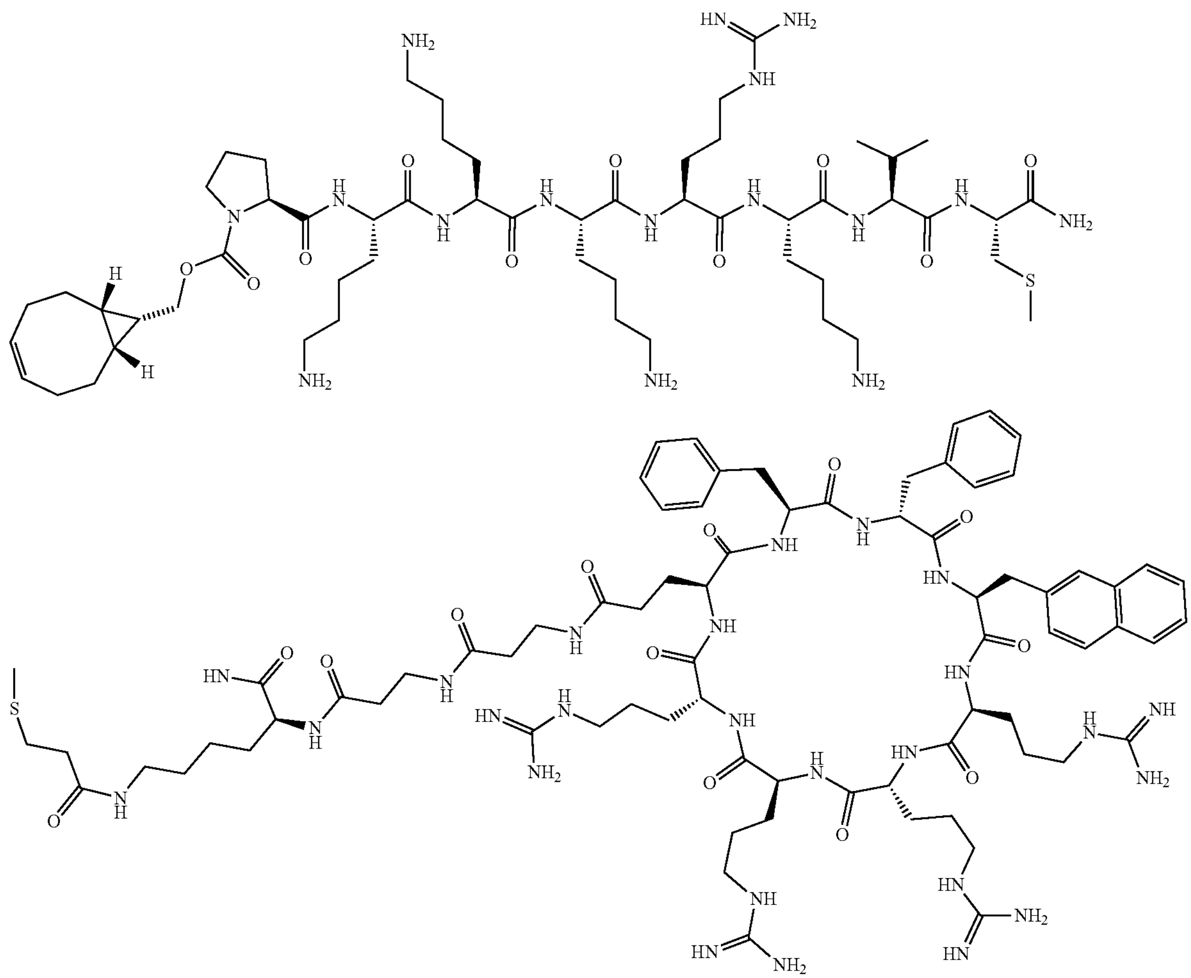
BCN-NLS-ss-CPP12
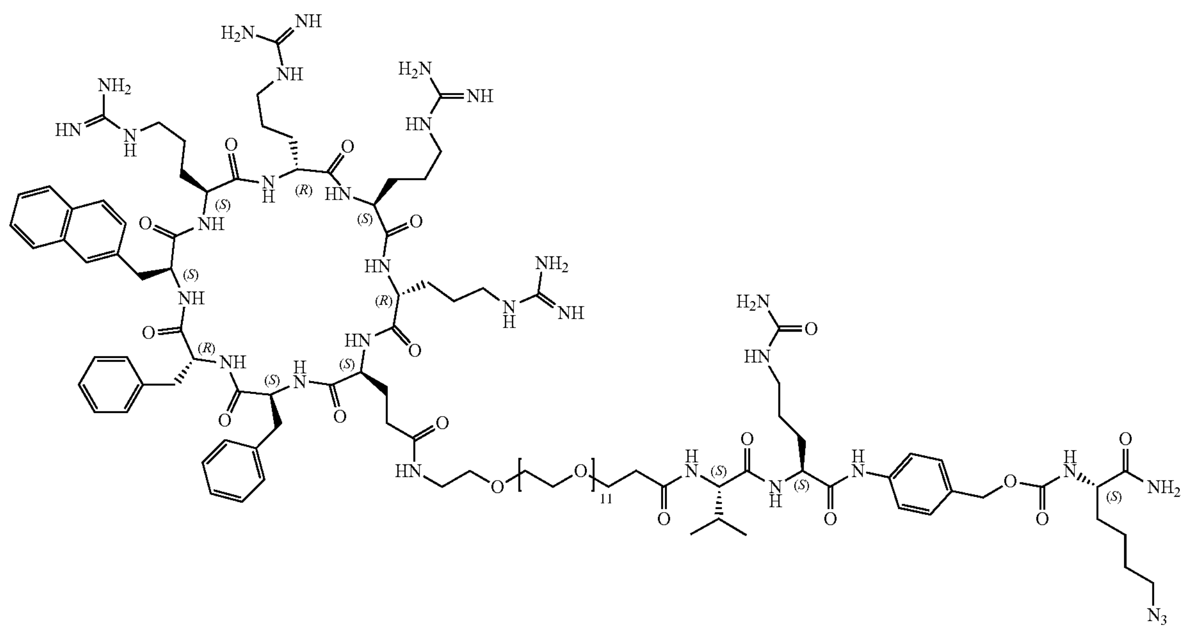
CPP12-PEG12-Val-Cit-PABC-Lys(N3)

-continued
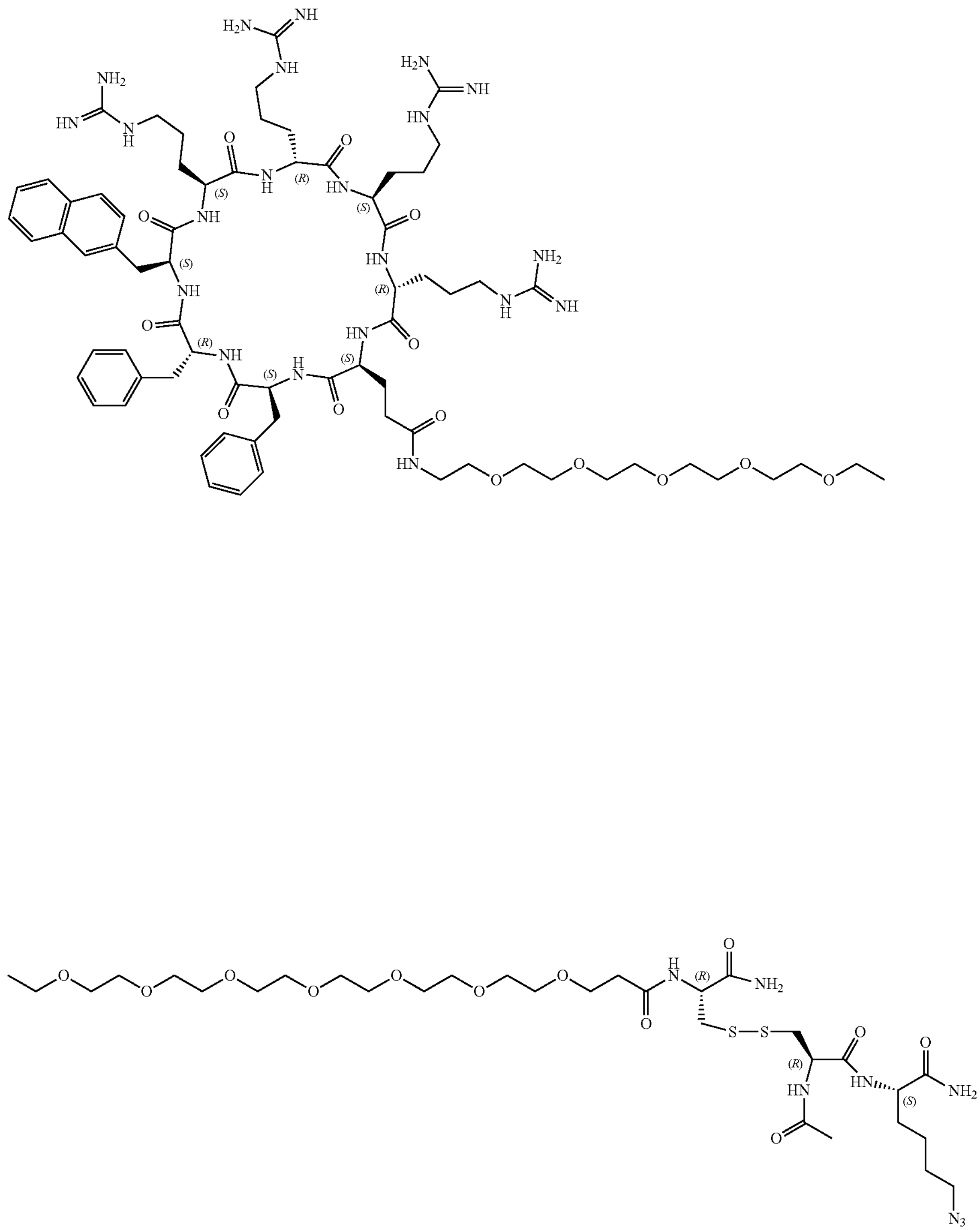
CPP12-PEG12-Cys-ss-Cys-Lys(N3)

-continued
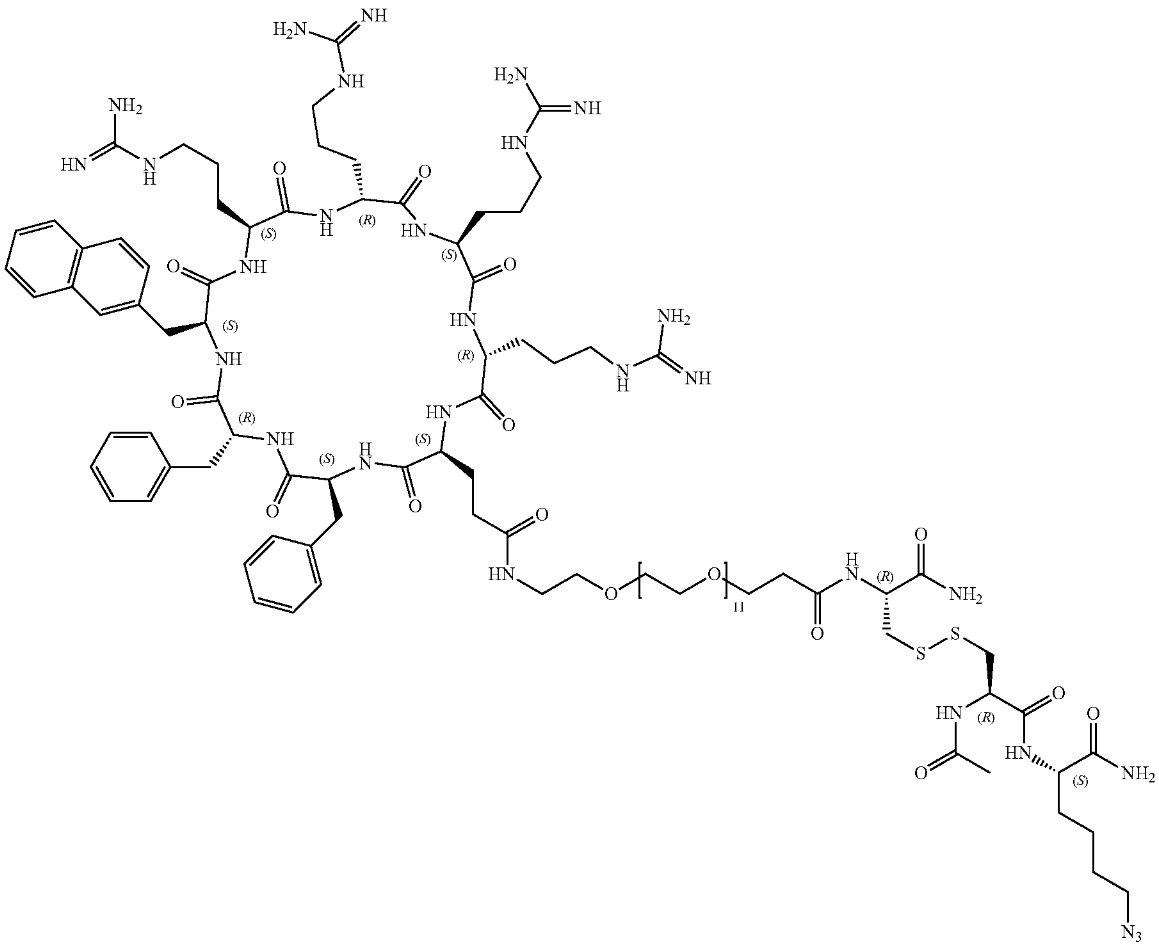
CPP12-PEG12-Cys-ss-Cys-Lys(N3)
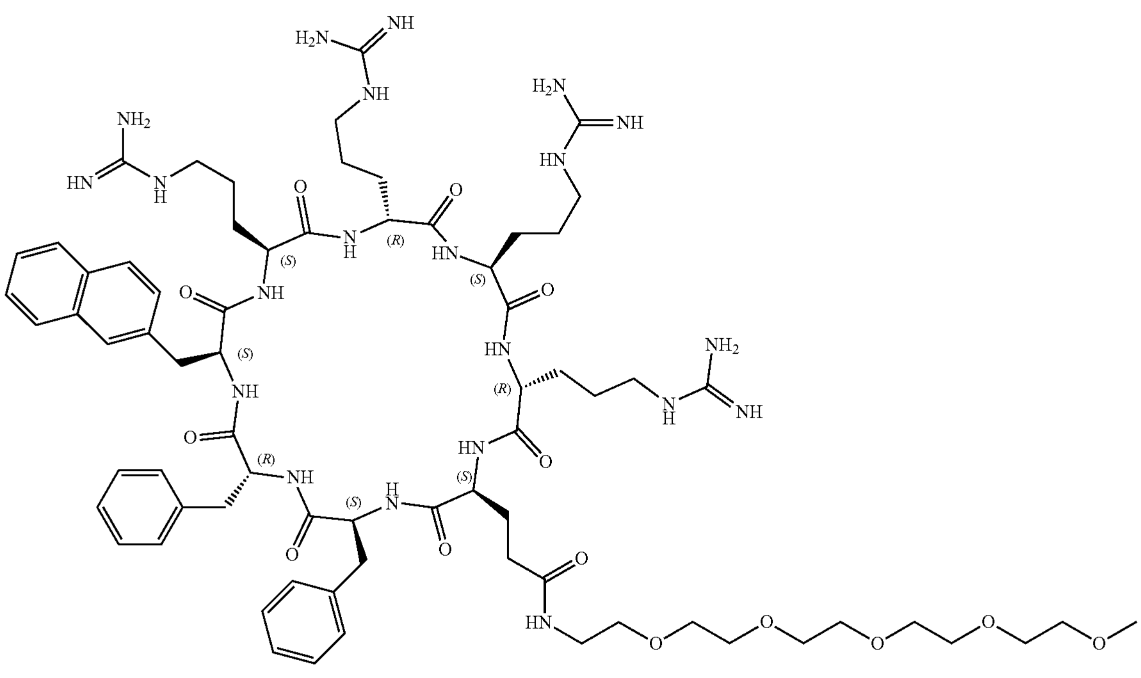

-continued
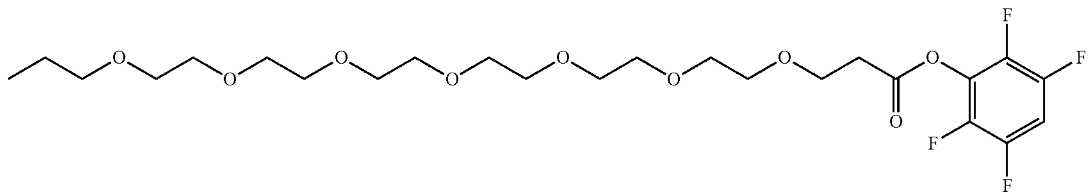
CPP12-PEG12-TFP ETRD802
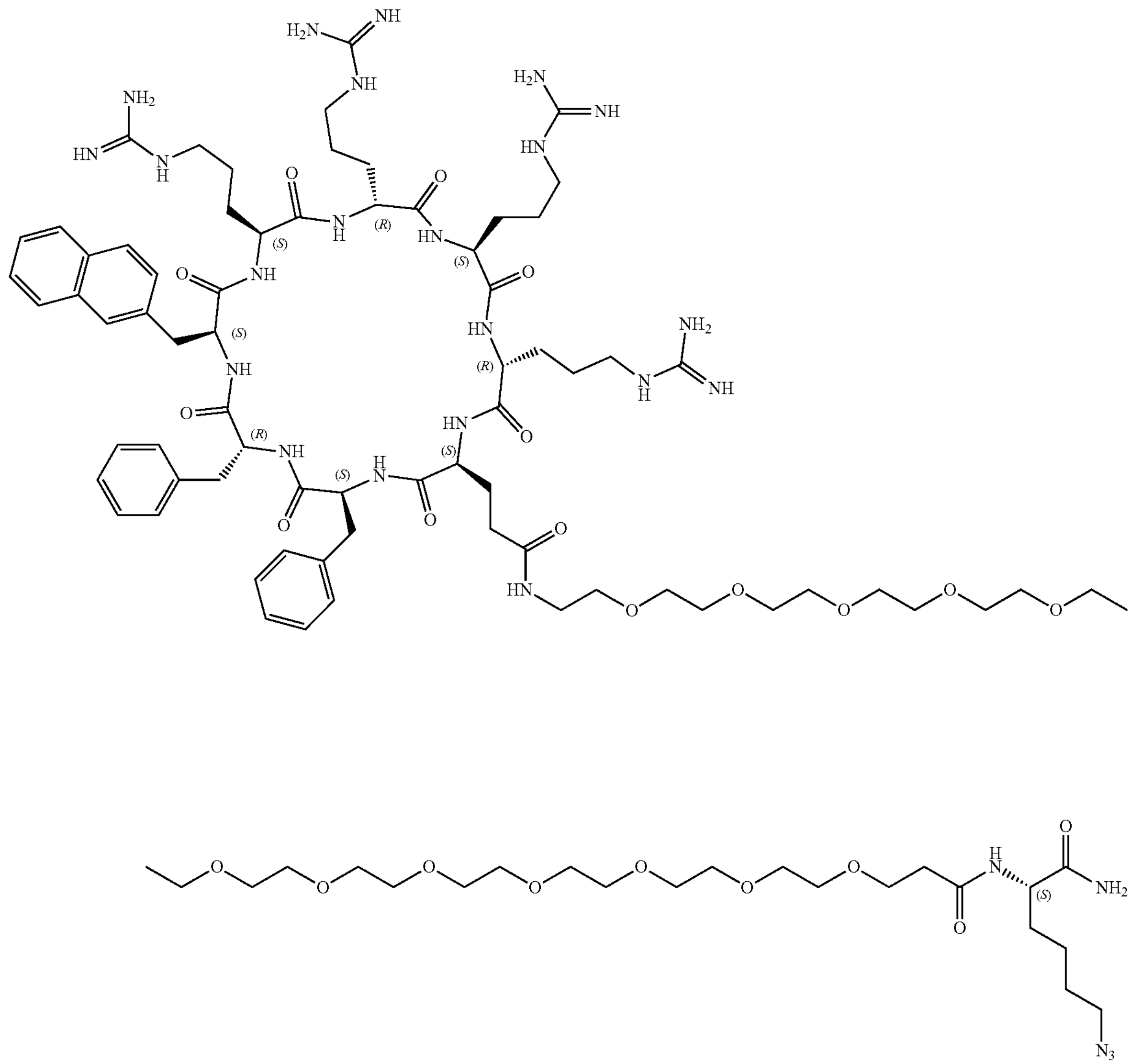
CPP12-PEG12-Lys(N3)

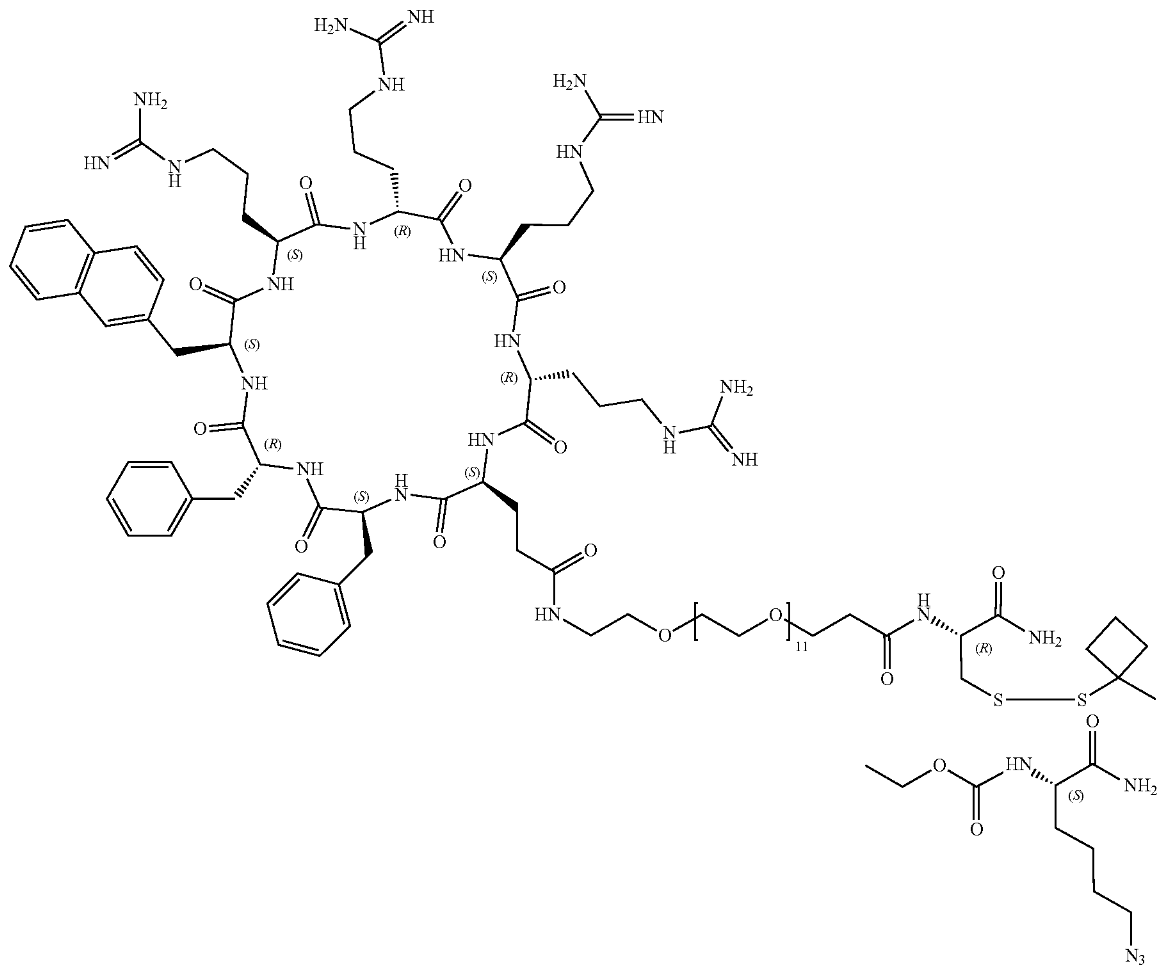
CPP12-PEG12-Cys-prodisulfide-Lys(N3)
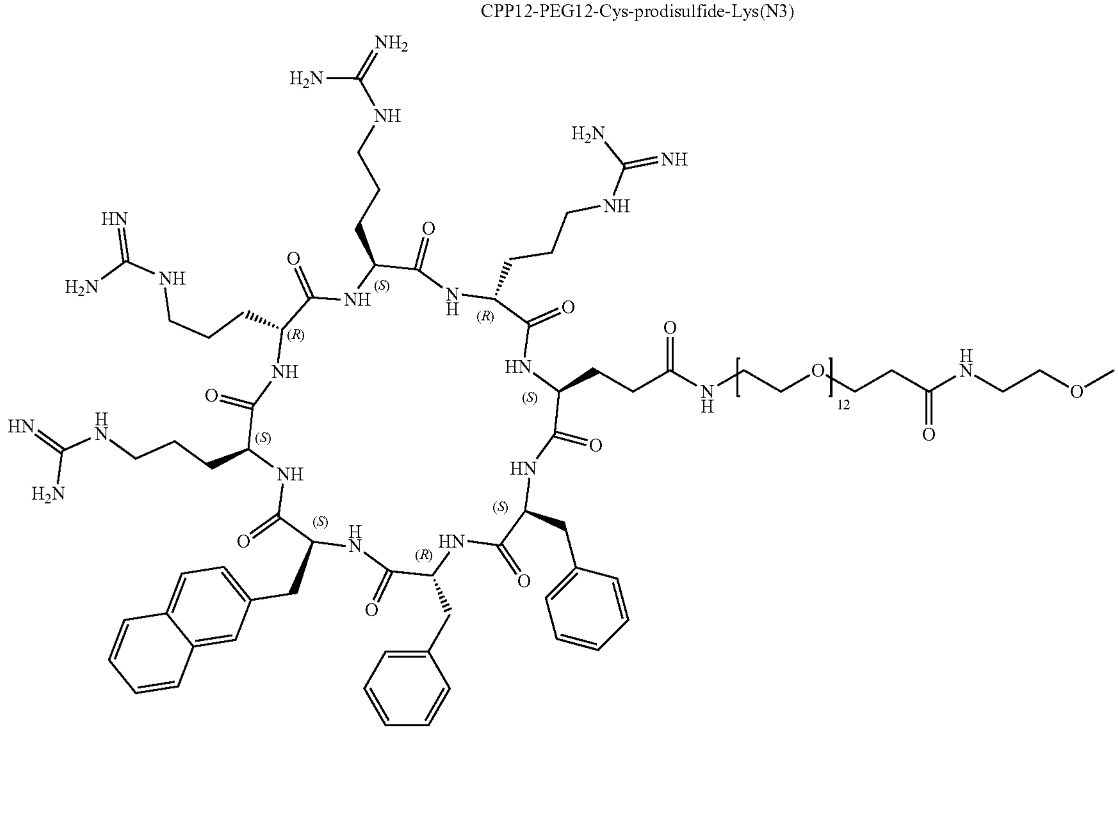

-continued
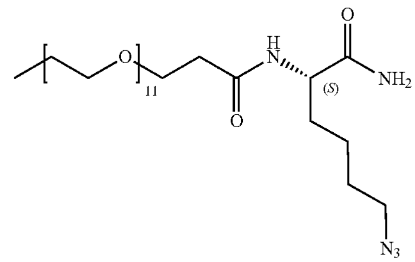
CPP12-PEG24-Lys(N3)
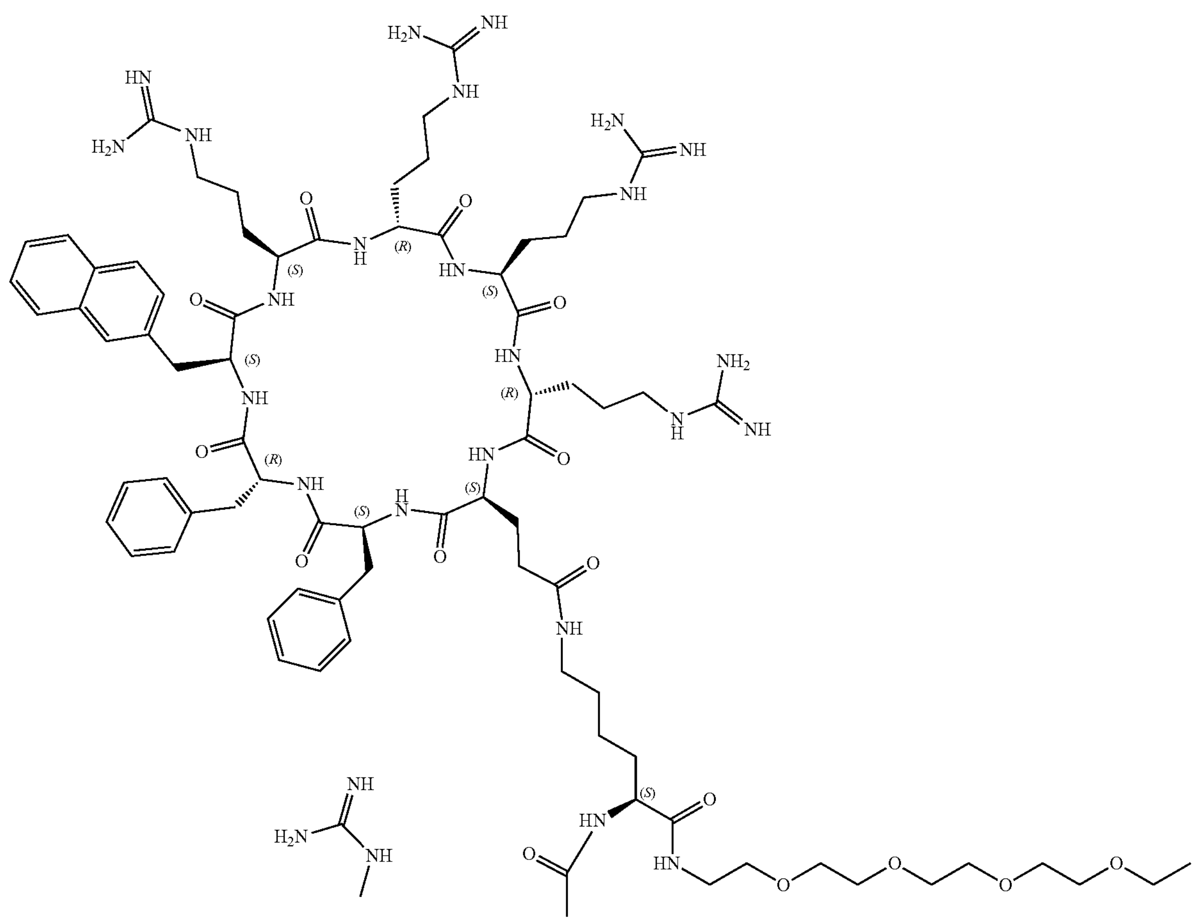

-continued
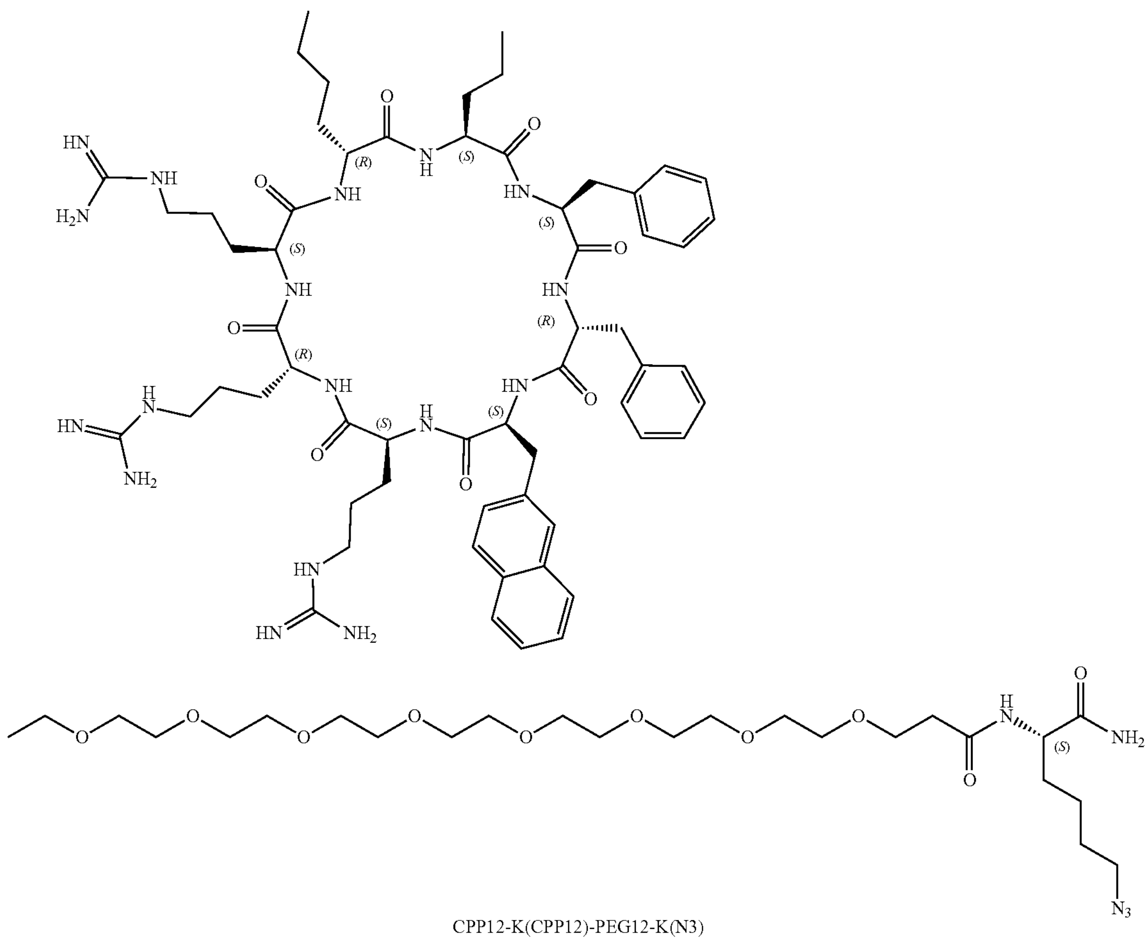
CPP12-K(CPP12)-PEG12-K(N3)
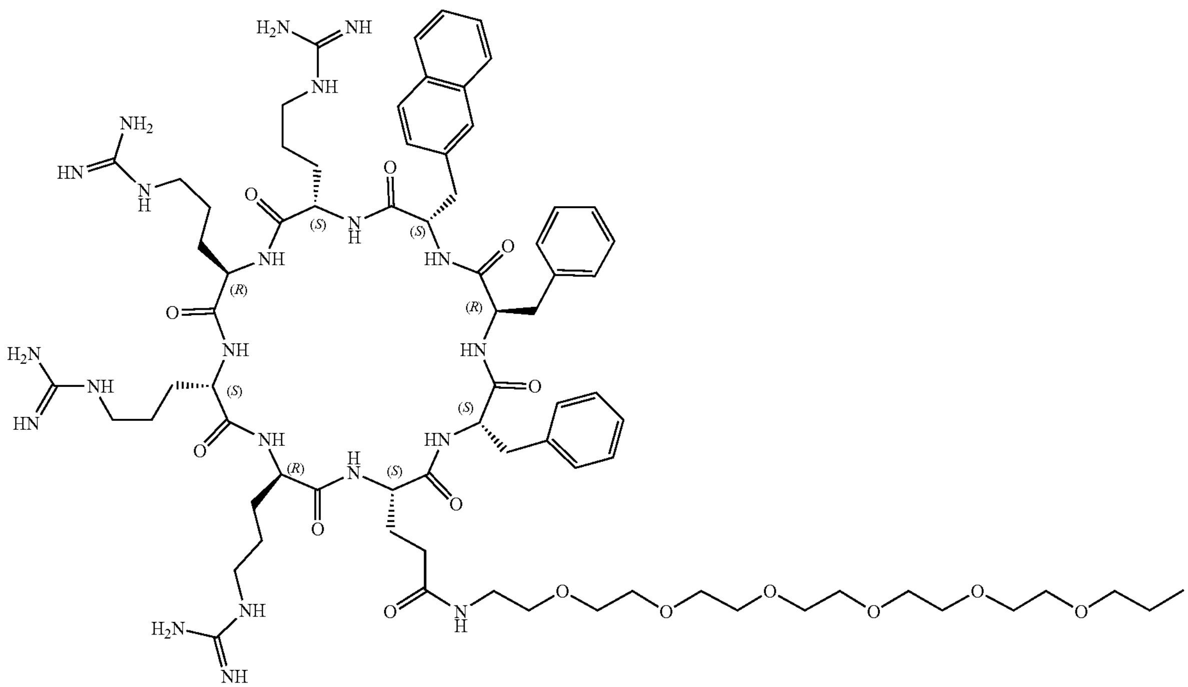

-continued
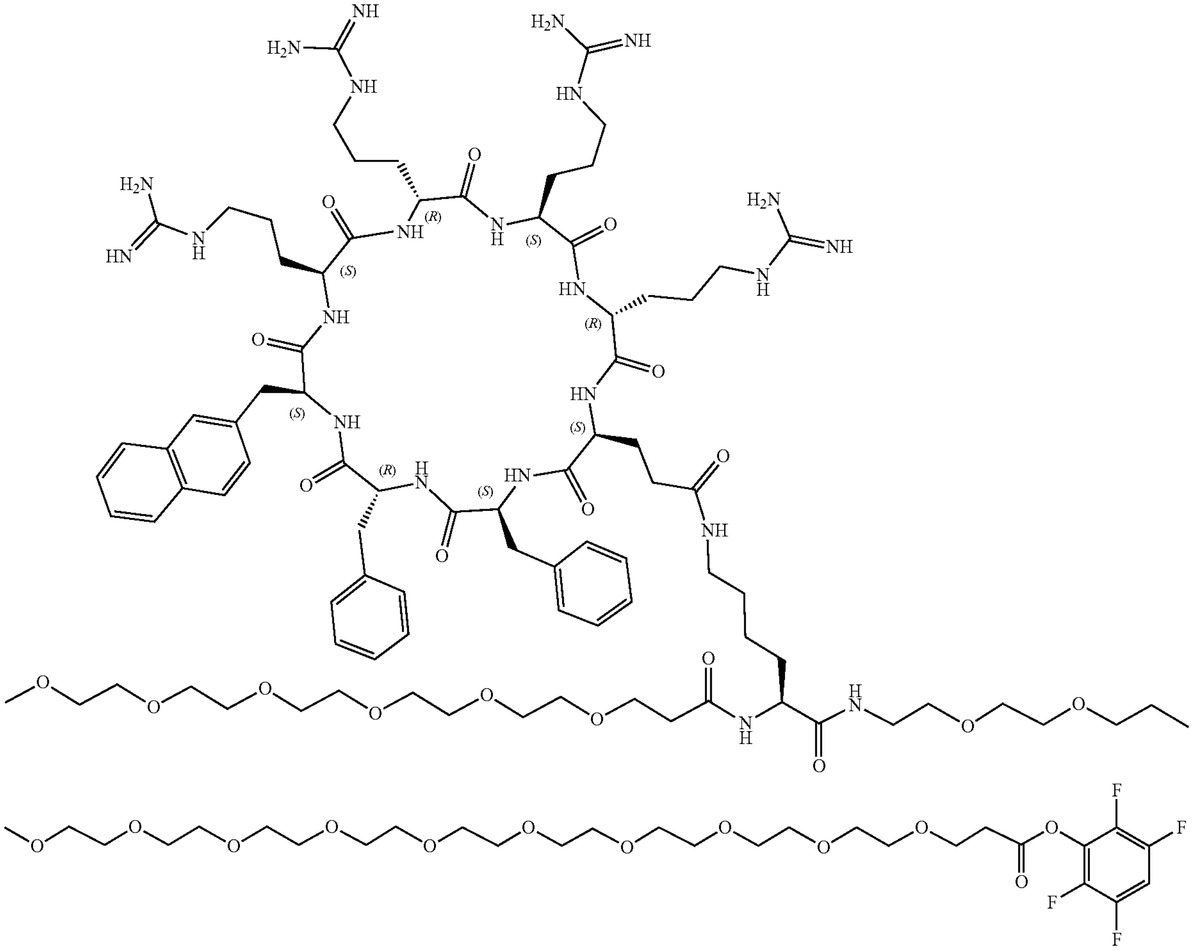
CPP12-PEG12-K(CPP12)-PEG12-TFP ETRD-344
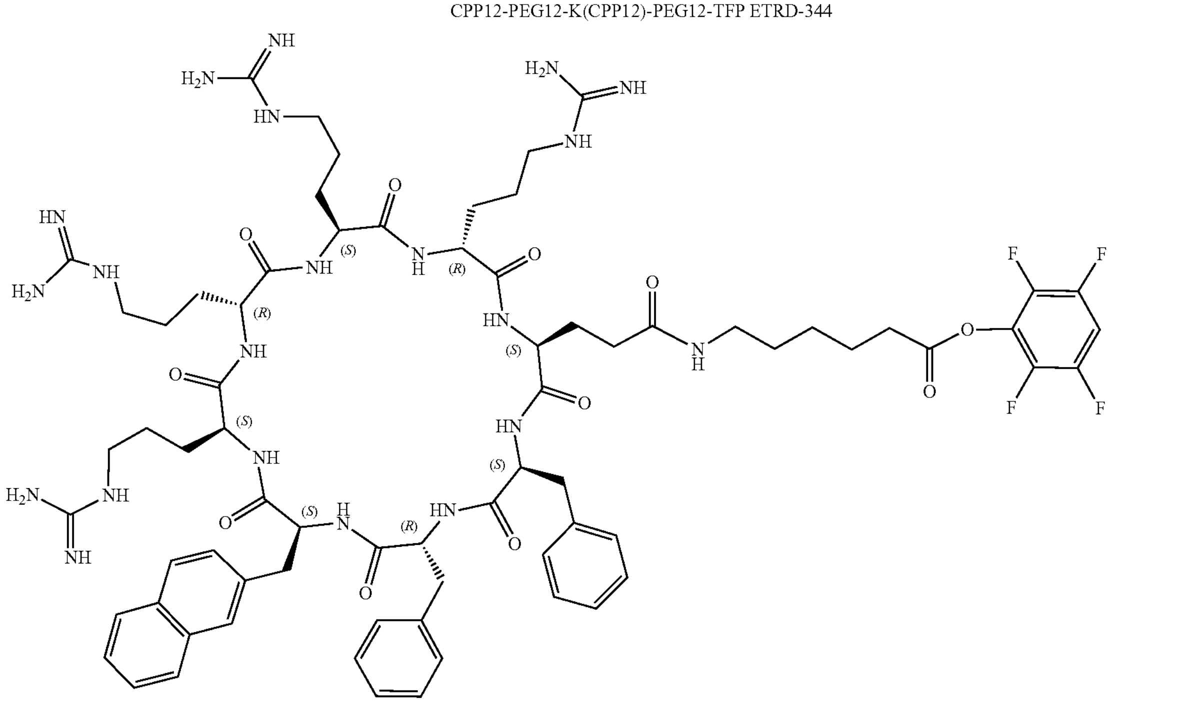
CPP12-C6-TFP -continued
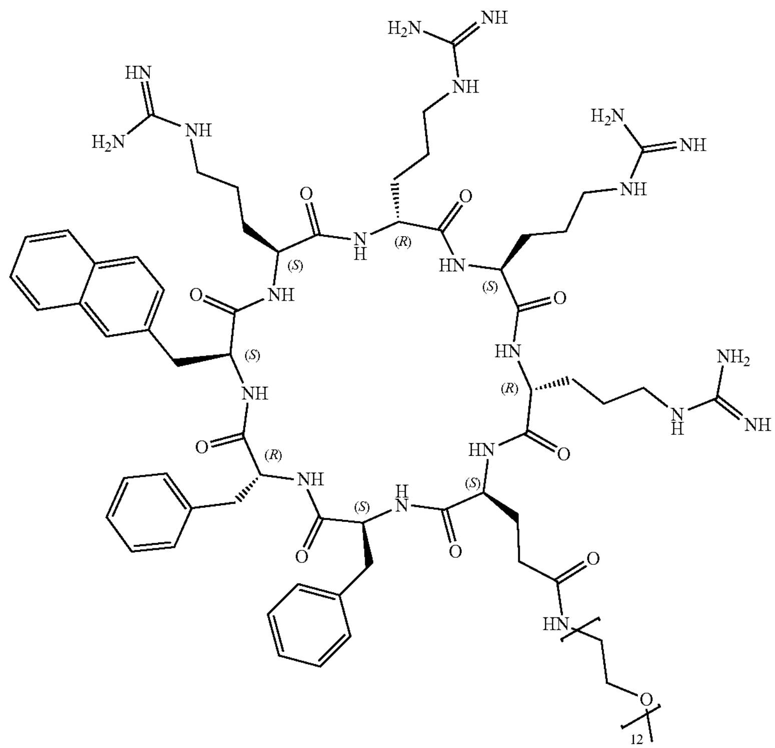
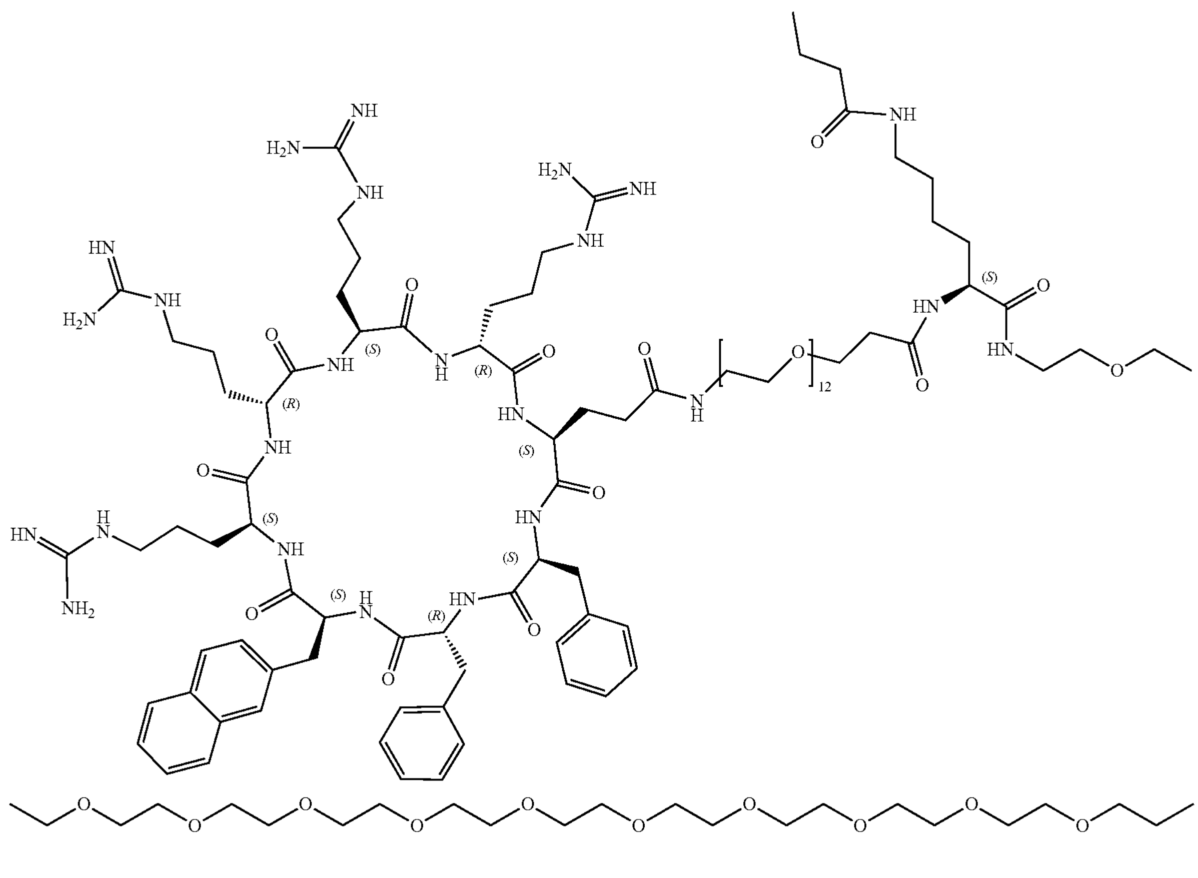

-continued
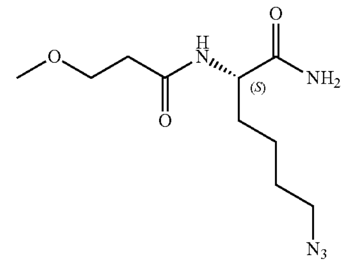
CPP12-PEG12-K(PEG12-CPP12)PEG12-K(N3)
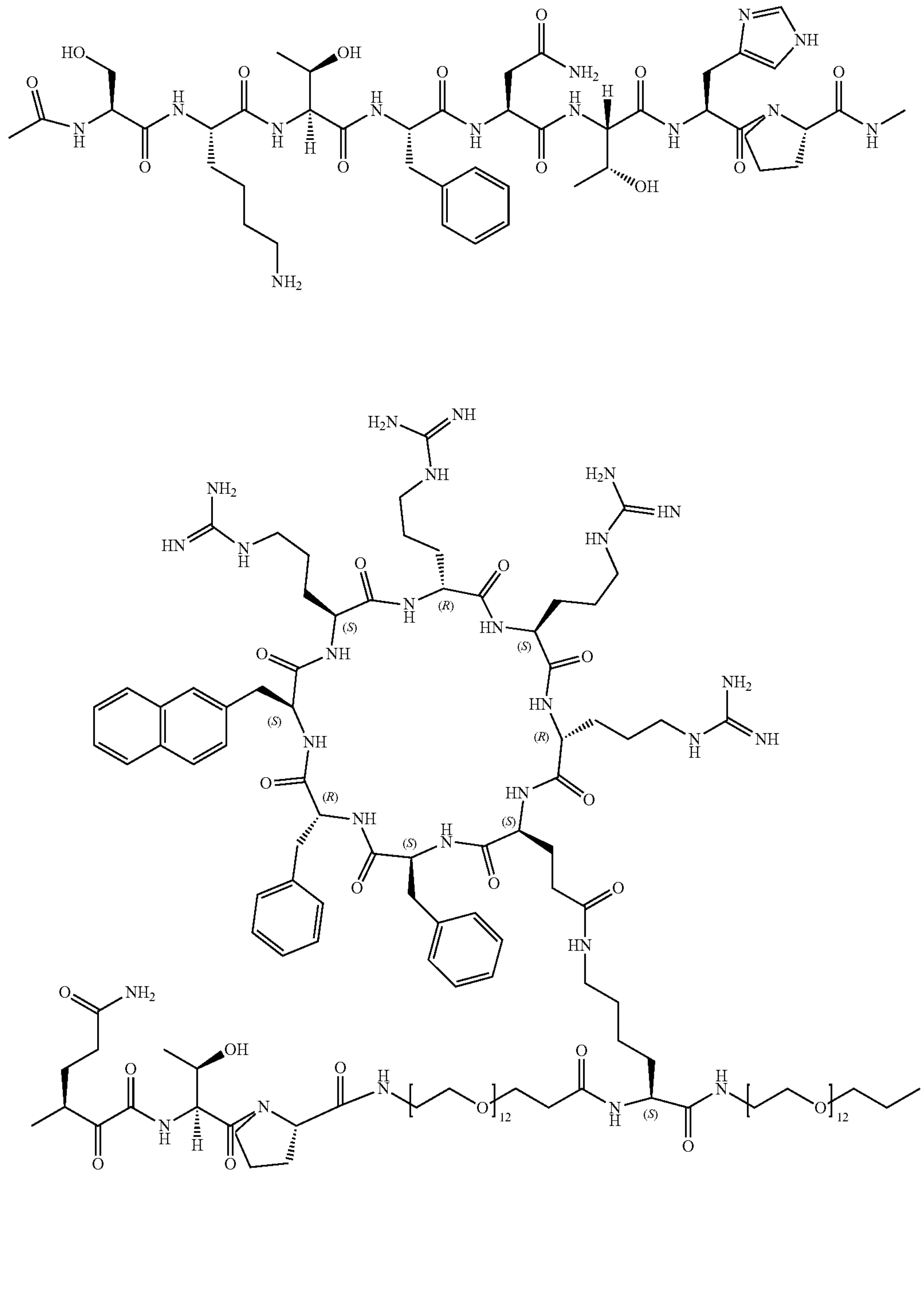

-continued
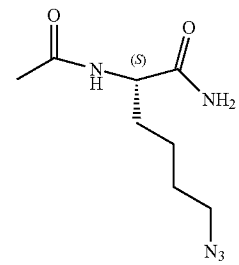
Ac-T9-PEG12-Lys(CPP12-PEG12)-K(N3)
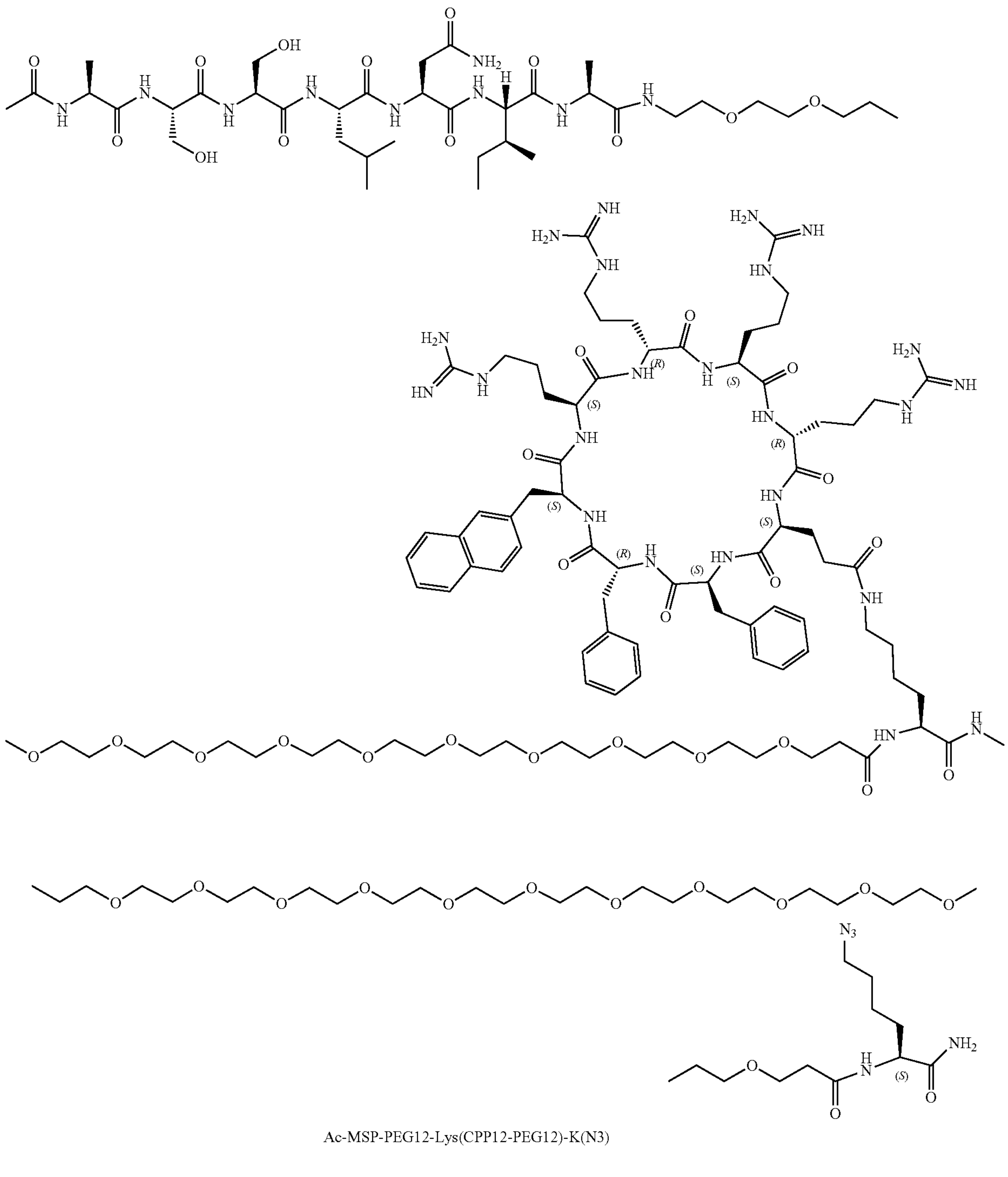
Ac-MSP-PEG12-Lys(CPP12-PEG12)-K(N3)

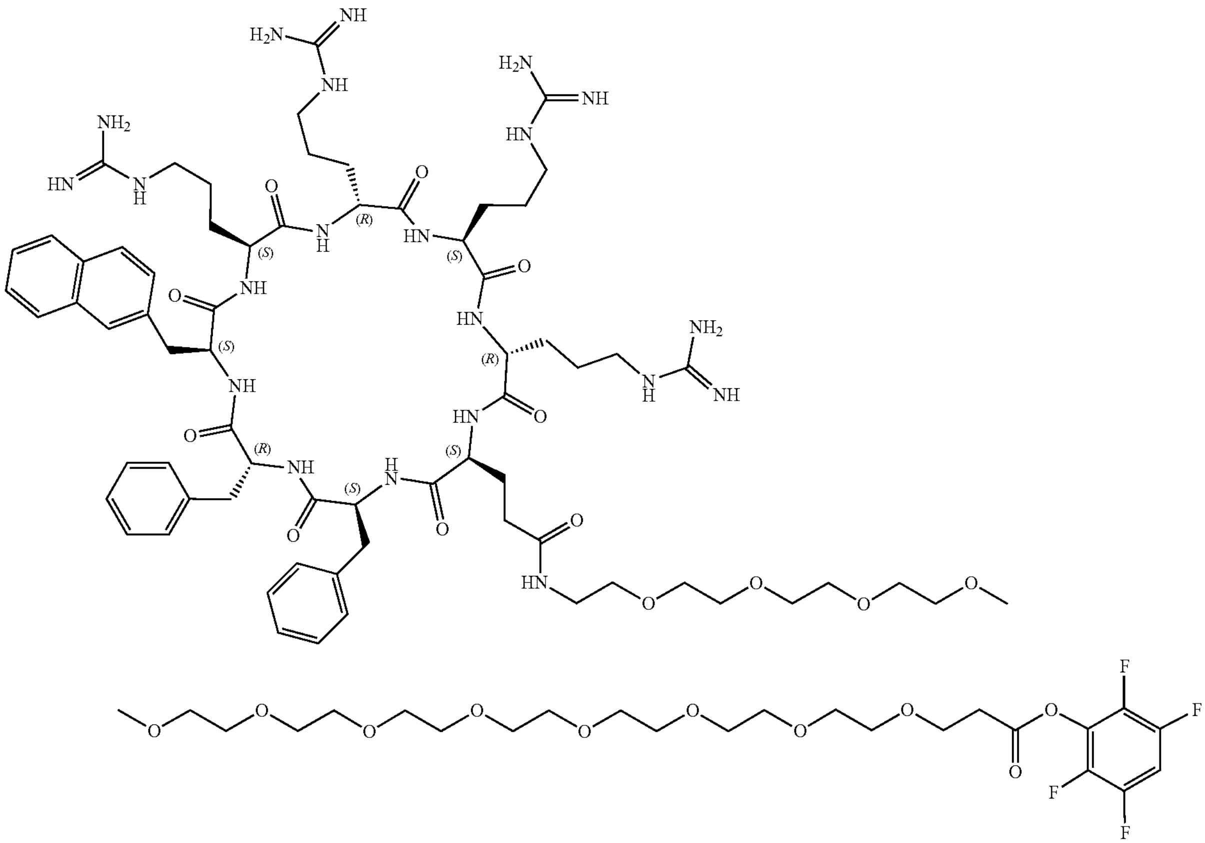
CPP12-PEG12-TFP
ETRD 802
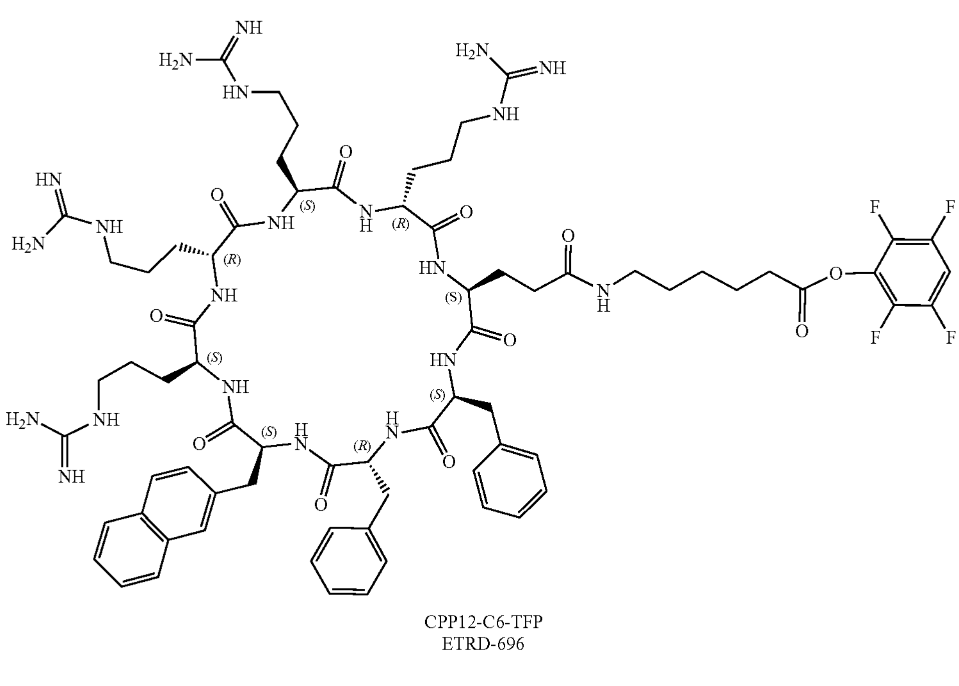
CPP12-C6-TFP
ETRD-696

-continued
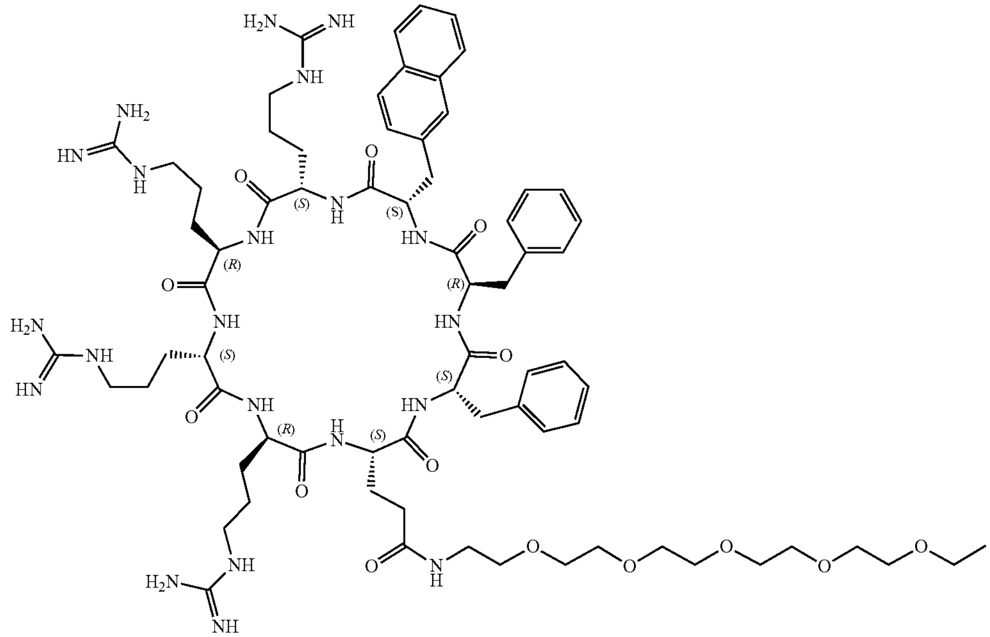
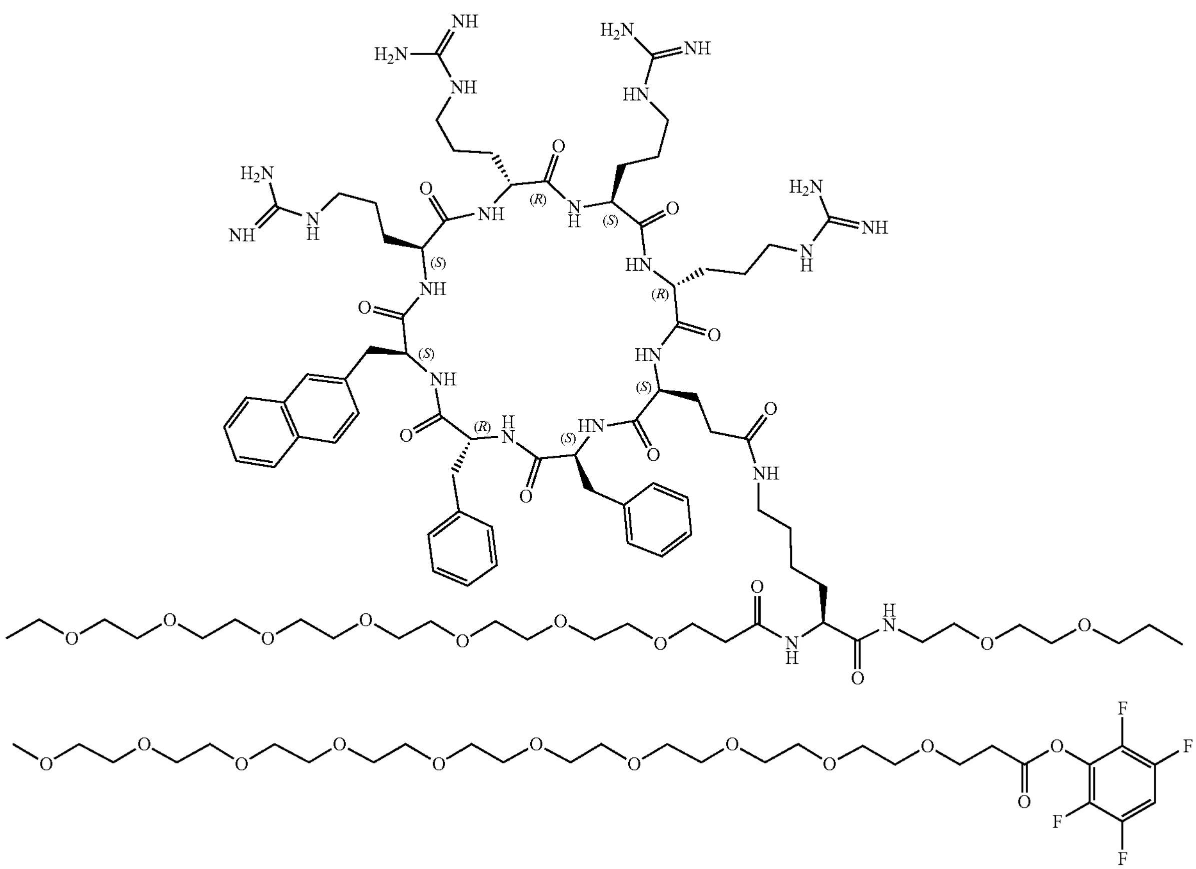
CPP12-PEG12-K(CPP12)-PEG12-TFP
ETRD-344

-continued
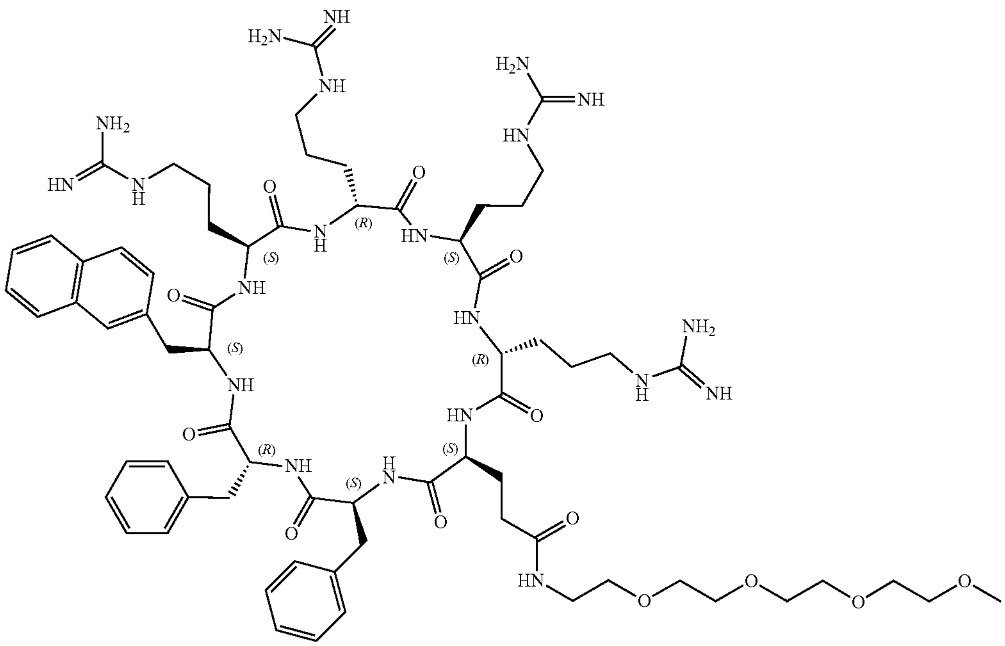
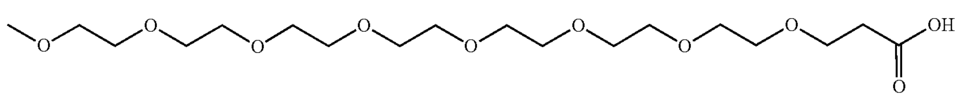
CPP12-PEG12-COOH
ETRD 802_OH
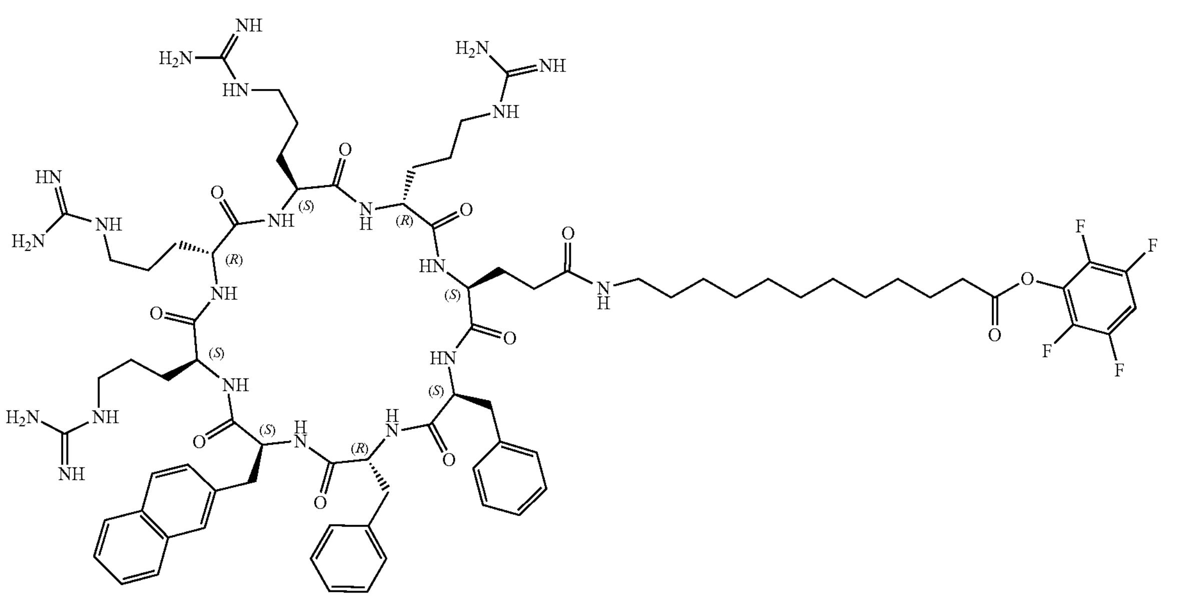
CPP12-C12-TFP
ETRD-695
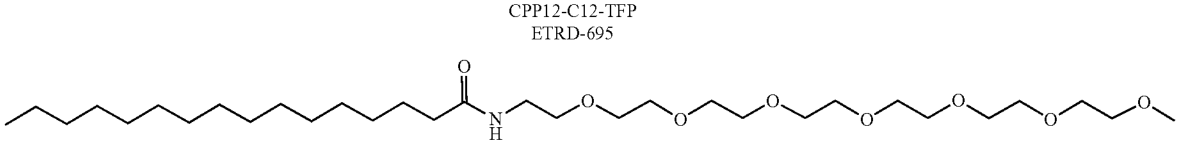

-continued
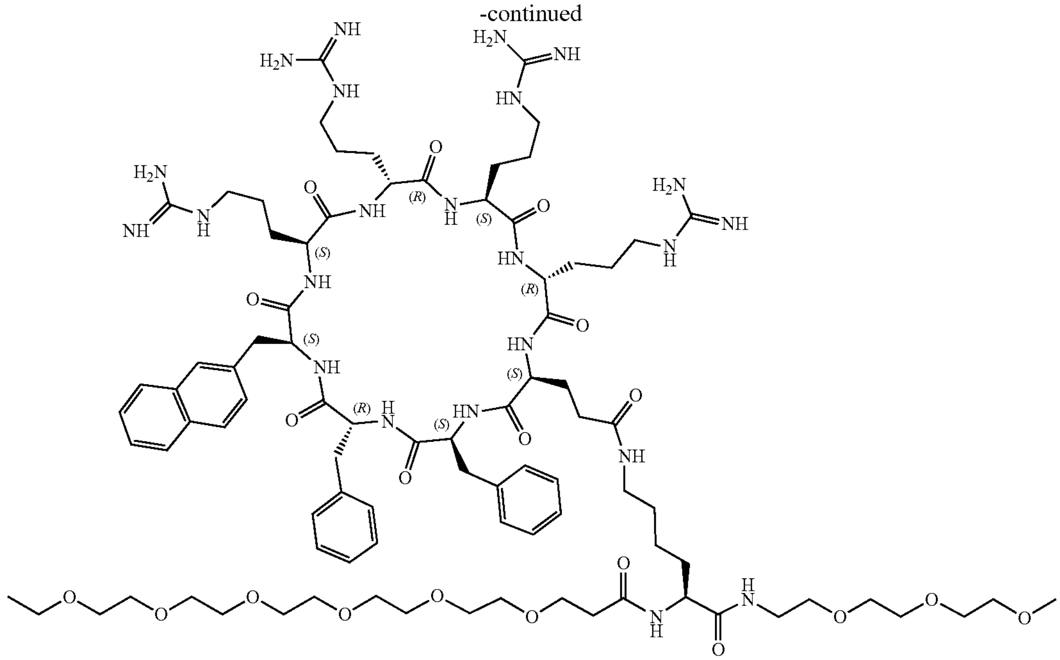
palmitoyl-PEG12-K(CPP12)-PEG12-TFP
ETRD-343
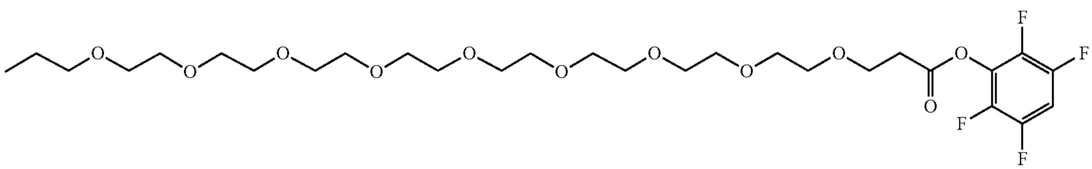
The following CPPs contain azide functional groups on the linker that may be utilized to facilitate addition of an AC. As shown below, in some embodiments, the CPP may also include an NLS conjugated to the side chain of an amino acid in the CPP.

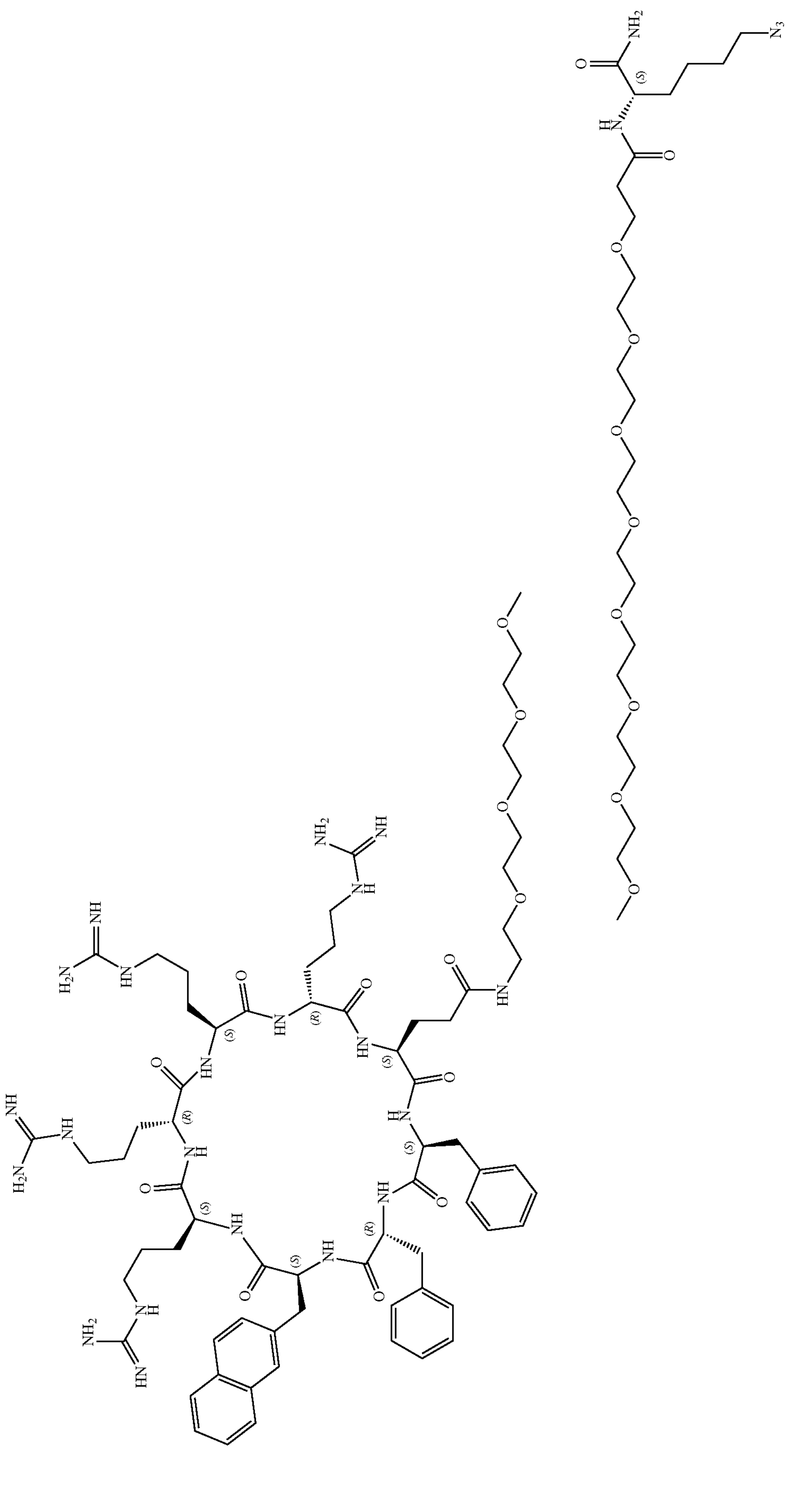
CPP12-PEG12-Lys(N3)
ETRD-617

-continued
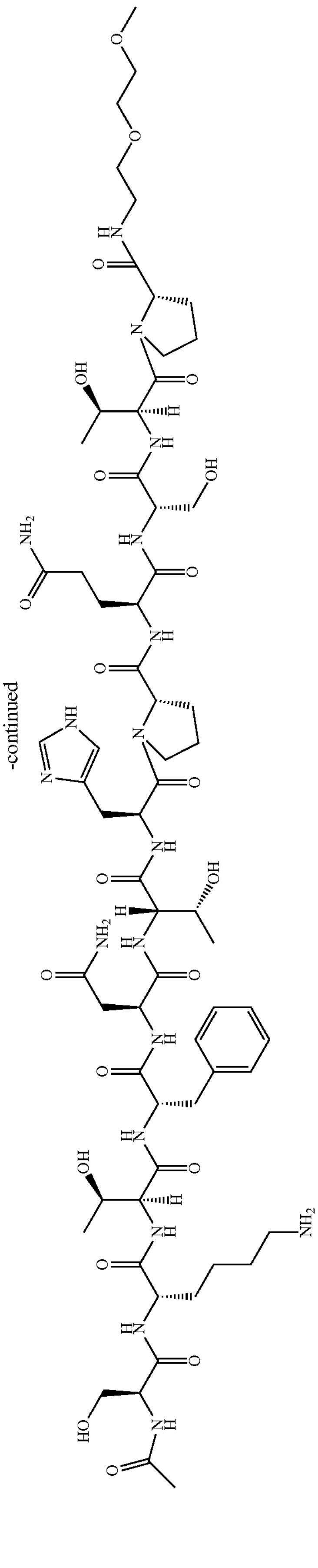
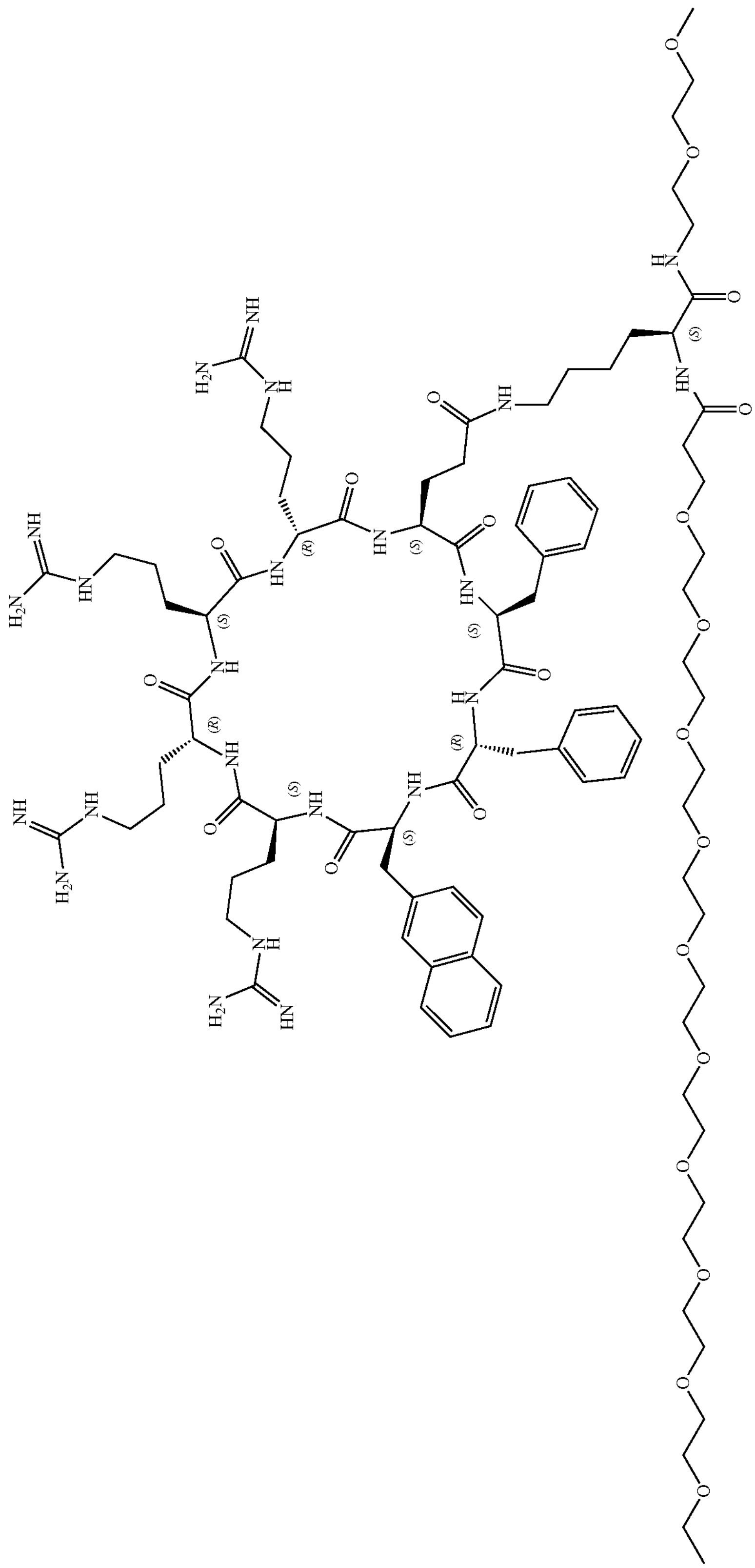

-continued
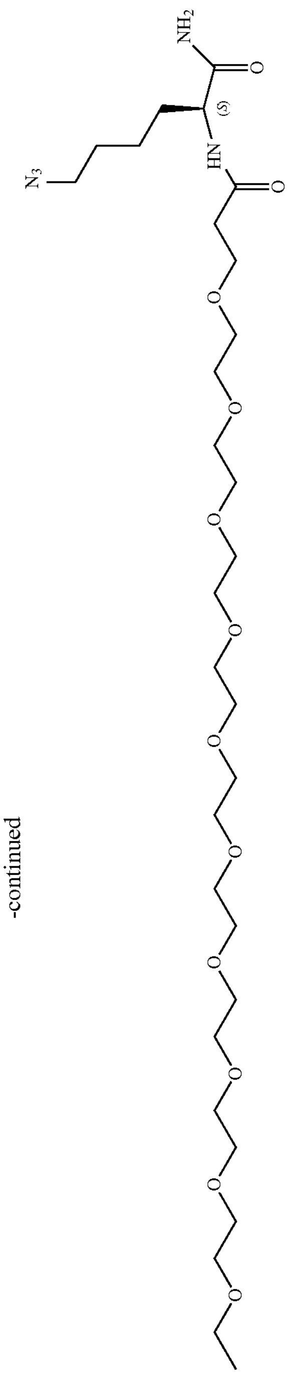
Ac-T9-PEG12-Lys(CPP12-PEG12)-K(N3)
ETRD 673

-continued
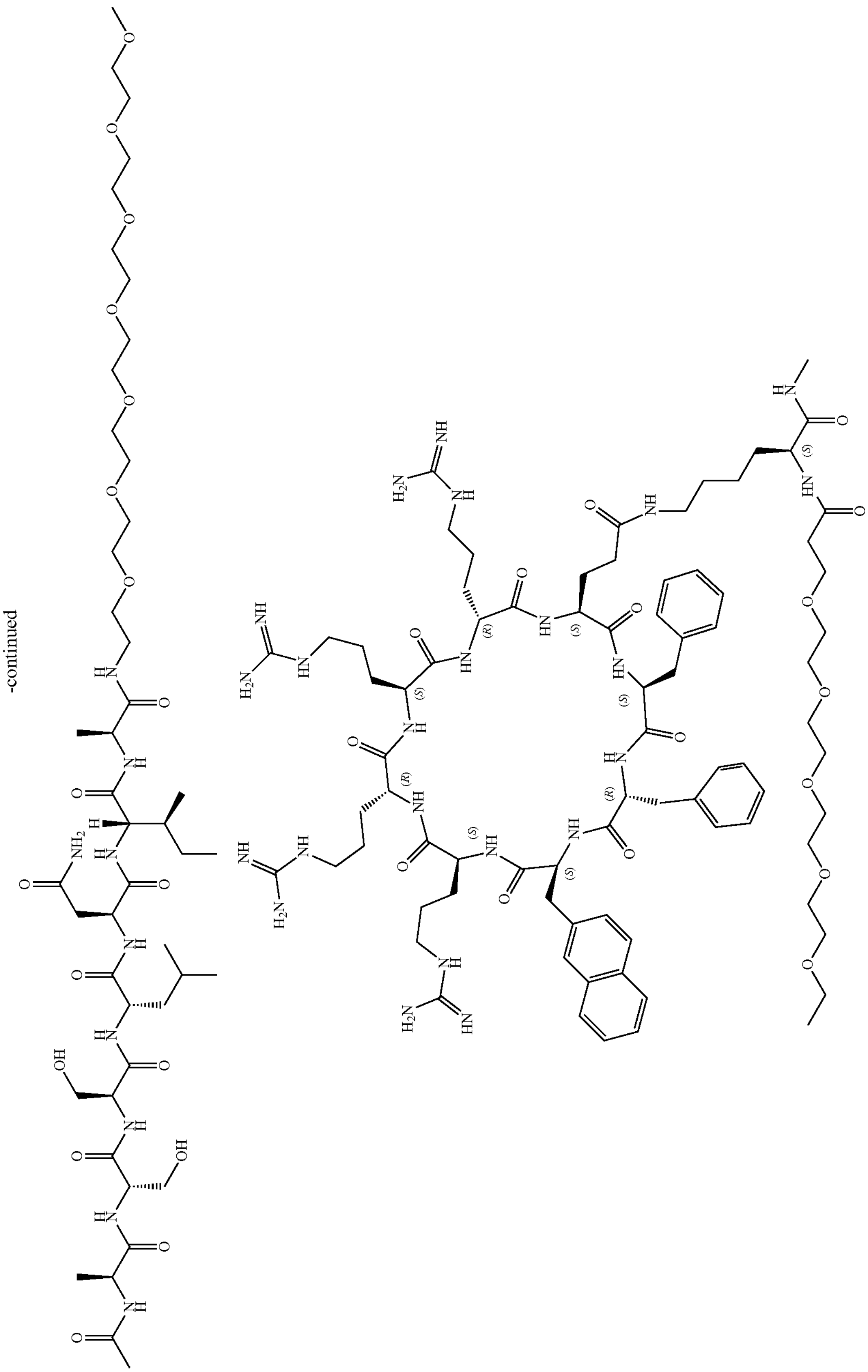

-continued
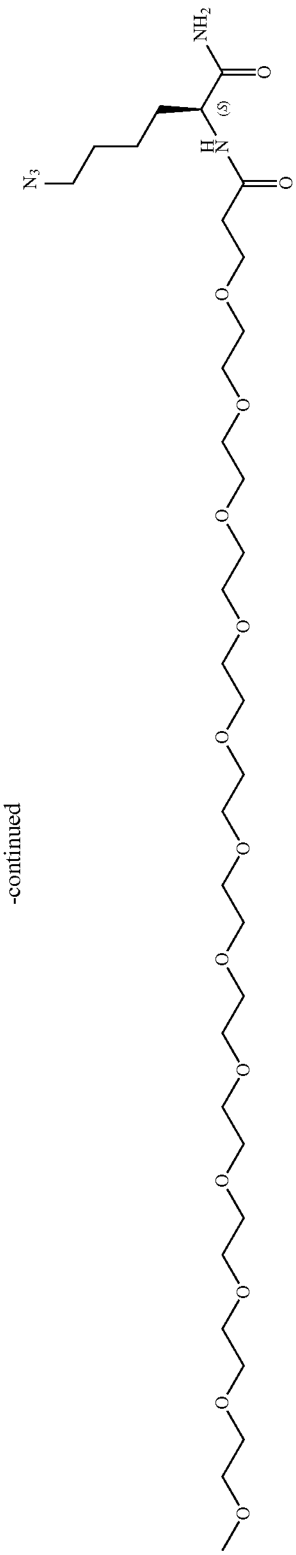
Ac-MSP-PEG12-Lys(CPP12-PEG12)-K(N3)
ETRD-675

-continued
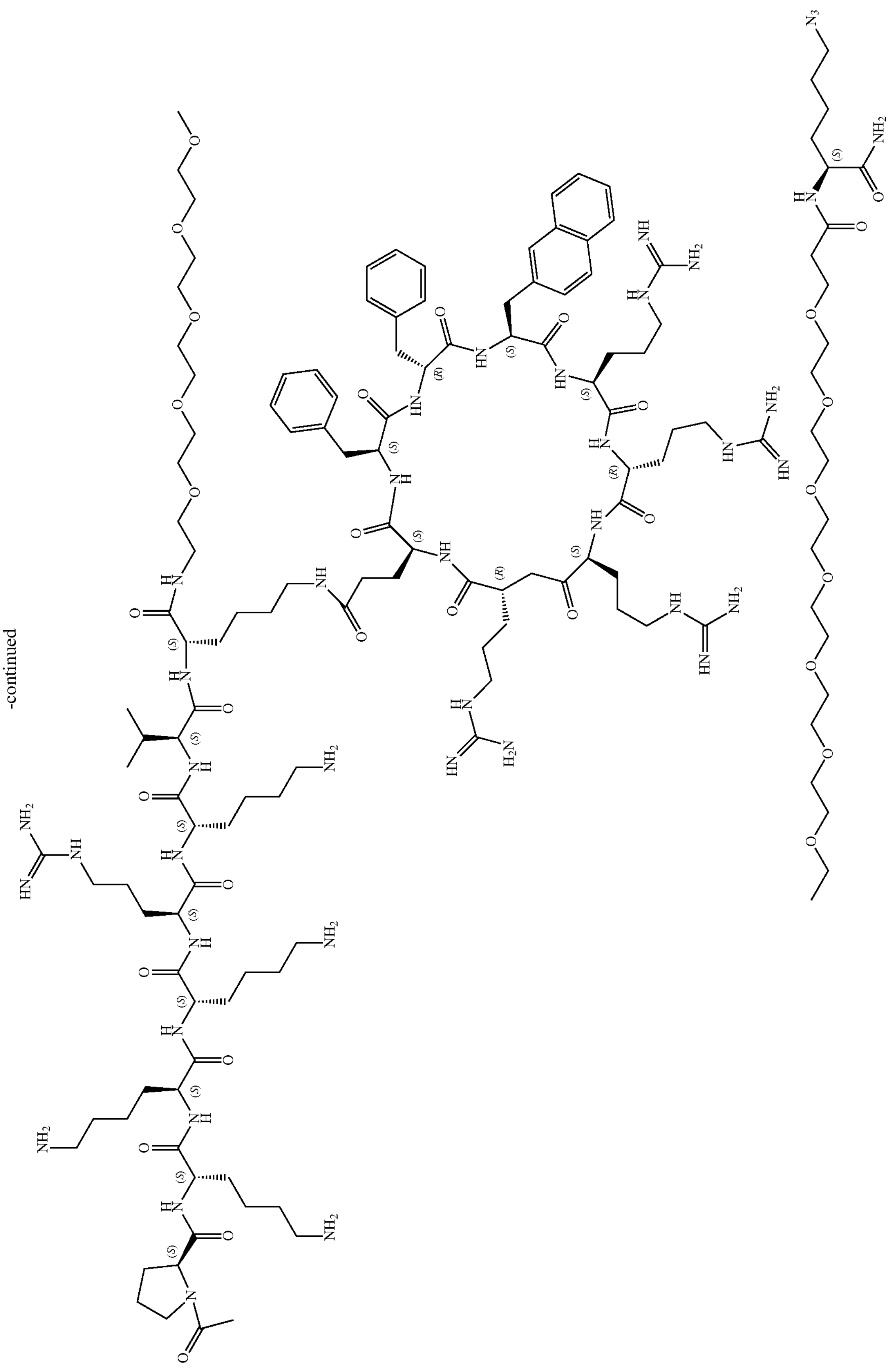
Ac-NLS-Lys(CPP12)-PEG12-K(n3)
ETRD-684

-continued
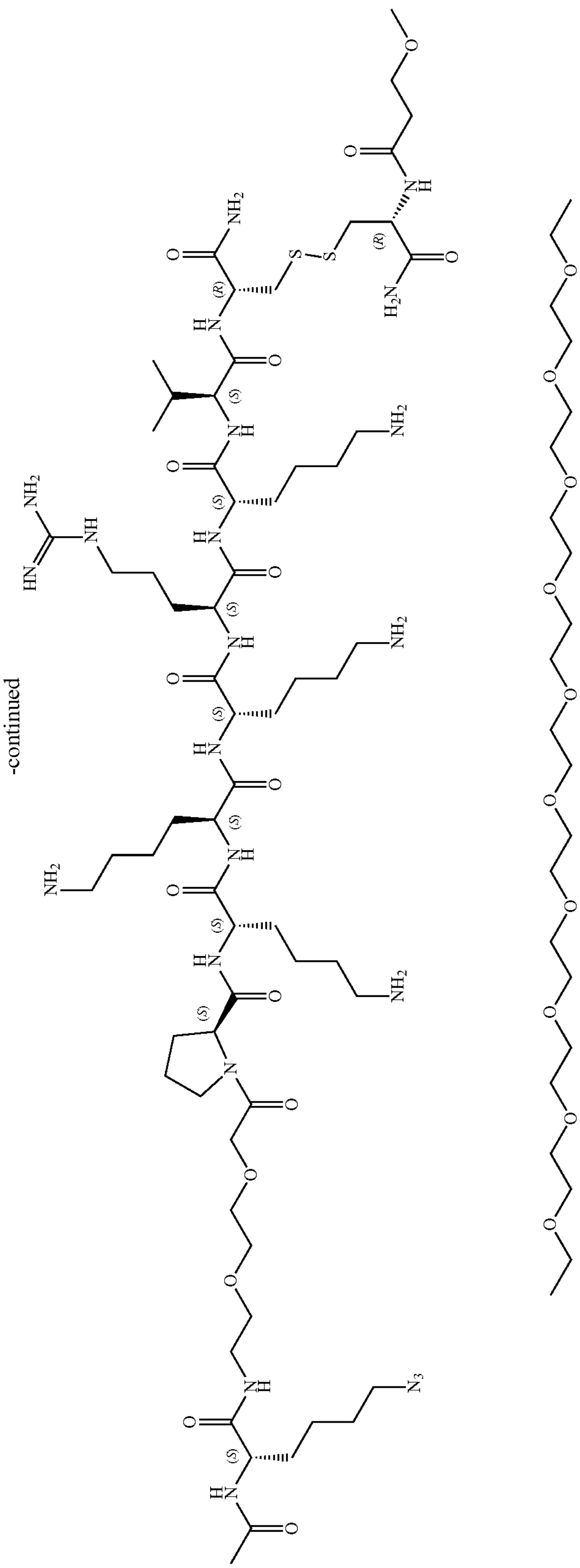

-continued
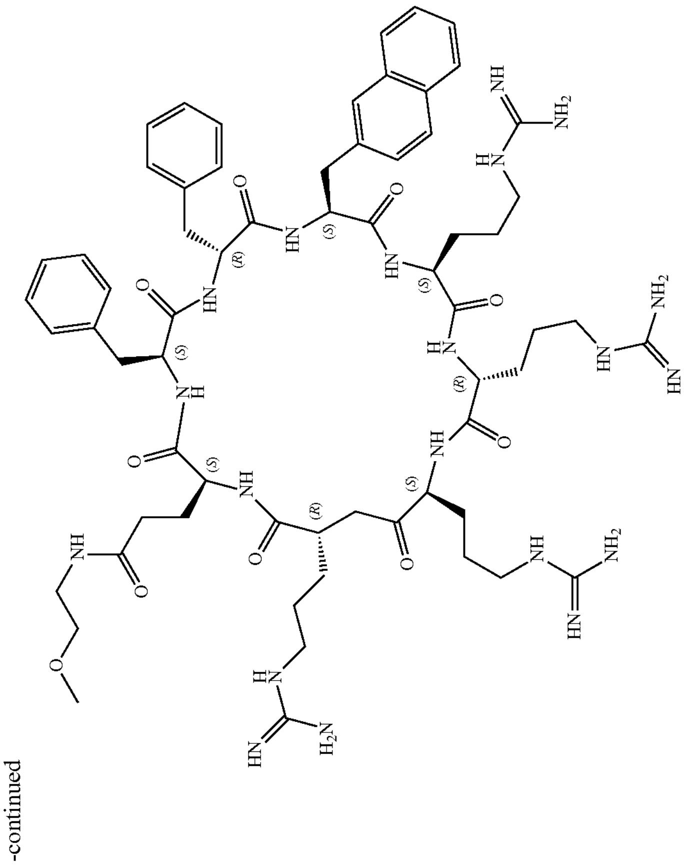
Lys(N3)-miniPEG-NLS-ss-PEG12-CPP12
ETRD-681

-continued
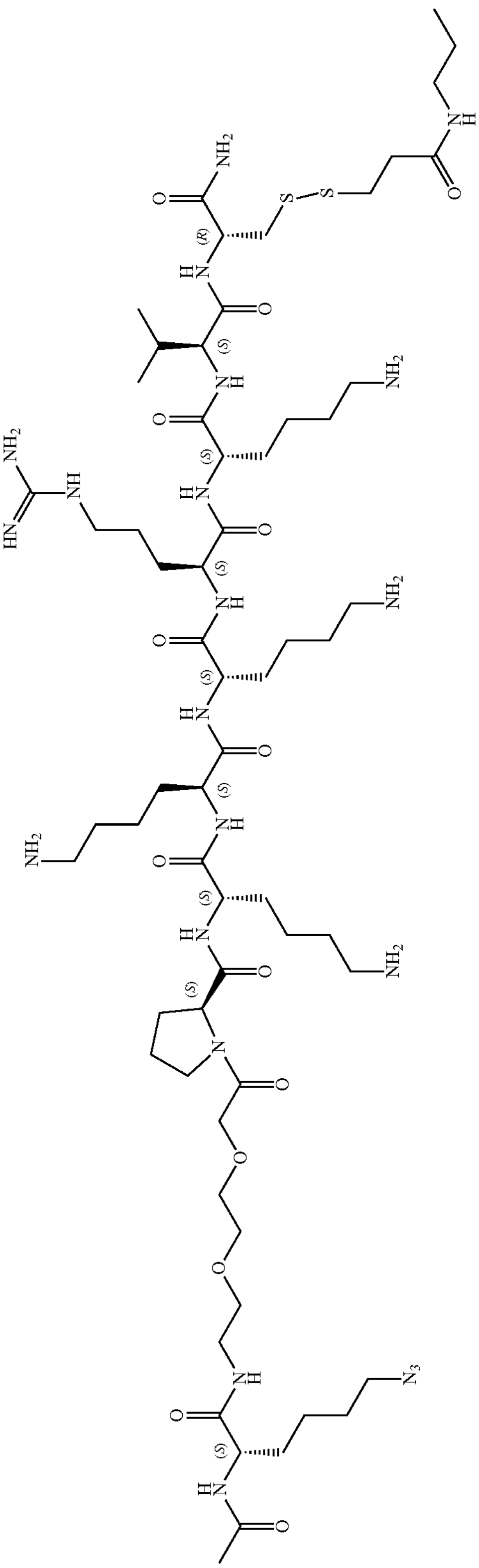

-continued
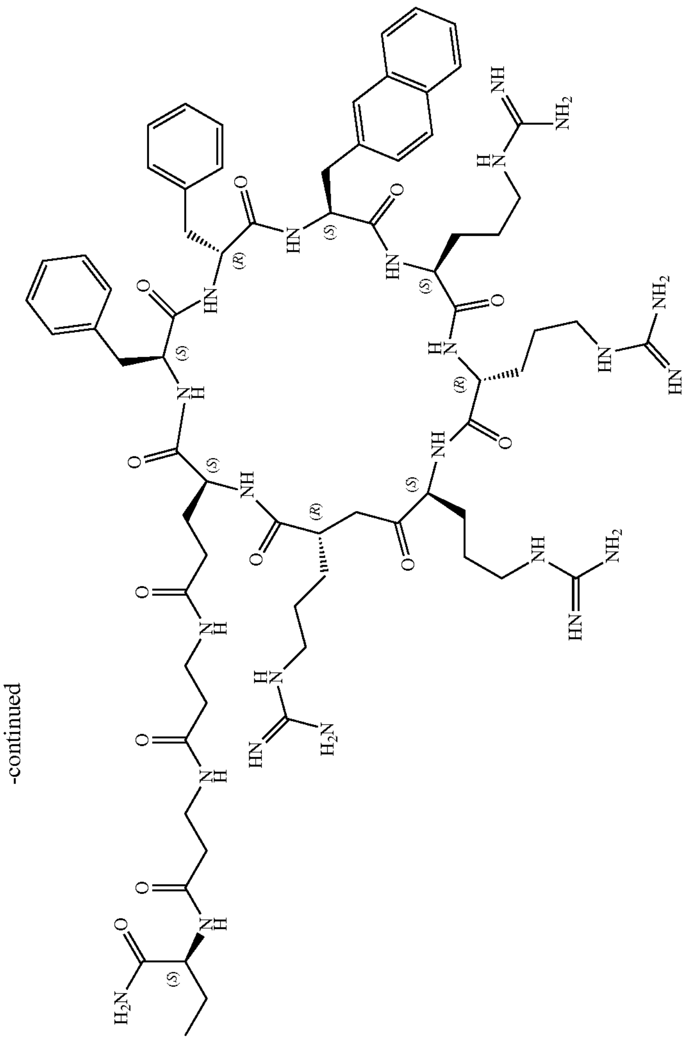
Lys(N3)-miniPEG-NLS-ss-Lys-BetaA-CPP12
ETRD-682

The structure below is a 3' cyclooctyne modified PMO used for a click reaction with CPPs and/or NLS containing an azide:

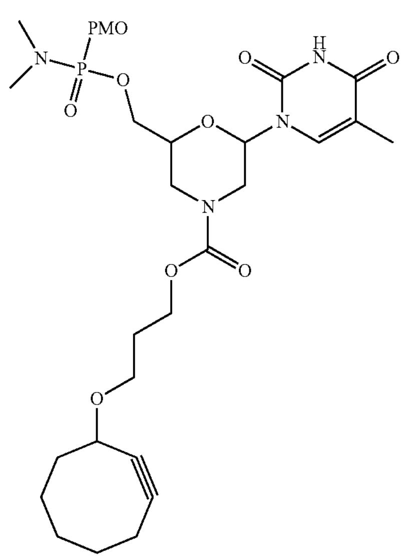

An example scheme of conjugation of a CPP and linker to the 3' end of an AC via an amide bond is shown below.

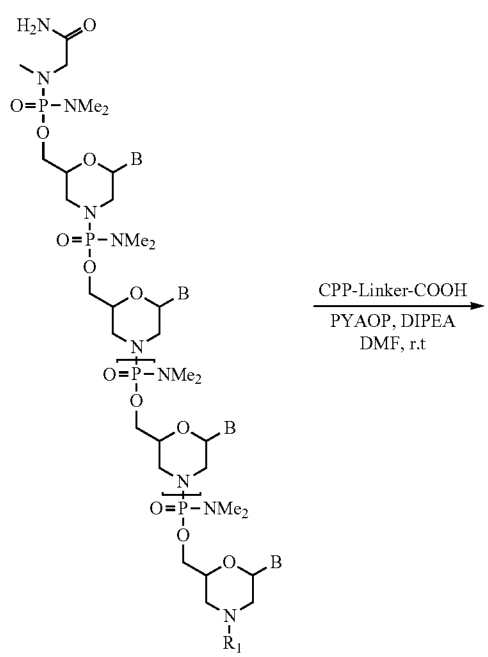

-continued

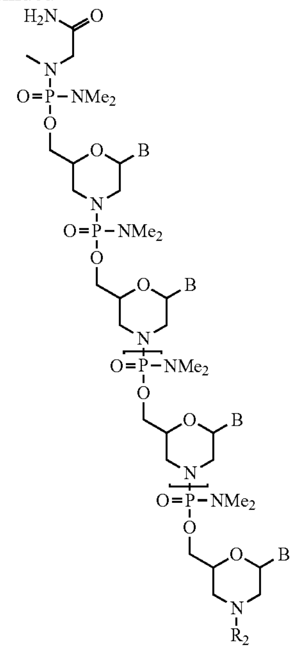

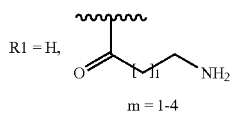

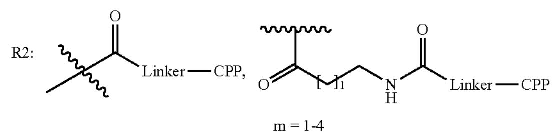

An example scheme of conjugation of a CPP and linker to a 3'-cyclooctyne modified PMO via strain-promoted azide-alkyne cycloaddition is shown below:

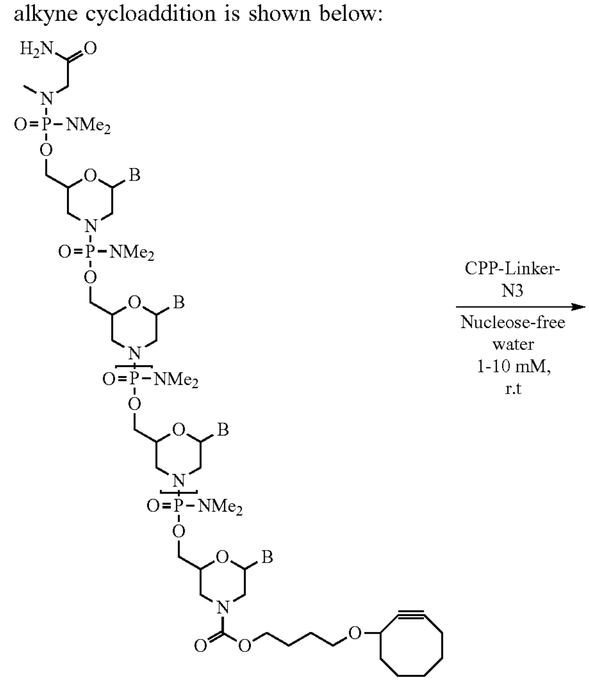

-continued
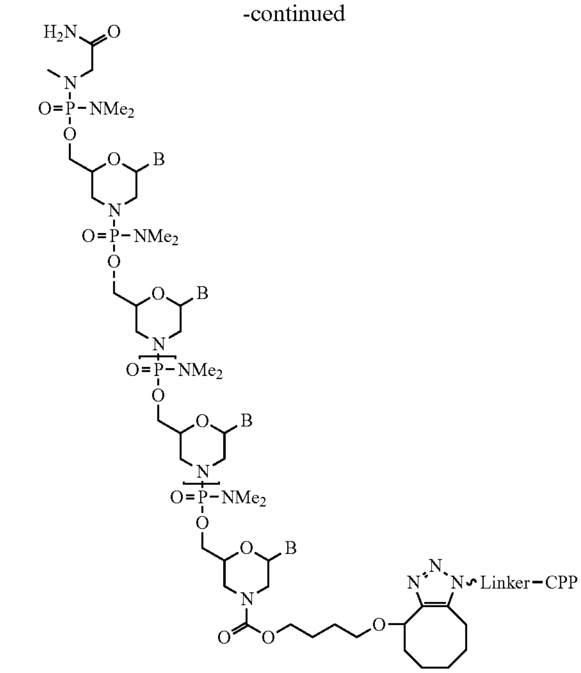
Mixture of regioisomers
An example of the conjugation chemistry used to connect an AC and CPP with an additional linker containing a polyethylene glycol moiety is shown below:
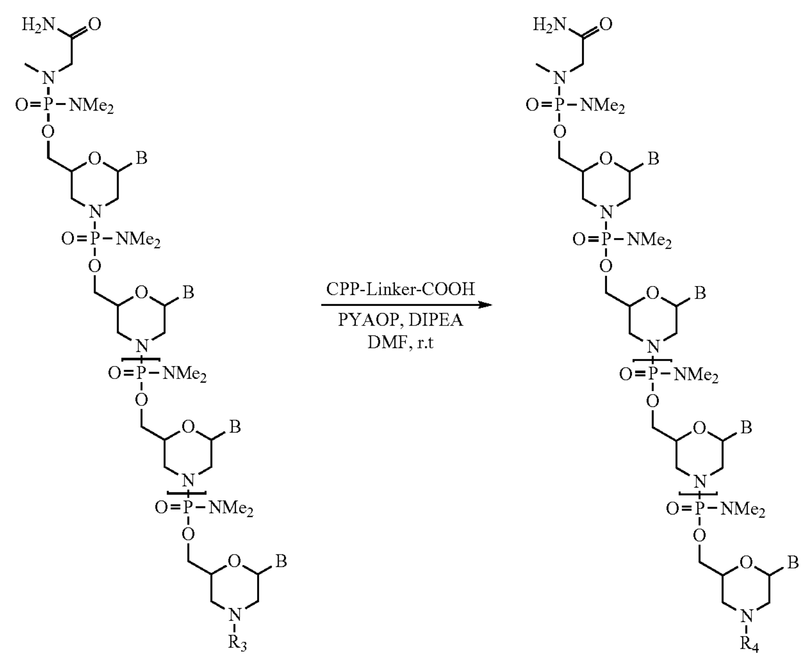
R3:
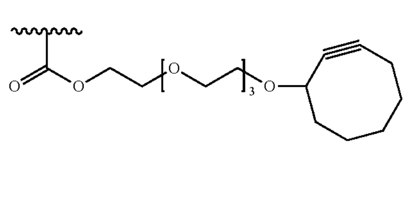

-continued
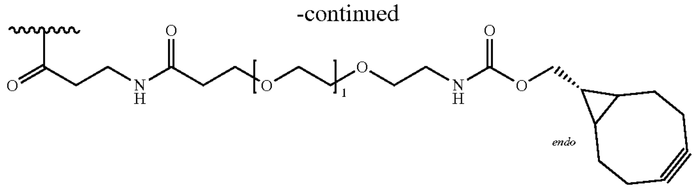
I = 0-12
R4:
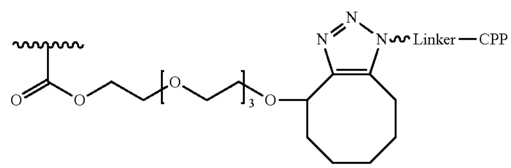
Mixture of regioisomers
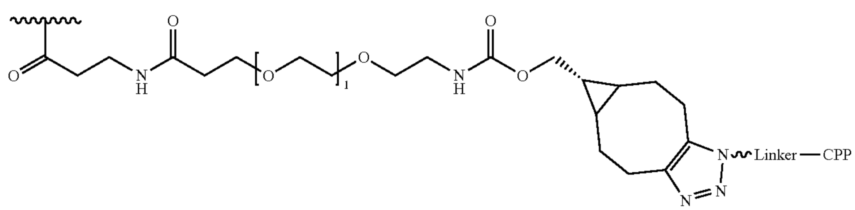
I = 0-12
Mixture of regioisomers
An example of conjugation of a CPP-linker to a 5'-cyclooctyne modified PMO via strain-promoted azide-alkyne cycloaddition (click chemistry) is shown below:
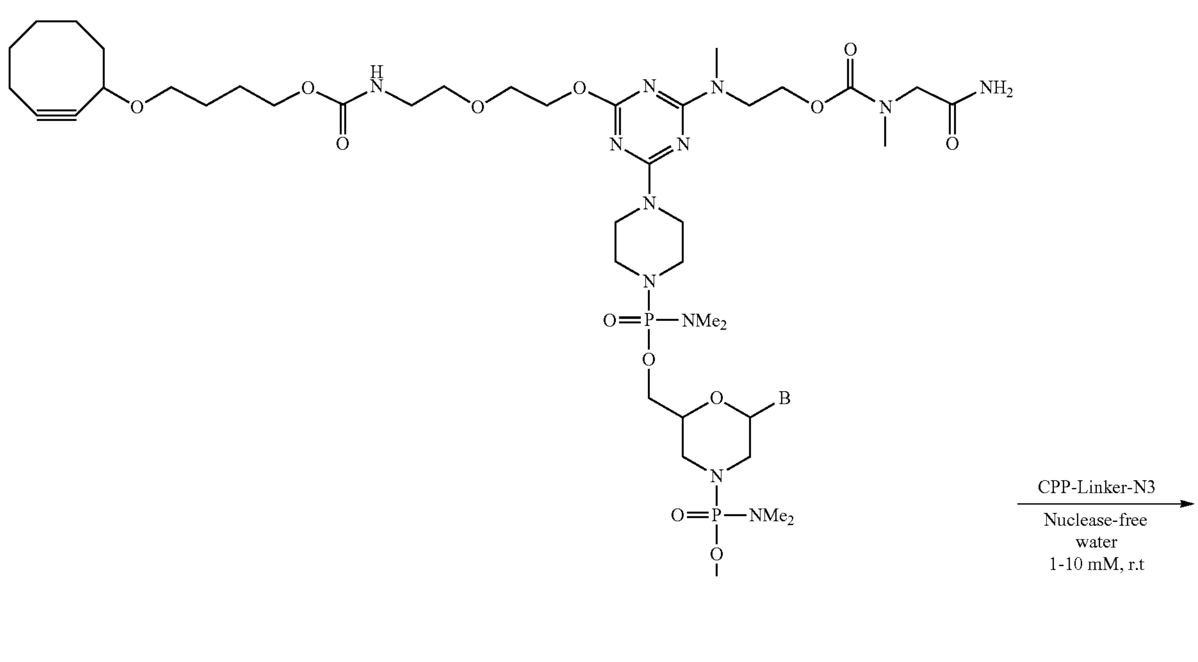

-continued
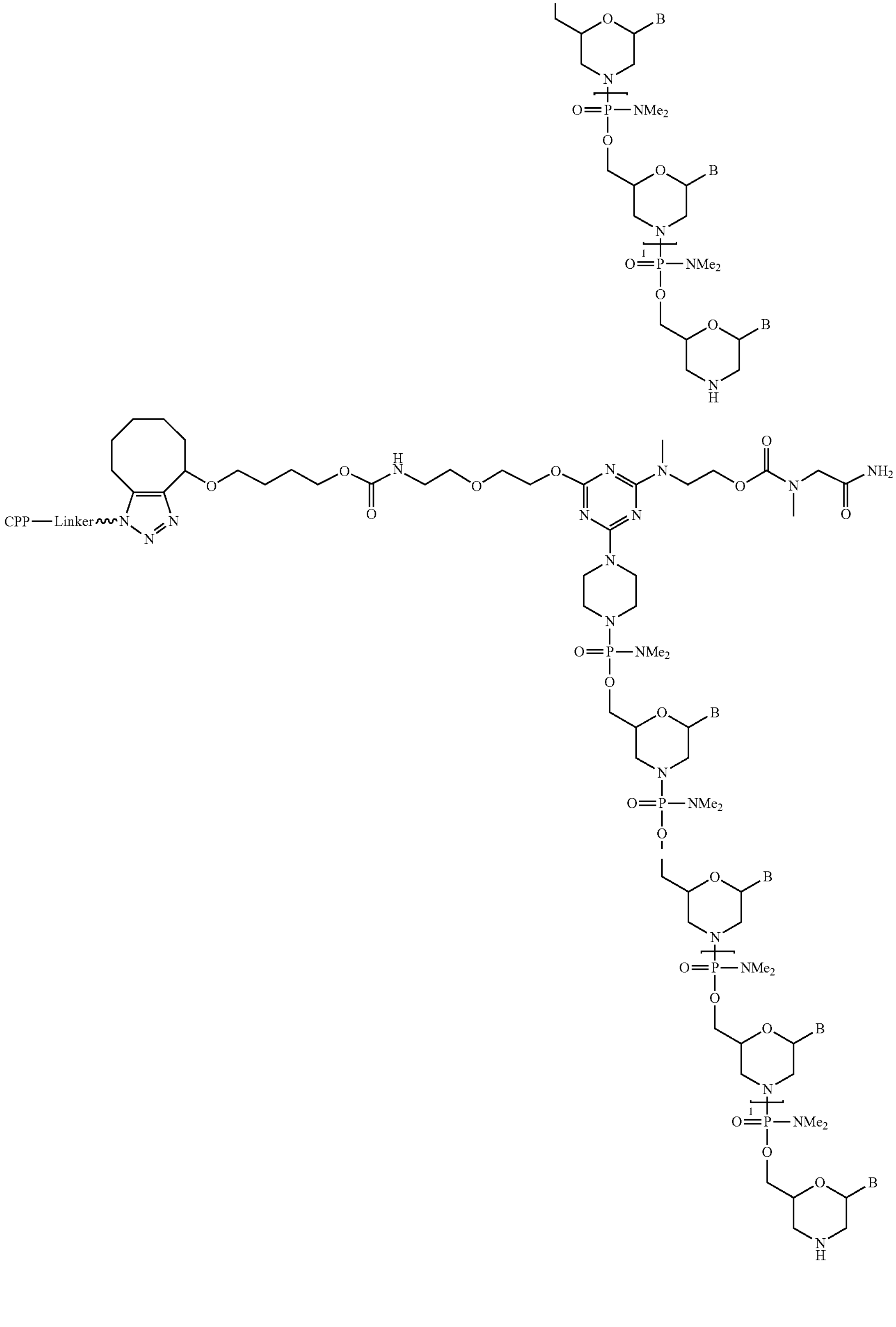

-continued
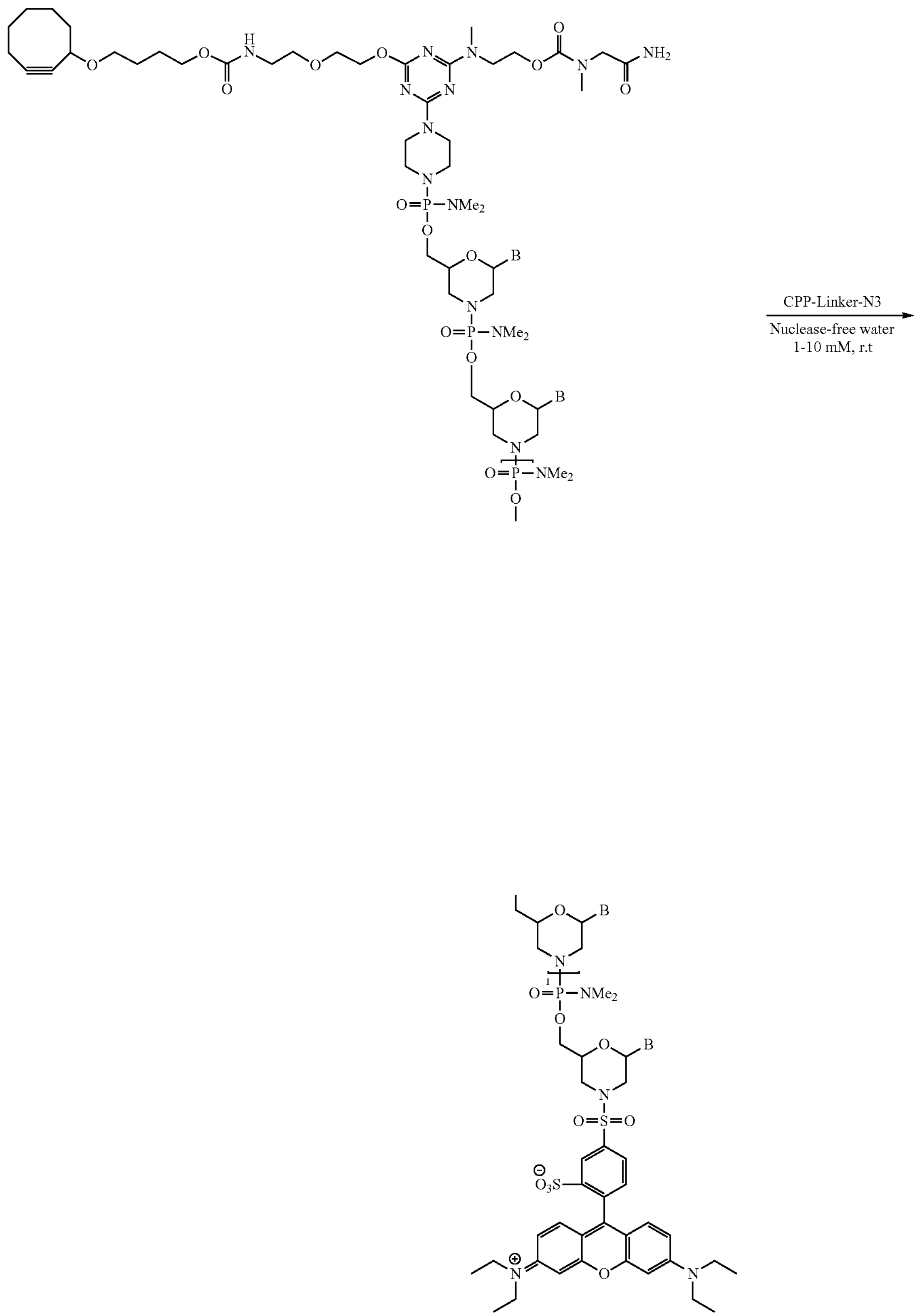

-continued
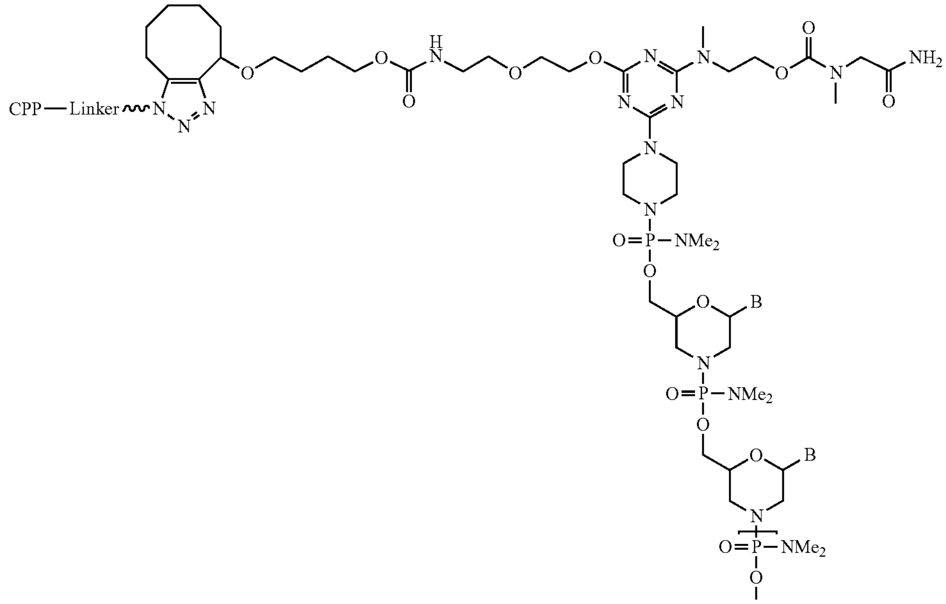
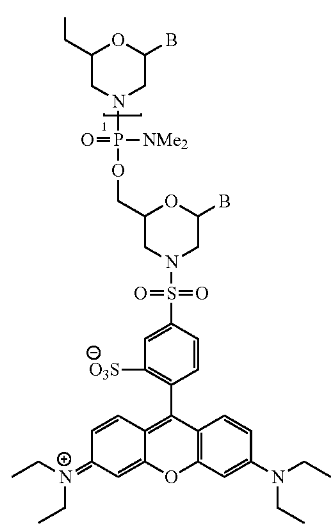
The following compounds contain an AC attached to a linker through click chemistry and a nuclear localization sequence attached to the linker via the C-terminus and the side chain of glutamine on a CPP. Alternative CPPs and/or AC that bind to different targets are envisioned.

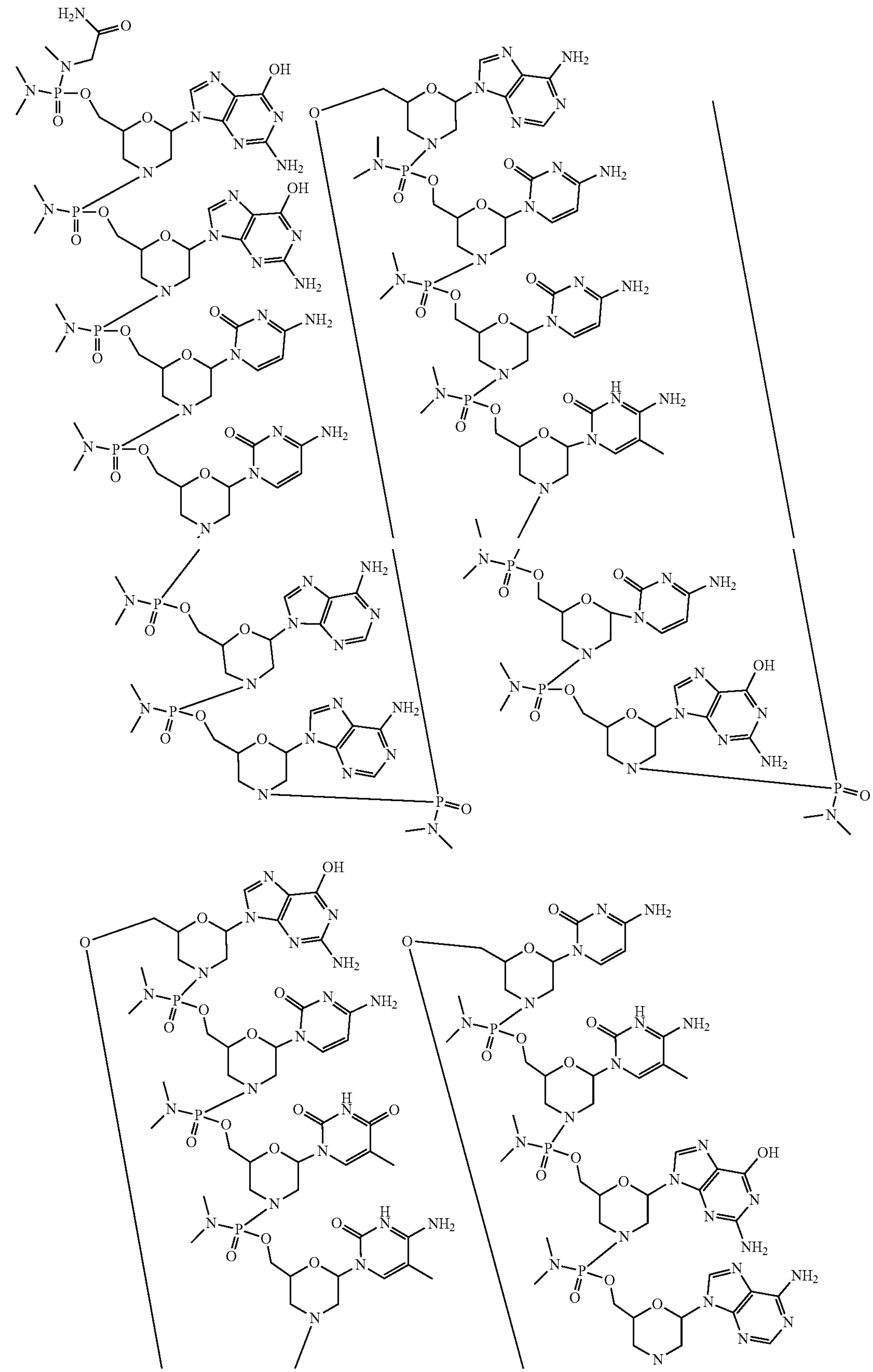

-continued
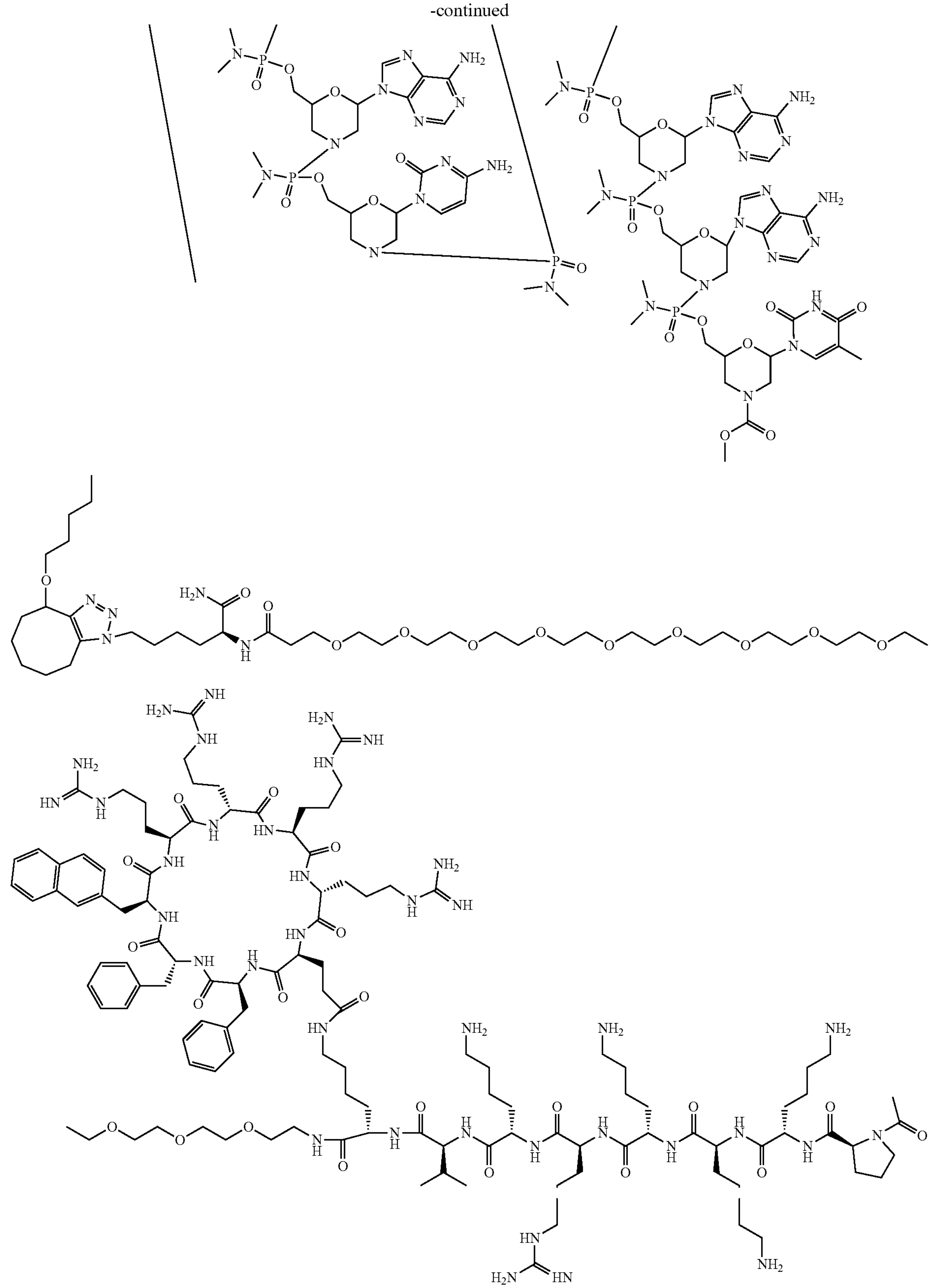

-continued
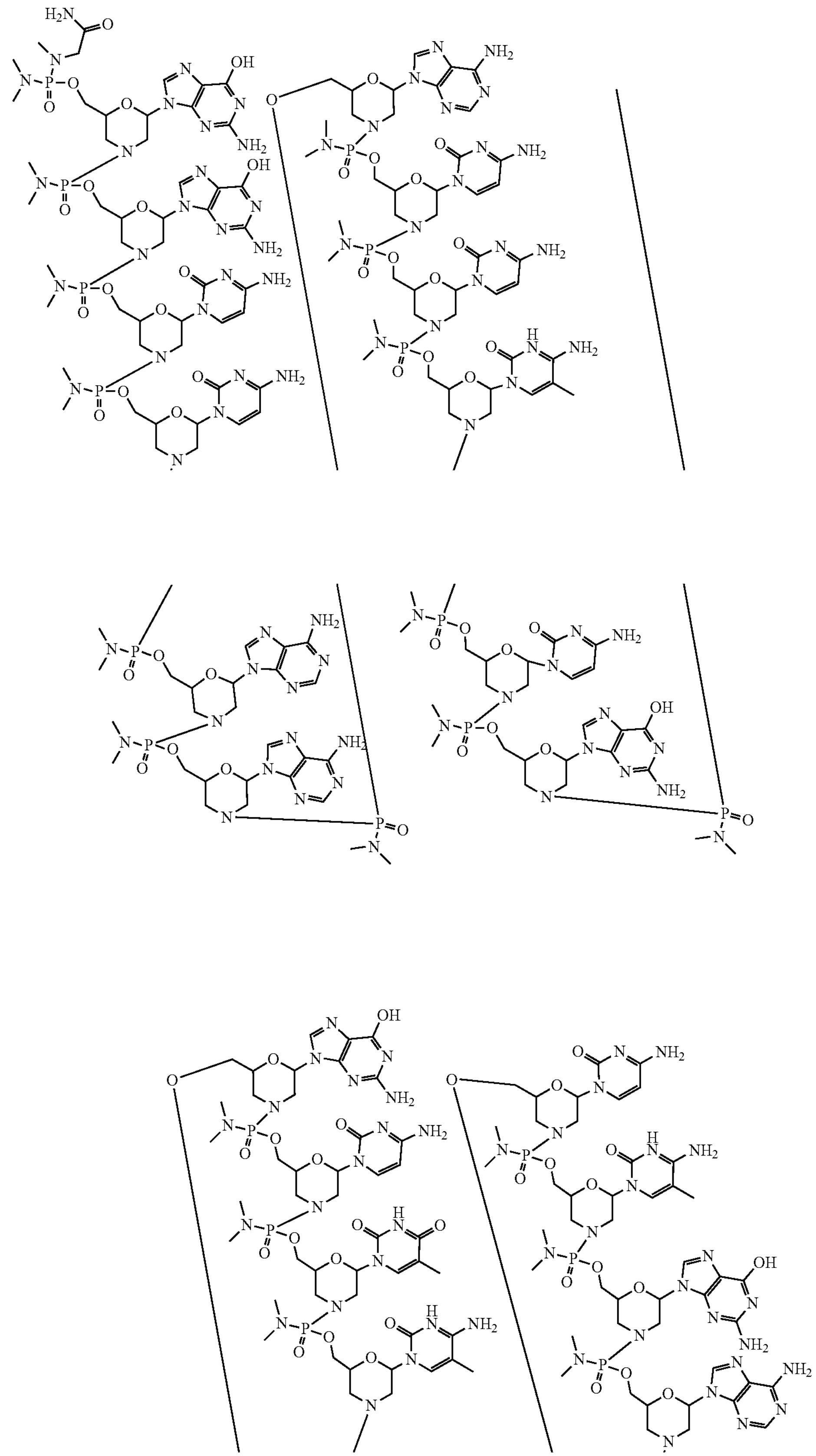

-continued

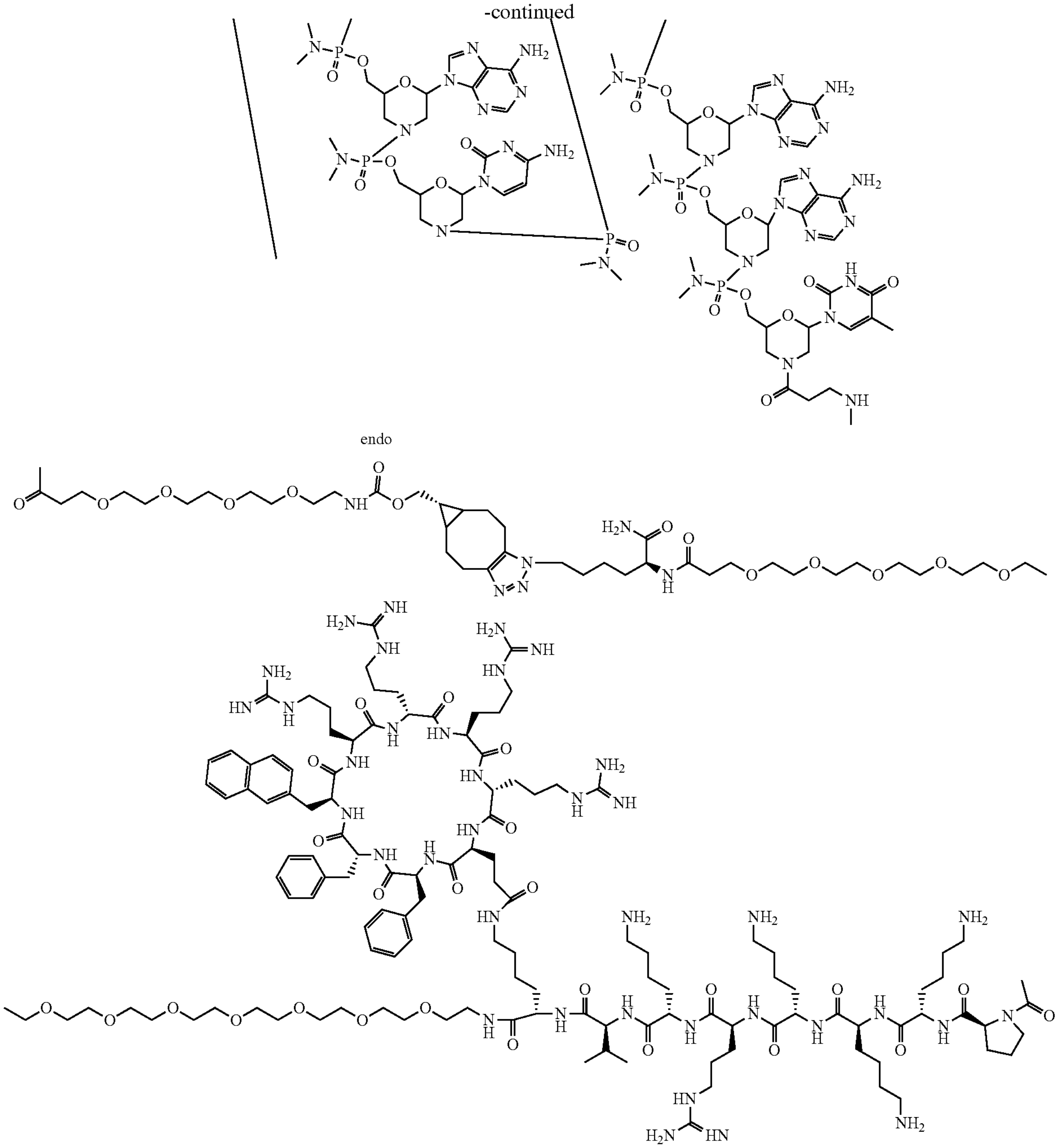

Methods of synthesizing oligomeric antisense compounds are known in the art. The present disclosure is not limited by the method of synthesizing the AC. In some embodiments, provided herein are compounds having reactive phosphorus groups useful for forming internucleoside linkages including for example phosphodiester and phosphorothioate internucleoside linkages. Methods of preparation and/or purification of precursors or antisense compounds are not a limitation of the compositions or methods provided herein. Methods for synthesis and purification of DNA, RNA, and the antisense compounds are well known to those skilled in the art.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds provided herein can be conveniently and routinely made through the well-known technique of solid phase synthesis. Equipment for such synthesis is sold by several vendors including, for example, Applied Biosystems (Foster City, CA). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral and parenteral routes of administration. As used herein, the term parenteral includes subcutaneous, intradermal, intravenous, intramuscular, intraperitoneal, intrasternal, and intrathecal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E.W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

Example 1A. Use of Cell-Penetrating Peptides Conjugated to Oligonucleotides for Restoring Protein Expression in Eukaryotic Cells The compounds of Table A are evaluated in Examples 1A and 1B. Exemplary experiments are described below for ENTR-0006. The same techniques are used to evaluate any compound of Table A.

TABLE A

Compounds that target EGFP-654

| Oligo# | Design | Sequence |
|---|---|---|
| ENTR-0006 | PMO-654 | 5'-GCT ATT ACC TTA ACC CAG-3' (SEQ ID NO: 221) |
| ENTR-0070 | PMO654-NH2 | 5'-GCT ATT ACC TTA ACC CAG-3' -C6-NH2 (all PMO monomers)(SEQ ID NO: 222) |
| ENTR-0059 | PMO654-LSR | cyclooctyne-5'-GCT ATT ACC TTA ACC CAG-3'-Lissamine Rho (all PMO monomers)(SEQ ID NO: 223) |
| ENTR-0123 | CPP12-PMO654-LSR | (CPP12-PEG12)-5'-GCT ATT ACC TTA ACC CAG-3'-Lissamine Rho (all PMO monomers)(SEQ ID NO: 224) |
| ENTR-0121 | PMO654-CPP12 | 5'-GCT ATT ACC TTA ACC CAG-3'-NH2 (all PMO monomers)+CPP12-PEG12-TFP-Amide chemistry (SEQ ID NO: 225) |
| ENTR-0106 | PMO654-3'-Asymmetric bidentate | 5'-GCT ATT ACC TTA ACC CAG-3'-NH2 (all PMO monomers)+CPP1212-TFP; Amide chemistry (SEQ ID NO: 226) |
| ENTR-0108 | 5'-Bidentate-PMO654-LSR | (CPP12-(bidentate-no linker)-PEG12)-5'-GCT ATT ACC TTA ACC CAG-3'-Lissamine Rho (all PMO monomers)(SEQ ID NO: 227) |
| ENTR-0109 | 5'-Bidentate-PMO654-LSR | (CPP12-(bidentate-PEG4)-PEG12)-5'-GCT ATT ACC TTA ACC CAG-3'-Lissamine Rho (all PMO monomers) (SEQ ID NO: 228) |

TABLE A-continued

| Compounds that target EGFP-654 | | |
|---|---|---|
| Oligo# | Design | Sequence |
| ENTR-0110 | 5'-Bidentate-PMO654-LSR | (CPP12-(bidentate-PEG12)-PEG12)-5'-GCT ATT ACC TTA ACC CAG-3'-Lissamine Rho (all PMO monomers) (SEQ ID NO: 229) |
| ENTR-0111 | 5'-Tridentate-PMO654-LSR | (CPP12-(tridentate-no linker)-PEG12)-5'-GCT ATT ACC TTA ACC CAG-3'-Lissamine Rho (all PMO monomers)(SEQ ID NO: 230) |
| ENTR-0112 | 5'-Tridentate-PMO654-LSR | (CPP12-(tridentate-PEG4)-PEG12)-5'-GCT ATT ACC TTA ACC CAG-3'-Lissamine Rho (all PMO monomers) (SEQ ID NO: 231) |
| ENTR-0113 | 5'-Tridentate-PMO654-LSR | (CPP12-(tridentate-PEG12)-PEG12)-5'-GCT ATT ACC TTA ACC CAG-3'-Lissamine Rho (all PMO monomers) (SEQ ID NO: 232) |
| ENTR-0047 | PMO654-NLS-ss-CPP12 | 5'-GCT ATT ACC TTA ACC CAG-3-NLS-ss-CPP12 (all PMO monomers)(SEQ ID NO: 233) |
| ENTR-0168 | NLS-CPP12-PMO654-LSR | (Ac-NLS-Lys(CPP12)-PEG12-K(N3))-5'-GCT ATT ACC TTA ACC CAG-3'-Lissamine Rho (all PMO monomers)(SEQ ID NO: 234) |
| ENTR-0203 | PMO654-CPP12-NLS | 5'-GCT ATT ACC TTA ACC CAG-3'-click-K-PEG12-Lys(CPP12)-NLS-Ac (all PMO monomers)(SEQ ID NO: 235) |
| ENTR-0207 | PMO654-NLS-CPP12 | 5'-GCT ATT ACC TTA ACC CAG-3'-click-Lys(N3)-miniPEG-NLS-ss-PEG12-CPP12 (all PMO monomers) (SEQ ID NO: 236) |

Figure 1:
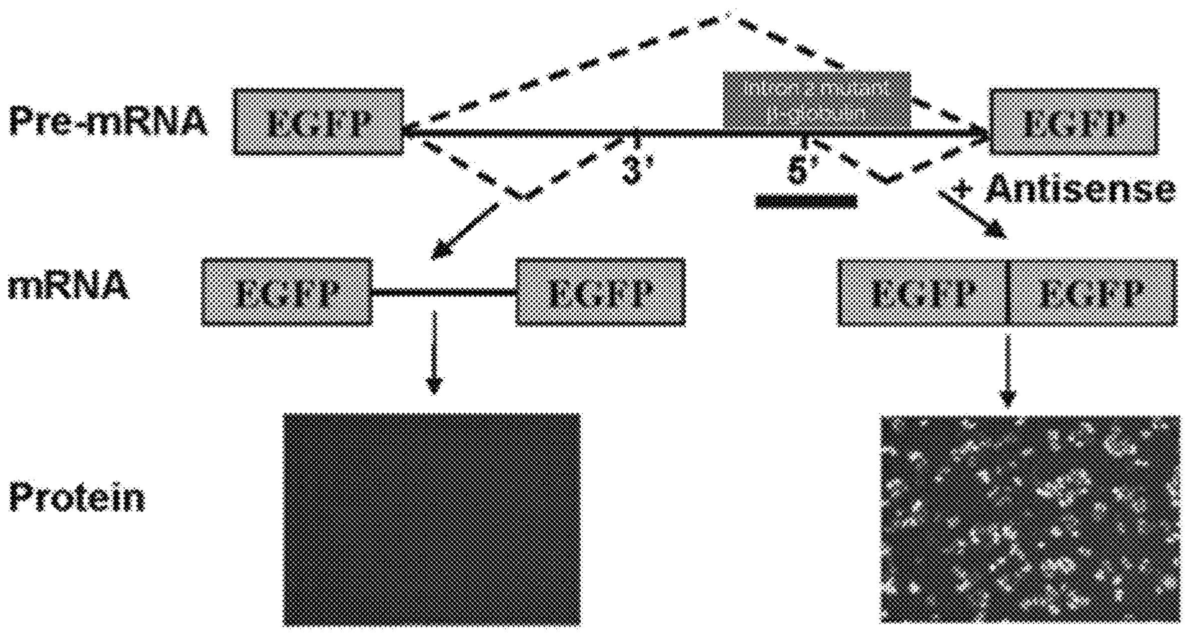
FIG. 1 shows a schematic of the experimental design for Example 1. The pre-mRNA line shows the coding sequence of EGFP (boxes) interrupted by intron 2 of the human p globin gene (thin line between boxes). The mutation at position 654 of the intron is also illustrated. The dotted lines above the pre-mRNA schematic show proper splicing of the intron. The dotted lines below the pre-mRNA schematic show improper splicing of the intron as a result of the mutation at position 654. The black bar shows the binding location of the designed antisense compound (AC). The mature, spliced mRNA line shows the mRNA sequence resulting from improper splicing (left) and from proper splicing (right). The protein line shows the lack of fluorescence from the nonfunctional protein resulting from translation of the improperly spliced mRNA sequence (left) and the restored fluorescence of the functional EGFP protein resulting from translation of the properly spliced mRNA sequence (right).

Target gene design. A missense EGFP gene ("EGFP-654") was designed with a mutated intron 2 of the human β globin gene interrupting the EGFP coding sequence. A mutation was introduced at nucleotide 654 of intron 2, which activated aberrant splice sites and led to retention of the intron fragment in spliced, mature mRNA, thereby preventing proper translation of EGFP. A schematic of the target gene, mutation site, splicing patterns, and resulting protein is provided in FIG. 1.

Oligonucleotide design. An antisense compound (AC) was designed to bind to and block the aberrant splice site of the target gene in order to correct pre-mRNA splicing and restore EGFP expression. The AC had the sequence "5'-GCTATTACCTTAACCCAG-3'" (SEQ ID NO:148) and was designed as a phosphorodiamidate morpholino oligomer (PMO) with a C6-thiol 5' modification (ENTR-0006, Table A). A schematic of the binding of the PMO to the target gene is provided in FIG. 1.

Cell penetrating peptide. A cell-penetrating peptide comprising cyclo(Phe-D-Phe-SNal-Arg-D-Arg-Arg-D-Arg-y-Glu)-b-Ala-b-Ala-Lys(Maleimide)-NH2 ("CPP12-Maleimide") (SEQ ID NO: 149) was formulated as a TFA salt. The peptide was synthesized using standard Fmoc chemistry according to the following procedure:

a. 1. DCM added to the vessel containing Rink amide resin (1 mmol, 1 g, 1.0 mmol/g) and Fmoc-Lys(Trt)-OH (1 eq) with $N_2$ bubbling.
b. 2. DIEA (4.0 eq) was added dropwise and mix for 4 hours.
c. 3. MeOH (0.2 mL) was added to the resin and mixed for 30 min.
d. 4. Solution was drained and washed with DMF for 5 times.
e. 5. 20% piperidine/DMF was added and reacted for 30 min.
f. 6. The solution was drained and washed with DMF for 5 times.
g. 7. Fmoc-amino acid solution was added to resin and mixed for 30 seconds, then activation buffer was added and mixed with $N_2$ bubbling for about 1 hour.
h. 8. Step 4 to 7 was repeated for the coupling of following amino acids. All couplings completions were confirmed by negative ninhydrin test. After couplings, resin was washed with DMF for 5 times.
i. 9. Allyl protecting group was removed by adding PhSiH3 (10eq) and Pd(PPh3)4 (0.1 eq) in DCM, repeat twice.
j. 10. Peptide was cyclized by HATU (1.0 eq) and DIEA (2 eq). The cyclization reaction was monitored by ninhydrin test. Resin was washed with DMF five times.
k. 11. The Trt protecting group was removed with 20% HIFP/80% DCM and the resulting primary amine was reacted with OAt activated 3-Maleimidopropionic acid using HATU/DIPEA for 2 hours
l. 12. After coupling, the resin was washed with MeOH for 3 times and dried under reduce pressure.

The table below shows the materials used for solid-phase peptide synthesis and coupling reagents:

| # | Materials | Coupling reagents |
|---|---|---|
| 1 | Fmoc-NH-PEG12-$CH_2CH_2COOH$ (1.0 eq) | DIEA (4.0 eq) |
| 2 | Fmoc-Glu-OAll (1.5 eq) | HATU (1.45 eq) and DIEA (3.0 eq) |
| 3 | D-Fmoc-Arg(Pbf)-OH (3 eq) | HBTU (2.85 eq) and DIEA (6.0 eq) |
| 4 | Fmoc-Arg(Pbf)-OH (3 eq) | HBTU (2.85 eq) and DIEA (6.0 eq) |
| 5 | D-Fmoc-Arg(Pbf)-OH (3 eq) | HBTU (2.85 eq) and DIEA (6.0 eq) |
| 6 | Fmoc-Arg(Pbf)-OH (3 eq) | HBTU (2.85 eq) and DIEA (6.0 eq) |
| 7 | Fmoc-3-(2-Nal)-Ala-OH (1.5 eq) | HATU (1.45 eq) and DIEA (3.0 eq) |

-continued

| # | Materials | Coupling reagents |
|---|---|---|
| 8 | D-Fmoc-Phe-OH (3 eq) | HBTU (2.85 eq) and DIEA (6.0 eq) |
| 9 | Fmoc-Phe-OH (3 eq) | HBTU (2.85 eq) and DIEA (6.0 eq) |
| 10 | Cyclization | HATU (1.00 eq) and DIEA (2.0 eq) |

The peptide was cleaved rom the solid-phase peptide synthesis resin an purified according to the following procedure:

a. Add cleavage buffer (95% TFA, 2.5% TIPS, 2.5% $H_2O$) to the flask containing the side chain protected peptide at room temperature and stir for 1 hour and repeat one time.
b. Filter and collect the peptide solution.
c. The peptide is concentrated under reduce press to give residue.
d. The resulting solid is dissolved in $CH_3CN$ and $H_2O$, then lyophilized to give crude peptide (2 g, 70.1% yield) as white solid.

Figure 2:
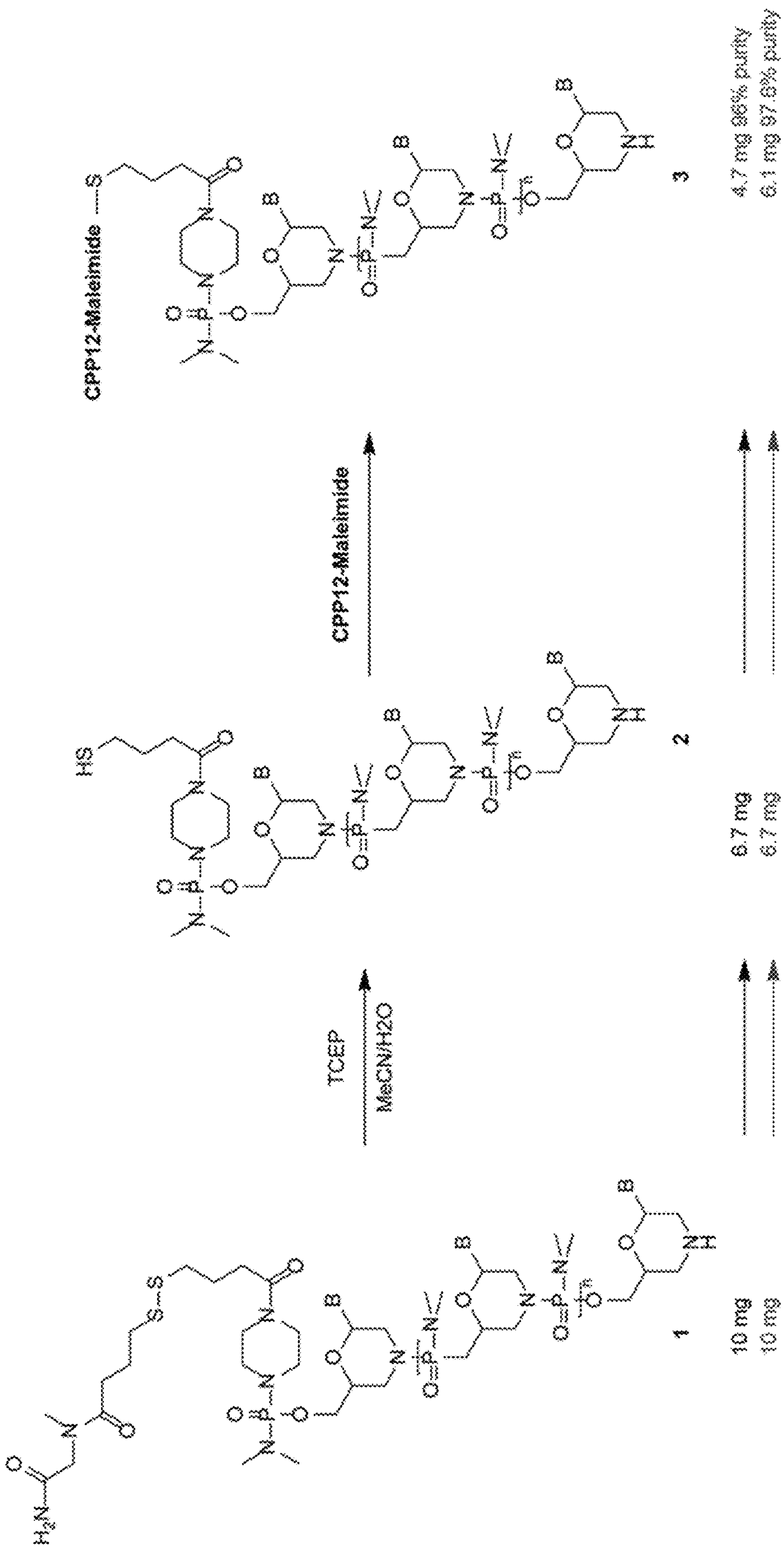
FIG. 2 shows the conjugation of an exemplary CPP and an exemplary AC, as described in Example 1.

CPP-AC conjugate formation. The steps of the conjugation process are shown in FIG. 2. Compound 1 was treated with 1M TCEP and MeCN/$H_2O$ to reduce the 5' end resulting in compound 2. To this solution of compound 2 (-13 mg, from reduction of −10 mg*2 PM0654-G) in $H_2O$/$CH_3CN$ (3:2, 2 mL) was added CPP12-Maleimide (4.5 mg, 1.2 eq, previously dissolved in $H_2O$/$CH_3CN$ (3:2), 98.4 uL) in one portion. Then to the mixture was added PB buffer (PH=7, 1 mL) and stirred for 1 hour at 25° C. Another batch (~12 mg) processed in parallel. LCMS shown the compound 1 was consumed completely and the solution was directly injected and purified by C18 reverse phase column. The mixture was first eluted with TEEA condition (2 mM TEAA in water, $CH_3CN$) and then eluted with TFA condition (0.07500 TFA in water, CH3CN) to give CPP12-Maleimide-PMO-654 (28 mg, 96.3% o purity, total yield: 56.8%).

Purification Conditions:

| Separation condition | |
|---|---|
| Dissolution condition | Dissolve in $H_2O$ |
| Instrument | GX-281D |
| Mobile Phase 1 | A: $H_2O$ (2 mM TEEA in $H_2O$)<br>B: $CH_3CN$ |
| Gradient 1 | 10-60% B 60 min. Separate the impurity that could be elute with TEEA condition. |
| Mobile Phase 2 | A: $H_2O$ (0.075% TFA in $H_2O$)<br>B: $CH_3CN$ |
| Gradient 2 | 20-50% B 60 min. Retention time: 14.5 min |
| Column | Luna 200*25 mm, C18, 10 um, 100Å + Gemini ® 150*30 mm, C18, 5 um, 110Å |
| Flow Rate | 20 mL/Min |
| Wavelength | 220/254 nm |
| Oven Tem. | Room temperature |

PMO synthesis protocol and linker installation at the 3' end. The following protocol was used to synthesize the PMO. For every step of the following synthesis protocol, it was ensured that the volume of reagent or solvent used completely covers resin (add more, if needed). Volumes listed below are estimates in number of milliliters per gram of resin used, which will increase during synthesis due to increasing resin size. All synthesis steps in the table were performed at room temperature. Prior to synthesis the resin is swelled in NMP for 1 hour. The resin was washed two times with DCM, followed by washing resin 2 times with 30DC TFE/DCM (15 mL/g of resin). The table below describes the PMO synthesis and linker installation protocol:

| Entry | Step | Volume | Time | Mixture |
|---|---|---|---|---|
| 1 | Wash | 7-24 mL/g | 15 seconds | 30% TFE/DCM |
| 2 | Deprotection | 7-24 mL/g | 15 minutes | CYTFA Solution |
| 3 | Deprotection | 7-24 mL/g | 15 minutes | CYTFA Solution |
| 4 | Wash | 7-24 mL/g | 15 seconds | DCM |
| 5 | Wash | 7-24 mL/g | 15 seconds | DCM |
| 6 | Neutral-ization | 7-24 mL/g | 5 minutes | Neutralization Solution |
| 7 | Neutral-ization | 7-24 mL/g | 5 minutes | Neutralization Solution |
| 8 | Wash | 7-24 mL/g | 15 seconds | DCM |
| 9 | Wash | 7-24 mL/g | 15 seconds | DCM or anhydrous DMI |
| 10 | Coupling | 4.6-7.3 mL/g | 4.25-5.0 hours | 3-6 eq monomer, 5-8 eq NEM in DMI (0.2-0.4M monomer & 0.5M NEM) |
| 11 | Wash | 7-24 mL/g | 15 seconds | DCM |
| 12 | Capping | 7-24 mL/g | 15 minutes | 0.55 M Benzoic anhydride + 0.55M NEM in NMP |
| 13 | Neutral-ization | 7-24 mL/g | 5 minutes | Neutralization Solution |
| 14 | Wash | 7-24 mL/g | 15 seconds | DCM |
| 15 | Wash | 7-24 mL/g | 15 seconds | 30% TFE/DCM |
| 16 | Wash | 7-24 mL/g | 15 seconds | 30% TFE/DCM |

CYTFA Solution=100 mM 4-cyanopyridine+100 mM TFA in 4:1 DCM:TFE+100 Ethanol.

Below are the solutions used for synthesis:

a. Neutralization Solution=5% DIPEA in 3:1 DCM:iP-rOH.
b. Coupling Solution=The number of equivalents and concentration will increase throughout synthesis using the following guide:
c. Residues 1–10=3 eq morpholino monomer, 5 eq NEM in DMI (0.2 M morpholino monomer, 0.5 M NEM), rt, 4.25 h.
d. Residue 1: couple for 5 h at rt.
e. Residues 11–20=4 eq morpholino monomer, 6.5 eq NEM in DMI (0.3 M morpholino monomer, 0.5 M NEM), rt, 4.25 h.
f. Residues 21–25=5 eq morpholino monomer, 8 eq NEM in DMI (0.3 M morpholino monomer, 0.5 M NEM), rt, 4.25 h.
g. Guanine morpholino monomers: couple for 4.75 h at rt.

Some couplings employed 6 eq morpholino monomer, 8 eq NEM in DMI (0.4 M morpholino monomer, 0.5 M NEM) at 45° C. for 4.75 hours.

The PMO synthesis resin with linker has the following structure:

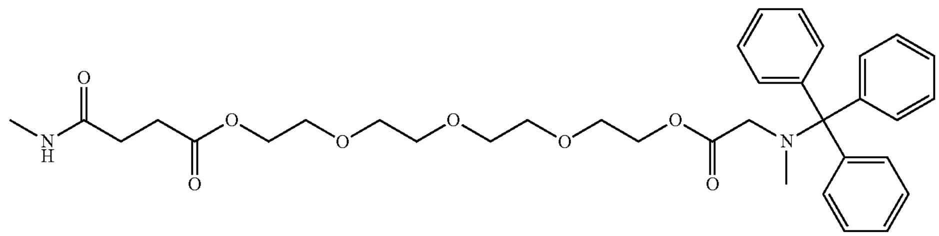 [SMILES: CNC(=O)CCC(=O)OCCOCCOCCOCCOC(=O)CN(C)C(c1ccccc1)(c1ccccc1)c1ccccc1]

The morpholino monomers used during coupling have the following structures:

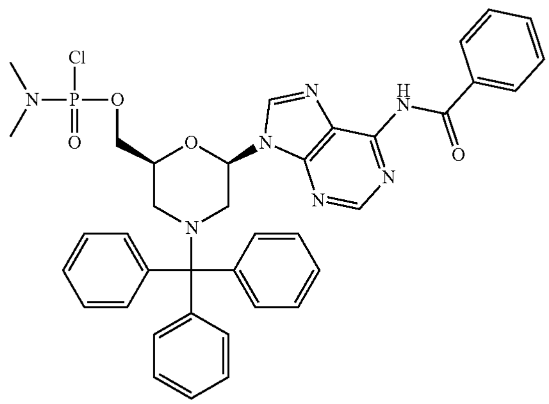

Adenine morpholino monomer

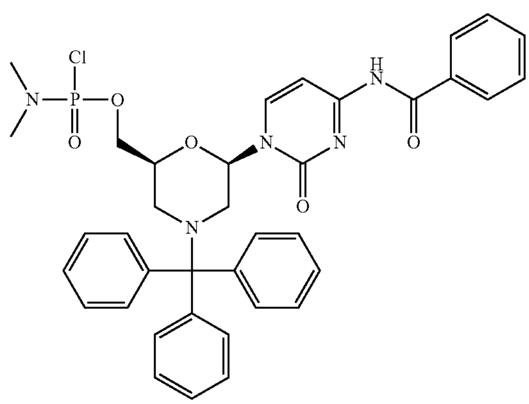

Cytosine morpholino monomer

-continued

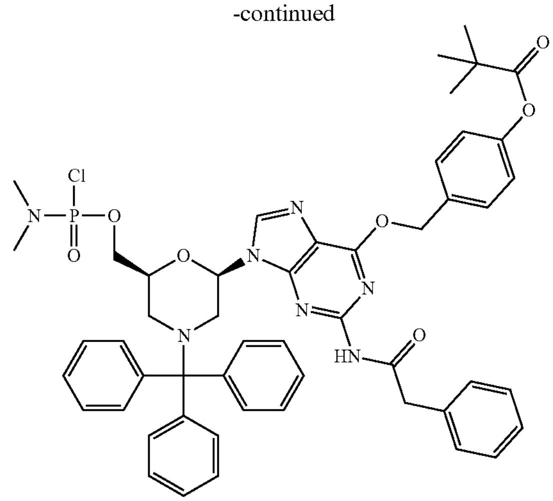

Guanine morpholino monomer

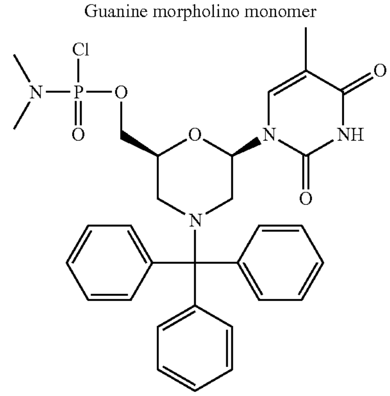

Thymine morpholino monomer

Below is the protocol for PMO synthesis:

Deprotection: Resin was first washed with 30% TFE/DCM solution and was allowed to stand for 15 seconds before draining. CYTFA solution was then added to the drained resin and reacted for 15 minutes. The resin was drained, then fresh CYTFA solution was added and reacted again for 15 minutes. The resin was drained and rinsed twice with DCM for 15 seconds before proceeding to neutralization.

Neutralization: Neutralization solution was added to the resin, stirred, and was allowed to stand for 5 minutes, then drained. A second wash of fresh neutralization solution was delivered to the resin, stirred, and reacted for 5 minutes. The resin was washed once with DCM and once with either DCM or anhydrous DMI before coupling.

Coupling: Using the guide listed above, two coupling solutions were made: 1) PMO monomer dissolved in DMI, and 2) NEM dissolved in DMI. These two solutions were mixed immediately before adding to the resin. The resin was stirred and reacted for 4.25-5 hours. The resin was washed one time with DCM.

Capping: A capping solution consisting of 0.55 M benzoic anhydride and 0.55 M NEM in NMP was added to the resin and reacted for 15 minutes. The resin was drained, and Neutralization solution was added to the resin to react for 5 minutes. The resin was drained again and was washed once with DCM, then twice with 30% TFE/DCM solution.

Post-synthesis: After the final coupling step, the resin-bound PMO can be stored until it is cleaved by washing the resin eight times with iPrOH, then drying the resin under vacuum at room temperature (Note: 3'-Trityl protecting group must still be on PMO for this). For PMO modifications at 3', the Trityl protecting group was removed, resin was neutralized, then appropriate bifunctional linker (TFA-protected amino or cyclooctyne) PFP ester (4 eq) in NMP and DIPEA (8 eq) were added to the resin and reacted for 3 hours. Solution was drained and resin was washed once with DCM, then twice with 30% TFE/DCM solution.

Cleavage: The following options can be utilized to perform PMO cleavage:

a. PMO was cleaved from resin with a 1:1 solution of ammonium hydroxide (25% ammonia, aqueous) and methylamine (8 mL/g) at 65° C. for 15 minutes.

b. PMO was cleaved from resin with ammonium hydroxide (25% ammonia, aqueous) at 65° C. for 16 hours.

c. PMO was cleaved from resin with 7M Ammonia in methanol solution (8 mL/g of resin) at 65° C. for 16 hours.

d. The deprotected PMO solution was then desalted prior to lyophilization and purification.

e. Resulting PMO was purified by Clarity 5 μm, C18 oligo reverse phase (250 mm×30 mm), AXIA packed, with 10-30% gradient over 40 min, flow rate of 30 mL/min, solvent A as water with 0.05% TFA and solvent B as Acetonitrile.

Design and preparation of CPP-PM0654 conjugates. Design of monovalent CPP-PMO (ENTR-0121, ENTR-0123), bivalent CPP-PMO (ENTR-0106, ENTR-0108, ENTR-0109 and ENTR-0110), trivalent CPP-PMO (ENTR-0111, ENTR-0112 and ENTR-0113) and mono CPP-NLS-PMO (ENTR-0047, ENTR-0168, ENTR-0203 and ENTR-0207) are shown in Table A. Specific structures of the conjugated AC are shown throughout this disclosure. For 3' covalent conjugation of primary amine modified PMOs, a solution of desired peptide-TFP ester in DMF (4 eq, 5 mM) was added to a solution of PMO-3'-primary amine (1 equivalent, 2 mM) in PBS-10X. Reaction proceed to completion in 4-8 hours at room temperature as confirmed by LCMS (Q-TOF), using BEH C18 column (130 Å, 1.7 μm, 2.1 mm×150 mm), buffer A: water, 0.1% FA), buffer B: acetonitrile, 0.1% FA), flow rate (0.3 mL/min), starting with 2% buffer B and ramping up to 70% for 11 min for a total of 20 min run. For 3' or 5' conjugation via click reaction, a solution of peptide-azide in nuclease-free water (1 mM) was added to the PMO-3'-cyclooctyne or cyclooctyne-5'-PMO solids. The mixture was vortexed to dissolve the peptide-PMO conjugate, centrifuged to settle the solution, and incubated at room temperature for 8-12 hours for completion as confirmed by LCMS (Q-TOF). For purifications, crude mixtures were diluted with DMSO, loaded onto a C18 reverse-phase column (150 mm*21.2 mm), flow rate of 20 mL/min and purified by an appropriate gradient over 20 min using water with 0.05% TFA and acetonitrile as solvents. Desired fractions were pooled, pH of the solution was adjusted to 5-6 by 1M NaOH and the solution underwent the lyophilization process, affording white lyophilized powder. For in vitro and in vivo formulations, the conjugates were reconstituted in appropriate amount of PBS or Saline for the desired concentration (2-10 mg/mL). Concentration of the non LSR labeled conjugates were measured by preparing 10, 20, and 50-fold dilutions in formulated buffer and reading the absorbance at 260 nm or 280 nm using a nanodrop. Once the linear range of dilution achieved, the absorbance was measured in triplicates and concentration was calculated using the average absorbance and $\varepsilon_{260}$ or $\varepsilon_{280}$. $\varepsilon_{280}$ for conjugates were calculated by the following formula: E280=100356+(n*3550); n=number of CPP. For LSR modified PMOs, the concentrations were measured at 566 nm with $\varepsilon_{566}$=100000 $LMol^{-1}Cm^{-1}$ The diluted samples were analyzed by LCMS (Q-TOF) for the conjugate identity confirmation. Table below summarizes the calculated MW and experimental MWs. All experimental MVWs reasonably matched the calculated average MVW with expected ±6 Da assay variation.

| Name | Calculated MW | Experimental Average MW | Purity |
|---|---|---|---|
| ENTR 0006 | 6038.19 | | |
| ENTR 0070 | 6151.27 | 6148.22 | >99 |
| ENTR 0059 | 7411.06 | 7409.78 | 99 |
| ENTR 0123 | 9409.43 | 9407.89 | 91 |
| ENTR 0121 | 7938.3 | 7933.15 | 97 |
| ENTR 0106 | 9893.56 | 9887.37 | 96 |
| ENTR 0108 | 10765.09 | 10763.74 | 90 |
| ENTR 0109 | 11259.8 | 11256.91 | 95 |
| ENTR 0110 | 11964.52 | 11961.21 | 99 |
| ENTR 0111 | 12120.7 | 12117.40 | 97 |
| ENTR 0112 | 12862.6 | 12858.85 | >99 |
| ENTR 0113 | 13919.86 | 13916.36 | 97 |
| ENTR 0047 | 9039.81 | 9034.81 | 99 |
| ENTR 0168 | 10444.78 | 10447.3 | 95 |
| ENTR 0203 | 9293.79 | 9295.2 | 92 |
| ENTR 0207 | 9532.05 | 9532.8 | >99 |

Target cells. HeLa cells were engineered to stably express EGFP-654 ("HeLa-654"). Untreated cells produced the improperly spliced mRNA retaining a portion of the intron sequence, resulting in non-functional missense EGFP protein expression.

Fluorescence assays. HeLa-654 cells were mock-treated (control), treated with the PMO alone at different concentrations (5 or 20 μM), or treated with the CPP12-PMO conjugate at different concentrations (0.6, 1.2, 1.8, 2.5, 5, or 10 μM) and incubated for 24 hours. The cells were then imaged with fluorescence microscopy and the fluorescence of the cells was quantified via FACS.

Figure 3:
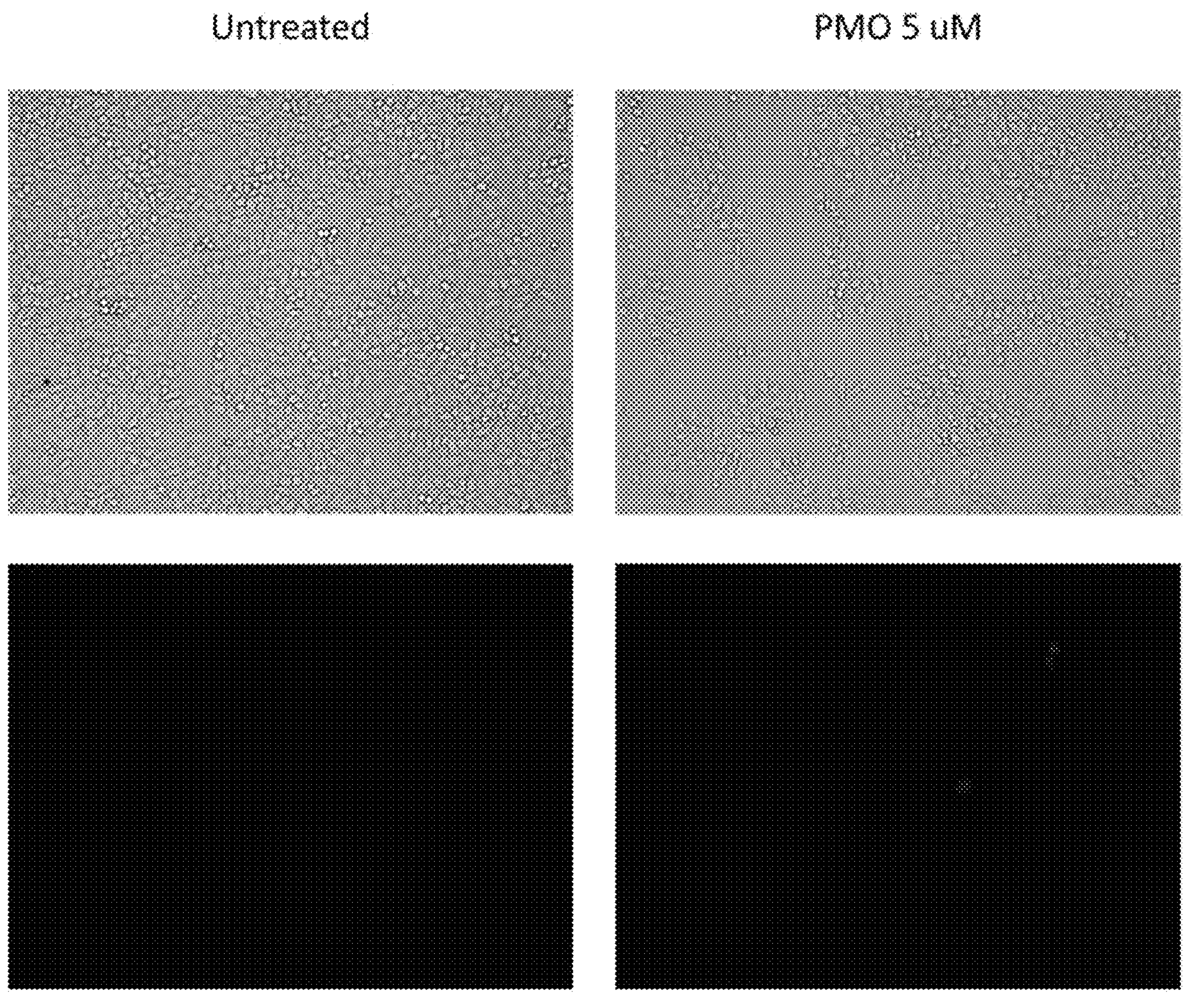
FIG. 3 shows the bright field microscopy (top) and fluorescence microscopy (bottom) imaging of untreated (mock-treated) control HeLa-654 cells (left) and 5 μM PMO-treated HeLa-654 cells (right), as described in Example 1.
Figure 4:
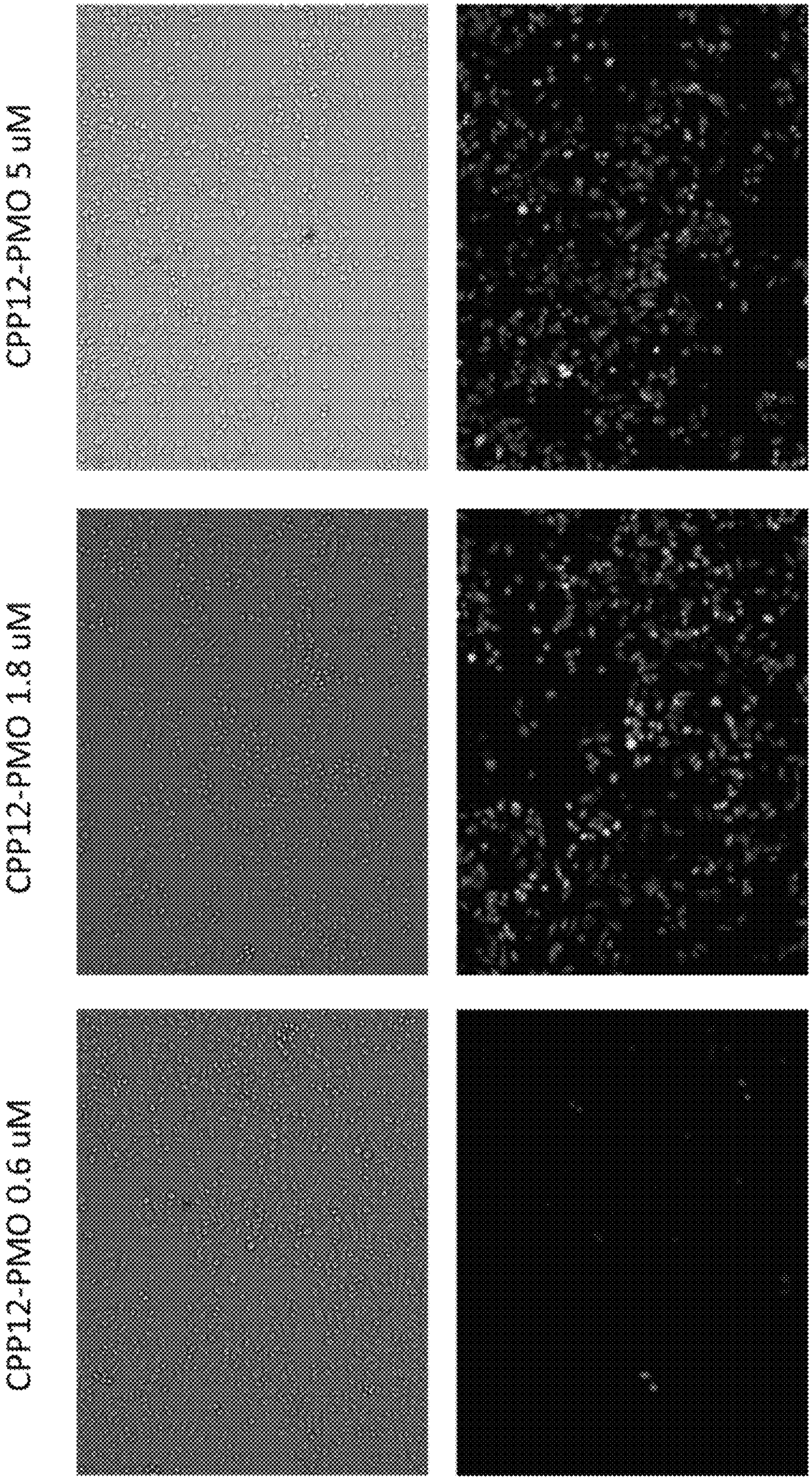
FIG. 4 shows the bright field microscopy (top) and fluorescence microscopy (bottom) imaging of HeLa-654 cells treated with 0.6 μM (left), 1.2 μM (middle), or 1.8 μM (right) CPP-PMO, as described in Example 1.
Figure 5:
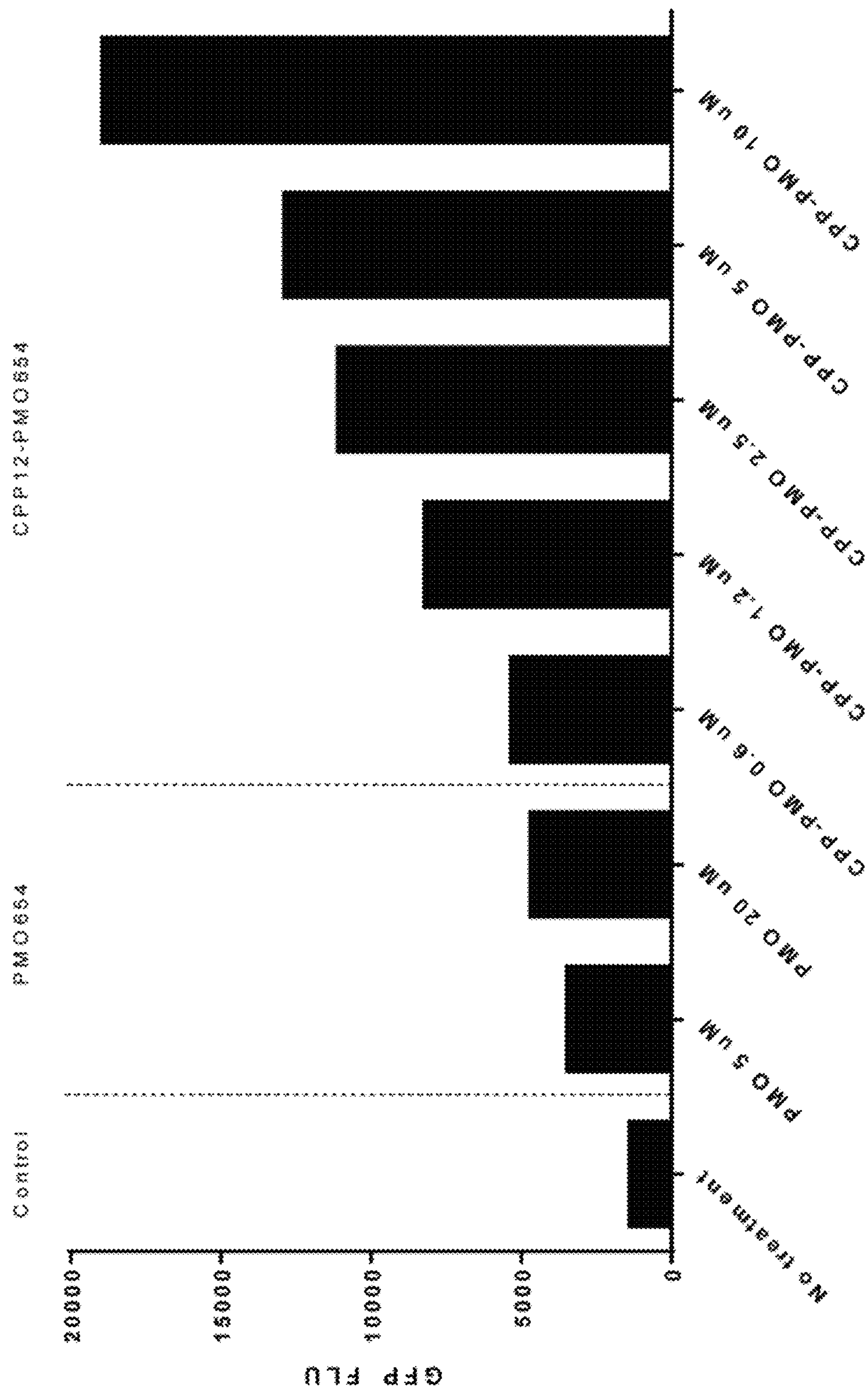
FIG. 5 shows the results of FACS analysis of untreated, PMO-treated (ENTR-0070, PM0654, Table A)-treated, and CPP-PMO-treated (ENTR-0121, CPP12-PM0654, Table A)HeLa-654 cells, as described in Example 1.

Results. FIG. 3 and FIG. 4 show the results of the fluorescence microscopy imaging of the mock-treated and treated cells. FIG. 3 demonstrates that mock-treated cells did not produce functional fluorescent EGFP protein and that treatment with 5 μM PMO barely increased the functional fluorescent protein expression. FIG. 4 shows that treatment with 0.6 μM CPP-PMO produced a small increase in fluorescence, and that treatment with 1.8 μM or 5 μM CPP-PMO produced a significant increase in fluorescence, indicating the proper splicing of the pre-mRNA sequence. FIG. 5 shows the results of the FACS quantification of fluorescence intensity for the control and treated cells, demonstrating that PMO treatment and CPP-PMO treatment produced dose-dependent increases in functional fluorescent protein production. The results shown in FIG. 5 also show the remarkable increase in efficacy of treatment with the PMO conjugated to CPP versus the PMO alone: treatment with 10 μM CPP-PMO produced nearly 4× the fluorescence reading at half the concentration, compared to 20 μM PMO treatment. These results demonstrate that CPP conjugated ACs are effective in binding to a target pre-mRNA sequence and restoring functional protein production.

Figure 34:
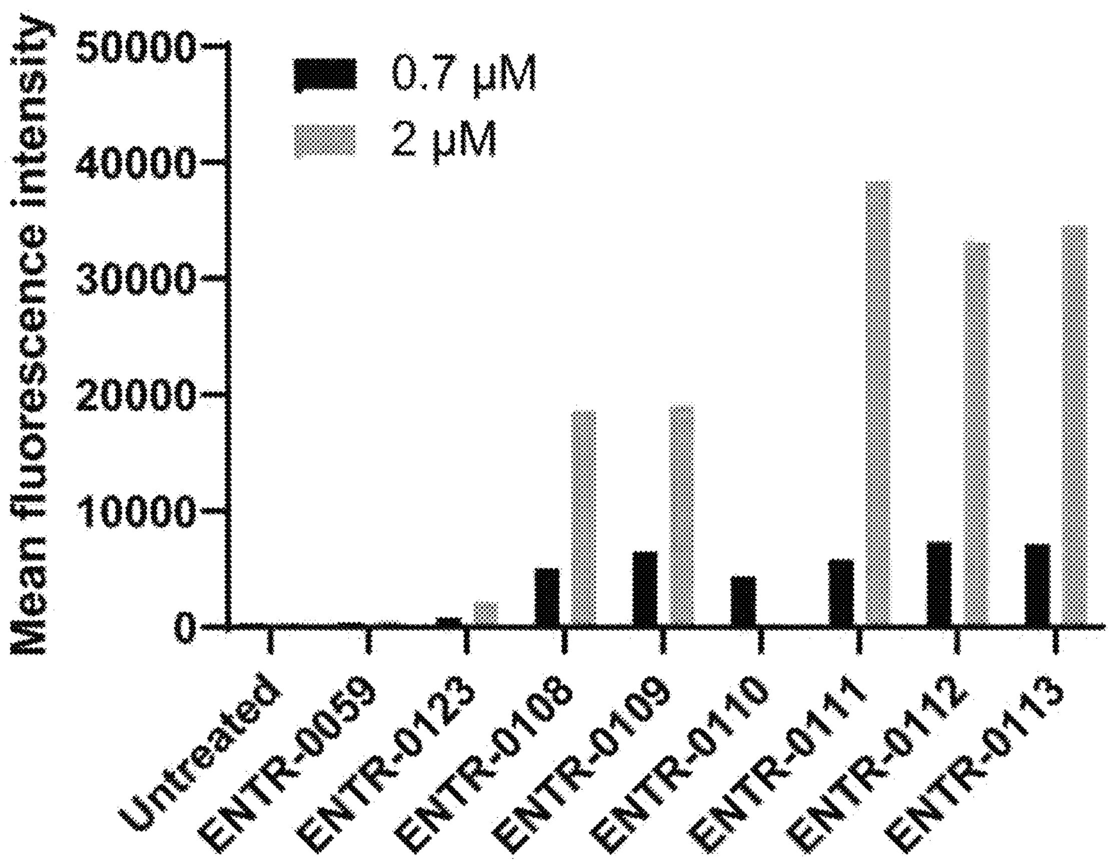
FIG. 34 shows the cellular uptake results of rhodamine (LSR) labeled PMO and CPP-PMO conjugates quantified by the fluorescent activated cell sorting analysis using HeLa-654 cells were treated with 0.7 μM or 2 μM of PMO-LSR (ENTR-0059, Table 1), monovalent CPP-PMO-LSR (ENTR-0123), bivalent CPP-PMO-LSR (ENTR-0108, ENTR-0109, or ENTR-0110, Table 1), or trivalent CPP-PMO-LSR (ENTR-0111, ENTR-0112, or ENTR-0113) for 48 hours, as described in Example 1.
Figure 35:
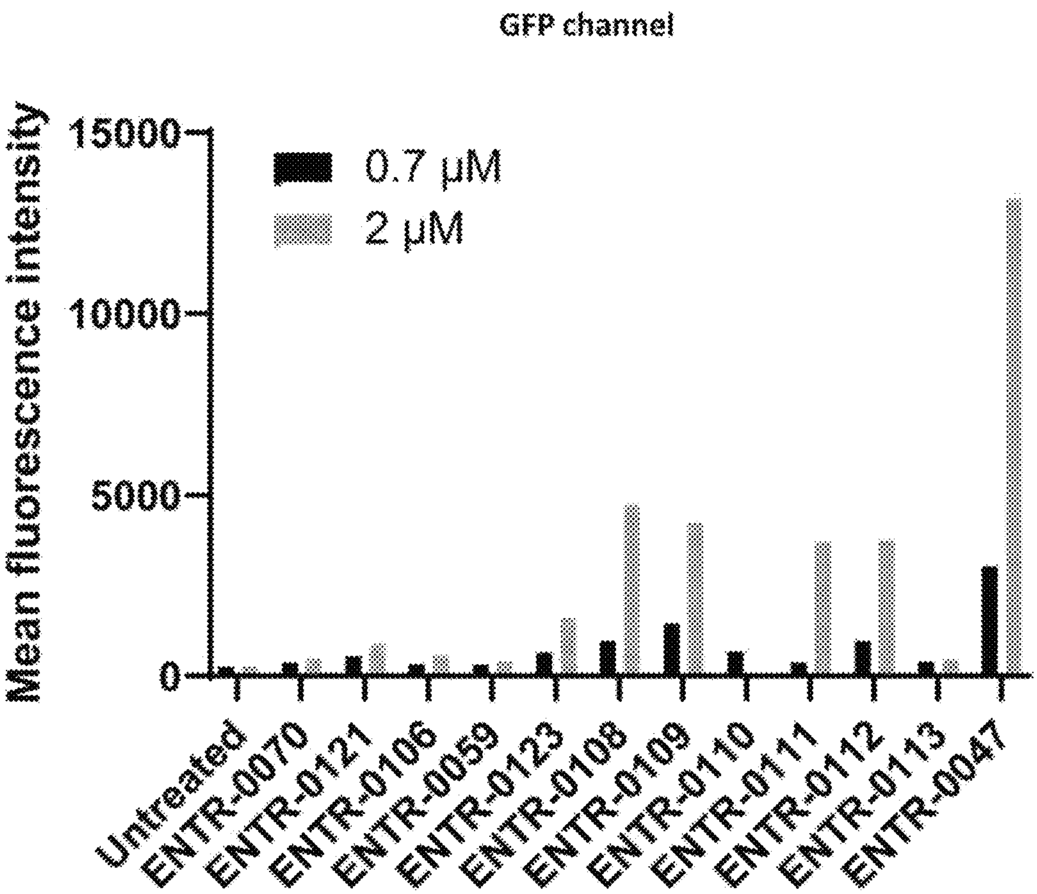
FIG. 35 shows the results of cellular activity as quantified by EGFP correction by fluorescent activated cell sorting analysis using HeLa-654 cells after treatment with medium, 0.7 μM or 2 μM of PMO (ENTR-0059 or ENTR-0070, Table 1), monovalent CPP-PMO conjugates (ENTR-0121 or ENTR-0123, Table 1), bivalent CPP-PMO conjugates (ENTR-0106, ENTR-0108, ENTR-0109 or ENTR-0110, Table 1), trivalent CPP-PMO (ENTR-0111, ENTR-0112, or ENTR-0113, Table 1) or CPP-NLS-PMO (ENTR-0047) for 48 hours, as described in Example 1.
Figure 36:
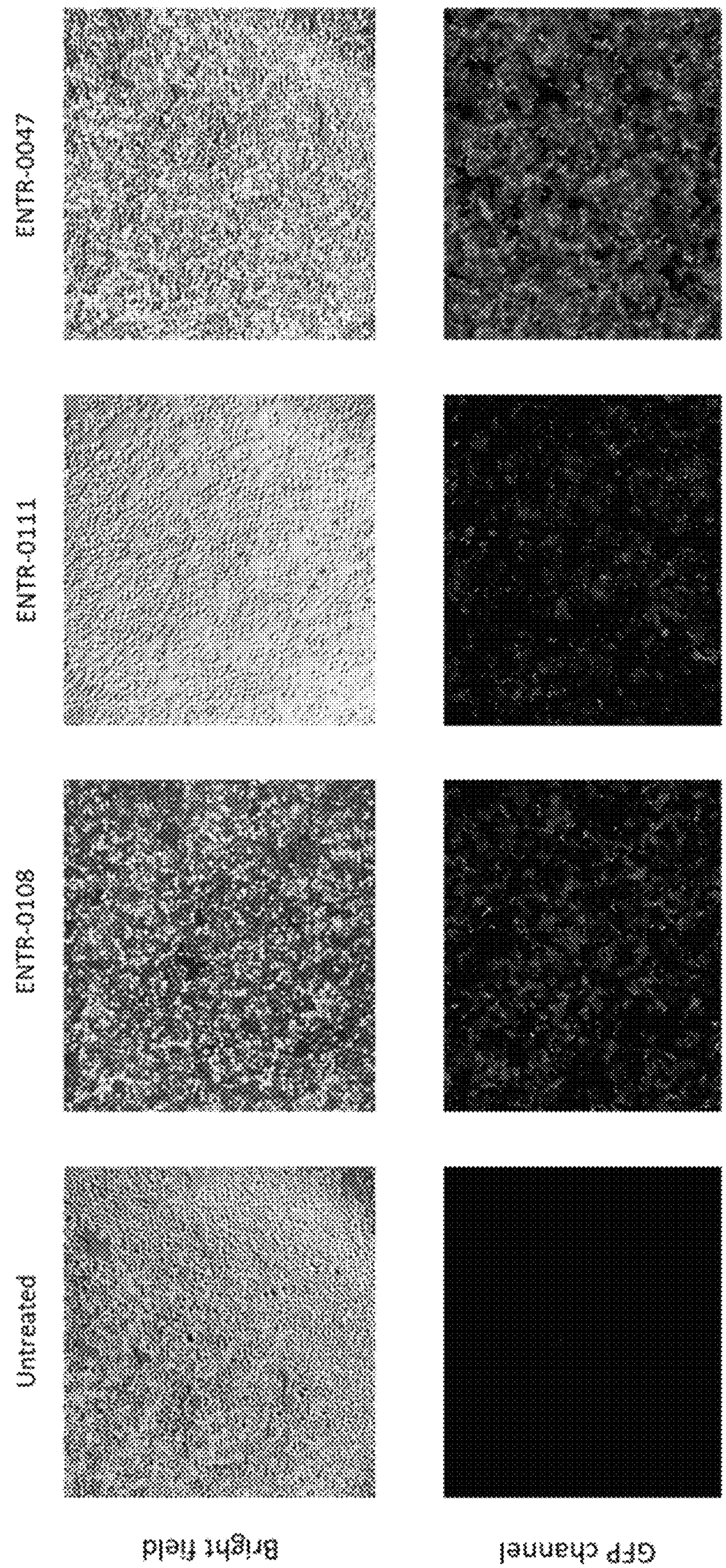
FIG. 36 shows the cellular activity of various CPP-conjugated PMO constructs on HeLa-654 cells after 48 hr treatment of medium, 2 μM bidentate CPP-PMO (ENTR-0108, Table 1), tridentate CPP-PMO (ENTR-0111, Table 1) and CPP-NLS-PMO (ENTR-0047, Table 1). Bright field microscopy (top) and fluorescence microscopy (bottom, GFP channel) images were captured as described in Example 1.
Figure 37:
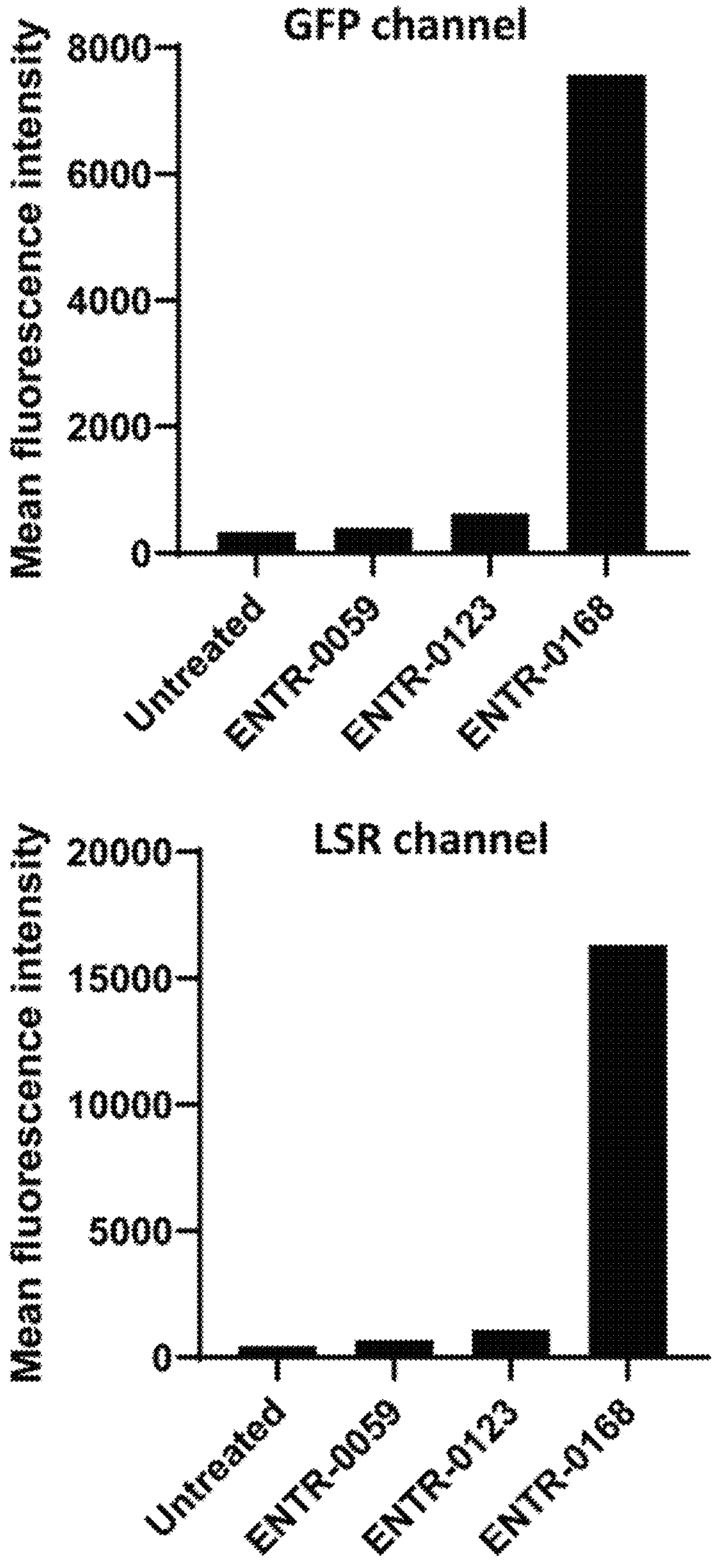
FIG. 37 shows the results of fluorescent activated cell sorting analysis (Top: GFP channel; Bottom: LSR channel) of HeLa-654 cells treated for 24 hr with 2 μM of PMO-LSR (ENTR-0059, Table 1), CPP-PMO-LSR (ENTR-0123, Table 1), or CPP-NLS-PMO-LSR (ENTR-0168, Table 1), as described in Example 1.

Structure activity relationship of CPP for PM0654 delivery. FIG. 34 shows the cellular uptake results of 0.7 μM or 2 μM rhodamine (LSR) labeled PMO and CPP-PMO conjugates quantified by FACS using HeLa-654 cells treated for 48 hours. Untreated and PMO (ENTR-0059) treated cells did not show lissamine-rhodamine (LSR) red fluorescent signal. Conjugation of mono-valent CPP12 (ENTR-0123) showed limited increase of the LSR fluorescence, while conjugation of bivalent (ENTR-0108, ENTR-0109) and trivalent (ENTR-0112, ENTR-0113) CPP12 modified PMOs significantly increase the cellular uptake in a dose dependent manner as indicated by the LSR fluorescence. FIG. 35 shows the cellular activity as quantified by GFP correction by FACS analysis treated with 0.7 μM or 2 μM PMO and CPP-PMO conjugates using HeLa-654 cells for 48 hours. Untreated and PMO (ENTR-0059 and ENTR-0070) treated cells show minimal GFP correction as expected. Monovalent CPP-PMO treated cells showed xx fold increase of GFP signal increase over PMO itself (comparing ENTR-0123 vs ENTR-0059). Additionally, the bivalent (ENTR-0108, ENTR-0109) and trivalent (ENTR-0112, ENTR-0113) conjugates significantly increase the GFP correction. Surprisingly, conjugation of PMO with monovalent CPP12 but with additional Nuclear Localization Sequence (PKKKRKV (SEQ ID NO: 131)) NLS sequence outperformed all the bivalent and trivalent CPP12 conjugation, by at least 3-fold (ENTR-0047). FIG. 36 shows the bright field microscopy and fluorescence microscopy images of HeLa-654 cells treated with vehicle PBS control (untreated), bidentate CPP-PMO (ENTR-0108), tridentate CPP-PMO (ENTR-0111), and CPP-NLS-PMO construct (ENTR-0047), which is consistent with FACS analysis shown in FIG. 35. To further explore different conjugation chemistry for the CPP-NLS constructs for PMO conjugation, EGFP654 cells were also treated with CPP-NLS-PMO conjugates (ENTR-0168) before analyzed by FACS and microscopic analysis. FIG. 37 shows that CPP-NLS-PMO-LSR (ENTR-0168) increased the GFP fluorescence by 10-fold and LSR fluorescence by 15-fold relative to monovalent CPP-PMO-LSR (ENTR-0123).

Figure 38:
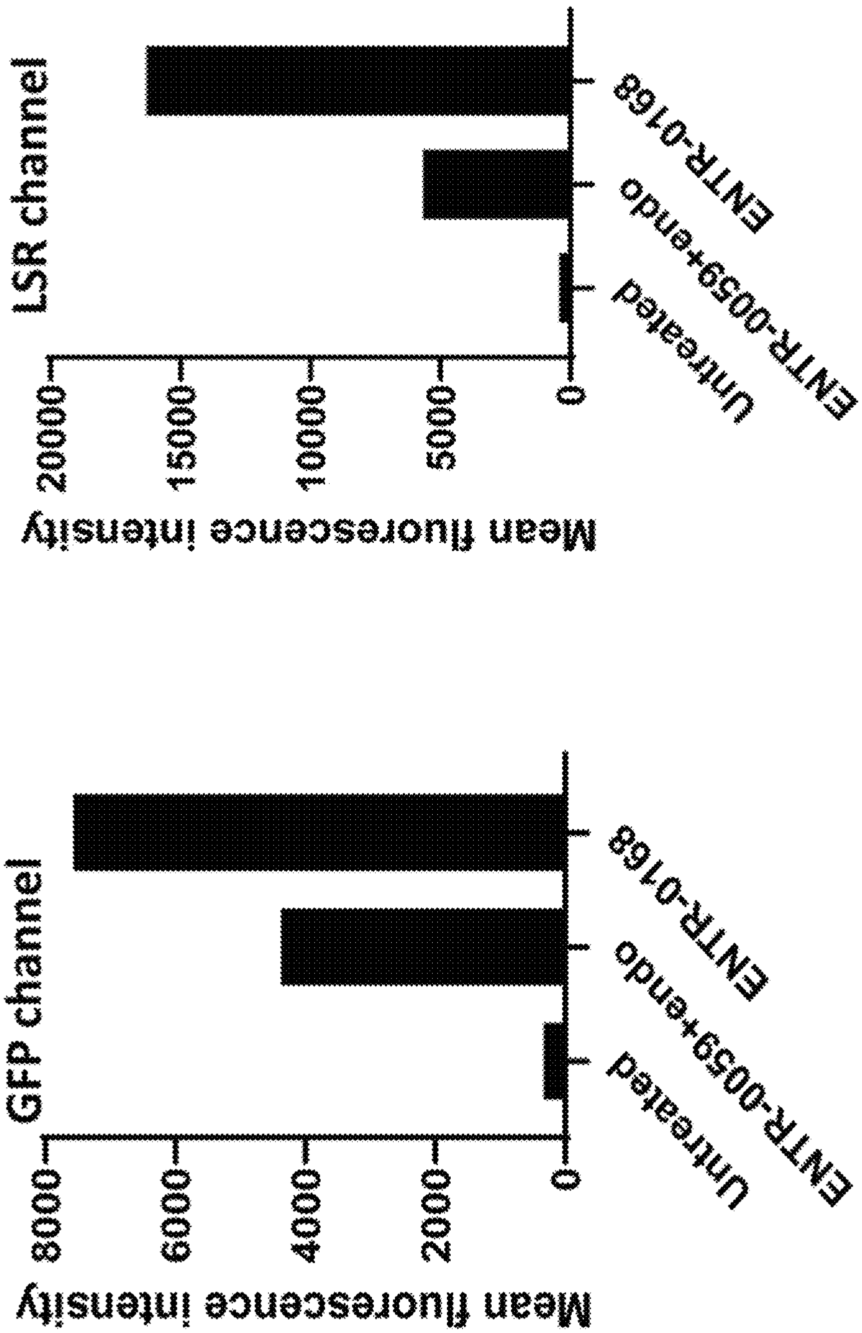
FIG. 38 shows the results of fluorescent activated cell sorting analysis (Top: GFP channel; Bottom: LSR channel)

Comparison of cellular uptake with transfection reagent. Endo-Porter (GENETOOLS, LLC) is a transfection reagent designed to deliver neutrally charged PMO oligos into cells and have been commonly used in the literature. The cellular uptake efficiency and cellular activity of CPP-NLS-mediated delivery was also compared to Endo-Porter mediated uptake as analyzed by FACS FIG. 38. and FIG. 39. ENTR-0168 exhibit higher GFP and LSR fluorescence than the commercially transfection reagent Endo-Porter transfected PMO (ENTR-0059+endo), indicating that CPP-NLS conjugation has higher functional cellular uptake capability than Endo-Porter. FIG. 39 shows the bright field microscopic and fluorescence microscopic images of the treated HeLa-654 cells, which confirms the findings from FACS analysis shown in FIG. 38. To ensure that LSR fluorescent dye label did not modulate the cellular uptake, two additional CPP-NLS-PMO for EGFP654 were also prepared: ENTR-0203 and ENTR-0207. ENTR-0207 contained a cleavable linker, whereas ENTR-0203 contained a non-cleavable linker.

The structure of ENTR-0203 is below:

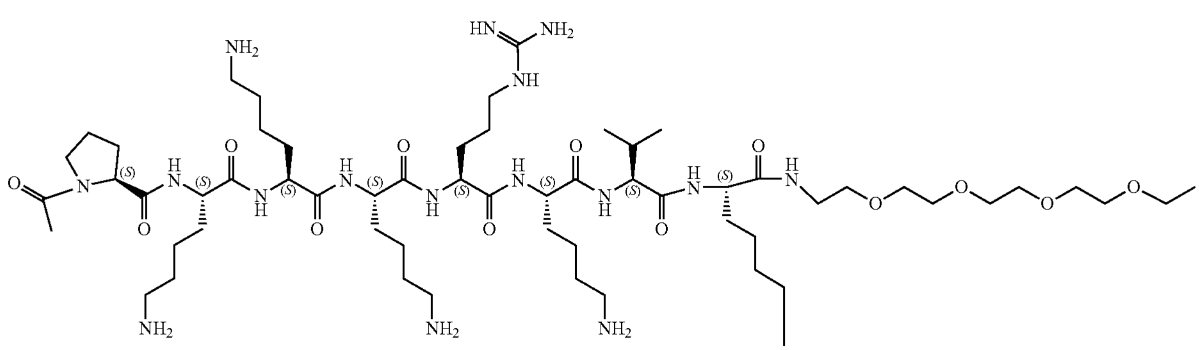

-continued
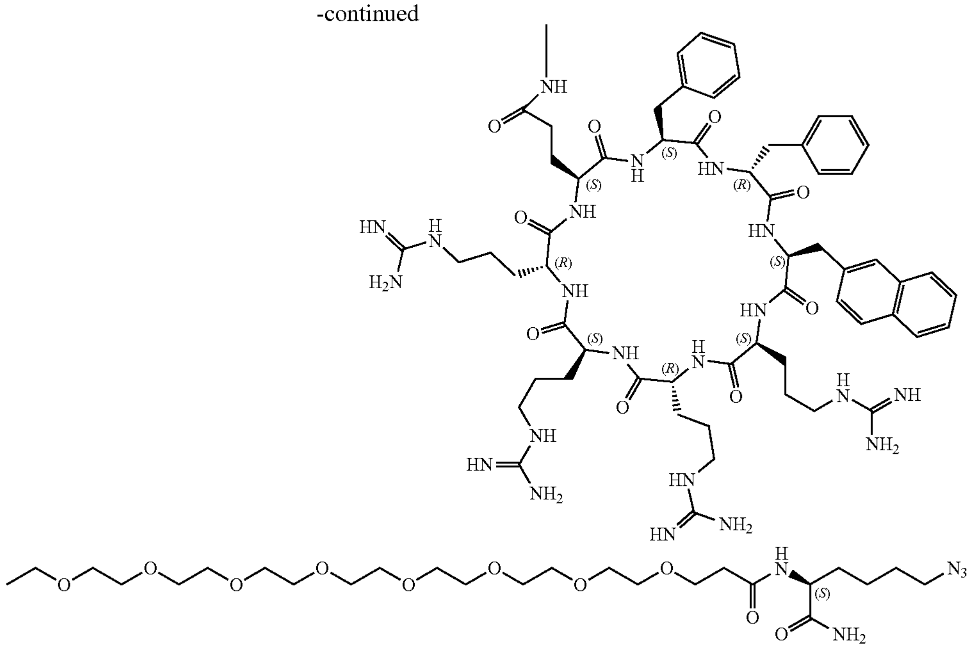
The structure of ENTR-0207 is below:

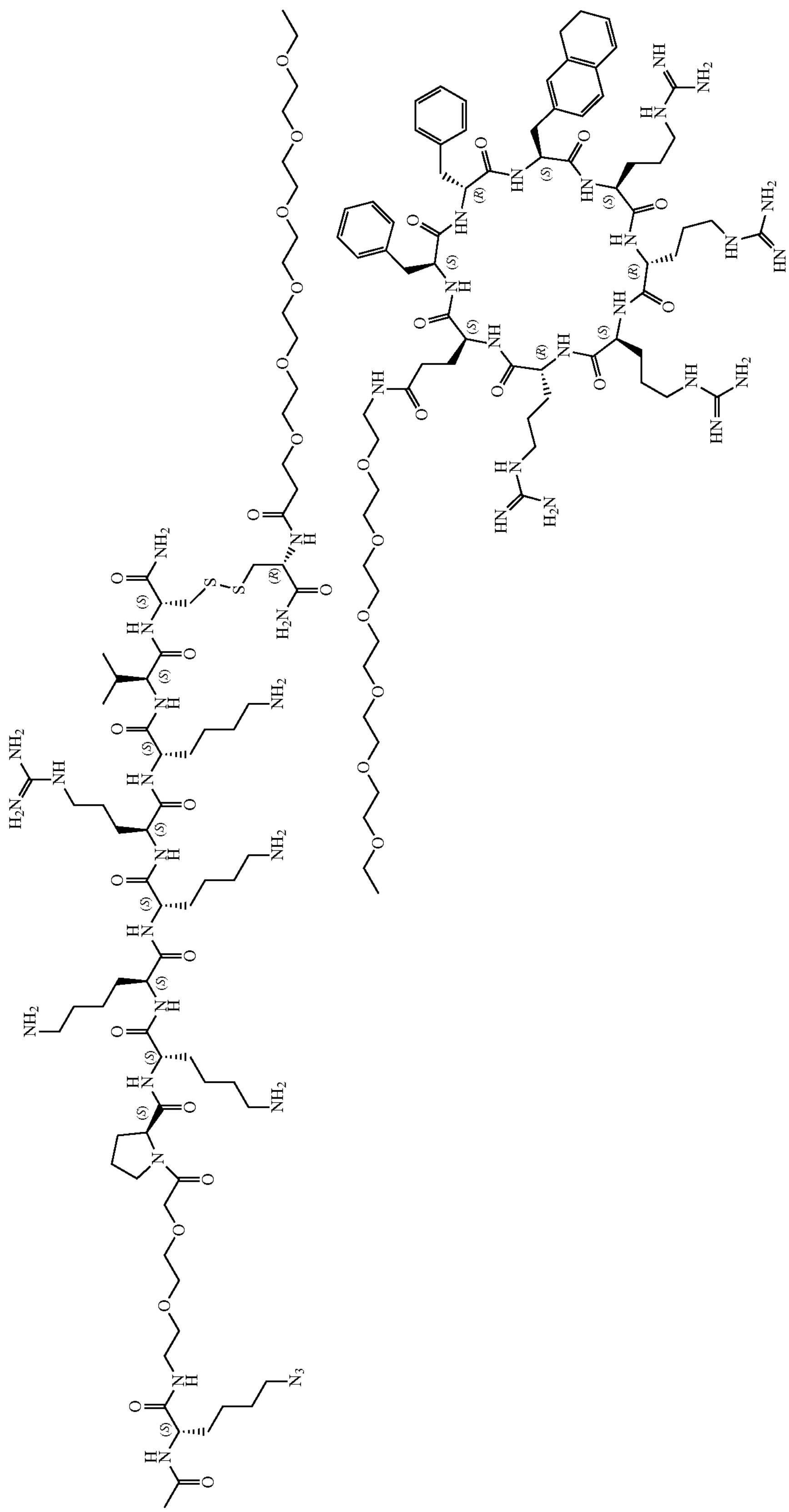

The table below provides additional information about the constructs evaluated:

| Identifier | Description | Sequence |
|---|---|---|
| ENTR-0047 | PMO654-NLS-ss-CPP12 | 5'-GCT ATT ACC TTA ACC CAG-3-NLS-ss-CPP12 (all PMO monomers)(SEQ ID NO: 233) |
| ENTR-0168 | NLS-CPP12-PMO654-LSR | (Ac-NLS-Lys(CPP12)-PEG12-K(N3))-5'-GCT ATT ACC TTA ACC CAG-3'-Lissamine Rho (all PMO monomers)(SEQ ID NO: 234) |
| ENTR-0203 | PMO654-CPP12-NLS | 5'-GCT ATT ACC TTA ACC CAG-3'-click-K-PEG12-Lys(CPP12)-NLS-Ac (all PMO monomers) (SEQ ID NO: 235) |
| ENTR-0207 | PMO654-NLS-CPP12 | 5'-GCT ATT ACC TTA ACC CAG-3'-click-Lys(N3)-miniPEG-NLS-ss-PEG12-CPP12 (all PMO monomers)(SEQ ID NO: 236) |

Both constructs showed dose dependent cellular activity (0-10 μM) as analyzed by the corrected GFP fluorescence (FIG. 24, FIG. 25, FIG. 26, FIG. 27).

Example 2. Use of Cell-Penetrating Peptides Conjugated to Oligonucleotides for Splicing Correction in Mice Mice. Mice used in this study were genetically engineered to express the missense EGFP-654 gene.

Study design. Mice expression EGFP-654 were injected with PBS, CPP-PMO (also called "CPP12-PMO"), or PMO without CPP, through IV/IP/IM administrations at different doses as indicated (IV=10 mpk, IP=30 mpk, IM=1/3/10 mpk). (IV: intravenous; IP: intraperitoneal; IM: intramuscular; mpk: mg of compound/kg of body weight) Each mouse received one injection per day for 4 days. Mice were sacrificed and tissue samples were collected either 24 or 96 hours after last injection. Total RNA were extracted from tissue samples and analyzed by RT-PCR to visualize the efficiency of splicing correction.

Figure 6:
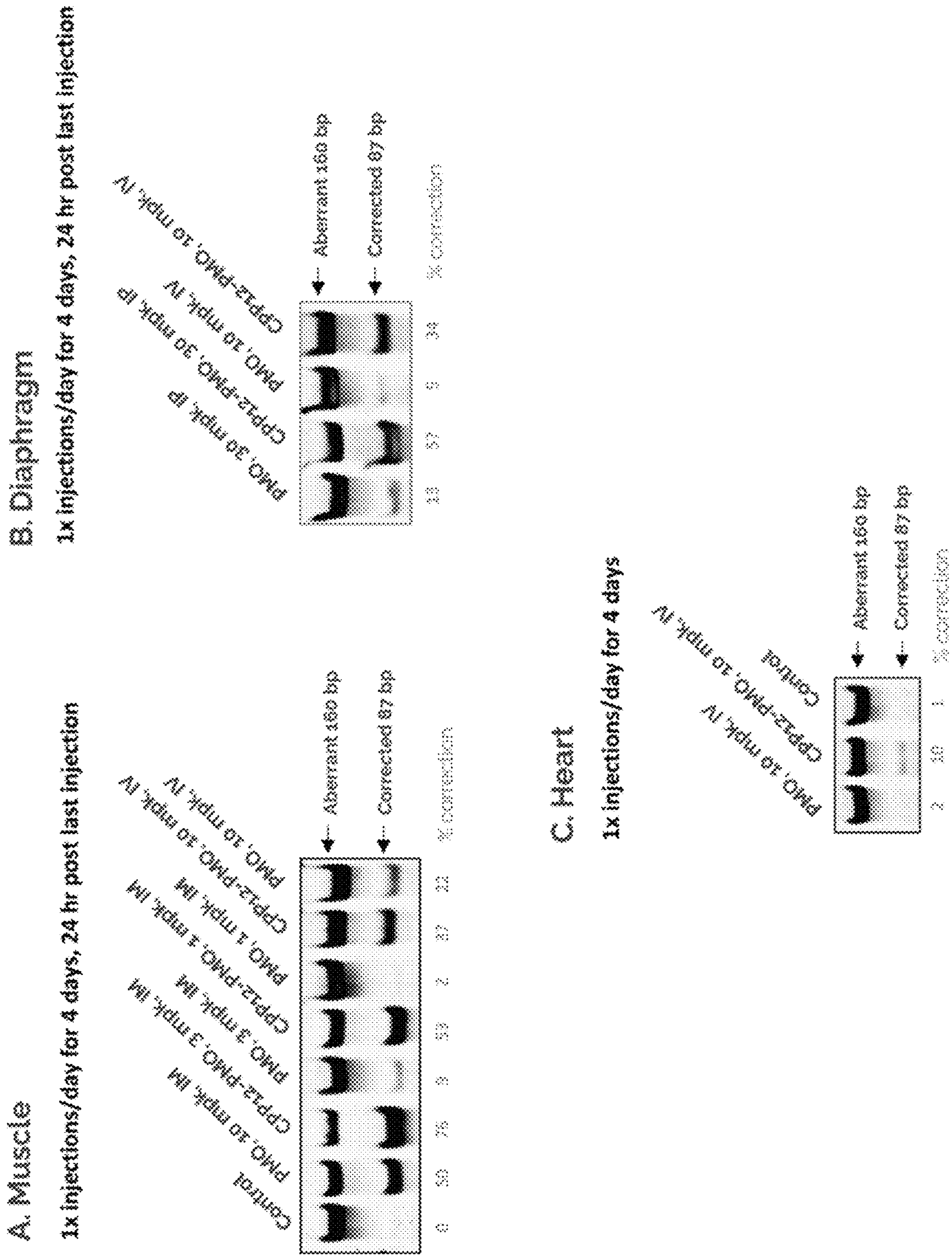
FIG. 6 shows the results of RT-PCR analysis of splicing correction of EGFP654 in mice tissue samples after PMO (ENTR-0070, PM0654, Table A) treatment or CPP-PMO (ENTR-0070, PM0654, Table 1) treatment, as described in Example 2.

Detection of splicing correction by RT-PCR. Untreated cells in control mice produced improperly spliced EGFP-654 mRNA retaining a portion of the intron sequence, resulting in non-functional missense EGFP mRNA expression. As shown in FIG. 6, RT-PCR using forward primer 5'-CGTAAACGGCCACAAGTTCAGCG-3' (SEQ ID NO: 150) and reverse primer 5'-GTGGTGCAGATGAACTTCAGGGTC3' (SEQ ID NO: 151) of the tissue samples without splicing correction resulted predominantly in an "aberrant", 160 bp gene fragment. On the other hand, splicing corrected EGFP-654 mRNAs displayed a "corrected", 87 bp fragment by RT-PCR.

Analysis of splicing correction. The degree (percentage) of splicing correction detected by RT-PCR was calculated using the following equation: % correction=(intensity of 87 bp fragment band)/(intensity of 160 bp fragment band+intensity of 87 bp fragment band). As shown in FIGS. 6A-C, PMO treatment increased the percentage of splicing corrected EGFP-654 in the tissue sample. Remarkably, as shown in Table B, tissue samples from CPP-PMO treated mice displayed a higher percentage of splicing correction as compared to samples from PMO treated mice, demonstrating that CPP conjugated ACs are more efficient at cell penetration and mediating splicing correction in mice.

TABLE B

| In vivo splice modulation potency | | | |
|---|---|---|---|
| Tissue | IM Muscle | IV diaphragm | IV heart |
| PMO | 2% | 5% | 1% |
| EEV12-PMO | 53% | 34% | 10% |
| Fold Difference | 26.5x | 6.8x | 10x |

Example 3A. Use of Cell-Penetrating Peptides Conjugated to Oligonucleotides for Splicing Correction of Dystrophin in Wild Type Mouse Model The compounds of Tables Bi, B2, B3, and B4 are evaluated in Examples 3A and 3B. Exemplary experiments are described below. The same techniques are used to evaluate any compounds of Table B1, Table B2, Table B3, or Table B4.

TABLE B1

| Compounds that target DMD | | |
|---|---|---|
| Oligo# | Design | Target |
| ENTR-0013 | 5'-GGC CAA ACC TCG GCT TAC CTG AAA T-3' (all PMO monomers)(SEQ ID NO: 237) | Murine DMD exon 23 |
| ENTR-0017 | 5'-GGC CAA ACC TCG GCT TAC CTG AAA T-3'-C3-NH2 (all PMO monomers)(SEQ ID NO: 238) | Murine DMD exon 23 |
| ENTR-0066 | Cyclooctyne-5'-GGC CAA ACC TCG GCT TAC CTG AAA T -3' (all PMO monomers)(SEQ ID NO: 239) | Murine DMD exon 23 |
| ENTR-0068 | NH2-5'-C3- GGCCAAACCTCGGCTTACCTGAAAT -3'-C3-NH2 (all PMO monomers)(SEQ ID NO: 240) | Murine DMD exon 23 |

TABLE B1-continued

| Compounds that target DMD | | |
|---|---|---|
| Oligo# | Design | Target |
| ENTR-0149 | 5'- GGC CAA ACC TCG GCT TAC CTG AAA T -3'-C4-cyclooctyne (all PMO monomers)(SEQ ID NO: 241) | Murine DMD exon 23 |

TABLE B2

| Compounds that target DMD | | |
|---|---|---|
| Oligo# | Design | Target |
| ENTR-0088 | (CPP12-PEG12-ValCitPABC)-5'- GGC CAA ACC TCG GCT TAC CTG AAA T -3' (all PMO monomers)(SEQ ID NO: 242) | Murine DMD exon 23 |
| ENTR-0093 | CPP12-PEG12-NH-5'-GGCCAAACCTCGGCTTACCTGAAAT -3'-NH-PEG12-CPP12 (all PMO monomers)(SEQ ID NO: 243) | Murine DMD exon 23 |
| ENTR-0098 | 5'-GGC CAA ACC TCG GCT TAC CTG AAA T-3'-C3-NH-PEG12-CPP12 (all PMO monomers) (SEQ ID NO: 244) | Murine DMD exon 23 |
| ENTR-0099 | 5'-CPP12-PEG12-Cys-ss-Cys-Lys(N3)-cyclooctyne-5'- GGC CAA ACC TCG GCT TAC CTG AAA T-3' (all PMO monomers)(SEQ ID NO: 245) | Murine DMD exon 23 |
| ENTR-0100 | CPP12-PEG12-Lys(N3)-cyclooctyne-5'- GGC CAA ACC TCG GCT TAC CTG AAA T -3' (all PMO monomers)(SEQ ID NO: 246) | Murine DMD exon 23 |
| ENTR-0115 | (CPP12-PEG12-Prodisulfide)-5'- GGC CAA ACC TCG GCT TAC CTG AAA T -3' (all PMO monomers)(SEQ ID NO: 247) | Murine DMD exon 23 |
| ENTR-0120 | (CPP12-PEG24)-5'- GGC CAA ACC TCG GCT TAC CTG AAA T -3' (all PMO monomers)(SEQ ID NO: 248) | Murine DMD exon 23 |
| ENTR-0161 | 5'- GGC CAA ACC TCG GCT TAC CTG AAA T -3'-C3NH-C6-CPP12 (all PMO monomers)(SEQ ID NO: 249) | Murine DMD exon 23 |
| ENTR-0089 | (CPP12-(bidentate-no linker)-PEG12)-5'- GGC CAA ACC TCG GCT TAC CTG AAA T -3' (all PMO monomers)(SEQ ID NO: 250) | Murine DMD exon 23 |
| ENTR-0090 | (CPP12-(bidentate-PEG12)-PEG12)-5'- GGC CAA ACC TCG GCT TAC CTG AAA T -3' (all PMO monomers)(SEQ ID NO: 251) | Murine DMD exon 23 |
| ENTR-0092 | 5'-GGC CAA ACC TCG GCT TAC CTG AAA T-3'-C3-NH-CPP1212; Amide chemistry (all PMO monomers)(SEQ ID NO: 252) | Murine DMD exon 23 |

TABLE B3

| Compounds that target DMD | | |
|---|---|---|
| Oligo# | Design | Peptide Fusion |
| ENTR-0119 | (T9-PEG12-CPP12-PEG12)-5'- GGC CAA ACC TCG GCT TAC CTG AAA T -3' (all PMO monomers)(SEQ ID NO: 253) | T9: SKTFNTHPQSTP (SEQ ID NO: 258) |
| ENTR-0163 | Ac-MSP-PEG12-Lys(CPP12-PEG12)-K(N3) + 5'- GGC CAA ACC TCG GCT TAC CTG AAA T -3' (SEQ ID NO: 254) | MSP: ASSLNIA (SEQ ID NO: 259) |

TABLE B3-continued

| Compounds that target DMD | | |
|---|---|---|
| Oligo# | Design | Peptide Fusion |
| ENTR-0164 | 5'- GGC CAA ACC TCG GCT TAC CTG AAA T -3'-C3NH-PEG4-BCN + Lys(N3)-miniPEG-NLS-ss-bA-bA-CPP12 (all PMO monomers)(SEQ ID NO: 255) | NLS: PKKKRKV (SEQ ID NO: 131) |
| ENTR-0165 | 5'- GGC CAA ACC TCG GCT TAC CTG AAA T -3'-C3NH-PEG4-BCN + Ac-NLS-Lys(CPP12)-PEG12-K(N3)(all PMO monomers)(SEQ ID NO: 256) | NLS: PKKKRKV (SEQ ID NO: 131) |
| ENTR-0201 | 5'- GGC CAA ACC TCG GCT TAC CTG AAA T -3'-click-K-PEG12-Lys(CPP12)-NLS-Ac (all PMO monomers)(SEQ ID NO: 257) | NLS: PKKKRKV (SEQ ID NO: 131) |

The compounds of Tables B1-B3 are evaluated in Examples 3A, 3B, 3C, and 3D. Exemplary experiments are described below.

Preparation and design of CPP-PMO targeting murine DMD exon 23. Design of monovalent CPP-PMO (ENTR-0092, ENTR-0098, ENTR-0100, ENTR-0120 and ENTR-0161), monovalent with cathepsin B cleavable linker (ENTR-0088), monovalent with cytosolic reducible linker by glutathione or GILT (ENTR-0099, ENTR-0115) bivalent CPP-PMO (ENTR-0089, ENTR-0090, ENTR-0093 and ENTR-0110), mono CPP with Muscle targeting moieties (ENTR-0119 and ENTR-0163) and mono CPP-NLS-PMO (ENTR-0164, ENTR-0165, ENTR-0201) are shown in Table B2 and B3. The following compounds were synthesized via 3', 5', or both covalent conjugation of primary amine modified PMOs: ENTR-0093, ENTR-0098, 0161, ENTR-0092. Briefly, a solution of desired peptide-TFP ester in DMF (6 eq, 5 mM) was added to a solution of PMO-3'-primary amine (1 equivalent, 2 mM) in PBS-10X. Reaction proceed to completion in 4-8 hours at room temperature as confirmed by LCMS (Q-TOF). For 3' or 5' conjugation via click reaction (ENTR-0088, ENTR-0099, ENTR-0100, ENTR-0120, ENTR-0089, ENTR-0090, ENTR-0119, ENTR-0163, ENTR-0164, ENTR-0165, ENTR-0201), a solution of peptide-azide in nuclease-free water (1 mM) was added to the PMO-3'-cyclooctyne or cyclooctyne-5'-PMO solids. The mixture was vortexed to dissolve the peptide-PMO conjugate, centrifuged to settle the solution, and incubated at room temperature for 8-12 hours for completion as confirmed by LCMS (Q-TOF). For purifications, crude mixtures were diluted with DMSO, loaded onto a C18 reverse-phase column (150 mm*21.2 mm), flow rate of 20 mL/min and purified by an appropriate gradient using water with 0.05% TFA and acetonitrile as solvents. Desired fractions were pooled, pH of the solution was adjusted to 5-6 by 1M NaOH and the solution underwent the lyophilization process, affording white lyophilized powder. For in vitro and in vivo formulations, the conjugates were reconstituted in appropriate amount of PBS or Saline for the desired concentration (2-10 mg/mL). Concentration of the non LSR labeled conjugates were measured by preparing 10, 20, and 50-fold dilutions in formulated buffer and reading the absorbance at 260 nm or 280 nm using a nanodrop. Once the linear range of dilution achieved, the absorbance was measured in triplicates and concentration was calculated using the average absorbance and $\varepsilon_{260}$ or $\varepsilon_{280}$. $\varepsilon_{280}$ for conjugates were calculated by the following formula: $\varepsilon_{280}$=138993+(n*3550); n=number of CPP. The diluted samples were analyzed by LCMS (Q-TOF) for the conjugate identity confirmation. Table below summarizes the calculated MVW and experimental MVWs. All experimental MVWs reasonably matched the calculated average MVW with expected ±6 Da assay variation.

| Name | Calculated MW | Experimental Average MW | Purity |
|---|---|---|---|
| ENTR-0013 | 8413.1 | 8410.02 | 99 |
| ENTR-0017 | 8487 | 8484 | 95 |
| ENTR-0066 | 9001.7 | 9003.8 | 95 |
| ENTR-0068 | 8751.07 | 8748.02 | 85 |
| ENTR-0149 | 8635.07 | 8635.8 | 82 |
| ENTR-0088 | 11404.89 | 11403.62 | 93 |
| ENTR-0093 | 12404.9 | 12400.2 | >99 |
| ENTR-0098 | 10311.46 | 10308.04 | >99 |
| ENTR-0099 | 11263.4 | 11260.43 | 90 |
| ENTR-0100 | 11000.1 | 10996.43 | 92 |
| ENTR-0115 | 11261.77 | 11259.53 | 98 |
| ENTR-0120 | 11599.17 | 11596.89 | 99 |
| ENTR-0161 | 9827 | 9825.8 | 98 |
| ENTR-0089 | 12355.7 | 12351.11 | 96 |
| ENTR-0090 | 13555.1 | 13550.96 | 97 |
| ENTR-0092 | 12266.79 | 12262.14 | 94 |
| ENTR-0119 | 13095.87 | 13092.55 | 96 |
| ENTR-0163 | 12426.1 | 12428.8 | 98 |
| ENTR-0164 | 11838.19 | 11836.3 | 97 |
| ENTR-0165 | 11944.31 | 11942.3 | 99 |
| ENTR-0201 | 11669.5 | 11669.5 | >99 |

Mice. This study used wild type mice with normal level of dystrophin expression and without DMD mutations or symptoms.

Study design. The composition and method described in Example 1 and 2 (ENTR-0013, TABLE B1 and ENTR-0098, Table B2) were applied to wild mice to evaluate the ability of the claimed compositions to skip exon 23 and thus treat DMD. The AC used in this study had the following sequence 5'-GGCCAAACCTCGGCTTACCTGAAAT-3' (SEQ ID NO: 260), which targeted exon 23. This sequence is referred to as PMO in this example. PBS, PMO conjugated to a CPP ("CPP-PMO," also called "CPP12-$PMO^{DMD}$" or "$PMO^{DMD}$-CPP 12"), or PMO without CPP (also called $PMO^{DMD}$) was administered via intramuscular (IM) or intravenous (IV) to MDX mice at the following doses: 1 mpk, 3 mpk, 10 mpk, 30 mpk; (mpk: mg of compound/kg of body weight). The CPP used was cCPP12, which has an amino acid sequence of FfΦRrRr. A schematic of preparation of $PMO^{DMD}$ and $PMO^{DMD}$-CPP12 is shown in FIG. 10A. Total RNA were extracted from tissue samples and analyzed by RT-PCR to visualize the efficiency of splicing correction.

Detection of splicing correction by RT-PCR. WT mice express normal level of full-length dystrophin mRNA in muscles. The delivery of PMO can alter the splicing and result in a truncated dystrophin mRNA after exon 23 skipping. The detection of splicing correction process is measured by RT-PCR where extracted RNAs from tissues are first reverse-transcribed into cDNA and are further analyzed by nested PCR using two primer sets: forward primer 5'-CAGAATTCTGCCAATTGCTGAG-3' (SEQ ID NO: 261) and reverse primer 5'-TTCTTCAGCTTGTGTCATCC-3' (SEQ ID NO: 262) for the first round PCR (outer primer set) and forward primer 5'-CCCAGTCTACCACCC-TATCAGAGC-3' (SEQ ID NO: 263) and reverse primer 5'-CCTGCCTTTAAGGCTTCCTT-3' (SEQ ID NO: 264) (inner primer set) for the second round PCR. The RT-PCR readout of tissues without splicing correction result in a 901 bp gene fragment and a new 689 bp gene fragment show up after splicing correction. The degree (percentage) of splicing correction detected by RT-PCR was calculated using the following equation: % correction=(intensity of 689 bp fragment band)/(intensity of 901 bp fragment band +intensity of 689 bp fragment band).

Figure 10:
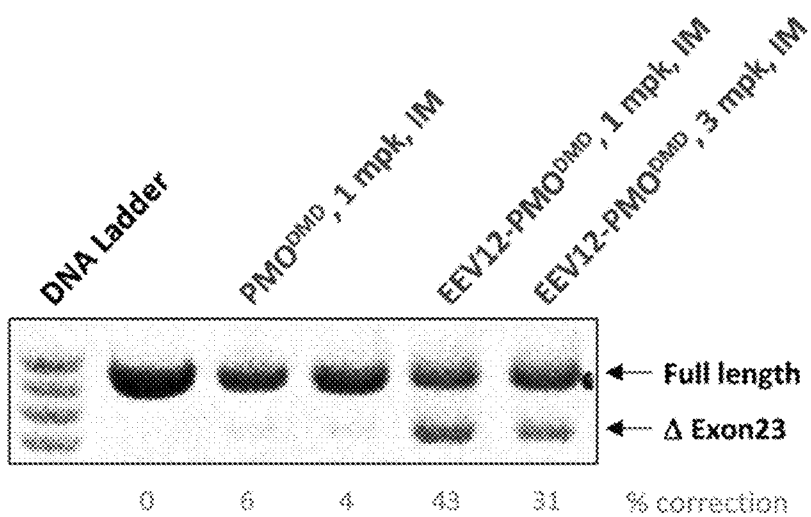
FIG. 10 shows the RT-PCR result of dystrophin exon skipping products in local muscle group post intramuscular administration (IM) of $PMO^{DMD}$ (ENTR-0013, Table B1) and CPP12-$PMO^{DMD}$ (ENTR-0014, Table B2) in wild type mice.
Figure 11:
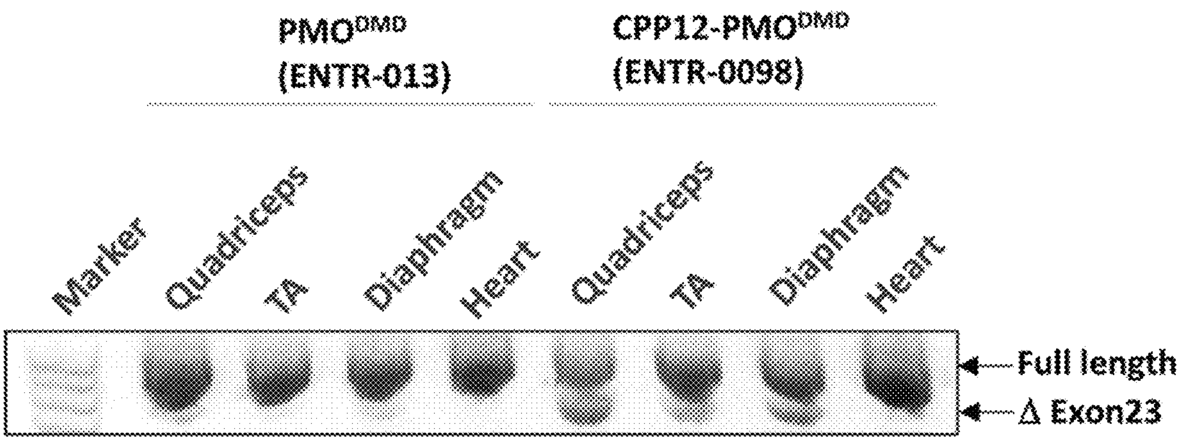
FIG. 11 shows dystrophin exon skipping products in various treated muscle groups post intravenous administration of $PMO^{DMD}$ (ENTR-0013, Table B1) and CPP12-$PMO^{DMD}$ (ENTR-0014, Table B2) in wild type mice.
Figure 12A:
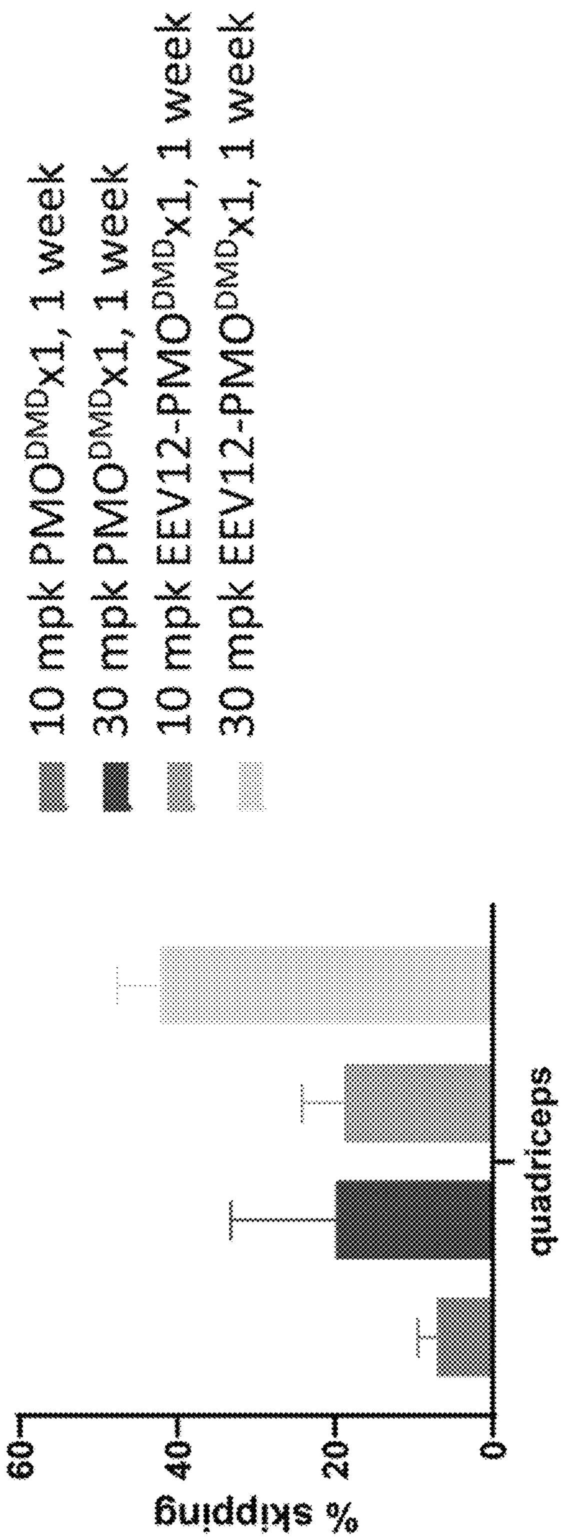
FIGS. 12A-D shows the percentage of exon skipping in MDX mice after delivery of $PMO^{DMD}$ or EEV12-$PMO^{DMD}$ in the quadriceps (FIG. 12A), transverse abdominus (TA) (FIG. 12B), diaphragm (FIG. 12C), and heart (FIG. 12D).
Figure 12B:
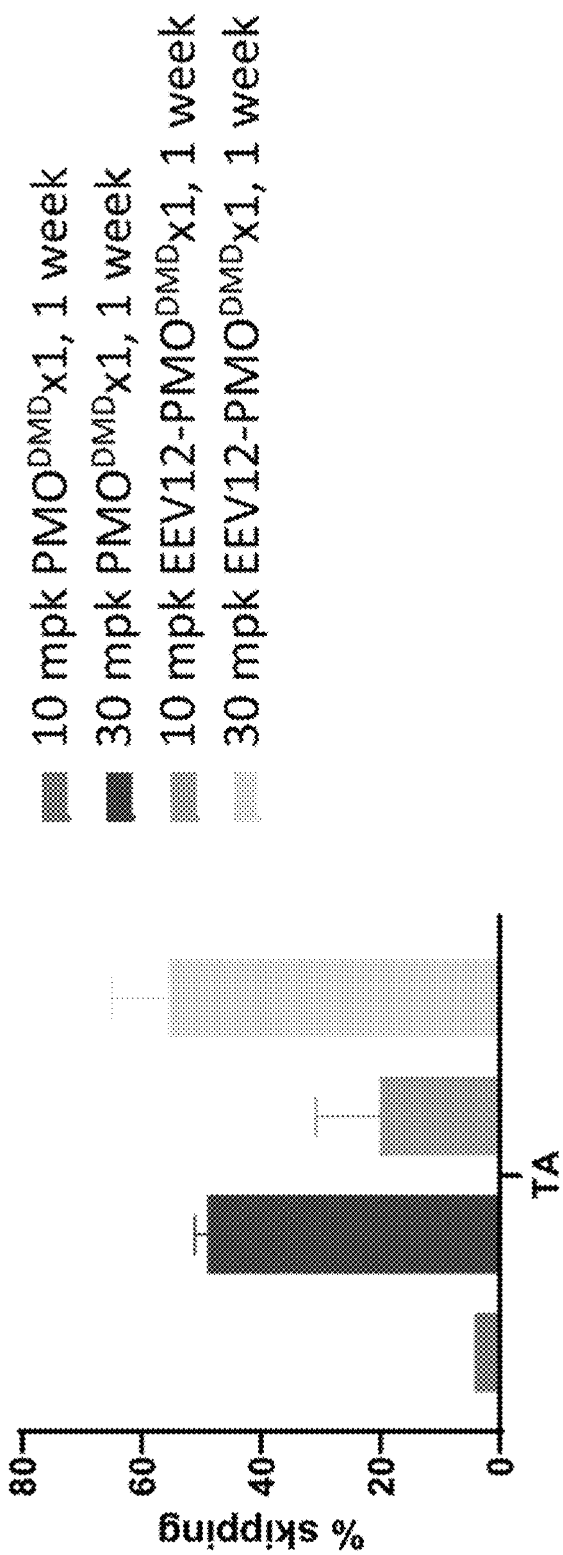
Figure 12C:
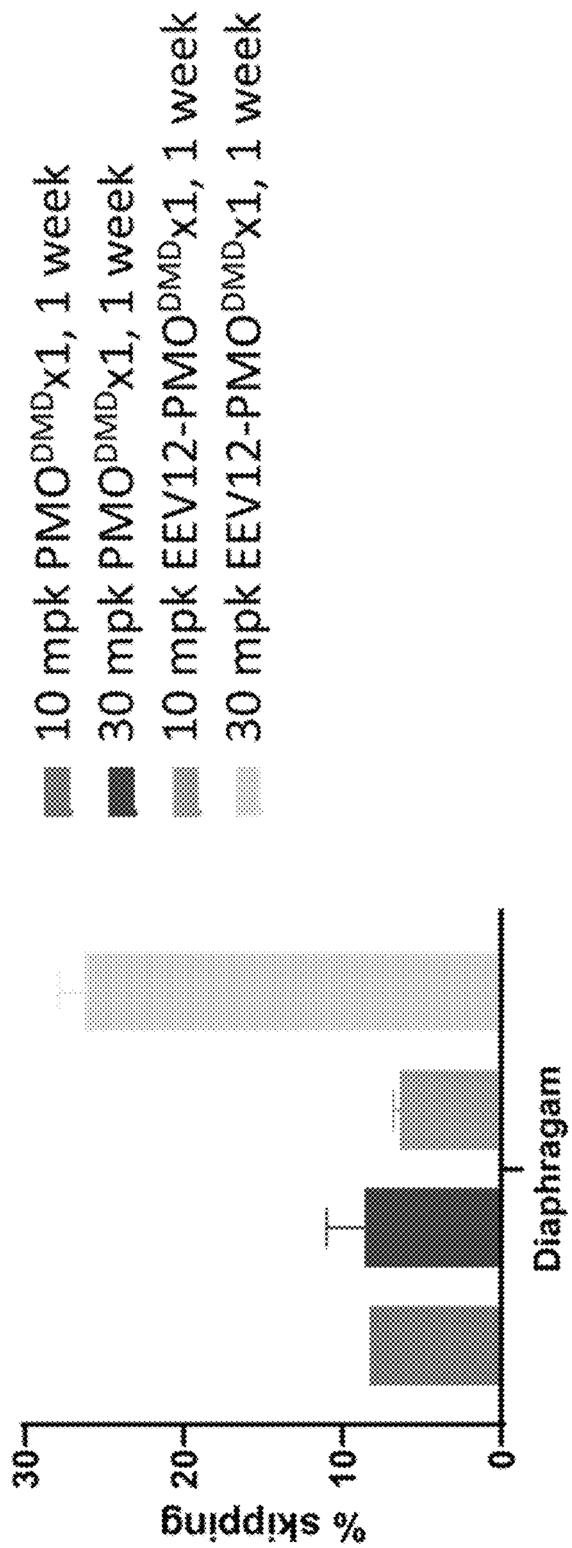
Figure 12D:
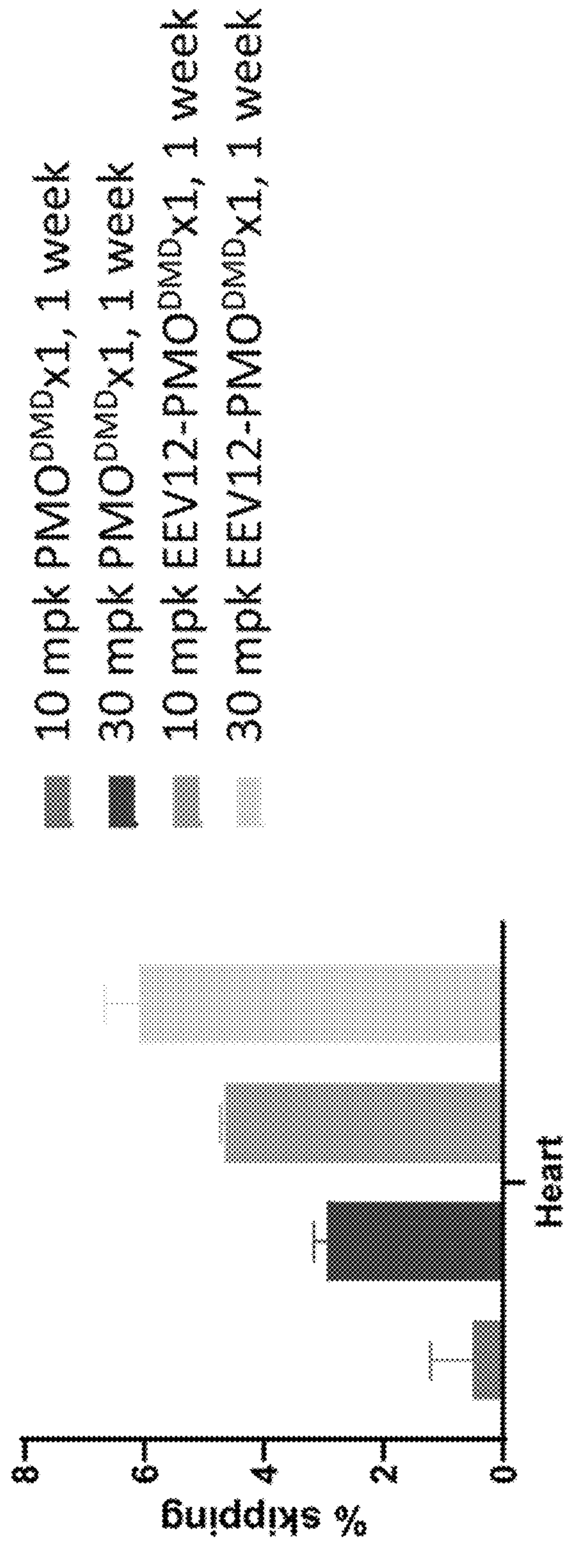
Figure 13A:
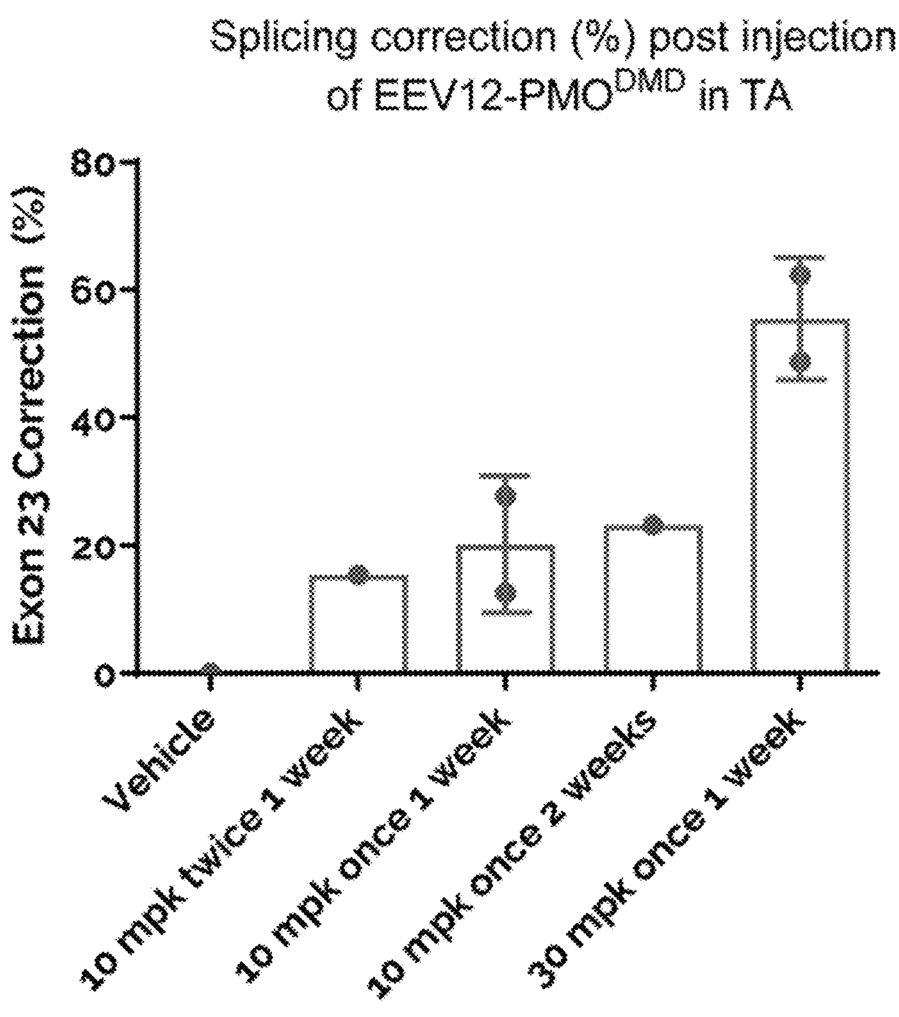
FIGS. 13A-D shows the percentage of exon 23 correction in MDX mice after delivery of EEV12-$PMO^{DMD}$ in the transverse abdominus (TA) (FIG. 13A), quadriceps (FIG. 13B), diaphragm (FIG. 13C), and heart (FIG. 13D).
Figure 13B:
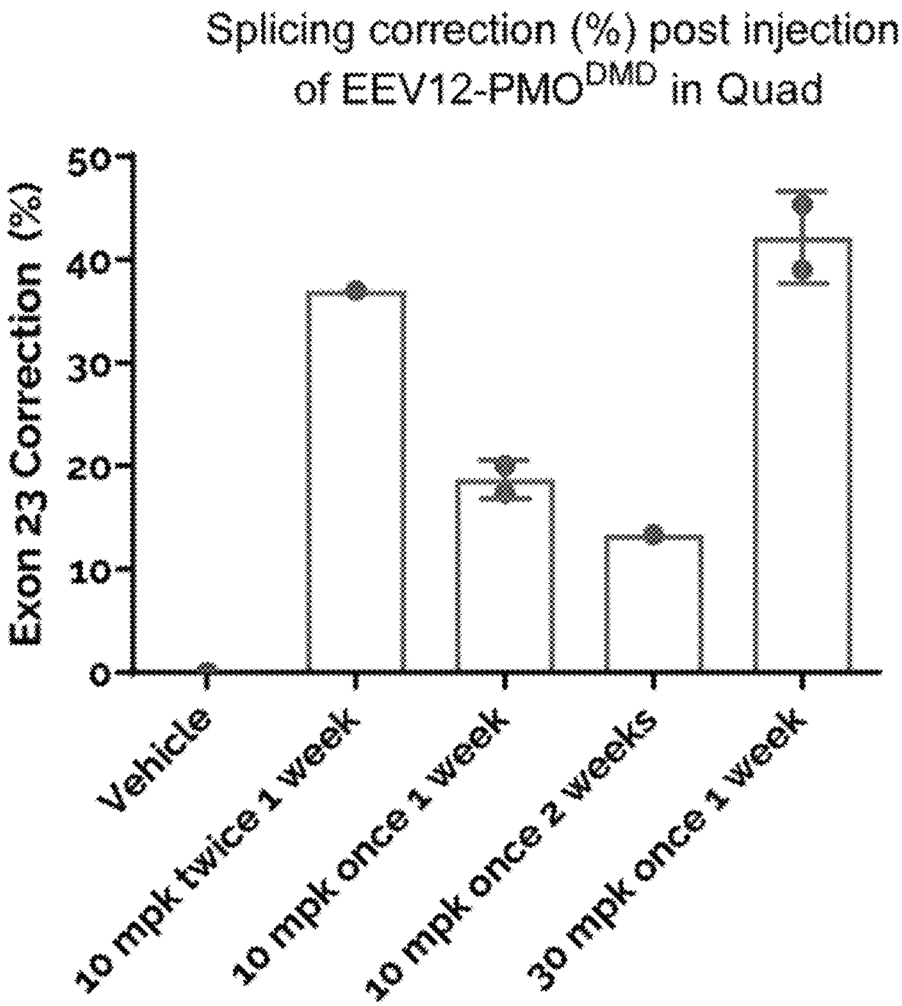
Figure 13C:
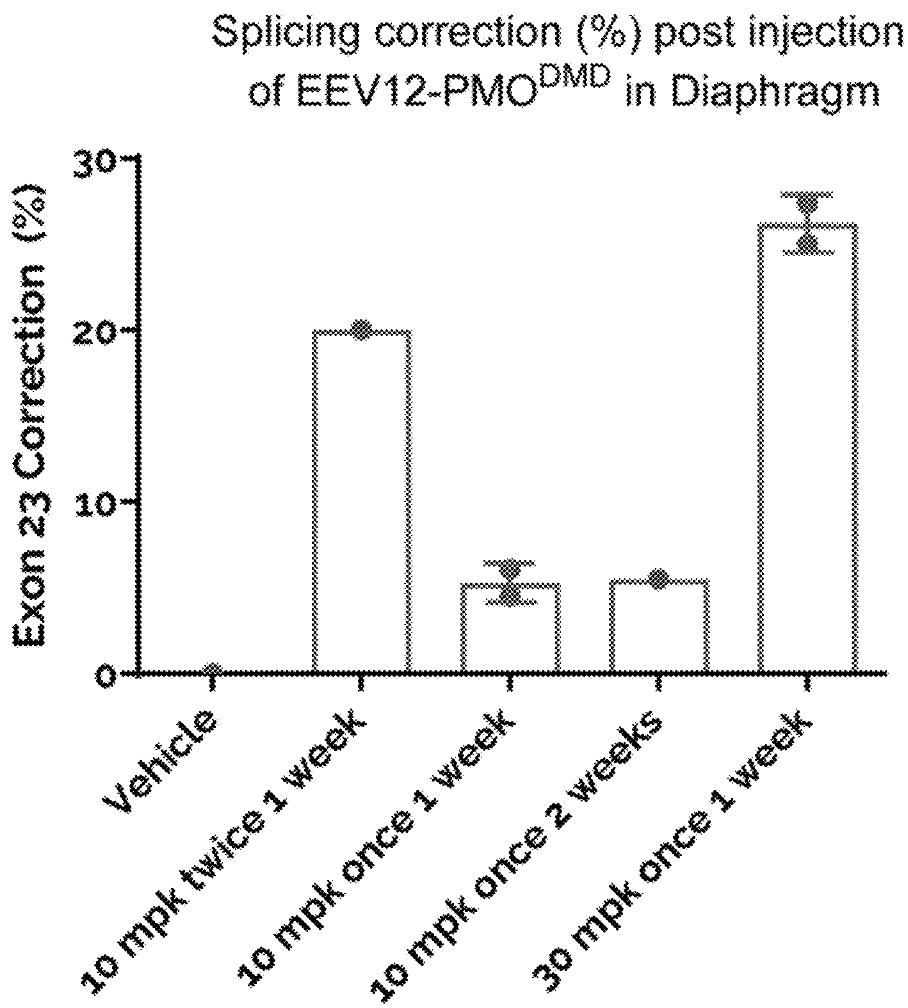
Figure 13D:
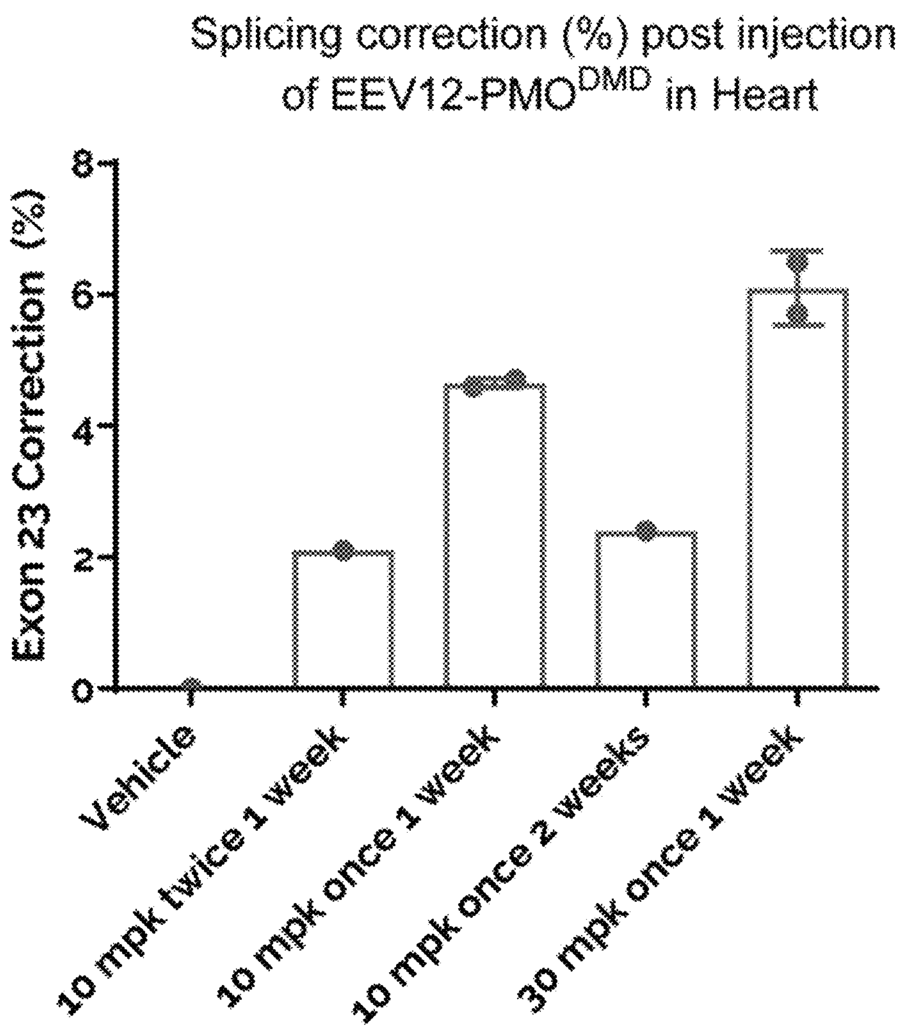
Figure 14A:
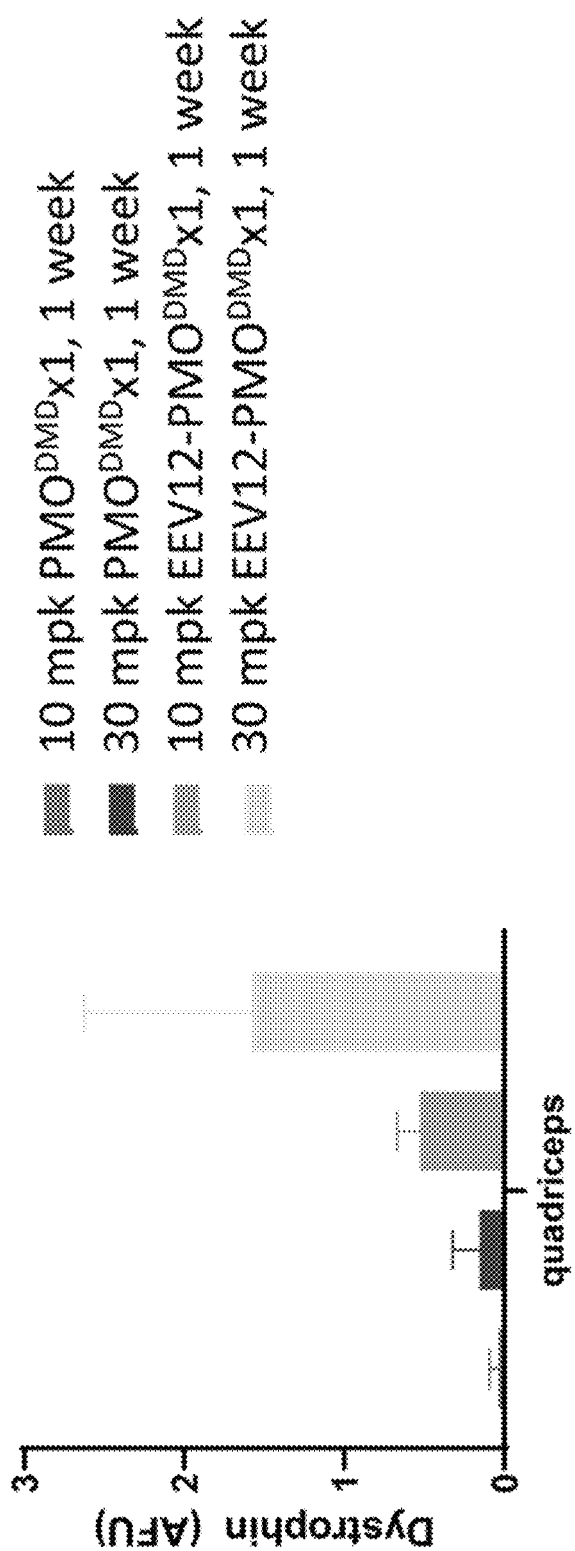
FIGS. 14A-D shows the amount of exon-23 corrected dystrophin detected after delivery of $PMO^{DMD}$ or EEV12-$PMO^{DMD}$ in the quadriceps (FIG. 14A), transverse abdominus (TA) (FIG. 14B), diaphragm (FIG. 14C), and heart (FIG. 14D) by Western Blot.
Figure 14B:
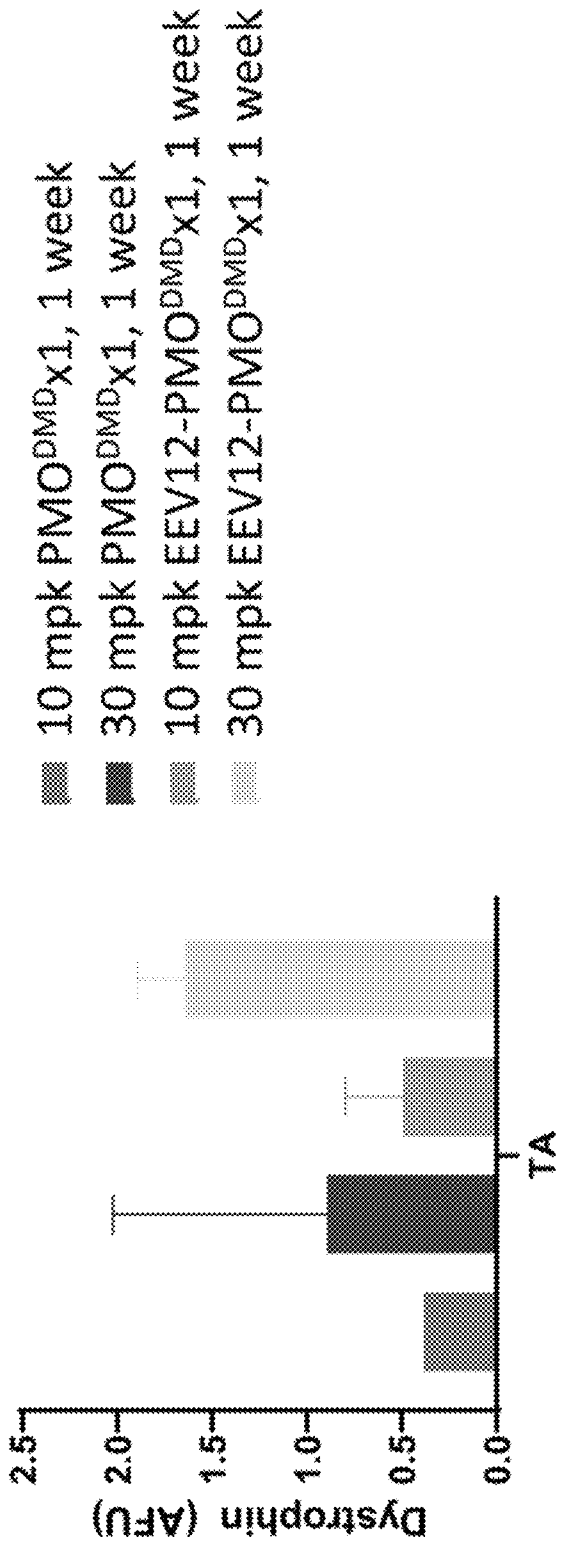
Figure 14C:
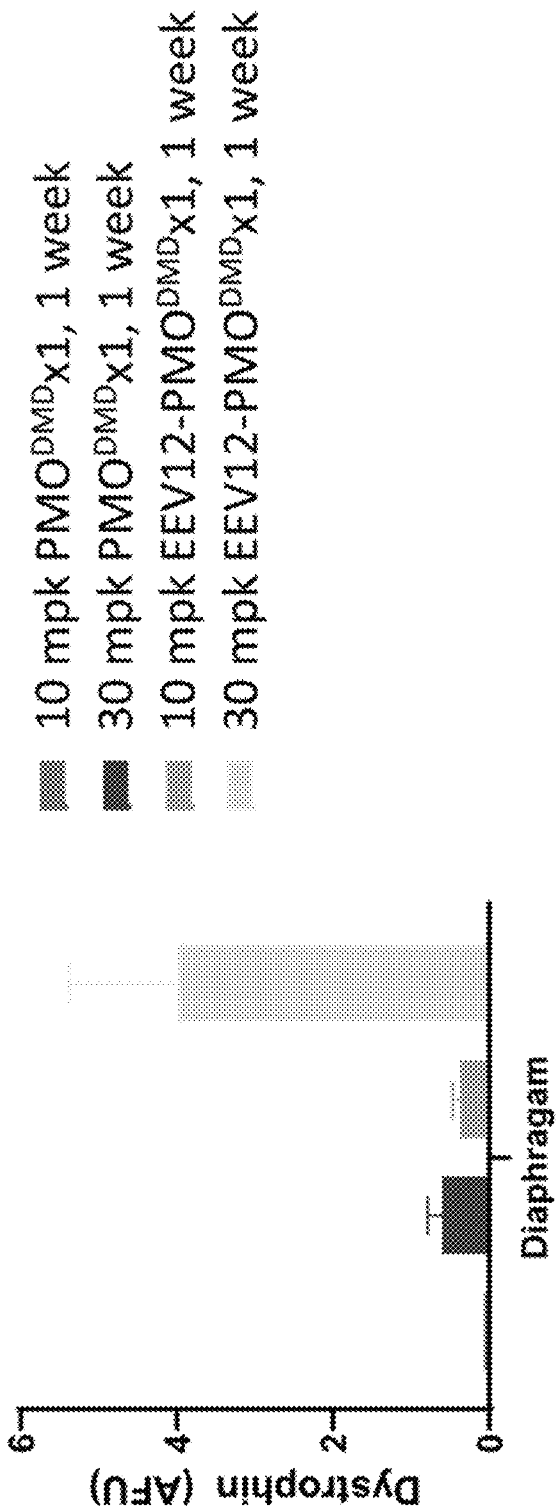
Figure 14D:
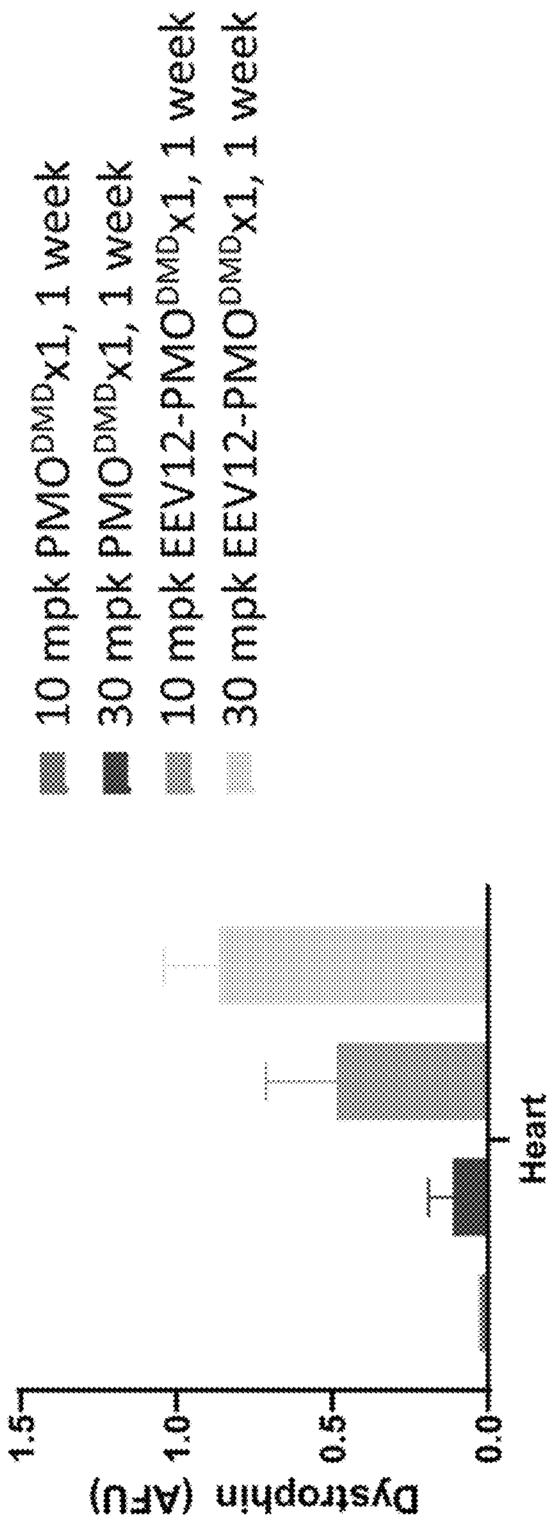
Figure 15A:
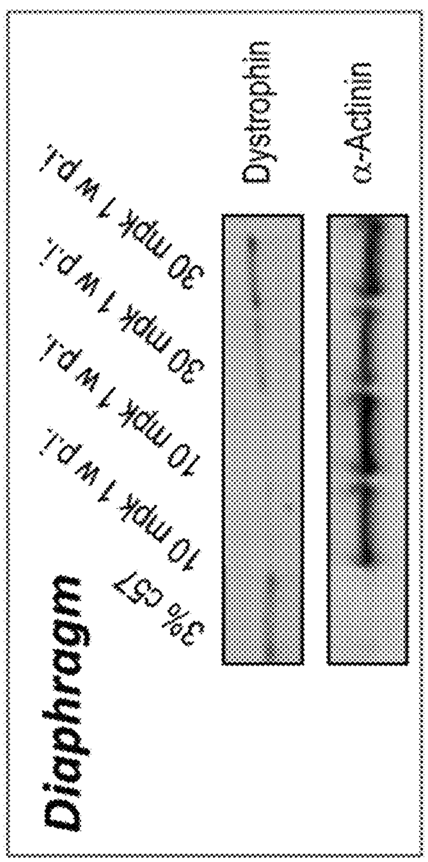
FIGS. 15A-D show Western Blots of exon-23 corrected dystrophin and α-actinin in the diaphragm (FIG. 15A), heart (FIG. 15B), quadriceps (FIG. 15C), and transverse abdominus (FIG. 15D) after intravenous delivery of 10 mpk or 30 mpk EEV12-$PMO^{DMD}$
Figure 15B:
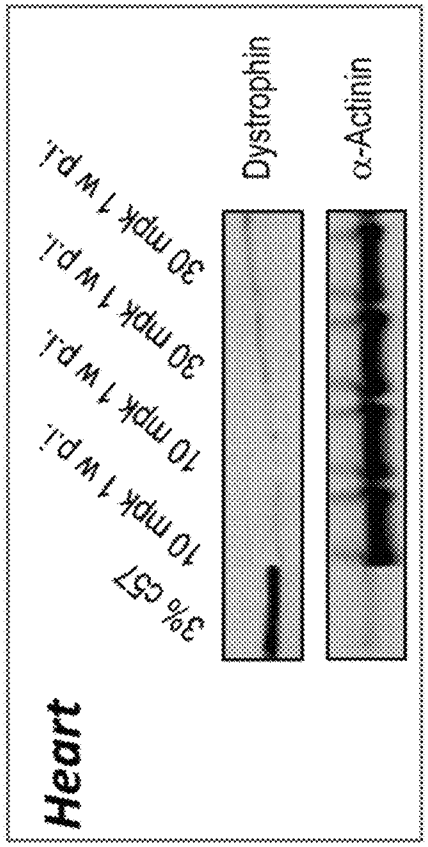
Figure 15C:
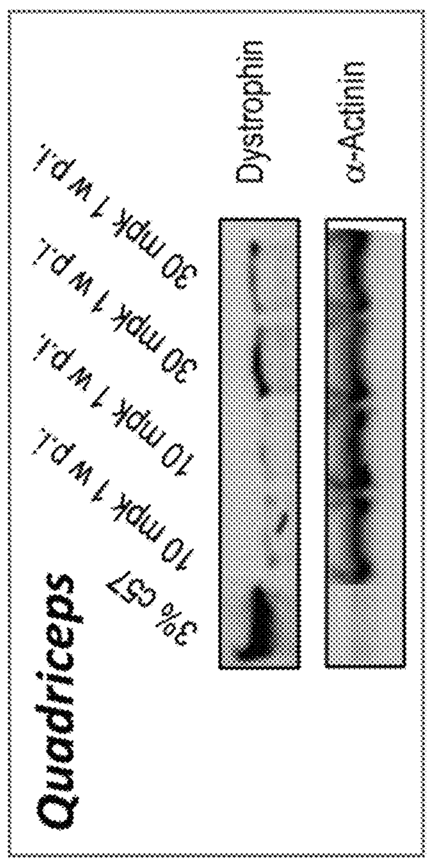
Figure 15D:
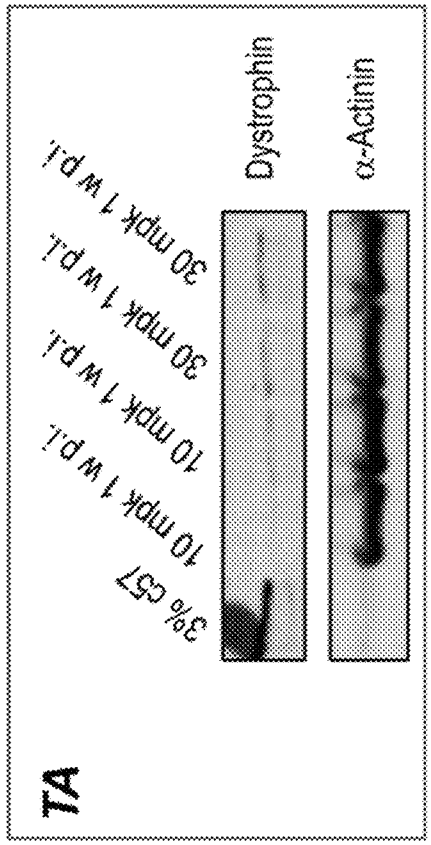
Figure 24:
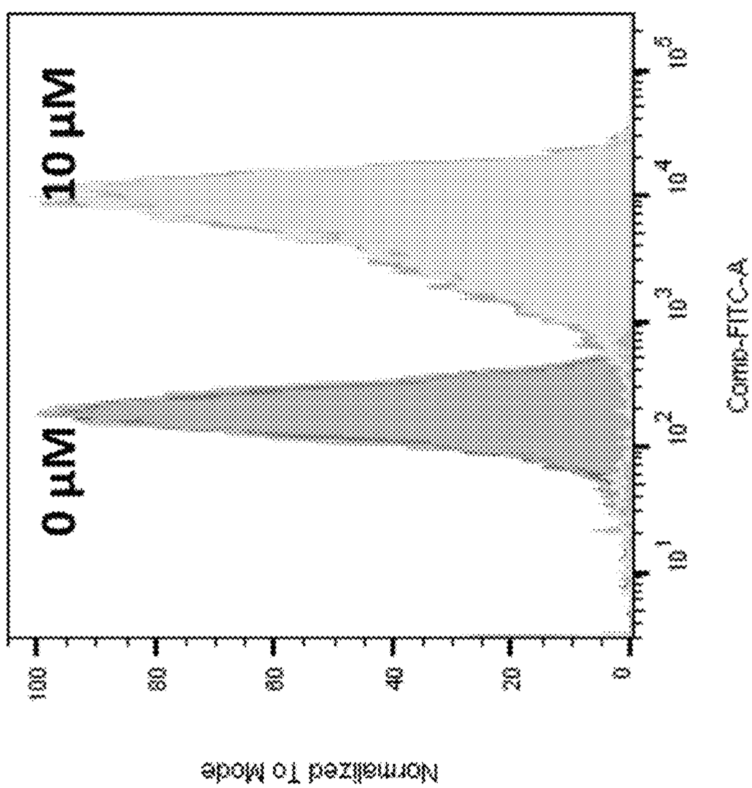
FIG. 24 show splicing correction of eGFP in HeLA-654 cells, as demonstrated by the fluorescence of HeLA-654 cells treated with 0 μM or 10 μM of ENTR-0203.
Figure 25:
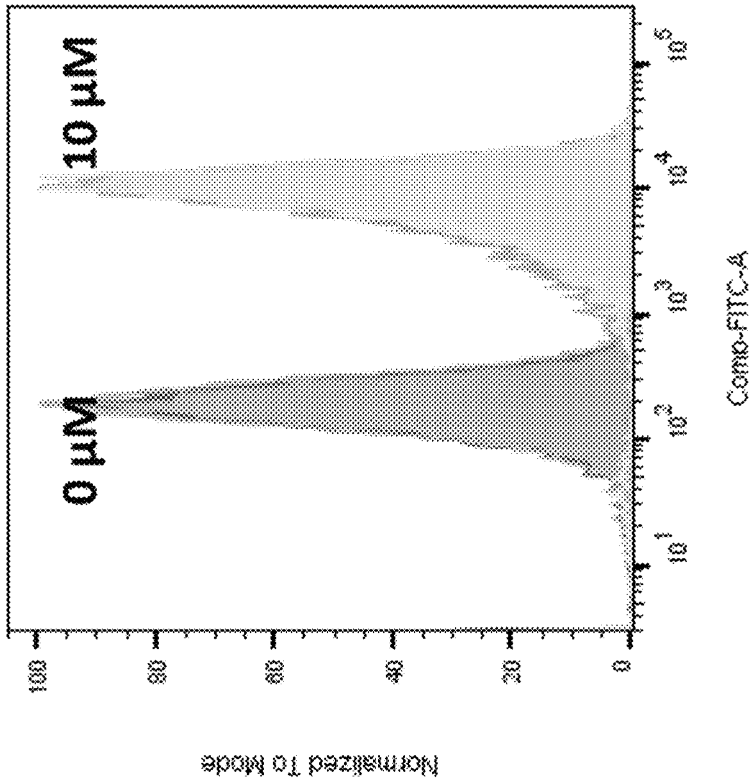
FIG. 25 shows splicing correction of eGFP in HeLA-654 cells, as demonstrated by the fluorescence of HeLA-654 cells treated with 0 μM or 10 μM of ENTR-0207.
Figure 26:
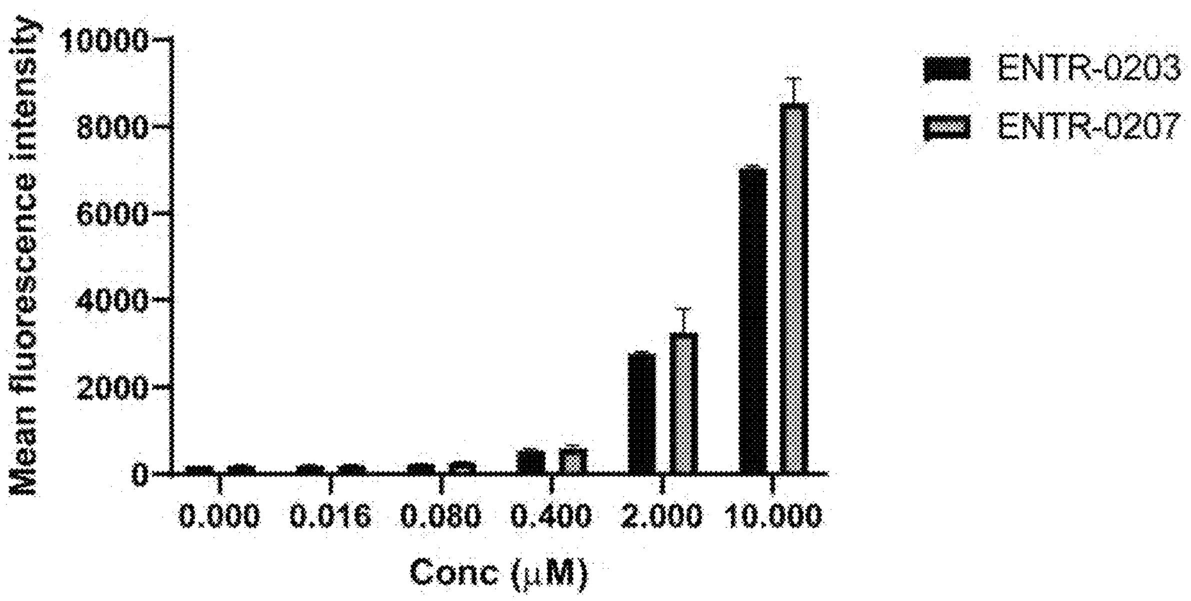
FIG. 26 shows the results of fluorescent activated cell sorting analysis of HeLa-654 cells treated for 24 hr with 0, 0.016 μM, 0.08 μM, 0.4 μM, 2 μM, 10 μM CPP-NLS-PMO constructs, including ENTR-0203 (non-cleavable linker, Table 1) and ENTR-0207 (cleavable linker, Table A), as described in Example 1.
Figure 27:
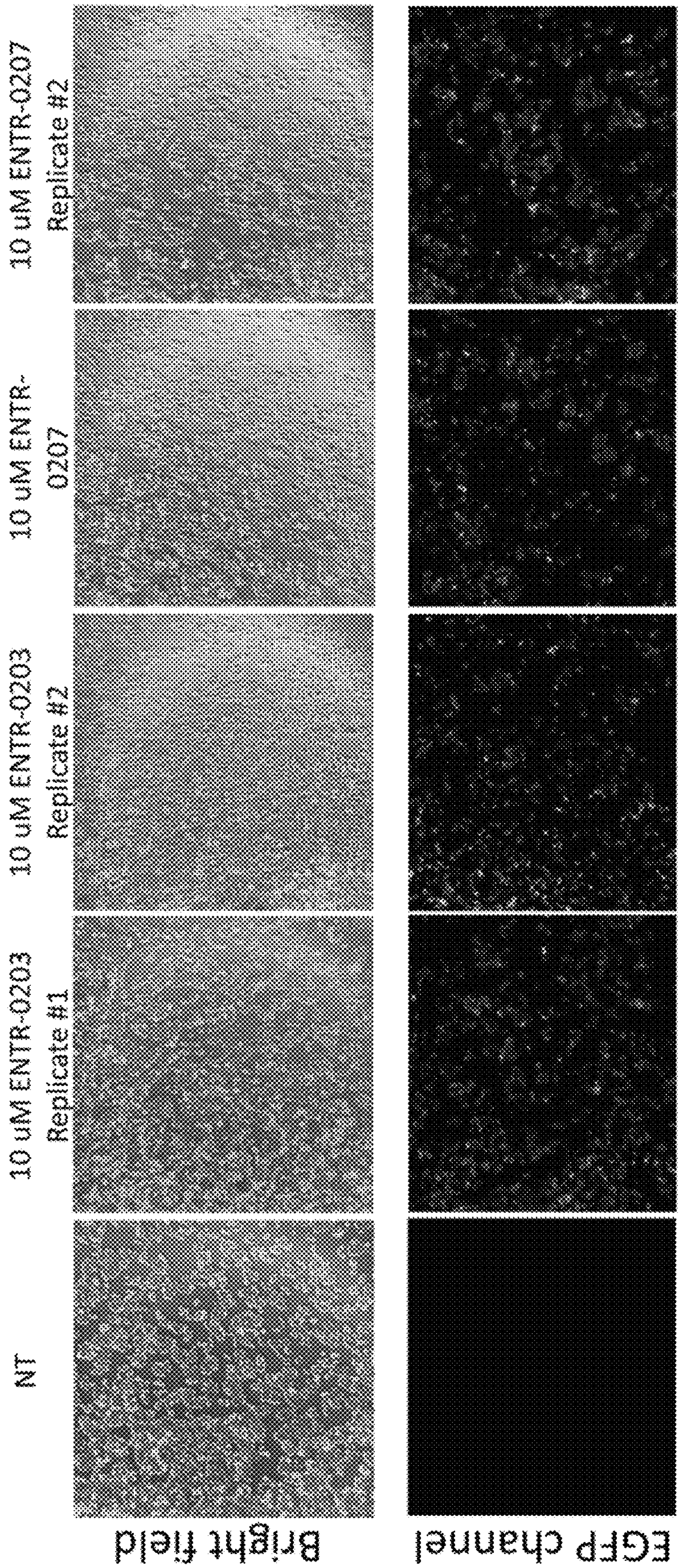
FIG. 27 shows fluorescence microscopy images of HeLA-654 cells treated with either 10 μM of ENTR-0203 or 10 μM of ENTR-0207.
Figure 28:
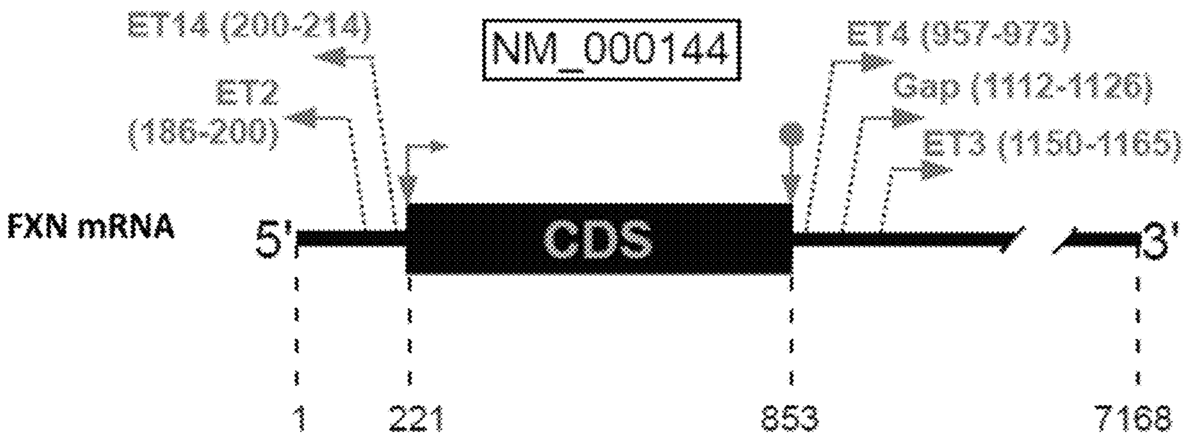
FIG. 28 shows a schematic of FXN mRNA.

In vivo activity in wild type mice. As shown in FIG. 10B, 24 hr after twice daily IM administration, WT mice (CD1) treated with CPP12-PMO$^{DMD}$ (ENTR-0098) produced significant amount of dystrophin mRNA lacking exon 23, whereas mice treated with PMO (ENTR-0013) alone produced only dystrophin mRNA containing exon 23 (similar to PBS treated control). WT mice (CD1) were also administrated intravenously with equal mole of material (8 mpk PMO, ENTR-0013, or 10 mpk CPP12-PMO, ENTR-0098). Five days post injection, the dystrophin mRNA products in quadriceps, transverse abdominis, diaphragm, and heart are analyzed by RT-PCR and shown in FIG. 11. In contrast to the low exon 23 skipping efficiency in PMO$^{DMD}$ treated mice tissues, the administration of CPP12-PMO$^{DMD}$ resulted in significantly increased amount of dystrophin mRNA with skipped exon 23 in quadriceps, transverse abdominis, diaphragm, and heart. To further confirm the findings, additional wild type mice (C57BL/10, n=5 per group) were administered intravenously with (equal mole) of 24 mpk PMO$^{DMD}$ (ENTR-0013) and 30 mpk CPP12-PMO$^{DMD}$ (ENTR-0098). One-week post injection, the dystrophin mRNA products in quadriceps, transverse abdominis, diaphragm, and heart were analyzed by RT-PCR and the percentage of exon 23 skipping are shown in FIG. 11. In contrast to the low exon 23 skipping efficiency in PMO$^{DMD}$ treated mice tissues, the administration of CPP12-PMO$^{DMD}$ resulted in significantly increased amount of dystrophin mRNA with skipped exon 23 in quadriceps, transverse abdominis, diaphragm, and heart, illustrating the effective delivery of oligonucleotide cargos by cyclic CPPs.

Example 3B. Use of Cell-Penetrating Peptides Conjugated to Oligonucleotides for Splicing Correction of Dystrophin in Mouse Model of DMD Mice. This study used C57BL/10ScSn-Dmdmdx/J (MDX) mice, which contain a C to T mutation resulting in a termination codon at position 2983 within exon 23 of the dystrophin muscular dystrophy gene (Dmd) on the X chromosome. Mice expressing this mutant allele produce a truncated dystrophin protein, and are thus a model of Duchenne's muscular dystrophy ("DMD").

Study design. The composition and method described in Example 3A and listed in Tables B2 and B3 were applied to MDX mice to evaluate the ability of the claimed compositions to skip exon 23 and thus treat DMD. The AC used in this study had the following sequence 5'-GGC-CAAACCTCGGCTTACCTGAAAT-3' (SEQ ID NO: 260), which targeted exon 23. This sequence is referred to as PMO in this example. PBS, PMO conjugated to a CPP ("CPP-PMO," also called "CPP12-PMO$^{DMD}$" or "PMO$^{DMD}$-CPP12"), PMO without CPP (also called PMO$^{DMD}$), PMO with various CPP12 through different linkers or multivalence (TABLE 3), PMO with CPP12 as well as various peptide fusions (TABLE 4) was administered via intravenous (IV) to MDX mice at the following doses: 10 mpk, 20 mpk, 30 mpk; (mpk: mg of compound/kg of body weight). The CPP used was cCPP12, which has an amino acid sequence of FfΦRrRr. A schematic of preparation of PMO$^{DMD}$ and PMO$^{DMD}$-CPP12 is shown in FIG. 10A. The structures of the compounds are provided throughout this disclosure. Total RNA was extracted from tissue samples and analyzed by RT-PCR to visualize the efficiency of splicing correction. Dystrophin protein level was analyzed by Western blot to evaluate the expression of dystrophin upon treatment.

Detection of dystrophin expression by Western Blot. Lysis buffer (9% SDS, 4% glycerol, 5 mM Tris, and 5% beta-mercaptoethanol, along with HALT protease inhibitors) was added to minced mouse tissue from either mouse heart, transverse abdominis, quadriceps, or diaphragm. Metal beads were used in conjunction with a Qiagen Tissuelyser to mechanically homogenize the tissue. Lysate was cleared by centrifugation, and the supernatant was subjected either to SDS-PAGE using 3-8% Tris Acetate gels followed by transfer to nitrocellulose membranes and western blotting followed by fluorescent imaging using the LICOR system or to the Jess Simple Western system using the 66-440 kDa capillary matrices. Dystrophin was detected using the anti-dystrophin antibodies from Abcam (Ab52777 or Ab154168); alpha-actinin was detected using anti-alpha-actinin antibodies from R&D Systems (MAB8279) or Abcam (ab68167). Traditional western blot bands were quantified using LICOR software. Jess Simple Western peaks were fit and the area under the peaks was calculated using the Simple Western software. Each run included a standard curve using wildtype mouse lysate diluted with different amounts of mdx mouse lysate from the respective tissue. The dystrophin detected in each sample was normalized to alpha-actinin as a loading control, and a linear regression was performed for the standard curve, which was used to determine the amount of dystrophin in each sample as a percentage of wildtype dystrophin levels.

Figure 42A:
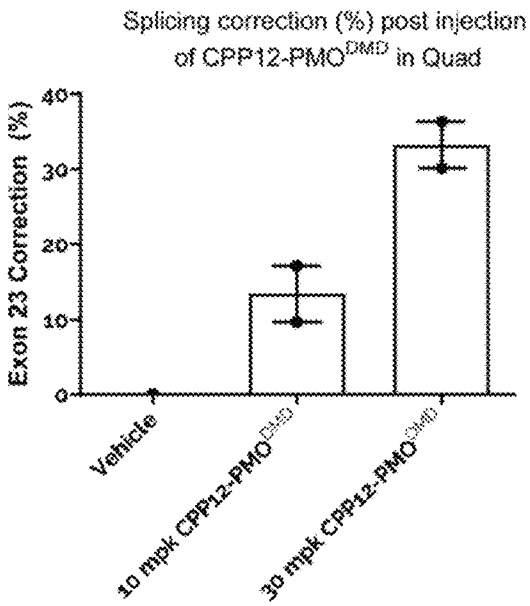
Figure 42B:
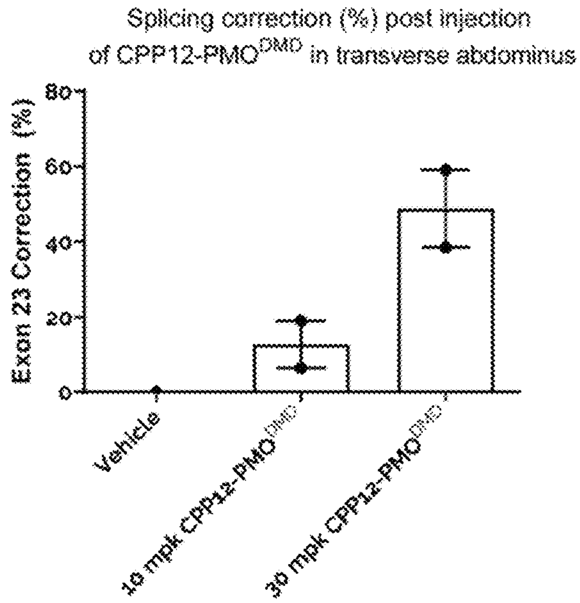
Figure 42C:
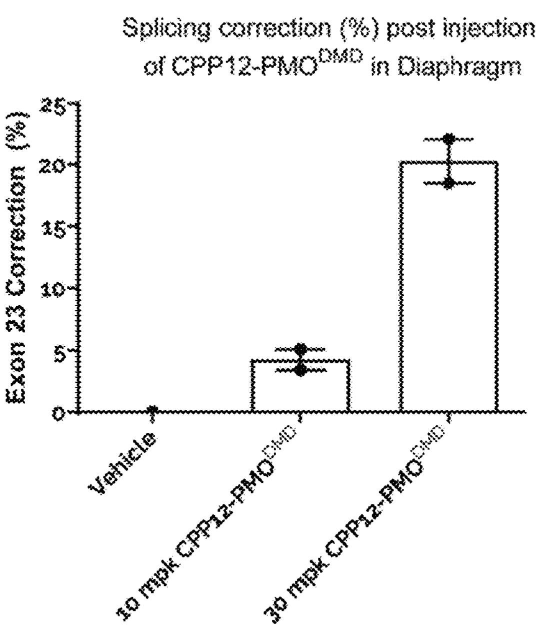
Figure 42D:
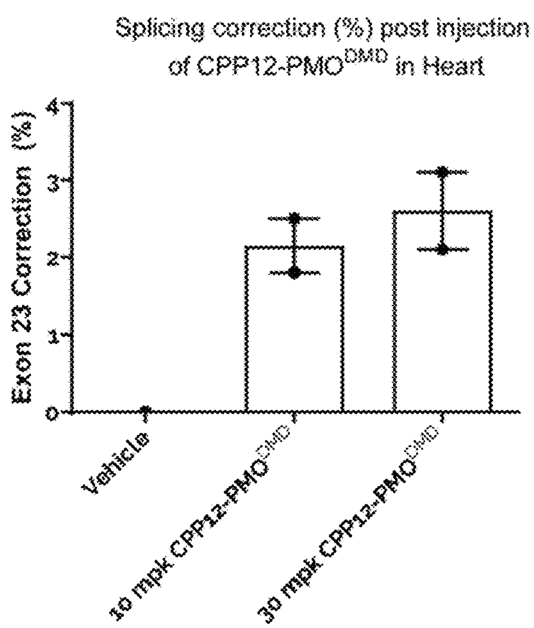

Dose dependent activity of CPP12-PMO in MDX mice. MDX mice were administered with 10 mpk or 30 mpk of CPP12-PMO$^{DMD}$ (ENTR-0098). One week post injection, the dystrophin mRNA products in various muscle groups (the quadriceps, transverse abdominis, diaphragm, and heart) were analyzed by RT-PCR and the quantification of exon 23 correction are shown in FIGS. 42A-D. FIGS. 42A-D show that compared to vehicle treated MDX mice where there are only minimal dystrophin mRNA product, the administration of CPP12-PMO$^{DMD}$ resulted in dose-dependent increased amount of dystrophin mRNA in the quadriceps (FIG. 42A), transverse abdominis (FIG. 42B), diaphragm (FIG. 42C), and heart (FIG. 42D).

Figure 43A:
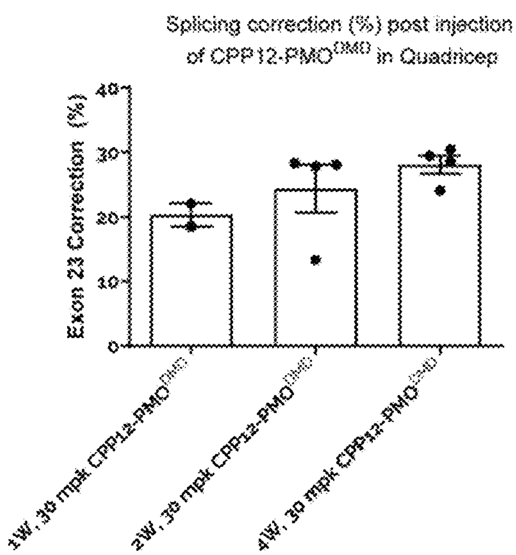
Figure 43B:
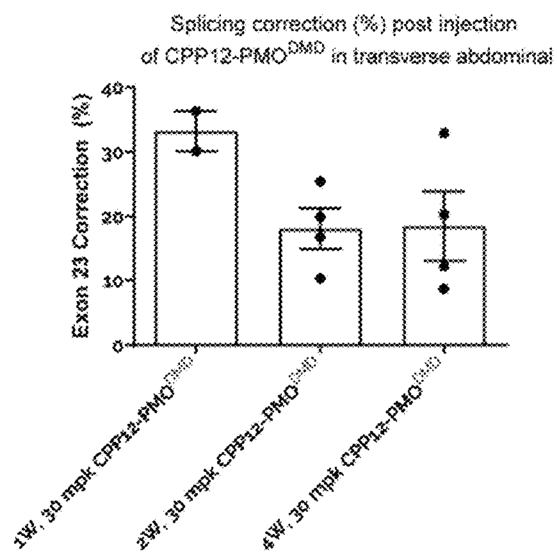
Figure 43C:
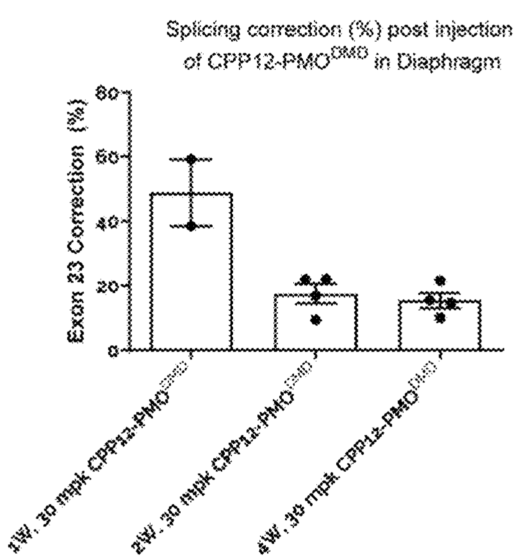
Figure 43D:
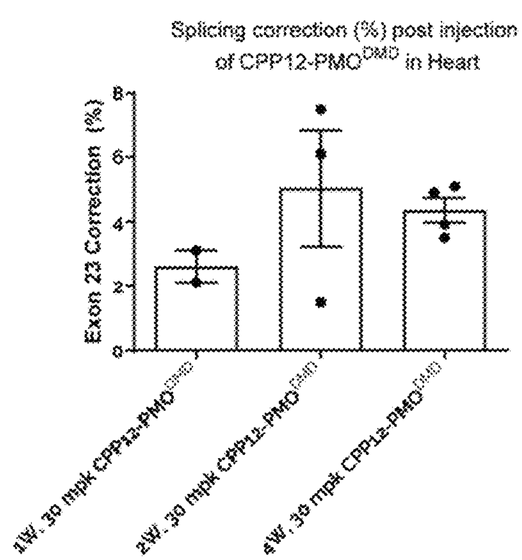

Duration of effects of CPP12-PMO in MDX mice. To evaluate the duration of effects of ENTR-0998, MDX mice were injected intravenously with 30 mpk CPP12-PMO (ENTR-0098) and various muscle groups were harvested 1 week (n=2), 2 weeks (n=4), or 4 weeks (n=4) post injection. FIGS. 43A-D show the effect of exon skipping and dystrophin mRNA correction is significant and consistent up to 4 weeks after a single IV injection in the quadriceps (FIG. 43A), transverse abdominis (FIG. 43B), diaphragm (FIG. 43C), and heart (FIG. 43D).

Correction of dystrophin protein expression with CPP12-PMO in MDX mice. MDX mice were injected with equal mole amount of PMO (8 mpk, ENTR-0013, n=3) or CPP12-PMO (10 mpk, ENTR-0098, n=2) intravenously, 1 week post injection, various muscle groups (quadriceps, transverse abdominis, diaphragm, and heart) were collected and analyzed by western blotting by blotting dystrophin and alpha-actinin (loading control) as shown in FIG. 44. Notably, mice administered with CPP12-PMO$^{DMD}$ exhibited enhanced dystrophin expression in a CPP-dependent manner. The degree of the dystrophin correction is also semi-quantified by image analysis using actinin as the loading control. As shown in FIGS. 45A-D, compared to that of PMO$^{DMD}$, CPP12-PMO$^{DMD}$ administration increased the dystrophin level in quadriceps (2.5 fold, FIG. 45A), transverse abdominis (4.8 fold, FIG. 45B), diaphragm (15.7 fold, FIG. 45C), and heart (>300 fold, FIG. 45D). Also by Western Blot analysis, FIGS. 46A-B show the sustainable dystrophin levels correction in heart muscles of MDX mice two weeks (FIG. 46A) and four weeks (FIG. 46B) after a single IV injection of 30 mpk CPP12-PMO$^{DMD}$ or 24 mpk (equal mole) PMO$^{DMD}$. The correction of dystrophin is consistent and as expected with the RT-PCR analysis as shown in FIGS. 42A-D and FIGS. 43A-D.

Structure activity relationship of CPP for PMO delivery in MDX mice. Table B4 shows the exon skipping activity one-week or 2-week of various muscle groups (Quadriceps, Heart, and Diaphragm) in MDX mice after a single IV injection of 20 mpk or 30 mpk of various CPP 12-connected PMO targeting the exon 23.

TABLE B4

Exon Skipping Activity in MDX Mice

| Animals | Injection | Oligo ID | Dosage (mpk) | Sac. | Exon 23 Skipping % Quad | Exon 23 Skipping % Heart | Exon 23 Skipping % Diaphragm |
|---|---|---|---|---|---|---|---|
| MDX | IV | ENTR-0098 | 30 | 2 w | 24.4 ± 7.4 | 5.0 ± 3.1 | 17.5 ± 5.9 |
| MDX | IV | ENTR-0100 | 30 | 2 w | 22.9 ± 16.5 | <1% | 11.6 ± 15.5 |
| MDX | IV | ENTR-0120 | 30 | 2 w | 0.4 ± 0.4 | <1% | 0.4 ± 0.2 |
| MDX | IV | ENTR-0088 | 30 | 2 w | 7.2 ± 3.3 | <1% | 0.0 ± 0.0 |
| MDX | IV | ENTR-0099 | 30 | 2 w | 25.6 ± 1.2 | <1% | 20.2 ± 0.0 |
| MDX | IV | ENTR-0115 | 30 | 2 w | 3.2 ± 3.4 | <1% | <1% |
| MDX | IV | ENTR-0161 | 20 | 1 w | 25.7 ± 5.1 | 1.1 ± 2.2 | 16.2 ± 10.7 |
| MDX | IV | ENTR-0098 | 10 | 1 w | 13.4 ± 3.7 | 2.2 ± 0.3 | 4.3 ± 0.8 |
| MDX | IV | ENTR-0089 | 10 | 1 w | <1% | <1% | <1% |
| MDX | IV | ENTR-0090 | 10 | 1 w | <1% | <1% | <1% |
| MDX | IV | ENTR-0092 | 10 | 1 w | <1% | <1% | <10% |
| MDX | IV | ENTR-0093 | 10 | 1 w | <1% | <1% | <1% |
| MDX | IV | ENTR-0119 | 30 | 2 w | 15.6 ± 8.3 | 5.0 ± 7.1 | 3.9 ± 4.7 |
| MDX | IV | ENTR-0163 | 20 | 1 w | 7.9 ± 3.7 | 0.0 ± 0.0 | 9.4 ± 1.8 |
| MDX | IV | ENTR-0164 | 20 | 1 w | 59.5 ± 2.2 | 29.1 ± 0.8 | 61.0 ± 13.7 |
| MDX | IV | ENTR-0165 | 20 | 1 w | 38.5 ± 2.5 | 30.5 ± 17.0 | 30.2 ± 2.8 |
| MDX | IV | ENTR-0201 | 20 | 1 w | 73.5 ± 8.4 | 60.5 ± 17.2 | 79.0 ± 6.8 |

The structures of examples of compounds comprising antisense oligonucleotides (underlined) (SEQ ID NO: 218) that target murine DMD and CPPs are shown below.

ENTR-0119:

ENTR-0119
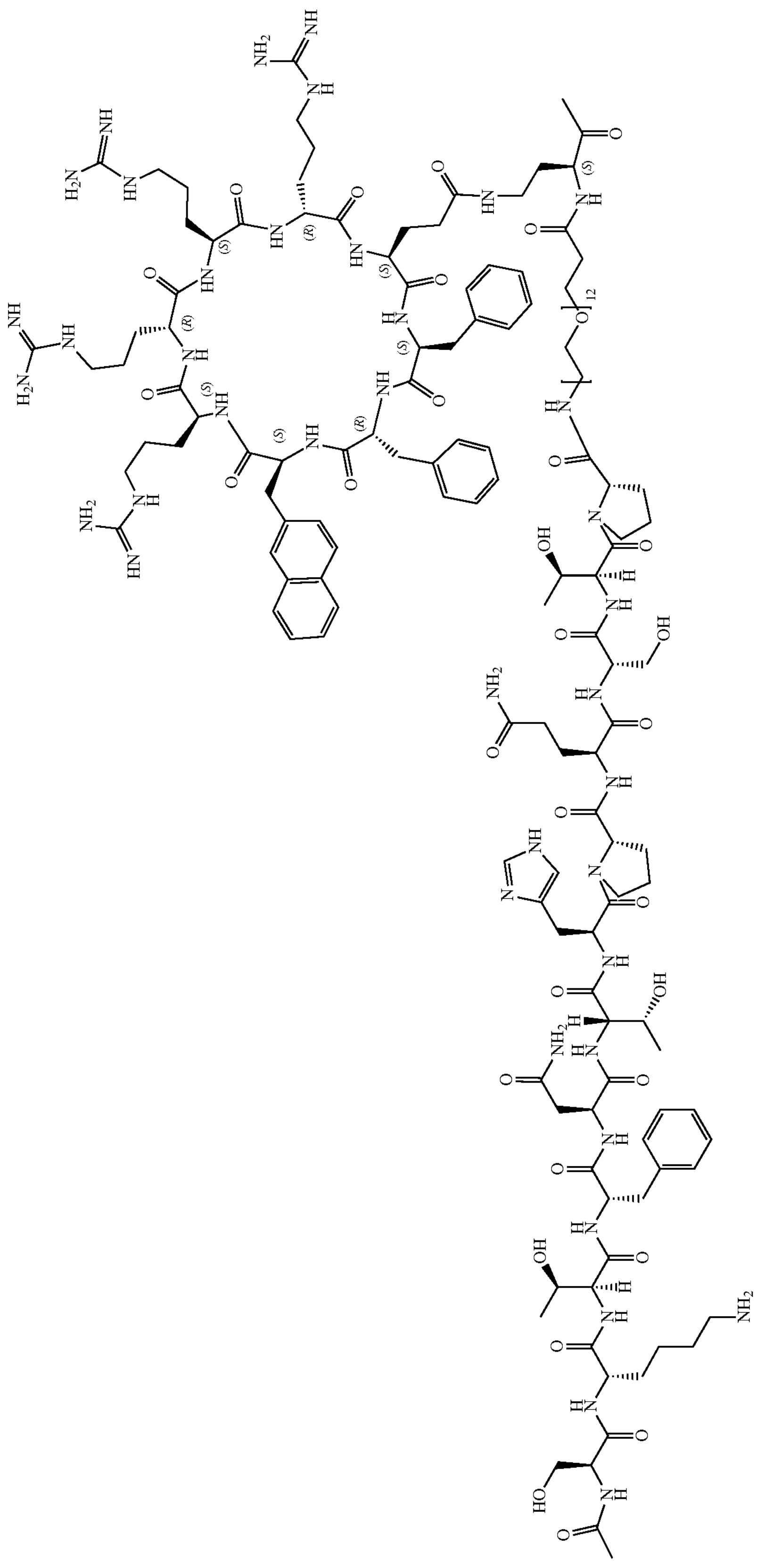

-continued
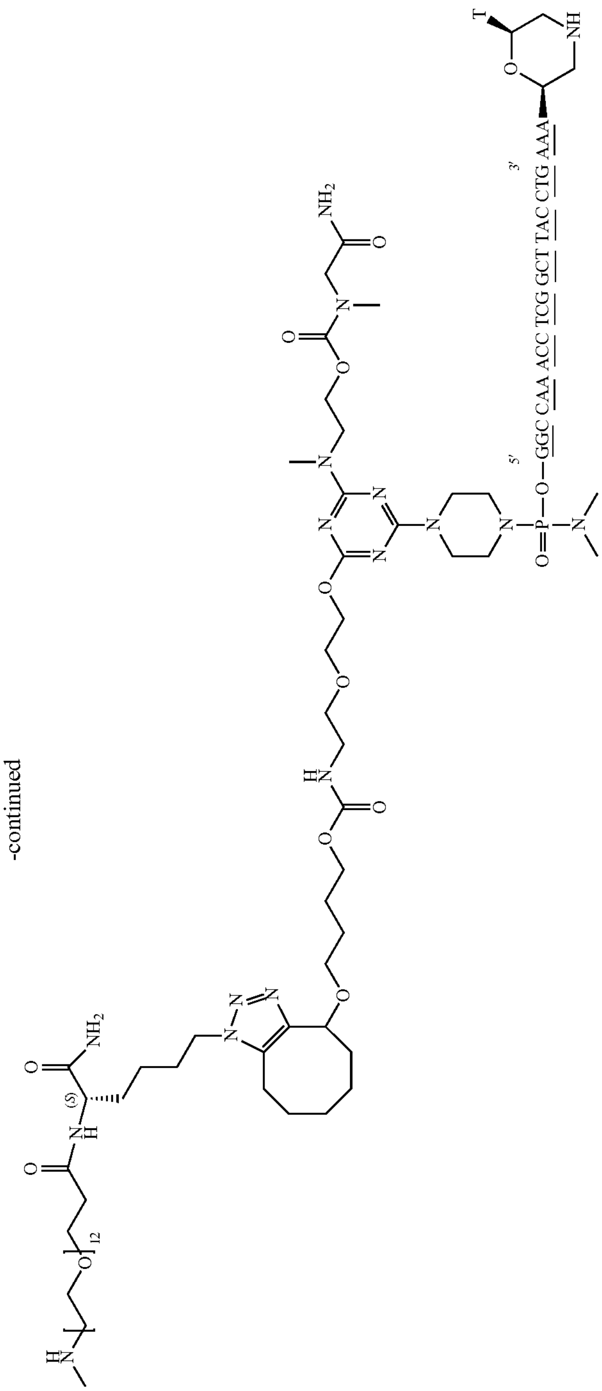

-continued
ENTR-0163
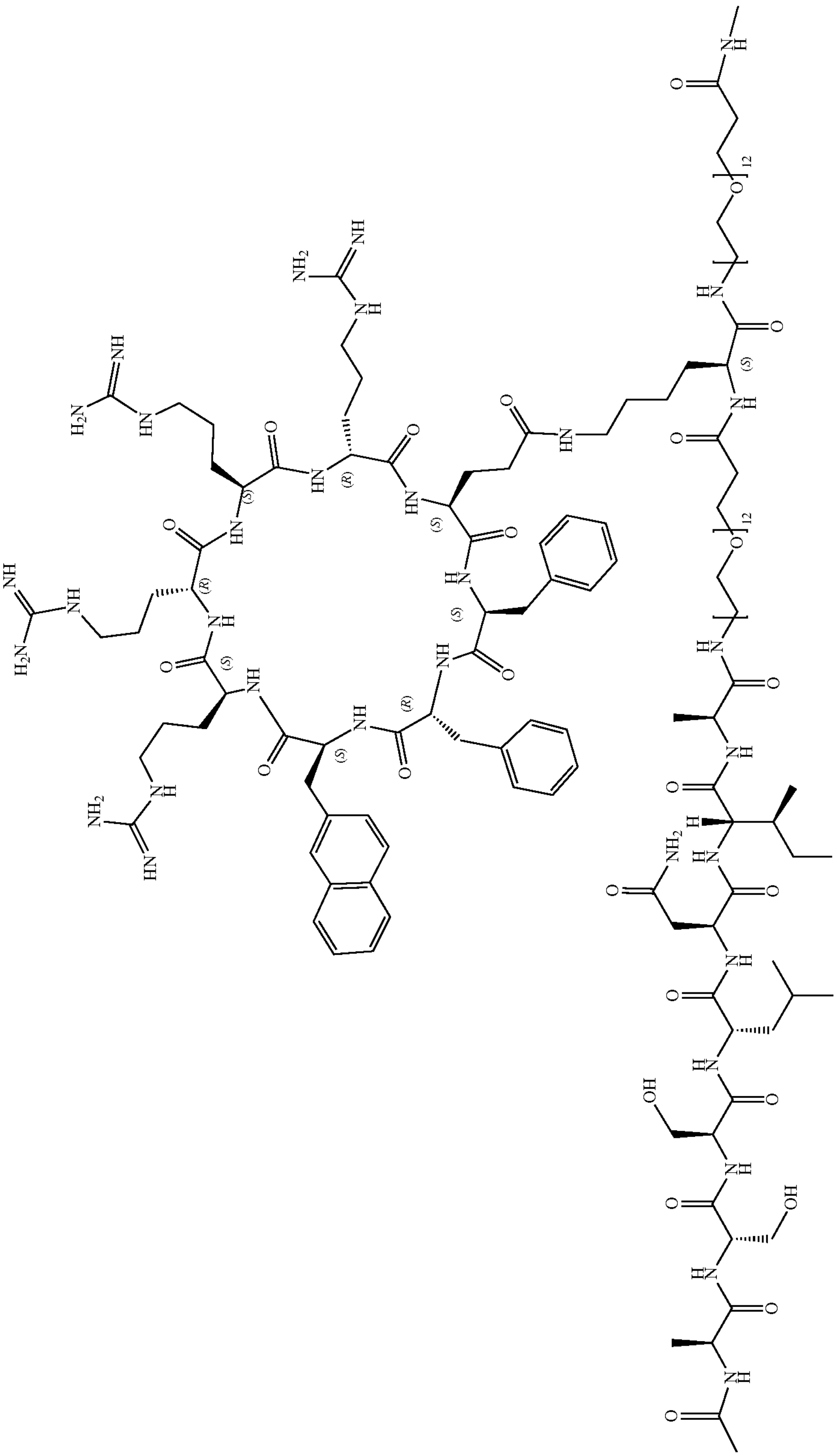

-continued
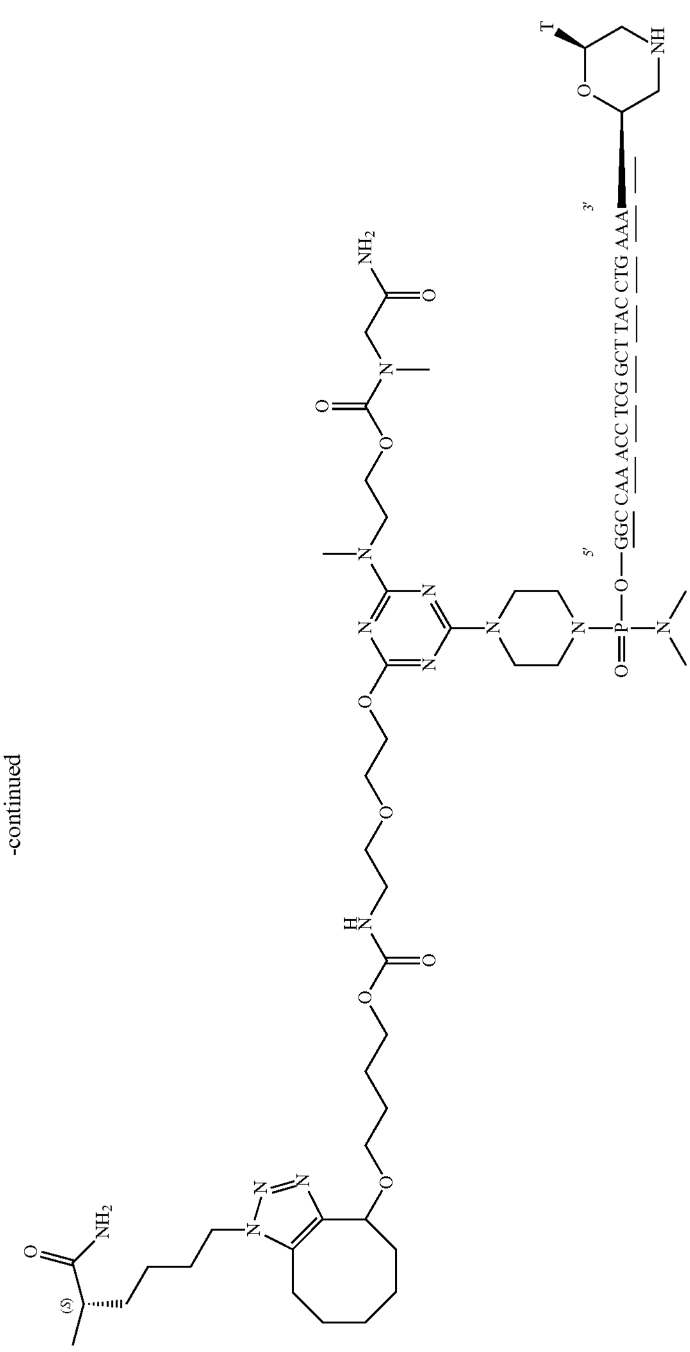
ENTR-0164
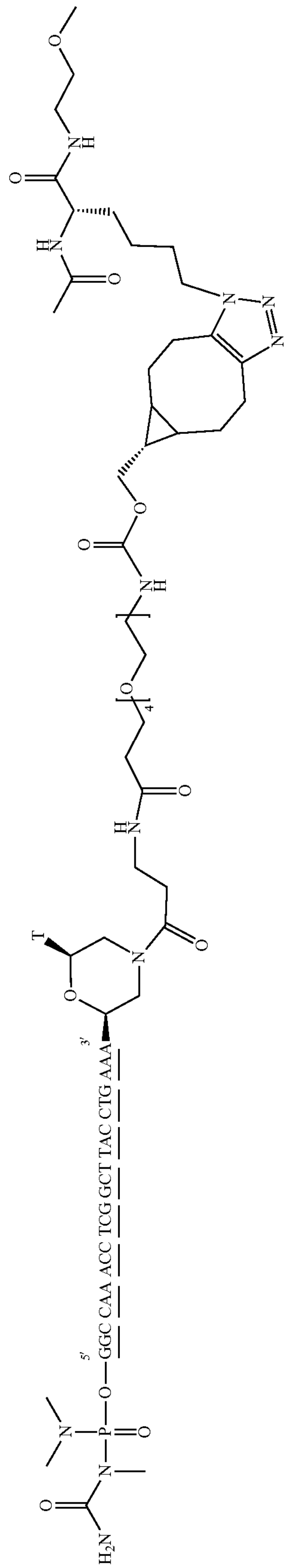

-continued
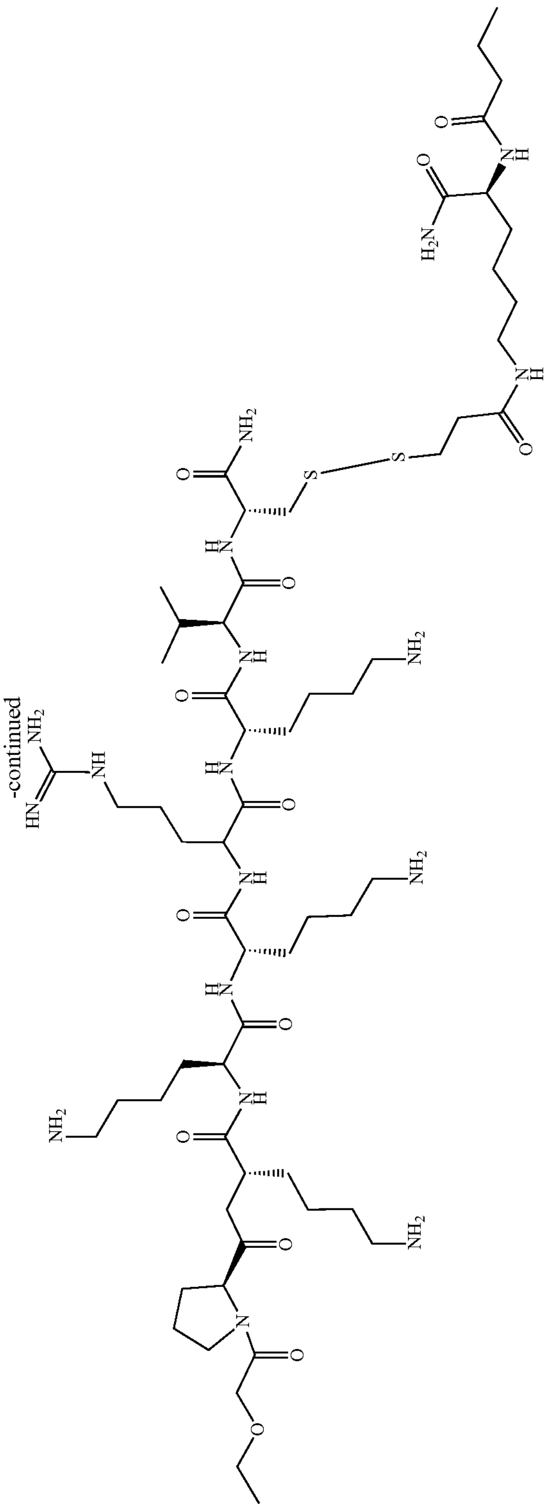

-continued
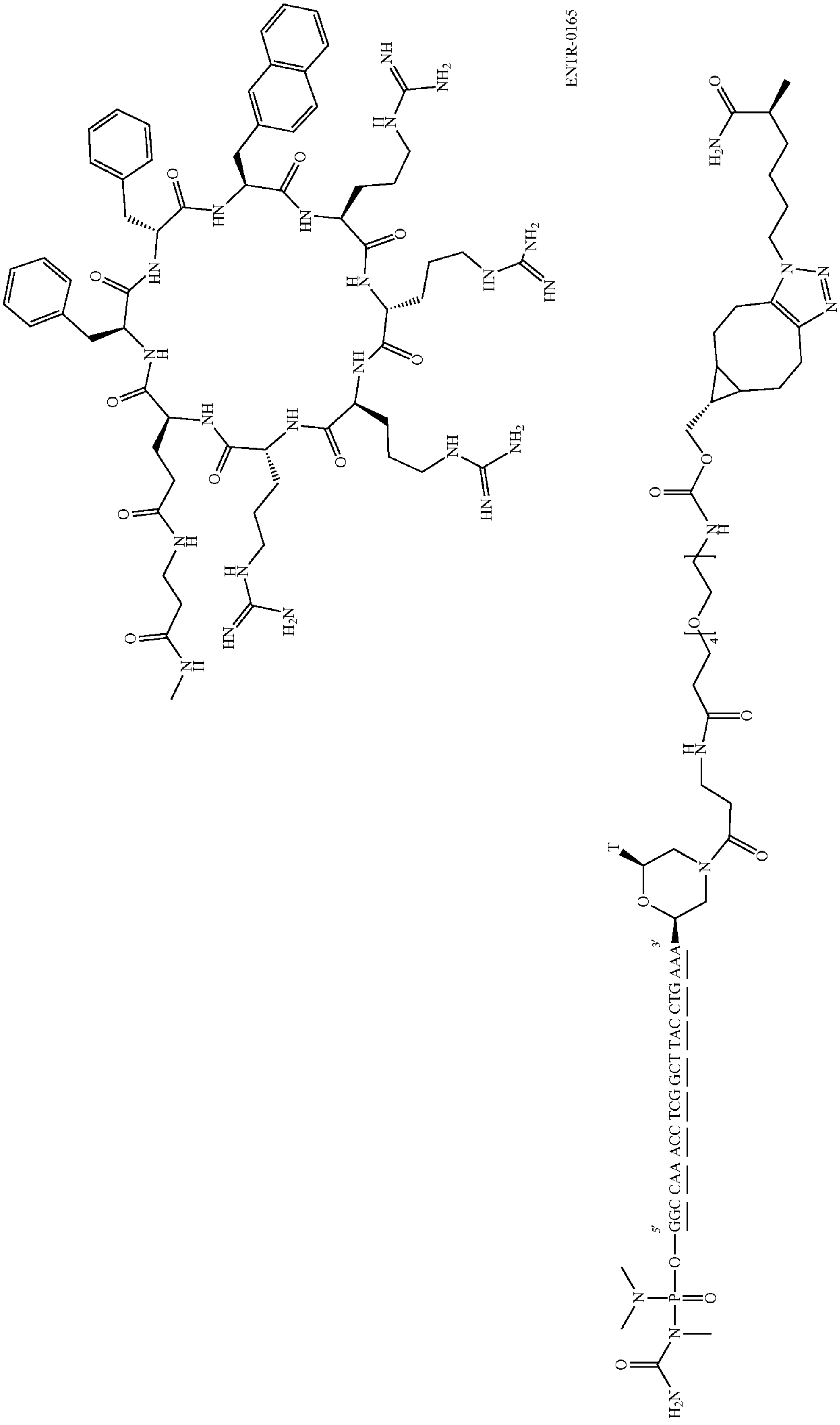
ENTR-0165

-continued
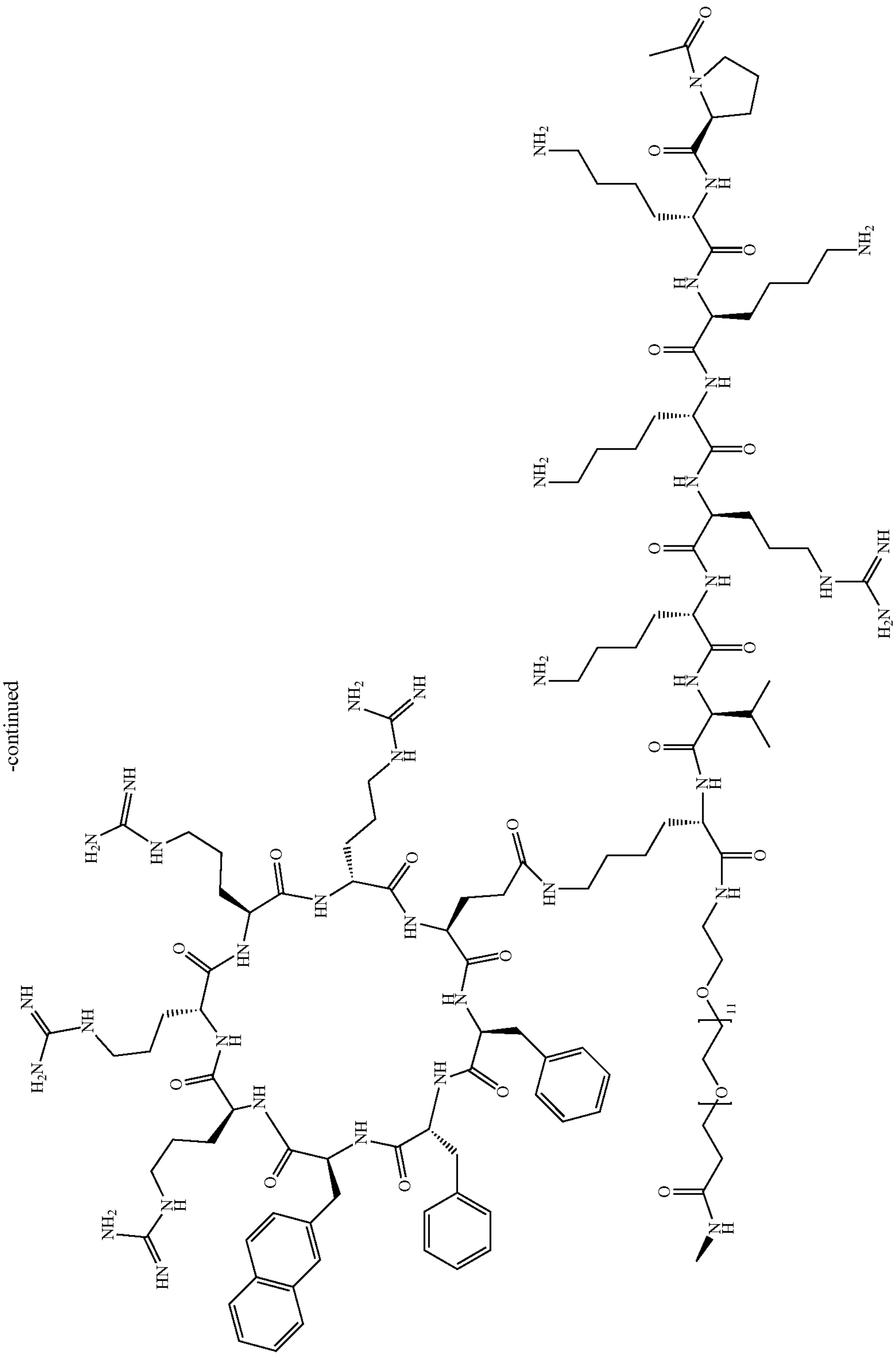

ENTR-0201
-continued
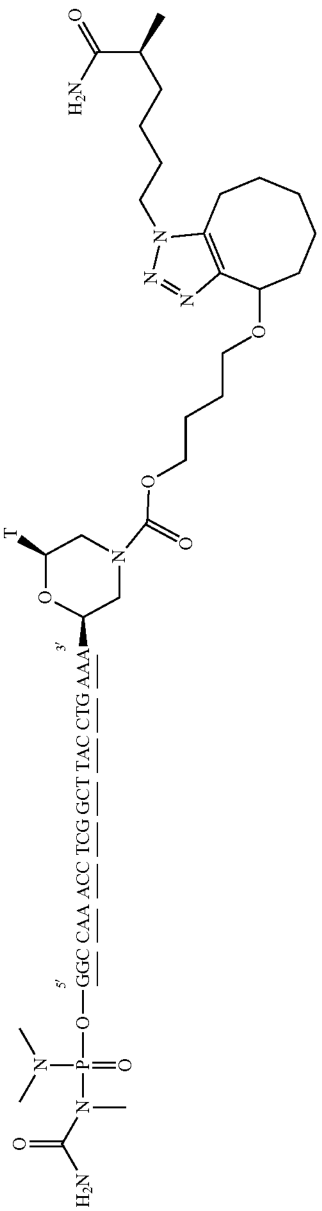

-continued
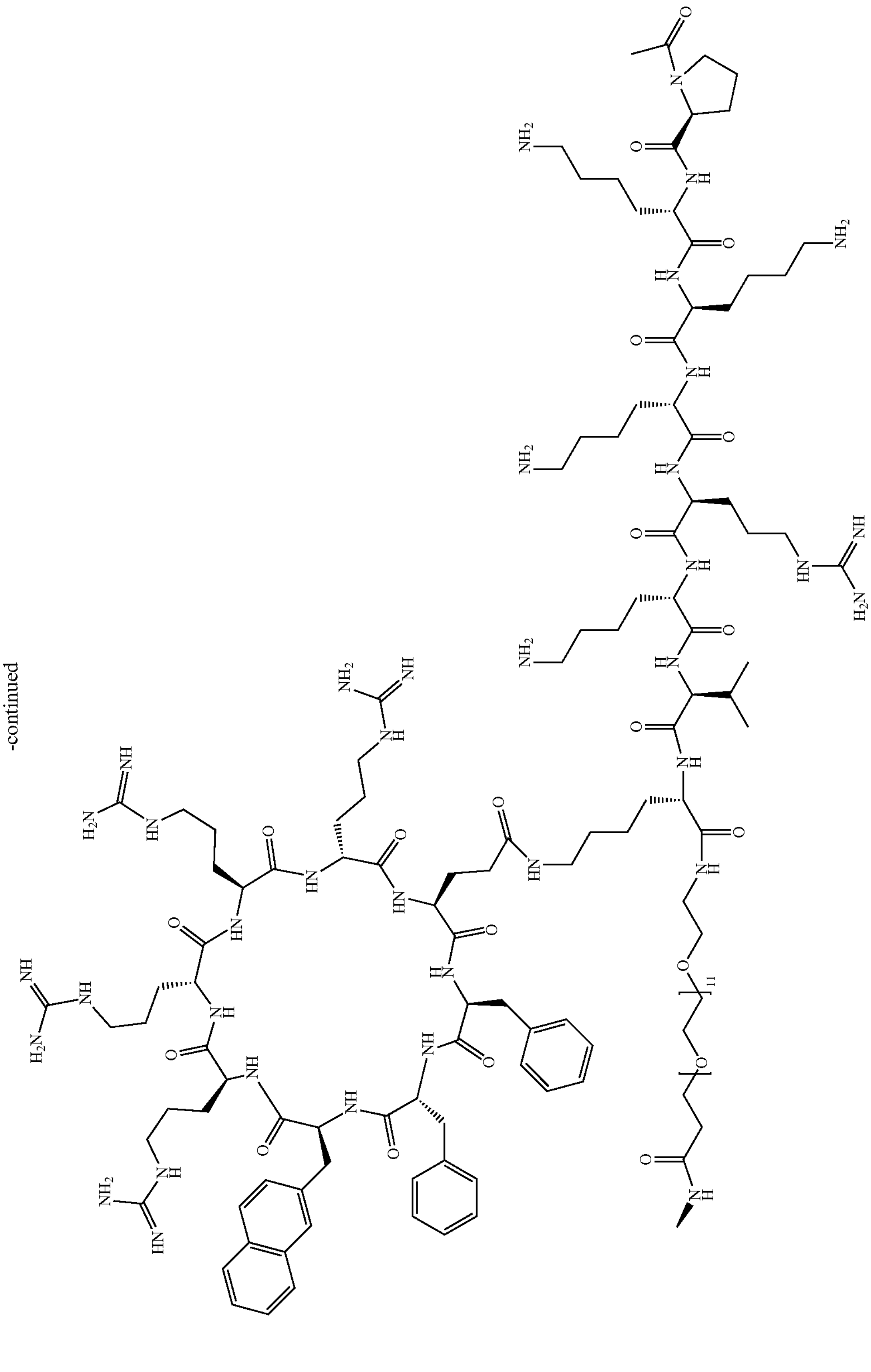

The activity of ENTR-098 is extracted from FIGS. 43A-D, and 2 week post single 30 mpk IV injection in MDX mice yielded robust exon skipping in quadricep (Quad) at 24.4±7.4%, in heart at 5.0±3.1%, as well as in diaphragm at 17.5±5.9%. Conjugation of mono-valent CPP12 to the 5' of PMO (e.g. ENTR-0100) vs the 3' of PMO (e.g. ENTR-0098) showed comparable exon skipping activity in Quad (22.9±16.5) and Diaphragm (11.6±15.5) but less in the heart (<1%) compared to that from ENTR-0098. The linker variants of ENTR-0098 also have significantly impact to the activity in MDX mice. For one example, further elongation of the linker between CPP12 and PMO from PEG12 to PEG24 (e.g. ENTR-0120) showed significantly reduced activity. For another example, replacing the amide bond linker as in ENTR-0100 to a cathepsin-B-cleavable linker (Val-CitPABC) as in ENTR-0088 significantly reduced the activity (comparing ENTR-0100 vs ENTR-0088). For another example, replacing the amide bond linker as in ENTR-0100 to a disulfide bond linker as in ENTR-0099 does not have any significant impact of the activity (comparing ENTR-0100 vs ENTR-0099). Interestingly, connecting the CPP and PMO with prodisulfide bond has a reduced activity as shown in ENTR-0115. For another example, replacing the PEG12 linker as in ENTR-0088 to all carbon chain ($C_6$ linker) as in ENTR-161 does not significantly modify the activity. To our surprise, connecting bivalent CPP12 to one PMO cargo molecule yielded significantly reduced activity (e.g. bivalent examples as in ENTR-0089, ENTR-0090, ENTR-0092 and ENTR-0093). Without being bound by theory, this may be due to limited biodistribution of these constructs to the target muscular tissues.

Figure 9:
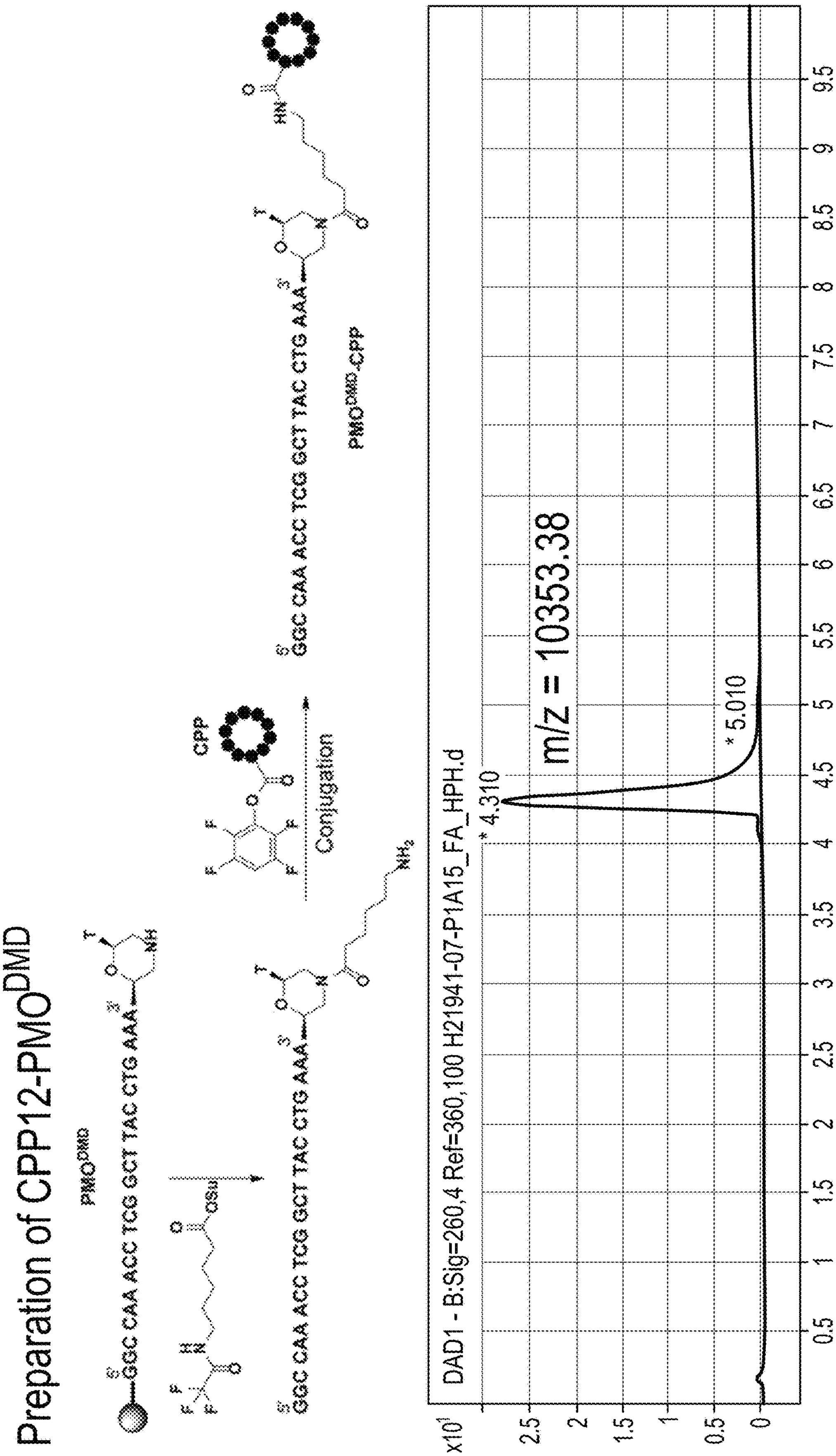
FIG. 9 shows an illustrative scheme for conjugating a CPPto an AC (SEQ ID NO: 214).

Example 3C. Use of Cell-Penetrating Peptides Conjugated to Oligonucleotides for Splicing Correction of Dystrophin in Mouse Model of DMD The study protocols of the previous examples were utilized to evaluate an additional AC that targets exon 23. The additional AC used had the following sequence 5'-GCTATTACCTTAACCCA-3' (PMO modifications) (SEQ ID NO: 152), which targeted exon 23. This sequence is referred to as PMO in this example. PBS, PMO conjugated to a CPP ("CPP-PMO," also called "EEV12-PMO$^{DMD}$" or "PMO$^{DMD}$-EEV12"), or PMO without CPP (also called PMO$^{DMD}$) was administered via intramuscular (IM) or intravenous (IV) to MDX mice at the following doses: 1 mpk, 3 mpk, 10 mpk, 30 mpk; mpk: mg of compound/kg of body weight. The CPP used was cCPP12, which has an amino acid sequence of FfΦRrRr (SEQ ID NO: 117). A schematic of preparation of PMO$^{DMD}$ and PMO$^{DMD}$-EEV12 is shown in FIG. 9. Total RNA were extracted from tissue samples and analyzed by RT-PCR to visualize the efficiency of splicing correction.

Figure 19A:
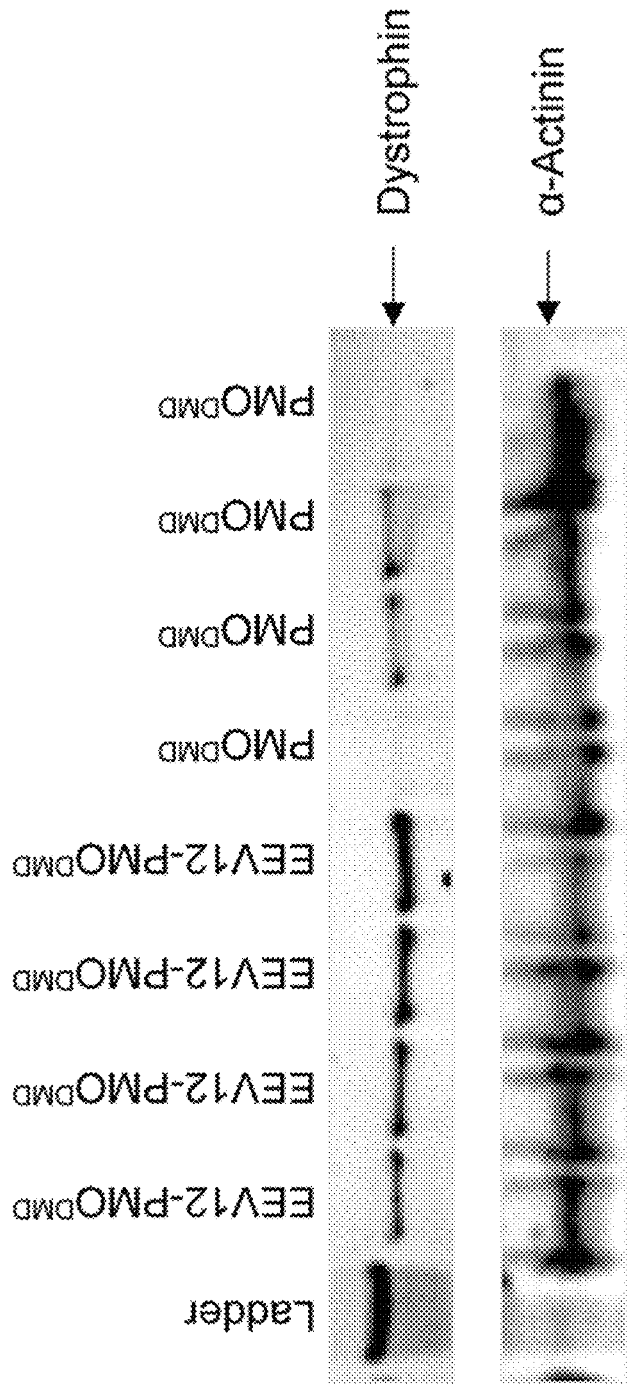
FIGS. 19A-B show the dystrophin levels in MDX mice two weeks (FIG. 19A) and four weeks (FIG. 19B) after treatment with 30 mpk EEV12-$PMO^{DMD}$ or 30 mpk $PMO^{DMD}$.
Figure 19B:
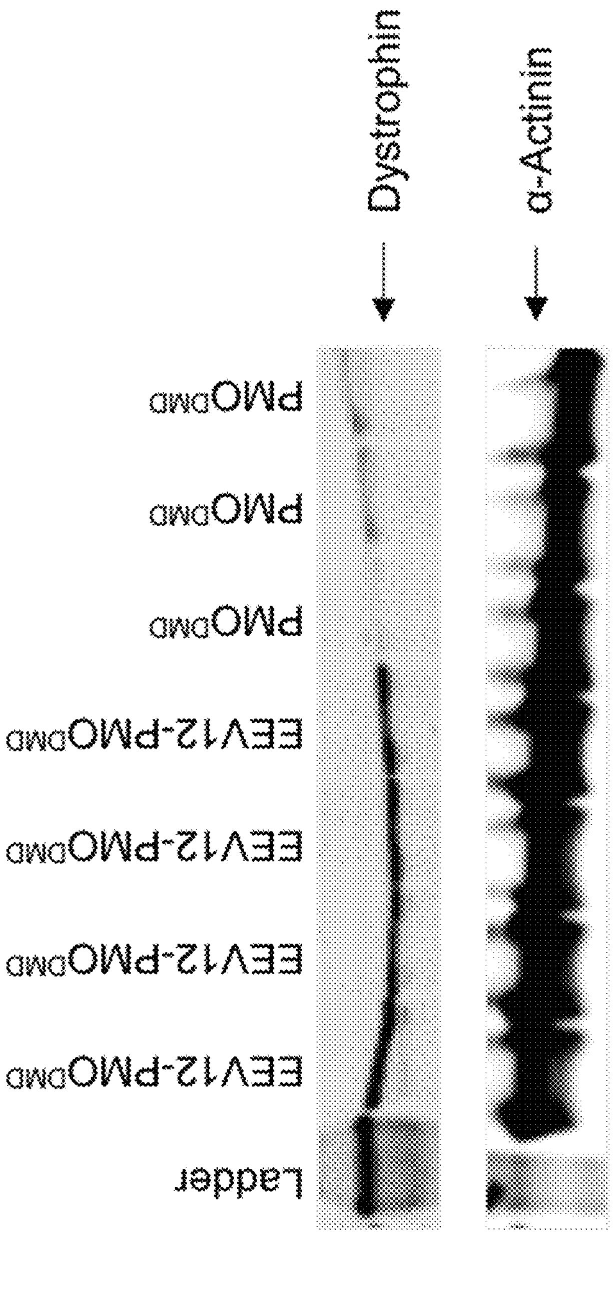
Figure 20A:
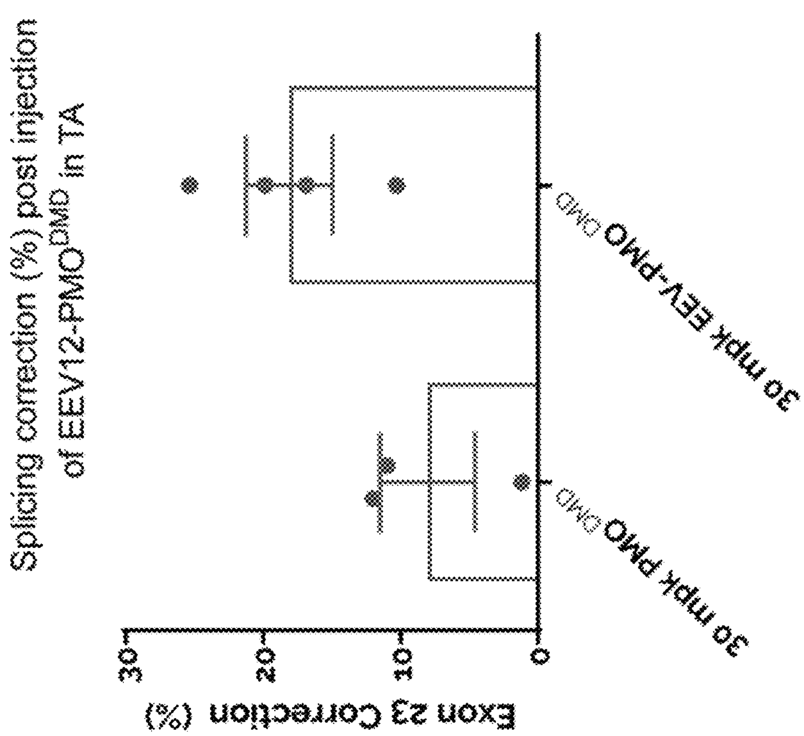
FIGS. 20A-D show the percentage of exon 23 corrected dystrophin products in transverse abdominus (FIG. 20A), quadriceps (FIG. 20B), diaphragm (FIG. 20C), and the heart (FIG. 20D) in MDX mice that were administered either 30 mpk of $PMO^{DMD}$ or 30 mpk of EEV12-$PMO^{DMD}$. Mice administered EEV12-$PMO^{DMD}$ exhibited enhanced splicing correction, compared to mice administered $PMO^{DMD}$ alone.
Figure 20B:
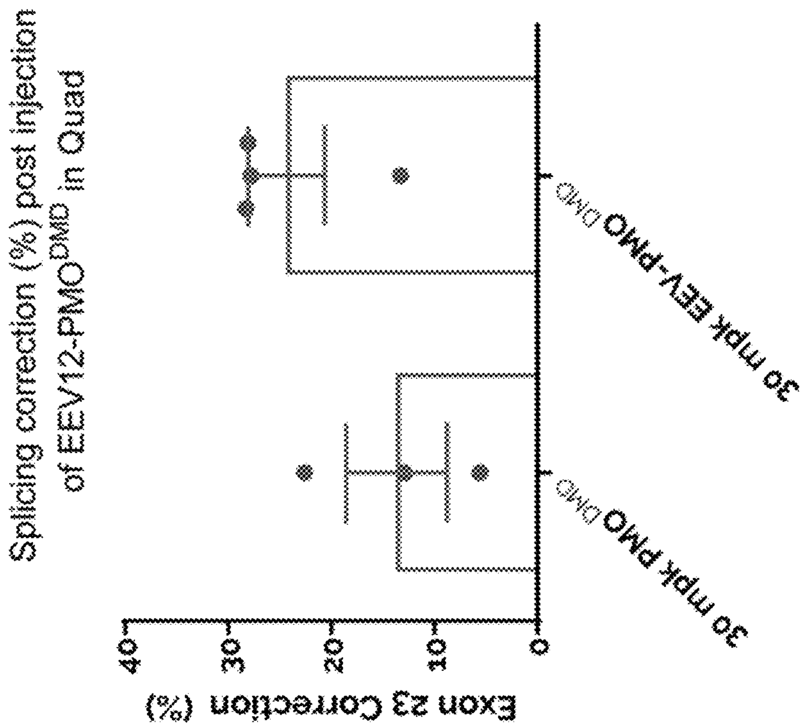
Figure 20D:
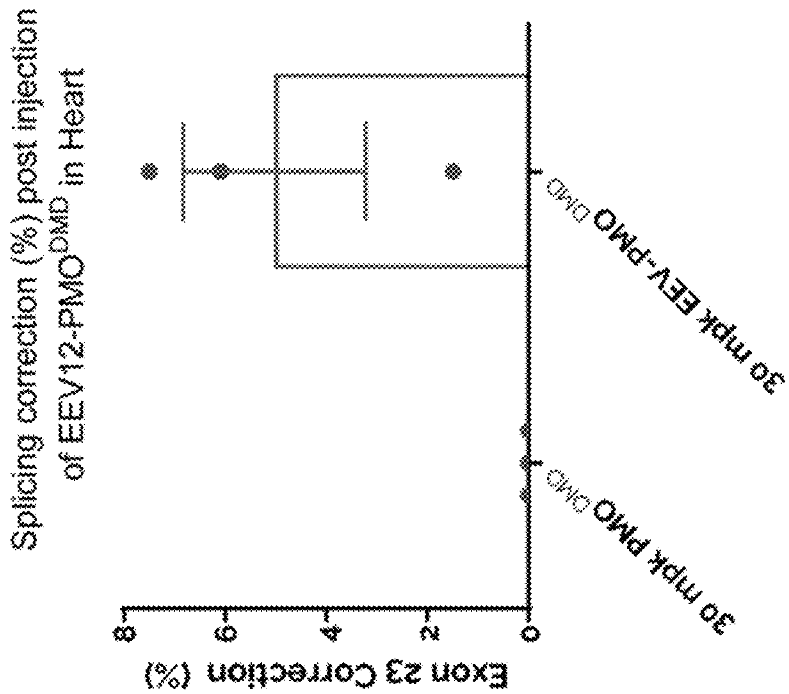
Figure 20C:
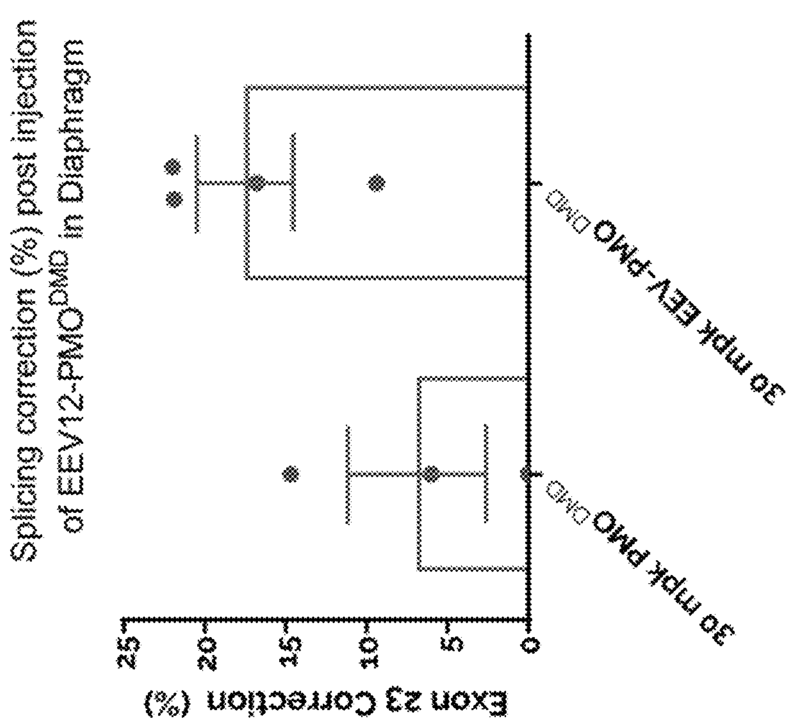

Detection of splicing correction by RT-PCR and Western Blot. As shown in FIG. 10, MDX mice treated with EEV12-PMO$^{DMD}$ produced dystrophin lacking exon 23, whereas MDX mice treated with PMO alone produced only dystrophin containing exon 23 (similar to untreated control). MDX mice were administered 10 mpk I.V. PMO$^{DMD}$ and EEV12-PMO$^{DMD}$. The dystrophin products in various muscle groups (e.g., the quadriceps, transverse abdominus, diaphragm, and heart) are shown in FIG. 11. FIG. 11 shows that in contrast to delivery of PMO$^{DMD}$ alone, the delivery of EEV12-PMO$^{DMD}$ to MDX mice resulted in corrected dystrophin splicing (e.g., dystrophin with excised exon 23) in the quadriceps, transverse abdominus, diaphragm, and heart. FIGS. 12A-D show the effect of the following IV dosage regimens on exon skipping efficacy: 10 mpk twice per week, 10 mpk once per week, 10 mpk once per two week, and 30 mpk once per week. Notably, 30 mpk EEV12-PMO$^{D}$ resulted in the highest percentage of exon skipping. The percentage of exon 23 corrected dystrophin products in quadriceps, transverse abdominus, diaphragm, and heart as determined by RT-PCR is shown in FIGS. 13A-D. FIGS. 20A-D show the percentage of exon 23 corrected dystrophin products in transverse abdominus (FIG. 20A), quadriceps (FIG. 20B), diaphragm (FIG. 20C), and the heart (FIG. 20D) in MDX mice that were administered either 30 mpk of PMO$^{DMD}$ or 30 mpk of EEV12-PMO$^{DMD}$. Mice administered EEV12-PMO$^{DMD}$ exhibited enhanced splicing correction, compared to mice administered PMO$^{DMD}$ alone. FIGS. 14A-D show exon skipping efficacy of the above-noted dosing regimens in quadriceps, transverse abdominus, diaphragm, and heart by Western Blot. FIGS. 19A-B show the dystrophin levels in MDX mice two weeks (FIG. 19A) and four weeks (FIG. 19B) after treatment with 30 mpk EEV12-PMO$^{DMD}$ or 30 mpk PMO$^{DMD}$. FIGS. 15A-D show dystrophin protein recovery in muscle groups from MDX mice treated with EEV12-PMO$^{DMD}$ at 10 mpk twice per week, 10 mpk once per week, 10 mpk once per two week, and 30 mpk once per week.

Example 3D. Use of Cell-Penetrating Peptide Coupled to an Oligonucleotide and Nuclear Localization Sequence for Splicing Correction of Exon 23 of DMD in an MDX Mouse Model Purpose. This study employs an MDX mouse model, a model of DMD, to study the effect of compositions comprising an AC, a CPP, and a nuclear localization sequence on dystrophin expression and muscle fiber damage.

Study design. Compositions comprising an AC having a sequence of 5'-GGCCAAACCTCGGCTTACCTGAAAT-3' (SEQ ID NO: 260), a cCPP12 (amino acid sequence is FfΦRrRr (SEQ ID NO: 117)), and a nuclear localization sequence PKKKRKV (SEQ ID NO: 131) (referred to herein as "ENTR-201" are applied to MDX mice to evaluate the ability of the compositions to skip exon 23 and thus treat DMD. A control composition lacks cCPP12 and a nuclear localization sequence. The sequence of the AC of the control composition is 5'-GGC CAA ACC TCG GCT TAC CTG AAA T-3' (SEQ ID NO: 260). The ENTR-201 composition is administered to the mice intravenously (IV) at a dose of 10 mg/kg once per week for four weeks or at a dose of 20 mpk once. The control composition is administered to mice intravenously (IV) at a dose of 20 mpk. Total RNA is extracted from tissue samples and analyzed by RT-PCR and protein is extracted from tissue sample and analyzed by Western Blot to visualize the efficiency of splicing correction and to detect dystrophin products. The percentage of exon 23 corrected products is evaluated. The dystrophin protein level is evaluated with respect to alpha-actinin (loading control) as well as in comparison to dystrophin expression in wild-type mice. Serum levels of creatine kinase, which is increased in DMD patients as a result of muscle fiber damage, were also evaluated by a commercially available kit purchased from Sigma Chemicals.

Evaluations of peptide fusions to the CPP12-PMO construct. To further increase the functional delivery of PMO, we also explored various peptides fusions for the CPP-PMO constructs as shown in Table B4. For one example, T9 peptide (SKTFNTHPQSTP (SEQ ID NO: 258)) (Y. Seow et al./Peptides 31 (2010) 1873-1877) and muscle specific peptide (MSP peptide, ASSLNIA (SEQ ID NO: 259) (Gao et al.

Molecular Therapy (2014) 22, 7: 1333-1341) which have been demonstrated to enhanced muscle targeting were also fused to CPP12 construct as in ENTR-0119 and ENTR-0163 respectively. As detailed in Table B4, neither of these peptide fusions improved the activity in MDX mice (comparing ENTR-0119, ENTR-0163 and ENTR-0098). Consistent with what we found the GFP correction in Example 1, CPP12 with a Nuclear Localization Sequence (PKKKRKV (SEQ ID NO: 131)) outperformed CPP12 alone significantly (e.g. ENTR-164, ENTR-0165, and ENTR-0201, Table B4). One week after a single intravenous dose at 20 mpk, ENTR-164 yielded 59.5±2.2%, 29.1±0.8%, and 61.0±13.7% exon 23 skipping in Quad, heart, and diaphragm respectively. One week after a single intravenous dose at 20 mpk, ENTR-165 yielded 38.5±2.5%, 30.5±17.0%, and 30.2±2.8% exon 23 skipping in Quad, heart, and diaphragm respectively. One week after a single intravenous dose at 20 mpk, ENTR-201 yielded 73.5±8.4%, 60.5±17.2%, and 79.0±6.8% exon 23 skipping in Quad, heart, and diaphragm respectively. The preparation of these NLS fusions were described in detail above. The structure of ENTR-164, ENTR-165 are shown above. Consistent with the exon skipping data, by ENTR-0164 and ENTR-0165 also significantly corrected the expression of dystrophin protein levels as analyzed by Western Blot shown in FIG. 47. By comparing to the level in respective tissues from wild type (C57BL/10) and using the actinin as loading control, percentage of dystrophin protein correction is further quantified to that of wild type and shown in FIGS. 48A-D. Instead of using the modified PMO with 3' amide bond formation, we also tested the incorporation of cyclooctyne on solid support by modifying the morpholino amino group with a bifunctional linker comprised of a cyclooctyne moiety for click reaction to a CPP-azide and a PFP easter to form a carbamate with PMO and thus produced the precursor which can be used for synthesis of ENTR-201. Similar to that of ENTR-165, ENTR-201 also demonstrated high exon skipping activity across all the muscle groups as shown in Table B4.

Activity of ENTR-201 in MDX mice. The study design in FIG. 50 and the table below outlines the injection, sample collection and bioanalysis to study the duration of effects of ENTR-201 after single IV injection.

| Group | N | Treatment | Dosage (mpk) | SAC time (p.i.) | Endpoints |
|---|---|---|---|---|---|
| 1 | 3 | PBS | 0 | 1 week | Exon skipping (RT-PCR) |
| 2 | 3 | ENTR-201 | 20 | 1 week | |
| 3 | 3 | ENTR-201 | 20 | 2 weeks | Dystrophin expression |
| 4 | 3 | ENTR-201 | 20 | 4 weeks | (Western blot and immunohistochemistry) |

After a single dose of ENTR-201 at 20 mg/kg on day 1, animals were sacrificed at 1 week, 2 weeks and 4 weeks post injection. Vehicle (PBS) only was used as a negative control. Heart, diaphragm, quadriceps and transverse abdominis were collected for RT-PCR to detect dystrophin exon 23 skipped product, and Western blot analysis to detect dystrophin protein expression (relative to alpha-actinin). Samples from 4 weeks post single IV injection of ENTR-201 at 20 mpk or PBS were also analyzed by immunohistochemistry staining to detect expression and distribution of dystrophin in various muscle tissues.

Figure 51A:
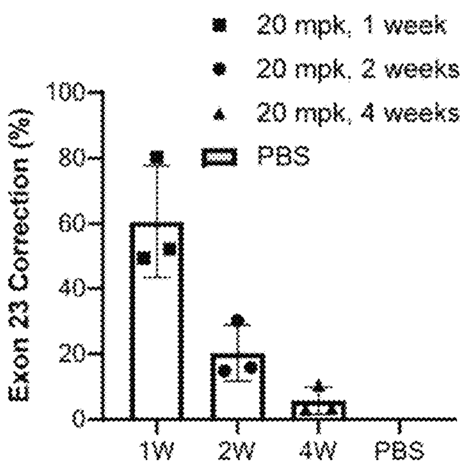
Figure 51B:
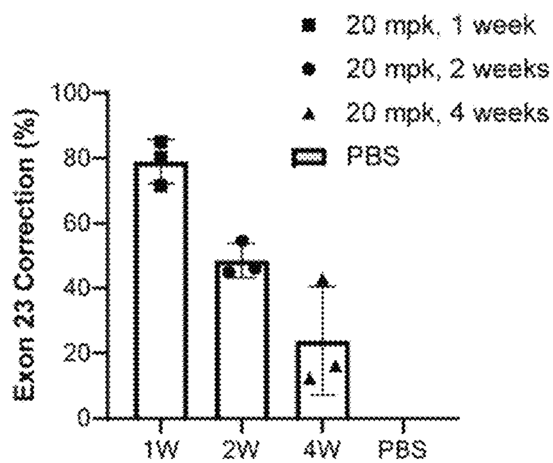
Figure 51C:
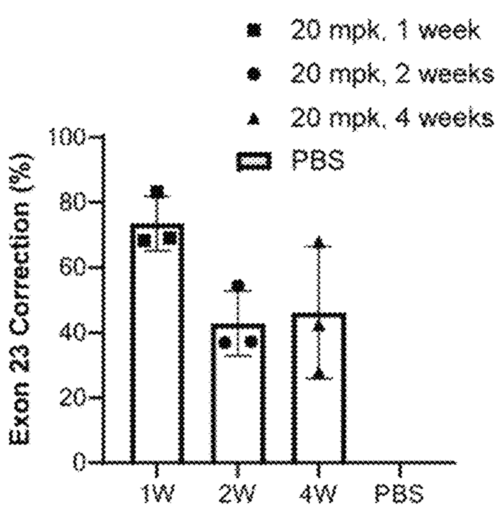
Figure 51D:
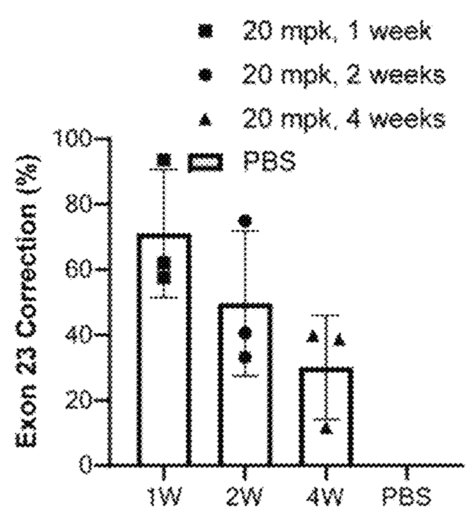
Figure 52A:
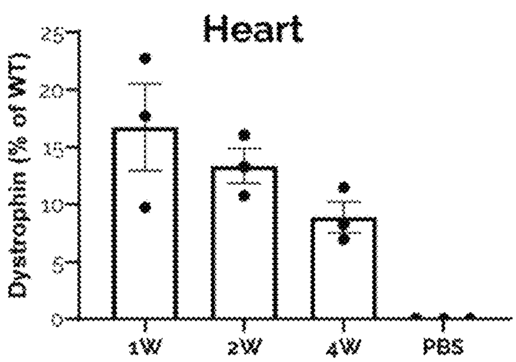
Figure 52B:
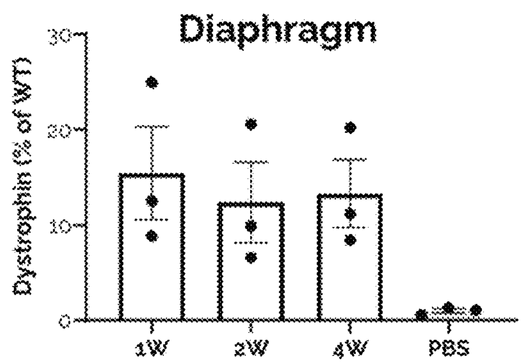
Figure 52C:
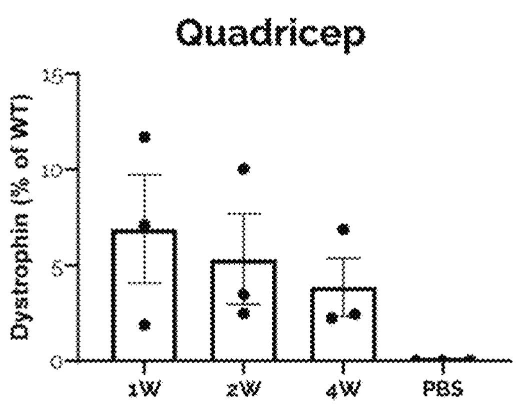
Figure 52D:
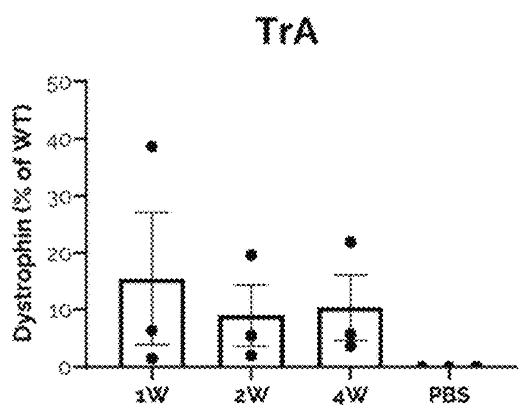

Treatment of mice with single dose 20 mg/kg ENTR-0201 resulted in splicing correction of dystrophin in the heart (FIG. 51A), diaphragm (FIG. 51B), quadriceps (FIG. 51C) and transverse abdominis (TrA) (FIG. 51D). ENTR-0201 delivers significant enhancements in exon skipping efficiency up to four weeks post single IV injection. The corresponding dystrophin protein levels were analyzed by Western Blot and summarized in FIG. 52A-D. Restored dystrophin protein sustained up to four weeks after single IV injection at 20 mpk in the heart (FIG. 52A), diaphragm (FIG. 52B), quadriceps (FIG. 52C) and transverse abdominis (TrA) (FIG. 52D). The level of protein correction is consistent with the RNA analysis. The tissue samples from the last injection were also analyzed by immunohistochemistry as shown in FIG. 53, which show that all the skeletal muscle fibers immunostained positive for dystrophin protein as visualized by brown color staining. The intensity of dystrophin expression was significant in the heart muscle tissue reaching near normal levels. Widespread uniform expression of dystrophin protein over multiple tissue sections within each of muscle group analyzed.

Activity of ENTR-201 in MDX mice after repeated dosage. The study design schemed in FIG. 54 and table below outlines the injection, sample collection and bioanalysis to study the activity of ENTR-201 after repeated dosage.

| Group | N | Treatment | Dosage (mpk) | Dosage Frequency | Endpoints |
|---|---|---|---|---|---|
| 1 | 3 | PBS | 0 | QW x 4 | Exon skipping (RT-PCR) |
| 2 | 3 | ENTR-013 | 20 | QW x 4 | |
| 3 | 3 | ENTR-201 | 10 | QW x 4 | Creatine Kinase Dystrophin Expression (Western blot and immunohistochemistry) |

Mice were treated with 10 mg/kg of ENTR-201 once every week for 4 weeks. ENTR-013 at 20 mg/kg (PMO only) and vehicle (PBS) only were used as control groups. All animals were sacrificed at 1 week post the last injection. Heart, diaphragm, quadriceps and transverse abdominis were collected for RT-PCR to detect dystrophin exon skipped products (FIGS. 55A-D), Western blot analysis and immunohistochemistry staining to detect dystrophin protein expression (FIGS. 56A-D and FIGS. 57A-D) to detect expression and distribution of dystrophin in various tissues. Serum creatine kinase level was quantified as a muscle functional biomarker (FIG. 58).

Treatment of MDX mice with 10 mg/kg ENTR-201 once per week for four weeks also resulted in significant splicing correction of dystrophin mRNA (FIGS. 55A-D) and dystrophin protein levels (FIGS. 56A-D) in various muscle tissues (heart, diaphragm, quadricep, and transverse abdominis (TrA)). In comparison to treatment with 20 mpk PMO, treatment with ENTR-201 at 10 mg/kg results in a higher amount of both splicing correction and dystrophin protein in all four muscle tissues (FIGS. 55A-D and FIGS. 56A-D). Notably, the mRNA correction and dystrophin protein expression in the heart are only observed in 10 mpk ENTR-201 treated MDX mice, not in 20 mg/kg PMO treated MDX mice. The findings from IHC study (FIG. 43) was also consistent with RT-PCR and WB analysis. Treatment with 10 mpk ENTR-201 once per week for four weeks also normalized the serum creatine kinase level, which is a muscle damage biomarker, suggesting that Oligo 201 treatment reduces muscle fiber damage in a DMD mouse model (FIG. 58). PMO (ENTR-0013) treatment alone in contract did not significantly reduce the elevated serum CK level (FIG. 58). Serum samples were collected one week after the last injection from repeated dosing study. Analysis of CK levels was performed using commercially available CK measurement kit (Millipore Sigma chemicals, MAK116) as per instructions from the manufacturer. Quantification of dystrophin protein showed nearly 40% cells are positive for dystrophin in cardiac tissue compared to 5% or less in vehicle treated or PMO alone treated cardia tissues (FIG. 59).

Figure 21A:
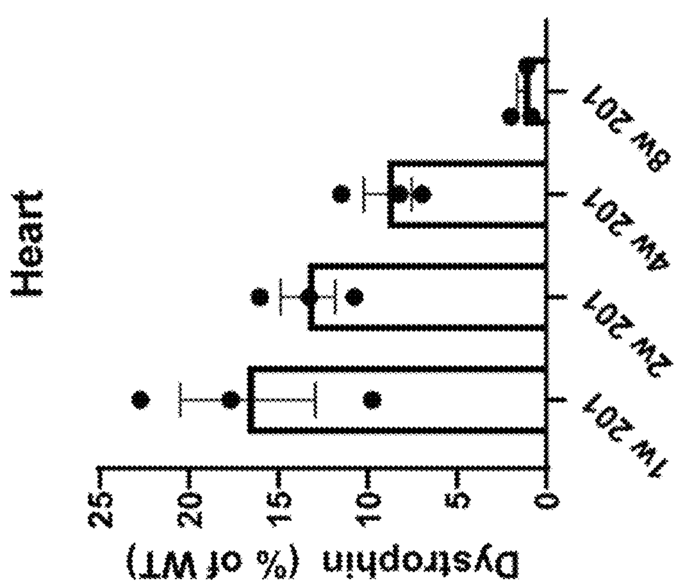
FIGS. 21A-B shows the effect of a composition called Oligo 201 comprising an AC, a nuclear localization sequence, and a CPP on exon 44 skipping in an MDX mouse model. The presence of an exon-skipped DMD product after treatment with Oligo 201 once a week is evaluated after one week, two weeks, four weeks, and eight weeks of treatment in the heart (FIG. 21A) and the diaphragm (FIG. 21B).
Figure 21B:
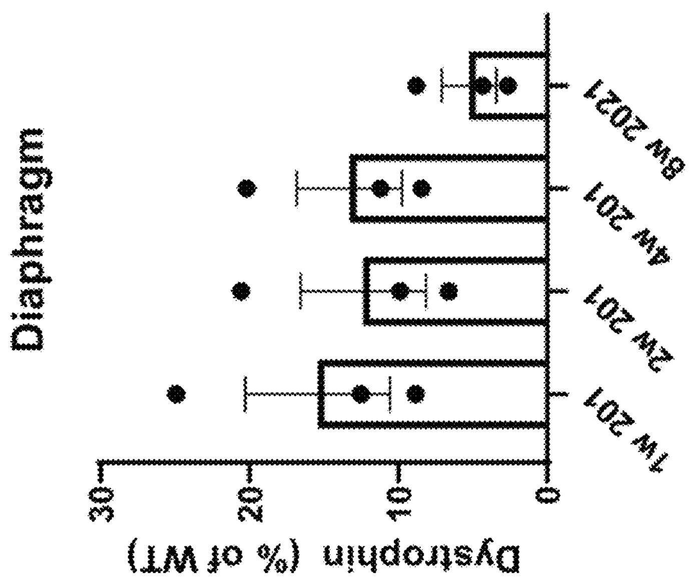
Figure 22A:
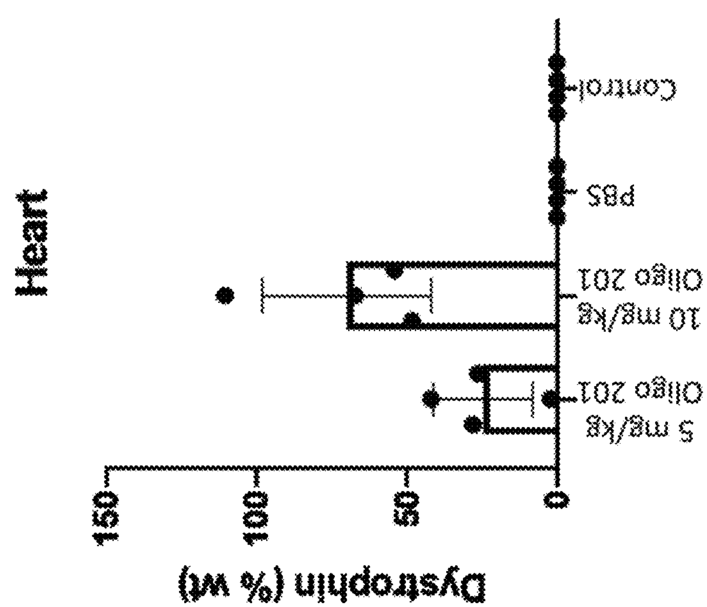
FIGS. 22A-D shows the effect of a composition called Oligo 201 comprising an AC, a nuclear localization sequence, and a CPP on exon 44 skipping in an MDX mouse model. The presence of an exon-skipped DMD product after treatment with 5 mg/kg Oligo 201 or 10 mg/kg Oligo 201 four times per week is evaluated in the heart (FIG. 22A) and diaphragm (FIG. 22B).
Figure 22B:
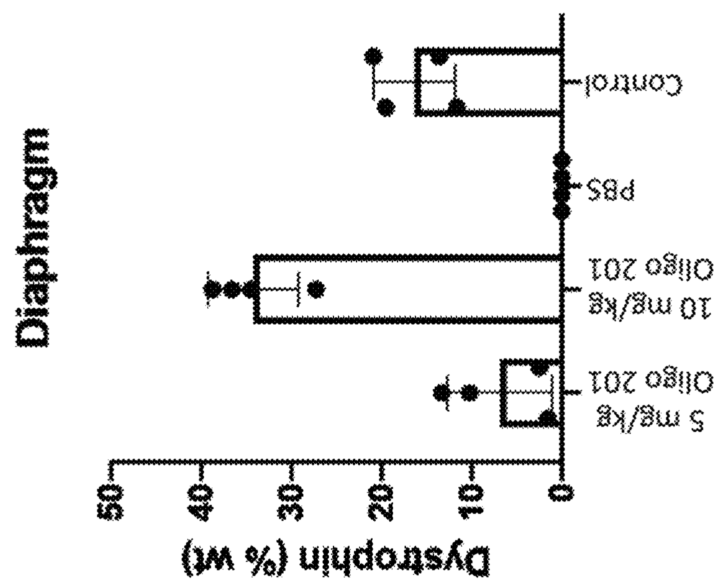
Figure 22C:
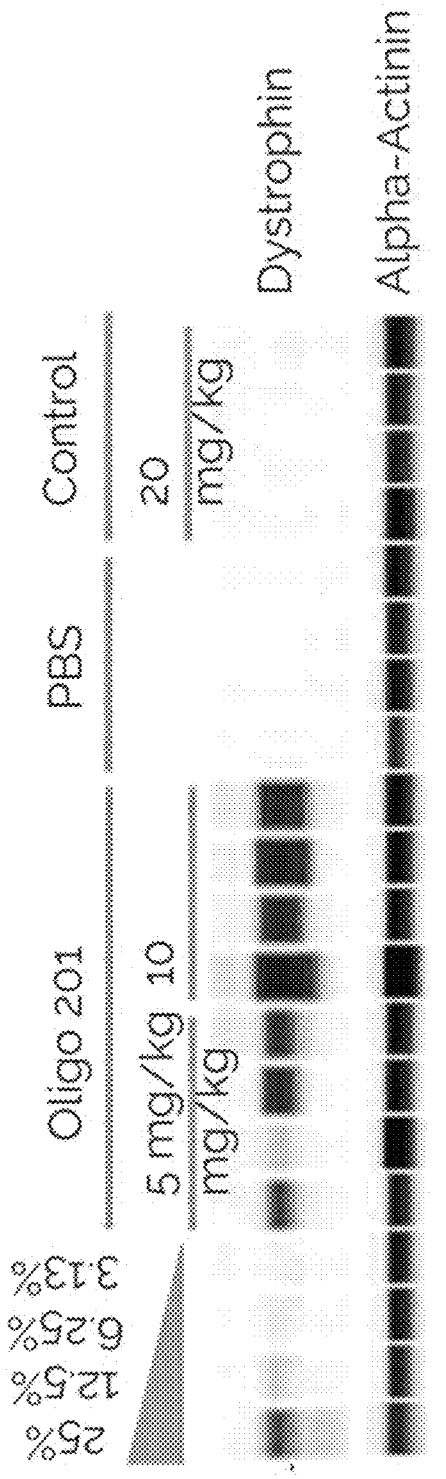
Figure 22D:
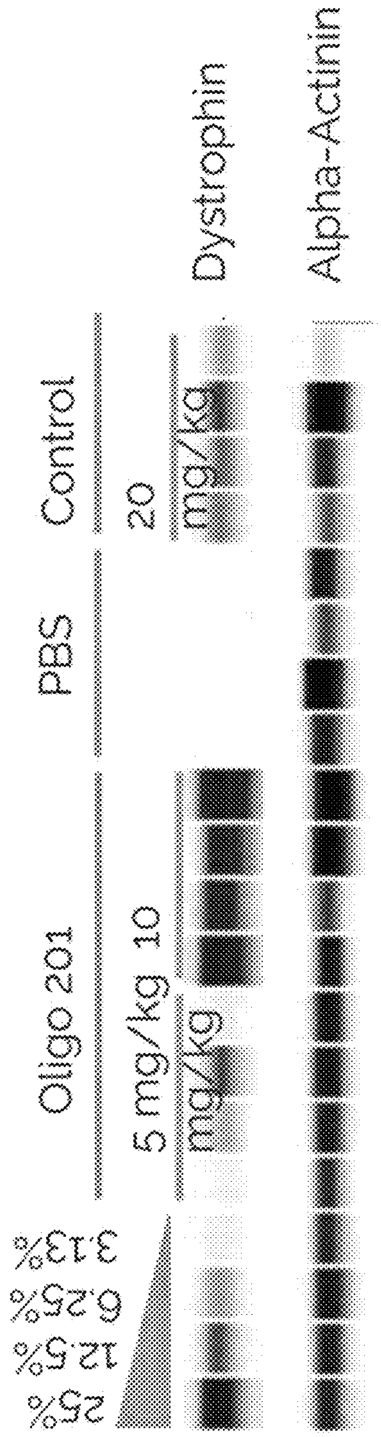
Figure 23:
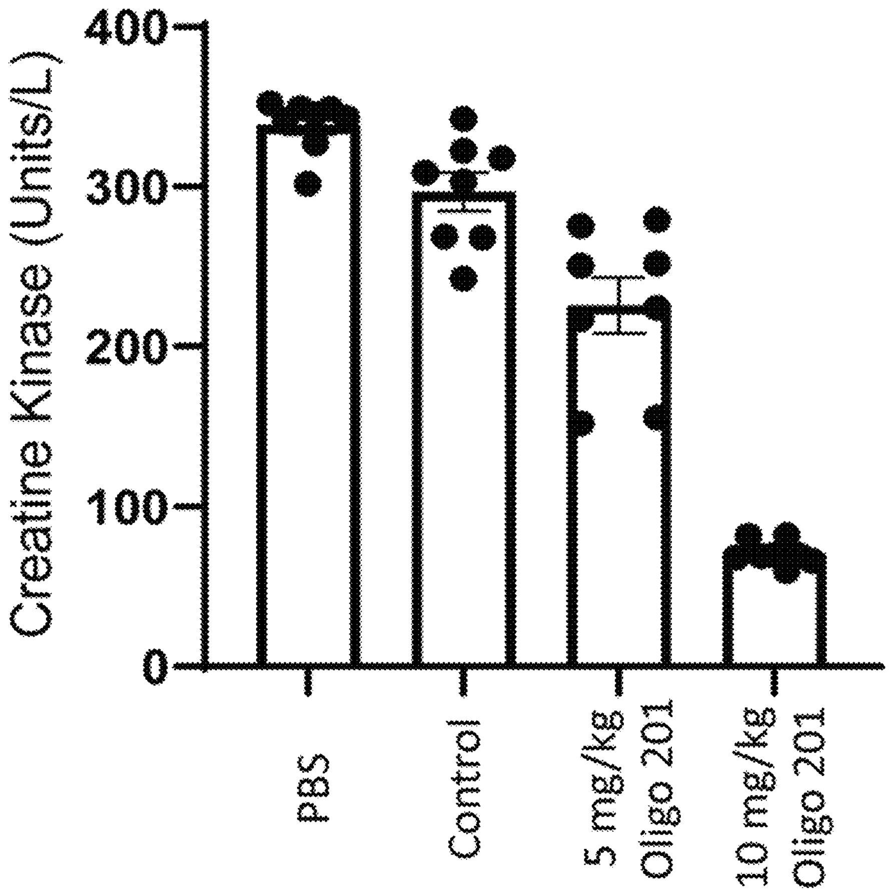
FIG. 23 shows the serum levels of creatine kinase in MDX mice treated with 5 mg/kg Oligo 201 or 10 mg/kg Oligo 201 four times per week.

Treatment of mice with 20 mg/kg Oligo 201 one time per week resulted in splicing correction of dystrophin in the heart (FIG. 21A) and in the diaphragm (FIG. 21B). Treatment of mice with 10 mg/kg Oligo 201 or 5 mg/kg Oligo 201 four times per week also resulted in splicing correction of dystrophin in the heart (FIG. 22A) and in the diaphragm (FIG. 22B). Treatment with Oligo 201 at 10 mg/kg results in a higher amount of splicing correction than treatment with 5 mg/kg in the heart (FIG. 22C) and diaphragm (FIG. 22D). Treatment with 5 mg/kg or 10 mg/kg Oligo 201 four times per week also resulted in a decrease in creatine kinase expression in comparison to control (FIG. 23), suggesting that Oligo 201 treatment reduces muscle fiber damage in patients with DIMD.

Example 4A. Use of Cell-Penetrating Peptides Conjugated to Oligonucleotides for CD33 Knockout in Human Macrophage Cells The compounds of Table C are evaluated in Example 4A and 4B. Exemplary experiments are described below.

absence of such a ligand binding domain, CD33 cannot inhibit microglial activation and phagocytosis of amyloid beta by microglial cells. Such a result is protective against AD. This example evaluated the efficacy of the platform described in Examples 1-5 for treating AD or cancer. Briefly, THP1 and glioblastoma cells were treated with AC having a nucleic acid sequence of 5'-GTAACTGTATTTGGTACTTCC-3' (SEQ ID NO: 153) ("$PMO^{CD33}$"), $PMO^{CD33}$ conjugated to a CPP ("CPP-$PMO^{CD33}$"), or $PMO^{CD33}$ conjugated to both CPP and NLS ("CPP-NLS-$PMO^{CD33}$"), in the presence of 10% fetal bovine serum (FBS). The CPP used was cCPP12, which has an amino acid sequence of FfΦRrRr (SEQ ID NO: 117).

PMO sequence development and optimization. The nucleic acid sequence 5'-CTGTATTTGGTACTT-3' (SEQ ID NO: 270) has previously been reported to induce human CD33 exon2 skipping in THP1 cells (Bergeijk P. et al. Molecular and Cellular Biol. 2019). We first modified the oligonucleotide chemistry from 2'-MOE modified RNA to phosphorodiamidate morpholino oligomers (PMO) as in the conjugated construct ENTR-085 but with moderate success (FIGS. 68A-B). To improve efficacy, we further developed a 21nt-long PMO, ENTR-036, TABLE 5, 5'-GTAACTGTATTTGGTACTTCC-3' (SEQ ID NO: 265) and its CPP conjugate (i.e. construct ENTR-087) showed superior efficacy (FIGS. 68A-B). Thus, PMO sequence ENTR-036 was used for subsequent studies.

TABLE C

| Compounds that target CD33 | | |
|---|---|---|
| Oligo# | Design | Note |
| ENTR-036 | 5'-GTA ACT GTA TTT GGT ACT TCC-3'-primary amine (all PMO monomers)(SEQ ID NO: 265) | $PMO^{CD33}$ Human CD33 exon 2 skipping |
| ENTR-081 | 5'-GTA ACT GTA TTT GGT ACT TCC-3'-PEG12CPP12 (all PMO monomers)(SEQ ID NO: 266) | CPP-$PMO^{CD33}$ Human CD33 exon 2 skipping |
| ENTR-085 | 5'-CTG TAT TTG GTA CTT-3' + CPP12-PEG12-K(CPP12)-PEG12-TFP (all PMO monomers)(SEQ ID NO: 267) | CPP-CPP-$PMO^{CD33}$ Human CD33 exon 2 skipping |
| ENTR-087 | 5'-GTA ACT GTA TTT GGT ACT TCC-3' + CPP12-PEG12-K(CPP12)-PEG12-TFP (all PMO monomers)(SEQ ID NO: 268) | CPP-CPP-$PMO^{CD33}$ Human CD33 exon 2 skipping |
| ENTR-179 | 5'-GTA ACT GTA TTT GGT ACT TCC-3' (Ac-NLS-Lys(CPP12)-PEG12-K(N3)- (all PMO monomers)(SEQ ID NO: 269) | CPP-NLS-$PMO^{CD33}$ Human CD33 exon 2 skipping |

Cells. Differentiated THP-1 cells (human monocyte cells) and glioblastoma cells (human neuronal cells) were used in this study.

Study design. CD33 is implicated in diseases such as cancer and Alzheimer's Disease ("AD"). Targeting CD33 expression represents a treatment strategy for AD and cancer.

Targeting CD33 expression represents a treatment strategy for AD and cancer. Skipping of exon 2 of the gene expressing CD33 produces D2-CD33, a CD33 isoform that lacks a binding domain of sialic acid. (FIGS. 60A-B). In the Detection of exon 2 skipping by RT-PCR and flow cytometry. Reverse Transcription followed by semi-quantitative PCR analysis revealed that treatment of THP1 cells for 48 hours in the presence of 10% FBS with CPP-CPP-$PMO^{CD33}$ (ENTR-087) resulted in skipping of exon 2 and the production of D2-CD33, a CD33 isoform that lacks a ligand binding domain (FIG. 61A and FIG. 61B). Treatment of THP1 cells with $PMO^{CD33}$ (ENTR-036) alone resulted in a lower amount of exon skipping in comparison to treatment with CPP-CPP-$PMO^{CD33}$. Exon 2 skipping was dependent on the dose of CPP-CPP-$PMO^{CD33}$ (ENTR-087) (FIG. 62A and FIG. 62B). Flow cytometry revealed reduced production of CD33 in cells treated with CPP-CPP-PMO$^{CD33}$ (ENTR_036) in comparison to untreated (NT) cells (FIGS. 61A-B).

Dose-dependent Exon 2 skipping induced by CPP-NLS-PMO$^{CD33}$ in THP1 cells CD33 mRNA from differentiated THP1 cells (human monocyte cells) with various concentrations of CPP-NLS-PMO$^{CD33}$(ENTR-179), PMO$^{CD33}$ (ENTR-036) with Endoporter (6 μL/mL) transfection reagent, or PMO$^{CD33}$ (ENTR_036) alone for 48 hours in the presence of 10% FBS were analyzed by RT-PCR (FIGS. 61A-B). Result shows dose-dependent skipping of exon 2 CD33 by CPP-NLS-PMO$^{CD33}$ treatment, with significant improvement over transfection (over 2-fold) and over 1000-fold improvement compared to unconjugated PMO. CD33 mRNA of glioblastoma cells (human neuronal cell line, U-87 MG) treated with various concentrations of CPP-NLS-PMO$^{CD33}$ (ENTR-179) for 48 hours in the presence of 10% FBS were analyzed by RT-PCR (FIG. 65). Result shows dose-dependent skipping of exon 2 CD33 by CPP-NLS-PMO$^{CD33}$ treatment.

Duration of effects of CPP-PMO$^{CD33}$ in differentiated THP1 cells. Differentiated THP1 cells (human monocyte cells) treated with CPP-PMO$^{CD33}$ (ENTR-087) for 1 day, and cells were continued to be cultured with full growth medium. 2-8 days post incubation, cells were harvested and the CD33 mRNA were analyzed (FIGS. 66A-B). Result shows that uptaken CPP-PMO$^{CD33}$ can induce CD33 exon 2 skipping for a sustained period of time (>8 days).

Exon 2 skipping induced by monovalent CPP-PMO$^{CD33}$ and bivalent CPP-PMO$^{CD33}$ CD33 mRNA of differentiated THP1 cells (human monocyte cells) treated by PMO$^{CD33}$ (ENTR-036), monovalent CPP-PMO$^{CD33}$ (ENTR-081), and bivalent CPP-PMO (ENTR-087) for 48 hours were analyzed by RT-PCR (FIG. 67). Result shows effect of bivalent CPP-PMO$^{CD33}$ is more potent than CPP-PMO$^{CD33}$ in inducing CD33 exon 2 skipping.

Example 4B. Use of Cell-Penetrating Peptides Conjugated to Oligonucleotides for CD33 Knockout in Human Macrophage Cells This example used the protocols of Example 4A to evaluate an AC having a nucleic acid sequence of 5'-GTAACTGTATTTGGTACTTCC-3' ("PMO$^{CD33}$") (SEQ ID NO: 153) or PMO$^{CD33}$ conjugated to a CPP ("EEV-PMO$^{CD33}$") in the presence of 10% fetal bovine serum (FBS). The CPP used was cCPP12, which has an amino acid sequence of FfΦRrRr (SEQ ID NO: 117).

Figure 16A:
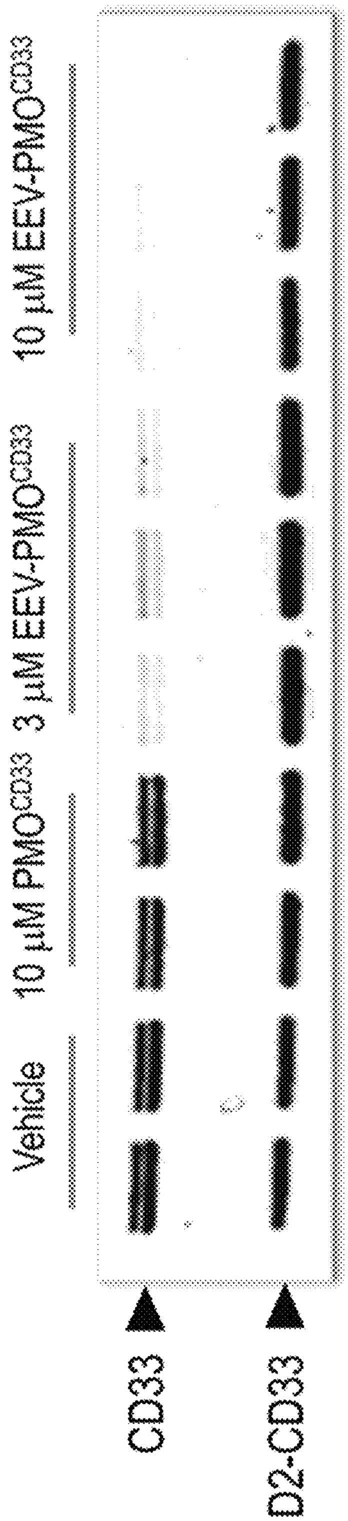
FIGS. 16A-B show a real-time PCR analysis of exon 2 skipping of CD33 (FIG. 16A) and quantification of full length CD33 versus D2-CD33 transcripts (FIG. 16B) after treatment with EEV-$PMO^{CD33}$ (also called "ENTR_087") or $PMO^{CD33}$ (also called "ENTR_036"). $PMO^{CD33}$ is an antisense compound that targets exon 2 of CD33.
Figure 16B:
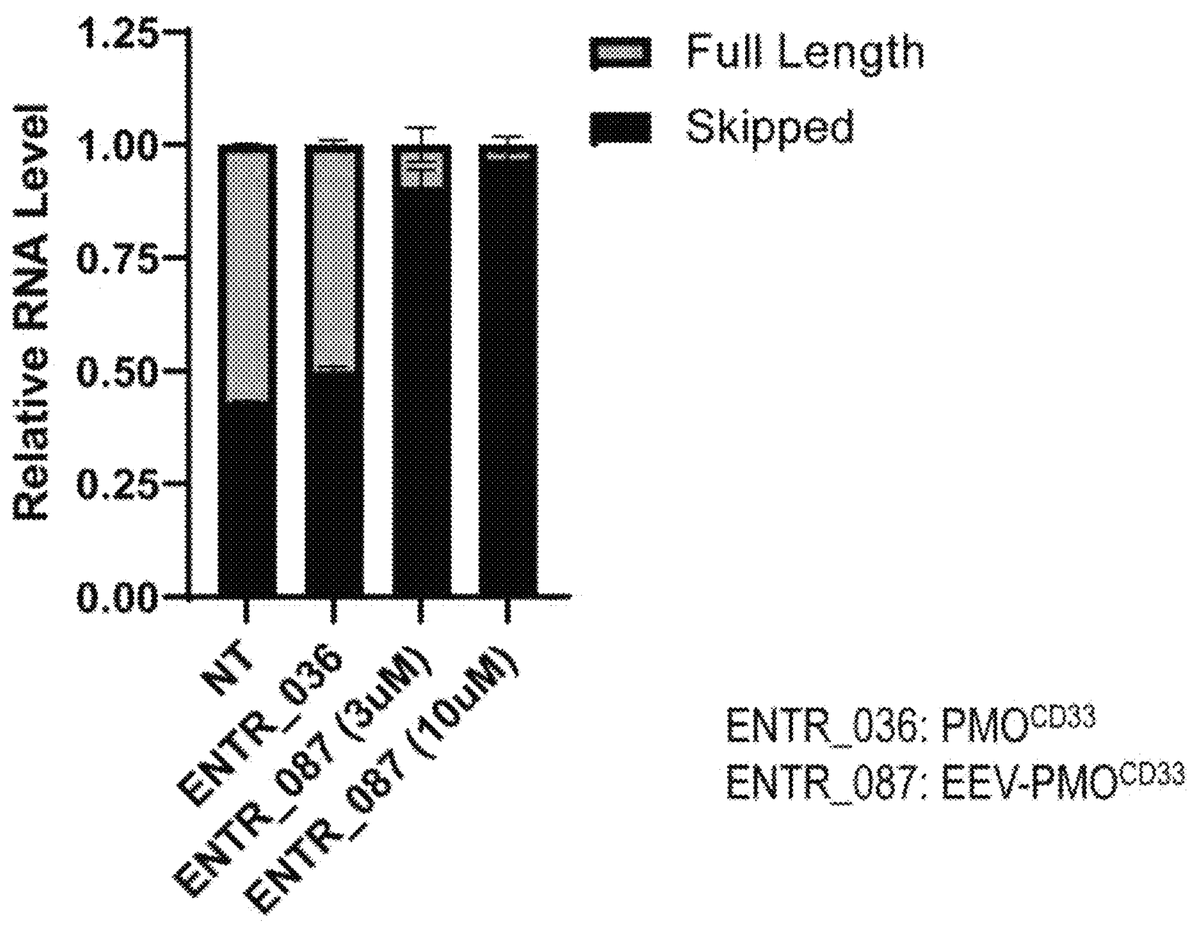
Figure 17A:
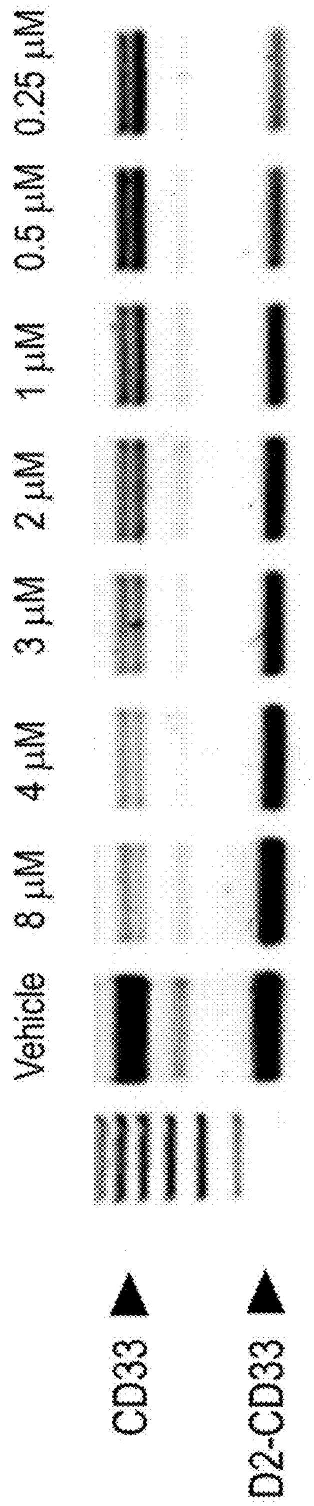
FIGS. 17A-B show the dose dependence of real-time PCR analysis of exon 2 skipping of CD33 (FIG. 17A) and quantification of full length CD33 versus D2-CD33 transcripts by dose (FIG. 17B) after treatment with EEV-$PMO^{CD33}$. The PMO targeted exon 2 of CD33.
Figure 17B:
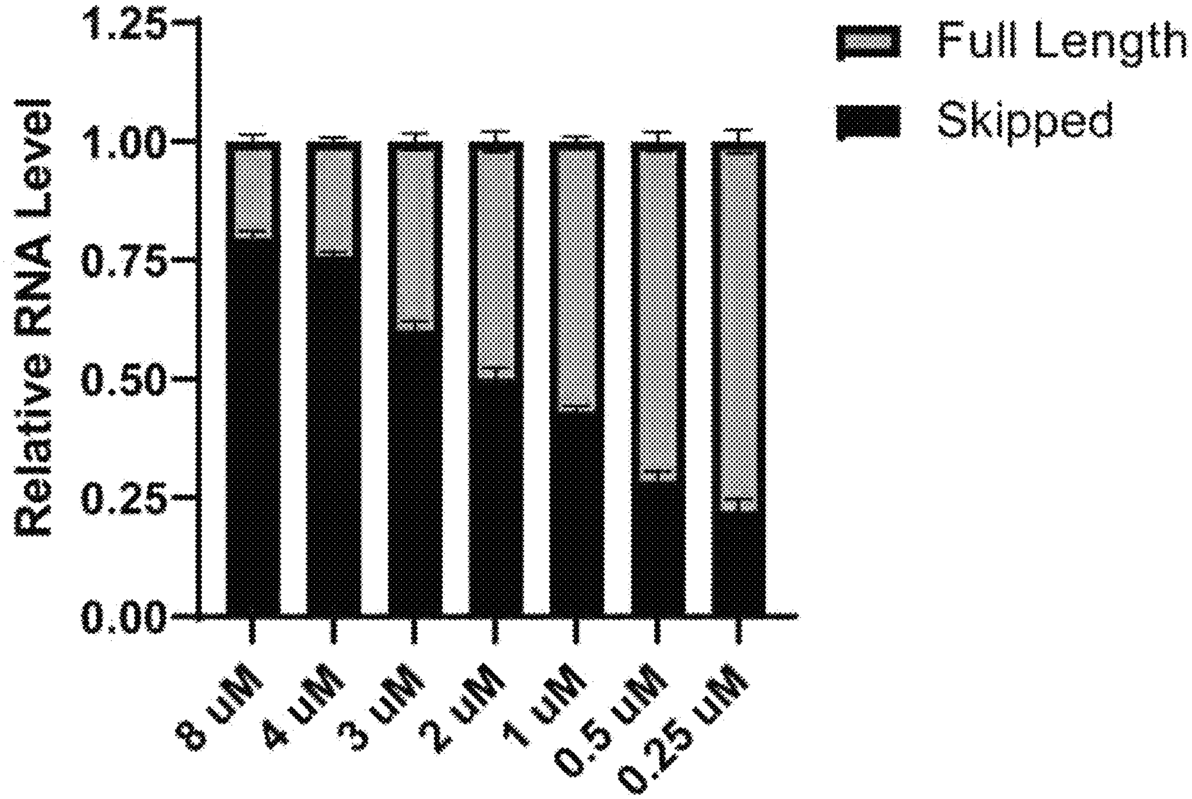
Figure 18:
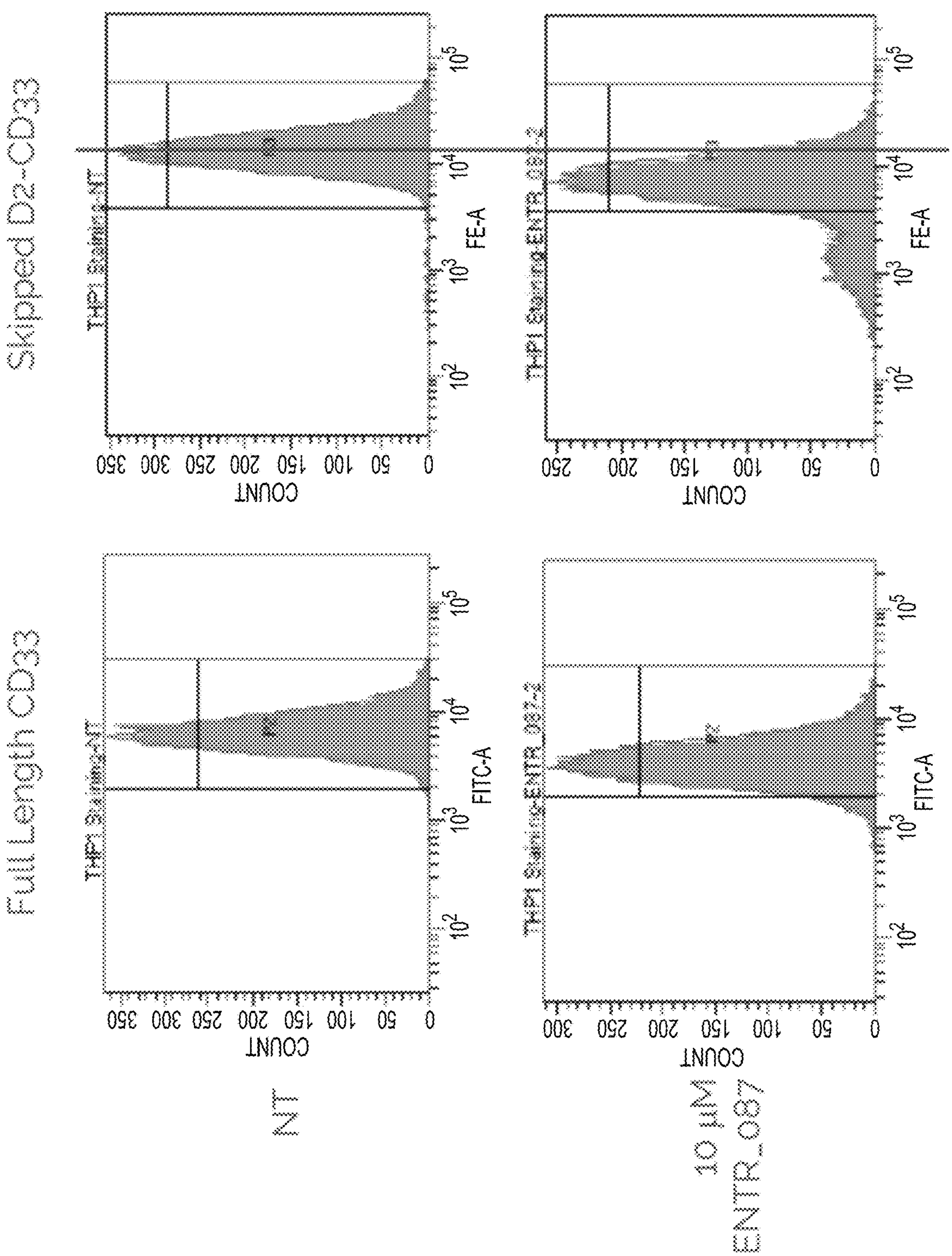
FIG. 18 shows flow cytometry analysis of THP1 cells after treatment with EEV-$PMO^{CD33}$ compared to untreated ("NT") cells.

Detection of exon 2 skipping by RT-PCR and flow cytometry. RT-PCR analysis revealed that treatment of THP1 cells for 48 hours in the presence of 10% FBS with EEV-PMO$^{CD33}$ resulted in skipping of exon 2 and the production of D2-CD33, a CD33 isoform that lacks a ligand binding domain (FIG. 16A and FIG. 16B). Treatment of THP1 cells with PMO$^{CD33}$ alone resulted in a lower amount of exon skipping in comparison to treatment with EEV-PMO$^{CD33}$. Exon 2 skipping was dependent on the dose of EEV-PMO$^{CD33}$ (FIG. 17A and FIG. 17B). Flow cytometry revealed reduced production of CD33 in cells treated with EEV-PMO$^{CD33}$ in comparison to untreated (NT) cells (FIG. 18).

Figure 29:
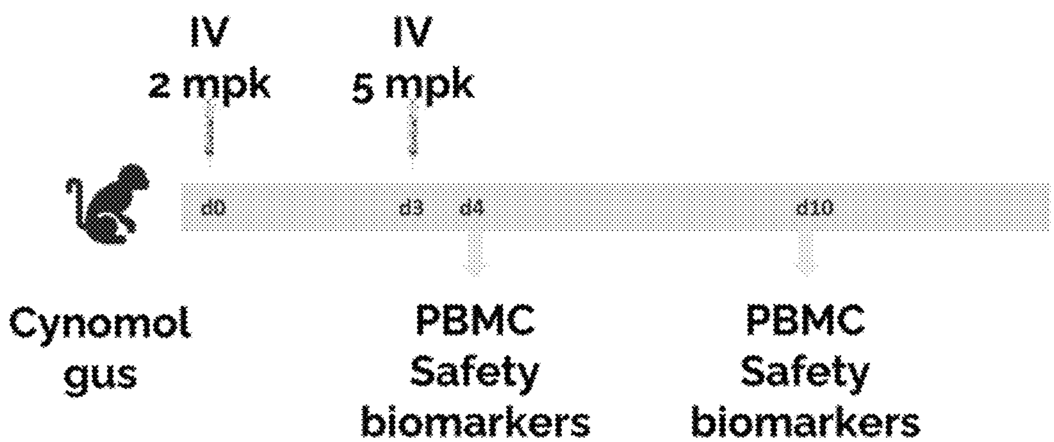
FIG. 29 shows the study design of to evaluate pharmacodynamic effects of CPP-conjugated AC and unconjugated AC against CD33 in cyno monkeys.

Example 4C. Use of Cell-Penetrating Peptides Conjugated to Oligonucleotides for Production of D2-CD33 in Nonhuman Primates The CPP-PMO$^{CD33}$ (ENTR-081 and ENTR-179) described in Examples 4A-C is used animal studies, e.g. in rodents, monkeys, and humans. Animals or humans are administered intravenously or intrathecally via various doses (0.5, 1, 2.5, 5, 10, 20, 40 mpk) of a CPP-PMO$^{CD33}$ or PMO conjugates that targets exon skipping (exon 2 of human CD33 or exon 5 of monkey CD33) of the gene expressing CD33. FIG. 29 shows the study design. The results show that the oligonucleotide therapeutics induce exon skipping of target CD33 gene, downregulate CD33 level and can treat AD.

NHP Study design. To explore the tolerability of CPP-PMO on non-human primate (NHP), two CPP-PMO constructs as well as PMO itself are dosed in staggered fashion at 2 mpk and 5 mpk through intravenous infusion on d0 and d3, respectively. Oligonucleotides include "PMO$^{CD33}$" (ENTR-036), PMO$^{CD33}$ conjugated to a CPP ("CPP-PMO$^{CD33}$", ENTR-081), or PMO$^{CD33}$ conjugated to both CPP and NLS ("CPP-NLS-PMO$^{CD33}$", ENTR-179), and are formulated in saline (0.9% w/v sodium chloride). The CPP used was CPP12, which has a cyclic amino acid sequence of FfΦRrRr (SEQ ID NO: 117). PBMCs (peripheral blood mononuclear cells) were isolated at 1 day (d4) and 7 days (10) post 5 mpk injection to detect splicing correction. Blood, serum and urine samples were collected at 1 day and or 7 days post each injection for hematology, clinical chemistry, coagulation, urinalysis, cytokine and histamine analysis.

Figure 30:
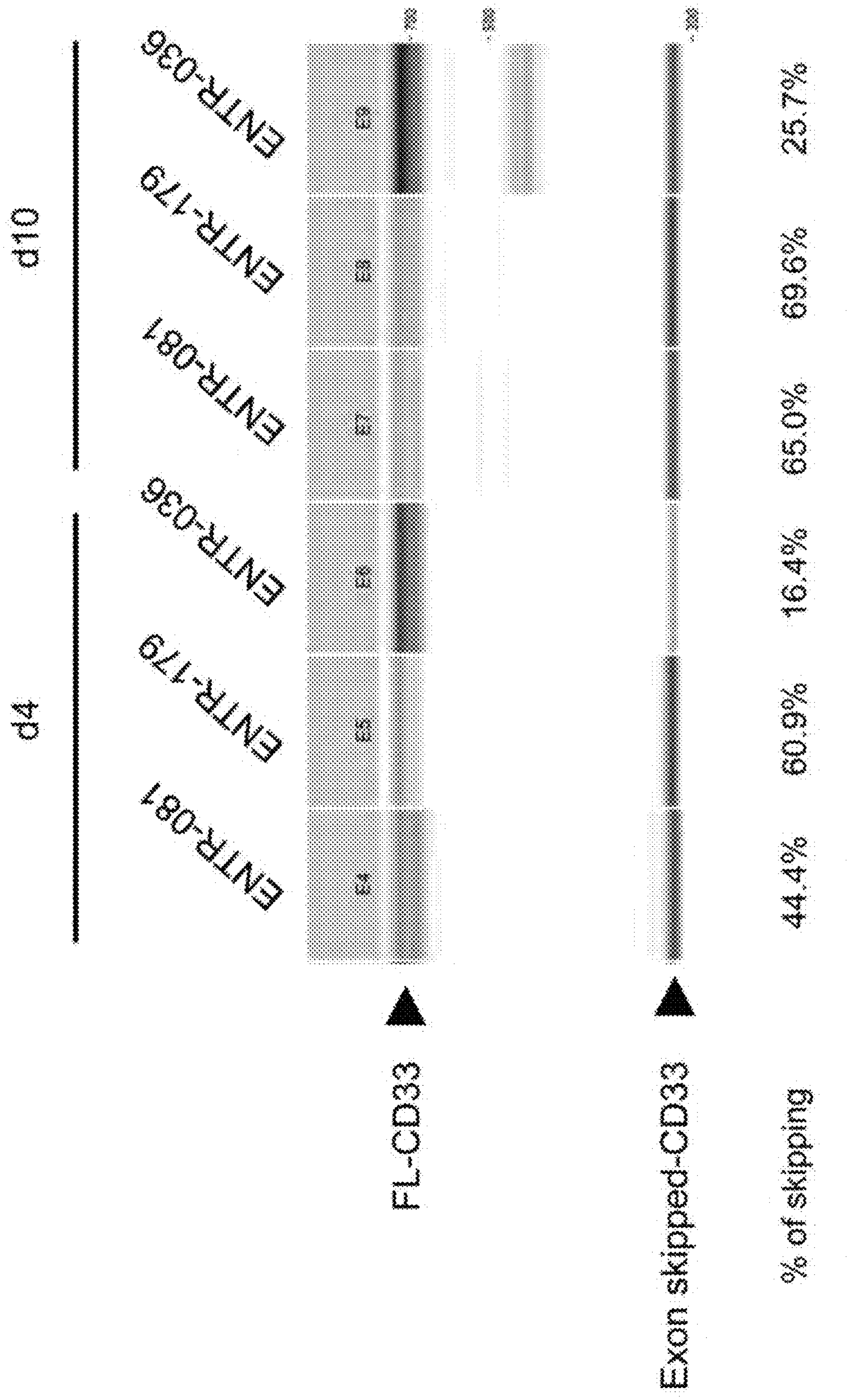
FIG. 30 shows RT-PCR analysis of exon skipping of CD33 gene in peripheral mononuclear blood cells (PBMCs) of cyno monkey after intravenous infusion of CPP-$PMO^{CD33}$ (also called "ENTR-081", TABLE 5), CPP-NLS-$PMO^{CD33}$ (also called "ENTR-179, TABLE C), or $PMO^{CD33}$ (also called "ENTR-036", TABLE 5).

Detection of exon exclusion by RT-PCR. Although human and non-human primates share high sequence homology of CD33 gene, the 5'-UTR and splicing pattern is different. The sequence coding for the IgV domain of CD33 is located in exon 2 for human and located in exon 5 for non-human primate CD33 gene. Therefore, the skipping of exon 2 in human CD33 (D2-CD33), resulting in ΔIgV-CD33 protein, corresponds to the skipping of exon 5 of non-human primate CD33. Monkey PBMC was collected at specified time points mentioned above. Total RNA was extracted, and RT-PCR was conducted using forward primer 5'-CTCAGACATGCCGCTGCT-3' (SEQ ID NO: 271) and reverse primer 5'-TTGAGCTGGATGGTTCTCTCCG-3' (SEQ ID NO: 272) resulting in full length CD33 mRNA (FL-CD33) at 700 bp and Exon-5 skipped CD33 mRNA (D5-CD33) at 320 bp. Reverse Transcription followed by semi-quantitative PCR analysis revealed that treatment of monkey PBMC cells showed that IV administration of CPP-PMO$^{CD33}$ (ENTR-081) and CPP-NLS-PMO$^{CD33}$ (ENTR-179), but not PMO, resulted in skipping of exon 5 of CD33 gene and the production of D2-CD33. And the activity of both ENTR-081 and ENTR-179 last for at least 7 days post treatment (FIG. 30).

Example 5. Conjugation of Oligonucleotide with Cell Penetrating Peptide

Figure 7A:
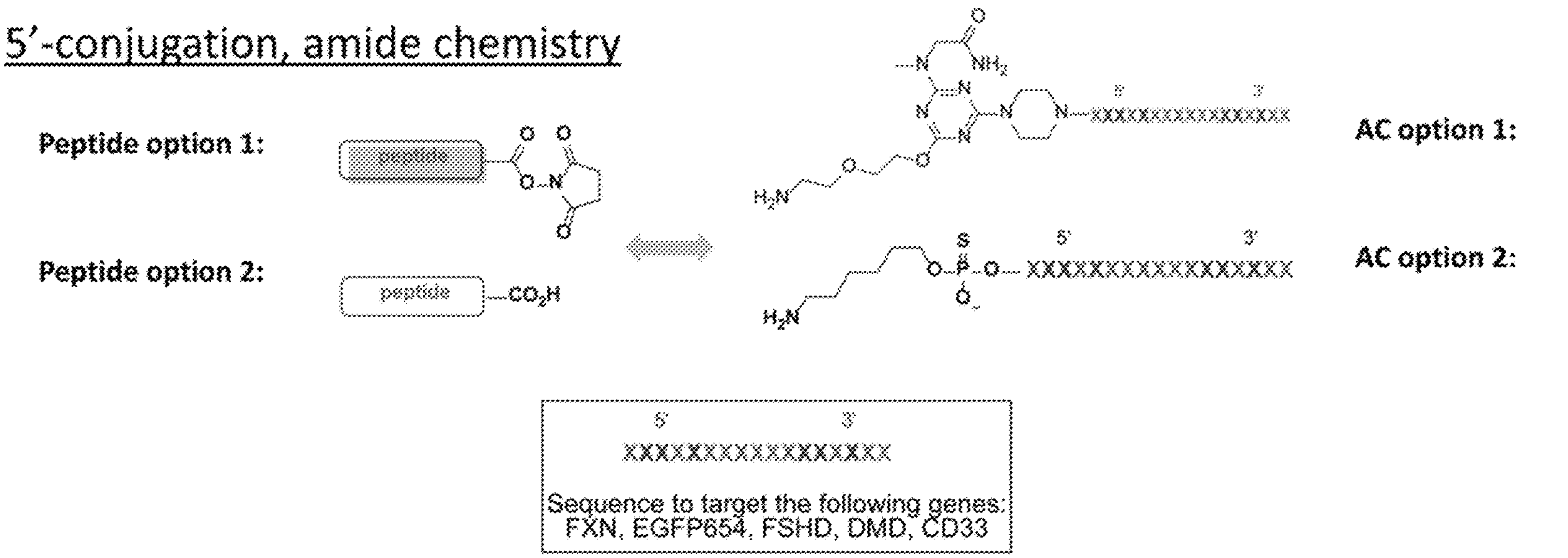
FIGS. 7A-D illustrate conjugation chemistries for connecting AC with peptides.
Figure 7B:
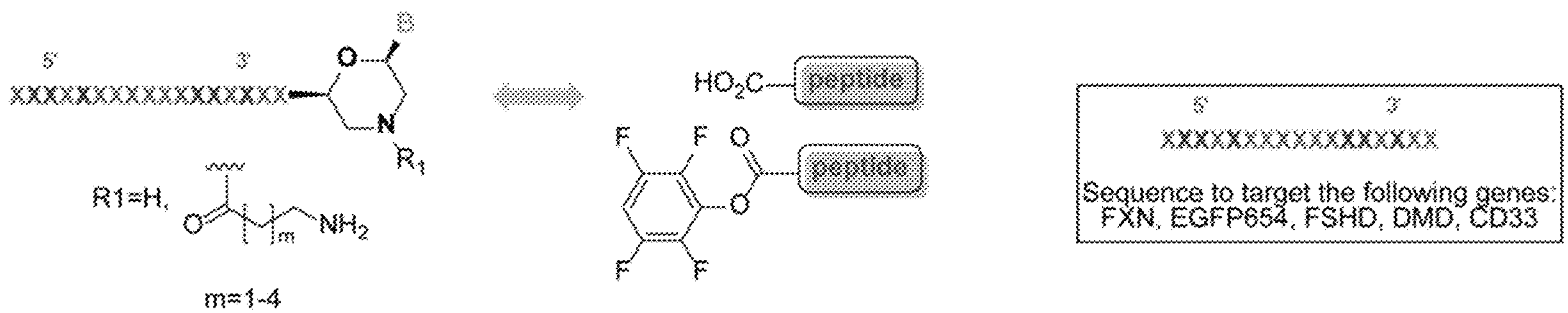
Figure 7C:
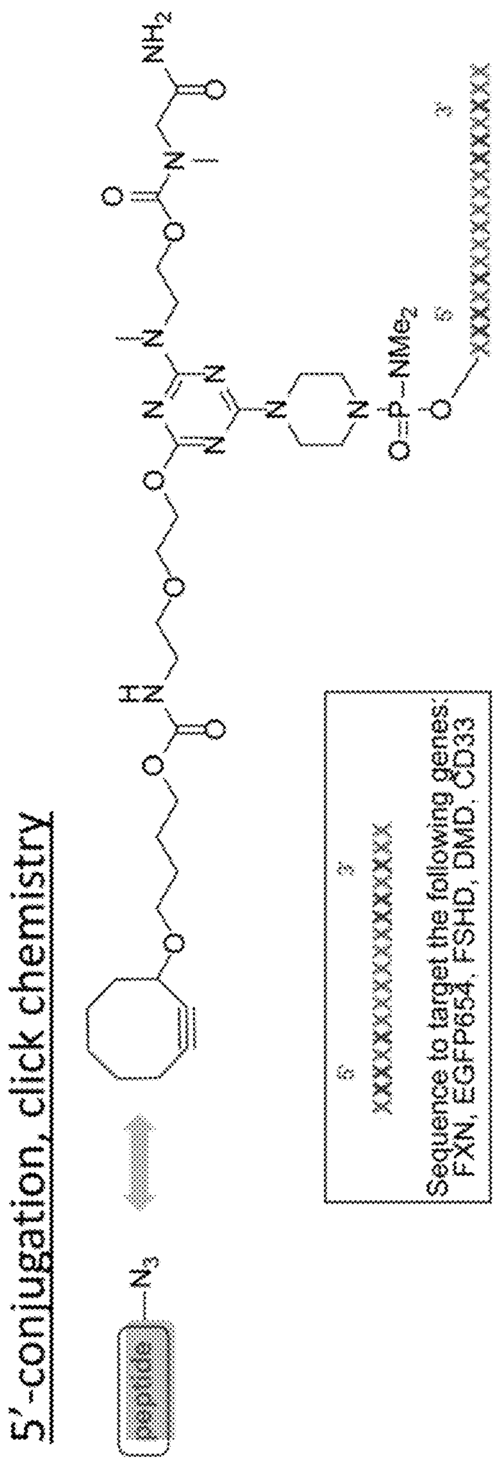
Figure 7D:
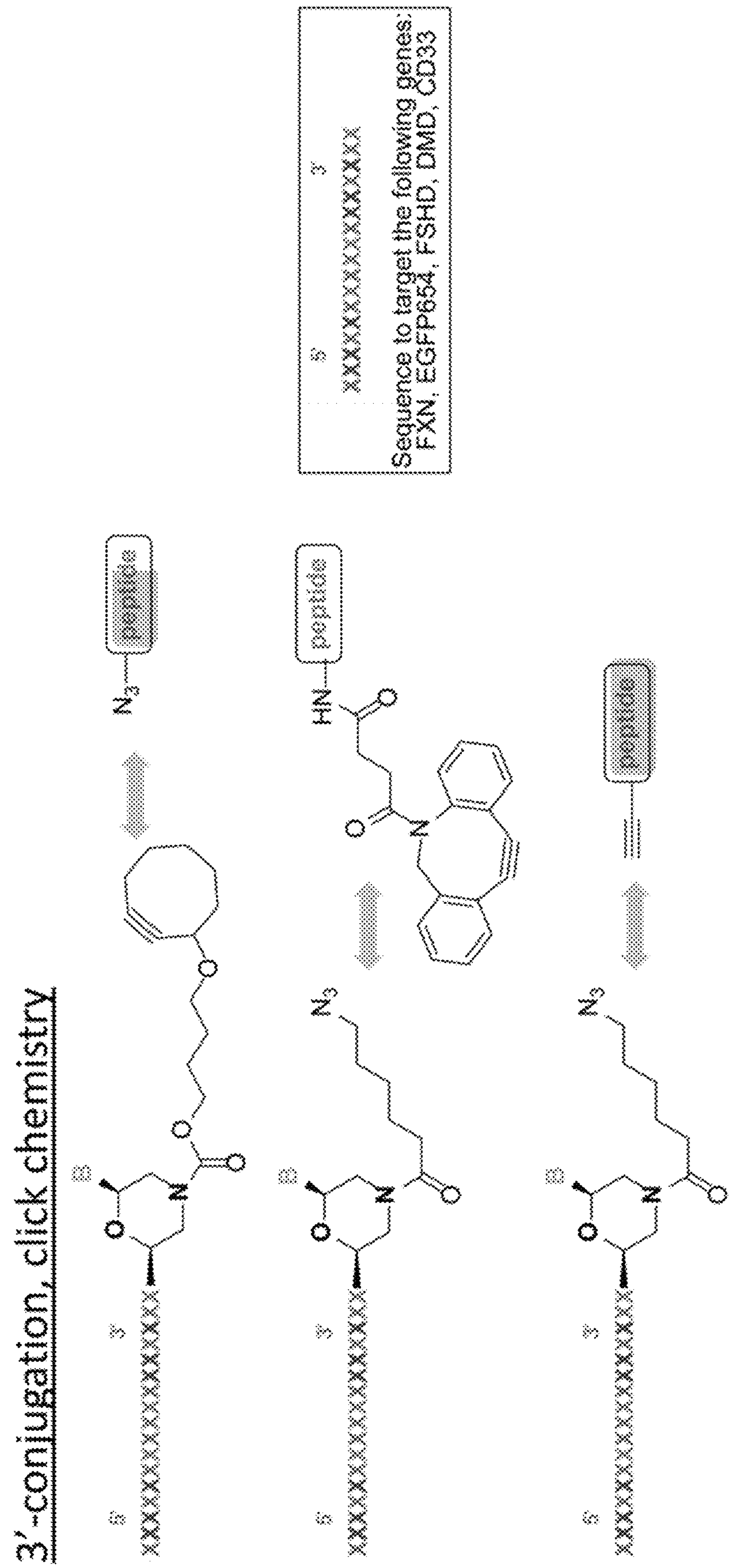

Conjugation of PMO oligos with cell penetrating peptides. As shown in FIG. 7*b*, phosphorodiamidate morpholino oligomer (PMO) was conjugated to cell penetrating peptide (CPP) via either amide bond formation (left) or click chemistry. The linker/CPP can be installed either on the 5' end, or on the 3' end of the oligonucleotide.

Figure 8:
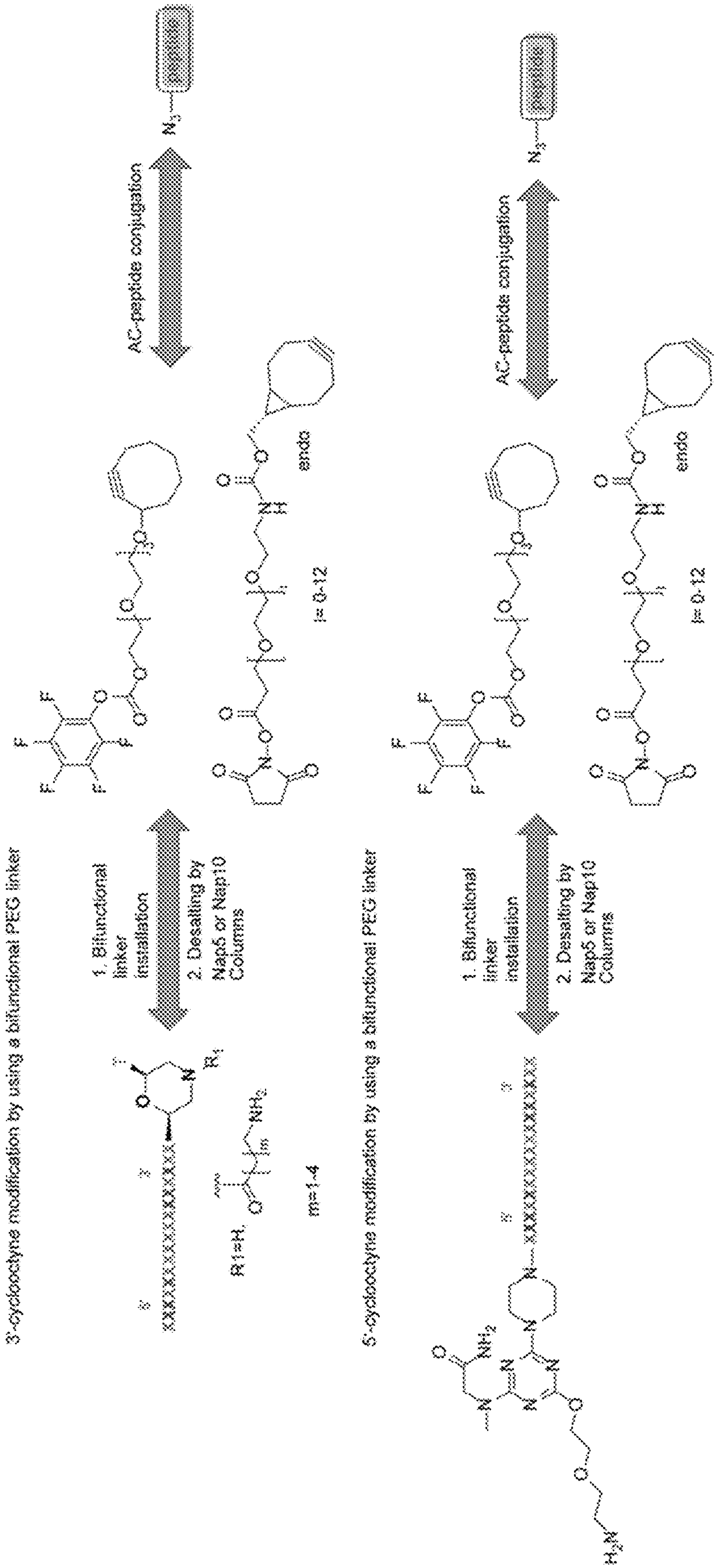
FIG. 8 shows the conjugation chemistry for connecting AC and CPP with additional linker modality containing a polyethylene glycol (PEG) moiety.

Synthesis of oligonucleotide-peptide conjugate with PEG spacer. As shown in FIG. 8, an oligonucleotide-peptide conjugate was synthesized with PEG (polyethylene glycol) linker inserted between oligonucleotide moiety and peptide. Briefly, the 3' or 5' amino group of the AC was conjugated to a bifunctional PEG linker comprising a OSU or TFP or PFP activating carbonate functionality and cyclooctyne. The carbonate is reacted with 3' or 5' amino group of AC to form stable carbamate. The excess bifunctional reagent and other small molecules were removed by desalting column (Nap 10 or Nap 5). The resulting solution was concentrated to 1-2 mM modified AC concentration and conjugated with the designated peptide-azide. The click reaction was allowed to proceed for 8-12 hours for completion monitored by LC-MS.

Synthesis of oligonucleotide-peptide conjugate for various gene targets. As shown in Table D, FIG. 7A, FIG. 71B, and FIG. 8, for each target selected from the group consisting of FXN, EGFP654, CD33, and DMD, the antisense compounds with specific oligonucleotide sequence were conjugated to corresponding peptides.

TABLE E

| Compositions Evaluated | |
|---|---|
| | Composition |
| 1 | CPP conjugated to gRNA of RNP comprising gRNA and Cas9 |
| 2 | CPP conjugated to Cas9 of RNP comprising gRNA and Cas9 |
| 3 | CPP conjugated to gRNA of RNP comprising gRNA and Cas9 and linker |
| 4 | CPP conjugated to Cas9 of RNP comprising gRNA and Cas9 and linker |

TABLE D

| Compositions Evaluated | | | |
|---|---|---|---|
| Oligo chemistry | Name (oligo chemistry) | Design | Target |
| PMO | $PMO^{GAA}$-CP12 | 5'-CTT CTT CTT CTT CTT CTT CTT CTT C-CP12 (SEQ ID NO: 154) (all PMO monomers; CP12 = peptide) | FXN |
| O-MOE | O-$MOE^{GAA}$-CP12 | CP12-5'-CTT CTT CTT CTT CTT CTT-3' (SEQ ID NO: 155) (all 2'-O-MOE RNA monomers; all PS bonds; CP12 = peptide) | FXN |
| LNA | $LNA^{GAA}$-CP12 | CP12-5'-LnT-dC-LnT-LnT-dC-LnT-LnT-dC-LnT-LnT-dC-LnT-LnT-dC-LnT-LnT-dC-LnT-LnT (SEQ ID NO: 156)(LnT = LNA T; dC = DNA C; all PS bonds; CP12 = peptide) | FXN |
| PMO | PMO654-CP12 | 5'-GCT ATT ACC TTA ACC CAG-3' -CP12 (SEQ ID NO: 157) (all PMO monomers; CP12 = peptide) | EGFP654 |
| PMO | PMO654-CP12-R1 | 5'-GCT ATT ACC TTA ACC CAG-3' -CP12-R1 (SEQ ID NO: 158) (all PMO monomers; CP12 = peptide; R1 = lipid group) | EGFP654 |
| PMO | PMO654-CP1212 | 5'-GCT ATT ACC TTA ACC CAG-3' -CP1212 (SEQ ID NO: 159) (all PMO monomers; CP1212 = peptide) | EGFP654 |
| PMO | PMO654-Pip | 5'-GCT ATT ACC TTA ACC CAG-3' -Pip (SEQ ID NO: 160) (all PMO monomers; Pip = peptide) | EGFP654, control |
| PMO | $PMO^{FM10}$-CP12 | 5'-GGG CAT TTT AAT ATA TCT CTG AAC T-3' - CP12 (SEQ ID NO: 161) (all PMO monomers; CP12 = peptide) | FSHD |
| PMO | $PMO^{DMD}$-CP12 | 5'-GGC CAA ACC TCG GCT TAC CTG AAA T-3' - CP12 (SEQ ID NO: 162) | DMD |
| PMO | $PMO^{DMD}$-CP12-R1 | 5'-GGC CAA ACC TCG GCT TAC CTG AAA T-3' - CP12-R1 (SEQ ID NO: 163) (all PMO monomers; CP12 = peptide; R1 = lipid group) | DMD |
| PMO | $PMO^{CD33}$-CP12 | 5'-GTA ACT GTA TTT GGT ACT TCC-3' - CP12 (SEQ ID NO: 164) | CD33 |

Cell penetrating peptides. Examples of cell penetrating peptides are presented in FIG. 9.

Example 6. Intracellular Delivery of CRISPR Gene-Editing Machinery

CPP conjugated to CRISPR gene-editing machinery. Various compositions comprising a CPP from Table 4 and CRISPR gene-editing machinery (Table E) are prepared. The gRNA is labeled with a fluorescent dye.

TABLE E-continued

| Compositions Evaluated | |
|---|---|
| | Composition |
| 5 | CPP conjugated to linker of RNP comprising gRNA and Cas9 and linker |

Target cells. HeLa cells

Study Design. HeLa cells are cultured in six-well plates ($5\times10^5$ cells per well) for 24 hours. After 24 hours, HeLa cells are incubated with the compositions of Table 7. As a negative control, the HeLa cells are incubated with CRISPR gene-editing machinery in the absence of CPP. The uptake efficiency of the compositions comprising a CPP and CRISPR gene-editing machinery is evaluated using fluorescence.

Example 7. Gene-Editing Using Cell-Penetrating Peptides Conjugated to CRISPR Gene-Editing Machinery Study Design. Various compositions comprising a CPP from Table 4 and CRISPR gene-editing machinery (Table F) are prepared to evaluate their ability to cleave human target DNA. The protocol described in U.S. Publication No. 2014/0068797, which is incorporated by reference herein, in its entirety, is used to evaluate the ability of the compositions to make gene edits. Composition 9 serves as a control to evaluate the effect of the CPP on gene editing. Compositions 10-13 are negative controls which lack either an gRNA or Cas9. Cas9 is labeled with green fluorescent protein (GFP) in the compositions of Table F.

Briefly, human EK293T cells are transfected with the compositions of Table F. Western blotting is performed to confirm that Cas9 enters the BEK293T cells. Northern blotting is performed to confirm that the gRNA enters the EK293T cells. Fluorescence microscopy is performed to visualize Cas9. A Surveyor assay is performed to assess site-specific genome cleavage.

TABLE F

CPPs conjugated to RNP

| | Composition |
|---|---|
| 1 | (a) CPP conjugated to Cas9<br>(b) CPP conjugated to gRNA |
| 2 | CPP conjugated to gRNA of RNP comprising gRNA and Cas9 |
| 3 | CPP conjugated to Cas9 of RNP comprising gRNA and Cas9 |
| 4 | CPP conjugated to gRNA of RNP comprising gRNA and Cas9 and linker |
| 5 | CPP conjugated to Cas9 of RNP comprising gRNA and Cas9 and linker |
| 6 | CPP conjugated to linker of RNP comprising gRNA and Cas9 and linker |
| 7 | (a) soluble Cas9<br>(b) CPP conjugated to gRNA |
| 8 | (a) soluble gRNA<br>(b) CPP conjugated to Cas9 |
| 9 | (a) RNP comprising Cas9 and gRNA |
| 10 | CPP conjugated to Cas9 |
| 11 | CPP conjugated to gRNA |
| 12 | CPP conjugated to Cas9 through linker |
| 13 | CPP conjugated to gRNA through linker |

EMBODIMENTS

Embodiment 1. A compound comprising:

(a) a cell penetrating peptide (CPP) sequence and (b) an antisense compound (AC) that is complementary to a target sequence in a pre-mRNA sequence.

Embodiment 2. The compound of Embodiment 1, wherein the AC comprises at least one modified nucleotide or nucleic acid selected from a phosphorothioate (PS) nucleotide, a phosphorodiamidate morpholino nucleotide, a locked nucleic acid (LNA), a peptide nucleic acid (PNA), a nucleotide comprising a 2'-O-methyl (2'-OMe) modified backbone, a 2'O-methoxy-ethyl (2'-MOE) nucleotide, a 2',4' constrained ethyl (cEt) nucleotide, and a 2'-deoxy-2'-fluoro-beta-D-arabinonucleic acid (2'F-ANA), and wherein hybridization of the AC with the target sequence reduces or prevents splicing.

Embodiment 3. The compound of Embodiment 1, wherein the AC comprises small interfering RNA (siRNA), microRNA (miRNA), ribozymes, immune stimulating nucleic acids, antisense, antagomir, antimir, microRNA mimic, supermir, UI adaptor, aptamer, or a CRISPR gene-editing machinery.

Embodiment 4. The compound of Embodiment 1, wherein the CPP is conjugated, directly or indirectly, to the AC.

Embodiment 5. The compound of Embodiment 4, wherein the CPP is conjugated to the 5' end or the 3' end of the AC.

Embodiment 6. The compound of Embodiment 4, wherein the CPP is conjugated to the backbone of the AC.

Embodiment 7. The compound of any one of Embodiment 4-6, further comprising a linker (L), which conjugates the CPP to the AC.

Embodiment 8. The compound of Embodiment 7, wherein the L is covalently bound to the 5' end of the AC.

Embodiment 9. The compound of Embodiment 7, wherein the L is covalently bound to the 3' end of the AC.

Embodiment 10. The compound of Embodiment 7, wherein the L is covalently bound to the backbone of the AC.

Embodiment 11. The compound of any one of Embodiment 7-10, wherein the L is covalently bound to the side chain of an amino acid on the CPP.

Embodiment 12. The compound of Embodiment 7, having a structure according to Formula I-A or Formula I-B:

CPP-L-AC Formula I-A or

AC-L-CPP Formula I-B, wherein L of Formula I-A is covalently bound to the side chain of an amino acid on the CPP and to the 5' end of the AC, and L of Formula I-B is covalently bound to the side chain of an amino acid on the CPP and the 3' end of the AC.

Embodiment 13. The compound of any one of Embodiment 7-12, wherein L comprises one or more D or L amino acids, each of which is optionally substituted; alkylene, alkenylene, alkynylene, carbocyclyl, or heterocyclyl, each of which is optionally substituted; or $—(R^1—X—R^2)z-$, wherein each of $R^1$ and $R^2$, at each instance, are independently selected from alkylene, alkenylene, alkynylene, carbocyclyl, and heterocyclyl, each X is independently $NR^3$, $—NR^3C(O)—$, S, and O, wherein $R^3$ is independently selected from H, alkyl, alkenyl, alkynyl, carbocyclyl, and heterocyclyl, each of which is optionally substituted, and z is an integer from 1 to 20; or combinations thereof.

Embodiment 15. The compound of any one of Embodiment 8-14, wherein L has a structure according to Formula II:

(II)

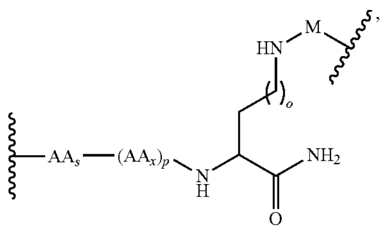

wherein

M is a group that conjugates L to an oligonucleotide;

$AA_s$ is a side chain or terminus of an amino acid on the CPP;

$AA_x$ is an amino acid;

o is an integer from 0 to 10; and p is an integer from 0 to 5.

Embodiment 16. The compound of Embodiment 15, wherein p is 2 and each $AA_x$ is R alanine Embodiment 17. The compound of Embodiment 15 or 16, wherein M is present and comprises an alkylene, alkenylene, alkynylene, carbocyclyl, or heterocyclyl, each of which is optionally substituted.

Embodiment 18. The compound of any one of Embodiments 15-17, wherein M is present and selected from the group consisting of:

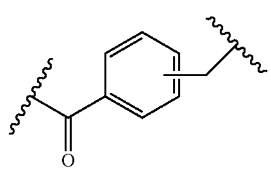,

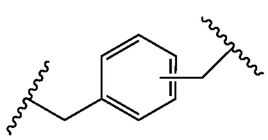,

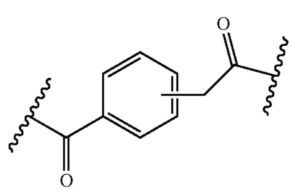,

-continued

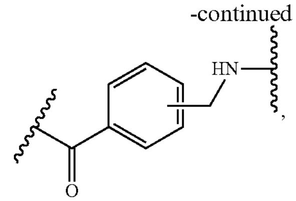,

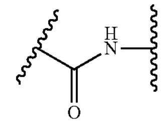,

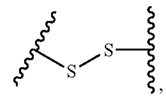,

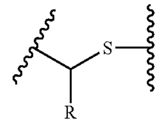,

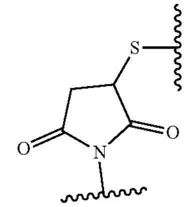,

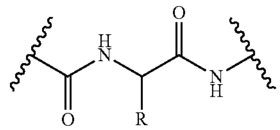,

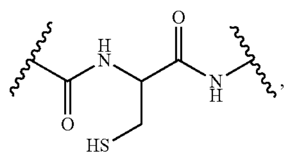,

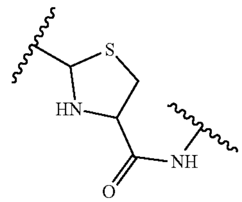,

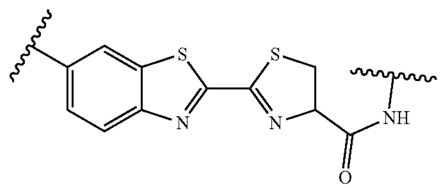,

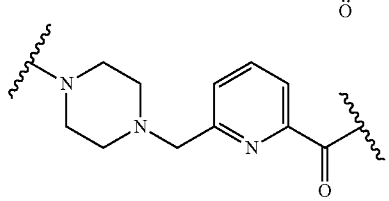, and

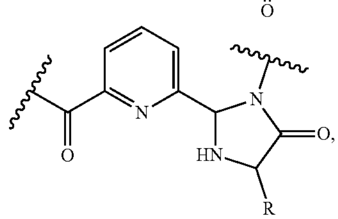

wherein R is alkyl, alkenyl, alkynyl, carbocyclyl, or heterocyclyl; or wherein M is selected from the group consisting of:

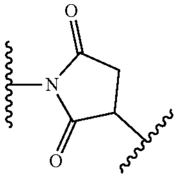,

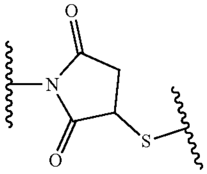,

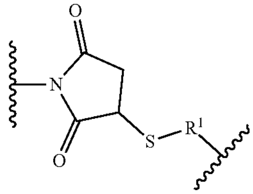,

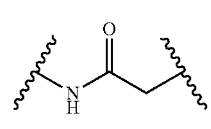,

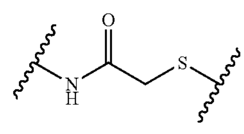,

-continued

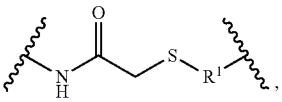
,
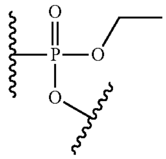
,
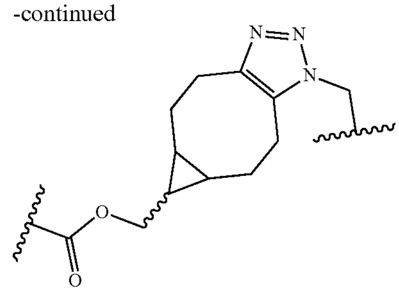
,
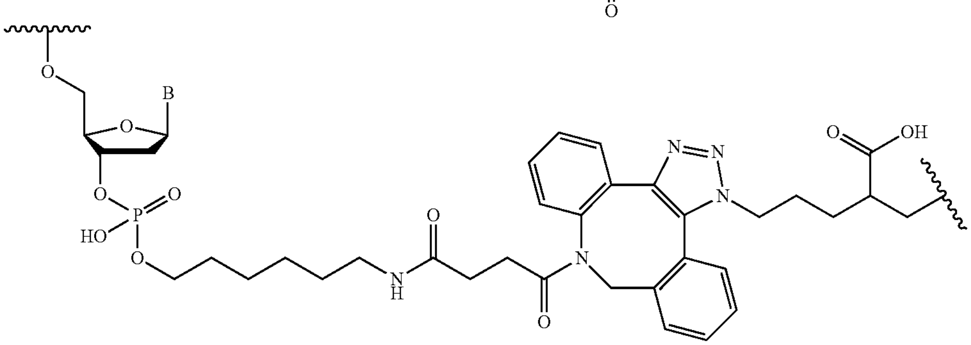
, and
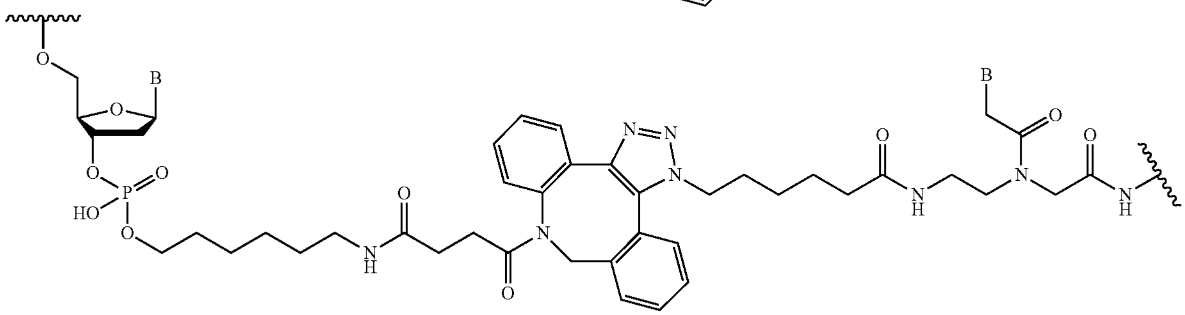
.

wherein: $R^1$ is alkylene, cycloalkyl, or

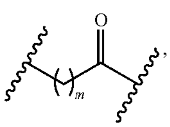
, wherein m is 0 to 10 wherein each R is independently an alkyl, alkenyl, alkynyl, carbocyclyl, or heterocyclyl.

Embodiment 18. The compound of any one of Embodiment 14-17, wherein M is

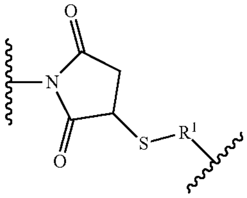
.

Embodiment 19. The compound of Embodiment 18, wherein $R^1$ is

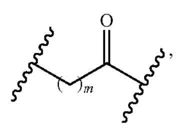
, and m is 2.

Embodiment 20. The compound of Embodiment 19, wherein L-M has the following structure

II-C

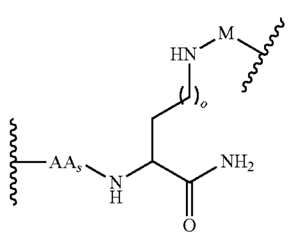

wherein:

$AA_s$ is a side chain or terminus of an amino acid on the cCPP;

o is an integer from 0 to 10.

Embodiment 21. The compound of any of the preceding Embodiments having the following structure

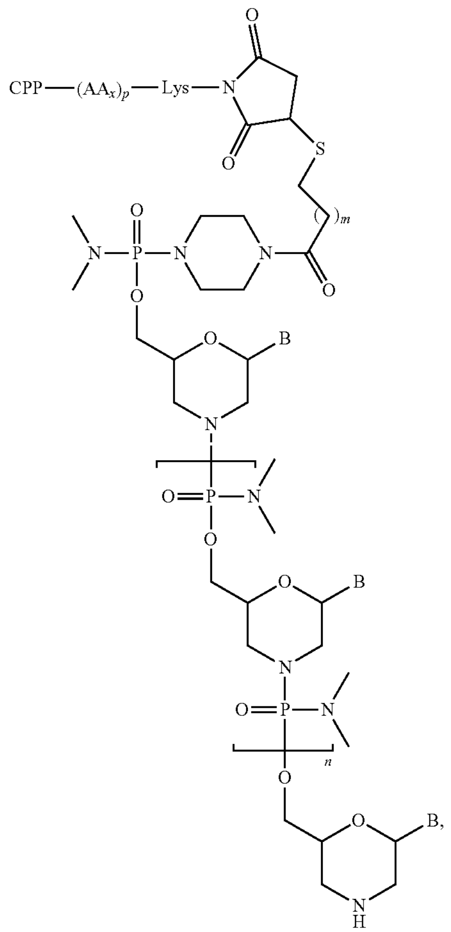

wherein each B is independently a nucleobase; and n is 1 to 50.

Embodiment 22. The compound of any one of Embodiments 12-21, wherein the cCPP has a sequence comprising Formula III:

III

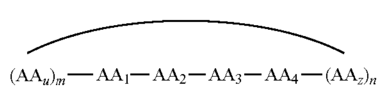

wherein:

each of $AA_1$, $AA_2$, $AA_3$, and $AA_4$, are independently selected from a D or L amino acid, each of $AA_u$ and $AA_z$, at each instance and when present, are independently selected from a D or L amino acid, and m and n are independently selected from a number from 0 to 6; and wherein:

at least two of $AA_u$, at each instance and when present, $AA_1$, $AA_2$, $AA_3$, $AA_4$, and $AA_z$, at each instance and when present, are independently arginine, and at least two of $AA_u$, at each instance and when present, $AA_1$, $AA_2$, $AA_3$, $AA_4$, and $AA_z$, at each instance and when present, are independently a hydrophobic amino acid.

Embodiment 23. The compound of Embodiment 22, wherein the cCPP has a sequence comprising any one of Formula IV-A-D:

IV-A

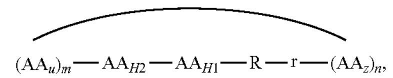

IV-B

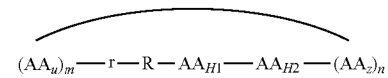

IV-C

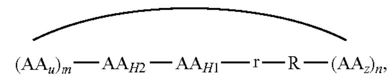

and

IV-D

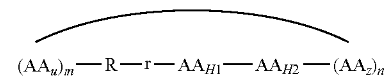

wherein:

each of $AA_{H1}$ and $AA_{H2}$ are independently a D or L hydrophobic amino acid;

at each instance and when present, each of $AA_U$ and $AA_Z$ are independently a D or L amino acid; and m and n are independently selected from a number from 0 to 6.

Embodiment 24. The compound of any one of Embodiments 1-23, wherein M is present and covalently bound to the 5' end of the AC or the 3' end of the AC.

Embodiment 25. The compound of any one of Embodiments 1-24, wherein M is present and is covalently bound to the 5' end of the AC.

Embodiment 26. The compound of any one of Embodiments 1-25, wherein M is present and is covalently bound to the backbone of the AC.

Embodiment 27. The compound of any one of Embodiments 114-26, wherein u is 0.

Embodiment 28. The compound of any one of Embodiments 14-27, wherein p is 1.

Embodiment 29. The compound of any one of Embodiments 14-28, wherein q is 12.

Embodiment 30. The compound of any one of Embodiments 1-29, wherein the AC is complementary to a target sequence comprising an intron, comprising by an exon, or bridging an intron/exon junction.

Embodiment 31. The compound of any one of Embodiments 1-30, wherein the AC is complementary to a target sequence comprising an intronic silencer sequence (ISS) or terminal stem loop (TSL) sequence of the target pre-mRNA.

Embodiment 32. The compound of any one of Embodiments 1-31, wherein the AC is complementary to part or all of a splice site.

Embodiment 33. The compound of Embodiment 32, wherein the splice site is a splice donor site, a splice acceptor site, a cryptic splice site, or a mutation-induced aberrant splice site.

Embodiment 34. The compound of any one of Embodiments 1-33, wherein hybridization of the AC with its target sequence results in exon skipping or exon inclusion.

Embodiment 35. The compound of any one of Embodiments 1-34, wherein the AC is 5-50 nucleotides in length.

Embodiment 36. The compound of any one of Embodiments 1-35, wherein the AC comprises one or more modified nucleotides or nucleic acids that affect one or more of nuclease resistance, pharmacokinetics, and affinity.

Embodiment 37. The compound of any one of Embodiments 1-36, wherein the AC comprises one or more phosphorodiamidate morpholino nucleosides, 2'-O-methylated nucleosides, and/or locked nucleic acids (LNAs).

Embodiment 38. The compound of any one of Embodiments 1-37, wherein the target gene is involved in the pathogenesis of a disease.

Embodiment 39. The compound of any one of Embodiments 1-38, wherein the target gene is involved in the pathogenesis of a genetic disease.

Embodiment 40. The compound of any one of Embodiments 1-39, wherein the target gene is involved in the pathogenesis of a cancer, an autoimmune disease, an inflammatory disease, or an infection.

Embodiment 41. The compound of any one of Embodiments 1-40, wherein the target sequence in the pre-mRNA comprises a mutation-induced aberrant splice site.

Embodiment 42. The compound of any one of Embodiments 1-41, wherein hybridization of the AC with the target sequence suppresses aberrant splicing of the target pre-mRNA.

Embodiment 43. The compound of any one of Embodiments 1-42, wherein hybridization of the AC with the target sequence induces preferential expression of one or more protein isomers encoded by the target gene.

Embodiment 44. The compound of any one of Embodiments 1-43, wherein hybridization of the AC with the target sequence suppresses expression of one or more protein isomers encoded by the target gene.

Embodiment 45. The compound of any one of Embodiments 1-44, wherein the target protein produced by splicing and translation of the target pre-mRNA is not functional or is less functional than a wild type target protein in the absence of AC hybridization to the target sequence.

Embodiment 46. The compound of any one of Embodiments 1-45, wherein hybridization of the AC with the target sequence suppresses expression of the target protein that would have been expressed from the target pre-mRNA in the absence of AC hybridization.

Embodiment 47. The compound of any one of Embodiments 1-46, wherein hybridization of the AC with the target sequence results in expression of a re-spliced target protein having one or more improved functions or characteristics compared to the expressed target protein in the absence of AC hybridization.

Embodiment 48. The compound of Embodiment 47, wherein the one or more improved characteristics comprise function and/or activity.

Embodiment 49. The compound of Embodiment 47 or 48, wherein the re-spliced target protein comprises an active fragment of a wild type target protein.

Embodiment 50. The compound of any one of Embodiments 1-49, wherein hybridization of the AC with the target sequence results in expression of a re-spliced target protein that ameliorates or rescues aspects of a disease phenotype associated with the target gene.

Embodiment 51. A pharmaceutical composition comprising the compound of any one of Embodiments 1-50.

Embodiment 52. A cell comprising a compound of any one of Embodiments 1-50.

Embodiment 53. A method of modulating the splicing of a target pre-mRNA in a subject in need thereof, comprising administering a compound of any one of Embodiments 1-50.

Embodiment 54. The method of Embodiment 53, wherein the compound suppresses expression of the target protein translated from the target pre-mRNA in the absence of the compound.

Embodiment 55. The method of Embodiment 53 or 54, wherein administration of the compound results in the expression of a re-spliced target protein.

Embodiment 56. The method of Embodiment 55, wherein the re-spliced target protein has one or more improved characteristics compared to the target protein.

Embodiment 57. The method of Embodiment 56, wherein the one or more improved characteristics are selected from the list consisting of: function, activity, binding, and enzymatic activity.

Embodiment 58. The method of Embodiment 53, wherein administration of the compound results in the increased expression of one or more protein isomers encoded by the target gene.

Embodiment 59. The method of Embodiment 53, wherein administration of the compound results in the decreased expression of one or more protein isomers encoded by the target gene.

Embodiment 60. A method of treating a genetic disease in a subject in need thereof, comprising administering a compound of any one of Embodiments 1-50.

Embodiment 61. The method of Embodiment 60, wherein administration of the compound modulates splicing or expression of a target gene.

Embodiment 62. The method of Embodiment 60 or 61, wherein administration of the compound modulates splicing of the target pre-mRNA.

Embodiment 63. The method of any one of Embodiments 60-62, wherein administration of the compound results in an increase in the expression of a wild type target protein or an active fragment thereof.

Embodiment 64. The method of any one of Embodiments 60-63, wherein administration of the compound results in expression of a re-spliced target protein that is more highly expressed, functional, and/or active than the target protein expressed in the absence of the compound.

Embodiment 65. The method of Embodiment 64, wherein the re-spliced target protein comprises an active fragment of a wild type target protein.

Embodiment 66. The method of any one of Embodiments 60-65, wherein the genetic disease is a central nervous system disorder, a neuromuscular disorder, or a musculoskeletal disorder.

Embodiment 67. The method of any one of Embodiments 60-66, wherein the genetic disease is Duchenne muscular dystrophy, R thalassemia, dystrophin Kobe, osteogenesis imperfect, cystic fibrosis, Merosin-deficient congenital muscular dystrophy type 1A, or spinal muscular atrophy.

Embodiment 68. The method of any one of Embodiments 60-67, wherein the disease is Duchenne muscular dystrophy.

Embodiment 69. A composition comprising:

(a) a cell penetrating peptide (CPP) sequence; and (b) CRISPR gene-editing machinery, wherein the CPP is conjugated to the CRISPR gene-editing machinery.

Embodiment 70. The composition of Embodiment 69, wherein the CPP is conjugated to the CRISPR gene-editing machinery through a linker.

Embodiment 71. The composition of Embodiment 69, wherein the CRISPR gene-editing machinery comprises a gRNA, nuclease, or combination thereof.

Embodiment 72. The composition of Embodiment 71, wherein the CRISPR gene-editing machinery comprises a nuclease, wherein the nuclease is Cas9.

Embodiment 73. The method of Embodiment 68, wherein the AC has a nucleic acid sequence of 5'-GCTATTACCTTAACCCA-3' (SEQ ID NO: 152).

Embodiment 74. The method of Embodiment 73, wherein the AC is a phosphorodiamidate morpholino oligomer (PMO).

Embodiment 75. The method of any one of Embodiments 68, 73, and 74, wherein the CPP is cCPP12

Embodiment 76. A method of treating Alzheimer's Disease in a subject in need thereof, comprising administering a compound of any one of Embodiments 1-50.

Embodiment 77. The method of Embodiment 68, wherein the AC has a nucleic acid sequence of 5'-GTAACTGTATTTGGTACTTCC-3' (SEQ ID NO: 153).

Embodiment 78. The method of Embodiment 77, wherein the AC is a phosphorodiamidate morpholino oligomer (PMO).

Embodiment 79. The method of any one of Embodiments 76-78, wherein the CPP is cCPP12.

Embodiment 80. The compound of any one of any of the preceding Embodiments, comprising a nuclear localization sequence.

Embodiment 81. The compound or method of preceding Embodiments, wherein the CPP is cyclic.

The invention claimed is:

1. A compound of the formula ETRD-684:

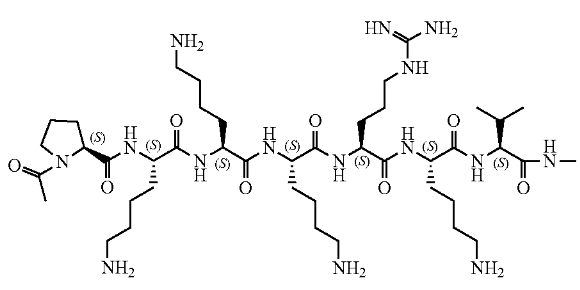

-continued

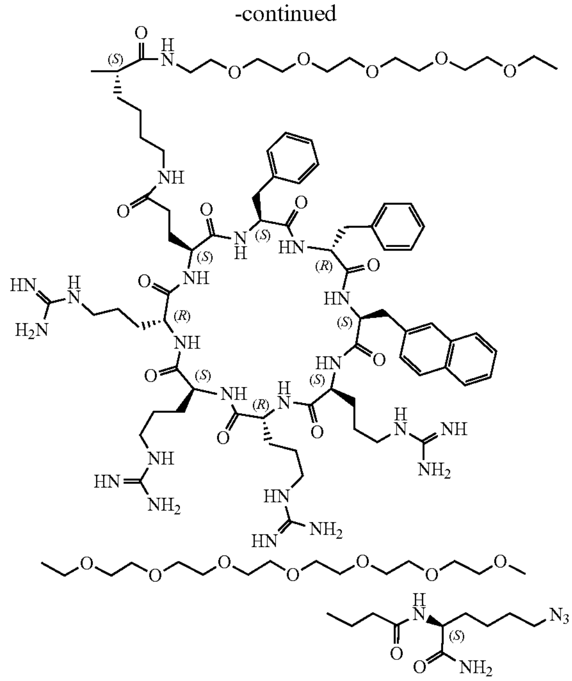

ETRD-684.

* * * * *